(12) United States Patent
Allen et al.

(10) Patent No.: US 8,022,062 B2
(45) Date of Patent: Sep. 20, 2011

(54) 6-SUBSTITUTED 2,3,4,5-TETRAHYDRO-1H-BENZO[D]AZEPINES AS 5-HT$_{2C}$ RECEPTOR AGONISTS

(75) Inventors: John Gordon Allen, Newbury Park, CA (US); Karin Briner, Indianapolis, IN (US); Michael Philip Cohen, Indianapolis, IN (US); Christopher Stanley Galka, Carmel, IN (US); Sarah Lynne Hellman, Indianapolis, IN (US); Maria Angeles Martinez-Grau, Alcobendas (ES); Matthew Robert Reinhard, Indianapolis, IN (US); Michael John Rodriguez, Indianapolis, IN (US); Roger Ryan Rothhaar, Reelsville, IN (US); Michael Wade Tidwell, Indianapolis, IN (US); Frantz Victor, Indianapolis, IN (US); Andrew Caerwyn Williams, Basingstoke (GB); Deyi Zhang, Carmel, IN (US); Michael Philip Mazanetz, Notts (GB)

(73) Assignee: Eli Lilly and Company, Indianapolis, IN (US)

( * ) Notice: Subject to any disclaimer, the term of this patent is extended or adjusted under 35 U.S.C. 154(b) by 644 days.

(21) Appl. No.: 10/598,302

(22) PCT Filed: Feb. 18, 2005

(86) PCT No.: PCT/US2005/005418
§ 371 (c)(1),
(2), (4) Date: Jun. 9, 2008

(87) PCT Pub. No.: WO2005/082859
PCT Pub. Date: Sep. 9, 2005

(65) Prior Publication Data
US 2009/0099155 A1    Apr. 16, 2009

Related U.S. Application Data

(60) Provisional application No. 60/547,681, filed on Feb. 25, 2004.

(51) Int. Cl.
| | |
|---|---|
| *A61P 3/04* | (2006.01) |
| *A61P 25/22* | (2006.01) |
| *A61P 25/24* | (2006.01) |
| *A61P 25/30* | (2006.01) |
| *A61K 31/55* | (2006.01) |
| *C07D 223/16* | (2006.01) |
| *C07D 401/12* | (2006.01) |
| *C07D 417/12* | (2006.01) |
| *C07D 413/12* | (2006.01) |
| *C07D 403/12* | (2006.01) |
| *C07D 409/12* | (2006.01) |
| *C07D 405/12* | (2006.01) |
| *C07D 413/14* | (2006.01) |
| *C07D 417/06* | (2006.01) |
| *C07D 403/06* | (2006.01) |

(52) U.S. Cl. .................. 514/217.01; 540/594
(58) Field of Classification Search ............. 514/217.01; 540/594
See application file for complete search history.

(56) References Cited

U.S. PATENT DOCUMENTS
| | | | |
|---|---|---|---|
| 4,265,890 A | 5/1981 | Holden et al. | |
| 5,698,766 A | 12/1997 | Julius et al. | |

FOREIGN PATENT DOCUMENTS
| | | |
|---|---|---|
| EP | 285 287 A2 | 5/1988 |
| WO | WO 93/03015 A | 2/1993 |
| WO | WO 93/04686 A | 3/1993 |
| WO | WO 02/074746 A1 | 9/2002 |
| WO | WO 03/006466 | 1/2003 |

OTHER PUBLICATIONS

Kilpatrick, et al., "The alpha 2-adreneceptor antagonist SK & F 104078 has high affinity for 5-HT1A and 5-HT2 receptors European Journal of Pharmacology", 166(2) 315-18 coden, 1989.

Database WPI- Section Ch, Week 200274, Derwent Publications LTD., London, GB; Class B02, AN 2002-691852 XP002328506, 2002.

Teacott, et al, "Eating disorder and epilepsy in mice lacking 5-HT2$_C$ serotonin receptors" *Nature*, vol. 374, 542-546, 1995.

Upton, et al, "Studies on the role of 5-HT2$_C$ and 5-HT2$_B$ receptors in regulating generalized seizure threshold in rodents" *European J. O Pharmacology*, 359, 33-40.

Vickers, et al, "Oral administration of the 5-HT2$_C$ receptor agonist, mCPP, reduces body weight gain in rats over 28 days as a result of maintained hypophagia" *Psychopharmacology*, 167; 274-280 (2003).

(Continued)

*Primary Examiner* — Brenda Coleman
(74) *Attorney, Agent, or Firm* — R. Craig Tucker

(57) ABSTRACT

The present invention provides 6-substituted 2,3,4,5-tetrahydro-1H-benzo[d]azepines of Formula I as selective 5-HT$_{2C}$ receptor agonists for the treatment of 5-HT$_{2C}$ associated disorders including obesity, obsessive/compulsive disorder, depression, and anxiety:

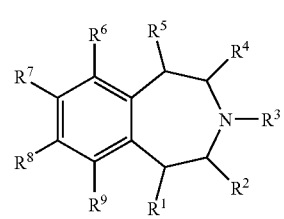

I where:
R$^6$ is —C≡C—R$^{10}$, —O—R$^{12}$, —S—R$^{14}$, or —NR$^{24}$R$^{25}$;
and other substituents are as defined in the specification.

22 Claims, No Drawings

OTHER PUBLICATIONS

Martin, et al, "Influence of the 5-HT$_{2C}$ receptor antagonist, SB-242084, in tests of anxiety" *Pharmacology Biochemistry and Behavior:* 71:615-625 (2002).

Chou-Green, et al, "Compulsive behavior in the 5-HT$_{2C}$ receptor knockout mouse" *Physiology & Behavior,* 78, 641-649 (2003).

Frank, et al, "Sleep and Sleep Homeostasis in Mice Lacking the 5-HT$_{2C}$ Receptor" *Neuropsychopharmacology,* 27:5, 869-873 (2002).

Leysen, et al, "Ligands for the 5-HT$_{2C}$ receptor as potential Antidepressants and Anxiolytics" *Trends In Drug Research II,* 49-61 (1998).

Fitzgerald, et al., Chapter 3: 5-HT$_{2C}$ Receptor Modulators : Progress in Development of New CNS Medicines: *Annual Reports in Medicinal Chemistry* 37, 21, 2002.

6-SUBSTITUTED 2,3,4,5-TETRAHYDRO-1H-BENZO[D]AZEPINES AS 5-HT$_{2C}$ RECEPTOR AGONISTS

This U.S. national stage application of International Application PCT/US2005/005418, filed Feb. 18, 2005, claims priority to U.S. provisional application Ser. No. 60/547,681, filed Feb. 25, 2004.

The neurotransmitter serotonin (5-hydroxytryptamine, 5-HT) has a rich pharmacology arising from a heterogeneous population of at least seven receptor classes. The serotonin 5-HT$_2$ class is further subdivided into at least three subtypes, designated 5-HT$_{2A}$, 5-HT$_{2B}$, and 5-HT$_{2C}$. The 5-HT$_{2C}$ receptor has been isolated and characterized (Julius, et al., U.S. Pat. No. 4,985,352), and transgenic mice lacking the 5-HT$_{2C}$ receptor have been reported to exhibit seizures and an eating disorder resulting in increased consumption of food (Julius et al., U.S. Pat. No. 5,698,766). The 5-HT$_{2C}$ receptor has also been linked to various other neurological disorders including obesity (Vickers et al., Psychopharmacology, 167: 274-280 (2003)), hyperphagia (Tecott et al., Nature, 374: 542-546 (1995)), obsessive compulsive disorder (Martin et al., Pharmacol. Biochem. Behav., 71: 615 (2002); Chou-Green et al., Physiology & Behavior, 78: 641-649 (2003)), depression (Leysen, Kelder, Trends in Drug Research II, 29: 49-61 (1998)), anxiety (Curr. Opin. Invest. Drugs 2(4), p. 317 (1993)), substance abuse, sleep disorder (Frank et al., Neuropsychopharmacology 27: 869-873 (2002)), hot flashes (EP 1213017 A2), epilepsy (Upton et al., Eur. J. Pharmacol., 359: 33 (1998); Fitzgerald, Ennis, Annual Reports in Medicinal Chemistry, 37: 21-30 (2002)), and hypogonadism (Curr. Opin. Invest. Drugs 2(4), p. 317 (1993)).

Certain substituted 2,3,4,5-tetrahydro-1H-benzo[d]azepine compounds have been disclosed as useful therapeutics as for example:

U.S. Pat. No. 4,265,890 describes certain substituted 2,3,4,5-tetrahydro-1H-benzo[d]azepine compounds as dopaminergic receptor antagonists for use as antipsychotics and antiemetics, inter alia.

EP 0 285 287 describes certain substituted 2,3,4,5-tetrahydro-1H-benzo[d]azepine compounds for use as agents to treat gastrointestinal motility disorders, inter alia.

WO 93/03015 and WO 93/04686 describe certain substituted 2,3,4,5-tetrahydro-1H-benzo[d]azepine compounds as alpha-adrenergic receptor antagonists for use as agents to treat hypertension and cardiovascular diseases in which changes in vascular resistance are desirable, inter alia.

WO 02/074746 A1 describes certain substituted 2,3,4,5-tetrahydro-1H-benzo[d]azepine compounds as 5-HT$_{2C}$ agonists for the treatment of hypogonadism, obesity, hyperphagia, anxiety, depression, sleep disorder, inter alia.

WO 03/006466 A1 describes certain substituted tricyclic hexahydroazepinoindole and indoline compounds as 5-HT ligands and consequently their usefulness for treating diseases wherein modulation of 5-HT activity is desired.

High affinity 5-HT$_{2C}$ receptor agonists would provide useful therapeutics for the treatment of the above mentioned 5-HT$_{2C}$ receptor-associated disorders including obesity, hyperphagia, obsessive/compulsive disorder, depression, anxiety, substance abuse, sleep disorder, hot flashes, and hypogonadism. High affinity 5-HT$_{2C}$ receptor agonists that are also selective for the 5-HT$_{2C}$ receptor, would provide such therapeutic benefit without the undesirable adverse events associated with current therapies. Achieving selectivity for the 5-HT$_{2C}$ receptor, particularly as against the 5-HT$_{2A}$ and 5-HT$_{2B}$ receptors, has proven difficult in designing 5-HT$_{2C}$ agonists. 5-HT$_{2A}$ receptor agonists have been associated with problematic hallucinogenic adverse events. (Nelson et al., Naunyn-Schmiedeberg's Arch. Pharm., 359: 1-6 (1999)). 5-HT$_{2B}$ receptor agonists have been associated with cardiovascular related adverse events, such as valvulopathy. (V. Setola et al., Mol. Pharmacology, 63: 1223-1229 (2003), and ref. cited therein).

Previous references to substituted 2,3,4,5-tetrahydro-1H-benzo[d]azepine compounds as potential therapeutics have predominately recited their uses as alpha adrenergic and/or dopaminergic modulators. Adrenergic modulators are often associated with the treatment of cardiovascular diseases (Frishman, Kotob, Journal of Clinical Pharmacology, 39: 7-16 (1999)). Dopaminergic receptors are primary targets in the treatment of schizophrenia and Parkinson's disease (Seeman, Van Tol, Trends in Pharmacological Sciences, 15: 264-270 (1994)). It will be appreciated by those skilled in the art that selectivity as against these and other physiologically important receptors will generally also be preferred characteristics for therapeutics for the specific treatment of 5-HT$_{2C}$ associated disorders as described above.

The present invention provides selective 5-HT$_{2C}$ agonist compounds of Formula I:

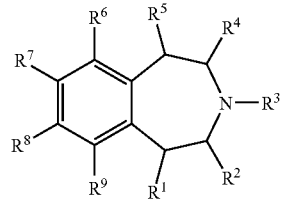

I where:

$R^1$ is hydrogen, fluoro, or ($C_1$-$C_3$)alkyl;

$R^2$, $R^3$, and $R^4$ are each independently hydrogen, methyl, or ethyl;

$R^5$ is hydrogen, fluoro, methyl, or ethyl;

$R^6$ is —C≡C—$R^{10}$, —O—$R^{12}$, —S—$R^{14}$, or —N$R^{24}R^{25}$;

$R^7$ is hydrogen, halo, cyano, ($C_1$-$C_6$)alkyl optionally substituted with 1 to 6 fluoro substituents, ($C_2$-$C_6$)alkenyl optionally substituted with 1 to 6 fluoro substituents, ($C_3$-$C_7$)cycloalkyl, ($C_1$-$C_6$)alkoxy optionally substituted with 1 to 6 fluoro substituents, ($C_1$-$C_6$)alkylthio optionally substituted with 1 to 6 fluoro substituents, Ph$^1$-($C_0$-$C_3$)alkyl, Ph$^1$-($C_0$-$C_3$)alkyl-O—, or Ph$^1$-($C_0$-$C_3$)alkyl-S—;

$R^8$ is hydrogen, halo, cyano, or —SCF$_3$;

$R^9$ is hydrogen, halo, cyano, —CF$_3$, —SCF$_3$, or ($C_1$-$C_3$) alkoxy optionally substituted with 1 to 6 fluoro substituents;

$R^{10}$ is —CF$_3$, ethyl substituted with 1 to 5 fluoro substituents, ($C_3$-$C_6$) alkyl optionally substituted with 1 to 6 fluoro substituents, ($C_3$-$C_7$)cycloalkyl($C_0$-$C_3$)alkyl, Ar$^1$—($C_0$-$C_3$)alkyl, Ph$^1$-($C_0$-$C_3$)alkyl, or 3-($C_1$-$C_4$)alkyl-2-oxo-imidazolidin-1-yl-($C_1$-$C_3$)alkyl;

$R^{12}$ is Ph$^2$-($C_1$-$C_3$)alkyl, Ar$^2$—($C_1$-$C_3$)alkyl, ($C_1$-$C_6$)alkyl-S—($C_2$-$C_6$)alkyl, ($C_3$-$C_7$)cycloalkyl-S—($C_2$-$C_6$)alkyl, phenyl-S—($C_2$-$C_6$)alkyl, Ph$^2$-S—($C_2$-$C_6$)alkyl, phenylcarbonyl-($C_1$-$C_3$)alkyl, Ph$^2$-C(O)—($C_1$-$C_3$)alkyl, ($C_1$-$C_6$) alkoxycarbonyl($C_3$-$C_6$)alkyl, ($C_3$-$C_7$)cycloalkyl-OC(O)—($C_3$-$C_6$)alkyl, phenyloxycarbonyl-($C_3$-$C_6$)alkyl, Ph$^2$-OC(O)—($C_3$-$C_6$)alkyl, Ar$^2$—OC(O)—($C_3$-$C_6$)alkyl, ($C_3$-$C_7$)cycloalkyl-NH—C(O)—($C_2$-$C_4$)alkyl-, Ph$^1$-NH—C(O)—($C_2$-$C_4$)alkyl-, Ar$^2$—NH—C(O)—($C_2$-$C_4$) alkyl-, or $R^{13}$—C(O)NH—($C_2$-$C_4$)alkyl;

$R^{13}$ is $(C_3-C_7)$cycloalkyl$(C_0-C_3)$alkyl, $Ph^2$, $Ar^2$, or $(C_1-C_3)$ alkoxy optionally substituted with 1 to 6 fluoro substituents, $Ph^1$-NH- or N-linked Het$^1$;

$R^{14}$ is $Ar^2$ which is not N-linked to the sulfur atom, $Ph^2$, $R^{15}$-L-, tetrahydrofuranyl, tetrahydropyranyl, or phenylmethyl substituted on the methyl moiety with a substituent selected from the group consisting of $(C_1-C_3)$-n-alkyl substituted with hydroxy, $(C_1-C_3)$alkyl-O—$(C_1-C_2)$-n-alkyl, $(C_1-C_3)$alkyl-C(O)—$(C_0-C_2)$-n-alkyl, and $(C_1-C_3)$alkyl-O—C(O)—$(C_0-C_2)$-n-alkyl, wherein when $R^{14}$ is $Ph^2$ or $Ar^2$, wherein $Ar^2$ is pyridyl, then $R^{14}$ may also, optionally be substituted with phenyl-CH═CH— or phenyl-C≡C—, said phenyl-CH═CH— or phenyl-C≡C— being optionally further substituted with 1 to 3 substituents independently selected from the group consisting of halo, cyano, —SCF$_3$, $(C_1-C_6)$alkyl optionally further substituted with 1 to 6 fluoro substituents, and $(C_1-C_6)$alkoxy optionally further substituted with 1 to 6 fluoro substituents, and wherein when $Ar^2$ is pyridyl, the pyridyl may alternatively, optionally be substituted with $R^{28}R^{29}N$—C(O)—, and optionally further substituted with one methyl, —CF$_3$, cyano, or —SCF$_3$ substituent, or with 1 to 2 halo substituents, and wherein the tetrahydrofuranyl and tetrahydropyranyl may optionally be substituted with an oxo substituent, or with one or two groups independently selected from methyl and —CF$_3$;

$R^{15}$ is —OR$^{16}$, cyano, —SCF$_3$, $Ph^2$, $Ar^2$, quinolinyl, isoquinolinyl, cinnolinyl, quinazolinyl, phthalimido, benzothiophenyl optionally substituted at the 2-position with phenyl or benzyl, benzothiazolyl optionally substituted at the 2-position with phenyl or benzyl, benzothiadiazolyl optionally substituted with phenyl or benzyl, 2-oxo-dihydroindol-1-yl optionally substituted at the 3 position with gem dimethyl or $(C_1-C_6)$alkyl optionally further substituted with 1 to 6 fluoro substituents, 2-oxo-dihydroindol-5-yl optionally substituted at the 3 position with gem dimethyl or $(C_1-C_6)$alkyl optionally further substituted with 1 to 6 fluoro substituents, 2-oxo-imidazolidin-1-yl optionally substituted at the 3 position with gem dimethyl or $(C_1-C_6)$alkyl optionally further substituted with 1 to 6 fluoro substituents, 2-oxo-tetrahydropyridinyl optionally substituted at the 3 or 4 position with gem dimethyl or $(C_1-C_6)$alkyl optionally further substituted with 1 to 6 fluoro substituents, 2-oxo-tetrahydroquinolin-1-yl optionally substituted at the 3 position with gem dimethyl or $(C_1-C_6)$alkyl optionally further substituted with 1 to 6 fluoro substituents, 2-oxo-dihydrobenzimidazol-1-yl optionally substituted at the 3 position with gem dimethyl or $(C_1-C_6)$alkyl optionally further substituted with 1 to 6 fluoro substituents, —NR$^{17}$R$^{18}$, —C(O)R$^{22}$, or a saturated heterocycle selected from the group consisting of pyrrolidinyl, piperidinyl, morpholinyl, and thiomorpholinyl, tetrahydrofuranyl, and tetrahydropyranyl, wherein $Ph^2$ and $Ar^2$ when $Ar^2$ is pyridyl, may also optionally be substituted with phenyl-CH═CH— or phenyl-C≡C—, said phenyl-CH═CH— and phenyl-C≡C— being optionally further substituted on the phenyl moiety with 1 to 3 substituents independently selected from the group consisting of halo, cyano, —SCF$_3$, $(C_1-C_6)$ alkyl optionally further substituted with 1 to 6 fluoro substituents, and $(C_1-C_6)$alkoxy optionally further substituted with 1 to 6 fluoro substituents, and wherein $Ar^2$ may alternatively, optionally be substituted with a substituent selected from the group consisting of $(C_3-C_7)$cycloalkyl-$(C_0-C_3)$alkyl, Het$^1$-$(C_0-C_3)$alkyl, pyridyl-$(C_0-C_3)$alkyl, and phenyl-$(C_0-C_3)$alkyl, and optionally further substituted with one methyl, —CF$_3$, cyano, or —SCF$_3$ substituent, or with 1 to 2 halo substituents, said pyridyl-$(C_0-C_3)$alkyl and phenyl-$(C_0-C_3)$alkyl optionally being further substituted with 1-3 substituents independently selected from halo, —CH$_3$, —OCH$_3$, —CF$_3$, —OCF$_3$, —CN, and —SCF$_3$, and wherein when $Ar^2$ is pyridyl, the pyridyl may alternatively, optionally be substituted with $R^{28}R^{29}N$—C(O)—, or $(C_1-C_6)$alkyl-C(O)— optionally substituted with 1 to 6 fluoro substituents, and may be optionally further substituted with one methyl, —CF$_3$, cyano, or —SCF$_3$ substituent, or with 1 to 2 halo substituents, and wherein when $Ar^2$ is thiazolyl, the thiazolyl may alternatively, optionally be substituted with $(C_3-C_7)$cycloalkyl-$(C_0-C_3)$alkyl-NH—, and wherein the pyrrolidinyl, piperidinyl, morpholinyl, and thiomorpholinyl is substituted with oxo- on a carbon atom adjacent to the ring nitrogen atom, or is N-substituted with a substituent selected from the group consisting of $(C_1-C_6)$alkylcarbonyl, $(C_1-C_6)$alkylsulfonyl,
$(C_3-C_7)$cycloalkyl$(C_0-C_3)$alkyl-C(O)—,
$(C_3-C_7)$cycloalkyl$(C_0-C_3)$alkyl-S(O)$_2$—, $Ph^1$-$(C_0-C_3)$alkyl-C(O)—, and
$Ph^1$-$(C_0-C_3)$alkyl-S(O)$_2$—, and may optionally be further substituted with 1 or 2 methyl or —CF$_3$ substituents, and when oxo-substituted, may optionally be further N-substituted with a substituent selected from the group consisting of $(C_1-C_6)$alkyl optionally further substituted with 1 to 6 fluoro substituents, $(C_3-C_7)$cycloalkyl$(C_0-C_3)$alkyl, and $Ph^1$-$(C_0-C_3)$alkyl, and wherein tetrahydrofuranyl and tetrahydropyranyl may optionally be substituted with an oxo substituent, and/or with one or two groups independently selected from methyl and —CF$_3$;

L is branched or unbranched $(C_1-C_6)$alkylene, except when $R^{15}$ is —NR$^{17}$R$^{18}$ or $Ar^2$—N-linked to L, in which case L is branched or unbranched $(C_2-C_6)$alkylene, and when L is methylene or ethylene, L may optionally be substituted with gem-ethano or with 1 to 2 fluoro substituents, and when $R^{15}$ is $Ph^2$, $Ar^2$, or a saturated heterocycle, L may alternatively, optionally be substituted with a substituent selected from the group consisting of hydroxy, cyano, —SCF$_3$, $(C_1-C_6)$alkoxy optionally further substituted with 1 to 6 fluoro substituents, $(C_1-C_6)$alkoxycarbonyl optionally further substituted with 1 to 6 fluoro substituents, $(C_1-C_6)$alkylcarbonyloxy optionally further substituted with 1 to 6 fluoro substituents, $(C_3-C_7)$cycloalkyl-$(C_0-C_3)$ alkyl-O—, $(C_3-C_7)$cycloalkyl-$(C_0-C_3)$alkyl-O—C(O)—, and $(C_3-C_7)$cycloalkyl-$(C_0-C_3)$alkyl-C(O)—O—;

$R^{16}$ is hydrogen, $(C_1-C_6)$alkyl optionally substituted with 1 to 6 fluoro substituents, $(C_1-C_6)$alkylcarbonyl, $(C_3-C_7)$cycloalkyl$(C_0-C_3)$alkyl, $(C_3-C_7)$cycloalkyl$(C_0-C_3)$alkyl-C(O)—, $Ph^1$-$(C_0-C_3)$alkyl, $Ph^1$-$(C_0-C_3)$alkyl-C(O)—, $Ar^2$—$(C_0-C_3)$alkyl, or $Ar^2$—$(C_0-C_3)$alkyl-C(O)—, $R^{17}$ is $(C_1-C_4)$alkyl optionally substituted with 1 to 6 fluoro substituents, t-butylsulfonyl, $(C_3-C_7)$cycloalkyl$(C_0-C_3)$alkyl-C(O)—, $(C_3-C_7)$cycloalkyl$(C_0-C_3)$alkyl-sulfonyl, $Ph^1$-$(C_0-C_3)$alkyl, $Ph^1$-$(C_0-C_3)$alkyl-C(O)—, $Ph^1$-$(C_0-C_3)$ alkylsulfonyl, $Ar^2$—$(C_0$-$C_3)$alkyl, $Ar^2$—$(C_0$-$C_3)$alkyl-C(O)—, $Ar^2$—$(C_0$-$C_3)$alkylsulfonyl, $R^{19}$OC(O)—, or $R^{20}R^{21}$NC(O)—;

$R^{18}$ is hydrogen or $(C_1$-$C_4)$alkyl optionally substituted with 1 to 6 fluoro substituents, or $R^{17}$ and $R^{18}$, taken together with the nitrogen atom to which they are attached form $Het^1$ where $Het^1$ is substituted with oxo- on a carbon atom adjacent to the ring nitrogen atom, or $R^{17}$ and $R^{18}$, taken together with the nitrogen atom to which they are attached, form an aromatic heterocycle selected from the group consisting of pyrolyl, pyrazolyl, imidazolyl, 1,2,3-triazolyl, and 1,2,4-triazolyl, said aromatic heterocycle optionally being substituted with 1 to 2 halo substituents, or substituted with 1, to 2 $(C_1$-$C_4)$alkyl substituents optionally further substituted with 1 to 3 fluoro substituents, or mono-substituted with fluoro, nitro, cyano, —$SCF_3$, or $(C_1$-$C_4)$ alkoxy optionally further substituted with 1 to 3 fluoro substituents, and optionally further substituted with a $(C_1$-$C_4)$alkyl substituent optionally further substituted with 1 to 3 fluoro substituents;

$R^{19}$ is $(C_1$-$C_6)$alkyl optionally substituted with 1 to 6 fluoro substituents, $(C_3$-$C_7)$cycloalkyl$(C_0$-$C_3)$alkyl, $Ar^2$—$(C_0$-$C_3)$alkyl, or $Ph^1$-$(C_0$-$C_3)$alkyl, $R^{20}$ is $(C_1$-$C_6)$alkyl optionally substituted with 1 to 6 fluoro substituents, $(C_3$-$C_7)$cycloalkyl$(C_0$-$C_3)$alkyl, $Ar^2$—$(C_0$-$C_3)$alkyl, or $Ph^1$-$(C_0$-$C_3)$alkyl, $R^{21}$ is hydrogen or $(C_1$-$C_4)$alkyl optionally substituted with 1 to 6 fluoro substituents, or $R^{20}$ and $R^{21}$, taken together with the nitrogen atom to which they are attached, form $Het^1$;

$R^{22}$ is $(C_1$-$C_6)$alkyl optionally substituted with 1 to 6 fluoro substituents, $(C_3$-$C_7)$cycloalkyl$(C_0$-$C_3)$alkyl, $R^{23}$—O—, $Ph^1$-$(C_0$-$C_3)$alkyl, $Ar^2$—$(C_0$-$C_3)$alkyl, or $R^{32}R^{33}$N—, $R^{23}$ is $(C_1$-$C_6)$alkyl optionally substituted with 1 to 6 fluoro substituents, $(C_3$-$C_7)$cycloalkyl$(C_0$-$C_3)$alkyl, $Ph^1$-$(C_0$-$C_3)$alkyl, or $Ar^2$—$(C_0$-$C_3)$alkyl;

$R^{24}$ is $(C_1$-$C_6)$alkoxy$(C_2$-$C_5)$alkyl optionally substituted with 1 to 6 fluoro substituents, $(C_1$-$C_6)$alkylthio$(C_2$-$C_5)$alkyl optionally substituted with 1 to 6 fluoro substituents, $(C_3$-$C_7)$cycloalkyl$(C_0$-$C_1)$alkyl-O—$(C_1$-$C_5)$alkyl, $(C_3$-$C_7)$cycloalkyl$(C_0$-$C_1)$alkyl-S—$(C_1$-$C_5)$alkyl, phenyl$(C_1$-$C_3)$ n-alkyl, $Ph^2$-$(C_1$-$C_3)$-n-alkyl, $Ar^2(C_0$-$C_3)$ n-alkyl, phenyl$(C_0$-$C_1)$alkyl-O—$(C_1$-$C_5)$alkyl, phenyl$(C_0$-$C_1)$alkyl-S—$(C_1$-$C_5)$alkyl $Ph^1$-$(C_0$-$C_1)$alkyl-C(O)NH—$(C_2$-$C_4)$alkyl, $Ph^1$-$(C_0$-$C_1)$alkyl-NH—C(O)NH—$(C_2$-$C_4)$alkyl, pyridyl-$(C_0$-$C_1)$alkyl-C(O)NH—$(C_2$-$C_4)$alkyl, pyridyl-$(C_0$-$C_1)$alkyl-NH—C(O)NH—$(C_2$-$C_4)$alkyl, or $Ar^3(C_1$-$C_2)$alkyl, where $Ar^3$ is a bi-cyclic moiety selected from a group consisting of indanyl, indolyl, dihydrobenzofuranyl, benzofuranyl, benzothiophenyl, benzoxazolyl, benzothiazolyl, benzo[1,3]dioxolyl, naphthyl, dihydrobenzopyranyl, quinolinyl, isoquinolinyl, and benzo[1,2,3]thiadiazolyl, said $Ar^3$ optionally being substituted with $(C_1$-$C_6)$alkyl optionally further substituted with 1 to 6 fluoro substituents, phenyl$(C_0$-$C_1)$alkyl optionally further substituted with 1 to 6 fluoro substituents, or substituted with $(C_3$-$C_7)$cycloalkyl$(C_0$-$C_3)$alkyl, or substituted with 1-3 substituents independently selected from the group consisting of halo, oxo, methyl, and —$CF_3$, said phenyl$(C_1$-$C_3)$ n-alkyl, $Ph^2$-$(C_1$-$C_3)$ n-alkyl, or $Ar^2$ $(C_0$-$C_3)$ n-alkyl optionally being substituted on the n-alkyl moiety when present with $(C_1$-$C_3)$alkyl, dimethyl, gem-ethano, 1 to 2 fluoro substituents, or $(C_1$-$C_6)$alkyl-C(O)—, said $Ar^2(C_0$-$C_3)$ n-alkyl being alternatively optionally substituted with a substituent selected from the group consisting of $(C_3$-$C_7)$cycloalkyl-$(C_0$-$C_3)$alkyl, $Het^1$-$(C_0$-$C_3)$alkyl, pyridyl-$(C_0$-$C_3)$alkyl, phenyl-$(C_0$-$C_3)$ alkyl, pyridyl-$(C_0$-$C_3)$alkyl-NH—, phenyl-$(C_0$-$C_3)$alkyl-NH—, $(C_1$-$C_6)$alkyl-S—, and $(C_3$-$C_7)$cycloalkyl-$(C_0$-$C_3)$alkyl-S—, and optionally further substituted with one methyl, —$CF_3$, cyano, or —$SCF_3$ substituent, or with 1 to 2 halo substituents, said pyridyl-$(C_0$-$C_3)$alkyl and phenyl-$(C_0$-$C_3)$alkyl optionally being further substituted with 1-3 substituents independently selected from halo, —$CH_3$, —$OCH_3$, —$CF_3$, —$OCF_3$, —CN, and —$SCF_3$, and said $Ph^2$-$(C_1$-$C_3)$ n-alkyl and $Ar^2(C_0$-$C_3)$ n-alkyl where $Ar^2$ is pyridyl, also optionally being substituted on the phenyl or $Ar^2$ moiety, respectively, with phenyl-CH═CH— or phenyl-C≡C—, said phenyl-CH═CH— or phenyl-C≡C— being optionally further substituted with 1 to 3 substituents independently selected from the group consisting of halo, cyano, —$SCF_3$, $(C_1$-$C_6)$alkyl optionally further substituted with 1 to 6 fluoro substituents, and $(C_1$-$C_6)$alkoxy optionally further substituted with 1 to 6 fluoro substituents, and said $Ar^2(C_0$-$C_3)$ n-alkyl where $Ar^2$ is pyridyl, alternatively, optionally being substituted with $(C_1$-$C_6)$alkyl-C(O)— or $R^{28}R^{29}$N—C(O)—, and optionally further substituted with one methyl, —$CF_3$, cyano, or —$SCF_3$ substituent, or with 1 to 2 halo substituents, said phenyl$(C_0$-$C_1)$alkyl-O—$(C_1$-$C_5)$alkyl, or phenyl $(C_0$-$C_1)$alkyl-S—$(C_1$-$C_5)$alkyl optionally being substituted on the phenyl moiety with $(C_1$-$C_2)$—S(O)$_2$—, or with 1 to 5 independently selected halo substituents, or with 1 to 3 substituents independently selected from the group consisting of halo, cyano, —$SCF_3$, $(C_1$-$C_6)$alkyl optionally further substituted with 1 to 6 fluoro substituents, and $(C_1$-$C_6)$alkoxy optionally further substituted with 1 to 6 fluoro substituents, and said pyridyl-$(C_0$-$C_1)$alkyl-C(O)NH—$(C_2$-$C_4)$alkyl and pyridyl-$(C_0$-$C_1)$alkyl-NH—C(O)NH—$(C_2$-$C_4)$alkyl optionally being substituted on the pyridyl moiety with methyl, —$CF_3$, or 1 to 3 halo substituents;

$R^{25}$ is hydrogen, $(C_1$-$C_3)$alkyl optionally substituted with 1 to 6 fluoro substituents, or alkyl;

$R^{26}$ is hydrogen, $(C_1$-$C_6)$alkyl optionally substituted with 1 to 6 fluoro substituents, $(C_3$-$C_7)$cycloalkyl$(C_0$-$C_3)$alkyl;

$R^{27}$ is hydrogen or $(C_1$-$C_4)$alkyl optionally substituted with 1 to 6 fluoro substituents, or $R^{26}$ and $R^{27}$, taken together with the nitrogen atom to which they are attached, form $Het^1$;

$R^{28}$ is $(C_1$-$C_8)$alkyl optionally substituted with 1 to 6 fluoro substituents, $(C_3$-$C_8)$cycloalkyl$(C_0$-$C_3)$alkyl, tetrahydropyran-3-yl$(C_0$-$C_3)$alkyl, tetrahydropyran-4-yl$(C_0$-$C_3)$alkyl, tetrahydrofuranyl$(C_0$-$C_3)$alkyl, $Ph^1$-$(C_0$-$C_2)$ n-alkyl, or $Ar^2$—$(C_0$-$C_2)$ n-alkyl, said $Ph^1$-$(C_0$-$C_2)$ n-alkyl and $Ar^2$—$(C_0$-$C_2)$ n-alkyl optionally being substituted on the alkyl moiety when present with $(C_1$-$C_3)$alkyl, dimethyl, or gem-ethano;

$R^{29}$ is hydrogen or $(C_1$-$C_3)$alkyl;

$R^{30}$ is hydrogen, $(C_1$-$C_6)$alkyl optionally substituted with 1 to 6 fluoro substituents, $(C_3$-$C_7)$cycloalkyl$(C_0$-$C_3)$alkyl, $Ph^1$-$(C_0$-$C_3)$alkyl, or $Ar^2(C_0$-$C_3)$alkyl, $R^{31}$ is hydrogen or $(C_1$-$C_6)$alkyl optionally substituted with 1 to 6 fluoro substituents, or $R^{30}$ and $R^{31}$, taken together with the nitrogen atom to which they are attached, form $Het^1$, said Het$^1$ also optionally being substituted with phenyl optionally further substituted with 1 to 3 halo substituents;

R$^{32}$ and R$^{33}$ are each independently hydrogen or (C$_1$-C$_6$)alkyl optionally substituted with 1 to 6 fluoro substituents, or R$^{32}$ and R$^{33}$, taken together with the nitrogen atom to which they are attached, form Het$^1$, or R$^{32}$ is Ph$^1$(C$_0$-C$_1$)alkyl provided that R$^{33}$ is hydrogen;

Ar$^1$ is an aromatic heterocycle substituent selected from the group consisting of furanyl, thiophenyl, thiazolyl, oxazolyl, isoxazolyl, pyridyl, and pyridazinyl, any of which may optionally be substituted with 1 to 3 substituents independently selected from the group consisting of halo, (C$_1$-C$_3$)alkyl, (C$_1$-C$_3$)alkoxy, —CF$_3$, —O—CF$_3$, nitro, cyano, and trifluoromethylthio;

Ar$^2$ is an aromatic heterocycle substituent selected from the group consisting of pyrrolyl, pyrazolyl, imidazolyl, 1,2,3-triazolyl, 1,2,4-triazolyl, furanyl, oxazolyl, isoxazolyl, 1,2,3-oxadiazolyl, 1,2,4-oxadiazolyl, 1,3,4-oxadiazolyl, thiophenyl, thiazolyl, isothiazolyl, 1,2,3-thiadiazolyl, 1,3,4-thiadiazolyl, pyridyl, pyridazinyl, and benzimidazolyl, any of which may optionally be substituted with 1 to 3 substituents independently selected from the group consisting of halo, cyano, —SCF$_3$, (C$_1$-C$_6$)alkyl optionally further substituted with 1 to 6 fluoro substituents, and (C$_1$-C$_6$)alkoxy optionally further substituted with 1 to 6 fluoro substituents, and wherein pyridyl and pyridazinyl may also optionally be substituted with (C$_1$-C$_6$)alkylamino optionally further substituted with 1 to 6 fluoro substituents, (C$_3$-C$_7$)cycloalkyl(C$_0$-C$_3$)alkyl, or (C$_3$-C$_7$)cycloalkyl(C$_0$-C$_3$)alkyl-amino;

Het$^1$ is a saturated, nitrogen-containing heterocycle substituent selected from the group consisting of azetidinyl, pyrrolidinyl, piperidinyl, homopiperidinyl, morpholinyl, thiomorpholinyl, homomorpholinyl, and homothiomorpholinyl, any of which may optionally be substituted with (C$_1$-C$_6$)alkyl or with 2 methyl substituents;

Het$^2$ is a saturated, oxygen-containing heterocycle substituent selected from the group consisting of tetrahydrofuranyl and tetrahydropyranyl, any of which may optionally be substituted with (C$_1$-C$_6$)alkyl or with 2 methyl substituents;

Ph$^1$ is phenyl optionally substituted with 1 to 5 independently selected halo substituents, or with 1 to 3 substituents independently selected from the group consisting of halo, cyano, —SCF$_3$, (C$_1$-C$_6$)alkyl optionally further substituted with 1 to 6 fluoro substituents, and (C$_1$-C$_6$)alkoxy optionally further substituted with 1 to 6 fluoro substituents;

Ph$^2$ is phenyl substituted with:
a) 1 to 5 independently selected halo substituents; or
b) 1 to 3 substituents independently selected from the group consisting of halo, cyano, —SCF$_3$, nitro, hydroxy, (C$_1$-C$_6$)alkyl optionally further substituted with 1 to 6 fluoro substituents, and (C$_1$-C$_6$)alkoxy optionally further substituted with 1 to 6 fluoro substituents; or
c) 0, 1, or 2 substituents independently selected from the group consisting of halo, cyano, —SCF$_3$, methyl, —CF$_3$, methoxy, —OCF$_3$, nitro, and hydroxy, together with one substituent selected from the group consisting of
  i) (C$_1$-C$_{10}$)alkyl optionally further substituted with 1 to 6 fluoro substituents or mono-substituted with hydroxy, (C$_1$-C$_6$)alkoxy, (C$_3$-C$_7$)cycloalkyl(C$_0$-C$_3$)alkyloxy, Het$^2$-(C$_0$-C$_3$)alkyloxy, Ph$^1$-(C$_0$-C$_3$)alkyloxy,
  ii) (C$_1$-C$_{10}$)alkoxy-(C$_0$-C$_3$)alkyl optionally further substituted with 1 to 6 fluoro substituents, and optionally further substituted with hydroxy,
  iii) (C$_1$-C$_6$)alkyl-C(O)—(C$_0$-C$_5$)alkyl optionally further substituted with 1 to 6 fluoro substituents,
  iv) carboxy,
  v) (C$_1$-C$_6$)alkoxycarbonyl optionally further substituted with 1 to 6 fluoro substituents,
  vi) (C$_1$-C$_6$)alkyl-C(O)—(C$_0$-C$_3$)—O— optionally further substituted with 1 to 6 fluoro substituents,
  vii) (C$_1$-C$_6$)alkylthio-(C$_0$-C$_5$)alkyl optionally further substituted with 1 to 6 fluoro substituents,
  viii) (C$_1$-C$_6$)alkylsulfinyl-(C$_0$-C$_5$)alkyl optionally further substituted with 1 to 6 fluoro substituents,
  ix) (C$_1$-C$_6$)alkylsulfonyl-(C$_0$-C$_5$)alkyl optionally further substituted with 1 to 6 fluoro substituents,
  x) (C$_1$-C$_6$)alkylsulfonyl-(C$_0$-C$_3$)alkyl-O— optionally further substituted with 1 to 6 fluoro substituents,
  xi) (C$_3$-C$_7$)cycloalkyl(C$_0$-C$_3$)alkyl, optionally further substituted on the cycloalkyl with 1 to 4 substituents selected from methyl and fluoro,
  xii) (C$_3$-C$_7$)cycloalkyl(C$_0$-C$_3$)alkyl-O—, optionally further substituted on the cycloalkyl with 1 to 4 substituents selected from methyl and fluoro,
  xiii) (C$_3$-C$_7$)cycloalkyl(C$_0$-C$_3$)alkyl-C(O)—,
  xiv) (C$_3$-C$_7$)cycloalkyl(C$_0$-C$_3$)alkyl-O—C(O)—,
  xv) (C$_3$-C$_7$)cycloalkyl(C$_0$-C$_3$)alkyl-S—,
  xvi) (C$_3$-C$_7$)cycloalkyl(C$_0$-C$_3$)alkyl-S(O)—,
  xvii) (C$_3$-C$_7$)cycloalkyl(C$_0$-C$_3$)alkyl-S(O)$_2$—,
  xviii) Ph$^1$-(C$_0$-C$_3$)alkyl, optionally substituted on the alkyl moiety with 1 to 2 fluoro substituents,
  xix) Ph$^1$-(C$_0$-C$_3$)alkyl-O—, optionally substituted on the alkyl moiety with 1 to 2 fluoro substituents
  xx) Ph$^1$-(C$_0$-C$_3$)alkyl-C(O)—,
  xxi) Ph$^1$-(C$_0$-C$_3$)alkyl-O—C(O)—,
  xxii) Ph$^1$-(C$_0$-C$_3$)alkyl-C(O)—(C$_0$-C$_3$)alkyl-O—,
  xxiii) Ph$^1$-(C$_0$-C$_3$)alkylthio,
  xxiv) Ph$^1$-(C$_0$-C$_3$)alkylsulfinyl,
  xxv) Ph$^1$-(C$_0$-C$_3$)alkylsulfonyl,
  xxvi) Ar$^2$(C$_0$-C$_3$)alkyl,
  xxvii) Ar$^2$(C$_0$-C$_3$)alkyl-O—
  xxviii) Ar$^2$—(C$_0$-C$_3$)alkyl-S—,
  xxix) Ar$^2$(C$_0$-C$_3$)alkyl-C(O)—,
  xxx) Ar$^2$(C$_0$-C$_3$)alkyl-C(S)—,
  xxxi) Ar$^2$—(C$_0$-C$_3$)alkylsulfinyl,
  xxxii) Ar$^2$—(C$_0$-C$_3$)alkylsulfonyl,
  xxxiii) Het$^1$(C$_0$-C$_3$)alkyl-C(O)— optionally substituted on the Het$^1$ moiety with Ph$^1$,
  xxxiv) Het$^1$(C$_0$-C$_3$)alkyl-C(S)— optionally substituted on the Het$^1$ moiety with Ph$^2$,
  xxxv) N-linked Het$^1$-C(O)—(C$_0$-C$_3$)alkyl-O—,
  xxxvi) Het$^2$-(C$_0$-C$_3$)alkyloxy,
  xxxvii) R$^{26}$R$^{27}$N—,
  xxxviii) R$^{28}$R$^{29}$N—(C$_1$-C$_3$)alkoxy,
  xxxix) R$^{28}$R$^{29}$N—C(O)—,
  xl) R$^{28}$R$^{29}$N—C(O)—(C$_1$-C$_3$)alkyl-O—,
  xli) R$^{28}$R$^{29}$N—C(S)—,
  xlii) R$^{30}$R$^{31}$N—S(O)$_2$—,
  xliii) HON=C(CH$_3$)—, and
  xliv) HON=C(Ph$^1$)-,
or a pharmaceutically acceptable salt thereof, subject to the following provisos:
a) no more than two of R$^1$, R$^2$, R$^3$, R$^4$, and R$^5$ may be other than hydrogen;
b) when R$^2$ is methyl, then R$^1$, R$^3$, R$^4$, and R$^5$ are each hydrogen;
c) when R$^3$ is methyl, then R$^2$ and R$^4$ are each hydrogen;

d) when $R^3$ is methyl, $R^7$ and $R^8$ are each —OH, and $R^1$, $R^2$, $R^4$, $R^5$, and $R^9$ are each hydrogen, then $R^6$ is other than cyclohexylthio, furanylthio, or phenylthio; and e) When $R^{12}$ is $Ar^2$—$(C_1$-$C_3)$alkyl, then $R^7$ is other than hydrogen or $R^9$ is other than chloro.

This invention also provides pharmaceutical compositions which comprise a compound of Formula I, or a pharmaceutically acceptable salt thereof, in association with a pharmaceutically acceptable carrier, diluent, or excipient.

In another aspect of the present invention, there is provided a method for increasing activation of the 5-HT$_{2C}$ receptor in mammals comprising administering to a mammal in need of such activation an effective amount of a compound of Formula I, or a pharmaceutically acceptable salt thereof.

The present invention also provides a method for treating obesity in mammals comprising administering to a mammal in need of such treatment an effective amount of a compound of Formula I, or a pharmaceutically acceptable salt thereof.

The present invention also provides a method for treating obsessive/compulsive disorder in mammals comprising administering to a mammal in need of such treatment an effective amount of a compound of Formula I, or a pharmaceutically acceptable salt thereof.

Furthermore, the present invention provides a method for treating depression in mammals comprising administering to a mammal in need of such treatment an effective amount of a compound of Formula I, or a pharmaceutically acceptable salt thereof.

Furthermore, the present invention provides a method for treating anxiety in mammals comprising administering to a mammal in need of such treatment an effective amount of a compound of Formula I, or a pharmaceutically acceptable salt thereof.

In preferred embodiments of the above methods of treatment utilizing a compound of Formula I, or a pharmaceutically acceptable salt thereof, the mammal is a human.

In another aspect of the present invention, there is provided a compound of Formula I for use in selectively increasing activation of the 5-HT$_{2C}$ receptor and/or for use in treating a variety of disorders associated with decreased activation of 5-HT$_{2C}$ receptors. Preferred embodiments of this aspect of the invention include a compound of Formula I for use in the treatment of obesity, hyperphagia, obsessive/compulsive disorder, depression, anxiety, substance abuse, sleep disorder, hot flashes, and/or hypogonadism. Particularly preferred embodiments of this aspect of the invention include the treatment of obesity, obsessive/compulsive disorder, depression, and/or anxiety.

In another aspect of the present invention, there is provided the use of one or more compounds of Formula I in the manufacture of a medicament for the activation of 5-HT$_{2C}$ receptors in a mammal. In preferred embodiments of this aspect of the invention, there is provided the use of one or more compounds of Formula I in the manufacture of a medicament for the treatment of obesity, hyperphagia, obsessive/compulsive disorder, depression, anxiety, substance abuse, sleep disorder, hot flashes, and/or hypogonadism. Particularly preferred embodiments of this aspect of the invention include the use of one or more compounds of Formula I in the manufacture of medicaments for the treatment of obesity, obsessive/compulsive disorder, depression, and/or anxiety.

Additionally, the present invention provides a pharmaceutical formulation adapted for the treatment of obesity, or for the treatment of obsessive/compulsive disorder, or for the treatment of depression, or for the treatment of anxiety, each of which comprise a compound of Formula I in association with a pharmaceutically acceptable carrier, diluent or excipient.

In those instances where the disorders which can be treated by 5-HT$_{2C}$ agonists are known by established and accepted classifications, their classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision (ICD-10), provides classifications for many of the disorders described herein. The skilled artisan will recognize that there are alternative nomenclatures, nosologies, and classification systems for disorders described herein, including those as described in the DSM-IV and ICD-10, and that terminology and classification systems evolve with medical scientific progress.

The general chemical terms used throughout have their usual meanings. For example, the term "alkyl" refers to a branched or unbranched saturated hydrocarbon group. The term "n-alkyl" refers to an unbranched alkyl group. By way of illustration, but without limitation, the term "$(C_1$-$C_2)$alkyl" refers to methyl and ethyl. The term "$(C_1$-$C_3)$ n-alkyl" refers to methyl, ethyl, and propyl. The term "$(C_1$-$C_3)$alkyl" refers to methyl, ethyl, propyl, and isopropyl. The term "$(C_1$-$C_4)$ n-alkyl" refers to methyl, ethyl, n-propyl, and n-butyl. The term "$(C_1$-$C_4)$alkyl" refers to methyl, ethyl, propyl, isopropyl, n-butyl, isobutyl, sec-butyl, and tert-butyl. The term "$(C_1$-$C_6)$alkyl" refers to all branched and unbranched alkyl groups having from one to six carbon atoms. The term "$(C_3$-$C_6)$alkyl" refers to all branched and unbranched alkyl groups having from three to six carbon atoms. The term "$(C_2$-$C_6)$alkyl" refers to all branched and unbranched alkyl groups having from two to six carbon atoms.

$(C_x$-$C_y)$alkyl may also be used in conjunction with other substituents to indicate a branched or unbranched saturated hydrocarbon linker for the substituent, where x and y indicate the range of carbon atoms permitted in the linker moiety. By way of illustration, but without limitation, —$(C_0$-$C_1)$alkyl refers to a single bond or a methylene linker moiety; —$(C_0$-$C_2)$alkyl refers to a single bond, methylene, methyl-methylene, or ethylene linker moiety; —$(C_0$-$C_3)$alkyl further includes trimethylene, alpha- or beta-methyl ethylene, or ethyl methylene. —$(C_1$-$C_2)$alkyl, —$(C_1$-$C_3)$alkyl, —$(C_1$-$C_4)$alkyl, and —$(C_1$-$C_6)$alkyl refer to branched or unbranched alkylene linkers having from 1 to 2, 3, 4, or 6 carbons, respectively.

The term "alkenyl" refers to a branched or unbranched unsaturated hydrocarbon group. By way of illustration, but without limitation, the term "$(C_2$-$C_6)$alkenyl" refers to a branched or unbranched hydrocarbon group having from 2 to 6 carbon atoms and 1 or more carbon-carbon double bonds. Allyl means a propyl-2-en-1-yl moiety ($CH_2$=CH—$CH_2$—).

The term "$(C_3$-$C_7)$cycloalkyl" refers to cyclopropyl, cyclobutyl, cyclopentyl, cyclohexyl and cycloheptyl. Cycloalkylalkyl refers to a cycloalkyl moiety linked through a branched or unbranched alkylene linker, as for example, but without limitation, —$CH_2$—, —$CH_2CH_2$—, —$CH(CH_3)$—, —$CH_2CH_2CH_2$—, —$CH_2CH(CH_3)$—, —$CH(CH_3)CH_2$—, —$CH(CH_2CH_3)$—, and the like. $(C_3$-$C_7)$cycloalkyl$(C_0$-$C_{1, 2\, or\, 3})$alkyl, refers to cycloalkyls linked through a single bond (i.e. $C_0$-alkyl) or an alkylene linker. Each alkyl, cycloalkyl, and cycloalkylalkyl group may be optionally substituted as provided for herein.

The terms "alkoxy", "phenyloxy", "sulfonyloxy", and "carbonyloxy" refer to an alkyl group, phenyl group, sulfonyl group, or carbonyl group, respectively, that is bonded through an oxygen atom.

The terms "alkylthio", "trifluoromethylthio", "cycloalkylthio" ("cyclohexylthio"), "phenylthio", and "furanylthio" refer to an alkyl group, trifluoromethyl group, cycloalkyl (cyclohexyl) group, phenyl group, or furanyl group, respectively, that is bonded through a sulfur atom.

The terms "alkylcarbonyl", "alkoxycarbonyl", "phenylcarbonyl", and "phenyloxycarbonyl", refer to an alkyl, alkoxy, phenyl, or phenyloxy group bonded through a carbonyl moiety.

The term "alkylcarbonyloxy" refers to an alkylcarbonyl group bonded through an oxygen atom.

The terms "$(C_1-C_6)$alkylsulfinyl", "$Ph^1-(C_0-C_3)$alkylsulfinyl", and "$Ar^2—(C_0-C_3)$alkylsulfinyl", refer to an alkyl, $Ph^1-(C_0-C_3)$alkyl, or $Ar^2—(C_0-C_3)$alkyl, respectively, group bonded through a sulfinyl moiety (—SO—).

The terms "alkylsulfonyl" (t-butylsulfonyl), "$(C_3-C_7)$cycloalkylsulfonyl", "phenylsulfonyl", "$Ph^1-(C_0-C_3)$alkylsulfonyl", and "$Ar^2—(C_0-C_3)$alkylsulfonyl", refer to an alkyl (t-butyl), $(C_3-C_7)$cycloalkyl, phenyl, $Ph^1-(C_0-C_3)$alkyl, or $Ar^2—(C_0-C_3)$alkyl group bonded through a sulfonyl moiety ($—SO_2—$).

The term "phenylamino" refers to a phenyl group bonded through a nitrogen atom.

The term "N-linked" means that the referenced moiety is linked through its nitrogen atom, by way of illustration, but without limitation, N-linked $Het^1$ means the $Het^1$ moiety is linked through a nitrogen atom in the ring of the $Het^1$ moiety, and N-linked $Ar^2$ means the $Ar^2$ moiety is linked through a nitrogen atom in the ring of the $Ar^2$ moiety.

The term "halo" refers to fluoro, chloro, bromo, or iodo. Preferred halo groups are fluoro, chloro, and bromo. More preferred halo groups are fluoro and chloro.

The term "heterocycle" is taken to mean a saturated or unsaturated 4 to 7 membered ring containing from 1 to 3 heteroatoms selected from nitrogen, oxygen and sulfur, said ring optionally being benzofused. Exemplary saturated heterocycles, for the purposes of the present invention, include azetidinyl, pyrrolidinyl, piperidinyl, homopiperidinyl, tetrahydrofuranyl, tetrahydropyranyl, morpholinyl, thiomorpholinyl, piperazinyl, and the like. Exemplary unsaturated heterocycles include, but are not limited to, pyrrolyl, pyrazolyl, imidazolyl, 1,2,3-triazolyl, 1,2,4-triazolyl, furanyl, oxazolyl, isoxazolyl, 1,2,3-oxadiazolyl, 1,2,4-oxadiazolyl, 1,3,4-oxadiazolyl, thiophenyl, thiazolyl, isothiazolyl, 1,2,3-thiadiazolyl, 1,2,4-thiadiazolyl, 1,3,4-thiadiazolyl, pyridyl, pyridazinyl, and the like. Exemplary benzofused heterocyclic rings include, but are not limited to, indolyl, dihydroindolyl, indazolyl, benzisoxazolyl, benzimidazolyl, benzofuranyl, dihydrobenzofuranyl, benzoxazolyl, benzo[1,3]dioxolyl, benzothiophenyl, benzothiazolyl, quinolinyl, isoquinolinyl, benzopyranyl, dihydrobenzopyranyl, cinnolinyl, quinazolinyl and the like, all of which may be optionally substituted as provided for herein, which also includes optionally substituted on the benzene ring when the heterocycle is benzofused.

In one embodiment, preferred heterocycles include pyrrolidinyl, piperidinyl, homopiperidinyl, tetrahydrofuranyl, tetrahydropyranyl, pyrrolyl, pyrazolyl, imidazolyl, furanyl, isoxazolyl, 1,2,4-oxadiazolyl, thiophenyl, thiazolyl, 1,2,3-thiadiazolyl, pyridyl, pyridazinyl, indolyl, dihydroindolyl, benzimidazolyl, benzofuranyl, dihydrobenzofuranyl, benzoxazolyl, benzo[1,3]dioxolyl, benzothiophenyl, benzothiazolyl, quinolinyl, isoquinolinyl, and benzopyranyl, all of which may be optionally substituted as provided for herein.

In yet another embodiment, preferred heterocycles include pyridyl, pyridazinyl, and thiophenyl.

The terms "gem-", "geminal", or "geminate" refer to two identical substituents bonded to a common carbon atom, as for example, but without limitation, gem-methyl, meaning two methyl groups bound to a common carbon atom, as for instance in a 3,3-dimethyltetrahydrobenzofuranyl group. For the purposes of this application, gem-ethano means an ethylene substituent wherein both carbons are bound to the same carbon atom of the substituted group to form a cyclopropyl moiety, as for example, but without limitation, the ethano substituent on the 2-phenyl-(1,1-ethano)ethylamino group below:

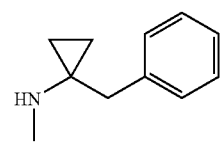

It is to be understood that when a basic definition of a group lists optionally allowable substituents, and in another place that group is said to also optionally be substituted with other recited substituents, then those other recited substituents are intended to be added to the list of optionally allowable substituents listed in the basic definition of the group. Conversely, if in another place that group is said to be alternatively, optionally substituted with other recited substituents, then those other recited substituents are intended to replace the list of optionally allowable substituents recited in the basic definition of the substituent. For example, but without limitation, $Ar^2$ has a basic definition that recites that any of the listed heteroaromatic groups may "optionally be substituted with 1 to 3 substituents independently selected from the group consisting of halo, cyano, $—SCF_3$, $(C_1-C_6)$alkyl optionally further substituted with 1 to 6 fluoro substituents, and $(C_1-C_6)$alkoxy optionally further substituted with 1 to 6 fluoro substituents, and wherein pyridyl and pyridazinyl may also optionally be substituted with $(C_1-C_6)$alkylamino optionally further substituted with 1 to 6 fluoro substituents, $(C_3-C_7)$cycloalkyl$(C_0-C_3)$alkyl, or $(C_3-C_7)$cycloalkyl$(C_0-C_3)$alkyl-amino." This is to be understood to mean that any of the listed heteroaromatic groups may optionally be substituted with [1 to 3 substituents independently selected from the group consisting of halo, cyano, $—SCF_3$, $(C_1-C_6)$alkyl optionally further substituted with 1 to 6 fluoro substituents, and $(C_1-C_6)$alkoxy optionally further substituted with 1 to 6 fluoro substituents], and that when $Ar^2$ is selected to be pyridyl or pyridazinyl, the list of substituents selectable for the 1 to 3 substituents is expanded to also include [$(C_1-C_6)$ alkylamino optionally further substituted with 1 to 6 fluoro substituents, $(C_3-C_7)$cycloalkyl$(C_0-C_3)$alkyl, and $(C_3-C_7)$cycloalkyl$(C_0-C_3)$alkyl-amino]. Likewise, in the definition of $R^{14}$, the terminology "wherein . . . $Ar^2$, wherein $Ar^2$ is pyridyl, then $R^{14}$ may also, optionally be substituted with phenyl-CH═CH— or phenyl-C≡C— . . . " is understood to mean that the list of substituents selectable for the 1 to 3 substituents optionally allowed on $Ar^2$=pyridyl is again expanded to also include [phenyl-CH═CH— or phenyl-C≡C— . . . ]. Conversely, later in the definition of $R^4$, the terminology "wherein when $Ar^2$ is pyridyl, the pyridyl may alternatively, optionally be substituted with $R^{28}R^{29}N—C(O)—$ and optionally further substituted with one methyl, $—CF_3$, cyano, or $—SCF_3$ substituent, or with 1 to 2 halo substituents", is understood to mean that when $R^{14}$ is selected to be A2=pyridyl, then the list of 1 to 3 independently selected substituents optionally allowable in the basic definition of $Ar^2$ may be superceded by "$R^{28}R^{29}N$—C(O)— and optionally further substituted with one methyl, —$CF_3$, cyano, or —$SCF_3$ substituent, or with 1 to 2 halo substituents."

The term "amino protecting group" as used in this specification refers to a substituent commonly employed to block or protect the amino functionality while reacting other functional groups on the compound. Examples of such amino protecting groups include the formyl group, the trityl group, the acetyl group, the trichloroacetyl group, the trifluoroacetyl group, the chloroacetyl, bromoacetyl, and iodoacetyl groups, carbamoyl-type blocking groups such as benzyloxycarbonyl, 9-fluorenylmethoxycarbonyl ("FMOC"), t-butoxycarbonyl (t-BOC), and like amino protecting groups. The species of amino protecting group employed is not critical so long as the derivatized amino group is stable to the conditions of subsequent reactions on other positions of the molecule and can be removed at the appropriate point without disrupting the remainder of the molecule.

The selection and use (addition and subsequent removal) of amino protecting groups is well known within the ordinary skill of the art. Further examples of groups referred to by the above terms are described by T. W. Greene and P. G. M. Wuts, "Protective Groups in Organic Synthesis", 3$^{rd}$ edition, John Wiley and Sons, New York, N.Y., 1999, chapter 7, hereafter referred to as "Greene".

The term "pharmaceutical" or "pharmaceutically acceptable" when used herein as an adjective, means substantially non-toxic and substantially non-deleterious to the recipient.

By "pharmaceutical composition" it is further meant that the carrier, solvent, excipients and/or salt must be compatible with the active ingredient of the composition (e.g. a compound of Formula I). It is understood by those of ordinary skill in this art that the terms "pharmaceutical formulation" and "pharmaceutical composition" are generally interchangeable, and they are so used for the purposes of this application.

The term "effective amount" means an amount of a compound of Formula I which is capable of activating 5-$HT_{2C}$ receptors and/or elicit a given pharmacological effect.

The term "suitable solvent" refers to any solvent, or mixture of solvents, inert to the ongoing reaction that sufficiently solubilizes the reactants to afford a medium within which to effect the desired reaction.

It is understood that compounds of the present invention may exist as stereoisomers. As such, all enantiomers, diastereomers, and mixtures thereof, are included within the scope of the present invention. Where specific stereochemistries are identified in this application, the Cahn-Prelog-Ingold designations of (R)13 and (S)— and the cis and trans designation of relative stereochemistry are used to refer to specific isomers and relative stereochemistry. Known optical rotations are designated by (+) and (−) for dextrorotatary and levorotatary, respectively. Where a chiral compound is resolved into its isomers, but absolute configurations or optical rotations are not determined, the isomers are arbitrarily designated as isomer 1, isomer 2, etc. While all enantiomers, diastereomers, and mixtures thereof, are contemplated within the present invention, preferred embodiments are single enantiomers and single diastereomers.

It is generally understood by those skilled in this art, that compounds intended for use in pharmaceutical compositions are routinely, though not necessarily, converted to a salt form in efforts to optimize such characteristics as the handling properties, stability, pharmacokinetic, and/or bioavailability, etc. Methods for converting a compound to a given salt form are well known in the art (see for example, Berge, S. M, Bighley, L. D., and Monkhouse, D. C., *J. Pharm. Sci.*, 66:1, (1977)). In that the compounds of the present invention are amines and therefore basic in nature, they readily react with a wide variety of pharmaceutically acceptable organic and inorganic acids to form pharmaceutically acceptable acid addition salts therewith. Such salts are also embodiments of this invention.

Typical inorganic acids used to form such salts include hydrochloric, hydrobromic, hydroiodic, nitric, sulfuric, phosphoric, hypophosphoric, metaphosphoric, pyrophosphoric acid, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include chloride, bromide, iodide, nitrate, acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, isobutyrate, phenylbutyrate, α-hydroxybutyrate, butyne-1,4-dicarboxylate, hexyne-1,4-dicarboxylate, caprate, caprylate, cinnamate, citrate, formate, fumarate, glycolate, heptanoate, hippurate, lactate, malate, maleate, hydroxymaleate, malonate, mandelate, nicotinate, isonicotinate, oxalate, phthalate, terephthalate, propiolate, propionate, phenylpropionate, salicylate, sebacate, succinate, suberate, benzenesulfonate, p-bromobenzenesulfonate, chlorobenzenesulfonate, ethylsulfonate, 2-hydroxyethylsulfonate, methylsulfonate (mesylate), naphthalene-1-sulfonate, naphthalene-2-sulfonate, naphthalene-1,5-sulfonate, p-toluenesulfonate, xylenesulfonate, tartrate, and the like.

It is well known that such compounds can form salts in various molar ratios with the acid to provide, for example, the hemi-acid, mono-acid, di-acid salt, etc. Where in the salt formation procedure, the acid is added in a specific stoichiometric ratio, unless otherwise analyzed to confirm, the salt is presumed, but not known, to form in that molar ratio. Terms such as "(acid)$_x$" are understood to mean that the molar ratio of the salt formed is not known and can not be presumed, as for example, but without limitation, (HCl) and (methanesulfonic acid)$_x$.

Abbreviations used herein are defined as follows:

"2B-3 ethanol" means ethanol denatured with toluene.
"AIBN" means 2,2'-azobisisobutyronitrile.
"Anal. Calc'd" or "Anal. Calcd" means calculated elemental analysis.
"APCI" means atmospheric pressure chemical ionization.
"bp" means boiling point.
"BINAP" means rac-2,2'-bis(diphenylphosphino)-1,1'binaphthyl.
"Boc" or "t-Boc" means tert-butoxycarbonyl.
"Brine" means a saturated aqueous sodium chloride solution.
"CV" means calorific value of oxygen.
"DBU" means 1,8-diazabicyclo[5.4.0]undec-7-ene.
"DCE" means 1,2-dichloroethane.
"DCM" means dichloromethane (i.e. methylene chloride, $CH_2Cl_2$).
"DIBAL-H" means diisobutylaluminum hydride.
"DIEA" means N,N-diisopropylethylamine.
"DMAP" means 4-(dimethylamino)pyridine.
"DME" means 1,2-dimethoxyethane.
"DMEA" means N,N-dimethylethylamine.
"DMF" means N,N-dimethylformamide.
"DMSO" means dimethylsulfoxide.

"DOI" means (±)-1-(2,5-dimethoxy-4-[$^{125}$I]-iodophenyl)-2-aminopropane.

"EDC" means 1-[3-(dimethylamino)propyl]-3-ethylcarbodiimide hydrochloride.

"EDTA" means ethylenediaminetetraacetic acid.

"EE" means energy expenditure.

"EtOAc" means ethyl acetate.

"GC-MS" means gas chromatography—mass spectrometry.

"GDP" means guanosine diphosphate.

"GTP" means guanosine triphosphate.

"GTPγ[$^{35}$S]" means guanosine triphosphate having the terminal phosphate substituted with $^{35}$S in place of an oxygen.

"HATU" means O-(7-azabenzotriazol-1-yl)-N,N,N',N'-tetramethyluronium hexafluorophosphate.

"HMPA" means hexamethylphosphoramide.

"HOBT" means 1-hydroxybenzotriazole hydrate.

"HPLC" means high-pressure liquid chromatography.

"HRMS" means high-resolution mass spectrometry.

"ISPA" means immunoadsorption scintillation proximity assay.

"m-CPBA" means meta-chloroperoxybenzoic acid.

"mp" means melting point.

"Ms" in a chemical structure means the methanesulfonyl moiety (—$SO_2CH_3$).

"MS (ES+)" means mass spectroscopy using electrospray ionization.

"MTBE" means methyl t-butyl ether.

"NBS" means N-bromosuccinimide.

"NMP" means 1-methyl-2-pyrrolidinone.

"NMR" means nuclear magnetic resonance.

"Pd/C" means palladium on activated carbon.

"RQ" means respiratory quotient.

"SCX chromatography" means chromatography on an SCX column or cartridge.

"SCX column" or "SCX cartridge", as used herein, refers to a Varian Bond Elute® silica based strong cation exchange resin column or disposable cartridge or equivalent.

"Sudan III" means 1-[(4-phenylazo)phenylazo]-2-naphthalenol.

"Tf" in a chemical structure means the trifluoromethanesulfonyl moiety (—$SO_2CF_3$).

"TFA" means trifluoroacetic acid.

"THF" means tetrahydrofuran.

"TLC" means thin layer chromatography.

While all of the compounds of the present invention are useful as $5-HT_{2C}$ agonists, certain classes are preferred, as for example, compounds having any of the following enumerated selections of substituents: Compounds wherein 1) $R^7$ is halo;
2) $R^7$ is chloro;
3) $R^7$ is ($C_1$-$C_6$)alkyl optionally substituted with 1 to 6 fluoro substituents;
4) $R^7$ is ($C_1$-$C_3$)alkyl optionally substituted with 1 to 6 fluoro substituents;
5) $R^7$ is —$CF_3$;
6) $R^7$ is ($C_3$-$C_6$)alkenyl optionally substituted with 1 to 6 fluoro substituents;
7) $R^7$ is ($C_3$-$C_6$)alkenyl;
8) $R^7$ is cyano;
9) $R^{1-5}$ are each hydrogen;
10) $R^4$ is methyl or ethyl;
11) $R^4$ is methyl;
12) $R^3$ is methyl;
13) $R^8$ is hydrogen;
14) $R^9$ is ($C_1$-$C_3$)alkoxy;
15) $R^9$ is methoxy;
16) $R^9$ is halo;
17) $R^9$ is chloro;
18) $R^6$ is —C≡C—$R^{10}$;
19) $R^{10}$ is $Ph^1$-($C_0$-$C_3$)alkyl;
20) $R^{10}$ is $Ph^1$-($C_1$-$C_2$)alkyl;
21) $R^{10}$ is Phenyl($C_0$-$C_3$)alkyl;
22) $R^{10}$ is ($C_3$-$C_7$)cycloalkyl($C_0$-$C_3$)alkyl;
23) $R^{10}$ is ($C_3$-$C_7$)cycloalkylmethyl;
24) $R^{10}$ is ($C_4$-$C_6$)alkyl;
25) $R^{10}$ is branched ($C_4$-$C_6$)alkyl;
26) $R^{10}$ is ($C_1$-$C_6$)alkyl substituted with 2-6 fluoro substituents;
27) $R^{10}$ is $Ar^1$—($C_0$-$C_3$)alkyl;
28) $R^{10}$ is $Ar^1$—($C_1$-$C_2$)alkyl;
29) $R^6$ is —O—$R^{12}$;
30) $R^{12}$ is $Ph^2$-($C_0$-$C_3$)alkyl;
31) $R^{12}$ is $Ph^2$-($C_1$-$C_2$)alkyl;
32) $R^{12}$ is $Ph^2$-($C_1$-$C_2$)alkyl and $Ph^2$ is substituted with 1-3 halo substituents;
33) $R^{12}$ is $Ph^2$-($C_1$-$C_2$)alkyl and $Ph^2$ is substituted with 1-3 fluoro substituents;
34) $R^{12}$ is $Ph^2$-($C_1$-$C_2$)alkyl and $Ph^2$ is substituted with cyano;
35) $R^{12}$ is $Ph^2$-($C_1$-$C_2$)alkyl and $Ph^2$ is substituted with $R^{30}R^{31}N$—$S(O)_2$—;
36) $R^{12}$ is $Ph^2$-($C_1$-$C_2$)alkyl, $Ph^2$ is substituted with $R^{30}R^{31}N$—$S(O)_2$—, $R^{30}$ is ($C_1$-$C_3$)alkyl optionally further substituted with 1-3 fluoro substituents and $R^{31}$ is hydrogen;
37) $R^{12}$ is $Ar^2$—($C_0$-$C_3$)alkyl;
38) $R^{12}$ is $Ar^2$—($C_1$-$C_2$)alkyl;
39) $R^{12}$ is $Ar^2$—($C_1$-$C_2$)alkyl and $Ar^2$ is pyridyl, thiazolyl, oxazolyl, or pyrazolyl, each optionally substituted with methyl;
40) $R^{12}$ is benzazolyl-($C_1$-$C_3$)alkyl;
41) $R^{12}$ is $Ph^2$-C(O)—($C_1$-$C_3$)alkyl,
42) $R^{12}$ is $Ph^2$-C(O)—($C_1$-$C_3$)alkyl and $Ph^2$ is substituted with 1 to 3 halo substituents;
43) $R^{12}$ is $Ph^2$-C(O)—($C_1$-$C_3$)alkyl and $Ph^2$ is substituted with 1 to 3 halofluoro substituents;
44) $R^{12}$ is $Ph^1$-S(O)—;
45) $R^{12}$ is ($C_1$-$C_6$)alkyl-O—C(O)—($C_3$-$C_6$)alkyl;
46) $R^{12}$ is ($C_1$-$C_3$)alkyl-O—C(O)—($C_3$-$C_6$)alkyl;
47) $R^{12}$ is $R^{13}$—C(O)NH—($C_2$-$C_4$)alkyl;
48) $R^{12}$ is $R^{13}$—C(O)NH—($C_2$-$C_4$)alkyl and $R^{13}$ is $Ph^1$;
49) $R^{12}$ is $R^{13}$—C(O)NH—($C_2$-$C_4$)alkyl, $R^{13}$ is $Ph^1$; substituted with 1 to 3 halo substituents;
50) $R^{12}$ is $R^{13}$—C(O)NH—($C_2$-$C_4$)alkyl and $R^{13}$ is ($C_3$-$C_7$)cycloalkyl;
51) $R^{12}$ is $R^{13}$—C(O)NH—($C_2$-$C_4$)alkyl and $R^{13}$ is pyridyl;
52) $R^{12}$ is $R^{13}$—C(O)NH—($C_2$-$C_4$)alkyl and $R^{13}$ is ($C_1$-$C_3$)alkoxy;
53) $R^{12}$ is $R^{13}$—C(O)NH—($C_2$-$C_4$)alkyl and $R^{13}$ is ($C_3$-$C_7$)cycloalkyl;
54) $R^6$ is —S—$R^{14}$;
55) $R^6$ is —S—$R^{14}$ and $R^{14}$ is $Ph^2$;
56) $R^6$ is —S—$R^{14}$, $R^{14}$ is $Ph^2$ substituted with 1 to 3 halo substituents;
57) $R^6$ is —S—$R^{14}$, $R^{14}$ is $Ph^2$ substituted with cyano;
58) $R^6$ is —S—$R^{14}$, $R^{14}$ is $Ph^2$; substituted with cyano and 1 to 2 halo substituents;
59) $R^6$ is —S—$R^{14}$ and $R^{14}$ is $Ar^2$;
60) $R^6$ is —S—$R^{14}$, $R^{14}$ is $Ar^2$, and $Ar^2$ is optionally substituted pyridyl or pyridazinyl;

61) $R^6$ is —S—$R^{14}$, $R^{14}$ is $Ar^2$, and $Ar^2$ is optionally substituted thiophenyl, thiazolyl, isothiazolyl, 1,2,3-thiadiazolyl, 1,3,4-thiadiazolyl;
62) $R^6$ is —S—$R^{14}$ and $R^{14}$ is tetrahydrofuranyl or tetrahydropyranyl;
63) $R^6$ is —S—$R^{14}$ and $R^{14}$ is tetrahydrofuranyl or tetrahydropyranyl and the tetrahydrofuranyl or tetrahydropyranyl is substituted with oxo on a carbon adjacent to the ring oxygen;
64) $R^6$ is —S—$R^{14}$ and $R^{14}$ is $R^5$-L-;
65) L is $(C_1-C_2)$alkylene;
66) L is branched $(C_2-C_3)$alkylene;
67) L is methyl-methylene;
68) L is di-methyl-methylene;
69) L is methyl-ethylene;
70) L is gem-di-methyl-ethylene;
71) L is gem-ethano-ethylene;
72) $R^{15}$ is $Ph^2$;
73) $R^{15}$ is $Ph^2$ substituted with 1 to 3 halo substituents;
74) $R^{15}$ is $Ph^2$ substituted with cyano;
75) $R^{15}$ is $Ph^2$ substituted with $(C_1-C_6)$alkoxy;
76) $R^{15}$ is $Ph^2$ substituted with $(C_1-C_6)$alkoxy optionally further substituted with 1 to 3 fluoro substituents;
77) $R^{15}$ is $Ph^2$ substituted with $(C_1-C_6)$alkoxy$(C_1-C_1)$alkyl;
78) $R^{15}$ is $Ph^2$ substituted with $(C_1-C_6)$alkoxy$(C_1-C_1)$alkyl further substituted with 1 to 3 fluoro substituents;
79) $R^{15}$ is $Ph^2$ substituted with $(C_1-C_6)$alkylthio;
80) $R^{15}$ is $Ph^2$ substituted with $(C_1-C_6)$alkylthio optionally further substituted with 1 to 3 fluoro substituents;
81) $R^{15}$ is $Ph^2$ substituted with $(C_1-C_6)$alkylthio$(C_1-C_1)$alkyl;
82) $R^{15}$ is $Ph^2$ substituted with $(C_1-C_6)$alkylthio$(C_1-C_1)$alkyl further substituted with 1 to 3 fluoro substituents;
83) $R^{15}$ is $Ph^2$ substituted with $(C_3-C_7)$cycloalkyl$(C_0-C_1)$alkyl;
84) $R^{15}$ is $Ph^2$ substituted with $(C_1-C_6)$alkysulfonyl$(C_0-C_1)$alkyl optionally further substituted with 1 to 3 fluoro substituents;
85) $R^{15}$ is $Ph^2$ substituted with $(C_1-C_6)$alkylsulfinyl$(C_0-C_1)$alkyl optionally further substituted with 1 to 3 fluoro substituents;
86) $R^{15}$ is $Ph^2$ substituted with $Ph^1$-$(C_0-C_1)$alkyl-sulfonyl;
87) $R^{15}$ is $Ph^2$ substituted with $Ph^1$-$(C_0-C_1)$alkyl;
88) $R^{15}$ is $Ph^2$ substituted with $R^{26}R^{27}N$—;
89) $R^{15}$ is $Ph^2$ substituted with $Het^1$;
90) $R^{15}$ is $Ph^2$ substituted with $(C_1-C_6)$alkyl-C(O)— optionally further substituted with 1 to 3 fluoro substituents;
91) $R^{15}$ is $Ph^2$ substituted with $(C_1-C_6)$alkyl-C(O)— optionally further substituted with 1 to 3 fluoro substituents;
92) $R^{15}$ is $Ph^2$ substituted with $Ph^1$;
93) $R^{15}$ is $Ph^2$ substituted with $Ph^1(C_0-C_3)$alkyl-O—;
94) $R^{15}$ is $Ph^2$ substituted with $Ph^1(C_0-C_3)$alkyl-C(O)—;
95) $R^{15}$ is $Ph^2$ substituted with $Ph^1(C_0-C_3)$alkyl-C(O)—;
96) $R^{15}$ is $Ph^2$ substituted with $Ar^2(C_0-C_3)$alkyl-C(O)—;
97) $R^{15}$ is $Ph^2$ substituted with $Ar^2(C_0-C_3)$alkyl-C(O)— and $Ar^2$ is pyrazolyl optionally further substituted as provided for in $Ar^2$;
98) $R^{15}$ is $Ph^2$ substituted with $R^{28}R^{29}N$—C(O)—;
99) $R^{15}$ is $Ph^2$ substituted with $R^{28}R^{29}N$—C(O)— and $R^{28}$ is $(C_1-C_6)$alkyl;
100) $R^{15}$ is $Ph^2$ substituted with $R^{28}R^{29}N$—C(O)— and $R^{28}$ is $(C_3-C_7)$cycloalkyl$(C_0-C_3)$alkyl;
101) $R^{15}$ is $Ph^2$ substituted with $R^{28}R^{29}N$—C(O)— and $R^{28}$ is $Ph^1$-$(C_0-C_2)$-n-alkyl optionally substituted on the alkyl moiety when present with $(C_1-C_3)$alkyl, dimethyl, or gem-ethano;
102) $R^{15}$ is $Ph^2$ substituted with $R^{28}R^{29}N$—C(O)— and $R^{28}$ is $Ar^2$—$(C_0-C_2)$-n-alkyl optionally substituted on the alkyl moiety when present with $(C_1-C_3)$alkyl, dimethyl, or gem-ethano;
103) $R^{15}$ is $Ph^2$ substituted with $Het^1$-C(O)—;
104) $R^{15}$ is $Ph^2$ substituted with $Het^1$-C(O)— further substituted with $Ph^1$;
105) $R^{15}$ is $Ar^2$;
106) $R^{15}$ is $Ar^2$ further substituted with methyl;
107) $R^{15}$ is $Ar^2$ further substituted with $(C_3-C_7)$cycloalkyl $(C_0-C_2)$alkyl, $Het^1$, pyridyl, or phenyl optionally further substituted with methyl, —$CF_3$, cyano, —$SCF_3$, or with 1 to 3 halo substituents;
108) $R^{15}$ is pyrrolyl, pyrazolyl, imidazolyl, 1,2,3-triazolyl, 1,2,4-triazolyl, furanyl, oxazolyl, isoxazolyl, 1,2,3-oxadiazolyl, 1,2,4-oxadiazolyl, 1,3,4-oxadiazolyl, thiophenyl, thiazolyl, isothiazolyl, 1,2,3-thiadiazolyl, or 1,3,4-thiadiazolyl, any of which may optionally be substituted with 1 to 3 substituents selected from the group consisting of halo, cyano, —$SCF_3$, $(C_1-C_6)$alkyl optionally further substituted with 1 to 6 fluoro, and $(C_1-C_6)$alkoxy optionally further substituted with 1 to 6 fluoro.
109) $R^{15}$ is pyridyl optionally further substituted as provided for in $Ar^2$;
110) $R^{15}$ is tetrahydrofuranyl or tetrahydropyranyl, either optionally being substituted with an oxo substituent, or with one or two groups selected independently from methyl and —$CF_3$;
111) $R^{15}$ is tetrahydrofuranyl or tetrahydropyranyl, being substituted with an oxo substituent, and optionally being further substituted with one or two groups selected independently from methyl and —$CF_3$;
112) $R^{15}$-L- is pyrid-2-yl-methyl;
113) $R^{15}$-L- is pyrid-3-yl-methyl;
114) $R^{15}$-L- is pyrid-2-yl-CH(CH$_3$)—;
115) $R^{15}$-L- is pyrid-3-yl-CH(CH$_3$)—;
116) $R^{15}$ is pyridazinyl optionally further substituted as provided for in $Ar^2$;
117) $R^{15}$-L- is pyridazin-2-yl-methyl;
118) $R^{15}$-L- is pyridazin-3-yl-methyl;
119) $R^{15}$-L- is pyridazin-2-yl-CH(CH$_3$)—;
120) $R^{15}$-L- is pyridazin-3-yl-CH(CH$_3$)—;
121) $R^{15}$ is pyridyl further substituted with $(C_3-C_7)$cycloalkyl$(C_0-C_2)$alkyl, $Het^1$, pyridyl, or phenyl optionally further substituted with methyl, —$CF_3$, cyano, —$SCF_3$, or with 1 to 3 halo substituents;
122) $R^{15}$ is pyridazinyl further substituted with $(C_3-C_7)$cycloalkyl$(C_0-C_2)$alkyl, $Het^1$, pyridyl, or phenyl optionally further substituted with methyl, —$CF_3$, cyano, —$SCF_3$, or with 1 to 3 halo substituents;
123) $R^{15}$ is $R^{22}$—C(O)—;
124) $R^{15}$ is $R^{22}$—C(O)— and $R^2$ is $(C_1-C_6)$alkyl optionally substituted with 1 to 6 fluoro substituents;
125) $R^{15}$ is $R^{22}$—C(O)— and $R^{22}$ is $(C_1-C_6)$alkoxy optionally substituted with 1 to 6 fluoro substituents;
126) $R^{15}$ is $R^{22}$—C(O)— and $R^{22}$ is $(C_3-C_7)$cycloalkyl$(C_0-C_3)$alkyl;
127) $R^{15}$ is $R^{22}$—C(O)— and $R^{22}$ is $(C_3-C_7)$cycloalkyl$(C_0-C_3)$alkyl-O—;
128) $R^{15}$ is $R^{22}$—C(O)— and $R^{22}$ is $Ph^1$-$(C_0-C_3)$alkyl;
129) $R^{15}$ is $R^{22}$—C(O)— and $R^{22}$ is $Ph^1$-$(C_0-C_3)$alkyl-O—;
130) $R^{15}$ is $R^{22}$—C(O)— and $R^{22}$ is $Ar^2$—$(C_0-C_3)$alkyl;

131) $R^{15}$ is $R^{22}$—C(O)— and $R^{22}$ is $Ar^2$—($C_0$-$C_3$)alkyl-O—;
132) $R^{15}$ is $R^{22}$—C(O)— and $R^{22}$ is $R^{32}R^{33}N$—;
133) $R^{15}$ is phthalimido;
134) $R^{15}$ is $R^{17}R^{18}N$—;
135) $R^{15}$ is $R^{17}R^{18}N$— and $R^{17}$ is ($C_1$-$C_3$)alkoxy-C(O)—;
136) $R^{15}$ is $R^{17}R^{18}N$— and $R^{17}$ is ($C_3$-$C_7$)cycloalkyl($C_0$-$C_2$)—C(O)—;
137) $R^{15}$ is $R^{17}R^{18}N$— and $R^{17}$ is $Ph^1$-($C_0$-$C_2$)—C(O);
138) $R^{15}$ is $R^{17}R^{18}N$— and $R^{17}$ is $Ar^2$—($C_0$-$C_2$)—C(O);
139) $R^{15}$ is $R^{16}O$—;
140) $R^{15}$ is $R^{16}O$— and $R^{16}$ is ($C_1$-$C_6$)oalkyl-C(O)—;
141) $R^{15}$ is $R^{16}O$— and $R^{16}$ is ($C_3$-$C_7$)cycloalkyl($C_0$-$C_2$)—C(O)—;
142) $R^6$ is $R^{24}R^{25}N$— and $R^{24}$ is ($C_1$-$C_6$)alkoxy($C_2$-$C_5$) alkyl optionally substituted with 1 to 6 fluoro substituents;
143) $R^6$ is $R^{24}R^{25}N$— and $R^{24}$ is ($C_1$-$C_6$)alkylthio($C_2$-$C_5$) alkyl optionally substituted with 1 to 6 fluoro substituents;
144) $R^6$ is $R^{24}R^{25}N$— and $R^{24}$ is ($C_3$-$C_7$)cycloalkyl($C_0$-$C_1$)alkyl-O—($C_1$-$C_5$)alkyl;
145) $R^6$ is $R^{24}R^{25}N$— and $R^{24}$ is ($C_3$-$C_7$)cycloalkyl($C_0$-$C_1$)alkyl-S—($C_1$-$C_5$)alkyl;
146) $R^6$ is $R^{24}R^{25}N$— and $R^{24}$ is phenyl($C_1$-$C_3$) n-alkyl optionally substituted on the n-alkyl moiety when present with ($C_1$-$C_3$)alkyl, dimethyl, or gem-ethano;
147) $R^6$ is $R^{24}R^{25}N$— and $R^{24}$ is $Ph^2$-($C_1$-$C_3$) n-alkyl optionally substituted on the n-alkyl moiety when present with ($C_1$-$C_3$)alkyl, dimethyl, or gem-ethano;
148) $R^6$ is $R^{24}R^{25}N$— and $R^{24}$ is $Ar^2$($C_0$-$C_3$) n-alkyl optionally substituted on the n-alkyl moiety when present with ($C_1$-$C_3$)alkyl, dimethyl, or gem-ethano;
149) $R^6$ is —$R^{24}R^{25}N$— and $R^{24}$ is $Ar^2$($C_0$-$C_3$) n-alkyl optionally substituted on the n-alkyl moiety when present with ($C_1$-$C_3$)alkyl, dimethyl, or gem-ethano, wherein $Ar^2$ contains a nitrogen atom, and $Ar^2$ is substituted;
150) $R^6$ is $R^{24}R^{21}N$— and $R^{24}$ is $Ar^2$($C_0$-$C_3$) n-alkyl optionally substituted on the n-alkyl moiety when present with ($C_1$-$C_3$)alkyl, dimethyl, or gem-ethano, wherein $Ar^2$ contains a nitrogen atom, and $Ar^2$ is substituted with ($C_1$-$C_6$)alkoxy optionally further substituted with 1 to 6 fluoro, ($C_1$-$C_6$)alkylamino optionally further substituted with 1 to 6 fluoro, or ($C_3$-$C_7$)cycloalkyl($C_0$-$C_2$)alkyl optionally further substituted with 1 to 6 fluoro;
151) $R^6$ is $R^{24}R^{25}N$— and $R^{24}$ is $Ar^2$($C_1$-$C_3$) n-alkyl optionally substituted on the n-alkyl moiety when present with ($C_1$-$C_3$)alkyl, dimethyl, or gem-ethano, and wherein $Ar^2$ is pyridyl or pyridazinyl and is substituted with ($C_1$-$C_6$)alkoxy optionally further substituted with 1 to 6 fluoro, ($C_1$-$C_6$)alkylamino optionally further substituted with 1 to 6 fluoro, or ($C_3$-$C_7$)cycloalkyl($C_0$-$C_2$) alkyl optionally further substituted with 1 to 6 fluoro;
152) $R^6$ is $R^{24}R^{25}N$— and $R^{24}$ is $Ar^2$($C_0$-$C_3$) n-alkyl optionally substituted on the n-alkyl moiety when present with ($C_1$-$C_3$)alkyl, dimethyl, or gem-ethano, and wherein $Ar^2$ is pyridyl substituted with $R^{28}R^{29}N$—C(O)— and $R^{28}$ is ($C_3$-$C_7$)cycloalkyl($C_0$-$C_2$)alkyl or $Ph^1$ and $R^{29}$ is hydrogen;
153) $R^6$ is $R^{24}R^{25}N$— and $R^{24}$ is $Ar^2$($C_0$-$C_3$) n-alkyl, wherein $Ar^2$ is pyridyl substituted with $R^{28}R^{29}N$—C(O)— and $R^{28}$ is ($C_3$-$C_7$)cycloalkyl or phenyl optionally substituted with 1 to 3 halo, preferably fluoro, and $R^{29}$ is hydrogen;
154) $R^6$ is $R^{24}R^{25}N$— and $R^{24}$ is $Ph^1$-($C_0$-$C_1$)alkyl-O—($C_1$-$C_5$)alkyl;
155) $R^6$ is $R^{24}R^{25}N$— and $R^{24}$ is $Ph^1$-($C_0$-$C_1$)alkyl-S—($C_1$-$C_5$)alkyl;
156) $R^6$ is $R^{24}R^{25}N$— and $R^{24}$ is $Ph^1$-($C_0$-$C_1$)alkyl-C(O)NH—($C_2$-$C_4$)alkyl,
157) $R^6$ is $R^{24}R^{25}N$— and $R^{24}$ is $Ph^1$-($C_0$-$C_1$)alkyl-NH—C(O)NH—($C_2$-$C_4$)alkyl;
158) $R^6$ is $R^{24}R^{25}N$— and $R^{24}$ is pyridyl-($C_0$-$C_1$)alkyl-C(O)NH—($C_2$-$C_4$)alkyl optionally substituted on the pyridyl moiety with methyl, —$CF_3$, or 1 to 3 halo substituents;
159) $R^6$ is $R^{24}R^{25}N$— and $R^{24}$ is pyridyl-($C_0$-$C_1$)alkyl-NH—C(O)NH—($C_2$-$C_4$)alkyl optionally substituted on the pyridyl moiety with methyl, —$CF_3$, or 1 to 3 halo substituents;
160) $R^6$ is $R^{24}R^{25}N$— and $R^{24}$ is $Ar^3$($C_1$-$C_2$)alkyl;
161) $R^6$ is $R^{24}R^{25}N$— and $R^{24}$ is $Ar^3$-methyl;

It will be understood that the above classes may be combined to form additional preferred classes. Exemplary combinations include, but are not limited to:

162) Any one of preferred embodiments 19) through 161) (the preferred selections for $R^6$), combined with any one of preferred embodiments 1) through 9) (the preferred selections for $R^7$);
163) Any one of preferred embodiments 19) through 161) (the preferred selections for $R^6$), wherein $R^7$ is halogen;
164) Any one of preferred embodiments 19) through 161) (the preferred selections for $R^6$), wherein $R^7$ is chloro;
165) A preferred combination according to 162), 163), or 164), wherein $R^{1-5}$, and $R^8$ are each hydrogen;
166) A preferred combination according to 162), 163), or 164), wherein $R^{1-5}$, $R^8$ and $R^9$, are each hydrogen.
167) Any one of preferred embodiments 37), 38), or 39), wherein $R^7$ is other than hydrogen;
168) Any one of preferred embodiments 37), 38), or 39), wherein $R^9$ is hydrogen;
169) Any one of preferred embodiments 37), 38), or 39), wherein $R^7$ is other than hydrogen and $R^9$ is hydrogen;
170) Any one of preferred embodiments 37), 38), or 39), wherein $R^7$ is chloro and $R^9$ is hydrogen;
171) compounds of formula (I) wherein $R^6$ is —C≡C—$R^{10}$ and wherein $R^{10}$ is selected from the values defined in any one of embodiments 19) to 28);
172) compounds of formula (I) wherein $R^6$ is —O—$R^{12}$ and wherein $R^{12}$ is selected from the values defined in any one of embodiments 30) to 53);
173) compounds of formula (I) wherein $R^6$ is —S—$R^{14}$ and wherein $R^{14}$ is selected from the values defined in any one of embodiments 55) to 63) or 64) wherein L is selected from the values of 65) to 71) and $R^{15}$ is selected from the values defined in any one of embodiments 72) to 141);
174) compounds of formula (I) wherein $R^6$ is $R^{24}R^{25}N$— and wherein $R^{24}$ is selected from the values defined in any one of embodiments 142) to 161);
175) compounds according to embodiment 172) wherein $R^{12}$ is selected from the values defined in any one of embodiments 37), 38) or 39);
176) compounds of formula (I) wherein $R^7$ is other than hydrogen;
177) compounds according to any one of embodiments 171) or 174) wherein $R^7$ is other than hydrogen;
178) compounds according to any one of embodiments 171) or 174) wherein $R^7$ is chloro;
179) compounds according to any one of embodiments 171) or 174) wherein $R^9$ is hydrogen;
180) compounds according to any one of embodiments 171) or 174) wherein $R^9$ is ($C_1$-$C_3$)alkoxy;

181) compounds according to any one of embodiments 171) or 174) wherein $R^9$ is methoxy;
182) compounds according to any one of embodiments 171) or 174) wherein $R^7$ is chloro and $R^9$ is hydrogen;
183) compounds according to any one of embodiments 171) or 174) wherein $R^7$ is chloro and $R^9$ is ($C_1$-$C_3$)alkoxy;
184) compounds according to any one of embodiments 171) or 174) wherein $R^7$ is chloro and $R^9$ is methoxy;
185) compounds according to any one of embodiments 171) or 185) wherein $R^9$ is hydrogen;
186) compounds according to any one of embodiments 171) or 185) wherein $R^9$ is ($C_1$-$C_3$)alkoxy;
187) compounds according to any one of embodiments 171) or 185) wherein $R^9$ is methoxy;
188) compounds according to any one of embodiments 171) or 187) wherein $R^{1-5}$ are each hydrogen;

Generally, when $R^6$ is —S—$R^{14}$, then $R^{15}$-L- is the more preferred $R^{14}$. When $R^{14}$ or $R^{15}$ is substituted $Ar^2$, para-substitution is preferred. When L is present, particularly preferred are methylene, and methyl-methylene. Particularly preferred $R^{15}$-L- is when $R^{15}$ is $Ph^2$ and L is methylene. Also particularly preferred is when $R^{15}$ is $Ph^2$ and L is methyl-methylene. Also particularly preferred is when $R^{15}$ is $Ar^2$ and L is methylene. Also particularly preferred is when $R^{15}$ is $Ar^2$ and L is methyl-methylene.

Also generally, when $R^6$ is —$NR^{24}R^{25}$, then $Ph^2$-($C_1$-$C_3$)-n-alkyl is particularly preferred over phenyl($C_1$-$C_3$)-n-alkyl.

Preferred compounds of formula (I) are those wherein
$R^6$ is —C≡C—$R^{10}$ and wherein $R^{10}$ is selected from the values defined in any one of embodiments 19) to 28); or
$R^6$ is —O—$R^{12}$ and wherein $R^{12}$ is selected from the values defined in any one of embodiments 30) to 53); or
$R^6$ is —S—$R^{14}$ and wherein $R^{14}$ is selected from the values defined in any one of embodiments 55) to 63) or embodiment 64) wherein L is selected from the values defined in any one of embodiments 65) to 71) and $R^{15}$ is selected from the values defined in any one of embodiments 72) to 111) and 121 to 141), or $R^{15}$-L- is selected from the values defined in any one of embodiments 112) to 120); or
$R^6$ is $R^{24}R^{25}N$— and wherein $R^{24}$ is selected from the values defined in any one of embodiments 143) to 161).

Particularly preferred compounds of formula (I) are those wherein $R^6$ is —O—$R^{12}$ and wherein $R^{12}$ is selected from the values defined in any one of embodiments 37), 38) or 39).

Further preferred compounds of formula (I) are those wherein $R^7$ is other than hydrogen. In particular, $R^7$ is preferably selected from the values defined in any one of embodiments 1) to 8). More preferably, $R^7$ is selected from halo (especially chloro), ($C_1$-$C_3$)alkyl optionally substituted with 1 to 6 fluoro substituents (especially methyl, ethyl, n-propyl or $CF_3$), and cyano.

Particularly preferred compounds of formula (I) are those wherein $R^7$ is halogen, and in particular wherein $R^7$ is chloro.

Preferred compounds of formula (I) are those wherein $R^9$ is ($C_1$-$C_3$)alkoxy, preferably methoxy, or halo, preferably chloro.

Also preferred are those compounds of formula (I) wherein $R^9$ is hydrogen.

Particularly preferred compounds of formula (I) are those wherein $R^7$ is other than hydrogen and $R^9$ is hydrogen, and most especially wherein $R^7$ is chloro and $R^9$ is hydrogen.

Further preferred compounds of formula (I) are those wherein $R^1$ is hydrogen.

Also preferred are those compounds of formula (I) wherein $R^2$ is hydrogen.

Also preferred are those compounds of formula (I) wherein $R^3$ is hydrogen or methyl, and especially wherein $R^3$ is hydrogen.

Another preferred class of compounds of formula (I) is that wherein $R^4$ is hydrogen, methyl or ethyl, particularly wherein $R^4$ is hydrogen or methyl, and especially wherein $R^4$ is hydrogen.

Further preferred are those compounds of formula wherein $R^5$ is hydrogen.

Also preferred are those compounds of formula (I) wherein $R^8$ is hydrogen.

One favored group of compounds of the present invention is that represented by formula (Ia), and pharmaceutically acceptable salts thereof:

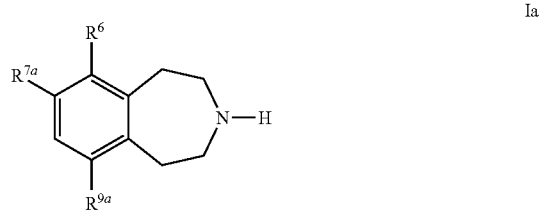

wherein
$R^{7a}$ is halogen, and especially chloro;
$R^{9a}$ is hydrogen, halogen or ($C_1$-$C_3$)alkoxy, particularly hydrogen, chloro or methoxy, and especially hydrogen; and
$R^6$ is as defined in relation to formula (I).

Specific preferred compounds of the present invention are those described in the Examples herein, including the free bases and the pharmaceutically acceptable salts thereof.

It will be appreciated that the preferred definitions of the various substituents recited herein may be taken alone or in combination and, unless otherwise stated, apply to the generic formula (I) for compounds of the present invention, as well as to the preferred class of compounds represented by formula (Ia).

The compounds of the invention can be prepared according to the following synthetic schemes by methods well known and appreciated in the art. Suitable reaction conditions for the steps of these schemes are well known in the art and appropriate substitutions of solvents and co-reagents are within the skill of the art. Likewise, it will be appreciated by those skilled in the art that synthetic intermediates may by isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of Formula I is dependent upon the particular compound being synthesized, the starting compound, and the relative liability of the substituted moieties as is well appreciated by those of ordinary skill in the art. All substituents, unless otherwise indicated, are as previously defined, and all reagents are well known and appreciated in the art.

Compounds of Formula I where $R^6$ is an acetylene-linked substituent may be prepared as illustrated in Scheme I where Pg is a suitable protecting group for a secondary amine such as, but not limited to, 2,2,2-trifluoroacetyl or tert-butoxycarbonyl, and variables $R^1$, $R^2$, $R^4$, $R^5$, $R^7$, $R^8$, $R^9$ and $R^{10}$ are as previously defined.

Scheme I

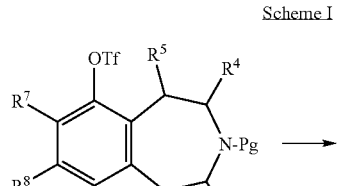

(a)

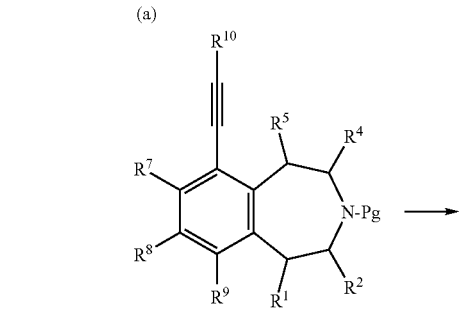

(b)

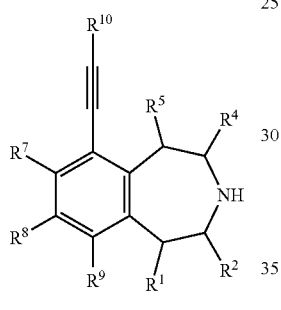

(Ia)

Mix the 6-triflate of the 2,3,4,5-tetrahydro-1H-benzo[d] azepines (a) with an appropriately substituted acetylene, a suitable palladium/copper catalyst mixture in a solvent, typically DMF, using triethylamine as base, and heat to afford the desired compound (b). Deprotection reaction and the standard extractive and chromatographic techniques afford the desired compound (Ia).

The appropriate 6-triflate of 2,3,4,5-tetrahydro-1H-benzo [d]azepines (a) may be prepared as described in Scheme II. Compound (a) may be prepared from 1-naphthol. 1-Naphthol can be converted to 5-hydroxy-1,4-dihydronaphthalene (c) by Birch reduction using ammonia and lithium metal at low temperature. Methylation of the 6-hydroxy group affords the compound (d). Ozonolysis of (d) and subsequent reduction with sodium borohydride provide the diol (e). After converting the two hydroxyl groups into two good leaving groups, for example methanesulfonates, cyclize the compound (f) to the 6-methoxy-2,3,4,5-tetrahydro-1H-benzo[d]azepines (g) with aqueous ammonia under pressure. Protect the ring nitrogen with a variety of alkyl halides, acid chlorides or anhydrides such as trifluoroacetic anhydride to give compound (h). Subsequently convert the methyl ether (h) to the phenol (i) with $BBr_3$ in dichloromethane or other methods well known in the literature [see for example, Greene and Wuts, Protective Groups in Organic Synthesis, 3rd Ed., John Wiley and sons, Chapter III, New York (1999)].

Functionalization of the aromatic ring to introduce substituents $R^7$, $R^8$ and $R^9$ are well known in the art and very depending on the substitution desired. Subsequent trifluoromethanesulfonylation of the 6-hydroxy (j) affords the desired 2,3,4,5-tetrahydro-1H-benzo[d]azepines (a).

Scheme II

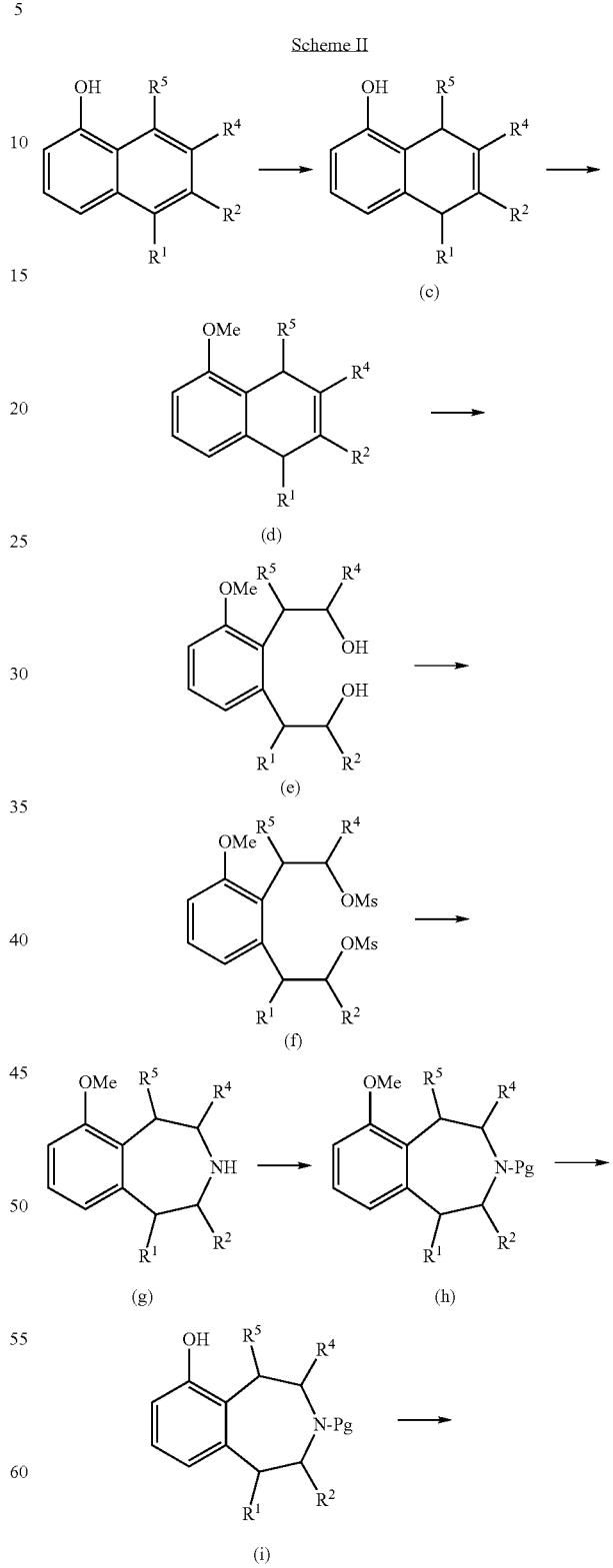

-continued

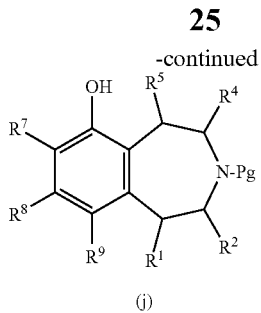
(j)

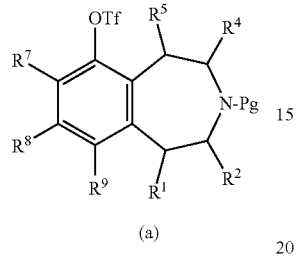
(a)

Alternately, compound (g) could be prepared from 1,2-bis (cyanomethyl)-3-methoxybenzene (1), previously described in the literature (*J. Med. Chem.* 1984, 27, 918-921), as shown in Scheme III below.

Scheme III

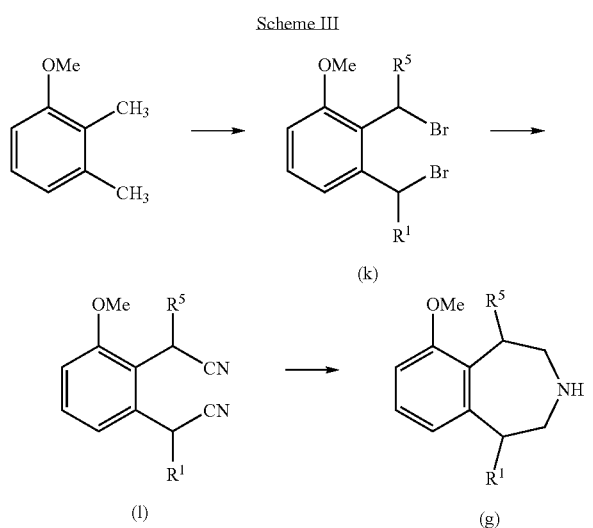

Compounds of Formula I where $R^6$ is an oxygen-linked substituent may be prepared as illustrated in Scheme IV where Pg is a suitable protecting group for secondary amine, such as 2,2,2-trifluoroacetyl or tert-butoxycarbonyl, and variables $R^7$, $R^9$ and $R^{12}$ are as previously defined.

Scheme IV

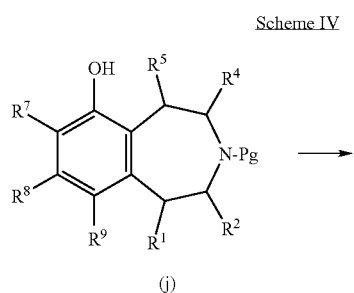
(j)

-continued

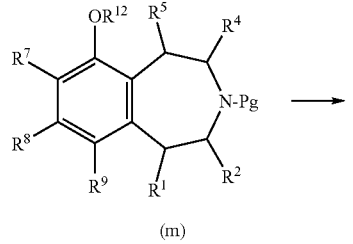
(m)

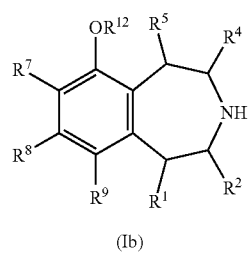
(Ib)

Compound (m) can be prepared by treating 6-hydroxy-2,3,4,5-tetrahydro-1H-benzo[d]azepines (j) with an appropriate alkylation reagent, such as an alkyl halide or sulfonate, and a base in a suitable solvent, typically acetone, ethanol or acetonitrile, followed by he standard extractive and chromatographic techniques. Deprotection of the ring nitrogen gives the compound (Ib). Alternately, compound (m) can be obtained by Mitsunobu reaction with an appropriate alcohol, a phosphine reagent such as triphenylphosphine, and diethyl azodicarboxylate (DEAD) or 1,1'-(azodicarbonyl)-dipiperidine in an anhydrous solvent, for example THF.

Compounds of Formula Ic where $R^6$ is a nitrogen-linked substituent may be prepared as illustrated in the Scheme V. The 6-triflate protected 2,3,4,5-tetrahydro-1H-benzo[d] azepines (a) can be converted to the compounds (n), under Buchwald conditions, by treatment with an appropriate amine (q) in the presence of an effective palladium catalyst, and a base in a suitable solvent, typically toluene or 1,4-dioxane under an inert atmosphere. Introduction of a second substituent $R^{25}$, if needed, may be performed. Standard workup and chromatographic techniques followed by deprotection, give the compound (Ic).

Alternately 6-amino-2,3,4,5-tetrahydro-1H-benzo[d] azepines (p) can be transformed to the desired compounds (n) by reaction with an appropriate bromide (r), and an appropriate base in a suitable solvent.

Bromides (r) are either commercially available or may be prepared by methods well known to the skilled artisan. Amines (q) are either commercially available or may be prepared by methods well known to the skilled artisan.

Scheme V
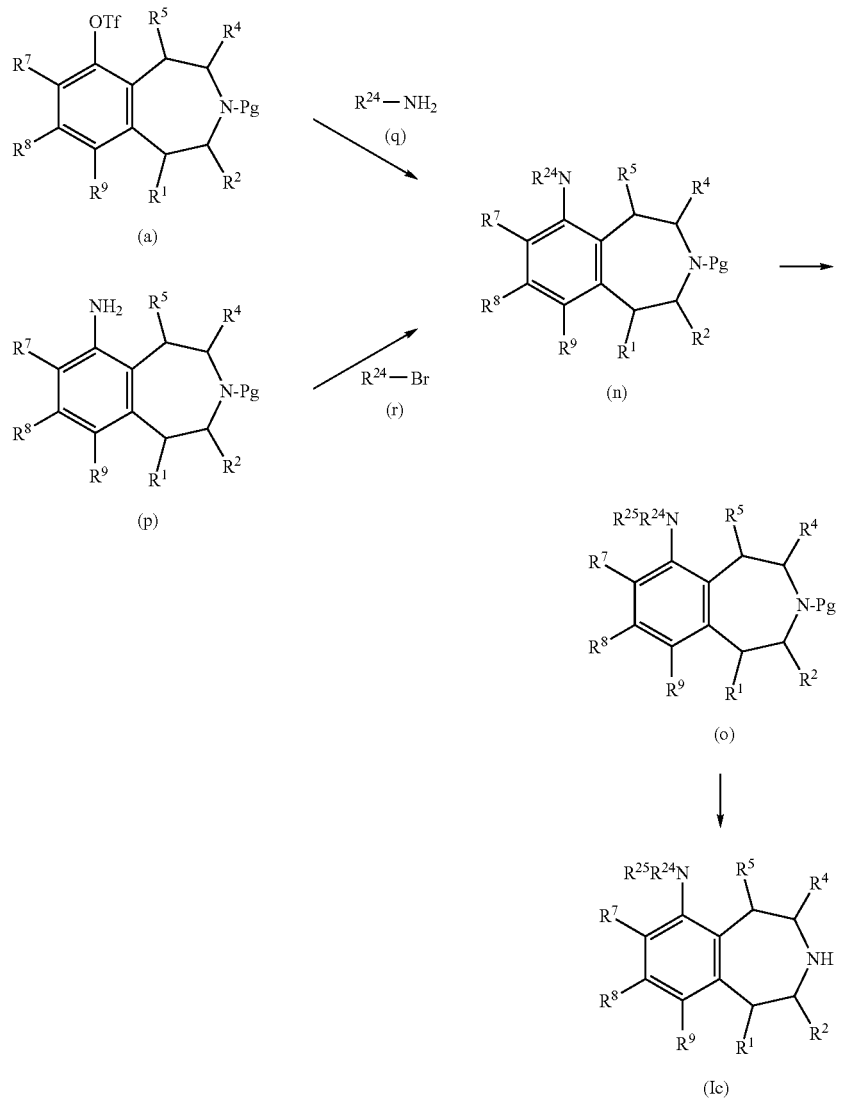
Compounds of Formula I where the $R^6$ is a sulfur-linked substituent may be prepared as illustrated in the Scheme VI.
Scheme VI
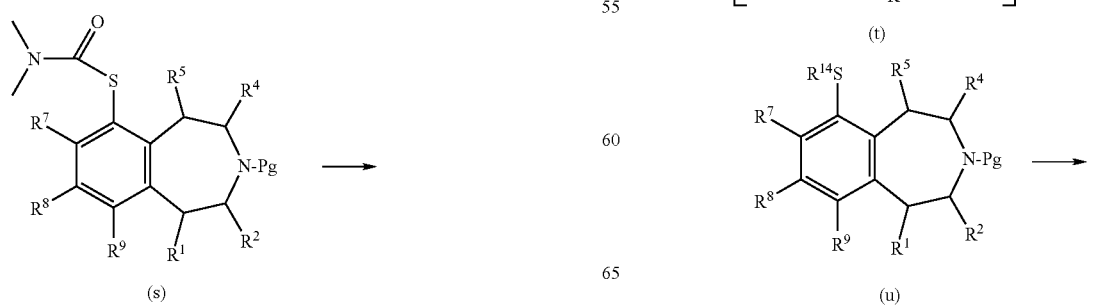

-continued

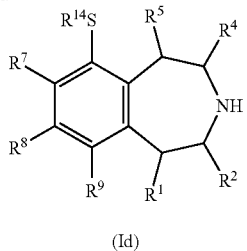

(Id)

Heat the appropriately substituted 3-(tert-butoxycarbonyl-6-dimethylcarbamoylthio-2,3,4,5-tetrahydro-1H-benzo[d]azepine (s) with an appropriate base in a suitable solvent, such as methanol, to obtain the intermediate thiol (t). Isolate the intermediate thiol (t), if required, and treat it with an appropriate electrophile (halide or alkyl sulfonate). Isolate the compound (u) by standard extractive and chromatographic techniques and deprotect to afford the desired compound (Id).

The requisite halides or alkyl sulfonates are either commercially available or may be prepared by methods well known to the skilled artisan.

The skilled artisan will also appreciate that not all of the substituents in the compounds of Formula I will tolerate certain reaction conditions employed to synthesize the compounds. These moieties may be introduced at a convenient point in the synthesis, or may be protected and then deprotected as necessary or desired, as is well known in the art. The skilled artisan will appreciate that the protecting groups may be removed at any convenient point in the synthesis of the compounds of the present invention. Methods for introducing and removing protecting groups used in this invention are well known in the art; see, for example, Greene and Wuts, Protective Groups in Organic Synthesis, 3$^{rd}$ Ed., John Wiley and sons, New York (1999).

The following Preparations and Examples are illustrative of methods useful for the synthesis of the compounds of the present invention. Exemplified compounds are also particularly preferred compounds of the present invention.

General Procedure 1-1

Dissolve the appropriately substituted 3-(2,2,2-trifluoroacetyl)-2,3,4,5-tetrahydro-1H-benzo[d]azepine in ammonia/methanol solution (1.0-7.0 M). Stir for 1-16 h at ambient temperature unless otherwise specified. Remove the volatiles in vacuo. Purify by chromatography on silica gel eluting with 1-20% 2M ammonia/methanol in DCM, or by SCX chromatography eluting with 1.0-7.0 M ammonia in methanol.

General Procedure 1-2

Dissolve the appropriately substituted 3-(2,2,2-trifluoroacetyl)-2,3,4,5-tetrahydro-1H-benzo[d]azepine (1.0 equiv.) in methanol. Add a 0.5 M aqueous solution of potassium carbonate (4.0 equiv.) and stir at ambient temperature for 6 h. Concentrate in vacuo and partition the residue between water and DCM. Extract the aqueous phase twice with DCM. Dry the combined organic extracts over Na$_2$SO$_4$, filter and concentrate in vacuo. If needed, purify by chromatography on silica gel eluting with 1-20% 2M ammonia/methanol in DCM, or by SCX chromatography eluting with 1.0-7.0 M ammonia in methanol.

General Procedure 1-3

Dissolve the appropriately substituted 3-(2,2,2-trifluoroacetyl)-2,3,4,5-tetrahydro-1H-benzo[d]azepine (1.0 equiv.) in methanol or ethanol (0.1 to 2M solution) and add from 10-50% by volume of a 1.0-5.0 N aqueous solution of sodium hydroxide or lithium hydroxide. Stir the reaction mixture at ambient temperature for 0.25-16 h and concentrate in vacuo. Partition the residue between EtOAc or DCM and water. Separate and dry the organic fraction over Na$_2$SO$_4$, filter, and concentrate in vacuo. Purify by SCX chromatography, followed by chromatography on silica gel eluting with 1-20% 2M ammonia/methanol in DCM or reverse phase HPLC.

General Procedure 1-4

Dissolve the appropriately substituted 3-tert-butoxycarbonyl-2,3,4,5-tetrahydro-1H-benzo[d]azepine in 4M hydrogen chloride in dioxane or 1M hydrogen chloride in ethyl ether and stir the mixture for 2-16 h at ambient temperature unless otherwise specified. Remove the solvent in vacuo. If a solid is obtained, wash the solid with ether and filter under vacuum to afford the desired hydrochloride salt. If an oil is obtained, dissolve the oil in the minimal volume of DCM, methanol or EtOAc and add ether to precipitate out the solid. Remove the solvent in vacuo, wash the solid with ether and filter. Dry the solid in vacuo or under a stream of nitrogen.

General Procedure 1-5

Dissolve the appropriately substituted 3-tert-butoxycarbonyl-2,3,4,5-tetrahydro-1H-benzo[d]azepine in a mixture of trifluoroacetic acid/DCM (from 1:0 to 1:10 ratio) and stir the reaction for 1-16 h at ambient temperature. Concentrate in vacuo and either subject the residue to SCX chromatography or partition the residue between saturated aqueous NaHCO$_3$ and DCM or EtOAc. Dry the organic layer over Na$_2$SO$_4$ and concentrate in vacuo. Purify by either chromatography on silica gel (eluting with 1-20% 2M ammonia/methanol in DCM) or reverse phase HPLC.

General Procedure 1-6

Add acetyl chloride (40 equiv.) to cold methanol (0° C.) and stir for 5 min. Then add a solution of the appropriately substituted 7-chloro-3-(tert-butoxycarbonyl)-2,3,4,5-tetrahydro-1H-benzo[d]azepine (1 equiv.) in methanol. Stir the reaction at ambient temperature for 12 h. Remove the solvent in vacuo, basify with saturated aqueous NaHCO$_3$ and extract three times with DCM. Dry the combined organic extracts over Na$_2$SO$_4$, filter and concentrate in vacuo. Purify by chromatography on silica gel, eluting with 1-20% 2M ammonia/methanol in DCM.

General Procedure 2-1

Dissolve the purified free base (1 equiv.) in acetone, ether or methanol and add a solution of succinic acid (1 equiv.) in a minimal volume of acetone or methanol. Stir for 1 h at ambient temperature. Concentrate to an oil, add a minimal volume of DCM and ethyl ether to precipitate out the salt. Alternatively, to precipitate out the salt, allow the reaction mixture to stand 1-16 h at ambient temperature, 4° C. or −10° C. and add ether or hexane. Filter and wash the solid with ether or hexane to obtain the succinate salt. Alternatively, evaporate the solvent in vacuo, wash the solid with ether and filter or decant the solvent to obtain the succinate as a solid. Dry the solid in vacuo or under a stream of nitrogen.

General Procedure 2-2

Dissolve the purified free base (1 equiv.) in a minimal volume of acetone, dioxane, methanol or DCM and add an excess of 4M hydrogen chloride in dioxane or a 1M solution of hydrogen chloride in ethyl ether. Stir for 1 h and evaporate the solvent to obtain the salt as a solid. Alternatively, allow the reaction mixture to stand 1 to 16 h at ambient temperature and add ether or hexane to precipitate out the salt. Filter and wash the solid with ether or hexane to obtain the salt as a solid. Alternatively, evaporate the solvent in vacuo, wash the solid with ether, filter or decant the solvent to obtain the hydrochloride salt as a solid. Dry the solid in vacuo or under a stream of nitrogen.

General Procedure 2-3

Dissolve the purified free base in methanol, add a solution of ammonium chloride (1 equiv.) in methanol and stir for 1 h. Slowly remove the volatiles in vacuo. Dissolve the residue in methanol and remove most of the solvent in vacuo. Add anhydrous ethyl ether or EtOAc to precipitate out the hydrochloride salt. Collect the solid, wash the solid with ether and then dry the solid in vacuo or under a stream of nitrogen.

General Procedure 2-4

Dissolve the purified free base (1.0 equiv.) in methanol. Add a 0.5 M solution of methanesulfonic acid in methanol (2.0 equiv). Mix well, stir for 1 h, then remove the solvent in vacuo. Dissolve the residue into a minimal volume of DCM. Add ethyl ether to precipitate out the solid. Remove the solvent in vacuo to form a foam. Dry in vacuo or under a stream of nitrogen to obtain the methanosulfonic acid salt General Procedure 2-5

Dissolve the purified free base (1 equiv.) in a minimal volume of acetone and add a solution of oxalic acid (1 equiv.) in a minimal volume of acetone. Allow the mixture to stand 10 min to 16 h at ambient temperature to −10° C., and/or add ether or hexane to precipitate out the solid. Filter and wash the solid with ether or hexane to obtain the oxalic acid salt as a solid. Dry the solid in vacuo or under a stream of nitrogen.

General Procedure 2-6

Dissolve the purified free base (1 equiv.) in a minimal volume of cyclohexane, isohexane, chloroform, dichloromethane, methanol or a mixture thereof and add a solution of (L)-tartaric acid in isopropanol or methanol. If a solid precipitate out, filter and wash the solid with ether, cyclohexane, isohexane or EtOAc. If no solid formation is observed, remove all the volatiles in vacuo to form a foam. Dry in vacuo or under a stream of nitrogen to obtain the tartaric acid salt.

General Procedure 3

Dissolve the appropriately substituted 3-tert-butoxycarbonyl-6-trifluoromethanesulfonyloxy-2,3,4,5-tetrahydro-1H-benzo[d]azepine or 7-chloro-3-(2,2,2-trifluoroacetyl)-6-trifluoromethanesulfonyloxy-2,3,4,5-tetrahydro-1H-benzo[d]azepine (1 equiv.), PdCl$_2$(PPh$_3$)$_2$ (0.1 equiv.), tetrabutyl ammonium iodide (3 equiv.), and copper(I) iodide (0.3 equiv.) in triethylamine/DMF (1:5). Stir the mixture for 5 min at ambient temperature, add the appropriately substituted acetylene (2 equiv.) and heat at 70° C. for 2-16 h in a sealed tube. Cool the reaction mixture to ambient temperature, dilute with EtOAc/hexane (1:1) and wash with water. Dry the organic fraction over Na$_2$SO$_4$, filter and concentrate in vacuo. Purify by chromatography on silica gel eluting with hexane/EtOAc mixtures.

Preparation 1

7-Chloro-3-(2,2,2-trifluoroacetyl)-6-trifluoromethanesulfonyloxy-2,3,4,5-tetrahydro-1H-benzo[d]azepine

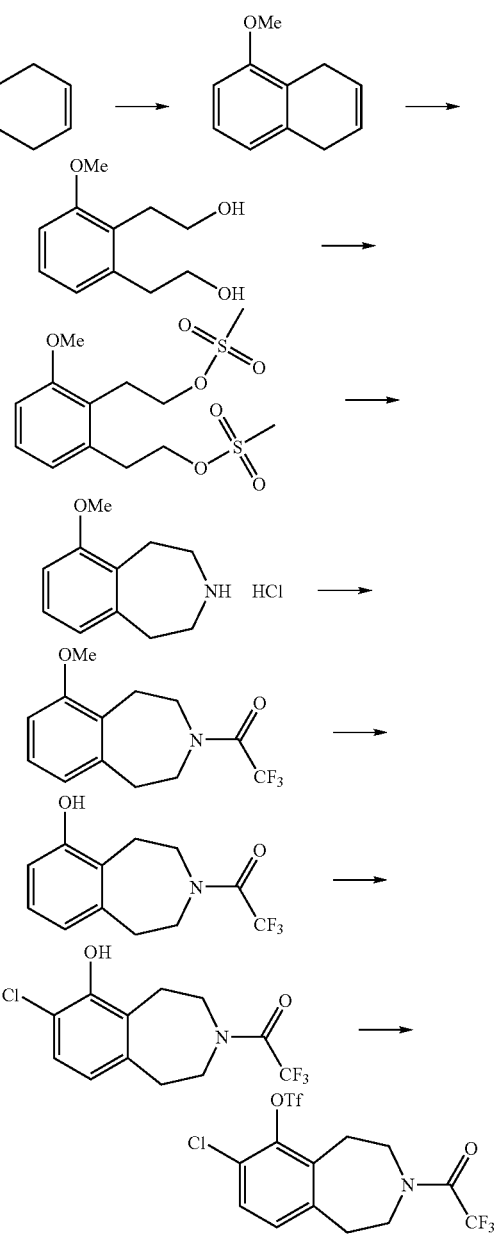

5-Methoxy-1,4-dihydronaphthalene: Add powdered potassium carbonate (193.1 g, 1.397 mol) to a solution of 5-hydroxy-1,4-dihydronaphthalene [68.08 g, 90% potency based on $^1$H-NMR, 0.4657 mol, from Societa Italiana Medicinala Scandicci, s.r.l., Reggello (Firenze), Italy] in ethanol (700 mL). Cool the solution to 0° C. with ice/water and add dimethyl sulfate (88.1 g, 66.1 mL, 0.699 mol) dropwise, maintaining the temperature between 5° C. and 10° C. Then heat the reaction mixture to 40° C. until the TLC (10:1 hexane/EtOAc) shows the absence of starting material (about 2 h). Filter off the solids by vacuum filtration and remove the solvent in vacuo. Dilute the residual brown oil with diethyl ether (500 mL), wash with 10% aqueous $NH_4OH$ (500 mL), water (500 mL), brine (500 mL), dry the organic layer over $Na_2SO_4$, filter and concentrate in vacuo to give the crude product as a brown oil (73 g). Purify the crude product by short path distillation under vacuum (bp 120-130° C./5 Torr) to give the desired intermediate as a clear oil (69.0 g, 92.5% potency corrected) (contains some 1,2,3,4-tetrahydro-5-methoxynaphthalene as an impurity). $^1H$ NMR (300 MHz, $CDCl_3$), δ7.15 (t, 1H, J=7.9), 6.72 (dd, 2H, J=15.7, 7.9), 5.93-5.88 (m, 2H), 3.83 (s, 3H), 3.42-3.39 (m, 2H), 3.30-3.28 (m, 2 H); $R_f$=0.58 eluting with 10:1 hexane/EtOAc.

2,3-Bis-(2-hydroxyethyl)-1-methoxybenzene: Charge a four-neck 5 L flask equipped with an over-head mechanical stirrer, reflux condenser, thermocouple, and gas dispersion apparatus with 5-methoxy-1,4-dihydronaphthalene (264.54 g, 89.5% potency based on $^1H$-NMR, 1.478 mol) in DCM (1.3 L) and 2B-3 ethanol (1 L). Add sudan III (10 mg) to give a faint red color. Cool the solution to −65° C. or lower, then pass $O_3$ through the solution until the solution turns a light yellow color and the TLC (10:1 hexane/EtOAc, $KMnO_4$ stain) shows the absence of the starting material (about 30 h). Transfer the solution via cannula into a slurry of $NaBH_4$ (97.8 g, 2.59 mol) in 2B-3 ethanol (500 mL) cooled in ice/water. It is important that the temperature be maintained at or above 0° C., as for example between 0° C. and 10° C., throughout the transfer to ensure the ozonide is completely reduced to the diol. After the transfer is complete, warm the solution to ambient temperature and stir for about 30 min. Cool the slurry to 0° C. with ice/water then slowly add acetone (540 mL, 7.4 mol) to remove excess $NaBH_4$. After all the solids dissolve, remove the solvent in vacuo. Dissolve the yellow solid in DCM (1 L) and water (1 L), separate the layers and extract the aqueous layer with DCM (750 mL). Wash the combined organic layers with brine (1.5 L), add toluene (750 mL) and remove the solvent in vacuo. Dissolve the solid in DCM (500 mL) with heating, then add toluene (750 mL) and concentrate the solution in vacuo to give the desired intermediate as a light yellow solid (283.7 g, 89% potency corrected, mp 82-83° C.) (contains 1,2,3,4-tetrahydro-5-methoxynaphthalene as an impurity (8.6%)). Further purify the product by vacuum drying overnight at 75° C., 5 Torr, to remove all but trace amount of the 1,2,3,4-tetrahydro-5-methoxynaphthalene impurity. $^1H$ NMR (300 MHz, $CDCl_3$), δ 7.16 (dd, 1H, J=8.2, 7.6), 6.83 (s, 1H, J=7.0), 6.76 (s, 1H, J=8.2), 3.85-3.77 (m, 7H), 3.01-2.91 (m, 4H), 2.35 (s, 2H); $^{13}C$ NMR (300 MHz, DMSO-$d_6$), δ 157.5, 138.9, 126.5, 125.2, 122.0, 108.4, 62.1, 60.5, 55.3, 36.1, 29.6; IR (KBr): 3006, 2960, 2886, 2829, 1583, 1461, 1440, 1264, 1091, 1041 $cm^{-1}$; MS (ES+) m/z 178 (M+H)$^+$; Anal. Calc'd for $C_{11}H_{16}O_3$: C, 67.32; H, 8.22; N, 0. Found: C, 67.26; H, 8.10; N, 0.21. $R_f$=0.23 eluting with 95:5 DCM/methanol.

2,3-Bis-(2-methanesulfonyloxyethyl)-1-methoxybenzene: To a slurry of 2,3-bis-(2-hydroxyethyl)-1-methoxybenzene (50.6 g, 0.258 mol, 1 equiv.) and triethylamine (78.3 g, 0.774 mol, 3 equiv.) in DCM (500 mL) at 0° C., add dropwise a solution of methanesulfonyl chloride (65.0 g, 0.567 mol, 2.2 equiv.) in DCM (100 mL) over 45 min. The addition is exothermic and the methanesulfonyl chloride is added at a rate to keep the temperature below 10° C. After the addition is complete, warm the reaction to ambient temperature. Wash the solution with water (2×500 mL), and then brine (750 mL). Dry the organic layer over $Na_2SO_4$, filter and concentrate in vacuo to obtain the desired intermediate as a dark yellow oil (87.4 g, 96.2%), which is used in the next reaction without further purification. An analytical sample is obtained by flash column chromatography eluting with 100% diethyl ether. $^1H$ NMR (300 MHz, $CDCl_3$), δ 7.20 (t, 1H, J=7.9), 6.82 (s, 1H, J=7.2), 6.80 (s, 1H, J=8.2), 4.41-4.34 (m, 4H), 3.83 (s, 3H), 3.16-3.09 (m, 4H), 2.91 (s, 3H), 2.87 (s, 3H); $^{13}C$ NMR (300 MHz, $CDCl_3$), δ 158.07, 136.55, 128.26, 123.34, 122.39, 109.24, 69.88, 69.08, 55.55, 37.35, 37.14, 32.57, 26.47; $^{13}C$ NMR (300 MHz, DMSO-$d_6$), δ157.58, 136.79, 127.81, 122.91, 122.00, 109.33, 70.19, 68.88, 55.55, 36.49, 36.47, 31.56, 25.72; IR (KBr): 1586.8, 1469.4, 1358.51, 1267.3, 1173.9, 1105.4, 972.4, 954.6, 914.3 $cm^{-1}$; MS (ES+) m/z 257 (M+H)$^+$; Anal. Calc'd. for $C_{13}H_{20}O_7S_2$: C, 44.31; H, 5.72; N, 0. Found: C, 44.22; H, 5.68; N, 0.13. $R_f$=0.72 eluting with 95:5 DCM/methanol.

6-Methoxy-2,3,4,5-tetrahydro-1H-benzo[d]azepine: Dissolve 2,3-bis-(2-methanesulfonyloxyethyl)-1-methoxybenzene (474.4 g, 1.346 mol) in acetonitrile (7 L) and split the mixture into two equal lots. In two separate runs, add concentrated aqueous $NH_4OH$ (3.5 L) and charge the solution to a pressure vessel (PARR apparatus). Heat the solution in a closed reactor to 100° C. over 20 min (internal pressure reaches about 100 psi), and maintain at 100° C. until the reaction is complete (about 1 h, HPLC monitored). Cool the reaction mixture to ambient temperature. Combine the two lots and remove the solvent in vacuo. Dissolve the residue in MTBE (3.5 L) and water (3.5 L). Adjust the pH to 6.5 using 2M aqueous NaOH or 1M aqueous HCl as appropriate (typically the pH is about pH=5.1 and the adjustment requires about 50 mL 2M aqueous NaOH). Discard the organic layer, adjust the aqueous layer to pH=13 using 50% NaOH (about 150 mL). Extract with MTBE (2×3.5 L), wash the combined organic layers with brine (3.5 L), dry over $Na_2SO_4$, filter and concentrate in vacuo to give the title compound as a crude yellow oil that solidifies upon standing (179.3 g). Use the material for the next step without further purification. Prepare an analytical sample by purification by two Kugelrohr distillations to give a clear oil that solidifies upon standing, mp 44.3-45.0° C. $^{13}C$ NMR (300 MHz, DMSO-$d_6$) □ 156.1, 144.4, 130.3, 126.2, 121.5, 108.9, 55.5, 48.2, 47.9, 39.9, 29.1; MS (ES+) m/z 163 (M+H)$^+$; Anal. Calc'd for $C_{11}H_{15}NO$: C, 74.54; H, 8.53; N, 7.90. Found: C, 74.28; H, 8.62; N, 7.86.

6-Methoxy-2,3,4,5-tetrahydro-1H-benzo[d]azepine Hydrochloride: Dissolve crude 6-methoxy-2,3,4,5-tetrahydro-1H-benzo[d]azepine (35.1 g, 0.198 mol) in 2B-3 ethanol (250 mL), heat the solution to reflux and add 2M HCl in ethanol (108.9 mL, 0.218 mol, 1.1 equiv.). Slowly add heptane (700 mL) over 10 min, then remove the heating mantle and cool the solution to ambient temperature, and finally continue the cooling with an ice/water mixture. Collect the resulting solid by vacuum filtration and wash with cold ethanol:heptane (1:2) (3×100 mL), air-dry for 15 min under vacuum, then further dry the product in a vacuum oven at 60° C. for 1 h to give the desired intermediate as a white granular solid (35.53 g, 63%): mp 246.6-246.9° C.; $^1H$ NMR (300 MHz, DMSO-$d_6$), δ 9.82 (broad s, 1H), 7.12 (dd, 1H, J=7.6, 7.9), 6.88 (d, 1H J=8.2), 6.78 (d, 1H, J=7.3), 3.75 (s, 3H), 3.20-3.00 (m, 8H); $^{13}C$ NMR (300 MHz, DMSO-$d_6$), δ 156.2, 141.3, 127.4, 127.2, 121.6, 109.7, 55.7, 44.9, 44.7, 31.6, 21.7; MS (ES+) m/z 178 (M+H)$^+$; Anal. Calc'd for $C_{11}H_{15}ClNO$: C, 62.12; H, 7.11; N, 6.59. Found: C, 61.95; H, 7.64; N, 6.58.

6-Methoxy-3-(2,2,2-trifluoroacetyl)-2,3,4,5-tetrahydro-1H-benzo[d]azepine: To a slurry of 6-methoxy-2,3,4,5-tetrahydro-1H-benzo[d]azepine hydrochloride (35.3 g, 0.165 mol, 1 equiv.) and triethylamine (69.1 mL, 0.496 mol, 3 equiv.) in DCM (300 mL) cooled at 0° C. with ice/water, add dropwise a solution of trifluoroacetic anhydride (25.7 mL, 0.182 mol, 1.1 equiv.) in DCM (40 mL) over 30 min, but at a rate that maintains the temperature below 10° C. After the addition is complete, warm the reaction mixture to ambient temperature and stir until the reaction is complete (verify by TLC using 9:1 CH₂Cl₂:methanol, about 2 h.). Wash the solution with water (2×350 mL), and then brine (350 mL), dry the organic layer over Na₂SO₄, filter and concentrate in vacuo to give desired intermediate as a yellow oil that solidifies upon standing (44.9 g, 96%). Use the material without further purification in the next step. Prepare an analytical sample by chromatography on silica gel eluting with 40% diethyl ether in hexane, mp 74-76° C. $^1$H NMR (300 MHz, CDCl₃), δ 7.16-7.11 (m, 1H), 6.81-6.74 (m, 2H), 3.81 (s, 3H), 3.79-3.64 (m, 4H), 3.11-3.07 (m, 2H), 2.99-2.95 (m, 2H); $^1$H NMR (300 MHz, DMSO-d₆), δ 7.13 (dd, 1H, J=1.5, 7.0), 7.08 (d, 1H, J=1.5), 6.88-6.74 (m, 1H), 3.75 (s, 3H), 3.67-3.61 (m, 4H), 3.04-2.92 (m, 4H); $^{13}$C NMR (300 MHz, DMSO-d₆), δ 156.43. 156.38, 155.06, 155.00, 154.60, 154.54, 154.14, 154.08, 141.31, 141.04, 127.44, 127.18, 127.05, 127.01, 122.27, 121.94, 121.90, 118.46, 114.64, 110.80, 109.52, 109.41, 55.63, 55.61, 47.11, 47.07, 46.67, 46.63, 45.61, 45.16, 35.90, 34.65, 26.18, 24.91; Anal. Calc'd for C₁₃H₁₄F₃NO₂: C, 57.14; H, 5.16; N, 5.13. Found: C, 57.17; H, 5.27; N, 5.08.

6-Hydroxy-3-(2,2,2-trifluoroacetyl)-2,3,4,5-tetrahydro-1H-benzo[d]azepine: To a 1M solution of BBr₃ (1.1 L, 1.6 equiv.), cooled at 0° C. with an ice-water bath, add 6-methoxy-3-(2,2,2-trifluoroacetyl)-2,3,4,5-tetrahydro-1H-benzo[d]azepine (187 g, 0.684 mol) in DCM (200 mL) over 1 h., while maintaining the temperature between 0° C. and 10° C. Warm the reaction mixture to ambient temperature and stir until HPLC indicates completion of the reaction (about 2 h.). Cool the solution to 0° C. and transfer it via cannula into an ice/water solution (1.2 L), thereby precipitating the product as a white solid. Add EtOAc (2 L) to dissolve most of the precipitate, separate the layers and concentrate the organic layer in vacuo. Extract the aqueous layer three times with EtOAc (2×2 L, 1×1 L). Wash the combined organic layers with water (2 L), and then brine (2 L), dry over Na₂SO₄, filter and concentrate in vacuo to give the desired intermediate as a light yellow solid (166.3 g, 94%). Use the product for the next step without further purification. Prepare an analytical sample by chromatography on silica gel eluting with 40% diethyl ether in hexane: mp 183.0-185.2° C. $^1$H NMR (300 MHz, DMSO-d₆), δ 9.39 (s, 1H), 6.94-6.88 (m, 1H), 6.72-6.68 (m, 1H), 6.61-6.57 (m, 1H), 3.67-3.32 (m, 4H), 2.99-2.86 (m, 4H); $^{13}$C NMR (300 MHz, DMSO-d₆), δ 154.50, 141.47, 141.18, 126.77, 126.64, 125.77, 125.33, 120.38, 120.32, 118.49, 114.67, 113.64, 113.47, 47.31, 47.27, 47.00, 46.96, 45.83, 45.49, 36.17, 34.93, 26.46, 25.18, 20.66, 14.00; MS (ES+) m/z 260 (M+H)⁺; Anal. Calc'd. for C₁₂H₁₂F₃NO₂: C, 55.60; H, 4.67; N, 5.40. Found: C, 55.51; H, 4.71; N, 5.29.

7-Chloro-6-hydroxy-3-(2,2,2-trifluoroacetyl)-2,3,4,5-tetrahydro-1H-benzo[d]azepine: Heat a mixture of 6-hydroxy-3-(2,2,2-trifluoroacetyl)-2,3,4,5-tetrahydro-1H-benzo[d]azepine (120 g, 0.4629 mol) and toluene (14.4 L) to 70° C. for 45 min until most of the starting material is dissolved. Add diisobutylamine (1.197 g, 1.62 mL, 9.26 mmol) followed by addition of sulfuryl chloride (62.48 g, 37.19 mL, 0.463 mol) in toluene (360 mL) over 20 min. Stir the reaction mixture for 50 min and then add additional sulfuryl chloride (4.536 g, 2.70 mL, 0.0336 mol) neat and stir the reaction mixture for 15 min at 70° C. Cool the reaction mixture to 24° C. over 30 min and then add 1N hydrochloric acid (2.00 L). Separate, wash the organic layer with saturated aqueous NaHCO₃ (2.00 L), brine (2.00 L) and then dry over Na2SO4. Filter and remove the solvent with a rotary evaporator at 70° C. until about 672.5 g remains using the minimum effective vacuum in order to maintain a vapor phase sufficient to prevent drying above the solvent line and self-seeding, thus preventing crystallization under these conditions. Using toluene heated to 70° C., transfer the light-yellow solution to a preheated (70° C.) 3-neck flask equipped with a mechanical stirrer. Lower the temperature to 58° C. over 1 h. If available, seed the solution with crystals of 7-chloro-6-hydroxy-3-(2,2,2-trifluoroacetyl)-2,3,4,5-tetrahydro-1H-benzo[d]azepine from a prior synthesis to enhance crystallization. After 30 min, reduce the temperature further to 55° C. and observe the initiation of the crystallization process. Hold the temperature at 55° C. for 2 h. followed by 4 h. at 45° C., then turn off the heat allowing the mixture to slowly reach 24° C. (ambient temperature). After stirring for 8 h. with the heat off, cool the mixture to 0° C. for 2 h. followed by 2 h. at −10° C. Collect the resulting dense, white, granular crystals by vacuum filtration at −10° C. Rinse the crystals twice with cold (−10° C.) toluene and vacuum dry at 50° C., 5 Torr, for 12 h., to obtain the desired intermediate as a white solid (120.7 g, 99.5% purity, 88.8%): mp 133-134° C. MS (ES+) m/z 294 (M+H)⁺. Anal. Calc'd for C₁₂H₁₁ClF₃NO₂: C, 49.08; H, 3.78; N, 4.77; Cl, 12.07. Found: C, 49.01; H, 3.63; N, 4.72; Cl, 12.32.

7-Chloro-3-(2,2,2-trifluoroacetyl)-6-trifluoromethanesulfonyloxy-2,3,4,5-tetrahydro-1H-benzo[d]azepine: Cool a solution of 7-chloro-6-hydroxy-3-(2,2,2-trifluoroacetyl)-2,3,4,5-tetrahydro-1H-benzo[d]azepine (60 g, 0.204 mol), triethylamine (62.6 mL, 0.448 mol, 2.2 equiv.), and DCM (590 mL) in an ice bath and add dropwise trifluoromethanesulfonic anhydride (43.5 mL, 0.258 mol, 1.26 equiv.) over 70 min. Remove the ice bath and stir the reaction mixture for 2 h Wash the reaction mixture sequentially with water (500 mL), 1N aqueous HCl (500 mL), water (500 mL), and brine (560 mL). Dry the organic layer over Na₂SO₄ and concentrate in vacuo to give the crude product as a brown solid (90 g). Dissolve the solid in warm toluene (200 mL). Further purify by plug filtration chromatography over silica gel (500 g) eluting sequentially with hexane (1 L), hexane/EtOAc (9:1, 1 L), hexane/EtOAc (4:1, 1 L), and hexane/EtOAc (7:3, 9 L). Pool the eluents and evaporate the solvent to obtain the product as a yellow tan solid (86.3 g). Dissolve the solid in warm EtOAc (86 mL) and then add hexane (700 mL). If available, seed the solution with crystals of 7-chloro-3-(2,2,2-trifluoroacetyl)-6-trifluoromethanelsulfonyloxy-2,3,4,5-tetrahydro-1H-benzo[d]azepine from a prior synthesis to enhance crystallization. Allow the mixture to stand at ambient temperature for 30 min. Cool the mixture at about −10° C. for 2 h., filter, rinse the crystals with cold (−110° C.) hexane/EtOAc, and air-dry on the filter under vacuum to obtain the title compound as a first crop of crystals (73.54 g). Concentrate the mother liquor to obtain a solid (12.7 g). Recrystallize the solid in a mixture of EtOAc/hexane (15 mL:211 mL) to obtain additional title compound (7.65 g, total yield: 81.19 g, 93%).

Preparation 2

3-(2,2,2-Trifluoroacetyl)-6-trifluoromethanesulfonyloxy-2,3,4,5-tetrahydro-1H-benzo[d]azepine

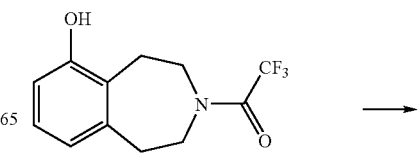

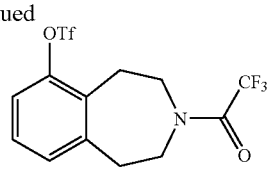

Cool a solution of 6-hydroxy-3-(2,2,2-trifluoroacetyl)-2,3,4,5-tetrahydro-1H-benzo[d]azepine (2 g, 7.72 mmol), triethylamine (1.4 mL, 10.1 mmol) and DCM (50 mL) in a cryogenic bath set at −30° C. and add dropwise trifluoromethanesulfonic anhydride (1.7 mL, 10.1 mmol) over 20 min. Stir at −30° C. for 2 h and then warm to ambient temperature overnight. Wash the reaction mixture sequentially with water (100 mL), 1N aqueous HCl (100 mL), water (200 mL), and brine (200 mL). Dry the organic layer over Na$_2$SO$_4$ and concentrate in vacuo to give the title compound as a colorless to light yellow oil (2.7 g, 89%) that was used without purification. Obtain an analytical sample by chromatography on silica gel eluting with hexane/EtOAc (9:1) to give the title compound as an off-white waxy solid. GC-MS m/z: 391 (M$^+$).

Preparation 3

3-tert-Butoxycarbonyl-6-trifluoromethanesulfonyloxy-2,3,4,5-tetrahydro-1H-benzo[d]azepine

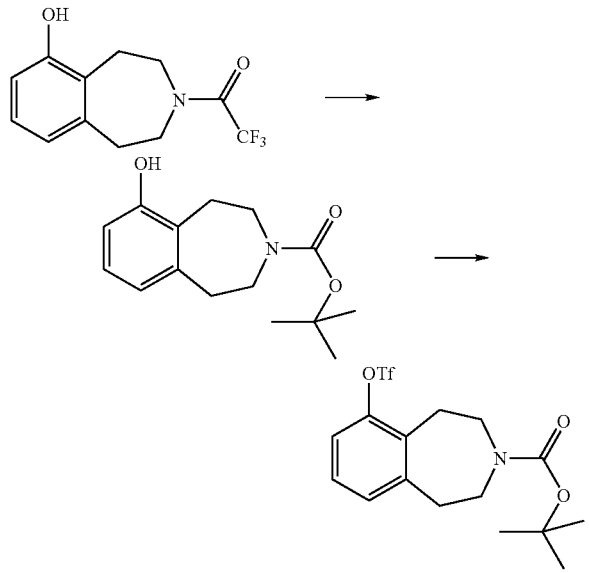

Dissolve 6-hydroxy-3-(2,2,2-trifluoroacetyl)-2,3,4,5-tetrahydro-1H-benzo[d]azepine (5 g, 19.3 mmol) in 7N ammonia in methanol (50 mL) and stir at ambient temperature for 16 h. Concentrate the reaction mixture to an oil and use without further purification. Dissolve the residue in a solvent mixture consisting of methanol (20 mL), DCM (10 mL) and water (100 mL), and add potassium carbonate (5 g) and di-tert-butyl-dicarbonate (5.05 g, 23.2 mmol). Stir the reaction mixture at ambient temperature for 16 h and concentrate in vacuo. Extract the aqueous phase with DCM, dry over Na$_2$SO$_4$, filter and concentrate. Use the residue without further purification. Dissolve the material in a mixture of DCM (300 mL) and pyridine (30 mL) and cool in an ice bath. Add dropwise to the stirred solution trifluoromethanesulfonic anhydride (5.84 mL, 34.7 mmol) and stir the reaction mixture for 2 h at ambient temperature. Dilute the reaction mixture with DCM (400 mL) and wash with 2.5N aqueous HCl. Dry the organic fraction over Na$_2$SO$_4$, filter and concentrate to give the title compound as a yellow solid (6.1 g, 80%). MS (ES+) m/z: 396 (M+H)$^+$.

Preparation 4

7-Fluoro-3-(2,2,2-trifluoroacetyl)-6-trifluoromethanesulfonyloxy-2,3,4,5-tetrahydro-1H-benzo[d]azepine

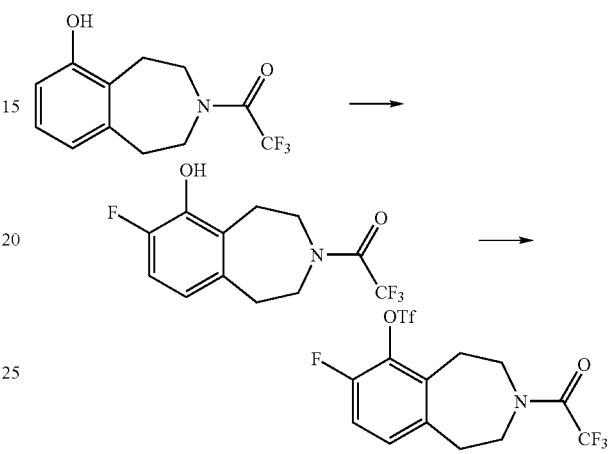

Add N-fluoro-4,6-bis(trifluoromethyl)-pyridinium 2-sulfonate (3.02 g, 9.6 mmol) to a stirred mixture of 6-hydroxy-3-(2,2,2-trifluoroacetyl)-2,3,4,5-tetrahydro-1H-benzo[d]azepine (2.5 g, 9.6 mmol) and hexafluoro-2-propanol (10 mL) in DCM (150 mL). Stir at ambient temperature for 16 h. Concentrate the reaction mixture and partition the residue between EtOAc and 1N aqueous HCl. Wash the organic fraction with saturated aqueous NaHCO$_3$, brine, dry over Na$_2$SO$_4$, filter and concentrate. Purify by chromatography on silica gel eluting with hexane/EtOAc (20:1, 10:1, 6:1, 5:1 and 3:1) to give 7-fluoro-6-hydroxy-3-(2,2,2-trifluoroacetyl)-2,3,4,5-tetrahydro-1H-benzo[d]azepine as a white solid (1.8 g, 68%). Dissolve 7-fluoro-6-hydroxy-3-(2,2,2-trifluoroacetyl)-2,3,4,5-tetrahydro-1H-benzo[d]azepine (1.5 g, 5.41 mmol) in a mixture of DCM (20 mL) and pyridine (2 mL) and cool in an ice bath. Add dropwise to the stirred solution a mixture of trifluoromethanesulfonic anhydride (1.64 mL, 9.74 mmol) in DCM and stir the reaction for 1.5 h at ambient temperature. Dilute the reaction with DCM (300 mL) and wash with 2.5N aqueous HCl. Dry the organic fraction over Na$_2$SO$_4$, filter and concentrate to give the title product as a white solid (2.2 g, 99%). MS (ES+) m/z: 410 (M+H)$^+$.

Preparation 5

3-tert-Butoxycarbonyl-7-chloro-6-hydroxy-2,3,4,5-tetrahydro-1H-benzo[d]azepine

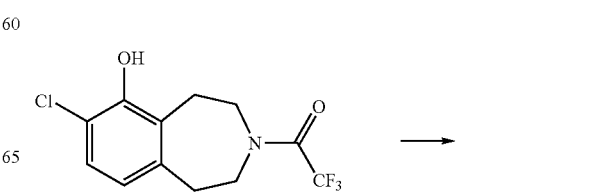

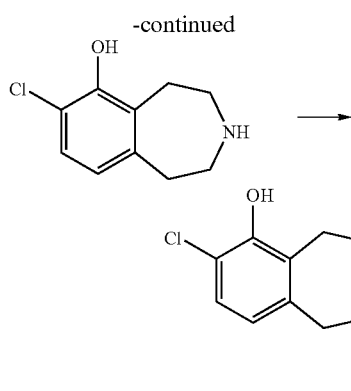

Dissolve 7-chloro-6-hydroxy-3-(2,2,2-trifluoroacetyl)-2,3,4,5-tetrahydro-1H-benzo[d]azepine (3 g, 10.2 mmol) in 7 N ammonia in methanol (50 mL) and stir at ambient temperature for 16 h. Concentrate the reaction mixture to an oil and use without further purification. Dissolve the residue in a solvent mixture consisting of DCM (25 mL) and saturated aqueous potassium carbonate solution (25 mL) and add di-tert-butyl-dicarbonate (2.2 g, 10.2 mmol). Stir the reaction mixture at ambient temperature for 4 h, concentrate in vacuo and extract the aqueous residue with DCM. Dry the organic fraction over $Na_2SO_4$, filter and concentrate in vacuo. Purify by chromatography on silica gel eluting with EtOAc/hexane (1:5) to give the title compound as a white solid (2.3 g, 76%). MS (ES−) m/z: 296 (M−H)⁻.

EXAMPLE 1

6-(3-Phenyl-prop-1-ynyl)-2,3,4,5-tetrahydro-1H-benzo[d]azepine Hydrochloride

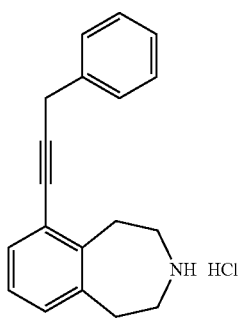

Use a method similar to the General Procedure 3 to couple 3-tert-butoxycarbonyl-6-trifluoromethanesulfonyloxy-2,3,4,5-tetrahydro-1H-benzo[d]azepine (0.6 g, 1.5 mmol) with 3-phenyl-1-propyne (0.38 mL, 3 mmol). Purify by chromatography on silica gel eluting with hexane/EtOAc (1:0, 40:1 and 20:1) to give 3-tert-butoxycarbonyl-6-(3-phenyl-prop-1-ynyl)-2,3,4,5-tetrahydro-1H-benzo[d]azepine as an orange oil (400 mg, 74%).

Use a method similar to the General Procedure 1-5 to deprotect 3-tert-butoxycarbonyl-6-(3-phenyl-prop-1-ynyl)-2,3,4,5-tetrahydro-1H-benzo[d]azepine (68 mg, 0.19 mmol). Purify by chromatography on silica gel eluting with DCM/2M ammonia in methanol (1:0, 20:1 and 10:1) to obtain the free base of the title compound. Use a method similar to the General Procedure 2-2 to give the title compound as a tan solid (48 mg, 85%). MS (ES+) m/z: 262 (M+H)⁺.

Examples 2-4 may be prepared essentially as described in Example 1 by using 3-tert-butoxycarbonyl-6-trifluoromethanesulfonyloxy-2,3,4,5-tetrahydro-1H-benzo[d]azepine and the appropriate alkyne. Overall yields and MS (ES+) data are shown in the Table below.

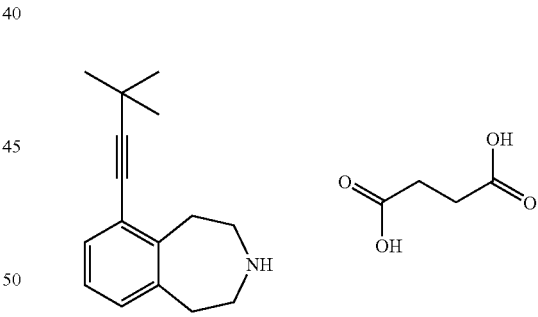

| Ex. | R | Compound | Yield (%) | MS (ES+) m/z |
|---|---|---|---|---|
| 2 | Benzyl | 6-(4-Phenyl-but-1-ynyl)-2,3,4,5-tetrahydro-1H-benzo[d]azepine Hydrochloride | 60 | 276 (M + H)⁺ |
| 3 | Cyclopentyl | 6-(3-Cyclopentyl-prop-1-ynyl)-2,3,4,5-tetrahydro-1H-benzo[d]azepine Hydrochloride | 73 | 254 (M + H)⁺ |
| 4 | Cyclohexyl | 6-(3-Cyclohexyl-prop-1-ynyl)-2,3,4,5-tetrahydro-1H-benzo[d]azepine Hydrochloride | 79 | 268 (M + H)⁺ |

EXAMPLE 5

6-(3,3-Dimethyl-but-1-ynyl)-2,3,4,5-tetrahydro-1H-benzo[d]azepine Succinate

Use a method similar to the General Procedure 3 to couple 3-tert-butoxycarbonyl-6-trifluoromethanesulfonyloxy-2,3,4,5-tetrahydro-1H-benzo[d]azepine (0.5 g, 1.3 mmol) with 3,3-dimethyl-1-butyne (0.311 mL, 2.5 mmol). Purify by chromatography on silica gel eluting with hexane/EtOAc (10:1) to give 3-tert-butoxycarbonyl-6-(3,3-dimethyl-but-1-ynyl)-2,3,4,5-tetrahydro-1H-benzo[d]azepine as a yellow oil (304 mg, 74%).

Use a method similar to the General Procedure 1-5 to deprotect 3-tert-butoxycarbonyl-6-(3,3-dimethyl-but-1-ynyl)-2,3,4,5-tetrahydro-1H-benzo[d]azepine. Purify by chromatography on silica gel eluting with DCM/2M ammonia in methanol (1:0, 50:1, 20:1, 15:1 and 10:1) to obtain the free base of the title compound. Use a method similar to the General Procedure 2-1 to give the title compound as a tan solid (171 mg, 53%). MS (ES+) m/z: 228 (M+H)+.

EXAMPLE 6

6-(3,3-Dimethyl-but-1-ynyl)-7-fluoro-2,3,4,5-tetrahydro-1H-benzo[d]azepine Succinate

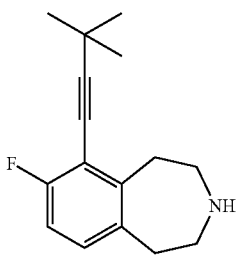 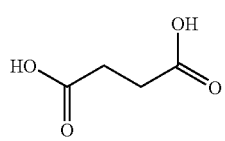

Use a method similar to the General Procedure 3 to couple 7-fluoro-3-(2,2,2-trifluoroacetyl)-6-trifluoromethanesulfonyloxy-2,3,4,5-tetrahydro-1H-benzo[d]azepine (1 g, 2.4 mmol) with 3,3-dimethyl-1-butyne (0.599 mL, 4.9 mmol). Purify by chromatography on silica gel eluting with hexane/ EtOAc (10:1) to give 6-(3,3-dimethyl-but-1-ynyl)-7-fluoro-3-(2,2,2-trifluoroacetyl)-2,3,4,5-tetrahydro-1H-benzo[d] azepine as a yellow oil (700 mg, 84%).

Use a method similar to the General Procedure 1-3 to deprotect 6-(3,3-dimethyl-but-1-ynyl)-7-fluoro-3-(2,2,2-trifluoroacetyl)-2,3,4,5-tetrahydro-1H-benzo[d]azepine. Purify by SCX chromatography followed by chromatography on silica gel eluting with DCM/2M ammonia in methanol (1:0, 50:1, 20:1, 15:1 and 10:1) to obtain the free base of the title compound. Use a method similar to the General Procedure 2-1 to give the title compound as a white solid (589 mg, 830%). MS (ES+) m/z: 246 (M+H)+.

General Procedure 4-1

Add 7-chloro-6-hydroxy-3-(2,2,2-trifluoroacetyl)-2,3,4, 5-tetrahydro-1H-benzo[d]azepine (1 equiv.), the appropriate alkylating agent (1.2 equiv.), ground $K_2CO_3$ (3 equiv.) and KI (0.1 equiv.) to a proper solvent (acetone, ethanol or acetonitrile) and heat to reflux for 6 to 16 h unless otherwise specified. Cool the reaction mixture to ambient temperature, quench with 1N aqueous HCl and extract the aqueous layer three times with EtOAc. Combine the organic fractions, wash with saturated aqueous $NaHCO_3$, brine, dry over $Na_2SO_4$, filter and concentrate in vacuo. Purify by chromatography on silica gel eluting with hexane/EtOAc mixtures.

General Procedure 4-2

Add 7-chloro-6-hydroxy-3-(2,2,2-trifluoroacetyl)-2,3,4, 5-tetrahydro-1H-benzo[d]azepine (1 equiv.), the appropriate alcohol (1.1 equiv.), triphenylphosphine (1.2 equiv.) and diethyl azodicarboxylate (1.1 equiv.) sequentially to anhydrous THF. Stir the mixture at ambient temperature under nitrogen. Re-add triphenylphosphine (1.2 equiv.) and diethyl azodicarboxylate (1.1 equiv.) if the reaction is not completed (monitored by TLC). Dilute the mixture with EtOAc, wash with saturated aqueous $NaHCO_3$, brine, dry over $Na_2SO_4$ and concentrate in vacuo. Purify by chromatography on silica gel eluting with hexane/EtOAc mixtures.

General Procedure 4-3

Add 7-chloro-6-hydroxy-3-(2,2,2-trifluoroacetyl)-2,3,4, 5-tetrahydro-1H-benzo[d]azepine (1 equiv.), the appropriate alcohol (1.2-1.5 equiv.) and triphenylphosphine (1.5 equiv.) sequentially to anhydrous THF. Stir the mixture at 0° C. under nitrogen for 10 min. Add 1,1'-(azodicarbonyl)dipiperidine (1.5 equiv.) and let the mixture warm to ambient temperature over 16 h. Dilute with ether, filter and concentrate in vacuo. Purify by chromatography on silica gel eluting with hexane/ EtOAc mixtures.

Preparation 6

7-Chloro-9-fluoro-3-(2,2,2-trifluoroacetyl)-6-trifluoromethanesulfonyloxy-2,3,4,5-tetrahydro-1H-benzo [d]azepine

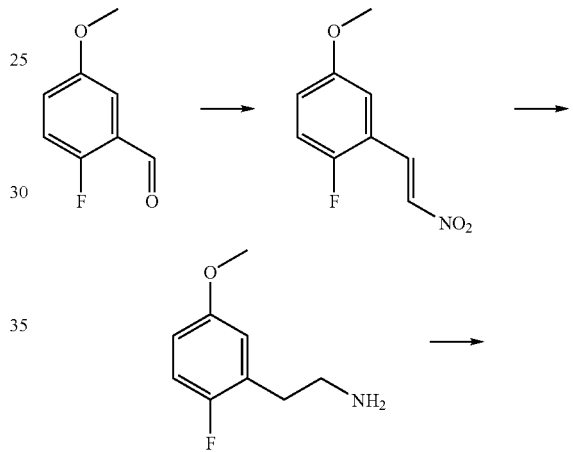

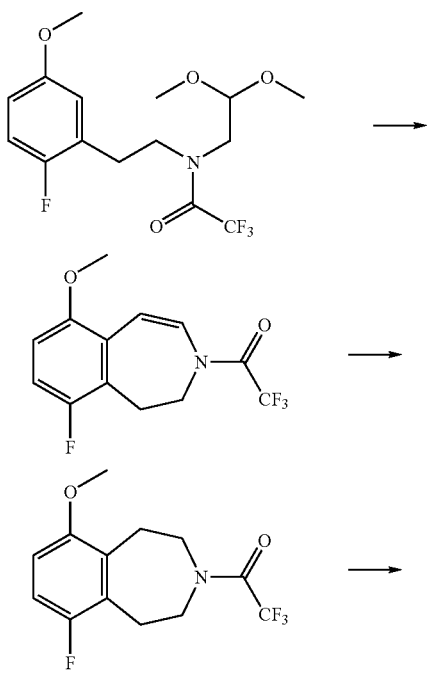

-continued

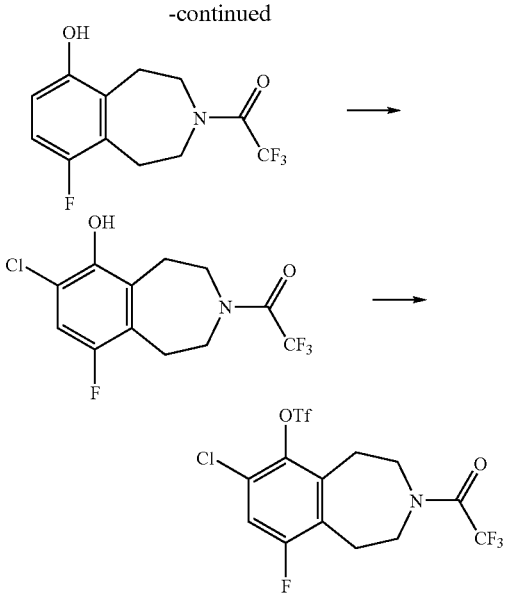

1-Fluoro-4-methoxy-2-(2-nitro-vinyl)-benzene: Heat 2-fluoro-5-methoxybenzaldehyde (15 g, 97.4 mmol) with nitromethane (32 mL, 584 mmol) and ammonium acetate (30 g, 390 mmol) in acetic acid (136 mL) under reflux for 30 min. Evaporate the solvent and dissolve the residue in ether. Wash the organic fraction with water, saturated aqueous NaHCO$_3$ and evaporate to give the desired intermediate (18.7 g, 97%). GC-MS m/z: 197 (M)$^+$.

2-(2-Fluoro-5-methoxyphenyl)-ethylamine: Cautiously add sulfuric acid (14.7 mL, 265 mmol) dropwise at 0° C. to lithium aluminum hydride (1M solution in THF, 565 mL) with efficient stirring. Warm the mixture to ambient temperature for 20 min and then cool back to 0° C. Add a solution of 1-fluoro-4-methoxy-2-(2-nitro-vinyl)-benzene (18.7 g, 95 mmol) in THF (150 mL) by cannula and stir 2.5 h at ambient temperature. Cool the mixture to 0° C., cautiously add water (4.6 mL) followed by 2N aqueous NaOH (4.6 mL) and water (6.5 mL). Remove the precipitate by filtration and evaporate the filtrate to give the desired intermediate (16 g, 100%). MS (ES+) m/z: 170 (+H)$^+$.

N-(2,2-Dimethoxy-ethyl)-2,2,2-trifluoro-N-[2-(2-fluoro-5-methoxy-phenyl)-ethyl]-acetamide: Dissolve 2-(2-fluoro-5-methoxyphenyl)-ethylamine (16 g, 95 mmol) and dimethoxy acetaldehyde (60% aqueous, 21.5 mL, 142 mmol) in methanol (500 mL). After 1.5 h, cautiously add sodium borohydride (5.39 g, 142 mmol) at 0° C. and then stir at ambient temperature for 3 h. Add acetone and evaporate the mixture. Dissolve the residue in DCM (250 mL), cool to 0° C. and add triethylamine (26.5 mL, 190 mmol) and trifluoroacetic anhydride (20.1 mL, 142 mmol). After 30 min, wash the mixture with 1N aqueous HCl (4×100 mL), brine and saturated aqueous NaHCO$_3$. Dry the organic layer over Na$_2$SO$_4$ and concentrate in vacuo. Purify by chromatography on silica gel to give the desired intermediate (19.7 g, 59%). MS (ES+) m/z: 322 (M-OMe)$^+$.

9-Fluoro-6-methoxy-3-(2,2,2-trifluoroacetyl)-2,3-dihydro-1H-benzo[d]azepine: Dissolve N-(2,2-dimethoxy-ethyl)-2,2,2-trifluoro-N-[2-(2-fluoro-5-methoxy-phenyl)-ethyl]-acetamide (5 g, 14.2 mmol) in chlorobenzene (100 mL). Add polyphosphoric acid (5 g) and P$_2$O$_5$ (2.5 g) and heat at 80° C. for 2 h. Add water to the hot mixture, cool to room temperature and extract with DCM. Dry the organic extracts over Na$_2$SO$_4$ and concentrate in vacuo to obtain the desired intermediate (3.0 g, 73%). MS (ES+) m/z: 290 (M+H)$^+$.

9-Fluoro-6-methoxy-3-(2,2,2-trifluoroacetyl)-2,3,4,5-tetrahydro-1H-benzo[d]azepine: Dissolve 9-fluoro-6-methoxy-3-(2,2,2-trifluoroacetyl)-2,3-dihydro-1H-benzo[d]azepine (9.4 g, 32.4 mmol) with 10% Pd/C (dry basis, Degussa type, 1.4 g, 0.65 mmol) in EtOAc/ethanol (1:1, 200 mL) and stir at ambient temperature under a balloon of hydrogen for 4.5 h. Filter the mixture through a pad of silica gel and evaporate the filtrate to obtain the desired intermediate (8.6 g, 91%). MS (ES+) m/z: 292 (M+H)$^+$.

9-Fluoro-6-hydroxy-3-(2,2,2-trifluoroacetyl)-2,3,4,5-tetrahydro-1H-benzo[d]azepine: Dissolve 9-fluoro-6-methoxy-3-(2,2,2-trifluoroacetyl)-2,3,4,5-tetrahydro-1H-benzo[d]azepine (8.1 g, 27.7 mmol) in DCM (250 mL), cool to 0° C. and add boron tribromide (5.24 mL, 55.5 mmol). Stir at ambient temperature for 1.5 h, wash the mixture with brine, dry the organic layer over Na$_2$SO$_4$ and concentrate in vacuo to obtain the desired intermediate (7.6 g, 99%). MS (ES+) m/z: 278 (M+H)$^+$.

7-Chloro-9-fluoro-6-hydroxy-3-(2,2,2-trifluoroacetyl)-2,3,4,5-tetrahydro-1H-benzo[d]azepine: Dissolve 9-fluoro-6-hydroxy-3-(2,2,2-trifluoroacetyl)-2,3,4,5-tetrahydro-1H-benzo[d]azepine (1.0 g, 3.6 mmol) in toluene (36 mL) with diisopropylamine (41 μL, 0.29 mmol). Warm to 60° C. and add dropwise a solution of sulfuryl chloride (0.32 mL, 3.97 mmol) in toluene (10 mL). After 2 h, wash the mixture with brine, dry the organic layer over Na$_2$SO$_4$ and evaporate onto silica gel. Purify by chromatography on silica gel eluting with EtOAc/hexane (0:1 to 1:0) to obtain the desired intermediate (1.0 g, 92%). MS (ES+) m/z: 312 (M+H)$^+$.

7-Chloro-9-fluoro-3-(2,2,2-trifluoroacetyl)-6-trifluoromethanesulfonyloxy-2,3,4,5-tetrahydro-1H-benzo[d]azepine: Cool a solution of 7-chloro-9-fluoro-6-hydroxy-3-(2,2,2-trifluoroacetyl)-2,3,4,5-tetrahydro-1H-benzo[d]azepine (2.5 g, 8.0 mmol), pyridine (3.25 mL, 40.2 mmol) and DCM (80 mL) at 0° C. and add dropwise trifluoromethanesulfonic anhydride (2.43 mL, 14.5 mmol) over 20 min. Stir at room temperature for 1 h. Wash the reaction mixture sequentially with 1N aqueous HCl, saturated NaHCO$_3$ solution and brine. Dry the organic fraction over Na$_2$SO$_4$ and concentrate in vacuo. Purify by chromatography on silica gel eluting with hexane/EtOAc (gradient from 19:1 to 1:1) to obtain the title compound (3.1 g, 87%).

Preparation 7

4-Bromomethyl-N-methyl-benzenesulfonamide

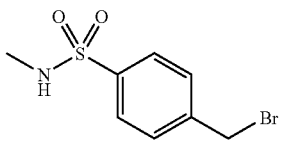

Mix 4-(bromomethyl)benzenesulfonyl chloride (2.7 g, 10 mmol), anhydrous potassium carbonate (1.4 g, 10 mmol) and anhydrous THF (60 mL) under nitrogen. Cool the mixture in an ice bath, add dropwise a 2M solution of methylamine in THF, and stir at this temperature for 30 min. Remove the ice bath and stir at ambient temperature for 16 h. Dilute with EtOAc then wash with 1N aqueous HCl. Separate the organic layer, dry over Na$_2$SO$_4$ and concentrate in vacuo. Purify by chromatography on silica gel eluting with hexane/EtOAc (1:0, 4:1, 7:3 and 13:7) to obtain the title compound (1.5 g, 71%). MS (ES+) m/z: 266 (M+H)⁺.

The compounds of Preparations 8-9 may be prepared essentially as described in Preparation 7 by using 4-(bromomethyl)benzenesulfonyl chloride and the appropriate amine. Yields and MS (ES+) data are shown in the Table below.

| Prep. | NH—R | Compound | Yield (%) | MS (ES+) m/z |
|---|---|---|---|---|
| 8 | NH—CH₂CH₃ | 4-Bromomethyl-N-ethyl-benzenesulfonamide | 43 | 278 (M + H)⁺ |
| 9 | NH—CH₂CH₂F | 4-Bromomethyl-N-(2-fluoroethyl)-benzenesulfonamide. | 39 | 296 (M + H)⁺ |

Preparation 10

Thiazol-2-yl-methanol

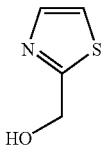

Mix under nitrogen 2-thiazolecarboxaldehyde (1.1 g, 10 mmol) and ethanol (30 mL). Add sodium borohydride (416 mg, 11 mmol) at 0° C. Stir and warm the mixture slowly to ambient temperature for 12 h. Quench with saturated aqueous ammonium chloride and concentrate in vacuo. Dilute the residue with EtOAc and wash with brine. Dry the organic fraction over Na₂SO₄ and concentrate in vacuo to obtain the title compound as an oil (1.0 g, 87%). MS (ES+) m/z: 116 (M+H)⁺.

Preparation 11

(1-Methyl-1H-pyrazol-3-yl)-methanol

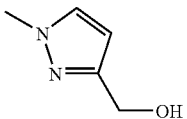

Dissolve 3-dimethoxymethyl-1-methylpyrazole (1.562 g, 10 mmol) in acetone (100 mL), add p-toluenesulfonic acid (190 mg, 1.0 mmol) and stir at ambient temperature for 12 h. Remove volatiles in vacuo, dissolve the residue in EtOAc, wash with saturated aqueous NaHCO₃, dry over Na₂SO₄, filter and concentrate in vacuo to afford an oil. Dissolve the oil in methanol (15 mL), add sodium borohydride (567 mg, 15 mmol) and stir the reaction mixture at ambient temperature for 12 h. Remove volatiles in vacuo, dissolve the residue in EtOAc, wash with saturated aqueous NaHCO₃, dry over Na₂SO₄, filter and concentrate in vacuo. Purify by chromatography on silica gel eluting with EtOAc/hexane (6:1) to give the title compound as an oil (530 mg, 47%).

Preparation 12

6-(2-Amino-ethoxy)-7-chloro-3-(2,2,2-trifluoro-acetyl)-2,3,4,5-tetrahydro-1H-benzo[d]azepine

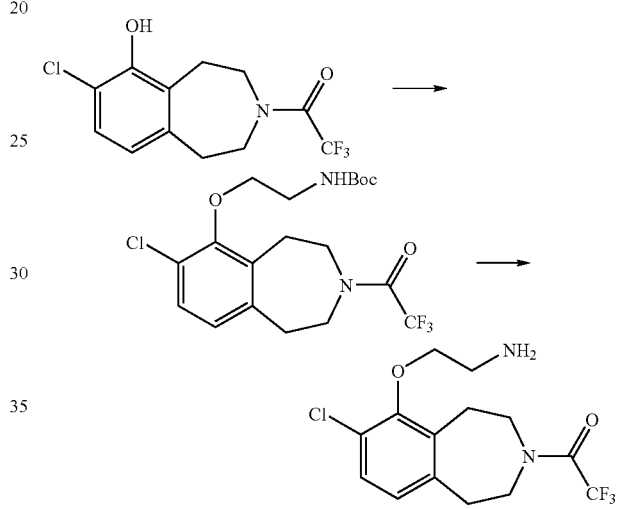

6-(2-tert-Butoxycarbonylamino-ethoxy)-7-chloro-3-(2,2,2-trifluoroacetyl)-2,3,4,5-tetrahydro-1H-benzo[d]azepine: Use a method similar to the General Procedure 4-3, using 7-chloro-6-hydroxy-3-(2,2,2-trifluoroacetyl)-2,3,4,5-tetrahydro-1H-benzo[d]azepine (277 mg, 0.94 mmol) and N-(tert-butoxycarbonyl)ethanolamine (244 mg, 1.51 mmol) to give, after chromatography on silica gel eluting with hexane/EtOAc (1:0 and 3:1), the desired intermediate (392 mg, 95%). MS (ES+) m/z: 337 (M+H–Boc)⁺.

6-(2-Amino-ethoxy)-7-chloro-3-(2,2,2-trifluoroacetyl)-2,3,4,5-tetrahydro-1H-benzo[d]azepine: Dissolve 6-(2-tert-butoxycarbonylamino-ethoxy)-7-chloro-3-(2,2,2-trifluoroacetyl)-2,3,4,5-tetrahydro-1H-benzo[d]azepine (997 mg, 2.28 mmol) in 4M hydrogen chloride in dioxane (15 mL) and stir at ambient temperature for 30 min. Concentrate to obtain the hydrochloride salt. Dissolve the salt in DCM and wash with saturated aqueous NaHCO₃. Extract the basic aqueous layer with DCM. Dry the combined organic extracts over MgSO₄, and concentrate in vacuo to afford the title compound (731 mg, 95%). MS (ES+) m/z: 337 (M+H)⁺.

The compounds of Preparations 13-14 may be prepared essentially as described in Preparation 12 by using 7-chloro-6-hydroxy-3-(2,2,2-trifluoroacetyl)-2,3,4,5-tetrahydro-1H-benzo[d]azepine and the appropriate alcohol. Overall yields and MS (ES+) data are shown in the Table below.

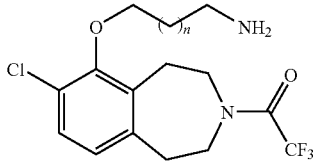

| Prep. | n | Compound | Yield (%) | MS (ES+) m/z |
|---|---|---|---|---|
| 13 | 1 | 6-(3-Amino-propoxy)-7-chloro-3-(2,2,2-trifluoroacetyl)-2,3,4,5-tetrahydro-1H-benzo[d]azepine | 94 | 351 (M + H)+ |
| 14 | 2 | 6-(4-Amino-butoxy)-7-chloro-3-(2,2,2-trifluoroacetyl)-2,3,4,5-tetrahydro-1H-benzo[d]azepine | 89 | 365 (M + H)+ |

EXAMPLE 7

7-Chloro-6-(4-fluorobenzyloxy)-2,3,4,5-tetrahydro-1H-benzo[d]azepine Succinate

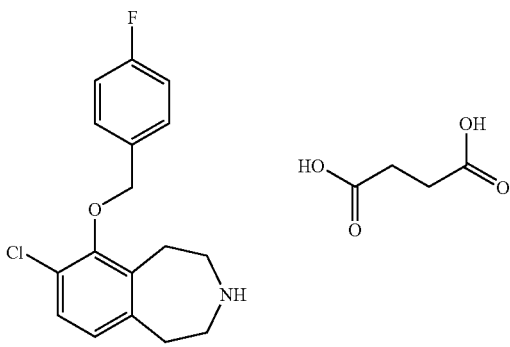

Prepare a slurry of sodium hydride (60% in mineral oil; 99 mg, 2.5 mmol) in DMF (4 mL) and heat to 65° C. Add a solution of 3-tert-butoxycarbonyl-7-chloro-6-hydroxy-2,3,4,5-tetrahydro-1H-benzo[d]azepine (250 mg, 0.84 mmol) in DMF (5 mL) dropwise and stir for 1 h. Add a solution of 4-fluorobenzyl bromide (191 mg, 1.0 mmol) in DMF (1 mL), stir at 65° C. for 1.5 h and cool to ambient temperature. Add water (1 mL) and concentrate the mixture to an oily residue. Partition the residue between EtOAc/hexane (1:1) and water. Dry the organic layer over Na$_2$SO$_4$, filter and concentrate in vacuo. Dissolve the residue in DCM, wash with 2N aqueous NaOH, dry the organic layer over Na$_2$SO$_4$, filter, and concentrate in vacuo. Purify by chromatography on silica gel eluting with hexane/EtOAc (20:1, 10:1 and 7:1) to give 3-tert-butoxycarbonyl-7-chloro-6-(4-fluorobenzyloxy)-2,3,4,5-tetrahydro-1H-benzo[d]azepine as an oil.

Use a method similar to General Procedure 1-5 to deprotect 3-tert-butoxycarbonyl-7-chloro-6-(4-fluorobenzyloxy)-2,3,4,5-tetrahydro-1H-benzo[d]azepine. Purify by SCX chromatography followed by chromatography on silica gel eluting with DCM/2M ammonia in methanol (1:0, 50:1, 20:1, 15:1 and 10:1) to give the free base of the title compound. Use a method similar to the General Procedure 2-1 to give the title compound as a white solid (178 mg, 50%). MS (ES+) m/z: 306 (M+H)+.

EXAMPLE 8

7-Chloro-6-(4-cyanobenzyloxy)-2,3,4,5-tetrahydro-1H-benzo[d]azepine Hydrochloride

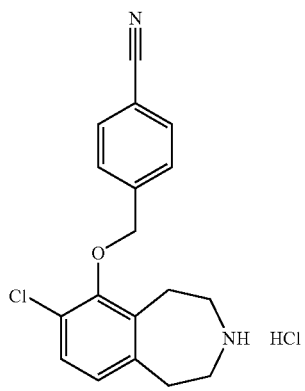

Combine 3-tert-butoxycarbonyl-7-chloro-6-hydroxy-2,3,4,5-tetrahydro-1H-benzo[d]azepine (200 mg, 0.67 mmol), potassium carbonate (111 mg, 0.8 mmol), and 4-cyanobenzyl bromide (263 mg, 1.34 mmol) in DMSO (5 mL) and heat the stirred mixture to 100° C. for 24 h. Cool to ambient temperature and partition the mixture between water and EtOAc/hexane (1:1). Wash the organic layer with brine and dry over Na$_2$SO$_4$, filter and concentrate in vacuo. Purify by chromatography on silica gel eluting with hexane/EtOAc (5:1) to give 3-tert-butoxycarbonyl-7-chloro-6-(4-cyanobenzyloxy)-2,3,4,5-tetrahydro-1H-benzo[d]azepine as an oil.

Use a method similar to the General Procedure 1-5 to deprotect 3-tert-butoxycarbonyl-7-chloro-6-(4-cyanobenzyloxy)-2,3,4,5-tetrahydro-1H-benzo[d]azepine. Purify by SCX chromatography to give the free base of the title compound. Use a method similar to the General Procedure 2-2 to give the title compound as an off-white solid (66 mg, 27%). MS (ES+) z/z: 313 (M+H)+.

EXAMPLE 9

7-Chloro-6-[2-(4-fluorophenyl)-2-oxo-oxy)]-2,3,4,5-tetrahydro-1H-benzo[d]azepine Hydrochloride

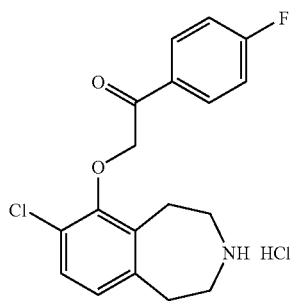

Use a method similar to the General Procedure 4-1, using 7-chloro-6-hydroxy-3-(2,2,2-trifluoroacetyl)-2,3,4,5-tetrahydro-1H-benzo[d]azepine (294 mg, 1.0 mmol) and 2-bromo-4'-fluoroacetophenone (260 mg, 1.2 mmol) to give, after purification by chromatography on silica gel eluting with hexane/EtOAc (7:1), 7-chloro-6-[2-(4-fluorophenyl)-2-oxo-ethoxy)]-3-(2,2,2-trifluoroacetyl)-2,3,4,5-tetrahydro-1H-benzo[d]azepine as a solid (402 mg, 93%). MS (ES+) m/z: 430 (M+H)$^+$.

Use a method similar to the General Procedure 1-1 to deprotect 7-chloro-6-[2-(4 fluorophenyl)-2-oxo-ethoxy)]-3-(2,2,2-trifluoroacetyl)-2,3,4,5-tetrahydro-1H-benzo[d]azepine (402 mg, 0.93 mmol). Purify by chromatography on silica gel eluting with DCM/2M ammonia in methanol (96:4) to give the free base of the title compound (278 mg, 89%). MS (ES+) m/z: 334 (M+H)$^+$. Use a method similar to the General Procedure 2-3 to give the title compound.

EXAMPLE 10

7-Chloro-6-(4-methylsulfamoyl-benzyloxy)-2,3,4,5-tetrahydro-1H-benzo[d]azepine Hydrochloride

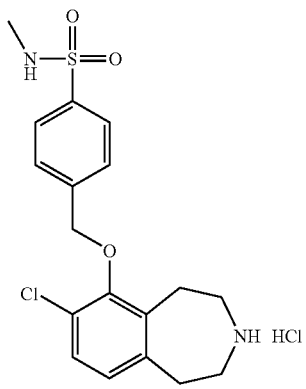

Dissolve under nitrogen 7-chloro-6-hydroxy-3-(2,2,2-trifluoroacetyl)-2,3,4,5-tetrahydro-1H-benzo[d]azepine (200 mg, 0.68 mmol) in acetone (30 mL). Add powdered anhydrous potassium carbonate (276 mg, 2.0 mmol) and powdered potassium iodide (11.3 mg, 0.068 mmol) followed by 4-bromomethyl-N-methyl-benzenesulfonamide (528 mg, 2.0 mmol). Stir the reaction mixture at ambient temperature for 12 h. Concentrate in vacuo, dilute with EtOAc and wash twice with 1N aqueous HCl. Separate the organic layer, dry over Na$_2$SO$_4$ and concentrate in vacuo. Purify by chromatography on silica gel eluting with hexane/EtOAc (1:0 and 4:1) to obtain 7-chloro-6-(4-methylsulfamoyl-benzyloxy)-3-(2,2,2-trifluoroacetyl)-2,3,4,5-tetrahydro-1H-benzo[d]azepine (201 mg, 60%).

Use a method similar to the General Procedure 1-1 to deprotect 7-chloro-6-(4-methylsulfamoyl-benzyloxy)-3-(2,2,2-trifluoroacetyl)-2,3,4,5-tetrahydro-1H-benzo[d]azepine (196 mg, 0.41 mmol). Purify by SCX column to give the free base of the title compound (110 mg, 70%). MS (ES+) m/z: 381 (M+H)$^+$. Use a method similar to the General Procedure 2-2 to obtain the title compound.

Examples 11-12 may be prepared essentially as described in Example 10 by using 7-chloro-6-hydroxy-3-(2,2,2-trifluoroacetyl)-2,3,4,5-tetrahydro-1H-benzo[d]azepine and the appropriate bromide. MS (ES+) data are shown in the Table below.

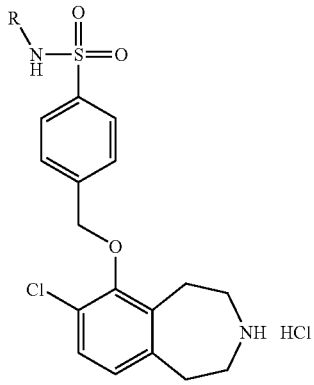

| Ex. | NH—R | Compound | MS (ES+) m/z |
|---|---|---|---|
| 11 | NH—CH$_2$—CH$_3$ | 7-Chloro-6-(4-ethylsulfamoyl-benzyloxy)-2,3,4,5-tetrahydro-1H-benzo[d]azepine Hydrochloride | 395 (M + H)$^+$ |
| 12 | NH—CH$_2$—CH$_2$F | 7-Chloro-6-[4-(2-fluoroethylsulfamoyl)-benzyloxy]-2,3,4,5-tetrahydro-1H-benzo[d]azepine Hydrochloride | 413 (M + H)$^+$ |

EXAMPLE 13

Allen 1

7-Chloro-9-fluoro-6-(4-fluorobenzyloxy)-3-(2,2,2-trifluoroacetyl)-2,3,4,5-tetrahydro-1H-benzo[d]azepine Hydrochloride

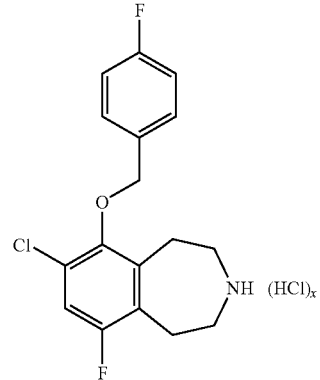

Dissolve 7-chloro-9-fluoro-6-hydroxy-3-(2,2,2-trifluoroacetyl)-2,3,4,5-tetrahydro-1H-benzo[d]azepine (0.25 g, 0.8 mmol) in DMF (8 mL), add potassium carbonate (0.56 g, 4.0 mmol) and 4-fluorobenzyl bromide (0.46 mL, 2.4 mmol). After 14 h at 90° C., dilute with ether and wash with brine. Dry the organic layer over Na$_2$SO$_4$ and evaporate onto silica gel. Purify by chromatography on silica gel eluting with EtOAc/hexane (0:1 to 1:0) to obtain 7-chloro-9-fluoro-6-(4-fluorobenzyloxy)-3-(2,2,2-trifluoroacetyl)-2,3,4,5-tetrahydro-1H-benzo[d]azepine.

Use a method similar to the General Procedure 1-1, using 7-chloro-9-fluoro-6-(4-fluorobenzyloxy)-3-(2,2,2-trifluoroacetyl)-2,3,4,5-tetrahydro-1H-benzo[d]azepine, to give the free base of the title compound. Use a method similar to the General Procedure 2-2 to obtain the title compound (275 mg, 95%). HRMS calc'd for C$_{17}$H$_{17}$NOF$_2$Cl 324.0902, found 324.0957.

EXAMPLE 14

7-Chloro-6-(pyridin-2-ylmethoxy)-2,3,4,5-tetrahydro-1H-benzo[d]azepine Succinate

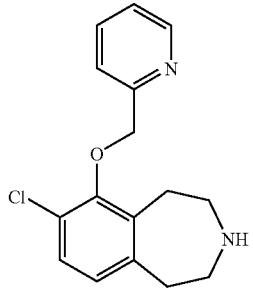
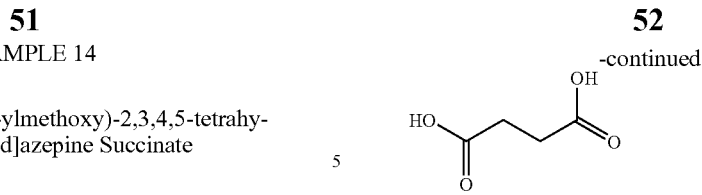

Prepare a slurry of sodium hydride (60% in mineral oil, 168 mg, 4.2 mmol) in DMF (4 mL) and heat to 65° C. Add dropwise a solution of 3-tert-butoxycarbonyl-7-chloro-6-hydroxy-2,3,4,5-tetrahydro-1H-benzo[d]azepine (250 mg, 0.84 mmol) in DMF (5 mL) and stir for 1 h. Add a solution of 2-(bromomethyl)-pyridine hydrobromide (256 mg, 1 mmol) in DMF (1 mL), stir at 65° C. for 0.5 h and cool to ambient temperature. Add water (1 mL) and concentrate the reaction mixture to an oily residue. Partition the residue between EtOAc/hexane (1:1) and water. Dry the organic layer over Na$_2$SO$_4$, filter and concentrate. Purify by chromatography on silica gel eluting with hexane/EtOAc (10:1, 5:1 and 3:1) to give 3-tert-butoxycarbonyl-7-chloro-6-(pyridin-2-ylmethoxy)-2,3,4,5-tetrahydro-1H-benzo[d]azepine as an oil.

Use a method similar to the General Procedure 1-5 to deprotect 3-tert-butoxycarbonyl-7-chloro-6-(pyridin-2-ylmethoxy)-2,3,4,5-tetrahydro-1H-benzo[d]azepine. Purify by SCX chromatography to give the free base of the title compound. Use a method similar to the General Procedure 2-1 to give the title compound as a white solid (228 mg, 67%). MS (ES+) m/z: 289 (M+H)$^+$.

EXAMPLE 15

7-Chloro-6-(pyridin-3-ylmethoxy)-2,3,4,5-tetrahydro-1H-benzo[d]azepine Disuccinate

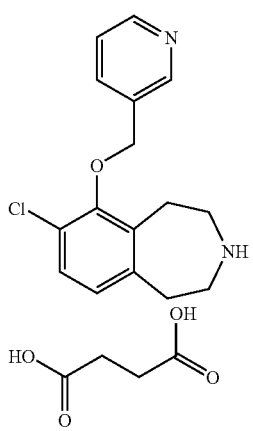

Use a method similar to the Example 14, using 3-tert-butoxycarbonyl-7-chloro-6-hydroxy-2,3,4,5-tetrahydro-1H-benzo[d]azepine (250 mg, 0.84 mmol) and 3-(bromomethyl)-pyridine hydrobromide (256 mg, 1 mmol) to give the free base of the title compound. Use a method similar to the General Procedure 2-1 with two equivalents of succinic acid to give the title compound as a white solid (354 mg, 80%). MS (ES+) m/z: 289 (M+H)$^+$.

EXAMPLE 16

7-Chloro-6-(thiazol-2-ylmethoxy)-2,3,4,5-tetrahydro-1H-benzo[d]azepine Hydrochloride

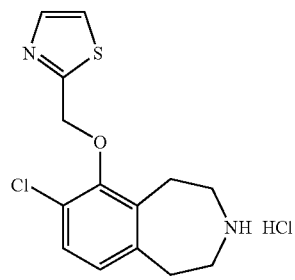

Use a method similar to the General Procedure 4-2, using 7-chloro-6-hydroxy-3-(2,2,2-trifluoroacetyl)-2,3,4,5-tetrahydro-1H-benzo[d]azepine and thiazol-2-yl-methanol (86.2 mg, 0.75 mmol) to give, after chromatography on silica gel eluting with hexane/EtOAc (9:1 and 7:3), 7-chloro-6-(thiazol-2-ylmethoxy)-3-(2,2,2-trifluoroacetyl)-2,3,4,5-tetrahydro-1H-benzo[d]azepine (163 mg, 61%). MS (ES+) m/z 391 (M+H)$^+$.

Use a method similar to the General Procedure 1-1 to deprotect 7-chloro-6-(thiazol-2-ylmethoxy)-3-(2,2,2-trifluoroacetyl)-2,3,4,5-tetrahydro-1H-benzo[d]azepine. Purify by chromatography on silica gel eluting with DCM/2M ammonia in methanol (94:6) to obtain the free base of the title compound (99 mg, 81%). MS (ES+) m/z: 295 (M+H)$^+$. Use a method similar to the General Procedure 2-2 to give the title compound.

EXAMPLE 17

7-Chloro-6-(thiazol-5-ylmethoxy)-2,3,4,5-tetrahydro-1H-benzo[d]azepine Hydrochloride

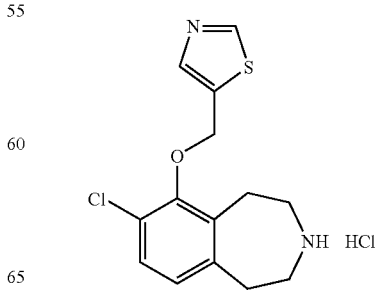

Use a method similar to the General Procedure 4-2, using 7-chloro-6-hydroxy-3-(2,2,2-trifluoroacetyl)-2,3,4,5-tetrahydro-1H-benzo[d]azepine (294 mg, 1.0 mmol) and 5-hydroxymethylthiazole (127 mg, 1.1 mmol) to give, after chromatography on silica gel eluting with EtOAc/hexane (1:3), 7-chloro-6-(thiazol-5-ylmethoxy)-3-(2,2,2-trifluoroacetyl)-2,3,4,5-tetrahydro-1H-benzo[d]azepine as an oil (350 mg, 89%). MS (ES+) m/z: 391 (M+H)⁺.

Use a method similar to the General Procedure 1-1 to deprotect 7-chloro-6-(thiazol-5-ylmethoxy)-3-(2,2,2-trifluoroacetyl)-2,3,4,5-tetrahydro-1H-benzo[d]azepine (350 mg, 0.90 mmol). Purify by chromatography on silica gel eluting with DCM/2M ammonia in methanol (95:5) to give the free base of the title compound (203 mg, 76%). MS (ES+) m/z: 295 (M+H)⁺. Use a method similar to the General Procedure 2-2 to give the title compound.

Examples 18-19 may be prepared essentially as described in Example 17 by using 7-chloro-6-hydroxy-3-(2,2,2-trifluoroacetyl)-2,3,4,5-tetrahydro-1H-benzo[d]azepine and the appropriate alcohol. Overall yields and MS (ES+) data are shown in the Table below.

| Ex. | O—R | Compound | Yield (%) | MS (ES+) m/z |
|---|---|---|---|---|
| 18 | (5-methylisoxazol-3-ylmethoxy) | 7-Chloro-6-(5-methyl-isoxazol-3-ylmethoxy)-2,3,4,5-tetrahydro-1H-benzo[d]azepine Hydrochloride | 47 | 293 (M + H)⁺ |
| 19 | (1-methyl-1H-pyrazol-3-ylmethoxy) | 7-Chloro-6-(1-methyl-1H-pyrazol-3-ylmethoxy)-2,3,4,5-tetrahydro-1H-benzo[d]azepine Hydrochloride | 39 | 292 (M + H)⁺ |

EXAMPLE 20

7-Chloro-6-(3-methylthio-propoxy)-2,3,4,5-tetrahydro-1H-benzo[d]azepine Succinate

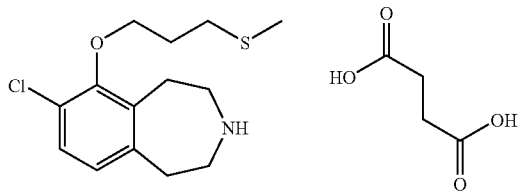

Use a method similar to the General Procedure 4-2, using 7-chloro-6-hydroxy-3-(2,2,2-trifluoroacetyl)-2,3,4,5-tetrahydro-1H-benzo[d]azepine and 3-(methylthio)-1-propanol (191 mg, 1.8 mmol) to give, after chromatography on silica gel eluting with EtOAc/hexane (1:8), 7-chloro-6-(3-methylthio-propoxy)-3-(2,2,2-trifluoroacetyl)-2,3,4,5-tetrahydro-1H-benzo[d]azepine as an oil (65 mg, 14%).

Use a method similar to the General Procedure 1-1 to deprotect 7-chloro-6-(3-methylthio-propoxy)-3-(2,2,2-trifluoroacetyl)-2,3,4,5-tetrahydro-1H-benzo[d]azepine (65 mg, 0.17 mmol). Purify by chromatography on silica gel eluting with DCM/2M ammonia in methanol (94:6) to give the free base of the title compound (25 mg, 51%). MS (ES+) m/z: 286 (M+1)⁺. Use a method similar to the General Procedure 2-1 to give the title compound.

EXAMPLE 21

7-Chloro-6-(4-methylthio-butoxy)-2,3,4,5-tetrahydro-1H-benzo[d]azepine Succinate

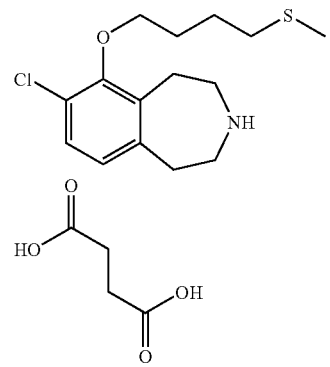

Use a method similar to the Example 20, using 7-chloro-6-hydroxy-3-(2,2,2-trifluoroacetyl)-2,3,4,5-tetrahydro-1H-benzo[d]azepine and 4-(methylthio)-1-butanol to give the title compound. MS (ES+) m/z: 300 (M+1)⁺.

EXAMPLE 22

7-Chloro-6-(3-pyridin-2-yl-propoxy)-2,3,4,5-tetrahydro-1H-benzo[d]azepine Hydrochloride

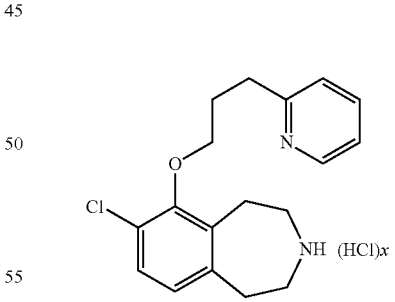

Use a method similar to the General Procedure 4-3, using 7-chloro-6-hydroxy-3-(2,2,2-trifluoroacetyl)-2,3,4,5-tetrahydro-1H-benzo[d]azepine (50 mg, 0.17 mmol) and 3-(2-pyridyl)-1-propanol (35 mg, 0.255 mmol) to give, after reverse phase HPLC (10-95% of solvent B in 12.8 min, 25 mL/min; solvent A: water, 0.1% trifluoroacetic acid; solvent B: acetonitrile, 0.1% trifluoroacetic acid; column: YMC SH-341-5, S-5□m, 12 nm, 100×20 mm), 7-chloro-6-(3-pyridin-2-yl-propoxy)-3-(2,2,2-trifluoroacetyl)-2,3,4,5-tetrahydro-1H-benzo[d]azepine.

Use a method similar to the General Procedure 1-1, using 7-chloro-6-(3-pyridin-2-yl-propoxy)-3-(2,2,2-trifluoro-acetyl)-2,3,4,5-tetrahydro-1H-benzo[d]azepine to give the free base of the title compound. Use a method similar to the General Procedure 2-2 to give the title compound as a solid (26 mg, 39%). MS (ES+) m/z: 317 (M+H)$^+$.

Examples 23-26 may be prepared essentially as described in Example 22 by using 7-chloro-6-hydroxy-3-(2,2,2-trifluoroacetyl)-2,3,4,5-tetrahydro-1H-benzo[d]azepine and the appropriate alcohol. Overall yields and MS (ES+) data are shown in the Table below.

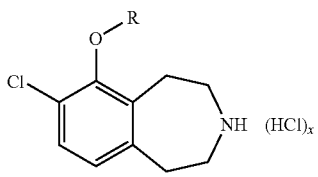

| Ex. | O—R | Compound | Yield (%) | MS (ES+) m/z |
|---|---|---|---|---|
| 23 | | 7-Chloro-6-[2-(4-methyl-thiazol-5-yl)-ethoxy]-2,3,4,5-tetrahydro-1H-benzo[d]azepine Hydrochloride | 83 | 323 (M + H)$^+$ |
| 24 | | 7-Chloro-6-(2-pyridin-2-yl-ethoxy)-2,3,4,5-tetrahydro-1H-benzo[d]azepine Hydrochloride | 83 | 303 (M + H)$^+$ |
| 25 | | 7-Chloro-6-(3-pyridin-3-yl-propoxy)-2,3,4,5-tetrahydro-1H-benzo[d]azepine Hydrochloride | 83 | 317 (M + H)$^+$ |
| 26 | | 6-[3-(1H-Benzimidazol-2-yl)-propoxy]-7-chloro-2,3,4,5-tetrahydro-1H-benzo[d]azepine Hydrochloride | 8 | 356 (M + H)$^+$ |

EXAMPLE 27

6-(2-Benzoylamino-ethoxy)-7-chloro-2,3,4,5-tetrahydro-1H-benzo[d]azepine Hydrochloride

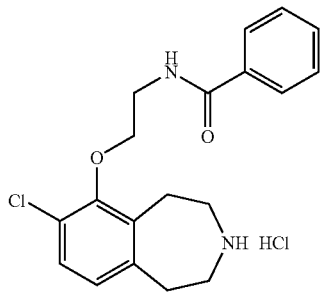

Combine benzoyl chloride (19.3 mg, 0.137 mmol), PS-morpholine (109 mg, 0.272 mmol), 6-(2-amino-ethoxy)-7-chloro-3-(2,2,2-trifluoroacetyl)-2,3,4,5-tetrahydro-1H-benzo[d]azepine (46 mg, 0.137 mmol) in DCM (1.5 mL) and stir at ambient temperature for 16 h. Filter the resin, wash with DCM and concentrate in vacuo. Purify by reverse phase HPLC (10-95% of solvent B in 12.8 min, 25 mL/min; solvent A: water, 0.1% trifluoroacetic acid; solvent B: acetonitrile, 0.1% trifluoroacetic acid; column: YMC SH-341-5, S-5 μm, 12 nm, 100×20 mm) to give 6-(2-benzoylamino-ethoxy)-7-chloro-3-(2,2,2-trifluoroacetyl)-2,3,4,5-tetrahydro-1H-benzo[d]azepine.

Use a method similar to the General Procedure 1-1, using 6-(2-benzoylamino-ethoxy)-7-chloro-3-(2,2,2-trifluoroacetyl)-2,3,4,5-tetrahydro-1H-benzo[d]azepine to give the free base of the title compound. Use a method similar to the General Procedure 2-2 to give the title compound as a solid (51 mg, 98%). MS (ES+) m/z: 345 (M+H)$^+$.

Examples 28-40 may be prepared essentially as described in Example 27, using 6-(2-amino-ethoxy)-7-chloro-3-(2,2,2-trifluoroacetyl)-2,3,4,5-tetrahydro-1H-benzo[d]azepine or 6-(3-amino-propoxy)-7-chloro-3-(2,2,2-trifluoroacetyl)-2,3,4,5-tetrahydro-1H-benzo[d]azepine or 6-(4-amino-butoxy)-7-chloro-3-(2,2,2-trifluoroacetyl)-2,3,4,5-tetrahydro-1H-benzo[d]azepine and the appropriate acyl chloride. Overall yields and MS (ES+) data are shown in the Table below.

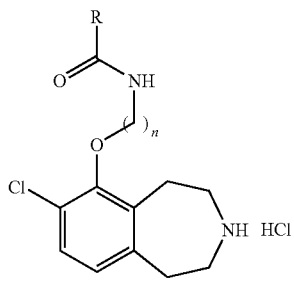

| Ex. | NH—CO—R | n | Compound | Yield (%) | MS (ES+) m/z |
|---|---|---|---|---|---|
| 28 | (4-Cl-C6H4)C(=O)NH— | 2 | 7-Chloro-6-[2-(4-chlorobenzoylamino)-ethoxy]-2,3,4,5-tetrahydro-1H-benzo[d]azepine Hydrochloride | 46 | 380 (M + H)+ |
| 29 | (3-Cl-C6H4)C(=O)NH— | 2 | 7-Chloro-6-[2-(3-chlorobenzoylamino)-ethoxy]-2,3,4,5-tetrahydro-1H-benzo[d]azepine Hydrochloride | 63 | 380 (M + H)+ |
| 30 | (2-Cl-C6H4)C(=O)NH— | 2 | 7-Chloro-6-[2-(2-chlorobenzoylamino)-ethoxy]-2,3,4,5-tetrahydro-1H-benzo[d]azepine Hydrochloride | 18 | 380 (M + H)+ |
| 31 | (4-F-C6H4)C(=O)NH— | 2 | 7-Chloro-6-[2-(4-fluorobenzoylamino)-ethoxy]-2,3,4,5-tetrahydro-1H-benzo[d]azepine Hydrochloride | 18 | 363 (M + H)+ |
| 32 | (pyridin-4-yl)C(=O)NH— | 2 | 7-Chloro-6-{2-[(pyridine-4-carbonyl)-amino]-ethoxy}-2,3,4,5-tetrahydro-1H-benzo[d]azepine Hydrochloride | 4 | 346 (M + H)+ |
| 33 | (cyclopropyl)C(=O)NH— | 2 | 7-Chloro-6-[2-(cyclopropanecarbonyl-amino)-ethoxy]-2,3,4,5-tetrahydro-1H-benzo[d]azepine Hydrochloride | 47 | 309 (M + H)+ |
| 34 | (pyrrolidin-1-yl)C(=O)NH— | 2 | 7-Chloro-6-{2-[(pyrrolidine-1-carbonyl)-amino]-ethoxy}-2,3,4,5-tetrahydro-1H-benzo[d]azepine Hydrochloride | 6 | 338 (M + H)+ |
| 35 | (cyclohexyl)C(=O)NH— | 2 | 7-Chloro-6-[2-(cyclohexanecarbonyl-amino)-ethoxy]-2,3,4,5-tetrahydro-1H-benzo[d]azepine Hydrochloride | 40 | 351 (M + H)+ |

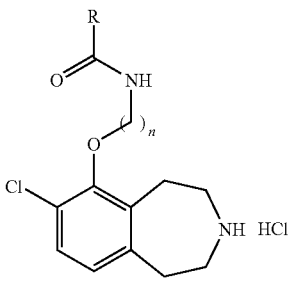

| Ex. | NH—CO—R | n | Compound | Yield (%) | MS (ES+) m/z |
|---|---|---|---|---|---|
| 36 | (ethyl carbamate structure) | 3 | 7-Chloro-6-(3-ethoxycarbonylamino-propoxy)-2,3,4,5-tetrahydro-1H-benzo[d]azepine Hydrochloride | 63 | 327 $(M + H)^+$ |
| 37 | (benzamide structure) | 3 | 6-(3-Benzoylamino-propoxy)-7-chloro-2,3,4,5-tetrahydro-1H-benzo[d]azepine Hydrochloride | 72 | 359 $(M + H)^+$ |
| 38 | (isonicotinamide structure) | 3 | 7-Chloro-6-{3-[(pyridine-4-carbonyl)-amino]-propoxy}-2,3,4,5-tetrahydro-1H-benzo[d]azepine Hydrochloride | 12 | 360 $(M + H)^+$ |
| 39 | (ethyl carbamate structure) | 4 | 7-Chloro-6-(4-ethoxycarbonylamino-butoxy)-2,3,4,5-tetrahydro-1H-benzo[d]azepine Hydrochloride | 49 | 341 $(M + H)^+$ |
| 40 | (benzamide structure) | 4 | 6-(4-Benzoylamino-butoxy)-7-chloro-2,3,4,5-tetrahydro-1H-benzo[d]azepine Hydrochloride | 56 | 373 $(M + H)^+$ |

EXAMPLE 41

7-Chloro-6-[2-(2-fluorobenzoylamino)-ethoxy]-2,3,4,5-tetrahydro-1H-benzo[d]azepine Hydrochloride

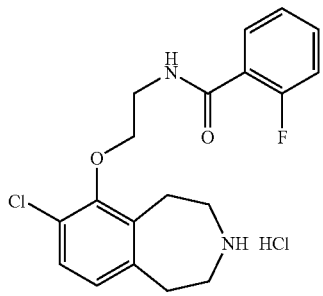

Dissolve 6-(2-amino-ethoxy)-7-chloro-3-(2,2,2-trifluoro-acetyl)-2,3,4,5-tetrahydro-1H-benzo[d]azepine (100 mg, 0.297 mmol) in DCM (5 mL). Add 2-fluorobenzoyl chloride (39 µL, 0.326 mmol), triethylamine (62 µL, 0.445 mmol) and stir at ambient temperature for 72 h under nitrogen atmosphere. Dilute with DCM, add 1M aqueous HCl and extract the aqueous phase with DCM. Dry the combined organic extracts over MgSO$_4$ and concentrate in vacuo. Purify by chromatography on silica gel eluting with hexane/EtOAc (7:3 and 2:1) to give 7-chloro-6-[2-(2-fluorobenzoylamino)-ethoxy]-3-(2,2,2-trifluoroacetyl)-2,3,4,5-tetrahydro-1H-benzo[d]azepine (111 mg, 820%).

Use a method similar to the General Procedure 1-1, using 7-chloro-6-[2-(2-fluorobenzoylamino)-ethoxy]-3-(2,2,2-trifluoroacetyl)-2,3,4,5-tetrahydro-1H-benzo[d]azepine to give the free base of the title compound. Use a method similar to the General Procedure 2-2 to give the title compound as a solid (12 mg, 95%). MS (ES+) m/z: 363 $(M+H)^+$.

EXAMPLE 42

7-Chloro-6-{2-[(pyridine-2-carbonyl)-amino]-ethoxy}-2,3,4,5-tetrahydro-1H-benzo[d]azepine Hydrochloride

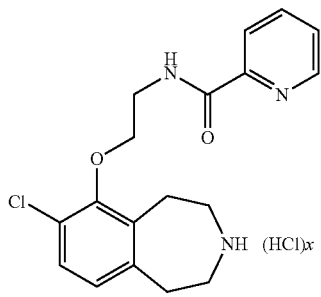

Combine picolinic acid (40 mg, 0.327 mmol), EDC (57 mg, 0.297 mmol) and HOBT (40 mg, 0.297 mmol) in DCM (3 mL). Stir for 10 min at ambient temperature. Add 6-(2-amino-ethoxy)-7-chloro-3-(2,2,2-trifluoroacetyl)-2,3,4,5-tetrahydro-1H-benzo[d]azepine (100 mg, 0.297 mmol). Stir for 16 h at ambient temperature. Dilute with DCM, add water and extract the aqueous layer with DCM. Wash the combined organic extracts with 1M aqueous NaOH and brine. Dry the organic layer over MgSO$_4$ and concentrate in vacuo. Purify by chromatography on silica gel eluting with hexane/EtOAc (3:2) to give 7-chloro-6-{2-[(pyridine-2-carbonyl)-amino]-ethoxy}-3-(2,2,2-trifluoroacetyl)-2,3,4,5-tetrahydro-1H-benzo[d]azepine (94 mg, 74%).

Use a method similar to the General Procedure 1-1, using 7-chloro-6-{2-[(pyridine-2-carbonyl)-amino]-ethoxy}-3-(2,2,2-trifluoroacetyl)-2,3,4,5-tetrahydro-1H-benzo[d]azepine to give the free base of the title compound. Use a method similar to the General Procedure 2-2 to give the title compound as a solid (81 mg, 72%). MS (ES+) m/z: 346 (M+H)$^+$.

EXAMPLE 43

7-Chloro-6-{2-[(pyridine-3-carbonyl)-amino]-ethoxy}-2,3,4,5-tetrahydro-1H-benzo[d]azepine Hydrochloride

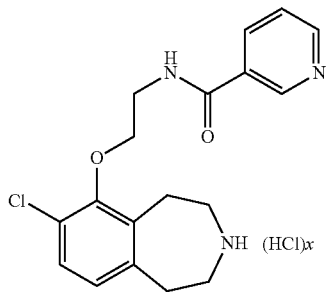

Use a method similar to Example 42, using nicotinic acid (40 mg, 0.327 mmol) and 6-(2-amino-ethoxy)-7-chloro-3-(2,2,2-trifluoroacetyl)-2,3,4,5-tetrahydro-1H-benzo[d]azepine (100 mg, 0.297 mmol) to give the title compound as a solid (105 mg, 93%). MS (ES+) m/z: 346 (M+H)$^+$.

EXAMPLE 44

7-Chloro-6-[2-(3-phenyl-ureido)-ethoxy]-2,3,4,5-tetrahydro-1H-benzo[d]azepine Hydrochloride

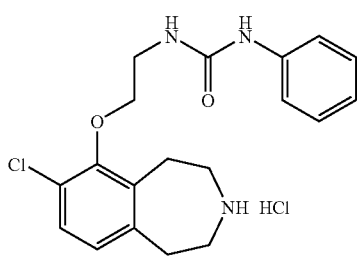

Combine phenyl isocyanate (16.3 mg, 0.137 mmol), 6-(2-amino-ethoxy)-7-chloro-3-(2,2,2-trifluoroacetyl)-2,3,4,5-tetrahydro-1H-benzo[d]azepine (46 mg, 0.137 mmol) in DCM (1.5 mL) and stir at ambient temperature for 16 h. Concentrate in vacuo. Purify by reverse phase HPLC (10-95% of solvent B in 12.8 min, 25 mL/min; solvent A: water, 0.1% trifluoroacetic acid; solvent B: acetonitrile, 0.1% trifluoroacetic acid; column: YMC SH-341-5, S-5 μm, 12 nm, 100×20 mm) to give 7-chloro-6-[2-(3-phenyl-ureido)-ethoxy]-3-(2,2,2-trifluoroacetyl)-2,3,4,5-tetrahydro-1H-benzo[d]azepine.

Use a method similar to the General Procedure 1-1, using 7-chloro-6-[2-(3-phenyl-ureido)-ethoxy]-3-(2,2,2-trifluoroacetyl)-2,3,4,5-tetrahydro-1H-benzo[d]azepine to give the free base of the title compound. Use a method similar to the General Procedure 2-2 to give the title compound as a solid (8 mg, 15%). MS (ES+) m/z: 360 (M+H)$^+$.

Examples 45-46 may be prepared essentially as described in Example 44 by using phenyl isocyanate and the appropriate 6-(3-amino-propoxy)-7-chloro-3-(2,2,2-trifluoroacetyl)-2,3,4,5-tetrahydro-1H-benzo[d]azepine or 6-(4-amino-butoxy)-7-chloro-3-(2,2,2-trifluoroacetyl)-2,3,4,5-tetrahydro-1H-benzo[d]azepine. Overall yields and MS (ES+) data are shown in the Table below.

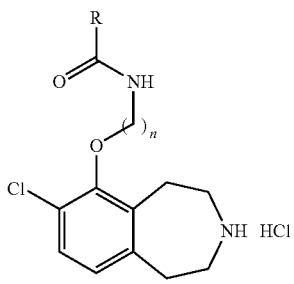

| Ex. | NH—CO—R | n | Compound | Yield (%) | MS (ES+) m/z |
|---|---|---|---|---|---|
| 45 | NH-C(O)-NH-phenyl | 3 | 7-Chloro-6-[3-(3-phenyl-ureido)-propoxy]-2,3,4,5-tetrahydro-1H-benzo[d]azepine Hydrochloride | 36 | 374 (M + H)+ |
| 46 | NH-C(O)-NH-phenyl | 4 | 7-Chloro-6-[4-(3-phenyl-ureido)-butoxy]-2,3,4,5-tetrahydro-1H-benzo[d]azepine Hydrochloride | 28 | 388 (M + H)+ |

EXAMPLE 48

7-Chloro-6-(3-methoxycarbonyl-propyloxy)-2,3,4,5-tetrahydro-1H-benzo[d]azepine Succinate

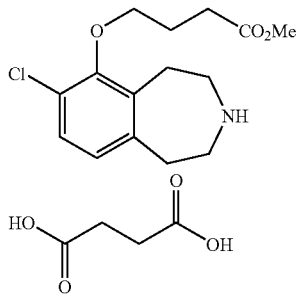

Add methyl 4-bromobutyrate (1.9 mL, 10.4 mmol) to a mixture of 3-tert-butoxycarbonyl-7-chloro-6-hydroxy-2,3,4,5-tetrahydro-benzo[d]azepine (310 mg, 1.0 mmol), DBU (0.23 mL, 1.6 mmol) and DMF (10 mL) at ambient temperature under nitrogen. Stir the reaction mixture for 16 h. Dilute with hexane/EtOAc (1:1, 60 mL), wash the mixture with 10% aqueous NaCl (4×25 mL), dry the organic layer over $Na_2SO_4$ and concentrate in vacuo. Purify by chromatography on silica gel eluting with hexane/EtOAc (19:1 to 2:3) to obtain 3-tert-butoxycarbonyl-7-chloro-6-(3-methoxycarbonyl-propyloxy)-2,3,4,5-tetrahydro-1H-benzo[d]azepine (303 mg, 73%). MS (ES+) m/z: 398 (+H)+.

Use a method similar to the General Procedure 1-5 to deprotect 3-tert-butoxycarbonyl-7-chloro-6-(3-methoxycarbonyl-propyloxy)-2,3,4,5-tetrahydro-1H-benzo[d]azepine (295 mg, 0.74 mmol). Purify by SCX chromatography followed by chromatography on silica gel eluting with DCM/2M ammonia in methanol (99:1 to 90:10) to give the free base of the title compound. Use a method similar to the General Procedure 2-1 to give the title compound (160 mg, 52%). MS (ES+) m/z: 298 (M+H)+.

General Procedure 5-1

Dissolve the appropriately substituted 3-(2,2,2-trifluoro-acetyl)-6-trifluoromethane-sulfonyloxy-2,3,4,5-tetrahydro-1H-benzo[d]azepine-(1 equiv.), palladium(II) acetate (0.1-0.4 equiv.), BINAP (0.2-0.8 equiv.; BINAP/catalyst ratio 2:1) and cesium carbonate (1.4-3.0 equiv.) in toluene (0.2-0.05 M solution). Add the amine (1-3 equiv.), degas the mixture with vacuum/nitrogen or argon purge and heat at 80-110° C. for 4-16 h. Cool the mixture to ambient temperature, dilute with EtOAc, filter through a pad of silica gel or through Celite® washing with EtOAc or ether, and evaporate the solvent to obtain the crude mixture. Alternatively, partition the reaction mixture between brine or saturated aqueous $NaHCO_3$ and EtOAc, ether or DCM, dry the organic layer over $Na_2SO_4$, and concentrate to obtain the crude mixture. Purify the crude mixture by chromatography on silica gel eluting with hexane/EtOAc mixtures and further SCX chromatography if needed.

General Procedure 5-2

Dissolve the appropriately substituted 3-(2,2,2-trifluoro-acetyl)-6-trifluoromethanesulfonyloxy-2,3,4,5-tetrahydro-1H-benzo[d]azepine (1 equiv.), tris(dibenzylideneacetone)dipalladium(0) (0.1-0.5 equiv.), BINAP (0.2-1.0 equiv.; BINAP/catalyst ratio 2:1) and cesium carbonate (1.4 equiv.) in toluene (0.05-0.5 M solution). Degas under vacuum and fill three times with nitrogen. Add the appropriately substituted amine (1.0-5.0 equiv.) and heat the mixture to 80-100° C. for 2-16 h in a sealed flask under a nitrogen atmosphere. Cool the reaction flask to ambient temperature, dilute the mixture with EtOAc or DCM, filter through Celite® and concentrate in vacuo. Purify by chromatography on silica gel eluting with hexane/EtOAc mixtures and further SCX chromatography if needed.

General Procedure 5-3

Add the appropriately substituted 3-(2,2,2-trifluoroacetyl)-6-trifluoromethanesulfonyloxy-2,3,4,5-tetrahydro-1H-benzo[d]azepine (1 equiv.), the appropriate amine (1.2-3.0 equiv.), palladium(II) acetate (0.2-0.4 equiv.), tris(dibenzylideneacetone)dipalladium(0) (0.1-0.2 equiv.), BINAP (0.6-1.2 equiv.; BINAP/catalysts ratio 2:1), cesium carbonate (2-2.5 equiv.) and toluene or 1,4-dioxane (0.05-0.2 M solution) to a flask, degas and fill three times with nitrogen. Heat the mixture at 80-100° C. for 10-16 h. Dilute the mixture with EtOAc, wash with saturated aqueous NaHCO$_3$ and brine, dry over Na$_2$SO$_4$, filter and concentrate in vacuo to give the crude mixture. Alternatively remove the volatiles from the reaction mixture to give directly the crude mixture, or filter the reaction mixture through Celite® and concentrate in vacuo. Purify by chromatography on silica gel eluting with hexane/EtOAc mixtures and further SCX chromatography if needed.

General Procedure 5-4

Combine 6-amino-7-chloro-3-(2,2,2-trifluoroacetyl)-2,3,4,5-tetrahydro-1H-benzo[d]azepine, the appropriate bromide (1.0-2.0 equiv.), potassium or cesium carbonate (1.0-2.0 equiv.) and toluene, DMF or acetonitrile in a sealed tube and heat at 50-150° C. for 3-72 h. Cool to ambient temperature and evaporate the solvent in vacuo to obtain the crude mixture. Alternatively, partition the reaction mixture between diethyl ether/brine (1:1), dry the organic layer over anhydrous Na$_2$SO$_4$ and concentrate to obtain the crude mixture. Purify by chromatography on silica gel eluting with hexane/EtOAc (1:0, 9:1, 4:1, 7:3 and 3:2).

General Procedure 6-1

Dissolve 4-(tert-butoxycarbonylamino-methyl)-benzoic acid (1 equiv.), HATU (1 equiv.), DIEA (2 equiv.) and the appropriately substituted amine (1 equiv.) in DCM or DCM/DMF and stir at ambient temperature for 4-16 h. Concentrate in vacuo, dissolve the residue in DCM and wash successively with saturated aqueous NaHCO$_3$, 1N aqueous HCl, water, brine, and dry over Na$_2$SO$_4$. Filter and concentrate the solution and use the material without further purification. Deprotect the residue using the General Procedure 1-5 and purify by SCX chromatography.

General Procedure 6-2

Dissolve 4-(tert-butoxycarbonylamino-methyl)-benzoic acid or 5-(tert-butoxycarbonylamino-methyl)-pyridine-2-carboxylic acid lithium salt (1 equiv.), HATU (1 equiv.), DIEA (2 equiv.) and the appropriately substituted amine (1 equiv.) in DCM or DCM/DMF and stir at ambient temperature for 4-16 h. Concentrate in vacuo, dissolve the residue in DCM and wash successively with saturated aqueous NaHCO$_3$, water, brine, and dry over Na$_2$SO$_4$. Filter and concentrate the solution and use the material without further purification. Deprotect the residue using the General Procedure 1-5 and purify by SCX chromatography.

General Procedure 6-3

Dissolve the appropriately substituted acetophenone (1.0-1.2 equiv.) in THF, add titanium(IV) ethoxide (33-35% TiO$_2$, 2.0 equiv.) and the corresponding (R)-2-methyl-2-propanesulfinamide or (S)-2-methyl-2-propanesulfinamide (1.0 equiv.). Heat the mixture to 40-60° C. for 2-16 h under a nitrogen atmosphere. Cool the reaction to −78° C., then add the cold mixture over 3-10 min to a slurry of THF/NaBH$_4$ (2-4 M) at −78° C. Allow the mixture to warm up to ambient temperature over 2-16 h. Pour the mixture into brine, filter the resulting slurry through Celite® and wash thoroughly with EtOAc. Concentrate in vacuo. Dilute the oil with EtOAc, wash with brine and extract the aqueous phase with EtOAc. Dry the combined organic extracts over Na$_2$SO$_4$ and concentrate in vacuo. Purify the crude sulfinamide on silica gel eluting with hexane/EtOAc mixtures to obtain the major diastereomer. Dissolve the major diastereomer in excess of 4M hydrogen chloride in dioxane, stir the mixture for 1 h and concentrate in vacuo to a solid. Slurry the solid in diethyl ether, then filter in vacuo to obtain the hydrochloride salt of the desired amine. The free base of the amine is prepared either via SCX chromatography or by basic extraction.

General Procedure 6-4

Add the appropriately substituted benzonitrile portion wise to a flask containing a slurry of lithium aluminum hydride (3.0-6.0 equiv.) in diethyl ether (0.1-0.3 M solution) under a nitrogen atmosphere. Stir the mixture for 1 h and quench slowly with water (0.5-2.0 mL), followed by 5N aqueous NaOH (0.5-2.0 mL). Filter the slurry through Celite® and wash the cake with diethyl ether. Concentrate in vacuo to obtain the desired amine. If additional purification is needed, dissolve the amine in ether and add an excess of 2M hydrogen chloride in ether. Filter to obtain the desired amine as the hydrochloride salt. Prepare the free base by using SCX chromatography or by dissolving the hydrochloride salt in an aqueous solution of cesium carbonate (1.0-5.0 equiv.) or saturated aqueous NaHCO$_3$ (1.0-5.0 equiv.). Extract the mixture with DCM or toluene, dry over Na$_2$SO$_4$ and concentrate in vacuo to obtain the amine.

General Procedure 6-5

Add BH$_3$-T complex (1-3 equiv., 1M solution in THF) dropwise to a solution of appropriately substituted benzonitrile in anhydrous THF at room temperature then stir overnight. Alternatively the reaction can be heated at reflux overnight Add either methanol or aqueous HCl (3 equiv.) cautiously at room temperature and stir vigorously until gaseous evolution stops. Concentrate in vacuo, basify and then extract into EtOAc. Wash the organic phase with brine, dry over MgSO$_4$ and concentrate in vacuo. Purify by SCX chromatography eluting with methanol followed by a solution of ammonia in methanol (3-7 M) to give the desired benzylamine.

Preparation 15

7-Cyano-3-(2,2,2-trifluoroacetyl)-6-trifluoromethanesulfonyloxy-2,3,4,5-tetrahydro-1H-benzo[d]azepine

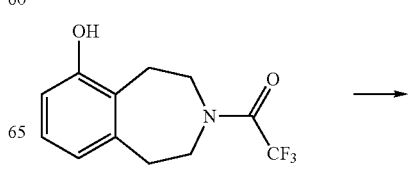

-continued

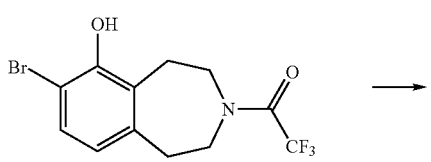

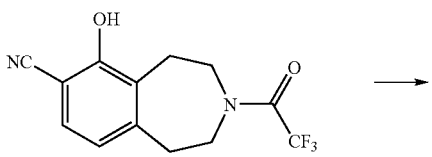

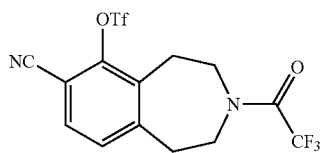

7-Bromo-6-hydroxy-(2,2,2-trifluoroacetyl)-2,3,4,5-tetrahydro-1H-benzo[d]azepine: Dissolve 6-hydroxy-3-(2,2,2-trifluoroacetyl)-2,3,4,5-tetrahydro-1H-benzo[d]azepine (18 g, 69.4 mmol) and DIEA (0.98 mL) in DCM (1.4 L). Add dropwise a solution of NBS (12.4 g, 69.4 mmol) in DCM (500 mL) over 75 min. Stir the reaction mixture at ambient temperature for 1 h, pour into water (500 mL) and extract the mixture with DCM. Wash the organic fraction with brine, dry over $Na_2SO_4$, filter and concentrate. Purify by chromatography on silica gel eluting with hexane/EtOAc (4:1) to give the desired intermediate as a white solid (20.9 g, 89%). MS (ES−) m/z: 337 (M−H)⁻.

7-Cyano-6-hydroxy-3-(2,2,2-trifluoroacetyl)-2,3,4,5-tetrahydro-1H-benzo[d]azepine: Add copper nitrile (2.6 g, 28 mmol) to a solution of 7-bromo-6-hydroxy-3-(2,2,2-trifluoroacetyl)-2,3,4,5-tetrahydro-1H-benzo[d]azepine (2.4 g, 7.0 mmol) in anhydrous NMP (45 mL), degas and purge with nitrogen and heat to 150° C. for 18 h. Allow the reaction mixture to cool to ambient temperature and then dilute with EtOAc/heptane (2:1) and filter through a silica pad. Dilute the filtrate with water, and extract the aqueous phase twice with EtOAc. Dry the combined organic extracts over $MgSO_4$, filter and concentrate in vacuo. Purify by chromatography on silica gel eluting with EtOAc/heptane (1:4 to 1:1) to obtain the desired intermediate as an orange oil (1.7 g, 86%). MS (ES−) m/z: 283 (M−H)⁻.

7-Cyano-3-(2,2,2-trifluoroacetyl)-6-trifluoromethanesulfonyloxy-2,3,4,5-tetrahydro-1H-benzo[d]azepine: Add dry pyridine (3 mL) to 7-cyano-6-hydroxy-3-(2,2,2-trifluoroacetyl)-2,3,4,5-tetrahydro-1H-benzo[d]azepine (1.1 g, 3.9 mmol) in anhydrous DCM (45 mL) and cool to 0° C. Add slowly trifluoromethanesulfonic anhydride (1.3 mL, 7.7 mmol), allow the reaction mixture to warm to ambient temperature and stir for 3 h. Dilute with DCM and wash with 2N aqueous HCl. Dry the organic layer over $MgSO_4$, filter and concentrate in vacuo to obtain the title compound as an orange/brown oil (1.6 g, 100%) that was used without purification. MS (ES−) m/z: 415 (M−H)⁻.

Preparation 16

3-(2,2,2-Trifluoroacetyl)-6-trifluoromethanesulfonyloxy-7-trifluoromethyl-2,3,4,5-tetrahydro-1H-benzo[d]azepine

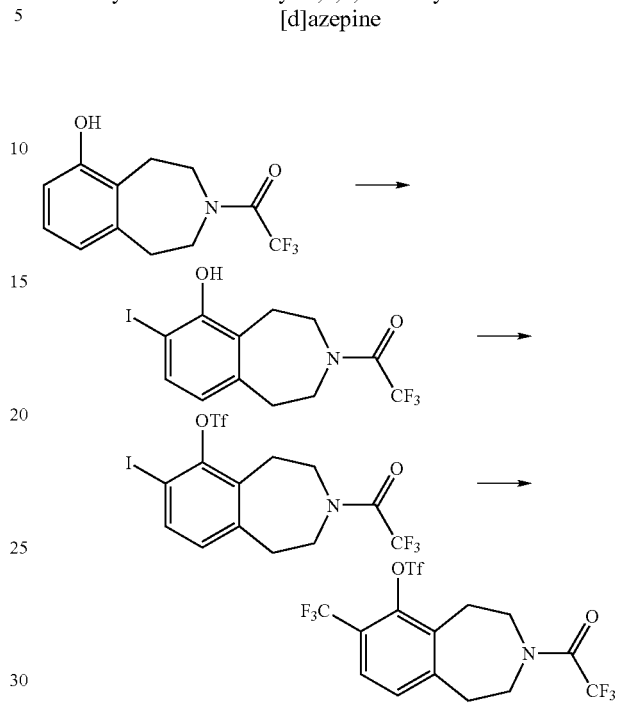

6-Hydroxy-7-iodo-3-(2,2,2-trifluoroacetyl)-2,3,4,5-tetrahydro-1H-benzo[d]azepine: Add 6-hydroxy-3-(2,2,2-trifluoroacetyl)-2,3,4,5-tetrahydro-1H-benzo[d]azepine (1.037 g, 4.0 mmol) and diisopropylamine (60.7 mg, 0.6 mmol) to anhydrous DCM (350 mL) and stir at 10-20° C. Add slowly a solution of N-iodosuccinimide (1.035 g, 4.6 mmol) in DCM (100 mL) over a period of 3 h. Stir the reaction mixture overnight and gradually warm to ambient temperature. Quench the reaction with saturated aqueous $NaHCO_3$, separate the organic layer, wash the organic layer with 0.1N aqueous HCl, brine, dry over $Na_2SO_4$, filter and concentrate in vacuo. Purify by chromatography on silica gel eluting with EtOAc/hexane (1:20 to 1:10) to give the desired intermediate as a white solid (1.0 g, 65%). MS (ES+) m/z: 386 (M+H)⁺.

7-Iodo-3-(2,2,2-trifluoroacetyl)-6-trifluoromethanesulfonyloxy-2,3,4,5-tetrahydro-1H-benzo[d]azepine: Add triethylamine (496 mg, 4.90 mmol) to a solution of 6-hydroxy-7-iodo-3-(2,2,2-trifluoroacetyl)-2,3,4,5-tetrahydro-1H-benzo[d]azepine (945 mg, 2.45 mmol) in DCM (30 mL) at 0° C. Add dropwise trifluoromethanesulfonic anhydride (1.244 g, 4.41 mmol) and stir at 0° C. for 1 h. Warm to ambient temperature overnight. Dilute the mixture with DCM, wash with water, saturated aqueous $NaHCO_3$ and brine. Dry over $Na_2SO_4$, filter and concentrate in vacuo. Purify by chromatography on silica gel eluting with EtOAc/hexane (1:6) to give the desired intermediate as a white solid (1.246 g, 98%). MS (ES+) m/z: 518 (M+H)⁺.

3-(2,2,2-Trifluoroacetyl)-6-trifluoromethanesulfonyloxy-7-trifluoromethyl-2,3,4,5-tetrahydro-1H-benzo[d]azepine: Add CuI (367 mg, 1.93 mmol), methyl 2,2-difluoro-2-(fluorosulfonyl)acetate (1.852 g, 9.64 mmol) and HMPA (1.728 g, 9.64 mmol) to a solution of 7-iodo-3-(2,2,2-trifluoroacetyl)-6-trifluoromethanesulfonyloxy-2,3,4,5-tetrahydro-1H-benzo[d]azepine (1.246 g, 2.41 mmol) in DMF (8 mL) and heat the mixture at 70° C. for 1.5 h. Add same amount of CuI, methyl 2,2-difluoro-2-(fluorosulfonyl)acetate, and HMPA and stir further for 4 h. Cool the mixture to ambient temperature, quench with saturated aqueous ammonium chloride, separate the organic layer, and extract the aqueous layer with EtOAc three times. Combine the organic layers, wash with saturated aqueous NaHCO$_3$, brine, dry over Na$_2$SO$_4$, filter and concentrate in vacuo. Purify by chromatography on silica gel eluting with EtOAc/hexane (1:20 to 1:10) to give the title compound as a white solid (321 mg, 29%) and to recover the starting material (741 mg, 59%). MS (ES+) m/z: 460 (M+H)$^+$.

Preparation 17

7-Ethyl-3-(2,2,2-trifluoroacetyl)-6-trifluoromethanesulfonyloxy-2,3,4,5-tetrahydro-1H-benzo[d]azepine

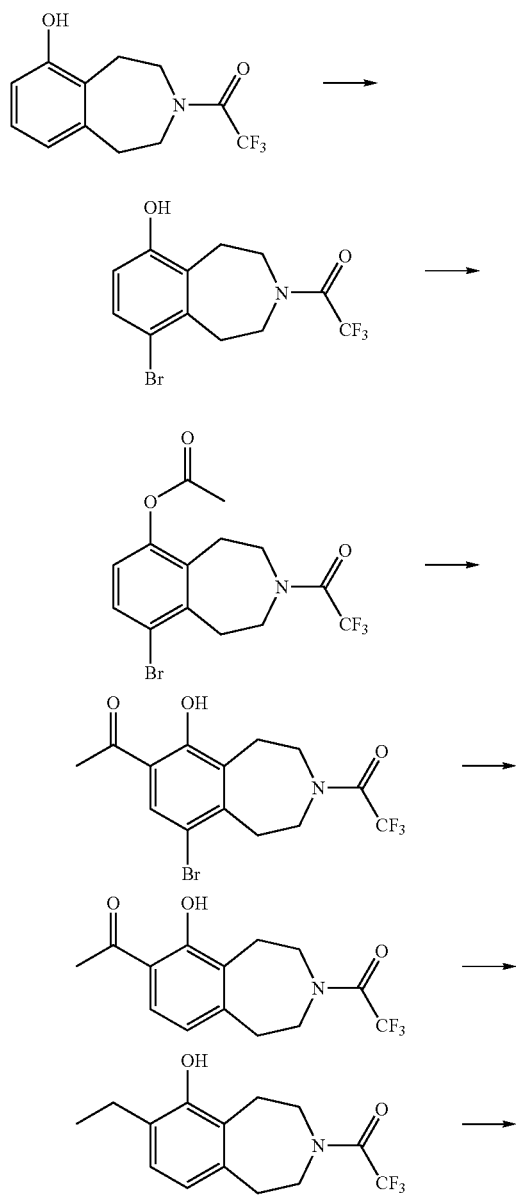

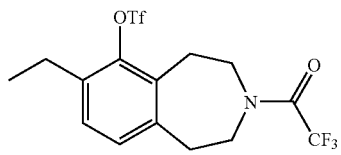

9-Bromo-6-hydroxy-3-(2,2,2-trifluoroacetyl)-2,3,4,5-tetrahydro-1H-benzo[d]azepine: Add dropwise bromine (10.8 mL, 0.21 mol) in acetonitrile (260 mL) to a slurry of 6-hydroxy-3-(2,2,2-trifluoroacetyl)-2,3,4,5-tetrahydro-1H-benzo[d]azepine (51.8 g, 0.2 mol) in acetonitrile (400 mL) at 0° C. cooling with ice-water to keep the temperature between 2-5° C. Warm the reaction to ambient temperature and stir for 30 min. Pour the mixture into ice-cold water (2 L) to obtain a white precipitate. Collect the solid by vacuum filtration, wash with water and dry under vacuum at 105° C. Recrystallize the crude material in toluene/heptane and cool the mixture in an ice bath. Collect the solid by vacuum filtration, wash with heptane and dry under vacuum at 105° C. to obtain the desired intermediate as a white solid (54.63 g, 81%). MS (ES+) m/z: 338 (M+H)$^+$.

6-Acetoxy-9-bromo-3-(2,2,2-trifluoroacetyl)-2,3,4,5-tetrahydro-1H-benzo[d]azepine: Under nitrogen atmosphere, mix 9-bromo-6-hydroxy-3-(2,2,2-trifluoroacetyl)-2,3,4,5-tetrahydro-1H-benzo[d]azepine (6 g, 17.8 mmol), anhydrous pyridine (0.06 mL, 0.72 mmol), DMAP (222 mg, 1.8 mmol) and acetic anhydride (30 mL). Heat the mixture at reflux for 8 h and then stir at ambient temperature for another 8 h. Concentrate in vacuo, dilute the residue in EtOAc, wash with 1N aqueous HCl, and then with saturated aqueous NaHCO$_3$. Dry the organic layer over Na$_2$SO$_4$, filter, and concentrate in vacuo to obtain the desired intermediate (5.64 g, 84%) that was used without further purification. MS (ES+) m/z: 380 (M+H)$^+$.

7-Acetyl-9-bromo-6-hydroxy-3-(2,2,2-trifluoroacetyl)-2,3,4,5-tetrahydro-1H-benzo[d]azepine: Under nitrogen atmosphere, mix 6-acetoxy-9-bromo-3-(2,2,2-trifluoroacetyl)-2,3,4,5-tetrahydro-1H-benzo[d]azepine (2.8 g, 7.4 mmol) and nitrobenzene (5 mL). Add anhydrous aluminum chloride (980 mg, 7.4 mmol). Heat at 180° C. for 2 h. Cool the mixture to ambient temperature. Add-concentrated HCl (10 mL) dropwise. Stir the mixture for 30 min. Add 1N aqueous HCl then extract with EtOAc. Dry the organic layer over Na$_2$SO$_4$, filter and concentrate in vacuo. Purify by chromatography on silica gel eluting with EtOAc/hexane (0:1 to 1:4) to afford the desired intermediate (833 mg, 30%). MS (ES−) m/z: 378 (M−H)$^−$.

7-Acetyl-6-hydroxy-3-(2,2,2-trifluoroacetyl)-2,3,4,5-tetrahydro-1H-benzo[d]azepine: Mix-acetyl-9-bromo-6-hydroxy-3-(2,2,2-trifluoroacetyl)-2,3,4,5-tetrahydro-1H-benzo[d]azepine (833 mg, 2.2 mmol), tetrakis(triphenylphosphine)palladium(0) (150 mg, 0.13 mmol) and sodium formate (224 mg, 3.3 mmol) in anhydrous DMF (15 mL). Degas twice then flush with argon. Keep the flask under argon and heat the reaction at 95° C. for 16 h. Dilute with EtOAc then wash with 1N aqueous HCl. Separate the organic layer, dry over Na$_2$SO$_4$, filter and concentrate in vacuo. Purify by chromatography on silica gel eluting with EtOAc/hexane (0:1, 1:9 and 1:4) to give the desired intermediate (448 mg, 68%). MS (ES+) m/z: 302 (+H)$^+$.

7-Ethyl-6-hydroxy-3-(2,2,2-trifluoroacetyl)-2,3,4,5-tetrahydro-1H-benzo[d]azepine: Under nitrogen dissolve 7-acetyl-6-hydroxy-3-(2,2,2-trifluoroacetyl)-2,3,4,5-tetrahydro-1H-benzo[d]azepine (1.0 g, 3.32 mmol) in anhydrous THF (100 mL). Cool the solution to 0° C., add boron trifluoride diethyl etherate (3.4 mL, 26.6 mmol) and sodium cyanoborohydride (836 mg, 13.3 mmol). Remove the ice bath and stir for 5 h at ambient temperature. Dilute with EtOAc and wash with 0.1N aqueous HCl. Separate the organic layer, dry over Na$_2$SO$_4$, filter and concentrate in vacuo. MS (ES−) m/z: 302 (M−H)$^−$. Mix the residue with trifluoroacetic acid (40 mL) and anhydrous DCM (50 mL) under nitrogen. Cool to 0° C. in an ice bath and add triethyl silane (3.5 mL, 21.9 mmol). After 15 min, remove the ice bath and stir at ambient temperature for 16 h. Concentrate in vacuo and purify by chromatography on silica gel eluting with EtOAc/hexane (1:9) to obtain the desired intermediate (698 mg, 73%). MS (ES−) m/z: 286 (M−H)$^−$.

7-Ethyl-3-(2,2,2-trifluoroacetyl)-6-trifluoromethanesulfonyloxy-2,3,4,5-tetrahydro-1H-benzo[d]azepine: Under nitrogen mix 7-ethyl-6-hydroxy-3-(2,2,2-trifluoroacetyl)-2,3,4,5-tetrahydro-1H-benzo[d]azepine (698 mg, 2.4 mmol), triethylamine (0.67 mL, 4.8 mmol) and anhydrous DCM (25 mL). Cool the mixture in an ice bath, add dropwise trifluoromethanesulfonic anhydride (0.81 mL, 4.8 mmol) and stir at ambient temperature for 3 h. Quench with water and extract three times with DCM. Wash the organic extracts with 0.1N aqueous HCl and brine. Dry over Na$_2$SO$_4$, filter and concentrate to obtain the title compound (1.0 g, 100%). MS (ES+) m/z: 420 (M+H)$^+$.

Preparation 18

7-Propyl-3-(2,2,2-trifluoroacetyl)-6-trifluoromethanesulfonyloxy-2,3,4,5-tetrahydro-1H-benzo[d]azepine

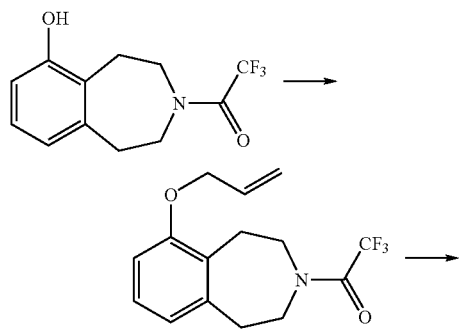

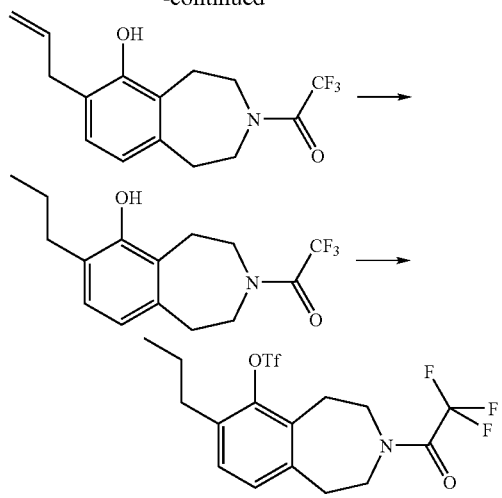

6-Allyloxy-3-(2,2,2-trifluoroacetyl)-2,3,4,5-tetrahydro-1H-benzo[d]azepine: Dissolve 6-hydroxy-3-(2,2,2-trifluoroacetyl)-2,3,4,5-tetrahydro-1H-benzo[d]azepine (1 g, 3.9 mmol) in acetone (5 mL) and add powdered potassium carbonate (2.8 g, 20 mmol). Add dropwise a solution of alkyl bromide (1.04 mL, 12 mmol) in acetone (3 mL) over 10 min and stir at ambient temperature overnight. Filter solids, wash with acetone and concentrate in vacuo to give the desired intermediate as an off-white solid (1.15 g, 98%). GC-MS m/z: 299 (M$^+$).

7-Allyl-6-hydroxy-3-(2,2,2-trifluoroacetyl)-2,3,4,5-tetrahydro-1H-benzo[d]azepine: Dissolve 6-alkyloxy-3-(2,7-trifluoroacetyl)-2,3,4,5-tetrahydro-1H-benzo[d]azepine (1.1 g, 3.7 mmol) in DCM (15 mL) and cool to −15° C. Add 1M boron trichloride in DCM (15 mL, 15 mmol) and warm to ambient temperature. Stir for 30 min at ambient temperature. Add water (50 mL) and extract the aqueous layer three times with DCM. Wash the combined organic extracts with water (100 mL), brine (100 mL), dry over MgSO$_4$, filter, and concentrate in vacuo to give the desired intermediate (980 mg, 89%) as a light yellow oil which solidified to an off-white solid upon standing at ambient temperature. MS (ES+) m/z: 300 (M+H)$^+$.

6-Hydroxy-7-propyl-3-(2,2,2-trifluoroacetyl)-2,3,4,5-tetrahydro-1H-benzo[d]azepine: Dissolve 7-alkyl-6-hydroxy-3-(2,2,2-trifluoroacetyl)-2,3,4,5-tetrahydro-1H-benzo[d]azepine (1.5 g, 5 mmol) in EtOAc (50 mL) containing 10% Pd/C (1.3 g). Stir at ambient temperature at 1 atm with H$_2$ (balloon) for 30 min. Filter the catalyst and wash with water (100 mL). Extract the resulting filtrate three times with EtOAc, wash the combined organic extracts with brine, dry over MgSO$_4$, filter and concentrate in vacuo to give the desired intermediate as a white solid (1.45 g, 97%). MS (ES+) m/z: 302 (M+H)$^+$.

7-Propyl-3-(2,2,2-trifluoroacetyl)-6-trifluoromethanesulfonyloxy-2,3,4,5-tetrahydro-1H-benzo[d]azepine: Cool a solution of 6-hydroxy-7-propyl-3-(2,2,2-trifluoroacetyl)-2,3,4,5-tetrahydro-1H-benzo[d]azepine (500 mg, 1.9 mmol), triethylamine (390 µL, 2.3 mmol) and DCM (20 mL) in a cryogenic bath set at −35° C. and add dropwise over 20 min trifluoromethanesulfonic anhydride (325 µL, 2.3 mmol). Stir at this temperature overnight. Wash the reaction mixture sequentially with water, 1N aqueous HCl, water, and brine. Dry the organic layer over Na$_2$SO$_4$ and concentrate in vacuo. Purify by chromatography on silica gel eluting with hexane/EtOAc (9:1) to obtain the title compound as an off-white waxy solid (550 mg, 75%). MS (ES+) m/z: 434 (M+H)$^+$.

Preparation 19

6-Amino-7-chloro-3-(2,2,2-trifluoroacetyl)-2,3,4,5-tetrahydro-1H-benzo[d]azepine

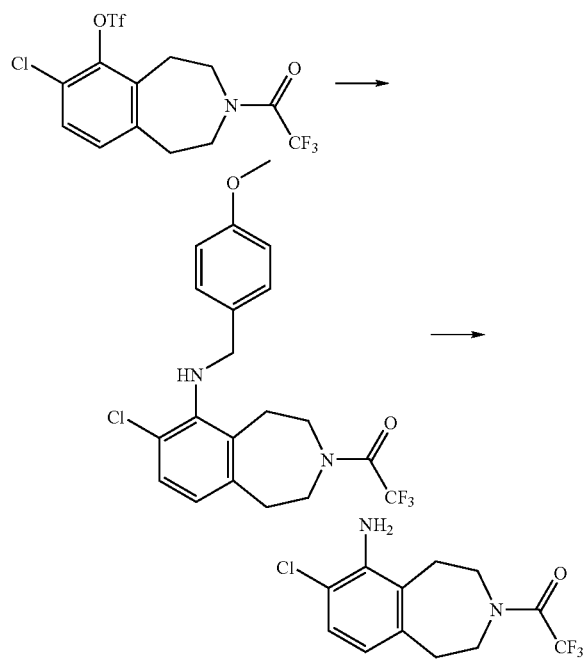

7-Chloro-6-(4-methoxybenzylamino)-3-(2,2,2-trifluoroacetyl)-2,3,4,5-tetrahydro-1H-benzo[d]azepine: Couple 7-chloro-3-(2,2,2-trifluoroacetyl)-6-trifluoromethanesulfonyloxy-2,3,4,5-tetrahydro-1H-benzo[d]azepine (15 g, 35.3 mmol), with 4-methoxybenzylamine (13.7 mL, 106 mmol) using tris(dibenzylideneacetone)-dipalladium(0) (1.62 g, 1.76 mmol), BINAP (4.40 g, 3.5 mmol) and cesium carbonate (16.1 g, 49.4 mmol) at 80° C. for 17 h. Filter the mixture through a pad of Celite® and evaporate the filtrate. Dissolve the residue in DCM and filter through a pad of silica gel. Evaporate the filtrate and purify by chromatography on silica gel eluting with hexane/EtOAc (1:0 to 2:3) to give the desired intermediate as a white solid (12.4 g, 86%). MS (ES+) m/z: 412 (M+H)+.

6-Amino-7-chloro-3-(2,2,2-trifluoroacetyl)-2,3,4,5-tetrahydro-1H-benzo[d]azepine: Treat 7-chloro-6-(4-methoxybenzylamino)-3-(2,2,2-trifluoroacetyl)-2,3,4,5-tetrahydro-1H-benzo[c]azepine (5.41 g, 13.1 mmol) with 2,3-dichloro-5,6-dicyano-1,4-benzoquinone (3.59 g, 15.8 mmol) in toluene (66 mL) at ambient temperature for 2 h. Dilute the mixture with EtOAc and wash with saturated aqueous NaHCO3 (5×100 mL). Extract the aqueous layer with ether, combine the organic extracts and evaporate to a volume of 300 mL. Extract the organic phase with 1N aqueous HCl (5×100 mL), and then wash the combined aqueous layers with ether (4×75 mL). Cool the aqueous phase to 0° C., neutralize with 5N aqueous NaOH (100 mL), and extract with DCM (5×200 mL). Wash the combined organic extracts with brine, dry over Na2SO4 and evaporate to obtain the title compound as a white solid (3.6 g, 94%). MS (ES+) m/z: 293 (M+H)+.

Preparation 20

6-(2-Amino-ethylamino)-7-chloro-3-(2,2,2-trifluoroacetyl)-2,3,4,5-tetrahydro-1H-benzo[d]azepine

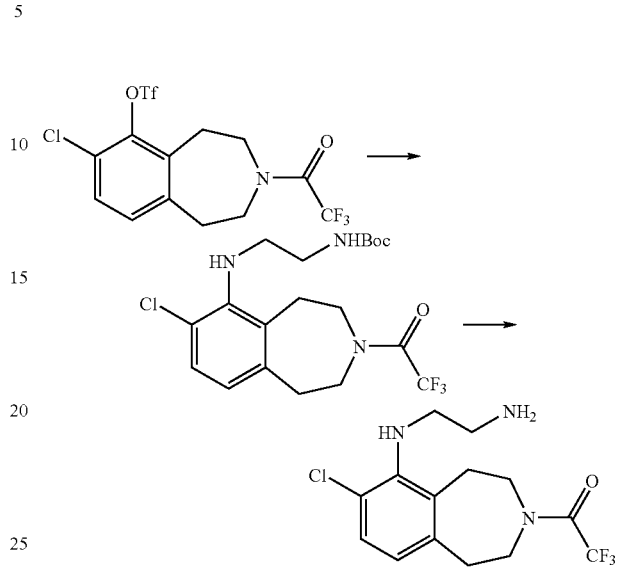

6-(2-tert-Butoxycarbonylamino-ethylamino)-7-chloro-3-(2,2,2-trifluoroacetyl)-2,3,4,5-tetrahydro-1H-benzo[d]azepine: Use a method similar to the General Procedure 5-1, using 7-chloro-3-(2,2,2-trifluoroacetyl)-6-trifluoromethanesulfonyloxy-2,3,4,5-tetrahydro-1H-benzo[d]azepine (150 mg, 0.352 mmol), palladium(II) acetate (8 mg, 0.0352 mmol), BINAP (22 mg, 0.0352 mmol), cesium carbonate (163 mg, 0.5 mmol), t-butyl N-(2-aminoethyl)-carbamate (254 mg, 1.59 mmol) and toluene (6 mL) to give, after chromatography on silica gel eluting with hexane/EtOAc (4:1), the desired intermediate (136 mg, 89%).

6-(2-Amino-ethylamino)-7 chloro-3-(2,2-trifluoroacetyl)-2,3,4,5-tetrahydro-1H-benzo[d]azepine: Dissolve 6-(2-tert-butoxycarbonylamino-ethylamino)-7-chloro-3-(2,2,2-trifluoroacetyl)-2,3,4,5-tetrahydro-1H-benzo[d]azepine (136 mg, 0.31 mmol) in 4M hydrogen chloride in dioxane (20 mL) and stir at ambient temperature for 25 min. Concentrate to afford the hydrochloride salt. Dissolve the salt in DCM and wash with saturated aqueous NaHCO3. Extract the basic aqueous layer with DCM, dry the organic layer over MgSO4, filter, and concentrate in vacuo to give the title compound (64 mg, 62%). MS (ES+) m/z: 336 (M+H)+.

Preparation 21

6-(3-Amino-propylamino)-7-chloro-3-(2,2,2-trifluoroacetyl)-2,3,4,5-tetrahydro-1H-benzo[d]azepine

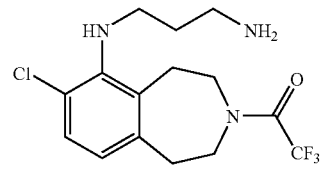

Use a method similar to the Preparation 20, using 7-chloro-3-(2,2,2-trifluoroacetyl)-6-trifluoromethanesulfonyloxy-2, 3,4,5-tetrahydro-1H-benzo[d]azepine (600 mg, 1.41 mmol) and tert-butyl N-(3-aminopropyl)-carbamate (1.11 g, 6.34 mmol) to give the title compound (34% overall).

Preparation 22

7-Chloro-6-(4-hydroxybenzylamino)-3-(2,2,2-trifluoroacetyl)-2,3,4,5-tetrahydro-1H-benzo[d]azepine

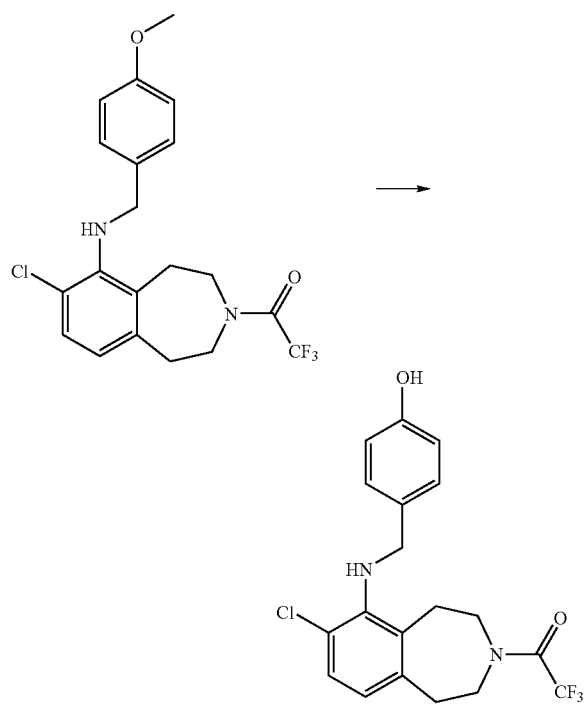

Dissolve 7-chloro-6-(4-methoxybenzylamino)-3-(2,2,2-trifluoroacetyl)-2,3,4,5-tetrahydro-1H-benzo[d]azepine (1.667 g) in DCM (40 mL). Add a 1M solution of boron tribromide in DCM (10 mL) at 0° C. Stir the reaction for 12 h and gradually raise to room temperature. Quench the reaction with saturated aqueous NaHCO₃ and extract with DCM three times. Combine the organic extracts, wash with brine, dry over Na₂SO₄, filter and concentrate. Purify by chromatography on silica gel eluting with EtOAc/hexane (1:3) to give the title compound as an oil (888 mg). MS (ES+) m/z: 399 (M+1)⁺.

Preparation 23

7-Chloro-6-(3-chloro-4-hydroxybenzylamino)-3-(2,2,2-trifluoroacetyl)-2,3,4,5-tetrahydro-1H-benzo[d]azepine

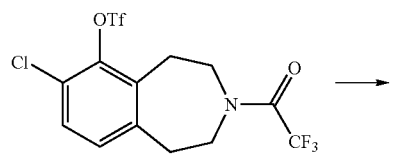

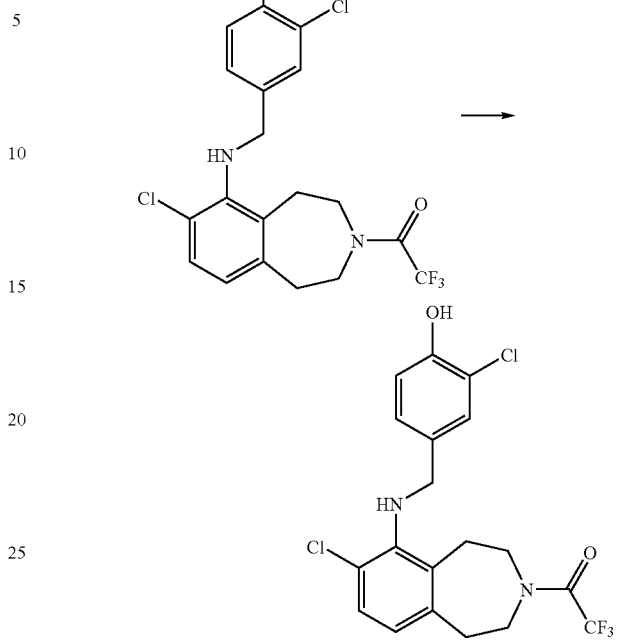

7-Chloro-6-(3-chloro-4-methoxybenzylamino)-3-(2,2,2-trifluoroacetyl)-2,3,4,5-tetrahydro-1H-benzo[d]azepine: Use a method similar to General Procedure 5-3, using 7-chloro-3-(2,2,2-trifluoroacetyl)-6-trifluoromethanesulfonyloxy-2,3,4,5-tetrahydro-1H-benzo[d]azepine (1.277 g, 3.0 mmol) and 3-chloro-4-methoxy-benzylamine (669 mg, 3.9 mmol) to give the desired intermediate as a slightly yellow oil (1.554 g, 100%).

7-Chloro-6-(3-chloro-4-hydroxybenzylamino)-3-(2,2,2-trifluoroacetyl)-2,3,4,5-tetrahydro-1H-benzo[d]azepine: Use a method similar to Preparation 22, using 7-chloro-6-(3-chloro-4-methoxybenzylamino)-3-(2,2,2-trifluoroacetyl)-2,3,4,5-tetrahydro-1H-benzo[d]azepine (1.36 g, 3.0 mmol) to give the title compound as an off-white solid (876 mg, 67% yield). MS (ES+) m/z: 433 (M+H)⁺. MS (ES−) m/z: 431 (M−H)⁻.

Preparation 24

3-(tert-Butoxycarbonyl)-6-(4-carboxy-benzylamino)-7-chloro-2,3,4,5-tetrahydro-1H-benzo[d]azepine

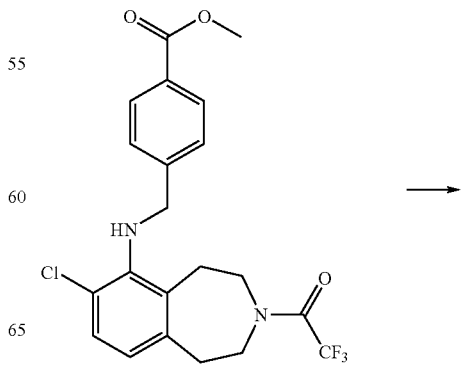

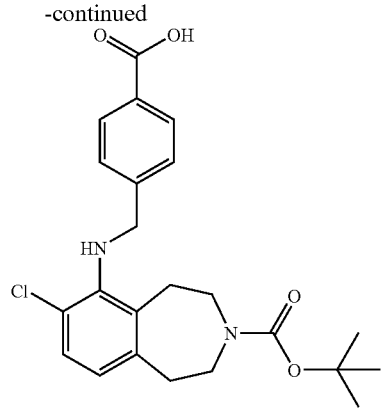

Combine 7-chloro-6-(4-methoxycarbonyl-benzylamino)-3-(2,2,2-trifluoroacetyl)-2,3,4,5-tetrahydro-1H-benzo[d]azepine (0.4 g, 0.82 mmol), potassium carbonate (4 g, 28.9 mmol), methanol (3 mL), water (3 mL) and heat at 50° C. for 2 h. Cool the reaction mixture to ambient temperature, add saturated aqueous $Na_2CO_3$ and dilute with DCM (10 mL). Add di-tert-butyl-dicarbonate (2.4 g, 10.9 mmol by portions. Separate the organic layer and extract the aqueous layer with DCM (3×10 mL). Combine the organic extracts, dry over anhydrous $Na_2SO_4$, evaporate the solvent and purify by chromatography on silica gel eluting with DCM and DCM/methanol (9:1) to give the title compound as a white solid (0.3 g, 80%). MS (ES+) m/z: 331 (M+H−Boc)+.

Preparation 25

2-Benzyloxyethylamine

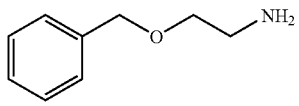

(2-Benzyloxyethyl)-carbamic acid tert-butyl ester: Dissolve tert-butyl-N-(2-hydroxyethyl)-carbamate (10 mL, 64.5 mmol) in anhydrous THY (500 mL) at 0° C. Add sodium hydride (60% in mineral oil, 3.1 g, 77.4 mmol) and stir for 30 min at 0° C. Add benzyl bromide (9.2 mL, 77 mmol) followed by tetrabutylammonium iodide (3.7 g, 10 mmol) and stir at ambient temperature overnight. Quench with water (500 mL), extract with diethyl ether (3×100 mL), wash the combined organic extracts with brine, dry over $MgSO_4$, filter, and evaporate to give the desired intermediate (5 g), that was used without further purification.

2-Benzyloxyethylamine: Dissolve (2-benzyloxyethyl)-carbamic acid tert-butyl ester (15 g) in DCM (50 mL), add trifluoroacetic acid (20 mL) and stir at 0° C. for 3 h. Concentrate and dissolve the residue in a minimal amount of DCM. Purify by chromatography on silica gel eluting sequentially with hexane/EtOAc (4:1 and 1:1), EtOAc and 2M ammonia in methanol to give the title compound (8.3 g, 85%).

Preparation 26

(R)-2-Benzyloxy-1-methyl-ethylamine

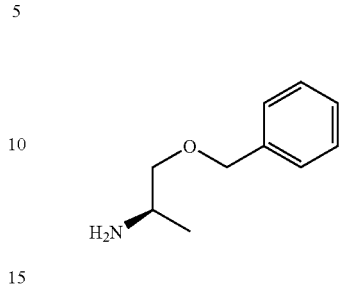

(R)-3-Benzyloxy-2-(tert-butoxycarbonylamino)-propane: Dissolve (R)-(+)-2-(tert-butoxycarbonylamino)-1-propanol (875 mg, 5 mmol) in anhydrous THF (50 mL). Add sodium hydride (60% in mineral oil, 210 mg, 5.2 mmol) and stir at 0° C. for 30 min. Add benzyl bromide (620 μL, 5.2 mmol) followed by tetrabutylammonium iodide (20 mg, 0.05 mmol) and stir for 3 h at ambient temperature. Pour the mixture into water (200 mL), extract with DCM (3×50 mL), wash with brine, dry over $MgSO_4$, filter and concentrate. Purify by chromatography on silica gel eluting with hexane/EtOAc (19:1) to give the desired intermediate as a colorless oil (800 mg, 60%).

(R)-2-Benzyloxy-1-methyl-ethylamine: Dissolve (R)-3-benzyloxy-2-(tert-butoxycarbonylamino)-propane (800 mg, 3 mmol) in DCM (10 mL), add trifluoroacetic acid (5 mL), and stir at 0° C. for 20 min. Evaporate and purify by SCX chromatography to give the title compound as a colorless oil (440 mg, 89%). MS (ES+) m/z: 166 (M+H)+.

Preparation 27

(R)-2-(4-Fluorobenzyloxy)-1-methyl-ethylamine

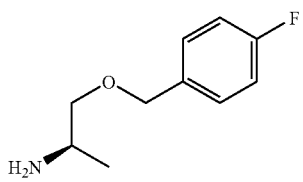

(R)-2-(tert-Butoxycarbonylamino)-3-(4-fluorobenzyloxy)-propane: Dissolve (R)-(+)-2-(tert-butoxycarbonylamino)-1-propanol (1.75 mg, 10.5 mmol) in anhydrous THF (50 mL). Add sodium hydride (60% in mineral oil, 480 mg, 12 mmol) and stir at 0° C. for 30 min. Add 4-fluorobenzyl bromide (1.5 mL, 12 mmol) followed by tetrabutylammonium iodide (370 mg, 0.1 mmol) and stir for 72 h at ambient temperature. Pour the mixture into water (500 mL), extract with DCM (3×150 mL), wash with brine, dry over $MgSO_4$, filter and concentrate in vacuo. Purify by chromatography on silica gel eluting with hexane/EtOAc (9:1) to give the desired intermediate as a yellow oil (2.18 g, 77%).

(R)-2-(4-Fluorobenzyloxy)-1-methyl-ethylamine: Dissolve-(R)-2-(tert-butoxycarbonylamino)-3-(4-fluorobenzyloxy)-propane (2.18 g, 7.7 mmol) in DCM (50 mL), add trifluoroacetic acid (25 mL), and stir at 0° C. for 20 min.

Evaporate and purify by SCX chromatography to give the title compound as a colorless oil (1.2 g, 85%). MS (ES+) m/z: 184 (M+H)⁺.

Preparation 28

(R)-1-Methyl-2-phenoxy-ethylamine

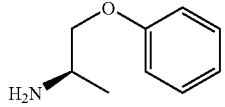

(R)-2-(tert-Butoxycarbonylamino)-3-phenoxy-propane: Dissolve (R)-(+)-2-(tert-butoxycarbonylamino)-1-propanol (1.75 g, 10 mmol) and phenol (0.95 g, 10 mmol) in anhydrous THF (75 mL). Cool to 0° C., add triphenylphosphine (4.0 g, 15 mmol) and diisopropylazodicarboxylate dropwise and stir at ambient temperature for 18 h. Pour the mixture into water (300 mL), basify to pH 10 with 5N aqueous NaOH, and extract with ethyl ether (3×100 mL). Wash the organic phase with brine, dry over MgSO₄, filter and concentrate. Purify by chromatography on silica gel eluting with hexane/EtOAc (9:1) to give the desired intermediate as an off-white solid (340 mg, 14%).

(R)-1-Methyl-2-phenoxy-ethylamine: Dissolve (R)-2-(tert-butoxycarbonylamino)-3-phenoxy-propane (340 mg, 1.35 mmol) in DCM (80 mL), add trifluoroacetic acid (35 mL), and stir at 0° C. for 2 h. Evaporate and purify by SCX chromatography to give the title compound as a colorless oil (186 mg, 91%). MS (ES+) m/z: 151 (M+H)⁺.

Preparation 29

4-(Aminomethyl)-2-methyl-thiazole

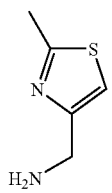

4-(Azidomethyl)-2-methyl-thiazole: Dissolve 4-(chloromethyl)-2-methyl-thiazole (350 mg, 2.37 mmol) and azidotrimethylsilane (315 µL, 2.37 mmol) in anhydrous THF (1 mL) under nitrogen. Add a 1M solution of tetrabutylammonium fluoride (3.6 mL, 3.56 mmol) in THF and stir at ambient temperature overnight. Pour the reaction mixture into water (10 mL), extract with ethyl ether (3×2 mL), wash the organic extra with brine, dry over MgSO₄, filter, and evaporate. Purify by chromatography on silica gel eluting with hexane/EtOAc (9:1) to give the desired intermediate as a colorless oil (165 mg, 45%).

4-(Aminomethyl)-2-methyl-thiazole: Add 4-(azidomethyl)-2-methyl-thiazole (165 mg, 1.07 mmol) to a slurry of methanol containing 10% Pd/C (75 mg) and stir vigorously under 1 atm H₂ for 1 h. Filter, evaporate the solvent, and purify by SCX chromatography to give the title compound (55 mg, 40%).

Preparation 30

2-Fluoro-4-phenoxy-benzylamine

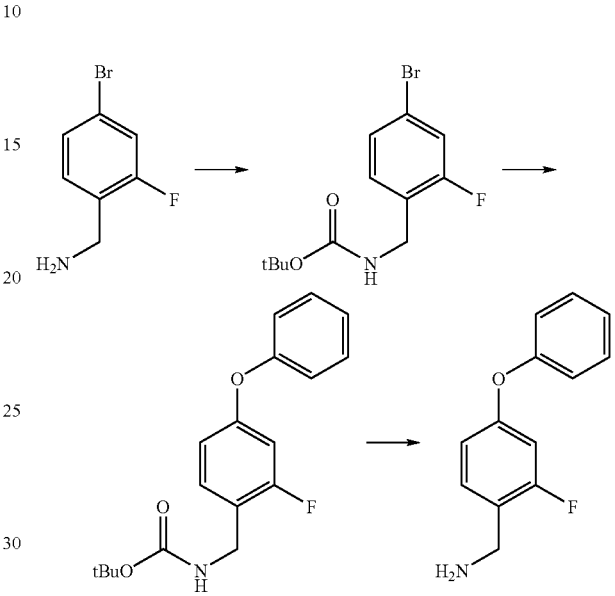

(4-Bromo-2-fluorobenzyl)-carbamic acid tert-butyl ester: Mix under nitrogen 4-bromo-2-fluorobenzylamine hydrochloride (7.2 g, 30 mmol), di-tert-butyl-dicarbonate (9.8 g, 45 mmol), and potassium carbonate (12.4 g, 90 mmol) in anhydrous THF (200 mL). Stir at ambient temperature for 16 h. Filter and concentrate in vacuo. Purify by chromatography on silica gel eluting with hexane/EtOAc (9:1) to obtain the desired intermediate (6.4 g, 70%). GC-MS m/z: 247 [M−C₄H₉)⁺].

(2-Fluoro-4-phenoxy-benzyl)-carbamic acid tert-butyl ester: Mix under argon atmosphere (4-bromo-2-fluorobenzyl)-carbamic acid tert-butyl ester (2.12 g, 7.0 mmol), phenol (1.32 g, 14 mmol), 2,2,6,6-tetramethylheptane-3,5-dione (129 mg, 0.7 mmol), and cesium carbonate (4.56 g, 14 mmol) in anhydrous NMP (15 mL). Degas the flask, fill with argon and add copper(I) chloride (346 mg, 3.5 mmol) quickly. Degas the flask then fill with argon and heat at 120° C. for 5 h. Cool to ambient temperature, dilute with EtOAc and filter. Wash the mixture sequentially with 0.5N aqueous HCl, 0.5N aqueous NaOH and brine. Separate the organic layer, dry over Na₂SO₄ and concentrate in vacuo. Purify by chromatography on silica gel eluting with hexane/EtOAc (1:0, 9:1 and 3:1) to obtain the desired intermediate (1.28 g, 58%). GC-MS m/z: 260 [M−C₄H₉)⁺].

2-Fluoro-4-phenoxy-benzylamine: Dissolve (2-fluoro-4-phenoxy-benzyl)-carbamic acid tert-butyl ester (2.44 g, 7.72 mmol) in DCM (200 mL). Add trifluoroacetic acid (50 mL) then stir at ambient temperature for 16 h. Evaporate the solvent, dissolve the residue in DCM and wash with 1N aqueous NaOH. Dry over Na₂SO₄ and concentrate in vacuo. Purify by SCX chromatography to obtain the title compound (557 mg, 33%). MS (ES+) m/z: 201 M+H−NH₃)⁺.

Preparation 31

2-Fluoro-4-(3'-fluorophenoxy)-benzylamine

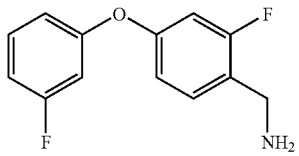

Use a method similar to Preparation 30, using (4-bromo-2-fluorobenzyl)-carbamic acid tert-butyl ester (2.12 g, 7.0 mmol) and m-fluorophenol (1.57 g, 14 mmol) to give the title compound (468 mg, 47% overall).

Preparation 32

4-2'-Fluorophenoxy)-benzylamine

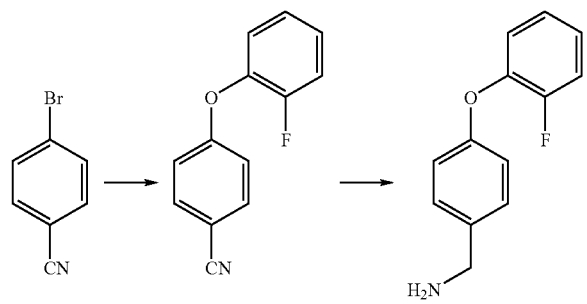

4-(2'-Fluorophenoxy)-benzonitrile: Mix under argon atmosphere 4-bromobenzonitrile (2.0 g, 11.3 mmol), 2-fluorophenol (2.5 g, 22.6 mmol), 2,2,6,6-tetramethylheptane-3,5-dione (203 mg, 1.1 mmol), and cesium carbonate (7.4 g, 22.6 mmol) in anhydrous NMP (19 mL). Degas the flask, fill with argon and add copper(I) chloride (554 mg, 5.6 mmol) quickly. Degas the flask then fill with argon and heat at 120° C. for 3 h. Cool to ambient temperature, dilute with EtOAc, filter and wash the filtrate sequentially with 2M aqueous HCl, 0.3M aqueous HCl, 2M aqueous NaOH and brine. Separate the organic layer, dry over $Na_2SO_4$ and concentrate in vacuo. Purify by chromatography on silica gel eluting with hexane/EtOAc (1:0 and 9:1) to obtain the desired intermediate (1.6 g, 66%). MS (ES+) m/z: 231 $(M+NH_4)^+$.

4-(2'-Fluorophenoxy)-benzylamine: Add 4-(2'-fluorophenoxy)-benzonitrile (1.5 g, 7.0 mmol) and ethanol wet Raney® activated nickel (0.4 g) to a Parr pressure vessel. Immediately add a 7N solution of ammonia in methanol (170 mL) and seal the vessel. Purge the reaction vessel with nitrogen, pressurize the reaction mixture with hydrogen (3400 KPa), seal the vessel, agitate the reaction and heat to 60° C. Continue the reaction for 18 h, turn off the heat and allow the reaction mixture to cool to ambient temperature. Vent the excess hydrogen from the vessel and purge the vessel with nitrogen. Filter the reaction mixture to remove the Raney® nickel. Concentrate in vacuo and purify by chromatography on silica gel eluting with DCM/2M ammonia in methanol (9:1) to obtain the title compound (1.2 g, 79%). MS (ES+) m/z: 201 $M+H-NH_3)^+$.

The compound of Preparation 33 may be prepared essentially as described in Preparation 32 using 4-bromobenzonitrile and 3-fluorophenol. Overall yield and MS (ES+) data are shown in the Table below.

| Prep. | Compound | Yield (%) | MS (ES+) m/z |
|---|---|---|---|
| 33 | 4-(3'-Fluorophenoxy)-benzylamine | 53 | 201 $(M + H - NH_3)^+$ |

Preparation 34

4-(3'-Isopropylphenoxy)-benzylamine

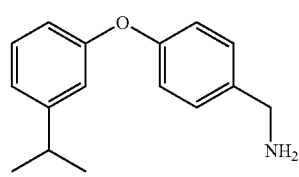

Use a method similar to Preparation 32 (Step 1), using 4-bromobenzonitrile (2.0 g, 11.3 mmol) and 3-isopropylphenol (3.08 g, 22.6 mmol) to give 4-(3'-isopropylphenoxy)-benzonitrile (885 mg, 33%). MS (ES+) m/z: 255 $(M+NH_4)^+$.

Use a method similar to the reduction procedure described in Preparation 45 (Step 2), using 4-(3'-isopropylphenoxy)-benzonitrile (875 mg, 3.7 mmol) to give the title compound (703 mg, 79%). MS (ES+) m/z: 225 $M+H-NH_3)^+$.

The compounds of Preparations 35-39 may be prepared essentially as described in Preparation 34 by using 4-bromobenzonitrile and the appropriate phenol. Overall yields and MS (ES+) data are shown in the Table below.

| Prep. | Compound | Yield (%) | MS (ES+) m/z |
|---|---|---|---|
| 35 | 4-(2'-Isopropylphenoxy)-benzylamine | 28 | 225 $(M + H - NH_3)^+$ |
| 36 | 4-(3'-Methylphenoxy)-benzylamine | 60 | 197 $(M + H - NH_3)^+$ |
| 37 | 4-(2'-Methylphenoxy)-benzylamine | 59 | 197 $(M + H - NH_3)^+$ |
| 38 | 4-(3',5'-Difluorophenoxy)-benzylamine | 24 | 219 $(M + H - NH_3)^+$ |
| 39 | 4-(3'-Chlorophenoxy)-benzylamine | 44 | 217 $(M + H - NH_3)^+$ |

Preparation 40

2-(4-Aminomethyl-phenoxy)-benzonitrile

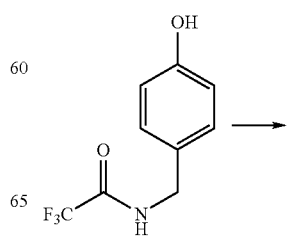

Preparation 44

3-(4-Aminomethyl-phenoxy)-benzonitrile

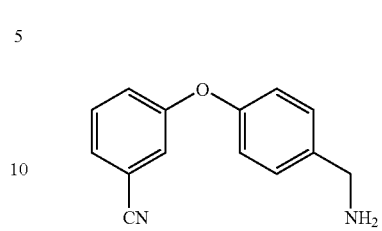

Use a method similar to Preparation 40 (Step 2), using 2,2,2-trifluoro-N-(4-hydroxybenzyl)-acetamide (1.0 g, 5.5 mmol) and 3-bromobenzonitrile (673 mg, 3.7° mmol). Purify by chromatography on silica gel eluting with hexane/EtOAc (1:0 and 3:1). Concentrate in vacuo. Dissolve the residue (287 mg, 0.89 mmol) in methanol (25 mL) and add 5N NaOH (7 mL). Stir at room temperature for 4 h. Dilute with DCM and add solid sodium chloride to the mixture. Extract the aqueous layer three times with DCM. Combine organic extracts, dry over $Na_2SO_4$ and concentrate in vacuo. Purify by chromatography on silica gel eluting with DCM/2M ammonia in methanol (94:6) to obtain the title compound (124 mg, 62%). MS (ES+) m/z: 500 (M+H)$^+$.

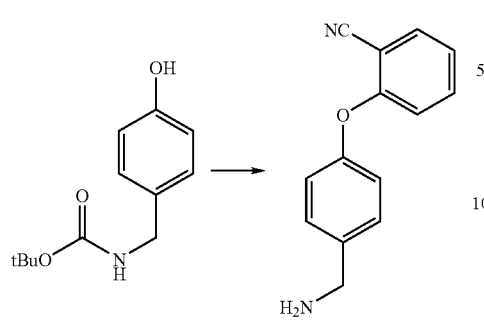

(4-Hydroxybenzyl)-carbamic acid tert-butyl ester: Mix 2,2,2-trifluoro-N-(4-hydroxybenzyl)-acetamide (8.8 g, 40 mmol), and 5N aqueous NaOH (20 mL) in methanol (100 mL). Stir at ambient temperature for 4 h. Adjust pH to about 8 with aqueous HCl. Add solid sodium bicarbonate (4.4 g, 52 mmol), di-tert-butyl-dicarbonate (9.3 g, 40 mmol) and DCM. Stir at ambient temperature for 16 h. Dilute with DCM, wash with 1N aqueous HCl and purify by chromatography on silica gel eluting with hexane/EtOAc (9:1 to 5:5) to obtain the desired intermediate (7.8 g, 87%). MS (ES−) m/z: 222 (M−H)$^-$.

2-(4-Aminomethyl-phenoxy)-benzonitrile: Mix under argon (4-hydroxybenzyl)-carbamic acid tert-butyl ester (1.5 g, 6.7 mmol), 2-bromobenzonitrile (813 mg, 4.5 mmol), 2,2,6,6-tetramethylheptane-3,5-dione (83 mg, 0.45 mmol), and cesium carbonate (2.2 g, 6.7 mmol) in anhydrous NMP (8.5 mL). Degas the flask and fill with argon. Add copper(I) chloride (223 mg, 2.25 mmol) quickly. Degas the flask, fill with argon and heat at 120° C. for 3 h. Cool to ambient temperature, dilute with EtOAc, filter and concentrate in vacuo. Purify by chromatography on silica gel eluting with hexane/EtOAc (1:0, 9:1 and 3:1). Evaporate the solvent and dissolve the residue in DCM (100 mL). Add trifluoroacetic acid (20 mL) and stir at ambient temperature for 16 h. Concentrate in vacuo, dissolve the residue in EtOAc and wash with 1N aqueous NaOH. Dry over $Na_2SO_4$ and concentrate in vacuo. Purify by SCX chromatography to obtain the title compound (385 mg, 38%). MS (ES+) m/z: 225 (M+H)$^+$.

The compounds of Preparation 4143 may be prepared essentially as described in Preparation 40 by using (4-hydroxybenzyl)-carbamic acid tert-butyl ester (1.5 g, 6.7 mmol) and the appropriate bromide. Overall yields and MS (ES+) data are shown in the Table below.

| Prep. | Compound | Yield (%) | MS (ES+) m/z |
|---|---|---|---|
| 41 | 4-(2'-Trifluoromethyl-phenoxy)-benzylamine | 13 | 251 (M + H − NH$_3$)$^+$ |
| 2 | 4-(3'-Trifluoromethyl-phenoxy)-benzylamine | 27 | 251 (M + H − NH$_3$)$^+$ |
| 43 | 4-(Pyridin-3-yloxy)-benzylamine | 11 | 201 (M + H)$^+$ |

Preparation 45

4-(3,3-Dimethylbutoxy)-benzylamine

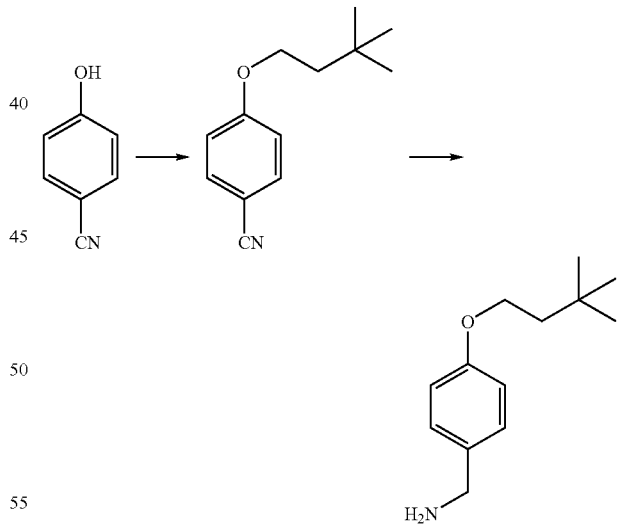

4-(3,3-Dimethylbutoxy)-benzonitrile: Mix 4-cyanophenol (1.2 g, 10 mmol), 1-bromo-3,3-dimethylbutane (5.3 g, 32 mmol), powdered potassium carbonate (4.14 g, 30 mmol), and powdered potassium iodide (166 mg, 1 mmol) in acetone (60 mL). Stir under inert atmosphere and heat at reflux for 48 h. Cool the reaction mixture to ambient temperature. Dilute with acetone, filter and evaporate. Purify by chromatography on silica gel eluting with hexane/EtOAc (10 and 9:1) to obtain the desired intermediate (1.8 g, 89%). MS (ES+) m/z: 221 (M+NH$_4$)$^+$.

4-(3,3-Dimethylbutoxy)-benzylamine: Mix lithium aluminum hydride (1.0 g, 26.6 mmol) and anhydrous ethyl ether (70 mL) under nitrogen atmosphere. Stir and cool to 0° C. in an ice bath. Add dropwise a solution of 4-(3,3-dimethylbutoxy)-benzonitrile (1.8 g, 8.87 mmol) in anhydrous ethyl ether (20 mL). Stir for 2 h at 0° C., remove the ice bath and stir at ambient temperature for 18 h. Cool the reaction flask in an ice bath and add carefully dropwise and sequentially water (1 mL), 2N aqueous NaOH (1 mL), and water (2 mL). Stir for 30 min. filter, separate the organic layer, dry over $Na_2SO_4$ and concentrate in vacuo to obtain the title compound (1.62 g, 88%). MS (ES+) m/z: 191 M+H−$NH_3)^+$.

The compounds of Preparations 46-48 may be prepared essentially as described in Preparation 45 by using 4-cyanophenol and the appropriate bromide. Overall yields and MS (ES+) data are shown in the Table below.

| Prep. | Compound | Yield (%) | MS (ES+) m/z |
|---|---|---|---|
| 46 | 4-Cyclohexylmethoxy-benzylamine | 90 | 203 (M + H − $NH_3)^+$ |
| 47 | 4-(2-Cyclohexylethoxy)-benzylamine | 94 | 217 (M + H − $NH_3)^+$ |
| 48 | 4-(2,2-Dimethylpropoxy)-benzylamine | 4 | 177 (M + H − $NH_3)^+$ |

Preparation 49

4-Benzyloxy-benzylamine

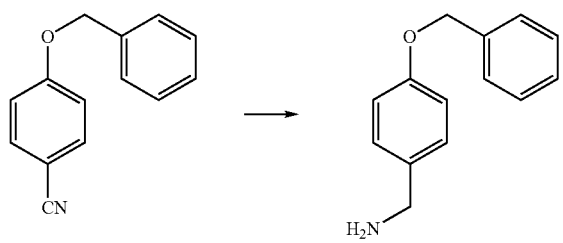

4-Benzyloxy-benzonitrile: Add 4-cyanophenol (1.191 g, 10 mmol), benzyl bromide (1.881 g, 11 mmol), potassium carbonate (3.455 g, 25 mmol) and potassium iodide (166 mg, 1 mmol) to acetonitrile (80 mL) and heat at reflux for 12 h. Cool, partition between EtOAc and water, separate he organic layer, and extract the aqueous layer with EtOAc. Combine the organic extracts, wash with brine, dry over $Na_2SO_4$, filter and concentrate. Purify by chromatography on silica gel eluting with EtOAc/hexane (1:6) to give the desired intermediate as a white solid (2.098 g, 100%). MS (ES+) m/z: 227 (M+$NH_4)^+$.

4-Benzyloxy-benzylamine: Use a method similar to Preparation 58, using 4-benzyloxy-benzonitrile (2.098 g, 10 mmol), to give the title compound as a white solid (2.021 g, 94%). MS (ES+) m/z: 197 M+H−$NH_3)^+$.

Preparation 50

(±)-4-(1-Phenylethoxy)-benzylamine

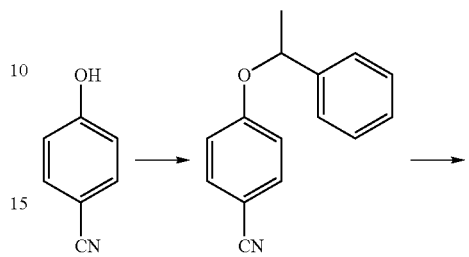

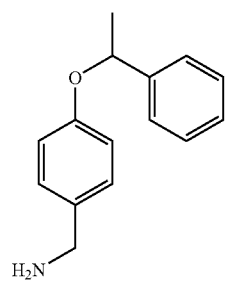

(±)-4-(1-Phenylethoxy)-benzonitrile: Add triphenylphosphine (7.869 g, 30 mmol) to a solution of sec-phenylethyl alcohol (1.467 g, 12 mmol), 4-cyanophenol (1.191 g, 10 mmol) and diethyl azodicarboxylate (4.528 g, 26 mmol) in anhydrous THF (50 mL) at 0° C. Stir the reaction at ambient temperature for 12 h. Dilute with EtOAc, wash with brine, dry over $Na_2SO_4$, filter and concentrate. Purify by chromatography on silica gel eluting with EtOAc/hexane (1:8) to give (±)-4-(1-phenylethoxy)-benzonitrile with a small amount of triphenylphosphine (2.49 g total).

(±)-4-(1-Phenylethoxy)-benzylamine: Use a method similar to Preparation 58, using crude (±)-4-(1-phenylethoxy)-benzonitrile, to give the title compound as a colorless oil (1.6 g, 70% two steps). MS (ES+) m/z: 211 M+H−$NH_3)^+$, 455.3 (2M+H)$^+$.

Preparation 51

4-(3,3-Dimethyl-2-oxo-butoxy)-benzylamine

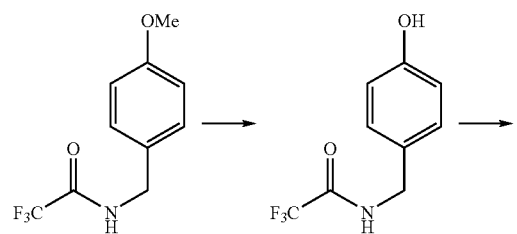

-continued

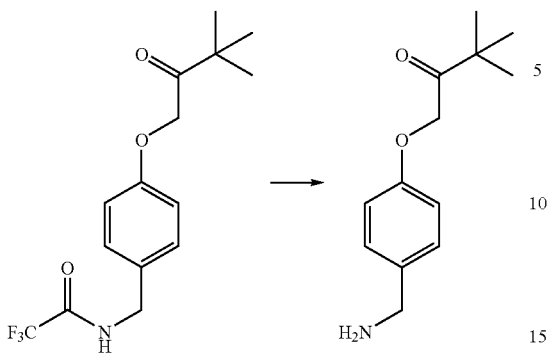

2,2,2-Trifluoro-N-(4-methoxybenzyl)acetamide: Mix under nitrogen atmosphere 4-methoxybenzylamine (13.7 g, 100 mmol) and N-methylmorpholine in anhydrous THF (300 mL). Cool to 0° C. in an ice bath. Add dropwise a solution of trifluoroacetic anhydride (15.6 mL, 110 mmol) in anhydrous THF (25 mL). Warm up to ambient temperature slowly and stir for 16 h. Concentrate in vacuo. Dissolve in EtOAc and wash successively with 1N aqueous NaOH, 1N aqueous HCl, and brine. Separate the organic layer, dry over $Na_2SO_4$ and concentrate in vacuo. Purify by chromatography on silica gel eluting with hexane/EtOAc (9:1 and 4:1) to obtain the desired intermediate (19 g, 81%). MS (ES−) m/z: 232 (M−H)−.

2,2,2-Trifluoro-N-(4-hydroxy-benzyl)-acetamide: Dissolve under nitrogen atmosphere 2,2,2-trifluoro-N-(4-methoxybenzyl)-acetamide (11.6 g, 50 mmol) in DCM (250 mL). Cool to 0° C. in an ice bath. Add dropwise 1M boron tribromide in DCM (100 mL, 100 mmol) and stir for 20 min after addition. Warm to ambient temperature and stir for 16 h. Cool the reaction mixture in an ice bath and quench very carefully with saturated aqueous $NaHCO_3$. Separate the organic layer. Extract the aqueous layer twice with chloroform. Dry the combined organic extracts over-$Na_2SO_4$ and concentrate in vacuo to obtain the desired intermediate (8.8 g, 40 mmol). MS (ES−) m/z: 218 (M−H)−.

N-[4-(3,3-Dimethyl-2-oxo-butoxy)-benzyl]-2,2,2-trifluoroacetamide: Mix 2,2,2-trifluoro-N-(4-hydroxy-benzyl)-acetamide (438 mg, 2.0 mmol), 1-bromopinacolone (430 mg, 2.4 mmol), anhydrous potassium carbonate (829 mg, 6.0 mmol) and potassium iodide (33 mg, 0.1 mmol) with acetone. Heat under reflux for 12 h. Acidify with 1N aqueous HCl and extract with EtOAc three times. Combine the organic extracts, wash with brine, dry over $Na_2SO_4$, filter and concentrate. Purify by chromatography on silica gel eluting with EtOAc/hexane (1:3) to give the desired intermediate as a colorless oil. MS (ES+) m/z: 335 $(M+NH_4)^+$. MS (ES−) m/z: 316 (M−H)−.

4-(3,3-Dimethyl-2-oxo-butoxy)-benzylamine: Add 5N aqueous NaOH (15 mL) to a solution of N-[4-(3,3-dimethyl-2-oxo-butoxy)-benzyl]-2,2,2-trifluoro-acetamide (552 mg, 1.74 mmol) in methanol (0 mL) and stir for 2 h at ambient temperature. Extract the mixture with DCM three times. Dry the combined organic extracts over $Na_2SO_4$, filter and concentrate. Purify by chromatography on silica gel eluting with DCM/2M ammonia in methanol (92:8) to give the title compound as a colorless oil (337 mg, 87%). MS (ES+) m/z: 205 $M+H-NH_3)^+$.

Preparation 52

N-(2-Chloro-acetyl)-piperidine

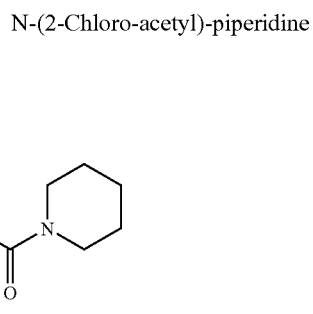

Add chloroacetyl chloride (1.242 g, 11.0 mmol) to a mixture of potassium carbonate (2.073 g, 15 mmol) and piperidine (852 mg, 10 mmol) in THF (50 mL) at 0° C. Stir the reaction for 12 h and gradually raise to room temperature. Dilute with water, extract with EtOAc three times. Combine the organic extracts and wash sequentially with saturated aqueous $NaHCO_3$, 0.1N aqueous HCl and brine. Dry over $Na_2SO_4$, filter and concentrate to give the title compound (1.65 g, 100%).

Preparation 53

4-Benzylthio-benzylamine

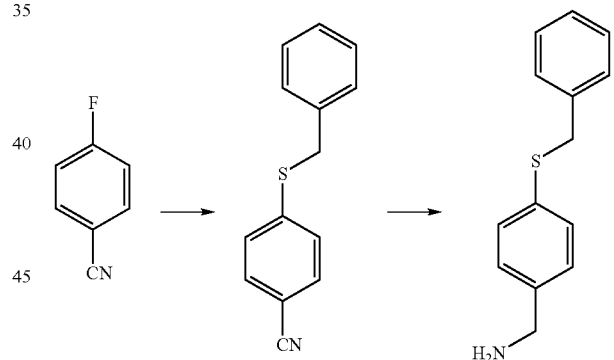

4-Benzylthio-benzonitrile: Mix under argon atmosphere 4-fluorobenzonitrile (1.21 g, 10 mmol), benzyl mercaptan (1.86 g, 15 mmol), and cesium carbonate (6.5 g, 20 mmol) in anhydrous NMP (20 mL). Degas the flask and fill with argon. Heat at 120° C. for 3 h. Cool to ambient temperature, dilute with EtOAc, filter and wash with 1N aqueous HCl. Separate the organic layer, dry over $Na_2SO_4$ and concentrate in vacuo. Purify by chromatography on silica gel eluting with hexane/EtOAc (1:0 and 9:1) to obtain the desired intermediate (689 mg, 31%). GC-MS m/z: 225 $(M^+)$.

4-Benzylthio-benzylamine: Use the reduction procedure described in Preparation 45 (Step 2), using 4-benzylthio-benzonitrile (689 mg, 3.1 mmol) to give, after SCX chromatography, the title compound (464 mg, 64%). MS (ES+) m/z: 213 $M+H-NH_3)^+$.

Preparation 54

4-(2,2,3,3,3-Pentafluoropropoxy)-benzylamine

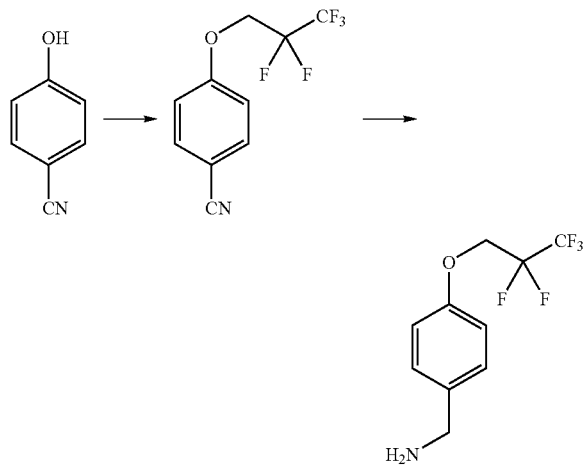

4-(2,2,3,3,3-Pentafluoropropoxy)-benzonitrile: Heat a mixture of 4-hydroxy-benzonitrile potassium fluoride complex (3.0 g, 16.9 mmol) and 1,1,1,2,2-pentafluoro-3-iodo-propane (10.8 g, 37.2 mmol) in DMSO (80 mL) to 130° C. for 20 h. Cool the mixture to ambient temperature, dilute with hexane/EtOAc (1:1, 200 mL) and wash with aqueous 10% NaCl (3×50 mL). Dry the organic layer, concentrate in vacuo and purify by chromatography on silica gel eluting with hexane/EtOAc (10:1, 10:2 and 10:3) to obtain the desired intermediate (1.1 g, 26%). GC-MS m/z: 251 (M$^+$).

4-(2,2,3,3,3-Pentafluoropropoxy)-benzylamine: Use a method similar to the General Procedure 64, using 4-(2,2,3,3,3-pentafluoropropoxy)-benzonitrile (1.1 g, 4.1 mmol), to obtain the title compound (1.1 g, 99%). GC-MS m/z: 254 (M$^+$–H).

Preparation 55

4-(2,2,3,3-Tetrafluoropropoxy)-benzylamine

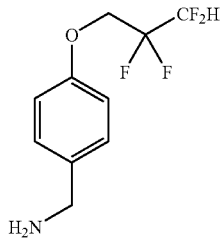

Use a method similar to Preparation 54, using 4-hydroxy-benzonitrile potassium fluoride complex (4.2 g, 23.7 mmol) and 1,1,2,2-tetrafluoro-3-iodo-propane (10 g, 41.3 mmol), to give the title compound (38% overall). GC-MS m/z: 236 (M$^+$–H).

Preparation 56

4-(2,2,2-Trifluoro-1,1-dimethyl-ethoxy)-benzylamine

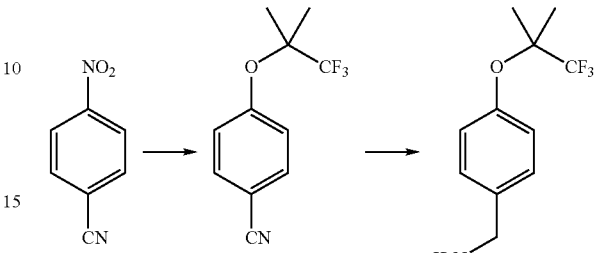

4-(2,2,2-Trifluoro-1,1-dimethyl-ethoxy)-benzonitrile: Add 2-trifluoromethyl-2-propanol (3.4 g, 27 mmol) slowly to a slurry of sodium hydride (0.6 g, 60% in mineral oil, washed with hexane) in HMPA (5 mL) under nitrogen. Stir the slurry for 15 min and add a solution of 4-nitrobenzonitrile (2.0 g, 13.5 mmol) in HMPA (10 mL). Stir the resulting purple slurry at ambient temperature for 16 h, dilute with diethyl ether (100 mL) and wash with 5% aqueous HCl (30 mL). Separate the layers and extract the aqueous layer with diethyl ether (2×50 mL). Combine the organic extracts and concentrate in vacuo. Purify by chromatography on silica gel eluting with hexane/EtOAc (9:1 to 1:1) to obtain the desired intermediate (780 mg, 25%). GC-MS m/z: 229 (M$^+$).

4-(2,2,2-Trifluoro-1,1-dimethyl-ethoxy)-benzylamine: Use a method similar to the General Procedure 64 to reduce 4-(2,2,2-trifluoro-1,1-dimethyl-ethoxy)-benzonitrile (780 mg, 3.4 mmol). Purify by chromatography on silica gel eluting with DCM/2M ammonia in methanol (40:1, 20:1 and 10:1) to obtain the title compound (780 mg, 98%). GC-MS m/z: 232 (M$^+$–H).

Preparation 57

(±)-4-(2,2,2-Trifluoro-1-methyl-ethoxy)-benzylamine

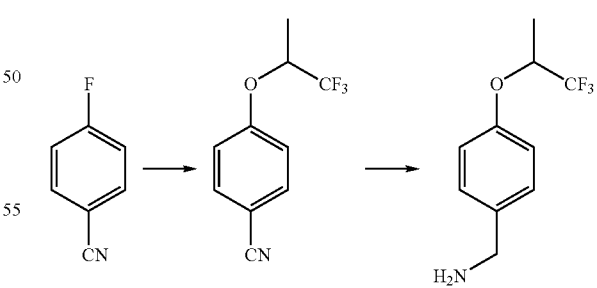

(±)-4-(2,2,2-Trifluoro-1-methyl-ethoxy)-benzonitrile: Add 1,1,1-trifluoro-2-propanol (3.8 g, 66 mmol) slowly to a slurry of sodium hydride (730 mg, 60% in mineral oil, washed with hexane) in HMPA (5 mL) under nitrogen. Stir the slurry for 15 min and add 4-fluorobenzonitrile (2 g, 16.5 mmol). Heat the slurry in a sealed flask to 90° C. for 16 h. Cool the mixture to ambient temperature and pour the mixture into a flask containing 5% aqueous HCl (20 mL). Extract the mixture with diethyl ether (3×50 mL), and wash with 5% aqueous HCl (25 mL). Dry the organic layer over Na₂SO₄ and concentrate in vacuo. Purify by chromatography on silica gel eluting with hexane/EtOAc (9:1) to obtain the desired intermediate (2.5 g, 70%). GC-MS m/z: 215 (M⁺).

(±)-4-(2,2,2-Trifluoro-1-methyl-ethoxy)-benzylamine: Use a method similar to the General Procedure 6-4, using (±)-4-(2,2,2-trifluoro-1-methyl-ethoxy)-benzonitrile (1.0 g, 4.6 mmol), to obtain the title compound (1.1 g, 95%). GC-MS m/z: 218 (M+H)⁺.

Preparation 58

3-Methoxybenzylamine

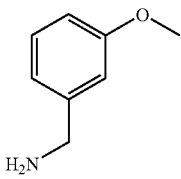

Add lithium aluminum hydride (3.795 g, 100 mmol) portion wise to a solution of 3-methoxybenzonitrile (5.326 g, 40 mmol) in anhydrous ethyl ether (200 mL) at 0° C. Stir for 1 h, warm to ambient temperature and continue to stir for 12 h. Quench the reaction with 0.1N aqueous NaOH, filter the solid, dry the filtrate over Na₂SO₄ and concentrate to give the title compound as a colorless oil (5.107 g, 93%). MS (ES+) m/z: 138 (M+H)⁺.

Preparation 59

3-(tert-Butyl)benzylamine

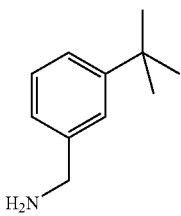

Dissolve 3-tert-butyltoluene (0.5 mL, 2.9 mmol) in carbon tetrachloride (20 mL). Add NBS (530 mg, 3 mmol) and irradiate the reaction mixture with a 250 watt sun-lamp with simultaneous heating to reflux for 1 h. Cool to ambient temperature, filter, and concentrate filtrate to dryness to give crude 1-bromomethyl-3-tert-butylbenzene. Dissolve crude 1-bromomethyl-3-tert-butylbenzene (600 mg) in anhydrous DMF. Add portion wise sodium azide (260 mg, 4 mmol) and stir at room temperature for 2 h. Pour the mixture into water (250 mL), extract with EtOAc (3×50 mL), wash combined organic extracts with brine, dry over MgSO₄, filter and evaporate solvent to give crude 1-azidomethyl-3-tert-butylbenzene, that was used without further purification. Dissolve crude 1-azidomethyl-3-tert-butylbenzene in methanol containing 10% Pd/C (75 mg) at 5° C., and stir the resulting slurry under 1 atm H₂ for 1 h. Filtrate, concentrate in vacuo and purify by chromatography on silica gel eluting sequentially with hexane/EtOAc (4:1 and 1:1), EtOAc, methanol and 2M ammonia in methanol to give the title compound (255 mg, 53% overall). MS (ES+) m/z: 164 (M+H)⁺.

Preparation 60

(3-Pyrrolidin-1-yl)benzylamine

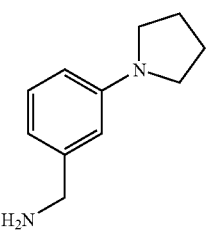

Slurry a mixture of (3-bromobenzyl)-carbamic acid tert-butyl ester (600 mg, 2.1 mmol, U.S. Pat. Appl. Publ. US 2003134885), pyrrolidine (450 mL, 5.2 mmol), tris(dibenzylideneacetone)dipalladium(0) (200 mg, 0.21 mmol), BINAP (400 mg, 0.63 mmol) and cesium carbonate (960 mg, 2.94 mmol) in anhydrous toluene (10 mL). Degas under vacuum, fill the system with nitrogen and heat in a sealed flask at 90° C. for 18 h. Cool to room temperature, dilute with diethyl ether, filter, and concentrate in vacuo. Dissolve the resulting residue in DCM (10 mL) and add trifluoroacetic acid (5 mL). Stir at ambient temperature for 1 h and concentrate in vacuo. Purify by chromatography on silica gel eluting sequentially with hexane/EtOAc (1:1), EtOAc and 2M ammonia in methanol. Purify again by SCX chromatography to give the title compound as a brown oil (300 mg, 85% overall). MS (ES+) m/z: 178 (M+H)⁺.

Preparation 61

(±)-C-(3-Methyl-2,3-dihydro-benzofuran-5-yl)-methylamine

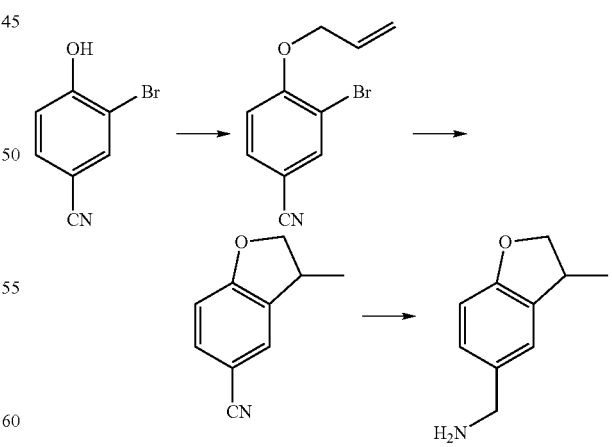

4-Allyloxy-3-bromo-benzonitrile: Mix 3-bromo-4-hydroxy-benzonitrile (1.520 g, 8.0 mmol), alkyl bromide (1.161 g, 9.6 mmol), potassium carbonate (3.317 g, 24 mmol) and potassium iodide (133 mg, 0.1 mmol) in acetone (80 mL). Heat the mixture to reflux for 12 h. Cool to ambient temperature, add EtOAc, wash the organic layer with water, and extract the aqueous layer twice with EtOAc. Dry the combined organic extracts over Na₂SO₄, filter and concentrate. Purify by chromatography on silica gel eluting with EtOAc/hexane (1:8) to obtain the desired intermediate.

(±)-3-Methyl-2,3-dihydro-benzofuran-5-carbonitrile: Add tri-n-butyltin hydride (5.821 g, 20 mmol) and AIBN (411 mg, 2.5 mmol) to a solution of 4-alkyloxy-3-bromo-benzonitrile (595 mg, 2.5 mmol). Heat the reaction at reflux for 20 h. Dilute with EtOAc and wash with water. Extract the aqueous layer with EtOAc three times. Combine the organic extracts, wash with brine, dry over Na₂SO₄, filter and concentrate in vacuo. Purify by chromatography on silica gel eluting with EtOAc/hexane (1:8) to give the desired intermediate as a white solid (474 mg, 100% with a trace amount of tributyltin derivative).

(±)-C-(3-Methyl-2,3-dihydro-benzofuran-5-yl)-methylamine: Use a method similar to Preparation 58, using (±)-3-methyl-2,3-dihydro-benzofuran-5-carbonitrile (474 mg, 2.98 mmol) to give the title compound as a colorless oil (410 mg, 84%).

The compounds of Preparations 62-64 may be prepared essentially as described in Preparation 61 by using 3-bromo-4-hydroxy-benzonitrile or 4-bromo-3-hydroxy-benzonitrile and the appropriately substituted alkyl bromide. MS (ES+) data are shown in the Table below.

| Prep. | Structure | Compound | MS (ES+) m/z |
|---|---|---|---|
| 62 | 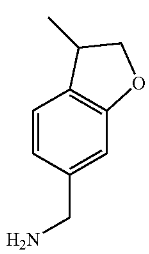 | (±)-C-(3-Methyl-2,3-dihydro-benzofuran-6-yl)-methylamine | 164 (M + H)⁺ |
| 63 | 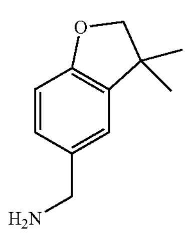 | C-(3,3-Dimethyl-2,3-dihydro-benzofuran-5-yl)-methylamine | ND |
| 64 | 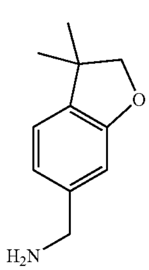 | C-(3,3-Dimethyl-2,3-dihydro-benzofuran-6-yl)-methylamine | 178 (M + H)⁺ |

ND = Not determined

Preparation 65

C-(2,2-Dimethyl-3-oxo-2,3-dihydro-benzofuran-5-yl)-methylamine

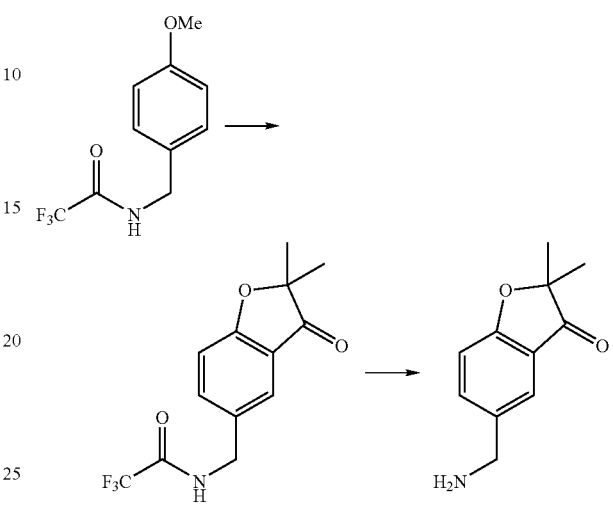

N-(2,2-Dimethyl-3-oxo-2,3-dihydro-benzofuran-5-ylmethyl)-2,2,2-trifluoro-acetamide: Add 2-bromoisobutyryl bromide (1.724 g, 7.5 mmol) to a solution of 2,2,2-trifluoro-N-(4-methoxy-benzyl)-acetamide (1.166 g, 5.0 mmol) in 1,2-dichloroethane (8 mL) at 15° C., then add powdered anhydrous iron(III) chloride (973 mg, 6.0 mmol). Stir the reaction at 15° C. for 3 h and at ambient temperature for 8 days. Add dropwise saturated aqueous potassium sodium tartrate, then water and EtOAc, and stir for 1 h. Filter off the solid, separate the organic layer, and extract the aqueous layer three times with EtOAc. Combine the organic extracts, wash with brine, dry over Na₂SO₄, filter and concentrate in vacuo. Purify by chromatography on silica gel eluting with EtOAc/hexane (1:3) to give the desired intermediate (253 mg, 17%).

C-(2,2-dimethyl-3-oxo-2,3-dihydro-benzofuran-5-yl)-methylamine: Dissolve N-(2,2-dimethyl-3-oxo-2,3-dihydro-benzofuran-5-ylmethyl)-2,2,2-trifluoro-acetamide (253 mg, 0.88 mmol) in 7M ammonia in methanol and stir at ambient temperature for 5 days. Remove volatiles in vacuo, purify by chromatography on silica gel eluting with DCM/2M ammonia in methanol (92:8) to give the title compound (44 mg, 26%). MS (ES+) m/z: 175 M+H−NH₃)⁺.

Preparation 66

C-(2,2-Dimethyl-3-oxo-2,3-dihydro-benzofuran-6-yl)-methylamine

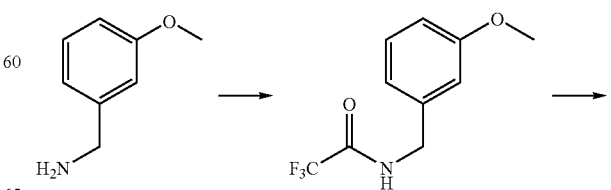

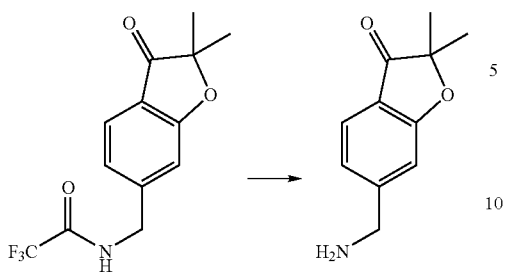

2,2,2-Trifluoro-N-(3-methoxy-benzyl)-acetamide: Add trifluoroacetic anhydride (6.3 g, 30 mmol) to a solution of 3-methoxybenzylamine (3.43 g, 25 mmol) and N-methylmorpholine (3.793 g, 37.5 mmol) in THF (80 mL) at 0° C. and stir at this temperature for 4 h. Warm to ambient temperature and stir for 12 h. Dilute with EtOAc, wash sequentially with water, 1N aqueous HCl, saturated aqueous NaHCO$_3$ and brine. Dry the organic layer over Na$_2$SO$_4$, filter and concentrate. Purify by chromatography on silica gel eluting with EtOAc/hexane (1:3) to give the desired intermediate (5.344 g, 91%).

C-(2,2-Dimethyl-3-oxo-2,3-dihydro-benzofuran-6-yl)-methylamine: Use a method similar to Preparation 65, using 2,2,2-trifluoro-N-(3-methoxy-benzyl)-acetamide (1.166 g, 5 mmol), to give the title compound (220 mg, 23% two steps). MS (ES+) m/z: 192 (M+H)$^+$.

Preparation 67

6-Aminomethyl-2,2-dimethyl-2H-chromene

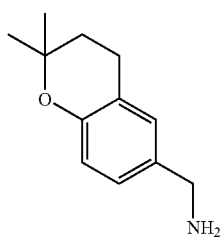

Add 2,2-dimethyl-2H-chromene-6-carbonitrile (1.5 g, 8.1 mmol) and ethanol wet Raney® activated nickel (0.4 g) to a Parr pressure vessel. Immediately add 7N ammonia in methanol (170 mL) and seal the vessel. Purge the reaction vessel with nitrogen, pressurize the reaction mixture with hydrogen (3400 KPa), seal the vessel, agitate the reaction and heat to 60° C. for 20 h. Turn off the heat and allow the reaction mixture to cool to ambient temperature. Vent the excess hydrogen from the vessel and purge the vessel with nitrogen. Filter the reaction mixture to remove the Raney® nickel. Purify by chromatography on silica gel eluting with DCM/2M ammonia in methanol (9:1) to obtain the title compound (1.5 g, 97%). MS (ES+) m/z: 175 M+H–NH$_3$)$^+$.

Preparation 68

4-(2-Methylthiazol-4-yl)-benzylamine

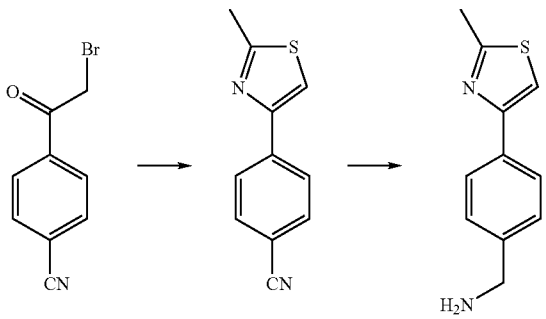

4-(2-Methylthiazol-4-yl)-benzonitrile: Suspend 4-cyanophenacyl bromide (515 mg, 2.23 mmol) in ethanol (15 mL). Add thioacetamide (171 mg, 2.23 mmol) and sodium bicarbonate (187 mg, 2.23 mmol) and heat the mixture under reflux for 2 h. Concentrate in vacuo and dissolve the residue in DCM. Wash the organic fraction with water, dry over Na$_2$SO$_4$, filter and concentrate to give a solid. Suspend the solid in ether/hexane and filter under vacuum washing with hexane to obtain the desired intermediate as a white solid (415 mg, 93%). GC-MS m/z: 200 (M$^+$).

442-Methylthiazol-4-yl)-benzylamine: Dissolve 4-(2-methylthiazol-4-yl)-benzonitrile (305 mg, 1.52 mmol) in anhydrous THF (50 mL). Add a 1M solution of lithium aluminum hydride in THF (3.05 mL, 3.05 mmol). Heat the mixture overnight under reflux. Cool the reaction mixture with ice/water and work-up sequentially with EtOAc and water. Filter the mixture over Celite®. Separate the organic phase, and extract the aqueous phase with chloroform. Dry the combined organic extracts over Na$_2$SO$_4$, filter and concentrate to obtain the title compound as an oil (120 mg) that was used without further purification. GC-MS m/z: 204

Preparation 69

4-(Pyridin-4-yl)-benzylamine

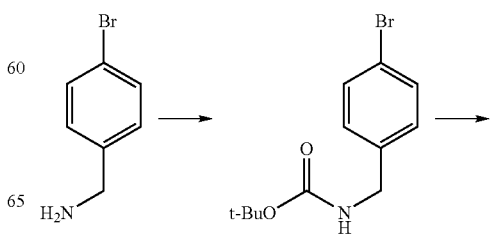

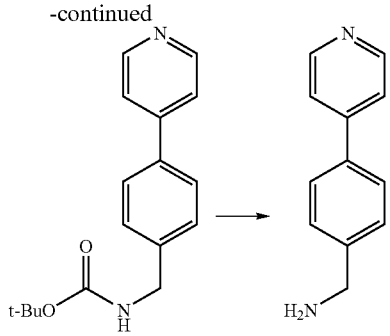

N-(tert-Butoxycarbonyl)-4-bromo-benzylamine: Add di-tert-butyl-dicarbonate (1.173 g, 5.375 mmol) and triethylamine (1.087 g, 1.0 mL, 10.75 mmol) to a stirred solution of 4-bromobenzylamine (1.0 g, 5.375 mmol) in anhydrous DCM (15 mL). Stir overnight at ambient temperature, dilute with DCM and wash with water. Separate the organic phase, dry over Na₂SO₄, filter and concentrate in vacuo. Purify by chromatography on silica gel eluting with hexane/EtOAc (1:0, 19:1 and 9:1) to obtain the desired intermediate as a solid (1.24 g, 81%).

N-(tert-Butoxycarbonyl)-4-(Pyridin-4-yl)-benzylamine: Dissolve N-(tert-butoxycarbonyl)-4-bromo-benzylamine (0.8 g, 2.807 mmol) in anhydrous DME (12 mL) under nitrogen. Add tetrakis(triphenylphosphine)palladium(0) (0.162 g, 0.14 mmol), pyridine-4-boronic acid (0.513 g, 4.211 mmol), and a 2M aqueous Na₂CO₃ solution (2.8 mL, 5.614 mmol). Heat the reaction overnight at 70° C. Cool the mixture to ambient temperature, dilute with EtOAc, and filter over Celite®. Wash the organic fraction with water, dry over Na₂SO₄, filter and concentrate in vacuo. Purify by chromatography on silica gel eluting with hexane/EtOAc (1:0, 4:1 and 1:1) to give the title compound as an oil (0.295 g, 37%). GC-MS m/z: 284 (M⁺).

4-(Pyridin-4-yl)-benzylamine: Dissolve N-(tert-butoxycarbonyl)-4-(4-pyridyl)-benzylamine (363 mg, 1.276 mmol) in anhydrous DCM (10 mL). Add 4N hydrogen chloride in dioxane (10 mL) and stir overnight at ambient temperature. Concentrate in vacuo to obtain the hydrochloride salt in pure form as a solid. Dissolve the solid in saturated aqueous NaHCO₃ and extract three times with DCM and three more times with EtOAc. Combine the organic extracts, dry over Na₂SO₄, filter and concentrate to obtain the title compound as a solid (166 mg, 71%). GC-MS m/z: 184 (M⁺).

Preparation 70

4-(Pyridin-2-yl)-benzylamine

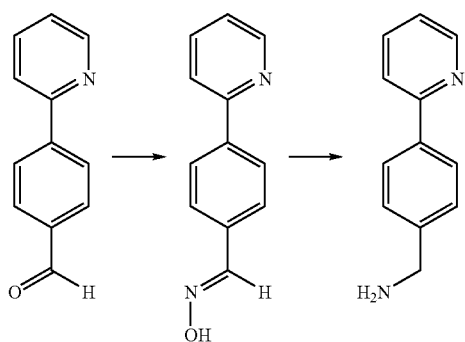

4-(2-Pyridyl)-benzaldehyde oxime: Add hydroxylamine hydrochloride (0.379 g, 5.458 mmol) and a solution of NaOH (0.327 g, 8.187 mmol) in water (2 mL) to a solution of 4-(2-pyridyl)-benzaldehyde (0.5 g, 2.729 mmol) in ethanol (10 mL). Heat the mixture at 80° C. for 2 h. Cool to ambient temperature and remove the solvent in vacuo. Partition the residue between EtOAc and water. Separate and dry the organic phase over Na₂SO₄, filter and concentrate in vacuo. Purify by chromatography on silica gel eluting with hexane/EtOAc (1:0 and 4:1) to obtain the desired intermediate (311 mg, 58%). GC-MS m/z: 198 (M⁺).

4-(Pyridin-2-yl)-benzylamine: Add Pd/C (10%, 50 mg) and concentrated HCl (2 mL) to a solution of 4-(2-pyridyl)-benzaldehyde oxime (0.29 g, 1.46 mmol) in absolute ethanol (20 mL). Hydrogenate the mixture at 50 psi for 2 h. Filter over Celite®, wash with ethanol and concentrate in vacuo to obtain the hydrochloride salt in pure form as a solid. Dissolve the solid in saturated aqueous NaHCO₃, extract the aqueous solution three times with DCM and three more times with EtOAc. Combine the organic extracts, dry over Na₂SO₄, filter and concentrate in vacuo to obtain the title compound as a solid (130 mg, 48%). GC-MS m/z: 184 (M⁺).

Preparation 71

4-(1-Methyl-1H-imidazol-2-yl)-benzylamine

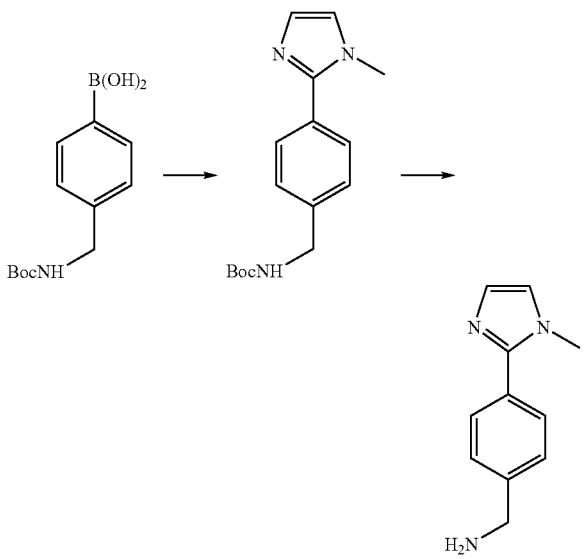

[4-(1-Methyl-1H-imidazol-2-yl)-benzyl]-carbamic acid tert-butyl ester: Add 4-(N-tert-Butoxycarbonyl-aminomethyl)phenylboronic acid (1.9 g, 7.4 mmol), 2-bromo-1-methyl-1H-imidazole (800 mg, 5.0 mmol), tetrakis(triphenylphosphine)-palladium(0) (287 mg, 0.25 mmol) and potassium carbonate (860 mg, 6.2 mmol) to a flask containing toluene (10 mL). Heat the mixture in a sealed flask at 90° C. for 16 h. Cool the mixture, dilute with EtOAc (50 mL), filter through Celite®, and concentrate in vacuo. Purify by chromatography on silica gel eluting with hexane/EtOAc/methanol (49:50:1) to obtain the desired intermediate (1.2 g, 83%). GC-MS m/z: 287 (M⁺).

4-(1-Methyl-1H-imidazol-2-yl)-benzylamine: Dissolve [4-(1-methyl-1H-imidazol-2-yl)-benzyl]-carbamic acid tert-butyl ester (500 mg, 1.7 mmol) in DCM (20 mL) and trifluoroacetic acid (5 mL). Stir the mixture for 1 h at ambient temperature. Concentrate in vacuo and purify by SCX chromatography to obtain the title compound (240 mg, 74%). MS (ES+) m/z: 188 (M+H)⁺.

Preparation 72

4-Ethanesulfonyl-benzylamine

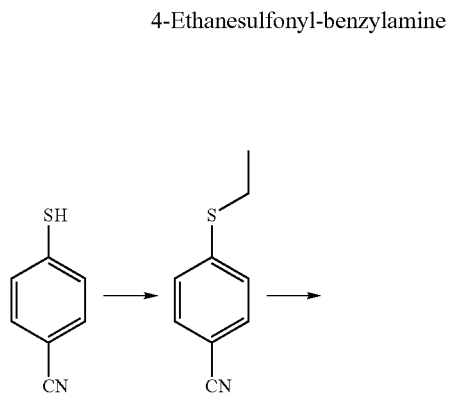

4-Ethylthio-benzonitrile: Combine 4-mercapto-benzonitrile (0.4 g, 2.96 mmol), bromoethane (1.4 mL, 8.88 mmol) and potassium carbonate (3.3 g, 23.7 mmol) in anhydrous DMF (7 mL) and heat at 60° C. for 17 h. Cool the reaction mixture to ambient temperature and partition between brine (20 mL) and EtOAc (20 mL). Separate the organic layer, dry over anhydrous Na₂SO₄ and concentrate. Purify by chromatography on silica gel eluting with hexane/EtOAc (1:0, 9:1 and 4:1) to obtain the desired intermediate as a colorless oil (0.4 g, 83%).

4-Ethanesulfonyl-benzonitrile: Dissolve 4-ethylthio-benzonitrile (0.4 g, 2.4 mmol) in TFA (10 mL) and add slowly hydrogen peroxide (30 w %, 10 mL) at 5° C. Stir the reaction mixture at ambient temperature for 2 h and partition between brine (20 mL) and DCM (20 mL). Separate the organic layer, dry over anhydrous Na₂SO₄ and concentrate to obtain the desired intermediate as a white solid (0.5 g, 100%). GC-MS m/z: 195 (M⁺).

4-Ethanesulfonyl-benzylamine: Combine 4-ethanesulfonyl-benzonitrile (0.7 g, 3.5 mmol), Raney® 3201 nickel (slurry in water, 0.1 g), 2N ammonia in methanol (20 mL) and hydrogenate at 50 psi for 17 h. Filter the reaction mixture through a pad of Celite® and concentrate in vacuo. Purify by SCX chromatography to obtain the title compound as a yellow oil (0.3 g, 43%).

Preparation 73

4-(2-Propanesulfonyl)-benzylamine

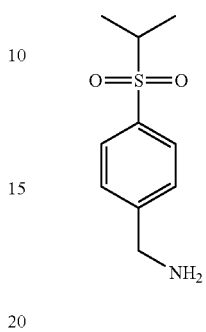

Use a method similar to Preparation 72, using 4-mercapto-benzonitrile (0.5 g, 3.7 mmol) and 2-bromopropane (1.4 g, 11.38 mmol), to obtain the title compound as a yellow oil (0.3 g, 39% overall).

Preparation 74

4-Aminomethyl-N-tert-butyl-benzamide

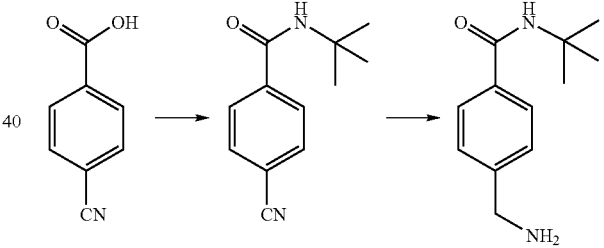

N-tert-butyl-4-cyano-benzamide: Combine 4-cyanobenzoic acid (30 mg, 2.07 mmol), tert-butylamine (0.5 mL, 4.13 mmol), triethylamine (0.4 mL, 2.89 mmol), and HATU (1.1 g, 2.89 mmol) in anhydrous DME (7 mL). Stir at ambient temperature for 17 h. Partition the reaction mixture between brine (15 mL) and diethyl ether (15 mL), separate the organic layer, dry over anhydrous Na₂SO₄ and concentrate in vacuo. Purify by chromatography on silica gel eluting with DCM to obtain the desired intermediate as a white solid (0.4 g, 89%). MS (ES+) m/z: 203 (M+H)⁺.

4-Aminomethyl-N-tert-butyl-benzamide: Combine N-tert-butyl-4-cyano-benzamide (0.4 g, 1.78 mmol), Raney® 3201 nickel (slurry in water, 0.03 g), 2N ammonia in methanol (20 mL) and hydrogenate at 50 psi for 1 h. Filter the reaction mixture through a pad of Celite®, remove the solvent and purify by SCX chromatography to obtain the title compound as a colorless oil (0.4 g, 95%). MS (ES+) m/z: 207 (M+H)⁺.

Preparation; 75

4-Aminomethyl-2-fluoro-N-tert-butyl-benzamide

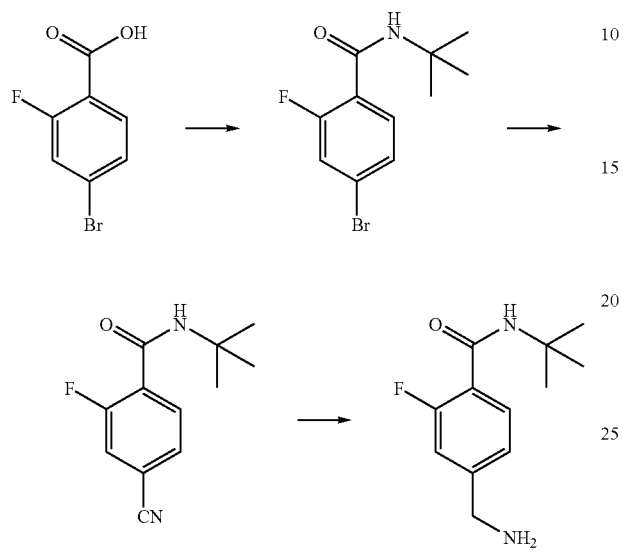

4-Bromo-N-tert-butyl-2-fluoro-benzamide: Combine 4-bromo-2-fluoro-benzoic acid (5.0 g, 22.83 mmol), thionyl chloride (10 mL, 0.137 mmol) in toluene (10 mL) and reflux for 2 h. Evaporate the reaction mixture to obtain 4-bromo-2-fluoro-benzoyl chloride (5.0 g, 93%) and use for the next step without further purification. Dissolve tert-butylamine (0.8 mL, 5.12 mmol) and triethylamine (0.8 mL, 6.32 mmol) in anhydrous DCM (20 mL), cool to 0° C. and add a solution of 4-bromo-2-fluoro-benzoyl chloride (1.0 g, 4.22 mmol) in anhydrous DCM (10 mL). Stir the reaction mixture at 0° C. for 10 min, warm to ambient temperature and continue to stir for 30 min. Wash the reaction mixture with brine (2×10 mL), dry the organic extracts over anhydrous $Na_2SO_4$, evaporate the solvent and purify by chromatography on silica gel eluting with DCM to obtain the desired intermediate as a white solid (1.0 g, 87%). MS (ES+) m/z: 275 $(M+H)^+$.

N-tert-Butyl-4-cyano-2-fluoro-benzamide: Combine 4-bromo-N-tert-butyl-2-fluoro-benzamide (1.0 g, 3.65 mmol) and copper(I) cyanide (0.7 g, 7.29 mmol) in anhydrous DMF (10 mL) and reflux for 17 h. Cool the reaction mixture to ambient temperature and treat with 50% (v/v) aqueous ethylenediamine (20 mL). Extract the reaction mixture with diethyl ether (3×10 mL), combine the organic extracts, wash with brine (2×10 mL) and dry the organic layer over $Na_2SO_4$. Evaporate the solvent and purify by chromatography on silica gel eluting with hexane/EtOAc (1:0, 9:1, 4:1, 7:3 and 3:2) to obtain the desired intermediate as a white solid (0.6 g, 77%). MS (ES+) m/z: 221 $(M+H)^+$.

4-Aminomethyl-2-fluoro-N-tert-butyl-benzamide: Combine N-tert-butyl-4-cyano-2-fluoro-benzamide (0.6 g, 1.78 mmol), Raney® 3201 nickel (slurry in water, 30 mg), 2N ammonia in methanol (30 mL) and hydrogenate at 50 psi for 1 h. Filter the reaction mixture through a pad of Celite®, concentrate in vacuo and purify by SCX chromatography to obtain the title compound as a colorless oil (0.6 g, 96%).

Preparation 76

4-Aminomethyl-2-fluoro-N-methyl-N'-propyl-benzamide

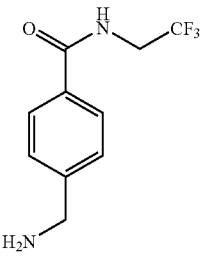

Use a method similar to Preparation 75, using 4-bromo-2-fluoro-benzoic acid (1.0 g, 4.56 mmol) and N-methyl-propylamine (0.5 mL, 5.05 mmol), to give the title compound as a colorless oil (0.5 g, 49%). GC-MS m/z: 224 $(M^+)$.

Preparation 77

4-Aminomethyl-N-(2,2,2-trifluoro-ethyl)-benzamide

Use the General Procedure 6-1, using 2,2,2-trifluoroethylamine (197 mg, 2 mmol) and 4-(tert-butoxycabonylaminomethyl)-benzoic acid, to give the title compound as a clear oil (440 mg, 94%). MS (ES+) m/z: 233 $(M+H)^+$.

The compounds of Preparations 78-93 may be prepared essentially as described in Preparation 77 by using 4-tert-butoxycabonylamino-methyl)-benzoic acid and the appropriate amine. Overall yields and MS (ES) data are shown in the Table below.

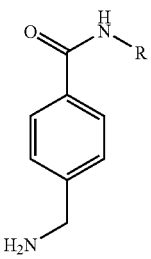

| Preparation | NH—R | Compound | Yield (%) | MS (ES) m/z |
|---|---|---|---|---|
| 78 | NH-C(CF3)(F)(F)-CH2- (2,2,3,3,3-pentafluoropropyl) | 4-Aminomethyl-N-(2,2,3,3,3-pentafluoro-propyl)-benzamide | 100 | 283 (M + H)+ |
| 79 | NH-CH(CH3)-CF3 | (±)-4-Aminomethyl-N-(2,2,2-trifluoro-1-methyl-ethyl)-benzamide | 78 | 247 (M + H)+ |
| 80 | NH-CH2-CH2-CF3 | 4-Aminomethyl-N-(3,3,3-trifluoro-propyl)-benzamide | 100 | 247 (M + H)+ |
| 81 | NH-CH(CH3)-CH2-CF3 | (±)-4-Aminomethyl-N-(3,3,3-trifluoro-1-methyl-propyl)-benzamide | 100 | 261 (M + H)+ |
| 82 | NH-cyclopentyl | 4-Aminomethyl-N-(cyclopentyl)-benzamide | 100 | 219 (M + H)+ |
| 83 | NH-cyclohexyl | 4-Aminomethyl-N-(cyclohexyl)-benzamide | 100 | 233 (M + H)+ |
| 84 | NH-cycloheptyl | 4-Aminomethyl-N-(cycloheptyl)-benzamide | 80 | 247 (M + H)+ |
| 85 | NH-(tetrahydropyran-4-yl) | 4-Aminomethyl-N-(tetrahydro-pyran-4-yl)-benzamide | 56 | ND |
| 86 | NH-(4-methylphenyl) | 4-Aminomethyl-N-(4-methyl-phenyl)-benzamide | 100 | 239 (M − H)− |
| 87 | NH-(4-chlorophenyl) | 4-Aminomethyl-N-(4-chloro-phenyl)-benzamide | 84 | 259 (M − H)− |
| 88 | NH-CH2-phenyl | 4-Aminomethyl-N-benzyl-benzamide | 59 | 241 (M + H)+ |
| 89 | NH-CH2-(3,4-difluorophenyl) | 4-Aminomethyl-N-(3,4-difluoro-phenyl)-benzamide | 100 | ND |

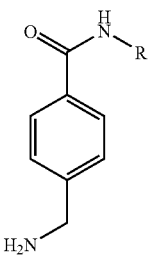

| Preparation | NH—R | Compound | Yield (%) | MS (ES) m/z |
|---|---|---|---|---|
| 90 | NH, CH(CH3)-Ph | (R)-4-Aminomethyl-N-(1-phenyl-ethyl)-benzamide | 94 | 255 (M + H)+ |
| 91 | NH, CH(CH3)-Ph | (S)-4-Aminomethyl-N-(1-phenyl-ethyl)-benzamide | 94 | 255 (M + H)+ |
| 92 | NH-C(CH3)2-Ph | 4-Aminomethyl-N-(1-methyl-1-phenyl-ethyl)-benzamide | 22 | 269 (M + H)+ |
| 93 | NH-CH(CH3)-CH2-Ph | (±)-4-Aminomethyl-N-(1-methyl-2-phenyl-ethyl)-benzamide | 85 | 269 (M + H)+ |

ND = Not determined

Preparation 94

4-(Piperidin-1-ylcarbonyl)-benzylamine

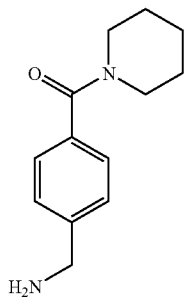

Use the General Procedure 6-1, using piperidine (373 mg, 4.4 mmol) and 4-(tert-butoxycabonylamino-methyl)-benzoic acid to give the title compound as a white solid (1.03 g, 100%). MS (ES+) m/z: 219 (M+H)+.

Preparation 95

4-Aminomethyl-N-cyclohexyl-2-fluoro-benzamide

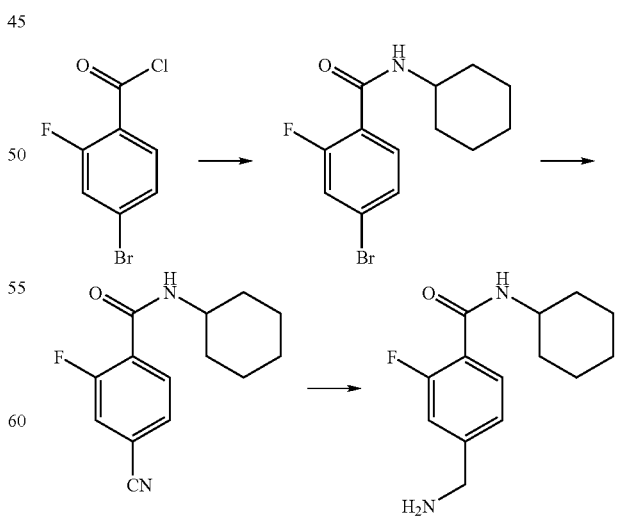

4-Bromo-N-cyclohexyl-2-fluoro-benzamide: Dissolve 4-bromo-2-fluoro-benzoyl chloride (1 g, 4.21 mmol) in DCM and cool the solution in an ice bath. Add triethylamine (0.87 mL, 6.32 mmol) and cyclohexylamine (502 mg, 5.1 mmol) and stir the mixture at ambient temperature for 2 h. Partition the reaction mixture between brine and DCM. Dry the organic layer over $Na_2SO_4$, filter and concentrate in vacuo to give the desired intermediate as a white solid (1.24 g, 98%).

4-Cyano-N-cyclohexyl-2-fluoro-benzamide: Heat a mixture of 4-bromo-N-cyclohexyl-2-fluoro-benzamide (1.24 g, 4.13 mmol) and copper cyanide (740 mg, 8.26 mmol) in DMF (20 mL) to reflux for 16 h. Cool the mixture to ambient temperature, add aqueous ethylenediamine and stir for 30 min. Extract the mixture with hexane/EtOAc (1:1), dry the organic layer over $Na_2SO_4$, filter and concentrate in vacuo. Purify the residue by chromatography on silica gel eluting with hexane/EtOAc (5:1) to give the desired intermediate as a white solid (620 mg, 61%). MS (ES−) m/z: 245 (M−H)⁻.

4-Aminomethyl-N-cyclohexyl-2-fluoro-benzamide: Dissolve 4-cyano-N-cyclohexyl-2-fluoro-benzamide (620 mg, 2.5 mmol) in 7N ammonia in methanol (150 mL) and hydrogenate at 500 psi pressure in the presence of Raney® nickel (500 mg) for 16 h at 60° C. Filter the mixture and concentrate in vacuo. Purify by SCX chromatography to give the title compound as a white solid (600 mg, 94%). MS (ES−) m/z: 251 (M−H)⁻.

Preparation 96

5-(Aminomethyl)-pyridine-2-carboxylic acid cyclohexylamide

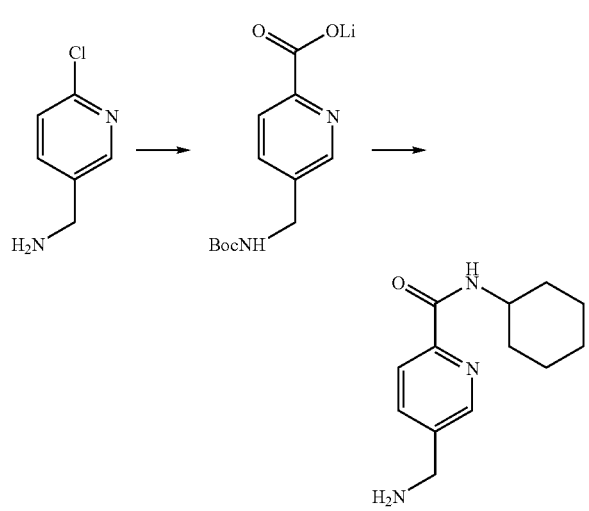

Lithium 5-(tert-butoxycarbonylamino-methyl)-pyridine-2-carboxylate: Dissolve 5-aminomethyl-2-chloro-pyridine (2 g, 14 mmol) and di-tert-butyl-dicarbonate (3.37 g, 15.4 mmol) in DCM (30 mL) and stir at room temperature for 2 h. Concentrate the reaction mixture and purify by chromatography on silica gel eluting with hexane/EtOAc (10:1 and 5:1) to give 5-(tert-butoxycarbonylamino-methyl)-2-chloro-pyridine as a yellow solid (3.6 g, 100%). MS (ES+) m/z: 243 (M+H)⁺. Dissolve 5-tert-butoxycarbonylamino-methyl)-2-chloro-pyridine (1 g, 4.12 mmol) in a mixture of ethanol (15 mL) and DMF (5 mL), and add potassium carbonate (427 mg, 3.09 mmol), palladium(II) acetate (92 mg, 0.4 mmol) and diphenylphosphinoferrocene (240 mg, 0.44 mmol). Pressurize the mixture 25 to 15 psi with carbon monoxide gas and heat the reaction mixture to 90° C. for 16 h. Filter the reaction mixture, concentrate the filtrate, and partition the residue between water and hexane/EtOAc (1:1). Dry the organic layer over $Na_2SO_4$, filter, and concentrate in vacuo. Purify the residue by chromatography on silica gel eluting with hexane/EtOAc (3:2) to give 5-(tert-butoxycarbonylamino-methyl)-pyridine-2-carboxylic acid ethyl ester as a brown oil (920 mg, 80%). MS (ES+) m/z: 281 (M+H)⁺. Dissolve 5-(tert-butoxycarbonylamino-methyl)pyridine-2-carboxylic acid ethyl ester (920 mg, 3.28 mmol) in a mixture of water/THF (1:2, 15 mL) and add lithium hydroxide (87 mg, 3.61 mmol). Stir the mixture at ambient temperature for 4 h and concentrate to a solid. Dry the material by azeotrope distillation with toluene to give the desired intermediate as a brown solid (1 g, 100%). MS (ES+) m/z: 253 (M+H)⁺.

5-(Aminomethyl)-pyridine-2-carboxylic acid cyclohexylamide: Use the General Procedure 6-2, using cyclohexylamine (1 mL), lithium 5-(tert-butoxycarbonylamino-methyl)-pyridine-2-carboxylate (1 g, 3.96 mmol) and DIEA (5 mL) as cosolvent, to give the title compound as a white solid (200 mg, 22%). MS (ES+) m/z: 234 (M+H)⁺.

Preparation 97

5-(Aminomethyl)-pyridine-2-carboxylic acid 4-fluoro-benzylamide

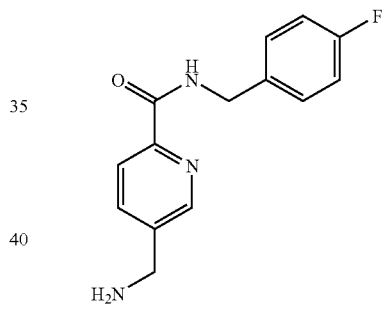

Use the General Procedure 6-2, using 4-fluoro-benzylamine (551 mg, 4.4 mmol), lithium 5-(tert-butoxycarbonylamino-methyl)-pyridine-2-carboxylate (740 mg, 2.93 mmol) and DIEA (2.6 mL) as cosolvent, to give the title compound as a white solid (200 mg, 26%). MS (ES+) m/z: 260 (M+H)⁺.

Preparation 98

2-Aminomethyl-5-(2,2,2-trifluoroethoxy)-pyridine

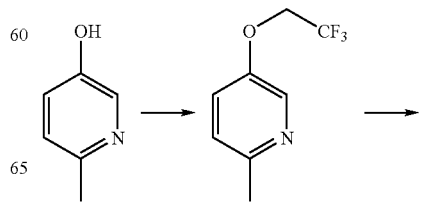

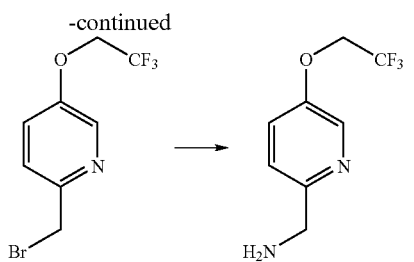

2-Methyl-5-(2,2,2-trifluoroethoxy)-pyridine: Add 5-hydroxy-2-methyl-pyridine (3.3 g, 30.6 mmol), potassium carbonate (17 g, 122.4 mmol) and 2-bromo-1,1,1-trifluoroethane (10 g, 61.2 mmol) to a flask containing DMF (60 mL) and heat to 95° C. for 20 h. Cool the mixture, dilute with aqueous 10% NaCl (20 mL) and extract with hexane/EtOAc (1:1, 100 mL). Filter the bi-phasic mixture through Celite®, separate and wash the organic layer with aqueous 10% NaCl (3×50 mL) and concentrate in vacuo. Purify by chromatography on silica gel eluting with hexane/EtOAc (9:1 to 1:1) to obtain the desired intermediate (4.1 g, 70%).

2-Bromomethyl-5-(2,2,2-trifluoroethoxy)-pyridine: Add 2-methyl-5-(2,2,2-trifluoroethoxy)-pyridine (2.5 g, 13.1 mmol), NBS (2.3 g, 13.1 mmol) and benzoyl peroxide (50 mg) to a flask containing carbon tetrachloride (30 mL). Heat the mixture at 80° C. in a sealed flask for 16 h. Cool the flask, add NBS (1.1 g, 6.5 mmol) and benzoyl peroxide (100 mg), then continue heating at 80° C. for an additional 5 h. Cool the mixture, dilute with DCM, then wash with saturated sodium bisulfite (10 mL). Collect the organic layer and concentrate in vacuo. Purify by chromatography on silica gel eluting with hexane/EtOAc (9:1) to obtain the desired intermediate (460 mg, 13%).

2-Aminomethyl-5-(2,2,2-trifluoroethoxy)-pyridine: Dissolve sodium azide (270 mg, 4.0 mmol) in DM (30 mL). Cool the solution to 0° C., then add 2-bromomethyl-5-(2,2,2-trifluoroethoxy)-pyridine (440 mg, 1.6 mmol) at 0° C. Slowly heat the mixture from 0° C. to 80° C. over 30 min. Cool the reaction, dilute with EtOAc (100 mL) and wash with 10% aqueous NaCl (3×25 mL). Collect the organic layer and concentrate in vacuo to a volume of 50 mL. Transfer the solution to a pressure vessel. Add 10% Pd/C (Degussa type E101, 50% water by wt, 500 mg) and pressurize the vessel under hydrogen (10 psi) for 1 h with stirring. Filter the mixture through Celite® and wash filter cake with warm methanol followed by DCM. Concentrate in vacuo, then purify by chromatography on silica gel eluting with DCM/2M ammonia in methanol (20:1) to obtain the title compound (180 mg, 54%). MS (ES+) m/z: 207 (M+H)+.

Preparation 99

2-Aminomethyl-5-(2,2,2-trifluoro-1,1-dimethyl-ethoxy)-pyridine

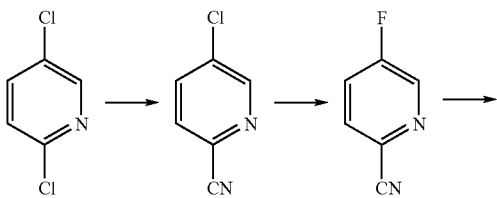

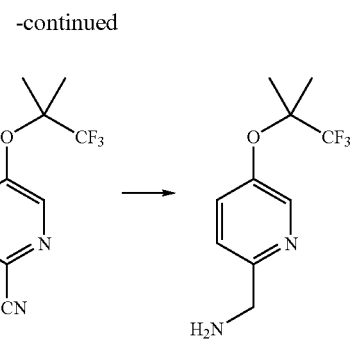

5-Chloro-pyridine-2-carbonitrile: Add 2,5-dichloropyridine (6.0 g, 40.5 mmol), zinc cyanide (2.9 g, 24.7 mmol), zinc dust (16 mg, 1.8 mmol) and 1,1'-[bis(diphenylphosphino)ferrocene]dichloropalladium(II) (20 mg, 0.98 mmol) to a flask containing DMF (40 mL). Heat the mixture to reflux for 5 h, then cool to ambient temperature. Dilute the mixture with EtOAc (300 mL) and wash with 10% aqueous NaCl (3×75 mL). Collect the organic layer, concentrate in vacuo and purify by chromatography on silica gel eluting with hexane/EtOAc (9:1 to 1:1) to obtain the desired intermediate (2.6 g, 46%).

5-Fluoro-pyridine-2-carbonitrile: Add 5-chloro-pyridine-2-carbonitrile (3.0 g, 21.7 mmol) and potassium fluoride (3.9 g, 67.1 mmol) to a flask containing NMP (75 mL). Heat the mixture to reflux for 16 h. Add additional potassium fluoride (1.0 g, 17.2 mmol) and NMP (10 mL), then continue heating at reflux for 3 h. Cool the mixture, dilute with EtOAc, then wash with saturated NaCl (3×50 mL). Collect the organic layer, concentrate in vacuo and purify by chromatography on silica gel eluting with hexane/EtOAc (20:1) to obtain the desired intermediate (1.5 g, 53%).

5-(2,2,2-Trifluoro-1,1-dimethyl-ethoxy)-pyridine-2-carbonitrile: Add 2-trifluoromethyl-2-propanol (1.1 g, 8.3 mmol) slowly to a slurry of sodium hydride (202 mg, 60% mineral oil, washed with hexane) in HMPA (3 mL) under nitrogen. Stir the slurry for 15 min, then add 5-fluoro-pyridine-2-carbonitrile (510 mg, 4.2 mmol). Stir the slurry for 16 h at ambient temperature. Adjust the mixture to pH 9 with sodium carbonate then extract with diethyl ether (3×50 mL). Collect the organic layer, dry over Na$_2$SO$_4$ and concentrate in vacuo. Purify by chromatography on silica gel eluting with hexane/EtOAc (95/5 to 80/20) to obtain the desired intermediate (768 mg, 79%). GC-MS m/z: 230 (Me).

2-Aminomethyl-5-(2,2,2-trifluoro-1,1-dimethyl-ethoxy)-pyridine: Add 5-(2,2,2-trifluoro-1,1-dimethyl-ethoxy)-pyridine-2-carbonitrile (580 mg, 2.5 mmol), 10% Pd/C (Degussa type E101, 50% water by wt, 400 mg) and trifluoroacetic acid (2 mL) in ethanol (20 mL) to a pressure vessel. Pressurize the vessel to 50 psi with hydrogen for 1 h. Filter the mixture through Celite® and wash the cake with warm ethanol followed by DCM under a nitrogen atmosphere. Concentrate in vacuo to obtain the crude product as the trifluoroacetic acid salt. Prepare the free base with SCX chromatography, then purify using silica gel chromatography eluting with DCM/2M ammonia in methanol (20:1) to obtain the title compound (261 mg, 45%). MS (ES+) m/z: 235 (M+H)+.

Preparation 100

(±)-2-Aminomethyl-5-(2,2,2-trifluoro-1-methyl-ethoxy)-pyridine

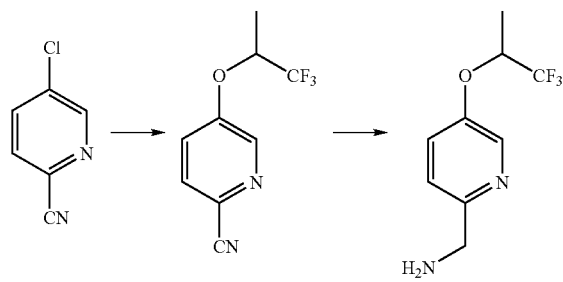

(±)-5-(2,2,2-Trifluoro-1-methyl-ethoxy)-pyridine-2-carbonitrile: Add 1,1,1-trifluoro-2-propanol (971 mg, 8.5 mmol) slowly to a slurry of sodium hydride (205 mg, 60% mineral oil, washed with hexane) in HMPA (8 mL) under nitrogen at 0° C. Allow the slurry to warm to ambient temperature and stir for 5 min. Add 5-chloro-pyridine-2-carbonitrile (590 mg, 4.2 mmol), then heat the mixture at 90° C. for 4 h. Adjust the mixture to pH 9 with sodium carbonate then extract with diethyl ether (2×50 mL). Dry the combined organic extracts over Na$_2$SO$_4$ and concentrate in vacuo. Purify by chromatography on silica gel eluting with hexane/EtOAc (95/5 to 80/20) to obtain the desired intermediate (818 mg, 89%). GC-MS m/z: 216 (M$^+$).

(±)-2-Aminomethyl-5-(2,2,2-trifluoro-1-methyl-ethoxy)-pyridine: Add (±)-5-(2,2,2-trifluoro-1-methyl-ethoxy)-pyridine-2-carbonitrile (810 mg, 3.7 mmol), 10% Pd/C (Degussa type E101, 50% water by wt, 300 mg), and trifluoroacetic acid (4 mL) in methanol (50 mL) to a pressure vessel. Pressurize the vessel to 40 psi with hydrogen for 0.25 h. Filter the mixture through Celite® and wash the cake with warm ethanol followed by DCM under a nitrogen atmosphere. Concentrate in vacuo to obtain the crude product as a trifluoroacetic acid salt. Prepare the free base with SCX ion chromatography, then purify by chromatography on silica gel eluting with DCM/2M ammonia in methanol (20:1) to obtain the title compound (676 mg, 82%). GC-MS m/z: 220 (M$^+$).

Preparation 101

2-Aminomethyl-5-fluoro-pyridine

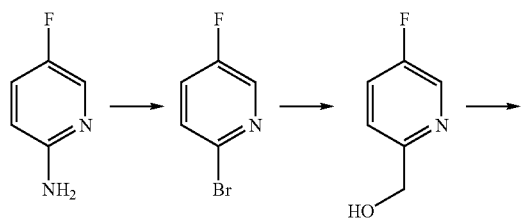

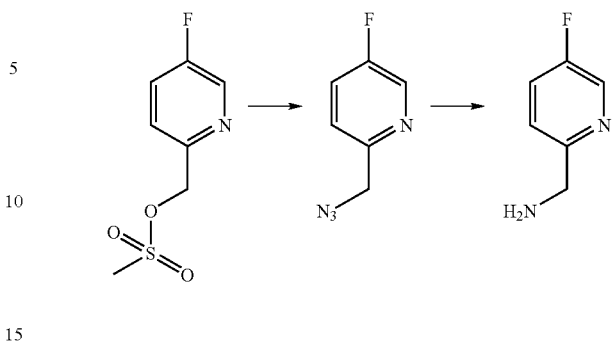

2-Bromo-5-fluoro-pyridine: Cool 48% hydrobromic acid (44 mL, 4.4 equiv.) in an ice/acetone bath to −5° C., then add 2-amino-5-fluoropyridine (10.0 g, 89.2 mmol, 1.0 equiv.) portion wise over 10 min and maintain the temperature below 5° C. throughout addition. Add bromine (14 mL, 3, equiv.) at 0° C. over 2 h and maintain the temperature at 0° C. throughout the addition. Stir the mixture for 30 min, then add a solution of sodium nitrite (15.4 g) in water (30 mL) via addition funnel over 2 h and maintain the temperature below 0° C. throughout the addition. Stir the mixture for 30 min., then add a solution of NaOH (34 g) in water (34 mL) over 1 h and maintain the temperature below 10° C. Stir the mixture for 3 min. Extract with diethyl ether (5×250 mL), dry the combined organic extracts over Na$_2$SO$_4$ and concentrate in vacuo to give the desired intermediate (12.1 g, 77%).

(5-Fluoro-pyridin-2-yl)-methanol: At −78° C. under nitrogen, add n-butyllithium (2.5 M in hexane, 16.4 mL, 40.9 mmol) via syringe to a solution of 2-bromo-5-fluoro-pyridine (6.0 g, 34.1 mmol) in toluene (220 mL), while keeping the reaction temperature below −60° C. Stir the mixture at −78° C. and then add DMF (3.4 mL, 44.3 mmol) and stir for 1 h at this temperature. Warm to −10° C. and quench with methanol (10 mL). Concentrate the mixture to half of the volume in vacuo. Dilute with methanol (150 mL), cool the mixture to −78° C. and add sodium borohydride (3.2 g, 85.2 mmol) portion wise over 5 min. Warm the mixture to ambient temperature and stir for 2 h. Quench with water (10 mL) and remove the organic solvent in vacuo to obtain an oil/water mixture. Extract with diethyl ether (3×100 mL), dry the combined organic extracts, wash with brine, dry and concentrate in vacuo to obtain the desired intermediate as an oil (3.9 g, 91%).

Methanesulfonic acid (5-fluoro-pyridin-2-yl)methyl ester: Add methanesulfonyl chloride (1.8 mL, 23.5 mmol) to a solution of (5-fluoro-pyridin-2-yl)-methanol (2.5 g, 19.7 mmol) and triethylamine (8.2 mL, 59.0 mmol) in DCM (150 mL) at 0° C. under nitrogen. Stir the mixture for 30 min and concentrate in vacuo. Dilute with water (20 mL) and extract the mixture with EtOAc (3×50 mL). Combine the organic extracts and concentrate in vacuo. Purify by chromatography on silica gel eluting with hexane/EtOAc to obtain the desired intermediate (2.2 g, 54%).

2-Aminomethyl-5-fluoro-pyridine: Dissolve methanesulfonic acid (5-fluoro-pyridin-2-yl)-methyl ester (1.5 g, 7.3 mmol) in DMF (5 mL) and add sodium azide (950 mg, 14.6 mmol). Stir the mixture for 30 min, then dilute with hexane/EtOAc (1:1, 50 mL). Wash the mixture with 10% aqueous NaCl (3×10 mL). Dry the combined organic extracts over Na₂SO₄ and remove half of the solvent in vacuo. Add EtOAc (20 mL) and a suspension of 10% Pd/C (200 mg) in EtOAc (2 mL). Stir the mixture for 1 h at ambient temperature in a pressurized vessel under 50 psi of hydrogen. Filter the slurry through Celite® and concentrate in vacuo to obtain 2-aminomethyl-5-fluoro-pyridine (613 mg, 60% yield, 80% purity by GC/MS). GC-MS m/z: 126 (M⁺).

Preparation 102

3-Aminomethyl-5-fluoro-pyridine

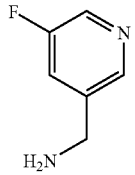

In a Parr Bottle add 2,6-dichloro-3-cyano-5-fluoropyridine (20 g, 0.105 mol), ethanol (336 mL), triethylamine (24 mL), and 5% Pd/C (4 g). Place on a Parr Shaker Apparatus under 60 psi hydrogen for 1 h at ambient temperature. Filter the reaction mixture and bubble ammonia gas into filtrate for 10 min. Add Raney® nickel (5.2 g) and place on a Parr Shaker Apparatus under 500 psi hydrogen for 18 h at 60-70° C. Filter the reaction mixture and concentrate in vacuo. Dissolve in methanol and add 1N hydrogen chloride in ether until form a precipitate. Cool in an ice bath, filter off the precipitate, wash the solid several times with ether, and dry to give the title compound as the hydrochloride salt (12 g, 70%). MS (ES+) m/z: 127 (M+H)⁺. Dissolve the hydrochloride salt in water, add 0.1 N aqueous NaOH to adjust to pH 10, extract with DCM, dry the organic layer over Na₂SO₄, filter and concentrate to give the title compound.

Preparation 103

3-Aminomethyl-4-trifluoromethyl-pyridine

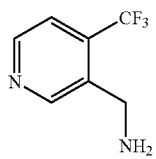

Add 4-trifluoromethyl-nicotinonitrile (1.0 g, 5.8 mmol) and ethanol wet Raney® activated nickel (0.2 g) to a Parr pressure vessel. Immediately add, at ambient temperature, 2B-ethanol (25 mL) previously saturated with ammonia gas and seal the vessel. Purge the reaction vessel with nitrogen, pressurize the reaction mixture with hydrogen (400 KPa), seal the vessel, agitate the reaction and heat to 40° C. Continue the reaction for 20 h then turn off the heat and allow the reaction mixture to cool to ambient temperature. Vent the excess hydrogen from the vessel and purge the vessel with nitrogen. Filter the reaction mixture to remove the Raney® nickel, wash with ethanol and concentrate in vacuo. Purify by SCX chromatography to give the title compound (560 mg, 55%). MS (ES+) m/z: 177 (M+H)⁺.

Preparation 104

2-Aminomethyl-6-fluoropyridine Dihydrochloride

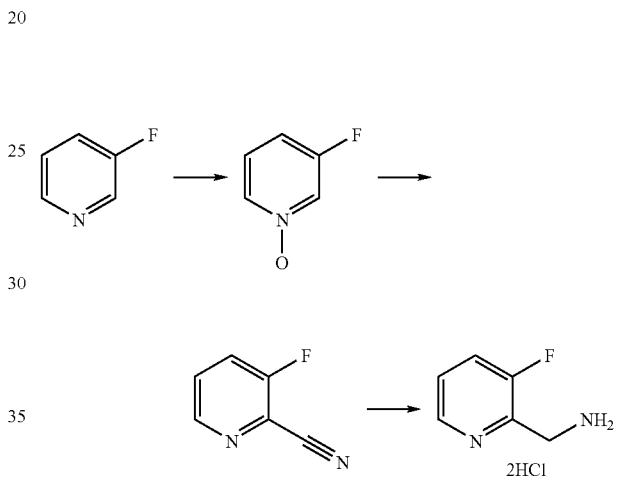

3-Fluoropyridine-N-Oxide: Dissolve 3-fluoropyridine (2.5 g, 25.749 mmol) in anhydrous DCM (75 mL). Add m-CPBA (70% suspension, 12.696 g, 51.499 mmol) and stir at ambient temperature overnight. Wash the reaction mixture with saturated aqueous NaHCO₃, dry the organic phase over Na₂SO₄, filter, and concentrate in vacuo. Purify by chromatography on silica gel eluting with DCM and DCM/methanol (97:3) to obtain the desired intermediate as a solid (1.413 g, 49%). MS (ES+) m/z: 115 (M+H)⁺.

2-Cyano-3-fluoropyridine: Dissolve 3-fluoropyridine-N-oxide (1.0 g, 8.687 mmol) in anhydrous acetonitrile (100 mL). Add triethylamine (1.319 g, 1.82 mL, 13.031 mmol), trimethylsilylcyanide (3.447 g, 4.63 mL, 34.749 mmol) and heat the mixture to reflux overnight. Cool to ambient temperature and concentrate in vacuo. Dissolve the residue in EtOAc and wash with saturated aqueous NaHCO₃. Dry the organic layer over Na₂SO₄, filter, and concentrate in vacuo. Purify by chromatography on silica gel eluting with hexane/EtOAc (1:0 and 17:3) to give the desired intermediate as a solid (746 mg, 70%). GC-MS m/z: 122 (M⁺).

2-Aminomethyl-3-fluoropyridine dihydrochloride: Dissolve 2-cyano-3-fluoropyridine (300 mg, 2.457 mmol) in absolute ethanol (12 mL). Add 10% Pd/C (93 mg) and concentrated HCl (0.614 mL, 7.37 mmol). Hydrogenate at 40 psi overnight. Filter through Celite® and concentrate in vacuo to give the title compound as a solid (440 mg, 90%). MS (ES+) m/z: 127 (M+H)⁺.

Preparation 105

2-Aminomethyl-6-fluoropyridine Dihydrochloride

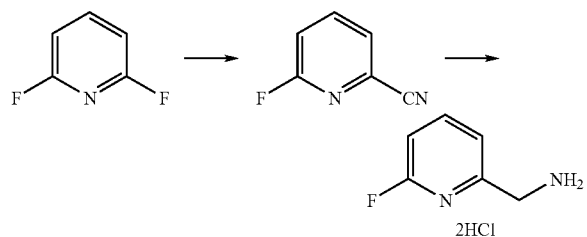

2-Cyano-6-fluoropyridine: Dissolve 2,6-difluoropyridine (12 g, 104.2 mmol) in anhydrous DMSO (5 mL). Add a solution of sodium cyanide (1.3 g, 26.53 mmol) in DMSO (60 mL) over 12 h using a syringe pump. Heat the mixture to 100° C. overnight. Cool to ambient temperature, dilute with EtOAc (500 mL), and wash with brine. Dry the organic phase over Na$_2$SO$_4$, filter, and concentrate in vacuo. Purify by chromatography on silica gel eluting with hexane/EtOAc (1:0 and 4:1) to give the desired intermediate as a solid (723 mg, 22%). GC-MS m/z: 122 (M⁺).

2-Aminomethyl-6-fluoropyridine Dihydrochloride: Dissolve 2-cyano-6-fluoropyridine (300 mg, 2.46 mmol) in absolute ethanol (12 mL). Add 10% Pd/C (93 mg) and concentrated HCl (0.614 mL, 7.37 mmol). Hydrogenate at 40 psi overnight. Filter through Celite® and concentrate to give the title compound as a solid (356 mg, 73%). MS (ES+) m/z: 127 (M+H)⁺.

Preparation 106

4-Aminomethyl-N-(pyridin-2-yl-methyl)-benzamide

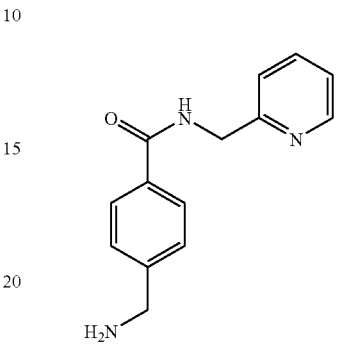

Use the General Procedure 6-2, using 2-(aminomethyl) pyridine (181 mg, 0.172 mL, 1.67 mmol) and 4-(tert-butoxycarbonylamino-methyl)-benzoic acid (420 mg, 1.67 mmol) to give the title compound as a solid (427 mg, 100%). MS (ES+) m/z: 242 (M+H)⁺.

The compounds of Preparations 107-1.17 may be prepared essentially as described in Preparation 106 by using 4-(tert-butoxycarbonylamino-methyl)-benzoic acid and the appropriate amine. Overall yields and MS (ES+) data are shown in the Table below.

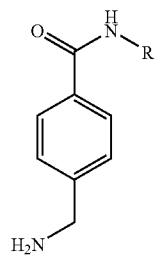

| Prep. | NHR | Compound | Yield (%) | MS (ES+) or GC-MS |
|---|---|---|---|---|
| 107 | NH—CH$_2$—thiophen-2-yl | 4-Aminomethyl-N-(thiophen-2-yl-methyl)-benzamide | 100 | 247 (M + H)⁺ |
| 108 | NH—CH$_2$—(3-fluoropyridin-2-yl) | 4-Aminomethyl-N-(3-fluoro-pyridin-2-ylmethyl)-benzamide | 58 | 259 (M)⁺ |
| 109 | NH—CH$_2$—(6-fluoropyridin-2-yl) | 4-Aminomethyl-N-(6-fluoro-pyridin-2-ylmethyl)-benzamide | 98 | 259 (M)⁺ |

-continued

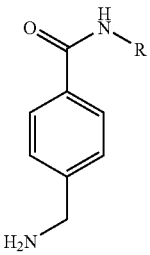

| Prep. | NHR | Compound | Yield (%) | MS (ES+) or GC-MS |
|---|---|---|---|---|
| 110 | 5-F pyridin-2-ylmethyl-NH | 4-Aminomethyl-N-(5-fluoro-pyridin-2-ylmethyl)-benzamide | 67 | 259 (M)+ |
| 111 | 3-CF3 pyridin-2-ylmethyl-NH | 4-Aminomethyl-N-(3-trifluoromethyl-pyridin-2-ylmethyl)-benzamide | 62 | 310 (M + H)+ |
| 112 | 4-CF3 pyridin-2-ylmethyl-NH | 4-Aminomethyl-N-(4-trifluoromethyl-pyridin-2-ylmethyl)-benzamide | 76 | 309 (M)+ |
| 113 | 5-CF3 pyridin-2-ylmethyl-NH | 4-Aminomethyl-N-(5-trifluoromethyl-pyridin-2-ylmethyl)-benzamide | 65 | 310 (M + H)+ |
| 114 | 2-thiophen-2-yl-ethyl-NH | 4-Aminomethyl-N-(2-thiophen-2-yl-ethyl)-benzamide | 100 | 261 (M + H)+ |
| 115 | 2-pyridin-2-yl-ethyl-NH | 4-Aminomethyl-N-(2-pyridin-2-yl-ethyl)-benzamide | 81 | 256 (M + H)+ |
| 116 | 2-pyridin-3-yl-ethyl-NH | 4-Aminomethyl-N-(2-pyridin-3-yl-ethyl)-benzamide | 97 | 256 (M + H)+ |
| 117 | 2-pyridin-4-yl-ethyl-NH | 4-Aminomethyl-N-(2-pyridin-4-yl-ethyl)-benzamide | 96 | 256 (M + H)+ |

Preparation 118

(±)-1-(3-Fluorophenyl)ethylamine

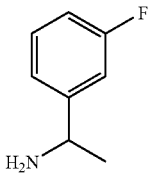

Add sodium cyanoborohydride (452 mg, 7.2 mmol) to a solution of 3-fluoroacetophenone (500 mg, 3.6 mmol) and ammonium acetate (2.8 g, 36 mmol) in methanol (11 mL). Stir the mixture for 96 h at ambient temperature under a nitrogen atmosphere. Adjust to pH 2 with 2M hydrogen chloride in diethyl ether. Concentrate the slurry in vacuo, dilute the residue with DCM and wash with 5N aqueous NaOH followed by saturated aqueous $NaHCO_3$. Dry the organic layer, concentrate in vacuo to half of the volume, and load the solution onto a SCX column (pre-wash column with methanol followed by DCM, then elute with 2M ammonia in methanol). Concentrate the fractions to half of the volume to remove ammonia, add excess of 2M hydrogen chloride in diethyl ether and concentrate to obtain the hydrochloride salt (70:30 mixture of title compound and dimer). Purify by chromatography on silica gel eluting with DCM/2M ammonia in methanol (20:1) to obtain the title compound (323 mg, 51%). MS (ES+) m/z: 140 (M+H)$^+$

Preparation 119

1-(3-Fluorophenyl)ethylamine, Isomer 2

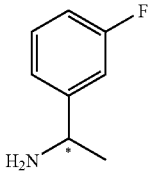

Set-up flask equipped with condenser, mechanical stirrer and addition funnel. Add 3-fluoroacetophenone (25 g, 0.18 mol) and formic acid (4.2 g, 0.09 mol) via addition funnel to a flask containing formamide (32.6 g, 0.72 mol) at 140° C. over 15 min, and then heat the mixture to 160° C. Add formic acid successively (4.2 g, 0.5 equiv.) via addition funnel to the flask every hour for 4 h while maintaining the reaction temperature at 160° C. Cool the reaction mixture, extract with toluene (3×100 mL), and concentrate the organic layer in vacuo. Add aqueous HCl (37%, 40 mL) to the residue and heat to reflux for 2 h. Cool to ambient temperature and wash the aqueous mixture with toluene (2×100 mL), then basify the aqueous mixture with 5N aqueous NaOH (120 mL). Extract the basic mixture with EtOAc (3×100 mL), dry the combined organic extracts over $Na_2SO_4$ and filter. Acidify the filtrate with 2M hydrogen chloride in diethyl ether to pH 2 and concentrate in vacuo to a solid. Suspend the solid in diethyl ether, filter and wash with diethyl ether. Dry the solid in a vacuo-oven at 50° C. to obtain (±)-1-(3-fluorophenyl)ethylamine hydrochloride (21.5 g, 68%). MS (ES+) m/z: 140 (M+H)$^+$.

Dissolve (±)-1-(3-fluorophenyl)ethylamine hydrochloride (42.5 g, 0.24 mol) in THF (520 mL) and saturated aqueous $NaHCO_3$ (430 mL). Add di-tert-butyl-dicarbonate (69 g, 0.31 mol) and stir for 16 h at ambient temperature. Separate the organic layer, dilute with EtOAc (300 mL) and wash with 2N aqueous NaOH (1×400 mL) and water (2×200 mL). Concentrate the organic layer in vacuo. Purify by chromatography on silica gel eluting with hexane/EtOAc (9:1) to obtain (±)-N-[1-(3-fluorophenyl)ethyl]-carbamic acid tert-butyl ester (56 g, 97%). GC-MS m/z: 183 [M–$C_4H_9$)$^+$].

Separate the racemic mixture of (±)N-[1-(3-fluorophenyl) ethyl]-carbamic acid tert-butyl ester by normal phase chiral chromatography (Chiralcel OD 8×34 cm, elute with 95:5, heptane/isopropanol). Using the General Procedure 1-4, deprotect the desired isomer [20.7 g, >95% ee (Chiralcel OD, 4.6×250 mm, eluent: 95:5 heptane/isopropanol with 0.2% DMEA, 1.0 mL/min)] to obtain the title compound (9.4 g, 78%). MS (ES+) m/z: 140 (M+H)$^+$.

Preparation 120

(±)-1-(2-Fluorophenyl)ethylamine

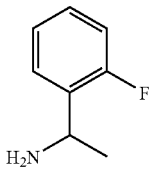

Add sodium cyanoborohydride (1.8 g, 29 mmol) to a solution of 2-fluoro-acetophenone (2.0 g, 14.5 mmol) and ammonium acetate (11.2 g, 145 mmol) in methanol (45 mL). Stir the mixture for 20 h at ambient temperature under a nitrogen atmosphere. Adjust the mixture to pH 1 with 2M hydrogen chloride in diethyl ether. Concentrate the slurry in vacuo, dilute the residue with DCM and wash with 5N aqueous NaOH. Dry the organic layer, concentrate carefully, as the amine is volatile, under reduced pressure to one third of the volume, and load the material onto an SCX column (pre-wash column with methanol, followed by DCM, elute with 2M ammonia in methanol). Concentrate the fraction to one half of the volume to remove the ammonia, then add excess 2M hydrogen chloride in diethyl ether and concentrate to obtain the hydrochloride salt. Purify by chromatography on silica gel eluting with DCM/2M ammonia in methanol (20:1) to obtain the title compound (280 mg, 13%). MS (ES+) m/z: 140 (M+H)$^+$.

Preparation 121

1-(2-Fluorophenyl)ethylamine, Isomer 1

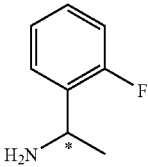

Use a method similar to the General Procedure 6-3, using 2-fluoroacetophenone (1.4 g, 9.9 mmol) and (R)-(+)-2-methyl-2-propanesulfinamide (1.0 g, 8.2 mmol). Purify by chromatography on silica gel eluting with hexane/EtOAc/2M ammonia in methanol (90:9:1 to 50:45:5). Add 4M hydrogen chloride in dioxane to obtain the title compound as the hydrochloride (600 mg, 35%). MS (ES+) m/z: 140 (M+H)$^+$. Dissolve the hydrochloride in an aqueous solution of cesium carbonate (1.5 equiv.) and extract with toluene to obtain the free base.

The compounds of Preparations 122-141 may be prepared essentially as described in Preparation 121 by using (R)-(+)-2-methyl-2-propanesulfinamide or (S)-(−)-2-methyl-2-propanesulfinamide and the appropriate acetophenone. Overall yields and mass spectrum data are shown in the Table below.

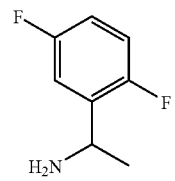

| Prep. | R | Compound | Yield (%) | MS (ES+) or GC-MS |
|---|---|---|---|---|
| 122 | 3-CN | 1-(3-Cyanophenyl)ethylamine, Isomer 1 | 37 | 130 $(M + H - NH_3)^+$ |
| 123 | 3-CN | 1-(3-Cyanophenyl)ethylamine, Isomer 2 | 49 | 130 $(M + H - NH_3)^+$ |
| 124 | 4-CN | 1-(4-Cyanophenyl)ethylamine, Isomer 1 | 49 | 130 $(M + H - NH_3)^+$ |
| 125 | 4-CN | 1-(4-Cyanophenyl)ethylamine, Isomer 2 | 49 | 130 $(M + H - NH_3)^+$ |
| 126 | 2-Cl | 1-(2-Chlorophenyl)ethylamine, Isomer 1 | 25 | 156 $(M + H)^+$ |
| 127 | 3-Cl | 1-(3-Chlorophenyl)ethylamine, Isomer 1 | 68 | 156 $(M + H)^+$ |
| 128 | 3-CF$_3$ | 1-(3-Trifluoromethylphenyl)-ethylamine, Isomer 1 | 40 | 190 $(M + H)^+$ |
| 129 | 4-CF$_3$ | 1-(4-Trifluoromethylphenyl)-ethylamine, Isomer 2 | 70 | 190 $(M + H)^+$ |
| 130 | 3-Cl, 4-F | 1-(3-Chloro-4-fluorophenyl)-ethylamine, Isomer 1 | 66 | 174 $(M + H)^+$ |
| 131 | 3-Cl-4-F | 1-(3-Chloro-4-fluorophenyl)-ethylamine, Isomer 2 | 68 | 174 $(M + H)^+$ |
| 132 | 2,3-diF | 1-(2,3-Difluorophenyl)-ethylamine, Isomer 1 | 20 | 141 $(M + H - NH_3)^+$ |
| 133 | 2,3-diF | 1-(2,3-Difluorophenyl)-ethylamine, Isomer 2 | 45 | 141 $(M + H - NH_3)^+$ |
| 134 | 2,4-diF | 1-(2,4-Difluorophenyl)-ethylamine, Isomer 1 | 58 | 158 $(M + H)^+$ |
| 135 | 2,4-diF | 1-(2,4-Difluorophenyl)-ethylamine, Isomer 2 | 49 | 158 $(M + H)^+$ |
| 136 | 3,5-diF | 1-(3,5-Difluorophenyl)-ethylamine, Isomer 1 | 26 | 158 $(M + H)^+$ |
| 137 | 3,5-diF | 1-(3,5-Difluorophenyl)-ethylamine, Isomer 2 | 83 | 158 $(M + H)^+$ |
| 138 | 3,4-diF | 1-(3,4-Difluorophenyl)-ethylamine, Isomer 1 | 67 | 158 $(M + H)^+$ |
| 139 | 3,4-diF | 1-(3,4-Difluorophenyl)-ethylamine, Isomer 2 | 77 | 158 $(M + H)^+$ |
| 140 | 3,4,5-triF | 1-(3,4,5-Trifluorophenyl)-ethylamine, Isomer 2 | 20 | 176 $(M + H)^+$ |
| 141 | 3,5-diCF$_3$ | 1-(3,5-bis-trifluoromethylphenyl)-ethylamine, Isomer 2 | 49 | 258 $(M + H)^+$ |
| 142 | 2-OCF$_3$ | 1-(2-Trifluoromethoxyphenyl)-ethylamine, Isomer 2 | 47 | ND |
| 143 | 2-Me | 1-(2-Methyl)-ethylamine, Isomer I | 13 | 136 $(M^+)$ |

ND = Not determined

Preparation 144

(±)-1-(2,5-Difluorophenyl)ethylamine

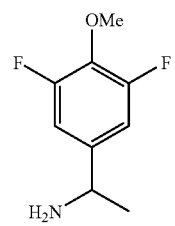

Slurry 2',5'-difluoroacetophenone (0.9 g, 5.76 mmol), ammonium acetate (4.44 g, 57.5 mmol) and sodium cyanoborohydride (755 mg, 12 mmol) in anhydrous methanol (25 mL) and stir for 18 h at ambient temperature. Acidify with 5N aqueous HCl (5 mL), dilute, extract with ethyl ether (3×150 mL), basify aqueous layer with 5N aqueous NaOH, extract with DCM (3×75 mL), wash the organic layer with brine, dry over MgSO$_4$, filter and concentrate in vacuo. Purify by SCX chromatography to give a mixture of (±)-1-(2,5-difluorophenyl)ethylamine and bis-[1-(±)-2,5-difluorophenyl)ethyl]-amine (total 400 mg, crude weight). MS (ES+) m/z: 158 (M+H)$^+$ and m/z: 298 (M+H)$^+$.

Preparation 145

(±)-1-(3,5-Difluoro-4-methoxyphenyl)ethylamine

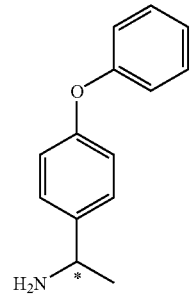

Slurry 3',5'-difluoro-4'-methoxyacetophenone (1.0 g, 5.0 mmol), ammonium acetate (4.14 g, 50 mmol) and sodium cyanoborohydride (630 mg, 20 mmol) in anhydrous methanol (35 mL) and stir for 18 h at ambient temperature. Acidify with 1N aqueous HCl (5 mL), dilute, extract with ethyl ether (3×150 mL), basify aqueous with 1N aqueous NaOH, extract with DCM (3×50 mL), wash the organic extracts with brine, dry over MgSO$_4$, filter and concentrate in vacuo. Purify by SCX chromatography to give crude the title compound as a yellow oil (380 mg).

Preparations 146 and 147

1-(4-Phenoxyphenyl)-ethylamine, Isomer 1 and Isomer 2

Mix 4-phenoxyacetophenone (5.3 g, 25 mmol), ammonium acetate (14.5 g, 187.5 mmol) and sodium cyanoborohydride (3.2 g, 50 mmol) in anhydrous methanol (200 mL). Stir for 18 h at ambient temperature. Acidify with 1N aqueous HCl (10 mL), dilute, extract with ethyl ether (3×150 mL), dry over MgSO$_4$, filter and concentrate in vacuo. Purify by chromatography on silica gel eluting sequentially with hexane/EtOAc (4:1, 1:1 and 0:1) and EtOAc/methanol (1:1) to give (±)-1-(4-phenoxyphenyl)-ethylamine (1.6 g, 30%). Dissolve the racemate (1.1 g, 5.2 mmol) in DCM (100 mL), add triethylamine (1.6 mL, 11.4 mmol) followed by di-tert-butyl-dicarbonate (1.7 g, 7.8 mmol). Purify by chromatography on silica gel eluting with hexane/EtOAc (9:1) to give [α-methyl-(4'-phenoxy)-benzylamino]carbamic acid tert-butyl ester as an off-white solid (1.3 mg, 81%). Separate via chiral chromatography (heptane/isopropanol/DMEA 95:5:0.2, 4.6×250 mm Chiralpak AD, 1 mL/min, UV detector at 260 nm) to give [α-methyl-(4'-phenoxy)benzylamino]carbamic acid tert-butyl ester, isomer 1 (315 mg, chiral HPLC: $t_R$=7.35 min; 99.1% ee) and [α-methyl-(4'-phenoxy)benzyl-aminocarbamic acid tert-butyl ester, isomer 2 (400 mg, chiral HPLC: $t_R$=8.7 min; 97.2% ee). Dissolve [α-methyl-(4'-phenoxy)benzylamino]carbamic acid tert-butyl ester isomer 1 or isomer 2 in DCM/trifluoroacetic acid (1:1, 20 mL) to give, after solvent evaporation and chromatography over SCX column, 1-(4-phenoxyphenyl)-ethylamine, isomer 1 (Preparation 146) and 1-(4-phenoxyphenyl)-ethylamine, isomer 2 (Preparation 147). MS (ES+) m/z: 214 (M+H)$^+$.

Preparation 148

(5-Fluoro-indan-1-yl)amine, Isomer 1

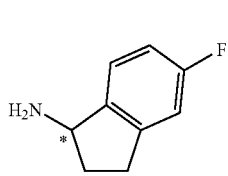

Use a method similar to the General Procedure 6-3 to react 5-fluoro-indan-1-one (1.5 g, 9.9 mmol) and (R)-(+)-2-methyl-2-propanesulfinamide (1.0 g, 8.3 mmol). Purify by chromatography on silica gel eluting with hexane/EtOAc (5:2). Add 4M hydrogen chloride in dioxane to obtain the title compound as the hydrochloride (254 mg, 16%). MS (ES+) m/z: 152 (M+H)$^+$. Dissolve the hydrochloride in an aqueous solution of cesium carbonate (1.5 equiv.) and extract with toluene to obtain the free base.

Preparation 149

1-Phenyl-cyclopropylamine

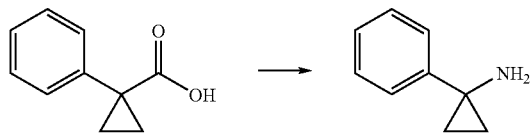

Dissolve 1-phenyl-cyclopropanecarboxylic acid (2.5 g, 15.4 mmol) in a mixture of sulfuric acid (12.5 mL) and DCM (25 mL). Add sodium azide (2.3 g, 35.4 mmol) by small portions at ambient temperature. Heat the reaction mixture at 50° C. for 8 h, cool to 0° C. and slowly add 2M aqueous NaOH until pH 11. Extract the reaction mixture with DCM (3×100 mL), combine the organic extracts and dry over anhydrous Na$_2$SO$_4$. Evaporate the solvent and purify by chromatography on silica gel eluting with DCM and DCM/2M ammonia in methanol (9:1) to obtain the title compound as a brown oil (1.1 g, 54%). MS (ES+) m/z: 134 (M+H)$^+$.

Preparation 150

1-(2,4-Dichlorophenyl)-cyclopropylamine

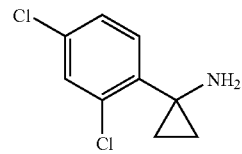

Use a method similar to Preparation 149, using 1-(2,4-dichlorophenyl)-cyclopropanecarboxylic acid (3.5 g, 15.4 mmol), to obtain the title compound as a yellow oil (1.0 g, 32%). MS (ES+) m/z: 203 (M+H)$^+$.

Preparation 151

4-Methylamino-benzo[1,3]dioxole

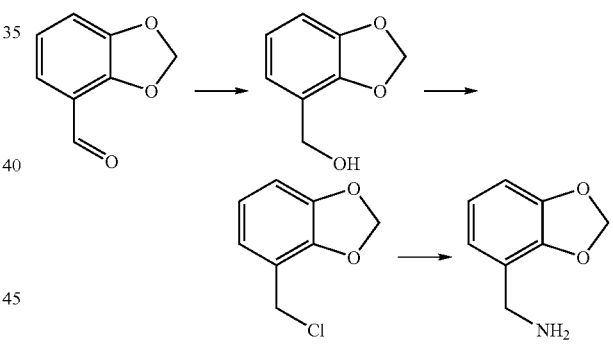

Benzo[1,3]dioxol-4-yl-methanol: Dissolve benzo[1,3]dioxole-4-carbaldehyde (2.0 g, 13.3 mmol) in anhydrous THF (30 mL) and treat with sodium borohydride (0.5 g, 13.3 mmol) at 0° C. Stir the reaction mixture for 30 min at ambient temperature and quench with water (30 mL). Extract the reaction mixture with DCM (3×10 mL), combine the organic extracts and dry over anhydrous Na$_2$SO$_4$. Remove the solvent to obtain the desired intermediate as a colorless oil (1.9 g, 94%).

4-Chloromethyl-benzo[1,3]dioxole: Dissolve benzo[1,3]dioxol-4-yl-methanol (1.9 g, 12.5 mmol) in thionyl chloride (3 mL, 41.1 mmol) and reflux the reaction mixture for 1 h. Concentrate in vacuo to obtain the desired intermediate as a yellow oil (1.9 g, 91%) that was used without further purification. GC-MS m/z: 170 (M$^+$).

4-Methylamino-benzo[1,3]dioxole: Dissolve 4-chloromethyl-benzo[1,3]dioxole (1.9 g, 11.1 mmol) in methanol (5 mL), cool the solution to 0° C. and saturate with anhydrous ammonia for 15 min. Keep the reaction mixture at 0° C. for 18

Preparation 152

6-Bromomethyl-benzothiazole

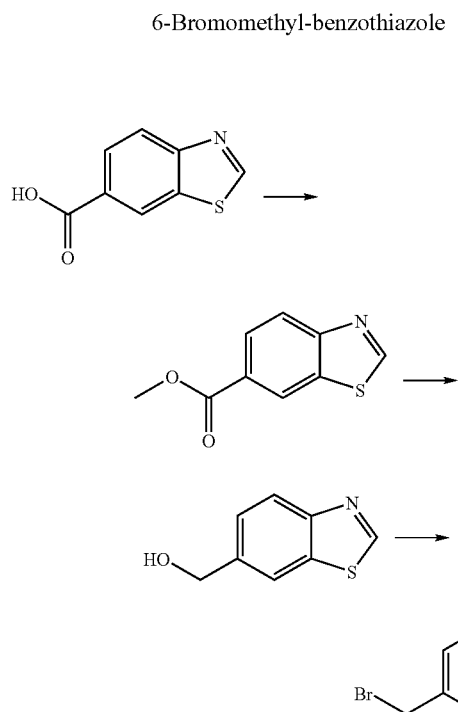

Benzothiazole-6-carboxylic acid methyl ester: Add 1-methyl-3-nitro-1-nitrosoguanidine (5.0 g, 33.9 mmol) to a mixture of diethyl ether (20 mL) and 1N aqueous NaOH (20 mL) at ambient temperature. Separate the organic layer and add it slowly to a solution of benzothiazole-6-carboxylic acid (1.0 g, 5.58 mmol) in THF (50 mL) at 0° C. Evaporate the solvent to obtain the desired intermediate as a yellow solid (1.1 g, 100%). MS (ES+) m/z: 194 (M+H)$^+$.

Benzothiazol-6-yl-methanol: Add slowly a solution of benzothiazole-6-carboxylic acid methyl ester (0.5 g, 2.59 mmol) in anhydrous THF (10 mL) to a suspension of lithium aluminum hydride (0.1 g, 2.85 mmol) in anhydrous THF (20 mL) at −10° C. and stir for 20 min at −10° C. Treat the reaction mixture with 2N aqueous NaOH until a granular precipitate starts to form and filter through a pad of Celite®. Evaporate the solvent and purify by chromatography on silica gel eluting with hexane/EtOAc (1:0, 9:1, 4:1, 7:3, 3:2 and 1:1) to obtain the desired intermediate as a yellow oil (0.4 g, 99%). MS (ES+) m/z: 166 (M+H)$^+$.

6-Bromomethyl-benzothiazole: Dissolve benzothiazol-6-yl-methanol (0.4 g, 2.55 mmol) in diethyl ether (10 mL) and add slowly a solution of phosphorus tribromide (0.7 g, 2.55 mmol) in diethyl ether (5 mL). Stir the reaction mixture for 2 h at ambient temperature, wash with brine, dry the organic phase over anhydrous Na$_2$SO$_4$, evaporate the solvent and purify by chromatography on silica gel eluting with hexane/EtOAc (1:0, 9:1 and 4:1) to obtain the title compound as a white solid (0.5 g, 86%). MS (ES+) m/z: 229 (M+H)$^+$.

Preparation 153

6-Bromomethyl-2-cyclohexyl-benzothiazole

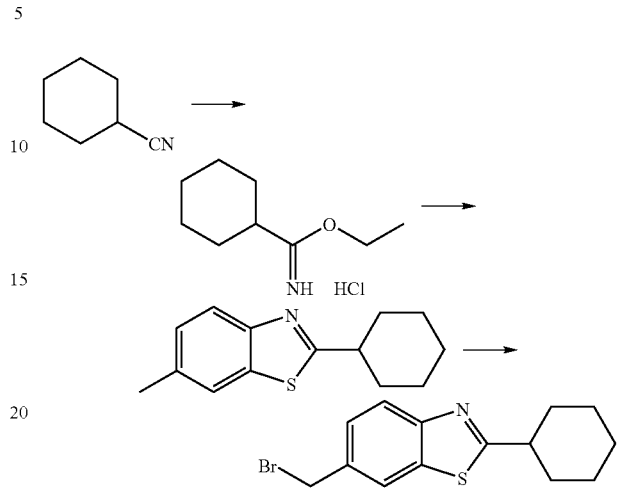

Cyclohexanecarboximidic acid ethyl ester, hydrochloride: Combine cyclohexanecarbonitrile (1.0 g, 9.20 mmol), ethanol (0.4 g, 9.20 mmol) and 4N hydrogen chloride in dioxane (8 mL) and stir the reaction mixture for 17 h at ambient temperature. Evaporate the solvent and triturate the residue with diethyl ether to obtain the desired intermediate as a white solid (1.4 g, 80%).

2-Cyclohexyl-6-methyl-benzothiazole: Combine 2-amino-5-methyl-benzenethiol zinc salt (1.0 g, 2.91 mmol, prepared as described in *Synth. Commun.* 1980, 10, 167-173), cyclohexanecarboximidic acid ethyl ester hydrochloride (1.1 g, 5.82 mmol), methanol (20 mL) and reflux the reaction mixture for 17 h. Evaporate the solvent and purify by chromatography on silica gel eluting with hexane/EtOAc (1:0 and 9:1) to obtain the desired intermediate as a white solid (1.15 g, 85%).

6-Bromomethyl-2-cyclohexyl-benzothiazole: Combine 2-benzyl-6-methyl-benzothiazole (0.6 g, 2.42 mmol), NBS (0.5 g, 2.54 mmol), AIBN (40 mg, 0.24 mmol), carbon tetrachloride (10 mL) and reflux for 3 h. Cool the reaction mixture to ambient temperature, dilute with chloroform and wash with water. Dry the organic extracts over anhydrous Na$_2$SO$_4$, concentrate in vacuo and purify by chromatography on silica gel eluting with hexane/EtOAc (1:0 and 9:1) to obtain the title compound as a white solid (0.4 g, 53%). MS (ES+) m/z: 311 (M+H)$^+$.

Preparation 154

6-Bromomethyl-2-phenyl-benzothiazole

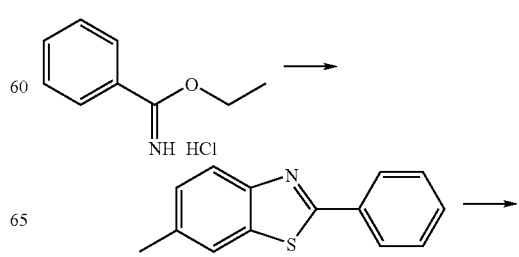

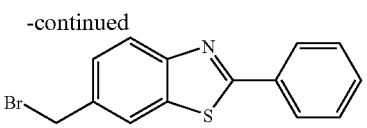

6-Methyl-2-phenyl-benzothiazole: Combine 2-amino-5-methyl-benzenethiol zinc salt (1.0 g, 2.91 mmol, prepared as described in *Synth. Commun.* 1980, 10, 167-173), ethyl benzimidate hydrochloride (1.1 g, 5.82 mmol), methanol (20 mL), and reflux the reaction mixture for 17 h. Evaporate the solvent and purify by chromatography on silica gel eluting with hexane/EtOAc (1:0 and 9:1) to obtain the desired intermediate as a white solid (1.1 g, 85%). MS (ES+) m/z: 226 (M+H)+.

6-Bromomethyl-2-phenyl-benzothiazole: Combine 6-methyl-2-phenyl-benzothiazole (0.2 g, 0.98 mmol), NBS (0.2 g, 1.02 mmol), AIBN (20 mg, 0.10 mmol), carbon tetrachloride (5 mL) and reflux for 3 h. Cool the reaction mixture to ambient temperature, dilute with chloroform and wash with water. Dry the organic extracts over anhydrous $Na_2SO_4$, concentrate and purify by chromatography on silica gel eluting with hexane/EtOAc (1:0, 9:1, 8:2 and 7:3) to obtain the title compound as a white solid (0.2 g, 69%).

Preparation 155

2-Benzyl-6-bromomethyl-benzothiazole

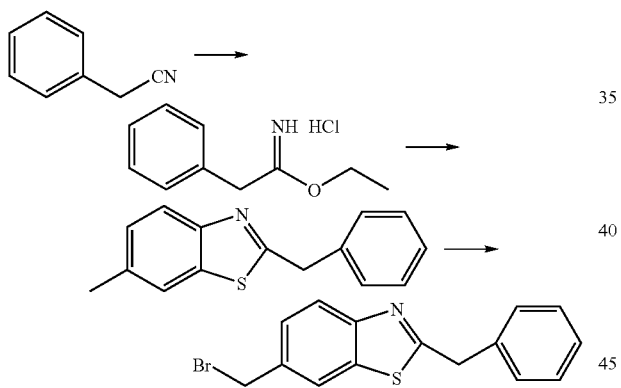

2-Phenyl-acetimidic acid ethyl ester, hydrochloride: Combine benzyl cyanide (1.0 g, 8.50 mmol), ethanol (0.4 g, 8.50 mmol) and 4N hydrogen chloride in dioxane (8 mL) and stir the reaction mixture at ambient temperature for 17 h. Evaporate the solvent and triturate the residue with diethyl ether to obtain the desired intermediate as a white solid (1.7 g, 100%).

2-Benzyl-6-methyl-benzothiazole: Combine 2-amino-5-methyl-benzenethiol zinc salt (1.0 g, 2.91 mmol, prepared as described in *Synth. Commun.* 1980, 10, 167-173), 2-phenyl-acetimidic acid ethyl ester hydrochloride (1.16 g, 5.82 mmol), methanol (20 mL) and reflux the reaction mixture for 17 h. Evaporate the solvent and purify by chromatography on silica gel eluting with hexane/EtOAc (1:0 and 9:1) to obtain the desired intermediate as a white solid (1.0 g, 72%). MS (ES+) m/z: 240 (M+H)+.

2-Benzyl-6-bromomethyl-benzothiazole: Combine 2-benzyl-6-methyl-benzothiazole (0.6 g, 2.51 mmol), NBS (0.5 g, 2.63 mmol), AIBN (40 mg, 0.25 mmol), carbon tetrachloride (10 mL) and reflux for 3 h. Cool the reaction mixture to ambient temperature, dilute with chloroform and wash with water. Dry the combined organic extracts over anhydrous $Na_2SO_4$, evaporate the solvent and purify by chromatography on silica gel eluting with hexane/EtOAc (1:0 and 9:1) to obtain the title compound as a white solid (0.2 g, 69%). MS (ES+) m/z: 319 (M+H)+.

Preparation 156

5-Bromomethyl-benzoxazole

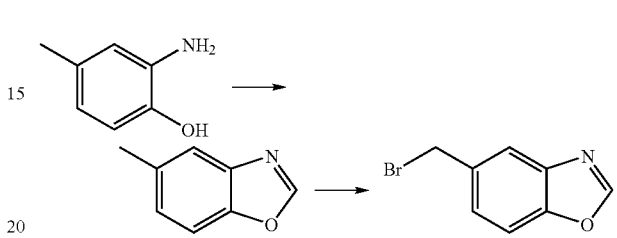

5-Methyl-benzoxazole: Combine 2-amino-4-methyl-phenol (1.0 g, 8.12 mmol), [(dimethylaminomethylene-aminomethylene)dimethylammonium chloride (Gold's reagent) (1.6 g, 9.91 mmol), anhydrous 1,4-dioxane (25 mL) and reflux for 17 h. Cool the reaction mixture to ambient temperature, evaporate the solvent and purify by chromatography on silica gel eluting with hexane/EtOAc (9:1) to obtain the desired intermediate as a yellow oil (0.7 g, 65%).

5-Bromomethyl-benzoxazol: Combine 5-methyl-benzoxazole (0.5 g, 3.75 mmol), NBS (0.7 g, 3.93 mmol), AIBN (60 mg, 0.37 mmol), chloroform (10 mL) and reflux for 1 h. Cool the reaction mixture to ambient temperature, dilute with chloroform and wash with water. Dry the organic extracts over anhydrous $Na_2SO_4$, evaporate the solvent and purify by chromatography on silica gel eluting with hexane/EtOAc (1:0, 9:1, 4:1 and 7:3) to obtain the title compound as a white solid (0.1 g, 13%).

Preparation 157

5-Methylamino-2-phenyl-benzoxazole

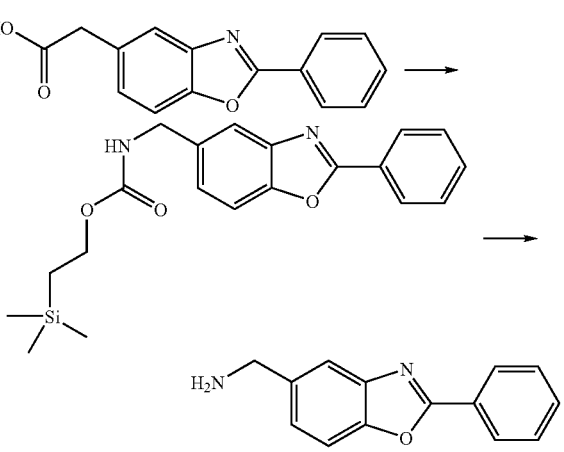

2-(Phenyl-benzoxazol-5-ylmethyl)-carbamic acid 2-trimethylsilanyl-ethyl ester: Combine (2-phenyl-benzoxazol-5-yl)acetic acid (1.0 g, 3.95 mmol), triethylamine (0.5 g, 4.34 mmol), and anhydrous toluene (20 mL), heat to reflux and slowly add diphenylphosphoryl azide (1.2 g, 4.15 mmol) in anhydrous toluene (8 mL). Continue to reflux for 3 h, cool to ambient temperature, add 2-trimethylsilylethanol (0.9 g, 7.89 mmol) to the reaction mixture and continue to reflux for 3 h. Evaporate the solvent and purify by chromatography on silica gel eluting with hexane/EtOAc (1:0, 9:1, 4:1 and 7:3) to obtain the desired intermediate as a yellow solid (0.4 g, 26%).

5-Methylamino-2-phenyl-benzoxazole: Dissolve (2-phenyl-benzoxazol-5-yl-methyl)-carbamic acid 2-trimethylsilanyl-ethyl ester (0.4, 0.99 mmol) in anhydrous THF (5 mL) and treat with 1M tetrabutylammonium fluoride in THF (1.5 mL, 1.54 mmol). Heat the mixture at reflux for 30 min evaporate the solvent and purify by SCX chromatography to obtain the title compound as a yellow oil (0.1 g, 27%).

Preparation 158

4-Aminomethyl-1-methylindole

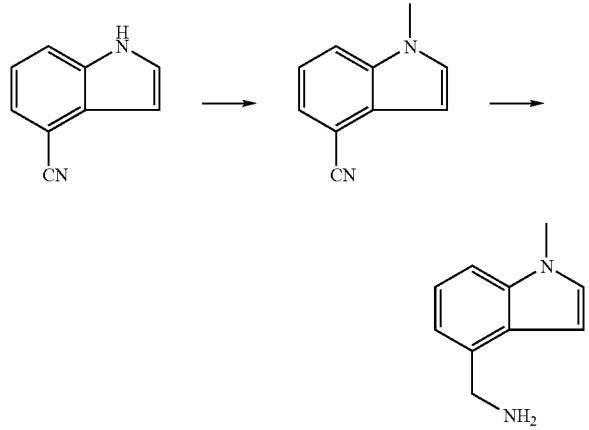

1-Methylindole-4-carbonitrile: Add slowly a solution of indole-4-carbonitrile (1.0 g, 7.04 mmol) in anhydrous DMF (5 mL) to a suspension of sodium hydride (60% dispersion in mineral oil, 0.6 g, 8.64 mmol) in anhydrous DMF (2 nm) at 0° C. and warm the reaction mixture to ambient temperature. Add iodomethane (0.7 mL, 10.6 mmol) and stir the reaction for 1 h at ambient temperature. Dilute the reaction mixture with 1M aqueous $NH_4OH$ (30 mL) and extract with diethyl ether (3×10 mL). Combine the organic extracts, dry over anhydrous $Na_2SO_4$, concentrate in vacuo and purify by chromatography on silica gel eluting with hexane/EtOAc (1:0, 9:1, 4:1 and 7:3) to obtain the desired intermediate as a yellow oil (1.0 g, 87%). GC-MS m/z: 156 (M+).

4-Aminomethyl-1-methylindole: Dissolve 1-methylindole-4-carbonitrile (1.0 g, 6.18 mmol) in anhydrous THF (10 mL) and add slowly to 1M lithium aluminum hydride in THF (12.4 mL, 12.37 mmol) at ambient temperature. Heat the reaction mixture at 50° C. for 17 h and cool to ambient temperature. Quench the reaction mixture with water until a granular precipitate starts to form and filter through a pad of Celite®. Evaporate the solvent and purify by SCX chromatography to obtain the title compound as a yellow oil (0.9 g, 91%). GC-MS m/z: 160 (M*).

Preparation 159

6-Aminomethyl-1-methylindole

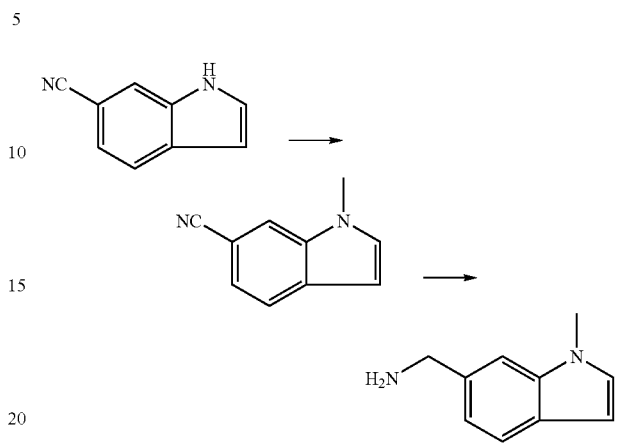

1-Methylindole-6-carbonitrile: Add slowly a solution of indole-6-carbonitrile (1.0 g, 7.04 mmol) in anhydrous DMF (5 mL) to a suspension of sodium hydride (60% dispersion in mineral oil, 0.6 g, 14.1 mmol) in anhydrous DMF (2 mL) at 0° C. and warm the reaction mixture to ambient temperature. Add iodomethane (0.7 mL, 1.06 mmol) and stir the reaction mixture for 1 h at ambient temperature. Dilute the reaction mixture with 1M aqueous $NH_4OH$ (30 mL) and extract with diethyl ether (3×10 mL). Combine the organic layers, dry over anhydrous $Na_2SO_4$, remove the solvent and purify by chromatography on silica gel eluting with hexane/EtOAc (1:0, 9:1, 4:1 and 7:3) to obtain the desired intermediate as a yellow oil (1.0 g, 87%). MS (ES+) m/z: 156 (M+H)+.

6-Aminomethyl-1-methylindole: Dissolve 1-methylindole-6-carbonitrile (0.97 g, 6.18 mmol) in anhydrous THF (10 mL) and add slowly to 1M lithium aluminum hydride in THF (1.24 mL, 1.24 mmol) at ambient temperature. Heat the reaction mixture at 50° C. for 17 h and cool to ambient temperature. Quench the reaction mixture with water until a granular precipitate starts to form and filter through a pad of Celite®. Evaporate the solvent and purify by SCX chromatography to obtain the title compound as a yellow oil (0.9 g, 91%). GC-MS m/z: 160 (M+).

Preparation 160

6-Aminomethyl-benzofuran

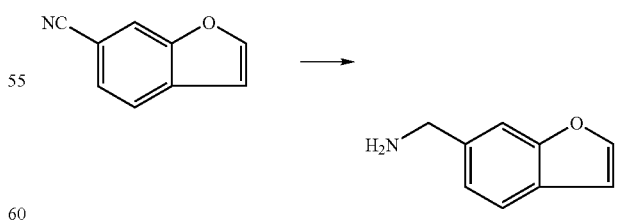

Dissolve benzofuran-6-carbonitrile (0.5 g, 3.28 mmol) in anhydrous THF (10 mL) and add slowly to 1M lithium aluminum hydride in THF (6.56 mL, 6.56 mmol) at ambient temperature. Heat the reaction mixture at 50° C. for 17 h and cool to ambient temperature. Quench the reaction mixture with water until a granular precipitate starts to form and filter Preparation 161

4-Aminomethyl-benzofuran

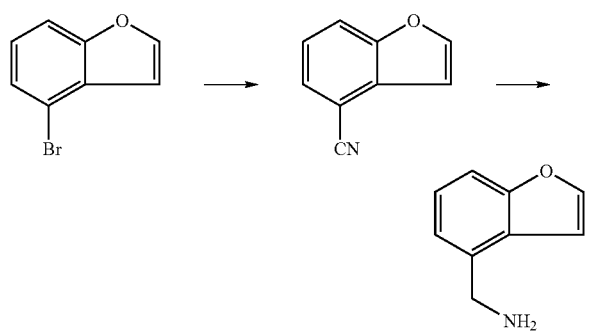

Benzofuran-4-carbonitrile: Combine 4-bromo-benzofuran (1.0 g, 5.07 mmol), copper(I) cyanide (0.9 g, 10.2 mmol), anhydrous DMF (16 ml) and reflux for 17 h. Cool the reaction mixture to ambient temperature, treat with 50% (v/v) aqueous ethylenediamine (25 mL). Extract the reaction mixture with diethyl ether (3×15 mL), combine the organic extracts, wash with brine (15 mL) and dry over anhydrous $Na_2SO_4$. Evaporate the solvent and purify by chromatography on silica gel eluting with hexane/EtOAc (1:0, 9:1 and 4:1) to obtain the desired intermediate as a colorless oil (0.3 g, 39%).

4-Aminomethyl-benzofuran: Dissolve benzofuran-4-carbonitrile (0.3 g, 1.96 mmol) in anhydrous THF (5 mL) and add slowly to 1M lithium aluminum hydride in THF (3.91 mL, 3.91 mmol) at ambient temperature. Heat the reaction mixture at 50° C. for 5 h and cool to ambient temperature. Quench the reaction mixture with water until a granular precipitate starts to form and filter through a pad of Celite®. Evaporate the solvent and purify by SCX chromatography to obtain the title compound as a brown oil (0.4 g, 79%). GC-MS m/z: 147 ($M^+$).

Preparation 162

4-Aminomethyl-benzo[b]thiophene

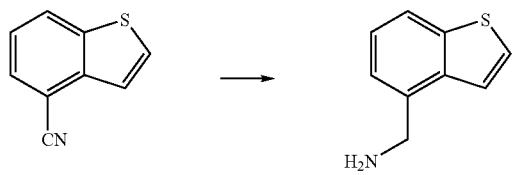

Add lithium aluminum hydride (1M solution in THF, 7.5 mL) to benzo[b]thiophene-4-carbonitrile (prepared as described in WO 0168653) (0.6 g, 3.8 mmol) at 0° C. in THF (38 mL). After 17 h at ambient temperature, cool to 0° C. and add sequentially water (1.89 mL), 2N aqueous NaOH (1.89 mL) and water (2.69 mL). Filter the solids and evaporate the filtrate to obtain the crude amine. Purify by SCX chromatography. Rinse the column with methanol, add a solution of the crude amine in methanol, wash the column with methanol and then elute with 1N ammonia in methanol. Concentrate to give the title compound (0.57 g, 93%). GC-MS m/z: 163 ($M^+$).

Preparation 163

6-Aminomethyl-benzo[b]thiophene

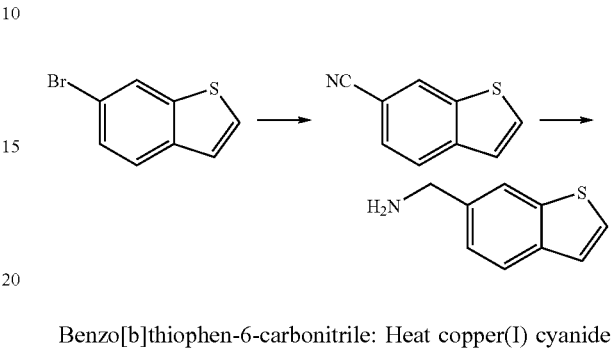

Benzo[b]thiophen-6-carbonitrile: Heat copper(I) cyanide (0.84 g, 9.4 mmol) and 6-bromobenzo[b]thiophene (prepared as described in WO 01/23381) (1.0 g, 4.7 mmol) at 160° C. for 13 h. Cool the mixture to 0° C., add 33% aqueous ethylenediamine (20 mL) and dilute with ether. Wash the organic mixture with brine, dry over $Na_2SO_4$ and evaporate. Purify by chromatography on silica gel eluting with EtOAc/hexane (0:1 to 1:3) to give the desired intermediate (0.58 g, 78%). GC-MS m/z: 159 ($M^+$).

6-Aminomethyl-benzo[b]thiophene: Add 1M lithium aluminum hydride in THF (7.3 mL) to benzo[b]thiophene-6-carbonitrile (0.6 g, 3.6 mmol) at 0° C. in THF (36 mL). After 15 h at ambient temperature, cool to 0° C. and add sequentially water (1.82 mL), 2N aqueous NaOH (1.82 mL) and water (2.60 mL). Filter the solid and evaporate the filtrate to obtain the crude amine. Purify by SCX chromatography. Rinse the column with methanol, add a solution of the crude amine in methanol, wash the column with methanol and then elute with 1N ammonia in methanol. Concentrate in vacuo to give the title compound (0.55 g, 92%).

Preparation 164

8-Bromomethyl-quinoline

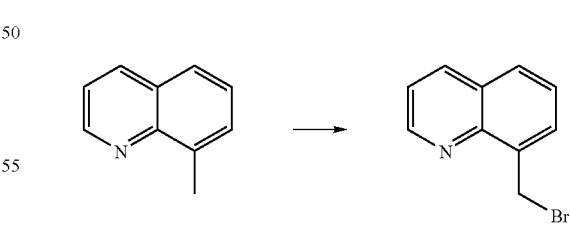

Combine 8-methyl-quinoline (1.0 g, 6.99 mmol), NBS (1.3 g, 7.13 mmol), benzoyl peroxide (6.0 mg, 0.03 mmol), carbon tetrachloride (30 mL) and reflux for 17 h. Cool the reaction mixture to ambient temperature and evaporate the solvent. Dissolve the residue in chloroform (30 mL), wash the organic solution with saturated aqueous $NaHCO_3$ (2×10 mL), brine (10 mL) and dry over anhydrous $Na_2SO_4$. Evaporate the solvent and purify by chromatography on silica gel eluting

Preparation 165

2-Aminomethyl-quinoline

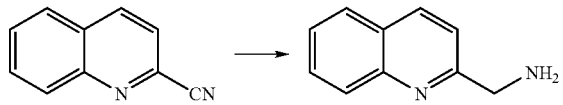

Combine quinoline-2-carbonitrile (0.2 g, 1.29 mmol), Raney® 3201 nickel (slurry in water, 0.05 g), 2N ammonia in methanol (10 mL) and hydrogenate at 50 psi for 15 min. Filter the reaction mixture through a pad of Celite®, remove the solvent and purify by SCX chromatography to obtain the title compound as a yellow oil (0.2 g, 98%). MS (ES+) m/z: 159 (M+H)+.

Preparation 166

3-Aminomethyl-quinoline Dihydrochloride

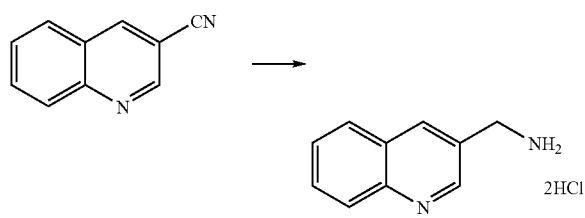

Combine quinoline-3-carbonitrile (1.0 g, 6.49 mmol), 10% Pd/C (0.2 g), 5% TFA in methanol (100 mL) and hydrogenate at 30 psi for 2 h. Filter the reaction mixture through a pad of Celite® and evaporate the solvent. Dissolve the residue in ethanol (10 mL), treat with 1N hydrogen chloride in diethyl ether (5 mL) and allow the mixture to stand at 5° C. for 18 h. Filter the precipitate, wash with ethanol and dry under vacuo to obtain the title compound as a white solid (0.6 g, 53%).

Preparation 167

2-Aminomethyl-isoquinoline Dihydrochloride

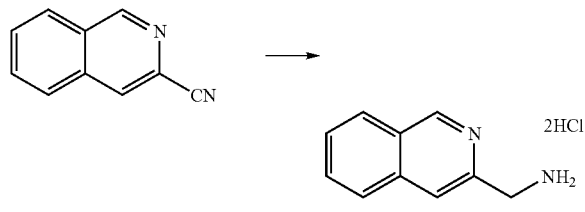

Combine isoquinoline-3-carbonitrile (1.0 g, 6.49 mmol), 10% Pd/C (0.2 g), 5% TFA in methanol (95 mL) and hydrogenate at 30 psi for 17 h. Filter the reaction mixture through a pad of Celite® and evaporate the solvent. Dissolve the residue in ethanol (10 mL), treat with 1N hydrogen chloride in diethyl ether (5 mL) and allow to stand at 5° C. for 18 h. Filter the precipitate, wash with ethanol and dry under vacuo to obtain the title compound as a white solid (0.6 g, 55%).

Preparation 168

6-Aminomethyl-quinoline

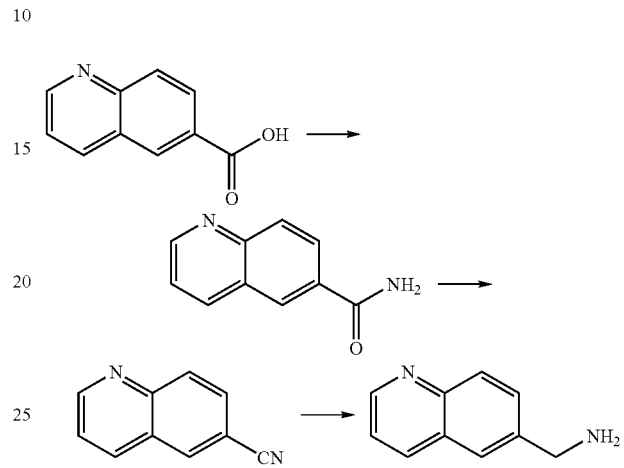

6-Quinolinecarboxamide: Combine 6-quinolinecarboxylic acid (2.0 g, 11.6 mmol), 1,1-carbonyldiimidazol (3.8 g, 23.45 mmol) in DCM (50 mL) and stir at ambient temperature for 1 h. Saturate the reaction mixture with anhydrous ammonia and continue to stir for 1 h. Quench the reaction mixture with water (100 mL) and extract with chloroform (3×50 mL). Combine the organic extracts, dry over anhydrous $Na_2SO_4$ and evaporate the solvent to obtain the desired intermediate as a white solid (1.6 g, 78%).

6-Quinolinecarbonitrile: Dissolve 6-quinolinecarboxamide (1.5 g, 8.95 mmol) in DCM (50 mL), add triethylamine (2.7 g, 26.8 mmol) and cool the reaction mixture to 0° C. Add trifluoroacetic acid anhydride (2.4 g, 11.16 mmol) to the reaction mixture and stir for 10 min at 0° C. Quench the reaction mixture with water (20 mL) and separate the organic layer. Extract aqueous layer with DCM (2×15 mL). Combine the organic extracts and dry over anhydrous $Na_2SO_4$. Evaporate the solvent to obtain the desired intermediate as a white solid (1.0 g, 73%). GC-MS m/z: 154 (M+).

6-Aminomethyl-quinoline: Combine 6-quinolinecarbonitrile (1.0 g, 6.49 mmol), Raney® 3201 nickel (slurry in water, 0.2 g), 2N ammonia in methanol (20 mL) and hydrogenate at 50 psi for 1 h. Filter the reaction mixture through a pad of Celite®, remove the solvent and purify by SCX chromatography to obtain the title compound as a yellow oil (0.8 g, 78%).

Preparation 169

(±)-2-(1-Aminoethyl)-5-methylthiophene

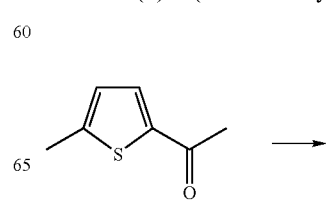

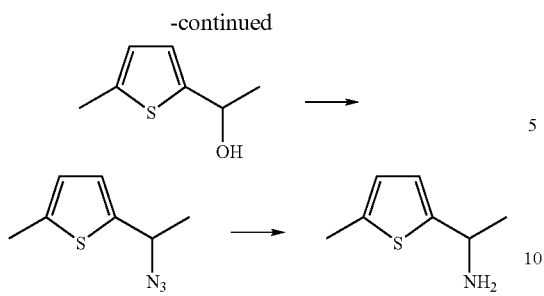

(±)-2-(1-Hydroxyethyl)-5-methylthiophene: Add sodium borohydride (270 mg, 7.13 mmol) to a solution of 2-acetyl-5-methylthiophene (1.0 g, 7.13 mmol) in methanol (40 mL). Stir the mixture for 1 h at room temperature. Remove the solvent in vacuo and partition the residue between water and DCM. Separate the organic phase, dry over $Na_2SO_4$, filter and concentrate to obtain the desired intermediate as an oil (0.995 g, 98%) that was used without further purification. GC-MS m/z 142 ($M^+$).

(±)-2-(1-Azidoethyl)-5-methylthiophene: Add DBU (1.228 g, 1.2 mL, 8.07 mmol) to a solution of (−)-2-(1-hydroxyethyl)-5-methylthiophene (0.955 g, 6.72 mmol) and diphenylphosphoryl azide (2.22 g, 1.74 mL, 8.07 mmol) in anhydrous toluene. Stir at room temperature for 18 h. Dilute the mixture with EtOAc and wash with water and 0.5N aqueous HCl. Dry the organic phase over $Na_2SO_4$, filter and concentrate. Purify by chromatography on silica gel eluting with hexane/EtOAc (1:0 and 19:1) to obtain the desired intermediate as an oil (0.875 g, 78%). GC-MS m/z 167 ($M^+$).

(±)-2-(1-Aminoethyl)-5-methylthiophene: Add lithium aluminum hydride (29 mg, 0.72 mmol) to a solution of (±)-2-(1-azidoethyl)-5-methylthiophene (100 mg, 0.59 mmol) in anhydrous THF (5 mL). Stir at room temperature overnight. Work-up the mixture with EtOAc and water. Filter the mixture over Celite®. Separate and wash the organic phase with brine. Dry over $Na_2SO_4$, filter and concentrate in vacuo. Purify by SCX chromatography. Rinse with DCM/methanol (1:1), load the crude mixture in methanol and elute sequentially with methanol and 1N ammonia in methanol to obtain the title compound as an oil (80 mg, 95%). GC-MS m/z 141 ($M^+$).

Preparations 170 and 171

1-(5-Phenyl-thiophen-2-yl)ethylamine, Isomers 1 and 2

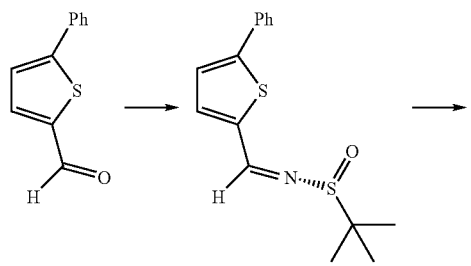

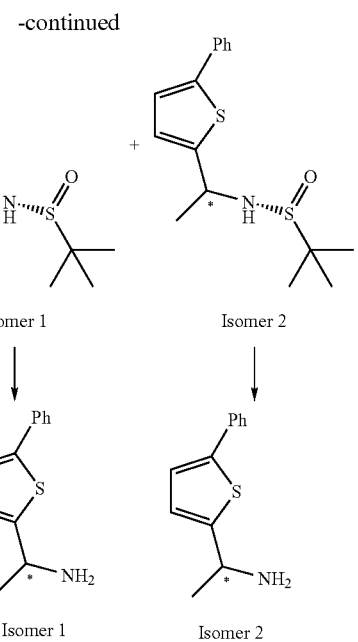

N-[(5-Phenylthiophen-2-yl)-methylene]-2-methylpropanesulfinamide: To a solution of 5-phenyl-2-thiophenecarboxaldehyde (1.25 g, 6.64 mmol) in anhydrous THF (50 mL), add titanium(IV) ethoxide (3.03 g, 2.78 mL, 13.28 mmol) and (R)-(+)-2-methyl-2-propanesulfinamide (0.965 g, 7.968 mmol) under nitrogen. Heat the reaction at 80° C. overnight Cool the mixture to room temperature and dilute with EtOAc. Add water and filter the resulting precipitate over Celite®. Separate and dry the organic phase over $Na_2SO_4$, filter and concentrate in vacuo to obtain the desired intermediate as a yellow solid (1.93 g, 100% yield) that was used without purification.

N-[1-(5-Phenylthiophen-2-yl)ethyl]-2-methylpropanesulfinamide (Isomer 1) and N-[1-(5-phenylthiophen-2-yl)ethyl]-2-methylpropanesulfinamide (Isomer 2): Add slowly methyllithium (8.1 mL, 12.92 mmol, 1.6 M solution in ether) to a solution of N-[(5-phenylthiophen-2-yl)-methylene]-2-methylpropanesulfinamide (1.883 g, 6.46 mmol) in anhydrous THF (50 mL) at −40° C. Warm the reaction to −20° C. and stir for 2 h. Warm to 0° C. and stir for an additional 2 h. Add saturated aqueous $NH_4Cl$ and extract with EtOAc. Dry the organic phase over $Na_2SO_4$, filter and concentrate in vacuo. Purify by chromatography on silica gel eluting with hexane/EtOAc (7:3 and 1:1) to obtain N-[1-(5-phenylthiophen-2-yl)ethyl]-2-methylpropanesulfinamide (Isomer 1) (575 mg, 30% yield) and N-[1-(5-phenylthiophen-2-yl)ethyl]-2-methylpropanesulfinamide (Isomer 2) (847 mg, 44% yield).

1-(5-Phenyl-thiophen-2-yl)ethylamine (Isomer 1, Preparation 170) Add 4N hydrogen chloride in dioxane (0.837 mL, 3.349 mmol) to a stirred solution of N-[1-(5-phenylthiophen-2-yl)ethyl]-2-methylpropanesulfinamide (Isomer 1) (515 mg, 1.675 mmol) in methanol (8 mL) at room temperature. Stir for 2 h and remove the solvent in vacuo to obtain a solid that was washed with ethyl ether. Dissolve the solid in DCM and wash with saturated aqueous $NaHCO_3$. Dry the organic phase over $Na_2SO_4$, filter and concentrate in vacuo to obtain the desired intermediate (236 mg, 69% yield).

1-(5-Phenyl-thiophen-2-yl)ethylamine (Isomer 2, Preparation 171) Add 4N hydrogen chloride in dioxane (1.112 mL, 4.449 mmol) to a stirred solution of N-[1-(5-phenylthiophen- 2-yl)ethyl]-2-methylpropanesulfinamide (Isomer 2) (684 mg, 2.225 mmol) in methanol (10 mL) at room temperature. Stir for 2 h and remove the solvent in vacuo to obtain a solid that was washed with ethyl ether. Dissolve the solid in DCM and wash with saturated aqueous NaHCO₃. Dry the organic phase over Na₂SO₄, filter and concentrate in vacuo to obtain the desired intermediate (347 mg, 77% yield).

EXAMPLE 49

6-(2-Benzoylamino-ethylamino)-7-chloro-2,3,4,5-tetrahydro-1H-benzo[d]azepine Hydrochloride

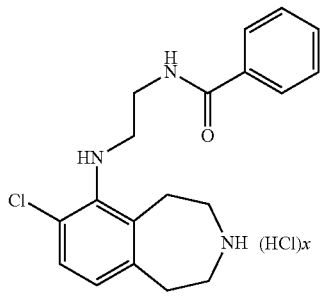

Dissolve 6-(2-amino-ethylamino)-7-chloro-3-(2,2,2-trifluoroacetyl)-2,3,4,5-tetrahydro-1H-benzo[d]azepine (70 mg, 0.208 mmol) in DCM (4 mL). Add benzoyl chloride (24 µL, 0.208 mmol), and triethylamine (44 µL, 0.312 mmol) and stir at ambient temperature for 24 h under nitrogen atmosphere. Dilute with DCM and add 1M aqueous HCl. Extract the aqueous layer with DCM. Dry the organic layer over MgSO₄ and concentrate in vacuo. Purify by chromatography on silica gel eluting with hexane/EtOAc (1:0, 7:3 and 1:1) to obtain 6-(2-benzoylamino-ethylamino)-7-chloro-3-(2,2,2-trifluoroacetyl)-2,3,4,5-tetrahydro-1H-benzo[d]azepine.

Use a method similar to the General Procedure 1-1, using 6-(2-benzoylamino-ethylamino)-7-chloro-3-(2,2,2-trifluoroacetyl)-2,3,4,5-tetrahydro-1H-benzo[d]azepine, to give the free base of the title compound. Use a method similar to the General Procedure 2-2 to give the title compound (77 mg, 90% overall). HPLC: $t_R$=2.64 min (20-80% of Solvent B in 7.5 min. Solvent A: water, 0.1% TFA. Solvent B: acetonitrile, 0.1% TFA. Column: C18-Metachem, 5 micron, 4.6×50).

Examples 50-52 may be prepared essentially as described in Example 49 by using 6-(2-amino-ethylamino)-7-chloro-3-(2,2,2-trifluoroacetyl)-2,3,4,5-tetrahydro-1H-benzo[d]azepine or 6-(3-amino-propylamino)-7-chloro-3-(2,2,2-trifluoroacetyl)-2,3,4,5-tetrahydro-1H-benzo[d]azepine and the appropriate benzoyl chloride. Overall yields and MS (ES+) data are shown in the Table below.

| Ex. | NH—CO—R | n | Compound | Yield (%) | MS (ES+) |
|---|---|---|---|---|---|
| 50 | 2-fluorobenzoyl | 2 | 7-Chloro-6-[2-(2-fluorobenzoylamino)-ethylamino]-2,3,4,5-tetrahydro-1H-benzo[d]azepine Hydrochloride | 40 | 362 (M + H)⁺ |
| 51 | benzoyl | 3 | 6-(3-Benzoylamino-propylamino)-7-chloro-2,3,4,5-tetrahydro-1H-benzo[d]azepine Hydrochloride | 90 | ND |
| 52 | 2-fluorobenzoyl | 3 | 7-Chloro-6-[3-(2-fluorobenzoylamino)-propylamino]-2,3,4,5-tetrahydro-1H-benzo[d]azepine Hydrochloride | 40 | 376 (M + H)⁺ |

ND = Not determined

EXAMPLE 53

7-Chloro-6-{2-[(pyridine-3-carbonyl)-amino]-ethylamino}-2,3,4,5-tetrahydro-1H-benzo[d]azepine Hydrochloride

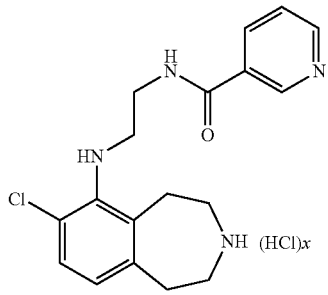

Dissolve nicotinic acid (28.2 mg, 0.23 mmol) in DCM (3 mL). Add EDC (40 mg, 0.208 mmol), HOBT (28.1 mg, 0.2081 mmol) and stir at ambient temperature for 10 min. Add 6-(2-amino-ethylamino)-7-chloro-3-(2,2,2-trifluoroacetyl)-2,3,4,5-tetrahydro-1H-benzo[d]azepine (70 mg, 0.208 mmol) and stir at ambient temperature for 10 hr. Dilute with DCM, add water and extract the aqueous layer three times with DCM. Wash combined organic extracts with 1N aqueous NaOH, and brine. Dry the organic layer over $MgSO_4$, concentrate in vacuo and purify by chromatography on silica gel eluting with hexane/EtOAc (1:0, 1:1, 3:7 and 1:9) to obtain 7-chloro-6-{2-[(pyridine-3-carbonyl)-amino]-ethylamino}-3-(2,2,2-trifluoroacetyl)-2,3,4,5-tetrahydro-1H-benzo[d]azepine.

Use a method similar to the General Procedure 1-1, using 7-chloro-6-{2-[(pyridine-3-carbonyl)-amino]-ethylamino}-3-(2,2,2-trifluoroacetyl)-2,3,4,5-tetrahydro-1H-benzo[d]azepine, to give the free base of the title compound. Use a method similar to the General Procedure 2-2 to give the title compound as a solid (92 mg, 98%). HPLC: $t_R$=1.38 min (20-80% of Solvent B in 7.5 min. Solvent A: water, 0.1% TFA. Solvent B: acetonitrile, 0.1% TFA. Column: C18 Metachem; 5 micron, 4.6×50).

EXAMPLE 54

7-Chloro-6-[3-(3-phenyl-ureido)-propylamino]-2,3,4,5-tetrahydro-1H-benzo[d]azepine Hydrochloride

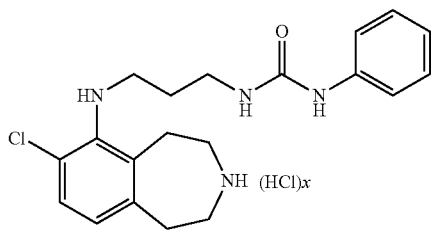

Combine phenyl isocyanate (15 μL, 0.137 mmol) and 6-(3-amino-propylamino)-7-chloro-3-(2,2,2-trifluoroacetyl)-2,3,4,5-tetrahydro-1H-benzo[d]azepine (48 mg, 0.137 mmol) in DCM and stir for 16 h. Concentrate, add DCM, filter and collect the solid to obtain 7-chloro-6-[3-(3-phenyl-ureido)-propylamino]-3-(2,2,2-trifluoroacetyl)-2,3,4,5-tetrahydro-1H-benzo[d]azepine (18 mg, 28%).

Use a method similar to the General Procedure 1-1, using 7-chloro-6-[3-(3-phenyl-ureido)-propylamino]-3-(2,2,2-trifluoroacetyl)-2,3,4,5-tetrahydro-1H-benzo[d]azepine, to give the free base of the title compound. Use a method similar to the General Procedure 2-2 to give the title compound (14 mg, 23%). MS (ES+) m/z: 373 (M+H)+.

EXAMPLE 55

6-(2-Phenoxy-ethylamino)-2,3,4,5-tetrahydro-1H-benzo[d]azepine Hydrochloride

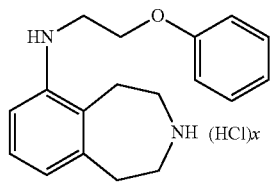

Use a method similar to the General Procedure 5-1, using 3-(2,2,2-trifluoroacetyl)-6-trifluoromethanesulfonyloxy-2,3,4,5-tetrahydro-1H-benzo[d]azepine (100 mg, 0.23 mmol) and phenoxyethylamine (63 mg, 0.4 mmol) to give, after chromatography on silica gel eluting with hexane/EtOAc (85:15) followed by SCX chromatography, 6-(2-phenoxyethylamino)-3-(2,2,2-trifluoroacetyl)-2,3,4,5-tetrahydro-1H-benzo[d]azepine as a yellow oil. MS (ES+) m/z: 379 (M+H)+.

Use a method similar to the General Procedure 1-1 to deprotect 6-(2-phenoxy-ethylamino)-3-(2,2,2-trifluoroacetyl)-2,3,4,5-tetrahydro-1H-benzo[d]azepine (75 mg, 0.19 mmol). Purify by SCX chromatography to give the free base of the title compound. Use a method similar to the General Procedure 2-2 to give the title compound as a white solid. MS (ES+) m/z: 283 (M+H)+.

Examples 56-61 may be prepared essentially as described in Example 55 by using 7-chloro-3-(2,2,2-trifluoroacetyl)-6-trifluoromethanesulfonyloxy-2,3,4,5-tetrahydro-1H-benzo[d]azepine and the appropriate amine. The yields for the Step 1 (General Procedure 5-1) and MS (ES+) data are shown in the Table below.

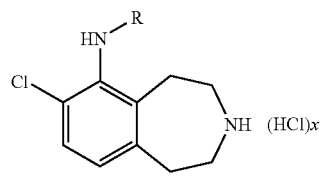

| Ex. | NH—R | Compound | Yield (%) | MS (ES+) m/z |
|---|---|---|---|---|
| 56 | | 7-Chloro-6-phenethylamino-2,3,4,5-tetrahydro-1H-benzo[d]azepine Hydrochloride | 47 | 301 (M + H)+ |
| 57 | | 7-Chloro-6-(3-fluoro-phenethylamino)-2,3,4,5-tetrahydro-1H-benzo[d]azepine Hydrochloride | 55 | 319 (M + H)+ |
| 58 | | 7-Chloro-6-[(thiazol-2-yl)methylamino]-2,3,4,5-tetrahydro-1H-benzo[d]azepine Hydrochloride | 21 | 294 (M + H)+ |
| 59 | | 7-Chloro-6-[(2-methyl-thiazol-4-yl)methylamino]-2,3,4,5-tetrahydro-1H-benzo[d]azepine Hydrochloride | 16 | 308 (M + H)+ |
| 60 | | 7-Chloro-6-(2-pyridin-2-yl-ethylamino)-2,3,4,5-tetrahydro-1H-benzo[d]azepine Hydrochloride | 86 | 302 (M + H)+ |
| 61 | | 7-Chloro-6-(2-thiophen-2-yl-ethylamino)-2,3,4,5-tetrahydro-1H-benzo[d]azepine Hydrochloride | 78 | ND |

ND = Not determined

EXAMPLE 62

7-Chloro-6-[(2-ethoxyethyl)amino]-2,3,4,5-tetrahydro-1H-benzo[d]azepine Succinate

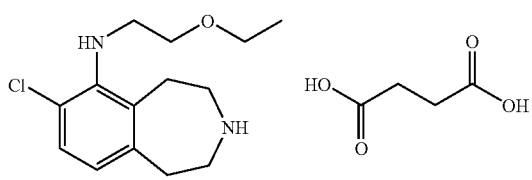

Use a method similar to the General Procedure 5-1, using 7-chloro-3-(2,2,2-trifluoroacetyl)-6-trifluoromethanesulfonyloxy-2,3,4,5-tetrahydro-1H-benzo[d]azepine (200 mg, 0.47 mmol) and 2-ethoxyethyl amine (105 μL, 1.0 mmol) to give, after chromatography on silica gel eluting with hexane/EtOAc (95:5) and additional SCX chromatography, 7-chloro-6-[(2-ethoxyethyl)amino]-3-(2,2,2-trifluoroacetyl)-2,3,4,5-tetrahydro-1H-benzo[d]azepine (32 mg, 19%). MS (ES+) m/z: 365 (M+H)+.

Use a method similar to the General Procedure 1-1 to deprotect 7-chloro-6-[(2-ethoxyethyl)amino]-3-(2,2,2-trifluoroacetyl)-2,3,4,5-tetrahydro-1H-benzo[d]azepine (30 mg, 0.08 mmol). Purify by SCX chromatography to give the free base of the title compound. Use a method similar to the General Procedure 2-1 to give the title compound as an oil (23.8 mg, 75% over 2 steps). MS (ES+) m/z: 269 (M+H)+.

Examples 63-68 may be prepared essentially as described in Example 62 by using 7-chloro-3-(2,2,2-trifluoroacetyl)-6-trifluoromethanesulfonyloxy-2,3,4,5-tetrahydro-1H-benzo[d]azepine and the appropriate amine. The yields for the Step 1 (General Procedure 5-1), optical rotations and MS (ES+) data are shown in the Table below.

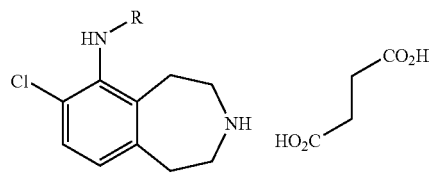

| Ex. | NH—R | Compound | Yield (%) | MS (ES+) m/z. | $[\alpha]^{20}_D$ (c, solvent) |
|---|---|---|---|---|---|
| 63 | NH−CH2CH2−O−propyl | 7-Chloro-6-[2-(1-propoxy)ethylamino]-2,3,4,5-tetrahydro-1H-benzo[d]azepine Succinate | 57 | 283 (M + H)+ | — |
| 64 | NH−CH2CH2−O−isopropyl | 7-Chloro-6-[2-(2-propoxy)ethylamino]-2,3,4,5-tetrahydro-1H-benzo[d]azepine Succinate | 75 | 283 (M + H)+ | — |
| 65 | NH−CH2CH2−O−CH2−Ph | 6-(2-Benzyloxy-ethylamino)-7-chloro-2,3,4,5-tetrahydro-1H-benzo[d]azepine Succinate | 37 | 331 (M + H)+ | — |
| 66 | (R)-NH−CH(CH3)−CH2−O−CH2−Ph | (R)-6-(2-Benzyloxy-1-methyl-ethylamino)-7-chloro-2,3,4,5-tetrahydro-1H-benzo[d]azepine Succinate | 15 | 345 (M + H)+ | ND |
| 67 | (R)-NH−CH(CH3)−CH2−O−Ph | (R)-6-(2-Phenoxy-1-methyl-ethylamino)-7-chloro-2,3,4,5-tetrahydro-1H-benzo[d]azepine Succinate | 15 | 331 (M + H)+ | +54.7° (c 0.5, CH3OH) |
| 68 | (R)-NH−CH(CH3)−CH2−O−(3-F-Ph) | (R)-6-[2-(4-Fluorobenzyloxy)-1-methyl-ethylamino]-7-chloro-2,3,4,5-tetrahydro-1H-benzo[d]azepine Succinate | 69 | 363 (M + H)+ | +22.6° (c 0.5, CH3OH) |

ND = Not determined

EXAMPLE 69

6-(2-Fluorobenzylamino)-2,3,4,5-tetrahydro-1H-benzo[d]azepine Hydrochloride

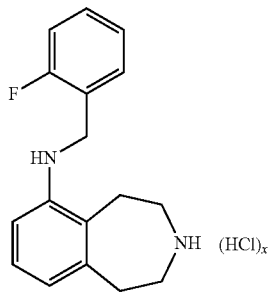

Use a method similar to the General Procedure 5-1, using 3-(2,2,2-trifluoroacetyl)-6-trifluoromethylsulfonyloxy-2,3,4,5-tetrahydro-1H-benzo[d]azepine (100 mg, 0.26 mmol) and 2-fluorobenzylamine (88 µL, 0.77 mmol) to give, after chromatography on silica gel eluting with hexane/EtOAc (9:1), 6-(2-fluorobenzylamino)-3-(2,2,2-trifluoroacetyl)-2,3,4,5-tetrahydro-1H-benzo[d]azepine as a yellow oil (45 mg, 48%). MS (ES+) m/z: 367 (M+H)$^+$.

Use a method similar to the General Procedure 1-1 to deprotect 6-(2-fluorobenzylamino)-3-(2,2,2-trifluoroacetyl)-2,3,4,5-tetrahydro-1H-benzo[d]azepine (40 mg, 0.11 mmol). Purify by SCX chromatography to give the free base of the title compound as a yellow oil (28 mg, 94%). Use a method similar to the General Procedure 2-2 to give the title compound as an off-white solid (29 mg, 95%). MS (ES+) m/z: 271 (M+H)$^+$.

Example 70 may be prepared essentially as described in Example 69 by using 3-(2,2,2-trifluoroacetyl)-6-trifluoromethylsulfonyloxy-2,3,4,5-tetrahydro-1H-benzo[d]azepine and 2,6-difluorobenzylamine. The yield for the Step 1 (General Procedure 5-1) and MS (ES+) data are shown in the Table below.

EXAMPLE 71

7-Chloro-6-(2-fluorobenzylamino)-2,3,4,5-tetrahydro-1H-benzo[d]azepine Hydrochloride

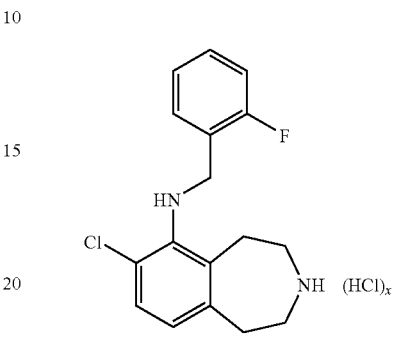

Use a method similar to the General Procedure 5-1 to couple 7-chloro-3-(2,2,2-trifluoroacetyl)-6-trifluoromethanesulfonyloxy-2,3,4,5-tetrahydro-1H-benzo[d]azepine and 2-fluorobenzyl amine. Purify by chromatography on silica gel eluting with hexane/EtOAc (9:1 and 4:1) to give 7-chloro-6-(2-fluorobenzylamino)-3-(2,2,2-trifluoroacetyl)-2,3,4,5-tetrahydro-1H-benzo[d]azepine as a yellow solid. MS (ES+) m/z: 401 (M+H)$^+$.

Use a method similar to the General Procedure 1-1 to deprotect 7-chloro-6-(2-fluorobenzylamino)-3-(2,2,2-trifluoroacetyl)-2,3,4,5-tetrahydro-1H-benzo[d]azepine. Purify by SCX chromatography to give the free base of the title compound as a yellow oil. Use a method similar to the General Procedure 2-2 to give the title compound as a light yellow solid. MS (ES+) m/z: 305 (M+H)$^+$.

Examples 72-80 may be prepared essentially as described in Example 71 by using 7-chloro-3-(2,2,2-trifluoroacetyl)-6-trifluoromethanesulfonyloxy-2,3,4,5-tetrahydro-1H-benzo[d]azepine and the appropriate amine. MS (ES+) data are shown in the Table below.

| Ex. | Structure | Compound | Yield (%) | MS (ES+) m/z |
|---|---|---|---|---|
| 70 | 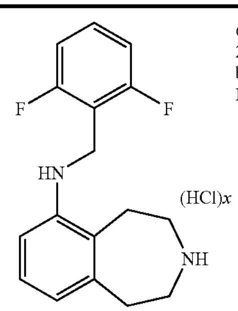 | 6-(2,6-Difluorobenzylamino)-2,3,4,5-tetrahydro-1H-benzo[d]azepine Hydrochloride | 69 | 289 (M + H)$^+$ |

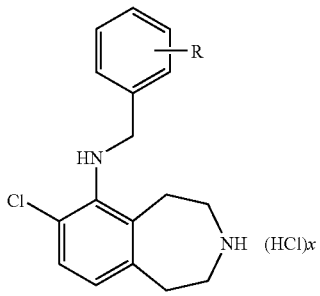

| Ex. | R | Compound | MS (ES+) m/z |
|---|---|---|---|
| 72 | 3-F | 7-Chloro-6-(3-fluorobenzylamino)-2,3,4,5-tetrahydro-1H-benzo[d]azepine Hydrochloride | 305 (M + H)⁺ |
| 73 | 4-F | 7-Chloro-6-(4-fluorobenzylamino)-2,3,4,5-tetrahydro-1H-benzo[d]azepine Hydrochloride | 305 (M + H)⁺ |
| 74 | 2,3-diF | 7-Chloro-6-(2,3-difluorobenzylamino)-2,3,4,5-tetrahydro-1H-benzo[d]azepine Hydrochloride | 323 (M + H)⁺ |
| 75 | 3,4-diF | 7-Chloro-6-(3,4-difluorobenzylamino)-2,3,4,5-tetrahydro-1H-benzo[d]azepine Hydrochloride | 323 (M + H)⁺ |
| 76 | 3,5-diF | 7-Chloro-6-(3,5-difluorobenzylamino)-2,3,4,5-tetrahydro-1H-benzo[d]azepine Hydrochloride | 323 (M + H)⁺ |
| 77 | 3,4,5-triF | 7-Chloro-6-(3,4,5-trifluorobenzylamino)-2,3,4,5-tetrahydro-1H-benzo[d]azepine Hydrochloride | 341 (M + H)⁺ |
| 78 | 3-CF$_3$ | 7-Chloro-6-(3-trifluoromethyl-benzylamino)-2,3,4,5-tetrahydro-1H-benzo[d]azepine Hydrochloride | 355 (M + H)⁺ |
| 79 | 3,5-diCF$_3$ | 7-Chloro-6-[3,5-bis(trifluoromethyl)benzylamino]-2,3,4,5-tetrahydro-1H-benzo[d]azepine Hydrochloride | 423 (M + H)⁺ |
| 80 | 4-O(CH$_2$)$_2$N(CH$_3$)$_2$ | 7-Chloro-6-{4-[2-(N,N-dimethylamino)ethoxy]benzylamino}-2,3,4,5-tetrahydro-1H-benzo[d]azepine Hydrochloride | 374 (M + H)⁺ |

EXAMPLE 81

6-(4-tert-Butylbenzylamino)-7-chloro-2,3,4,5-tetrahydro-1H-benzo[d]azepine Succinate

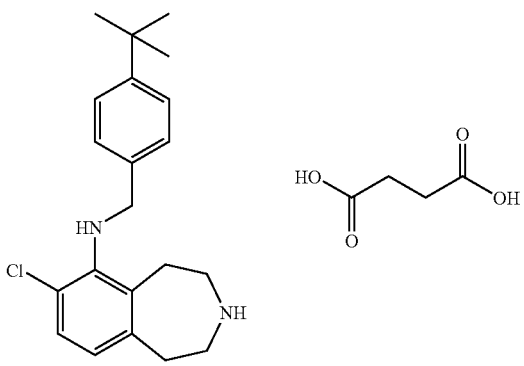

Use a method similar to the General Procedure 5-1 to couple 7-chloro-3-(2,2,2-trifluoroacetyl)-6-trifluoromethanesulfonyloxy-2,3,4,5-tetrahydro-1H-benzo[d]azepine (300 mg, 0.7 mmol) with 4-(tert-butyl)benzyl amine (375 μL, 2.1 mmol). Purify by chromatography on silica gel eluting with hexane/EtOAc (95:5) followed by SCX chromatography to give 6-(4-tert-butylbenzylamino)-7-chloro-3-(2,2,2-trifluoroacetyl)-2,3,4,5-tetrahydro-1H-benzo[d]azepine as a colorless oil (240 mg, 78%). MS (ES+) m/z: 439 (M+H)⁺.

Use a method similar to the General Procedure 1-1 to deprotect 6-(4-tert-butylbenzylamino)-7-chloro-3-(2,2,2-trifluoroacetyl)-2,3,4,5-tetrahydro-1H-benzo[d]azepine (235 mg, 0.54 mmol). Purify by SCX chromatography to give the free base of the title compound (161 mg, 87%). Use a method similar to the General Procedure 2-1 to give the title compound as an off-white gum (190 mg, 88%). MS (ES+) m/z: 343 (M+H)⁺.

Examples 82-88 may be prepared essentially as described in Example 81 by using 7-chloro-3-(2,2,2-trifluoroacetyl)-6-trifluoromethanesulfonyloxy-2,3,4,5-tetrahydro-1H-benzo[d]azepine and the appropriate amine. MS (ES+) data are shown in the Table below

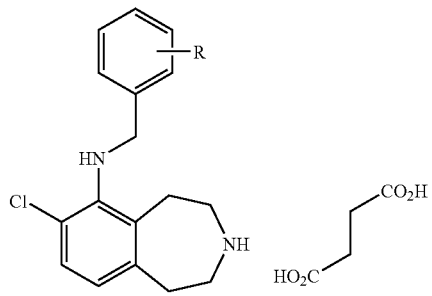

| Ex. | R | Compound | MS (ES+) m/z |
|---|---|---|---|
| 82 | 3-t-Bu | 6-(3-tert-Butylbenzylamino)-7-chloro-2,3,4,5-tetrahydro-1H-benzo[d]azepine Succinate | 343 (M + H)+ |
| 83 | 4-OCF$_3$ | 7-Chloro-6-(4-trifluoromethoxy-benzylamino)-2,3,4,5-tetrahydro-1H-benzo[d]azepine Succinate | 371 (M + H)+ |
| 84 | 4-F,3-CF$_3$ | 7-Chloro-6-[(4-fluoro-3-trifluoromethyl)benzylamino]-2,3,4,5-tetrahydro-1H-benzo[d]azepine Succinate | 373 (M + H)+ |
| 85 | 4-F,3-OCH$_3$ | 7-Chloro-6-[(4-fluoro-3-methoxy)benzylamino]-2,3,4,5-tetrahydro-1H-benzo[d]azepine Succinate | 321 (M + H)+ |
| 86 | 4-Ph | 7-Chloro-6-(4-phenylbenzylamino)-2,3,4,5-tetrahydro-1H-benzo[d]azepine Succinate | 363 (M + H)+ |
| 87 | 4-OPh | 7-Chloro-6-(4-phenoxy-benzylamino)-2,3,4,5-tetrahydro-1H-benzo[d]azepine Succinate | 379 (M + H)+ |
| 88 | 4-SO$_2$CH$_3$ | 7-Chloro-6-(4-methanesulfonyl-benzylamino)-2,3,4,5-tetrahydro-1H-benzo[d]azepine Succinate | 365 (M + H)+ |

EXAMPLE 89

7-Chloro-6-(4-cyanobenzylamino)-2,3,4,5-tetrahydro-1H-benzo[d]azepine Succinate

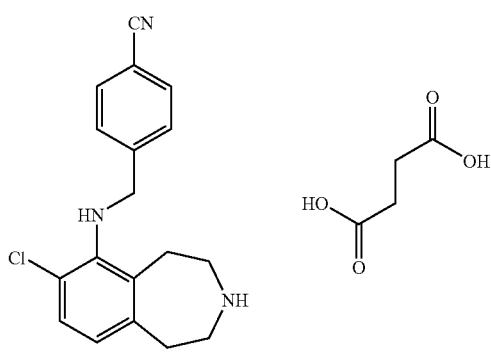

Use a method similar to the General Procedure 5-1 to react 7-chloro-3-(2,2,2-trifluoroacetyl)-6-trifluoromethanesulfonyloxy-2,3,4,5-tetrahydro-1H-benzo[d]azepine (504 mg, 1.2 mmol), 4-cyanobenzylamine (476 mg, 3.6 mmol), palladium (II) acetate (29 mg, 0.1 mmol), BINAP (148 mg, 0.2 mmol) and cesium carbonate (540 mg, 1.7 mmol) in toluene (5 mL). Purify by chromatography on silica gel eluting with isohexane/EtOAc (1:0 to 1:1) to give 7-chloro-6-(4-cyanobenzylamino)-3-(2,2,2-trifluoroacetyl)-2,3,4,5-tetrahydro-1H-benzo[d]azepine as a white gum (108 mg, 22%). MS (ES+) m/z: 408 (M+H)+.

Use a method similar to the General Procedure 1-2 to deprotect 7-chloro-6-(4-cyanobenzylamino)-3-(2,2,2-trifluoroacetyl)-2,3,4,5-tetrahydro-1H-benzo[d]azepine (98 mg, 0.2 mmol). Purify by preparative liquid chromatography eluting with a gradient of water/acetonitrile (19:1 to 1:19) to give the free base of the title compound (31 mg, 42%). MS (ES+) m/z: 312 (+H)+. Use a method similar to the General Procedure 2-1, using 7-chloro-6-(4-cyanobenzylamino)-2,3,4,5-tetrahydro-1H-benzo[d]azepine (31 mg, 0.1 mmol) to give the title compound as a beige solid (41 mg, 95%). MS (ES+) m/z: 312 (M+H)+.

EXAMPLE 90

7-Chloro-6-(3-phenyl-benzylamino)-2,3,4,5-tetrahydro-1H-benzo[d]azepine Succinate

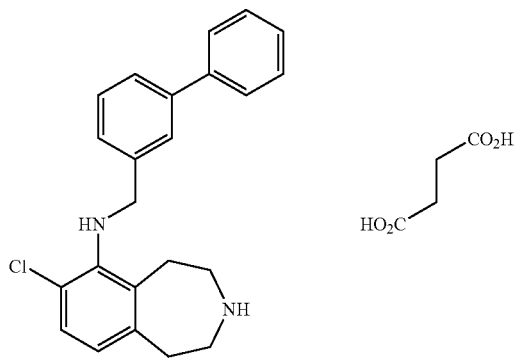

Use a method similar to the General Procedure 5-3 to couple 7-chloro-3-(2,2,2-trifluoroacetyl)-6-trifluoromethanesulfonyloxy-2,3,4,5-tetrahydro-1H-benzo[d] azepine (0.3 g, 0.706 mmol) with 3-phenyl-benzylamine (0.388 g, 2.117 mmol) using palladium(II) acetate (32 mg, 0.141 mmol), tris(dibenzylideneacetone)dipalladium(0) (65 mg, 0.070 mmol), BINAP (264 mg, 0.424 mmol) and cesium carbonate (460 mg, 1.412 mmol) in toluene (12 mL). Purify by chromatography on silica gel eluting with hexane/EtOAc (1:0, 19:1) to give 7-chloro-6-(3-phenyl-benzylamino)-3-(2,2,2-trifluoroacetyl)-2,3,4,5-tetrahydro-1H-benzo[d]azepine as an oil (0.257 g, 79%). MS (ES+) m/z: 459 (M+H)+.

Use a method similar to the General Procedure 1-2, using 7-chloro-6-(3-phenyl-benzylamino)-3-(2,2,2-trifluoroacetyl)-2,3,4,5-tetrahydro-1H-benzo[d]azepine (237 mg, 0.516 mmol), to give the free base of the title compound as an oil (188 mg, 100%) that was used without further purification.

Use a method similar to the General Procedure 2-1, using 7-chloro-6-(3-phenyl-benzylamino)-2,3,4,5-tetrahydro-1H-benzo[d]azepine (188 mg, 0.518 mmol) to give the title compound as a white solid (191 mg, 77%). MS (ES+) m/z: 363 (M+H)+.

EXAMPLE 91

7-Chloro-6-(4-chlorobenzylamino)-2,3,4,5-tetrahydro-1H-benzo[d]azepine Succinate

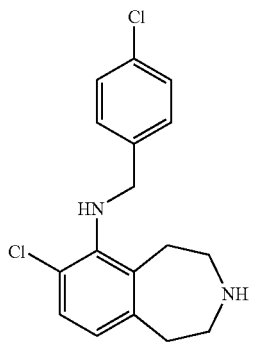
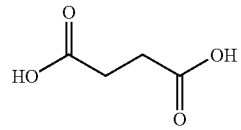

Use a method similar to the General Procedure 5-3 to couple 7-chloro-3-(2,2,2-trifluoroacetyl)-6-trifluoromethanesulfonyloxy-2,3,4,5-tetrahydro-1H-benzo[d]azepine (700 mg, 1.6 mmol) with 4-chlorobenzylamine (354 mg, 2.5 mmol). Purify by chromatography on silica gel eluting with hexane/EtOAc (1:0 and 9:1) and then SCX chromatography to give 7-chloro-6-(4-chlorobenzylamino)-3-(2,2,2-trifluoroacetyl)-2,3,4,5-tetrahydro-1H-benzo[d]azepine (459 mg, 69%). MS (ES+) m/z: 417 (M+H)$^+$.

Use a method similar to the General Procedure 1-1 to deprotect 7-chloro-6-[1-(4-chlorobenzylamino)-3-(2,2,2-trifluoroacetyl)-2,3,4,5-tetrahydro-1H-benzo[d]azepine. Purify by chromatography on silica gel eluting with DCM/2M ammonia in methanol (95:5) to give the free base of the title compound. MS (ES+) m/z: 321 (M+H)$^+$. Use a method similar to the General Procedure 2-1 to obtain the title compound.

Examples 92-98 may be prepared essentially as described in Example 91 by using 7-chloro-3-(2,2,2-trifluoroacetyl)-6-trifluoromethanesulfonyloxy-2,3,4,5-tetrahydro-1H-benzo[d]azepine and the appropriate amine. The yields for the Step 1 (General Procedure 5-3) and MS (ES+) data are shown in the Table below.

| Ex. | R | Compound | Yield (%) | MS (ES+) m/z |
|---|---|---|---|---|
| 92 | 3-Cl | 7-Chloro-6-(3-chlorobenzylamino)-2,3,4,5-tetrahydro-1H-benzo[d]azepine Succinate | 45 | 321 (M + H)$^+$ |
| 93 | 3-Cl,4-F | 7-Chloro-6-(3-chloro-4-fluoro-benzylamino)-2,3,4,5-tetrahydro-1H-benzo[d]azepine Succinate | 90 | 339 (M + H)$^+$ |
| 94 | 2-Cl,4-F | 7-Chloro-6-(2-chloro-4-fluoro-benzylamino)-2,3,4,5-tetrahydro-1H-benzo[d]azepine Succinate | 75 | 339 (M + H)$^+$ |
| 95 | 3-OCH$_3$ | 7-Chloro-6-(3-methoxy-benzylamino)-2,3,4,5-tetrahydro-1H-benzo[d]azepine Succinate | 84 | 316 (M + H)$^+$ |
| 96 | 2-F,4-CH$_3$ | 7-Chloro-6-(2-fluoro-4-methyl-benzylamino)-2,3,4,5-tetrahydro-1H-benzo[d]azepine Succinate | 53 | 319 (M + H)$^+$ |
| 97 | 3-OCF$_3$ | 7-Chloro-6-(3-trifluoromethoxy-benzylamino)-2,3,4,5-tetrahydro-1H-benzo[d]azepine Succinate | 85 | 371 (M + H)$^+$ |
| 98 | 3-Cl, 4-OCH$_3$ | 7-Chloro-6-(3-chloro-4-methoxy-benzylamino)-2,3,4,5-tetrahydro-1H-benzo[d]azepine Succinate | 100 | 351 (M + H)$^+$ |

Examples 99-106 may be prepared essentially as described in Example 91 by using 7-chloro-3-(2,2,2-trifluoroacetyl)-6-trifluoromethanesulfonyloxy-2,3,4,5-tetrahydro-1H-benzo[d]azepine and the appropriate amine. The yields for the Step 1 (General Procedure 5-3) and MS (ES+) data are shown in the Table below.

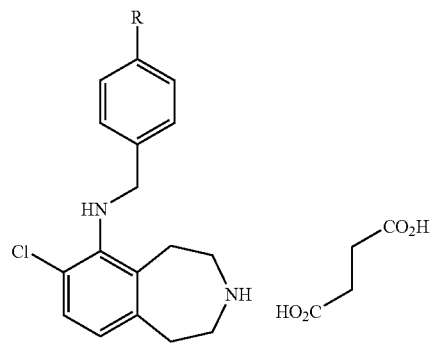

| Ex. | R | Compound | Yield (%) | MS (ES+) m/z |
|---|---|---|---|---|
| 99 | (4-benzyloxy) | 7-Chloro-6-(4-benzyloxy-benzylamino)-2,3,4,5-tetrahydro-1H-benzo[d]azepine Succinate | 87 | 393 (M + H)+ |
| 100 | (3,3-dimethyl-2-oxo-butoxy) | 7-Chloro-6-[4-(3,3-dimethyl-2-oxo-butoxy)-benzylamino]-2,3,4,5-tetrahydro-1H-benzo[d]azepine Succinate | 20 | 401 (M + H)+ |
| 101 | (2,2-dimethylpropoxy) | 7-Chloro-6-[4-(2,2-dimethylpropoxy)-benzylamino]-2,3,4,5-tetrahydro-1H-benzo[d]azepine Succinate | 23 | 373 (M + H)+ |
| 102 | (2-cyclohexylethoxy) | 7-Chloro-6-[4-(2-cyclohexylethoxy)-benzylamino]-2,3,4,5-tetrahydro-1H-benzo[d]azepine Succinate | 61 | 413 (M + H)+ |
| 103 | (1H-pyrazol-1-yl) | 7-Chloro-6-[4-(1H-pyrazol-1-yl)benzylamino]-2,3,4,5-tetrahydro-1H-benzo[d]azepine Succinate | 36 | 353 (M + H)+ |
| 104 | (pyridin-3-yloxy) | 7-Chloro-6-[4-(pyridin-3-yloxy)-benzylamino]-2,3,4,5-tetrahydro-1H-benzo[d]azepine Succinate | 42 | 380 (M + H)+ |
| 105 | (4-Benzylthio) | 6-(4-Benzylthio-benzylamino)-7-chloro-2,3,4,5-tetrahydro-1H-benzo[d]azepine Succinate | 21 | 409 (M + H)+ |

EXAMPLE 106

7-Chloro-6-(2-fluoro-4-phenoxy-benzylamino)-2,3,4,5-tetrahydro-1H-benzo[d]azepine Succinate

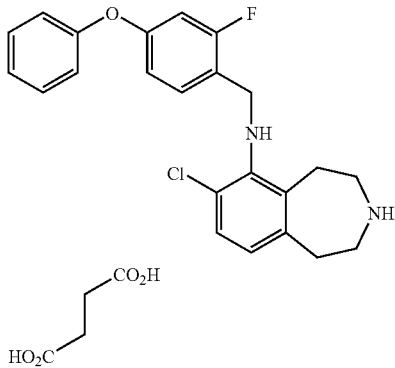

Using a method similar to the General Procedure 5-3, couple 7-chloro-3-(2,2,2-trifluoroacetyl)-6-trifluoromethanesulfonyloxy-2,3,4,5-tetrahydro-1H-benzo[d]azepine (1.1 g, 2.5 mmol) with 2-fluoro-4-phenoxy-benzylamine (550 mg, 2.5 mmol). Purify by chromatography on silica gel eluting with hexane/EtOAc (9:1) and then SCX chromatography to obtain 7-chloro-6-(2-fluoro-4-phenoxybenzylamino)-3-(2,2,2-trifluoroacetyl)-2,3,4,5-tetrahydro-1H-benzo[d]azepine. MS (ES+) m/z: 493 (M+H)$^+$.

Use a method similar to the General Procedure 1-1 to deprotect 7-chloro-6-(2-fluoro-4-phenoxy-benzylamino)-3-(2,2,2-trifluoroacetyl)-2,3,4,5-tetrahydro-1H-benzo[d]azepine. Purify by chromatography on silica gel eluting with DCM/2M ammonia in methanol (95:5) to give the free base of the title compound (468 mg, 47% overall). MS (ES+) m/z: 397 (M+H)$^+$. Use a method similar to the General Procedure 2-1 to obtain the title compound.

EXAMPLE 107

7-Chloro-6-[2-fluoro-4-(3'-fluorophenoxy)-benzylamino]-2,3,4,5-tetrahydro-1H-benzo[d]azepine Succinate

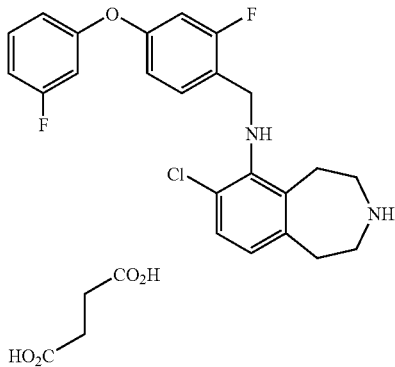

Use a method similar to the Example 106, using 7-chloro-3-(2,2,2-trifluoroacetyl)-6-trifluoromethanesulfonyloxy-2,3,4,5-tetrahydro-1H-benzo[d]azepine (426 mg, 1.0 mmol) and 2-fluoro-4-(3'-fluorophenoxy)-benzylamine (340 mg, 1.4 mmol) to give the free base of the title compound (162 mg, 39%). MS (ES+) m/z: 415 (M+H)$^+$. Use a method similar to the General Procedure 2-1 to obtain the title compound.

Examples 108-121 may be prepared essentially as described in Example 107 by using 7-chloro-3-(2,2,2-trifluoroacetyl)-6-trifluoromethanesulfonyloxy-2,3,4,5-tetrahydro-1H-benzo[d]azepine and the appropriate amine. The yields for the Step 1 (General Procedure 5-3) and MS (ES+) data are shown in the Table below.

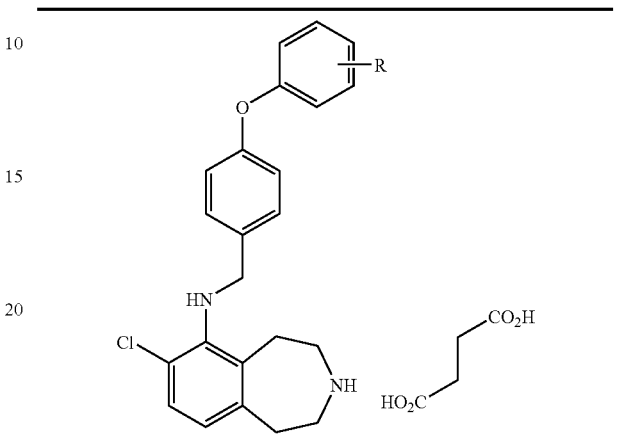

| Ex. | R | Compound | Yield (%) | MS (ES+) m/z |
|---|---|---|---|---|
| 108 | 2-F | 7-Chloro-6-[4-(2'-fluorophenoxy)-benzylamino]-2,3,4,5-tetrahydro-1H-benzo[d]azepine Succinate | 44 | 397 (M + H)$^+$ |
| 109 | 3-F | 7-Chloro-6-[4-(3'-fluorophenoxy)-benzylamino]-2,3,4,5-tetrahydro-1H-benzo[d]azepine Succinate | 23 | 397 (M + H)$^+$ |
| 110 | 4-F | 7-Chloro-6-[4-(4'-fluorophenoxy)-benzylamino]-2,3,4,5-tetrahydro-1H-benzo[d]azepine Succinate | 50 | 397 (M + H)$^+$ |
| 111 | 3-Cl | 7-Chloro-6-[4-(3'-chlorophenoxy)-benzylamino]-2,3,4,5-tetrahydro-1H-benzo[d]azepine Succinate | 45 | 413 (M + H)$^+$ |
| 112 | 3,5-diF | 7-Chloro-6-[4-(3',5'-difluorophenoxy)-benzylamino]-2,3,4,5-tetrahydro-1H-benzo[d]azepine Succinate | 36 | 415 (M + H)$^+$ |
| 113 | 4-CH$_3$ | 7-Chloro-6-[4-(4'-methylphenoxy)-benzylamino]-2,3,4,5-tetrahydro-1H-benzo[d]azepine Succinate | 54 | 393 (M + H)$^+$ |
| 114 | 3-CH$_3$ | 7-Chloro-6-[4-(3'-methylphenoxy)-benzylamino]-2,3,4,5-tetrahydro-1H-benzo[d]azepine Succinate | 45 | 393 (M + H)$^+$ |
| 115 | 2-CH$_3$ | 7-Chloro-6-[4-(2'-methylphenoxy)-benzylamino]-2,3,4,5-tetrahydro-1H-benzo[d]azepine Succinate | 54 | 393 (M + H)$^+$ |
| 116 | 3-$^i$Pr | 7-Chloro-6-[4-(3'-isopropylphenoxy)-benzylamino]-2,3,4,5-tetrahydro-1H-benzo[d]azepine Succinate | 49 | 421 (M + H)$^+$ |
| 117 | 2-$^i$Pr | 7-Chloro-6-[4-(2'-isopropylphenoxy)-benzylamino]-2,3,4,5-tetrahydro-1H-benzo[d]azepine Succinate | 40 | 421 (M + H)$^+$ |
| 118 | 2-CN | 7-Chloro-6-[4-(2'-cyanophenoxy)-benzylamino]-2,3,4,5-tetrahydro-1H-benzo[d]azepine Succinate | 79 | 404 (M + H)$^+$ |
| 119 | 3-CN | 7-Chloro-6-[4-(3'-cyanophenoxy)-benzylamino)-2,3,4,5-tetrahydro-1H-benzo[d]azepine Succinate | 37 | 404 (M + H)$^+$ |
| 120 | 2-CF$_3$ | 7-Chloro-6-[4-(2'-trifluoromethylphenoxy)-benzylamino]-2,3,4,5-tetrahydro-1H-benzo[d]azepine Succinate | 30 | 447 (M + H)$^+$ |
| 121 | 3-CF$_3$ | 7-Chloro-6-[4-(3'-trifluoromethylphenoxy)-benzylamino]-2,3,4,5-tetrahydro-1H-benzo[d]azepine Succinate | 37 | 447 (M + H)$^+$ |

EXAMPLE 122

7-Chloro-6-[4-(3'-cyanobenzyloxy)-benzylamino]-2,3,4,5-tetrahydro-1H-benzo[d]azepine Succinate

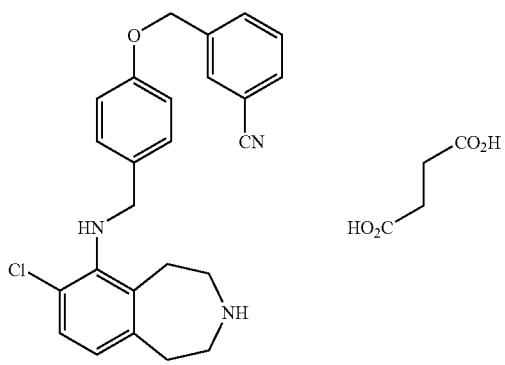

Mix 7-chloro-6-(4-hydroxy-benzylamino)-3-(2,2,2-trifluoroacetyl)-2,3,4,5-tetrahydro-1H-benzo[d]azepine (150 mg, 0.38 mmol), 3-cyanobenzyl bromide (90 mg, 0.46 mmol), powdered potassium carbonate (105 mg, 0.76 mmol), powdered potassium iodide (6.6 mg, 0.04 mmol) and acetone (30 mL). Stir and heat to reflux under nitrogen for 16 hr. Dilute with acetone, filter, concentrate in vacuo and purify by chromatography on silica gel eluting with hexane/EtOAc (1:0 and 4:1) to obtain 7-chloro-6-[4-(3'-cyanobenzyloxy)-benzylamino]-3-(2,2,2-trifluoroacetyl)-2,3,4,5-tetrahydro-1H-benzo[d]azepine (72.4 mg, 37%). MS (ES+) m/z 514 $(M+H)^+$.

Use a method similar to the General Procedure 1-1 to deprotect 7-chloro-6-[4-(3' cyanobenzyloxy)-benzylamino]-3-(2,2,2-trifluoroacetyl)-2,3,4,5-tetrahydro-1H-benzo[d]azepine. Purify by chromatography on silica gel eluting with DCM/2M ammonia in methanol (95:5) to give the free base of the title compound (42 mg, 71%). MS (ES+) m/z: 418 $(M+H)^+$. Use a method similar to the General Procedure 2-1 to obtain the title compound.

Examples 123-126 may be prepared essentially as described in Example 122 by using 7-chloro-6-(4-hydroxy-benzylamino)-3-(2,2,2-trifluoroacetyl)-2,3,4,5-tetrahydro-1H-benzo[d]azepine and the appropriate bromide. Overall yields and MS (ES+) data are shown in the Table below.

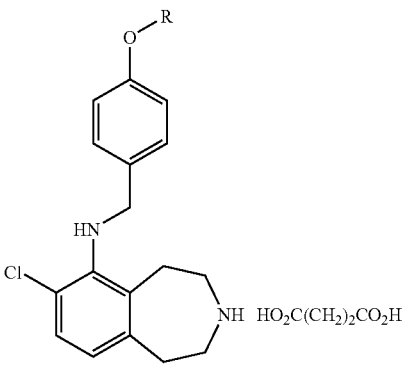

| Ex. | O—R | Compound | Yield (%) | MS (ES+) m/z |
|---|---|---|---|---|
| 123 | ![3-fluorobenzyl] | 7-Chloro-6-[4-(3'-fluorobenzyloxy)-benzylamino]-2,3,4,5-tetrahydro-1H-benzo[d]azepine Succinate | 75 | 411 $(M+H)^+$ |
| 124 | ![phenacyl] | 7-Chloro-6-[4-(2-oxo-2-phenyl-ethoxy)-benzylamino]-2,3,4,5-tetrahydro-1H-benzo[d]azepine Succinate | 45 | 421 $(M+H)^+$ |
| 125 | ![4-fluorophenacyl] | 7-Chloro-6-[4-(2-oxo-2-(4-fluorophenyl)-ethoxy)-benzylamino]-2,3,4,5-tetrahydro-1H-benzo[d]azepine Succinate | 17 | 439 $(M+H)^+$ |

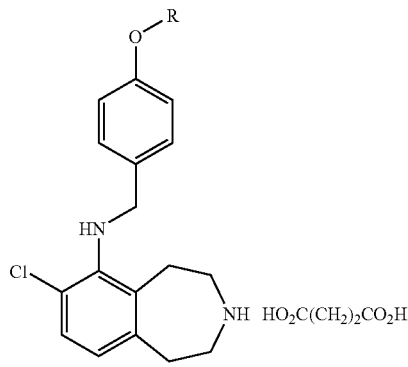

| Ex. | O—R | Compound | Yield (%) | MS (ES+) m/z |
|---|---|---|---|---|
| 126 |  | 7-Chloro-6-[4-(2-oxo-2-piperidin-1-yl-ethoxy)-benzylamino]-2,3,4,5-tetrahydro-1H-benzo[d]azepine Succinate | 44 | 428 (M + H)+ |

EXAMPLE 127

7-Chloro-6-[3-chloro-4-(3,3-dimethyl-2-oxo-butoxy)-benzylamino]-2,3,4,5-tetrahydro-1H-benzo[d]azepine Succinate

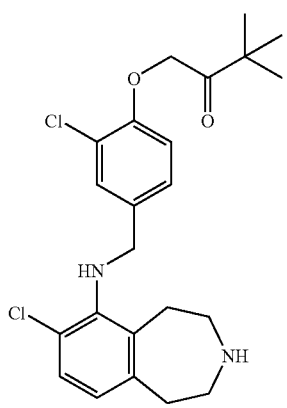

Use a method similar to the General Procedure 4-1 to react 7-chloro-6-(3-chloro-4-hydroxy-benzylamino)-3-(2,2,2-trifluoroacetyl)-2,3,4,5-tetrahydro-1H-benzo[d]azepine (438 mg, 1.01 mmol) and 1-bromopinacolone (217 mg, 1.21 mmol). Purify by chromatography on silica gel eluting with EtOAc/hexane (1:4) to give 7-chloro-6-[3-chloro-4-(3,3-dimethyl-2-oxo-butoxy)-benzylamino]-3-(2,2,2-trifluoroacetyl)-2,3,4,5-tetrahydro-1H-benzo[d]azepine as a colorless oil (441 mg, 82%). MS (ES+) m/z: 531 (M+H)+.

Use a method similar to the General Procedure 1-1 to deprotect 7-chloro-6-[3-chloro-4-(3,3-dimethyl-2-oxo-butoxy)-benzylamino]-3-(2,2,2-trifluoroacetyl)-2,3,4,5-tetrahydro-1H-benzo[d]azepine (441 mg, 0.83 mmol). Purify by chromatography on silica gel eluting with DCM/2M ammonia in methanol (93:7) to give the free base of the title compound (278 mg, 95%). MS (ES+) m/z: 435 (M+H)+. Use a method similar to the General Procedure 2-1 to give the title compound.

EXAMPLE 128

7-Chloro-6-(3-chloro-4-benzyloxy-benzylamino)-2,3,4,5-tetrahydro-1H-benzo[d]azepine Succinate

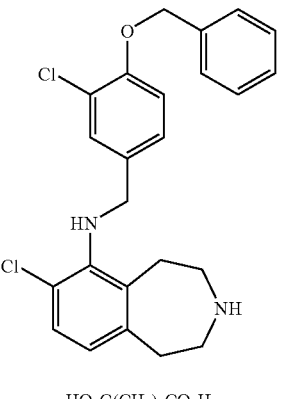

The title compound may be prepared essentially as described in Example 127, using 7-chloro-6-(3-chloro-4-hydroxy-benzylamino)-3-(2,2,2-trifluoroacetyl)-2,3,4,5-tetrahydro-1H-benzo[d]azepine and benzyl bromide (64%). MS (ES+) m/z: 427 (M+H)+.

EXAMPLE 129

(±)-7-Chloro-6-[4-(1-phenyl-ethoxy)-benzylamino]-2,3,4,5-tetrahydro-1H-benzo[d]azepine Succinate

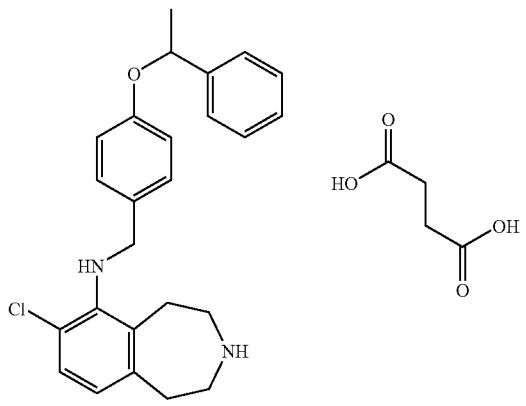

Use a method similar to the General Procedure 5-3, to couple 7-chloro-3-(2,2,2-trifluoroacetyl)-6-trifluoromethanesulfonyloxy-2,3,4,5-tetrahydro-1H-benzo[d]azepine (851 mg, 2.0 mmol) and (±)-4-(1-phenyl-ethoxy)-benzylamine (721 mg, 2.6 mmol). Purify by chromatography on silica gel eluting with EtOAc/hexane (1:8) to give (±)-7-chloro-6-[4-(1-phenyl-ethoxy)-benzylamino]-3-(2,2,2-trifluoroacetyl)-2,3,4,5-tetrahydro-1H-benzo[d]azepine (702 mg, 69%). MS (ES+) m/z: 503 (M+H)+.

Use a method similar to the General Procedure 1-1 to deprotect (±)-7-chloro-6-[4-(1-phenyl-ethoxy)-benzylamino]-3-(2,2,2-trifluoroacetyl)-2,3,4,5-tetrahydro-1H-benzo[d]azepine (702 mg, 1.40 mmol). Purify by chromatography on silica gel eluting with DCM/2M ammonia in methanol (92:8) to give the free base of the title compound (368 mg, 65%). MS (ES+) m/z: 407 (M+H)+. Use a method similar to the General Procedure 2-1 to obtain the title compound.

EXAMPLES 130 AND 131

(−)-7-Chloro-6-[4-(1-phenyl-ethoxy)-benzylamino]-2,3,4,5-tetrahydro-1H-benzo[d]azepine Succinate and (+)-7-Chloro-6-[4-(1-phenyl-ethoxy)-benzylamino]-2,3,4,5-tetrahydro-1H-benzo[d]azepine Succinate

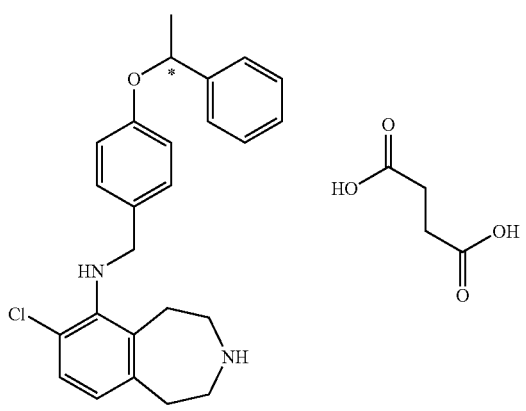

Separate the two enantiomers of Example 129 by chiral HPLC [Chiralcel OJ-H column, acetonitrile/methanol (20:80) with 0.2% DMEA; flow rate 1 mL/min; Isomer 1: $t_R$=5.0 min, Isomer 2: $t_R$=6.5 min].

Use a method similar to the General Procedure 2-1 to prepare the succinate of each enantiomer: (−)-7-chloro-6-[4-(1-phenyl-ethoxy)-benzylamino]-2,3,4,5-tetrahydro-1H-benzo[d]azepine Succinate, $[\alpha]^{20}_D$ −17.4° (c 0.5, CH$_3$OH), and (+)-7-chloro-6-[4-(1-phenyl-ethoxy)-benzylamino]-2,3,4,5-tetrahydro-1H-benzo[d]azepine Succinate, $[\alpha]^{20}_D$ +18.2° (c 0.5, CH$_3$OH).

EXAMPLE 132

7-Chloro-6-[4-(3,3-dimethylbutoxy)-benzylamino]-2,3,4,5-tetrahydro-1H-benzo[d]azepine Mesylate

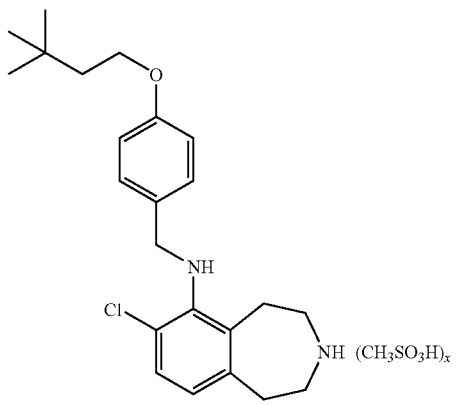

Use a method similar to the General Procedure 5-3 to couple 7-chloro-3-(2,2,2-trifluoroacetyl)-6-trifluoromethanesulfonyloxy-2,3,4,5-tetrahydro-1H-benzo[d]azepine (426 mg, 1.0 mmol) and 4-(3,3-dimethylbutoxy)-benzylamine (325 mg, 1.5 mmol). Purify by chromatography on silica gel eluting with hexane/EtOAc (1:0 and 9:1) and then SCX chromatography to obtain 7-chloro-6-[4-(3,3-dimethylbutoxy)-benzylamino]-3-(2,2,2-trifluoroacetyl)-2,3,4,5-tetrahydro-1H-benzo[d]azepine. MS (ES+) m/z: 483 (M+H)+.

Use a method similar to the General Procedure 1-1 to deprotect 7-chloro-6-[4-(3,3-dimethylbutoxy)-benzylamino]-3-(2,2,2-trifluoroacetyl)-2,3,4,5-tetrahydro-1H-benzo[d]azepine. Purify by chromatography on silica gel eluting with DCM/2M ammonia in methanol (95:5) to give the free base of the title compound (161 mg, 42% overall). MS (ES+) m/z: 387 (M+H)+. Use a method similar to the General Procedure 2-4 to obtain the title compound.

EXAMPLE 133

7-Chloro-6-(4-cyclohexylmethoxy-benzylamino)-2,3,4,5-tetrahydro-1H-benzo[d]azepine Mesylate

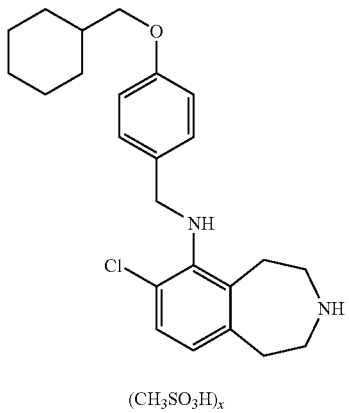

(CH$_3$SO$_3$H)$_x$

The title compound may be prepared essentially as described in Example 132, using 7-chloro-3-(2,2,2-trifluoroacetyl)-6-trifluoromethanesulfonyloxy-2,3,4,5-tetrahydro-1H-benzo[d]azepine and 4-cyclohexylmethoxy-benzylamine (27% yield, MS (ES+) m/z 399 (M+H)$^+$).

EXAMPLE 134

7-Chloro-6-(3-pyrrolidinyl-benzylamino)-2,3,4,5-tetrahydro-1H-benzo[d]azepine Succinate

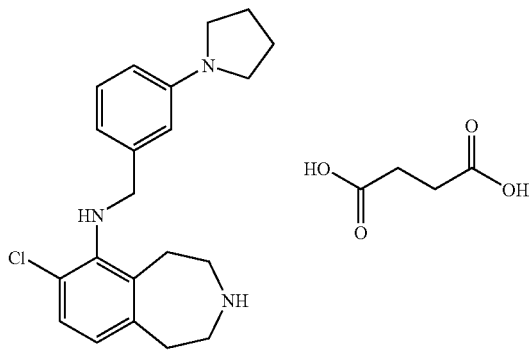

Use a method similar to the General Procedure 5-1, using 7-chloro-3-(2,2,2-trifluoroacetyl)-6-trifluoromethanesulfonyloxy-2,3,4,5-tetrahydro-1H-benzo[d]azepine (300 mg, 0.7 mmol) and 3-(pyrrolidin-1-yl)benzylamine (300 mg, 1.7 mmol) to give, after chromatography on silica gel eluting with hexane/EtOAc (19:1, 9:1, 4:1 and 3:2), 7-chloro-6-(3-pyrrolidinyl-benzylamino)-3-(2,2,2-trifluoroacetyl)-2,3,4,5-tetrahydro-1H-benzo[d]azepine as a yellow oil (195 mg, 62%). MS (ES+) m/z: 452 (M+H)$^+$.

Use a method similar to the General Procedure 1-1 to deprotect 7-chloro-6-(3-pyrrolidinyl-benzylamino)-3-(2,2,2-trifluoroacetyl)-2,3,4,5-tetrahydro-1H-benzo[d]azepine (195 mg, 0.43 mmol). Purify by SCX chromatography to give the free base of the title compound (136 mg, 89%). Use a method similar to the General Procedure 2-1, using 7-chloro-6-(3-pyrrolidinyl-benzylamino)-2,3,4,5-tetrahydro-1H-benzo[d]azepine (130 mg, 0.37 mmol), to give the title compound as an off-white gum (111 mg, 61%). MS (ES+) m/z: 356 (M+H)$^+$.

EXAMPLE 135

6-(4-Methoxybenzylamino)-7-chloro-2,3,4,5-tetrahydro-1H-benzo[d]azepine Hydrochloride

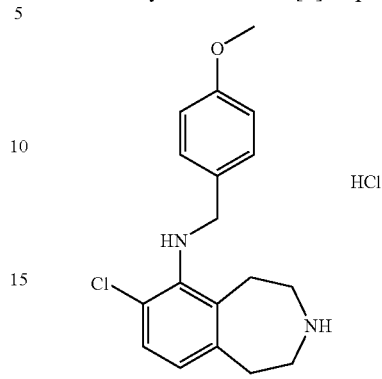

Use a similar method to the General Procedure 1-1, using 6-(4-methoxybenzylamino)-7-chloro-3-(2,2,2-trifluoroacetyl)-2,3,4,5-tetrahydro-1H-benzo[d]azepine (0.1 g, 0.24 mmol) to give the free base of the title compound. Use a similar method to the General Procedure 2-2 to give the title compound (75 mg, 80%). HRMS calcd for C$_{18}$H$_{21}$ClN$_2$O 317.1421, found 317.1410.

EXAMPLE 136

7-Chloro-6-[4-(2,2,3,3-tetrafluoropropoxy)-benzylamino]-2,3,4,5-tetrahydro-1H-benzo[d]azepine Succinate

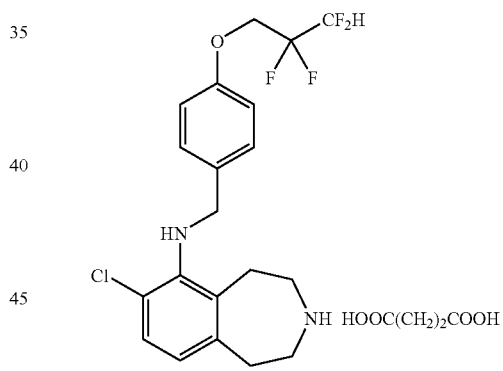

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (500 mg, 1.2 mmol) with 4-(2,2,3,3-tetrafluoropropoxy)-benzylamine (835 mg, 3.5 mmol) in toluene (10 mL). Purify by chromatography on silica gel eluting with hexane/EtOAc (10:1, 5:1 and 3:1) followed by SCX chromatography [pre-wash column with methanol followed by DCM, load material dissolved in DCM, then elute with DCM/2M ammonia in methanol (1:1) and concentrate in vacuo] to obtain 7-chloro-6-[4-(2,2,3,3-tetrafluoropropoxy)-3-(2,2,2-trifluoroacetyl)-2,3,4,5-tetrahydro-1H-benzo[d]azepine (600 mg, 99%).

Use a method similar to the General Procedure 1-3 to deprotect 7-chloro-6-[4-(2,2,3,3-tetrafluoropropoxy)-3-(2,2,2-trifluoroacetyl)-2,3,4,5-tetrahydro-1H-benzo[d]azepine (600 mg, 1.2 mmol). Purify by chromatography on silica gel eluting with DCM/2M ammonia in methanol (99:1 to 90:10) to give the free base of the title compound. Use a method similar to the General Procedure 2-1 to give the title compound (390 mg, 62%). MS (ES+) m/z: 417 (M+H)⁺.

Examples 137-138 may be prepared essentially as described in Example 136 by using 7-chloro-3-(2,2,2-trifluoroacetyl)-6-trifluoromethanesulfonyloxy-2,3,4,5-tetrahydro-1H-benzo[d]azepine and the appropriate amine. Overall yields and MS (ES+) data are shown in the Table below.

hexane/EtOAc (10:1, 5:1 and 3:1) followed by SCX chromatography [pre-wash column with methanol followed by DCM, load material dissolved in DCM, then elute with DCM/2M ammonia in methanol (1:1) and concentrate in vacuo] to give (±)-7-chloro-6-[4-(2,2,2-trifluoro-1-methyl-ethoxy)-benzylamino]-3-(2,2,2-trifluoroacetyl)-2,3,4,5-tetrahydro-1H-benzo[d]azepine (530 mg, 90%). GC-MS m/z: 494 (M⁺).

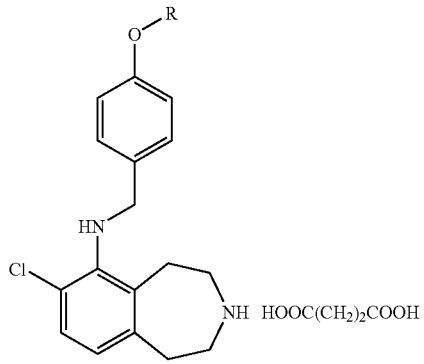

| Ex. | O—R | Compound | Yield (%) | MS (ES+) m/z |
|---|---|---|---|---|
| 137 | (pentafluoropropoxy group) | 7-Chloro-6-[4-(2,2,3,3,3-pentafluoropropoxy)-benzylamino]-2,3,4,5-tetrahydro-1H-benzo[d]azepine Succinate | 45 | 435 (M + H)⁺ |
| 138 | (2,2,2-trifluoro-1,2-dimethyl-ethoxy group) | 7-Chloro-6-[4-(2,2,2-trifluoro-1,2-dimethyl-ethoxy)-benzylamino]-2,3,4,5-tetrahydro-1H-benzo[d]azepine Succinate | 66 | 413 (M + H)⁺ |

EXAMPLES 139 AND 140

(−)-7-Chloro-6-[4-(2,2,2-trifluoro-1-methyl-ethoxy)-benzylamino]-2,3,4,5-tetrahydro-1H-benzo[d]azepine Succinate and (+)-7-Chloro-6-[4-(2,2,2-trifluoro-1-methyl-ethoxy)-benzylamino]-2,3,4,5-tetrahydro-1H-benzo[d]azepine Succinate

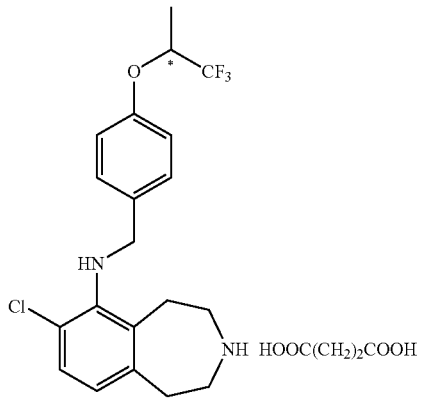

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (500 mg, 1.2 mmol) with (±)-4-(2,2,2-trifluoro-1-methyl-ethoxy)-benzylamine (515 mg, 2.3 mmol) in toluene (10 mL). Purify by chromatography on silica gel eluting with Use a method similar to the General Procedure 1-3 to deprotect (±)-7-chloro-6-[4-(2,2,2-trifluoro-1-methyl-ethoxy)-benzylamino]-3-(2,2,2-trifluoroacetyl)-2,3,4,5-tetrahydro-1H-benzo[d]azepine (520 mg, 1.1 mmol). Purify by chromatography on silica gel eluting with DCM/2M ammonia in methanol (99:1 to 90:10) to give (±)-7-chloro-6-[4-(2,2,2-trifluoro-1-methyl-ethoxy)-benzylamino]-2,3,4,5-tetrahydro-1H-benzo[d]azepine. Use a method similar to the General Procedure 2-1 to obtain (±)-7-chloro-6-[4-(2,2,2-trifluoro-1-methyl-ethoxy)-benzylamino]-2,3,4,5-tetrahydro-1H-benzo[d]azepine Succinate.

Separate the two enantiomers of (±)-7-chloro-6-[4-(2,2,2-trifluoro-1-methyl-ethoxy)-benzylamino]-2,3,4,5-tetrahydro-1H-benzo[d]azepine succinate by normal phase chiral chromatography (Chiralpak AD 8×30 cm, elute with 85:15 heptane/3A ethanol with 0.2% DMEA).

Use a method similar to the General Procedure 2-1 to obtain (−)-7-chloro-6-[4-(2,2,2-trifluoro-1-methyl-ethoxy)-benzylamino]-2,3,4,5-tetrahydro-1H-benzo[d]azepine Succinate [137 mg, 71% recovery, 980% ee (Chiralpak AD, 4.6× 150 mm, eluent: 85:15 heptane/isopropanol with 0.2% DMEA, 0.6 mL/min)]. MS (ES+) m/z: 399 (M+H)⁺. [α]²⁰_D −7.9° (c 0.5, MeOH).

Use a method similar to the General Procedure 2-1 to obtain (+)-7-chloro-6-[4-(2,2,2-trifluoro-1-methyl-ethoxy)-benzylamino]-2,3,4,5-tetrahydro-1H-benzo[d]azepine Succinate [133 mg, 69% recovery, 97% ee (Chiralpak AD, 4.6× 11150 mm, eluent: 85:15 heptane/isopropanol with 0.2% DMEA, 0.6 mL/min)]. MS (ES+) m/z: 399 (M+H)⁺. [α]²⁰_D +9.2° (c 0.5, MeOH).

EXAMPLE 141

6-(4-Acetyl-benzylamino)-7-chloro-2,3,4,5-tetrahydro-1H-benzo[d]azepine Succinate

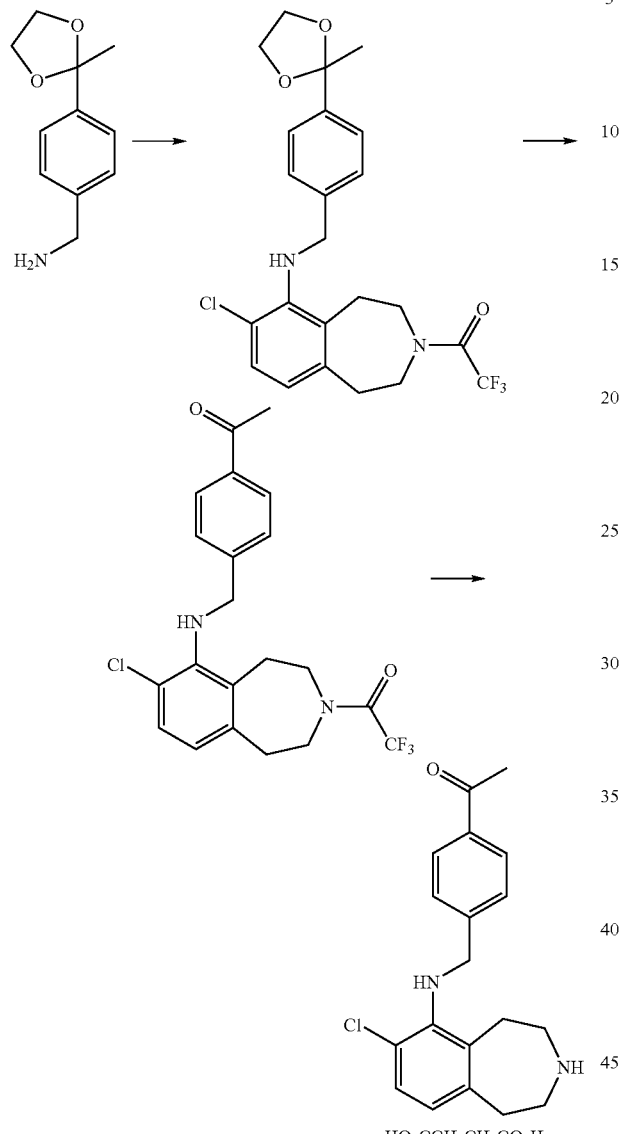

Use a method similar to the General Procedure 5-3 to couple 7-chloro-3-(2,2,2-trifluoroacetyl)-6-trifluoromethanesulfonyloxy-2,3,4,5-tetrahydro-1H-benzo[d]azepine (200 mg, 0.47 mmol) with 4-(2-methyl-[1,3]dioxolan-2-yl)-benzylamine (prepared by following the procedure described in *J. Med. Chem.* 1978, 21, 507) (182 mg, 0.94 mmol). Purify by chromatography on silica gel eluting with hexane/EtOAc (1:0, 19:1 and 9:1) to give 6-{4-(2-methyl-[1,3]dioxolan-2-yl)-benzylamino}-7-chloro-3-(2,2,2-trifluoroacetyl)-2,3,4,5-tetrahydro-1H-benzo[d]azepine as an oil (150 mg, 68%). GC-MS m/z 468 (M+).

Dissolve 6-{4-(2-methyl-[1,3]dioxolan-2-yl)benzylamino}-7-chloro-3-(2,2,2-trifluoroacetyl)-2,3,4,5-tetrahydro-1H-benzo[d]azepine (150 mg, 0.32 mmol) in methanol (5 mL) and add 1N aqueous HCl (1 mL). Stir the solution at ambient temperature for 2 h. Remove the solvent, dissolve the residue in DCM and wash with saturated aqueous NaHCO₃. Dry the organic phase over Na₂SO₄, filter and concentrate. Purify by chromatography on silica gel eluting with hexane/EtOAc (1:0, 9:1, 17:3 and 4:1) to obtain 6-(4-acetyl-benzylamino)-7-chloro-3-(2,2,2-trifluoroacetyl)-2,3,4,5-tetrahydro-1H-benzo[d]azepine as an oil (107 mg, 79%). GC-MS m/z/z 424 (M+).

Use a method similar to the General Procedure 1-2, using 6-(4-acetyl-benzylamino)-7-chloro-3-(2,2,2-trifluoroacetyl)-2,3,4,5-tetrahydro-1H-benzo[d]azepine (100 mg; 0.23 mmol), to give the free base of the title compound as an oil (76 mg, 99%) that was used without further purification.

Use a method similar to the General Procedure 2-1, using 6-(4-acetyl-benzylamino)-7-chloro-2,3,4,5-tetrahydro-1H-benzo[d]azepine (76 mg, 0.23 mmol), to give the title compound as a white solid (102 mg, 97%). MS (ES+) m/z: 329 (M+H)+.

EXAMPLE 142

6-(3-Acetylbenzylamino)-7-chloro-2,3,4,5-tetrahydro-1H-benzo[d]azepine Succinate

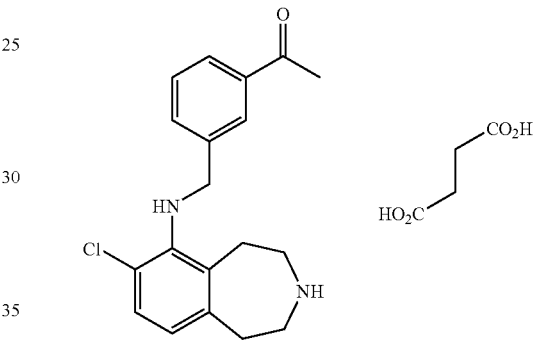

Use a method similar to Example 141, using 7-chloro-3-(2,2,2-trifluoroacetyl)-6-trifluoromethanesulfonyloxy-2,3,4, 5-tetrahydro-1H-benzo[d]azepine and 3-(2-methyl-[1,3]dioxolan-2-yl)-benzylamine (prepared by following the procedure described in *J. Med. Chem.* 2000, 43, 3315), to give the title compound as a solid. MS (ES+) m/z: 329 (M+H)+.

EXAMPLE 143

7-Chloro-6-[4-(1-hydroxyiminoethyl)-benzylamino]-2,3,4,5-tetrahydro-1H-benzo[d]azepine Succinate

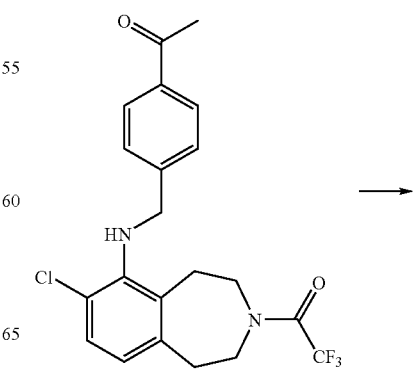

EXAMPLE 144

6-(4-Benzoyl-benzylamino)-7-chloro-2,3,4,5-tetrahydro-1H-benzo[d]azepine Succinate

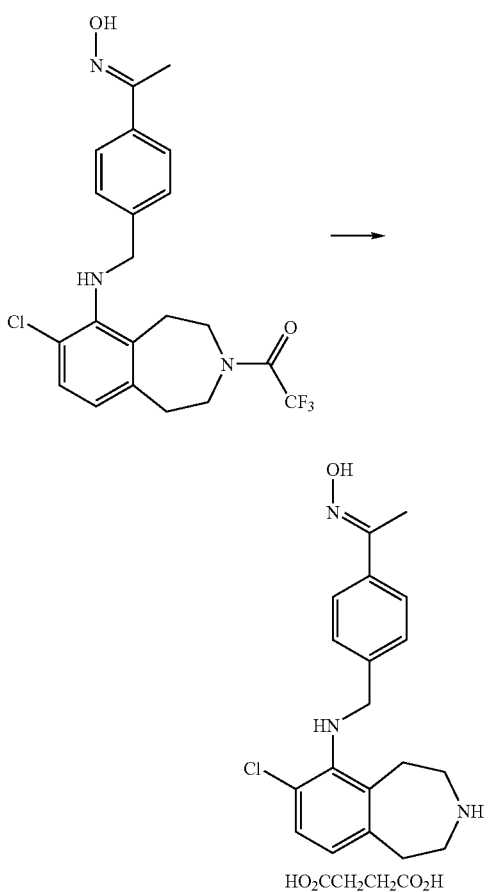

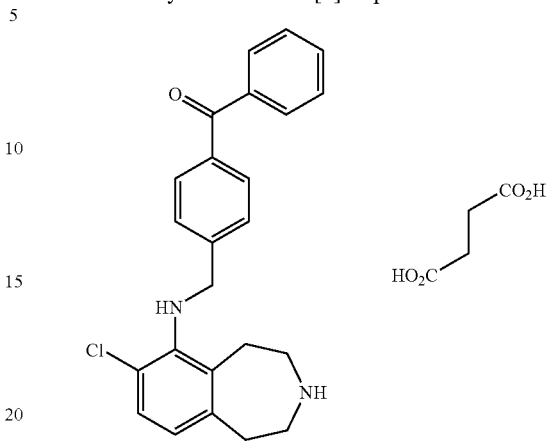

Use a method similar to the General Procedure 5-3 to couple 7-chloro-3-(2,2,2-trifluoroacetyl)-6-trifluoromethanesulfonyloxy-2,3,4,5-tetrahydro-1H-benzo[d]azepine (272 mg, 0.64 mmol) with 4-(aminomethyl)benzophenone (prepared by following the procedure described in *J. Biol. Chem.* 1993, 268 (19), 14230) (270 mg, 1.3 mmol). Purify by chromatography on silica gel eluting with hexane/ EtOAc (1:0, 9:1, 17:3 and 4:1) to give 6-(4-benzoyl-benzylamino)-7-chloro-3-(2,2,2-trifluoroacetyl)-2,3,4,5-tetrahydro-1H-benzo[d]azepine as an oil (300 mg, 96%).

Use a method similar to the General Procedure 1-2, using 6-(4-benzoyl-benzylamino)-7-chloro-3-(2,2,2-trifluoroacetyl)-2,3,4,5-tetrahydro-1H-benzo[d]azepine (80 mg, 0.16 mmol), to give 6-(4-benzoyl-benzylamino)-7-chloro-2,3,4,5-tetrahydro-1H-benzo[d]azepine as an oil (47 mg, 73%) that was used without further purification.

Use a method similar to the General Procedure 2-1, using 6-(4-benzoyl-benzylamino)-7-chloro-2,3,4,5-tetrahydro-1H-benzo[d]azepine (45 mg, 0.11 mmol), to give the title compound as a white solid (37 mg, 63%). MS (ES+) m/z: 391 (M+H)+.

Add hydroxylamine hydrochloride (19 mg, 0.27 mmol) and pyridine (0.04 mL, 0.54 mmol) to a solution of 6-(4-acetylbenzylamino)-7-chloro-3-(2,2,2-trifluoroacetyl)-2,3,4,5-tetrahydro-1H-benzo[d]azepine (115 mg, 0.27 mmol) in ethanol (10 mL). Heat the mixture to reflux for 2 h. Remove the solvent in vacuo and partition the residue between DCM and 0.1N aqueous HCl. Dry the organic phase over Na$_2$SO$_4$, filter and concentrate. Dissolve the oil into the minimum amount of ether and add hexane to precipitate the solid. Filter to obtain 7-chloro-6-[4-(1-hydroxyiminoethyl)-benzylamino]3-(2,2,2-trifluoroacetyl)-2,3,4,5-tetrahydro-1H-benzo[d]azepine as a solid (12 mg, 94%) that was used without further purification. MS (ES+) m/z: 440 (M+H)+.

Use a method similar to the General Procedure 1-2, using 7-chloro-6-[4-(1-hydroxyiminoethyl)-benzylamino]-3-(2,2,2-trifluoroacetyl)-2,3,4,5-tetrahydro-1H-benzo[d]azepine (100 mg, 0.23 mmol), to give 7-chloro-6-[4-(1-hydroxyiminoethyl)-benzylamino]-2,3,4,5-tetrahydro-1H-benzo[d]azepine as an oil (61 mg, 78%) that was used without ether purification.

Use a method similar to the General Procedure 2-1, using 7-chloro-6-[4-(1-hydroxyiminoethyl)benzylamino]-2,3,4,5-tetrahydro-1H-benzo[d]azepine (58 mg, 0.17 mmol) to give the title compound as a white solid (68 mg, 87%). MS (ES+) m/z: 344 (M+H)+.

EXAMPLE 145

7-Chloro-6-[4-(1-hydroxyiminobenzyl)-benzylamino]-2,3,4,5-tetrahydro-1H-benzo[d]azepine Succinate

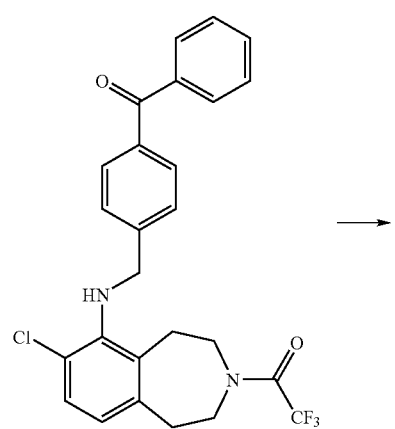

-continued

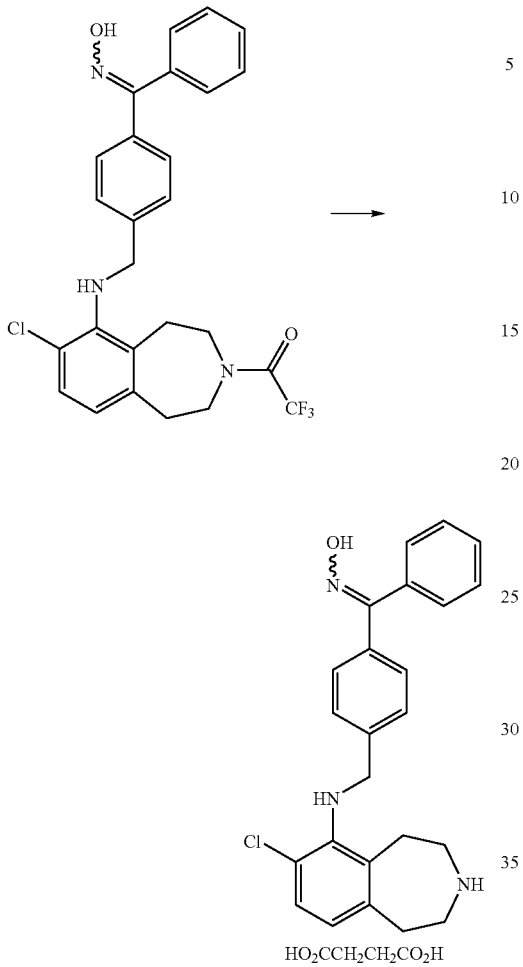

HO₂CCH₂CH₂CO₂H

Add hydroxylamine hydrochloride (52 mg, 0.75 mmol) and pyridine (0.1 mL) to a solution of 6-(4-benzoyl-benzylamino)-7-chloro-3-(2,2,2-trifluoroacetyl)-2,3,4,5-tetrahydro-1H-benzo[d]azepine (91 mg, 0.19 mmol) in ethanol (10 mL). Heat the mixture to reflux overnight. Remove the solvent in vacuo and partition the residue between DCM and 0.1N aqueous HCl. Dry the organic phase over Na₂SO₄, filter and concentrate. Purify by chromatography on silica gel eluting with hexane/EtOAc (1:0, 4:1 and 3:1) to give 7-chloro-6-[4-(1-hydroxyiminobenzyl)-benzylamino]-3-(2,2,2-trifluoroacetyl)-2,3,4,5-tetrahydro-1H-benzo[d]azepine as a mixture of E/Z isomers (93 mg, 99%).

Use a method similar to the General Procedure 1-2, using 7-chloro-6-[4-(1-hydroxyiminobenzyl)benzylamino]-3-(2,2,2-trifluoroacetyl)-2,3,4,5-tetrahydro-1H-benzo[d]azepine (97 mg, 0.19 mmol), to give 7-chloro-6-[4-(1-hydroxyiminobenzyl)-benzylamino]-2,3,4,5-tetrahydro-1H-benzo[d]azepine as an oil (68 mg, 87%) that was used without further purification.

Use a method similar to the General Procedure 2-1, using 7-chloro-6-[4-(1-hydroxyiminobenzyl)benzylamino]-2,3,4,5-tetrahydro-1H-benzo[d]azepine (65 mg, 0.16° mmol), to give the title compound as a white solid (67 mg, 80%). MS (ES+) m/z: 406 (M+H)⁺.

EXAMPLE 146

7-Chloro-6-[4-(pyridin-4-yl)-benzylamino]-2,3,4,5-tetrahydro-1H-benzo[d]azepine Succinate

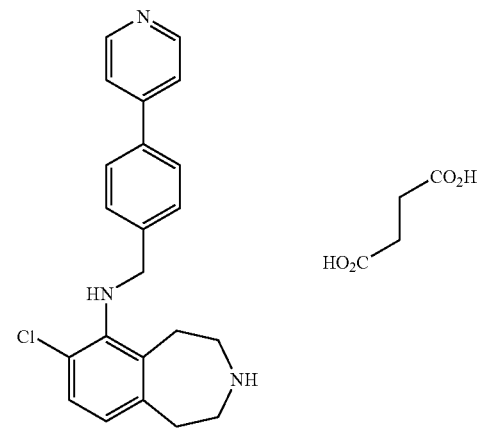

Use a method similar to the General Procedure 5-3, using 7-chloro-3-(2,2,2-trifluoroacetyl)-6-trifluoromethanesulfonyloxy-2,3,4,5-tetrahydro-1H-benzo[d]azepine (178 mg, 0.426 mmol) and a solution of 4-(pyridin-4-yl)-benzylamine (116 mg, 0.63 mmol) in THF/toluene (1:1, 8 mL). Purify by chromatography on silica gel eluting with hexane/EtOAc (1:0, 7:3 and 1:1) to give 7-chloro-6-[4-(4-pyridin-4-yl)-benzylamino]-3-(2,2,2-trifluoroacetyl)-2,3,4,5-tetrahydro-1H-benzo[d]azepine as an oil (120 mg, 63%). MS (ES+) m/z: 460 (M+H)⁺.

Use a method similar to the General Procedure 1-2, using 7-chloro-6-[1-(pyridin-4-yl)-benzylamino]-3-(2,2,2-trifluoroacetyl)-2,3,4,5-tetrahydro-1H-benzo[d]azepine (153 mg, 0.33 mmol), to give 7-chloro-6-[4-(pyridin-4-yl)-benzylamino]-2,3,4,5-tetrahydro-1H-benzo[d]azepine as an oil (110 mg, 91%) that was used without further purification. Use a method similar to the General Procedure 2-1, using 7-chloro-6-[pyridin-4-yl)-benzylamino]-2,3,4,5-tetrahydro-1H-benzo[d]azepine (105 mg, 0.289 mmol) to give the title compound as a white solid (123 mg, 88%). MS (ES+) m/z: 364 (M+H)⁺.

Examples 147-149 may be prepared essentially as described in Example 146 by using 7-chloro-3-(2,2,2-trifluoroacetyl)-6-trifluoromethanesulfonyloxy-2,3,4,5-tetrahydro-1H-benzo[d]azepine and the appropriate amine. Overall yields and MS (ES+) data are shown in the Table below.

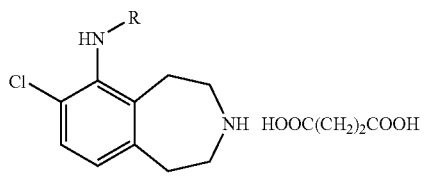
| Ex. | NH—R | Compound | Yield (%) | MS (ES+) m/z |
|---|---|---|---|---|
| 147 | | 7-Chloro-6-[4-(pyridin-2-yl)-benzylamino]-2,3,4,5-tetrahydro-1H-benzo[d]azepine Succinate | 32 | 364 (M + H)+ |
| 148 | | 7-Chloro-6-[4-(1,2,3-thiadiazol-4-yl)-benzylamino]-2,3,4,5-tetrahydro-1H-benzo[d]azepine Succinate | 23 | 371 (M + H)+ |
| 149 | | 7-Chloro-6-[4-(2-methylthiazol-4-yl)-benzylamino]-2,3,4,5-tetrahydro-1H-benzo[d]azepine Succinate | 22 | 384 (M + H)+ |

EXAMPLE 150

(−)-7-Chloro-6-[4-(4-phenyl-4,5-dihydro-1H-imidazol-2-yl)-benzylamino]-2,3,4,5-tetrahydro-1H-benzo[d]azepine Hydrochloride

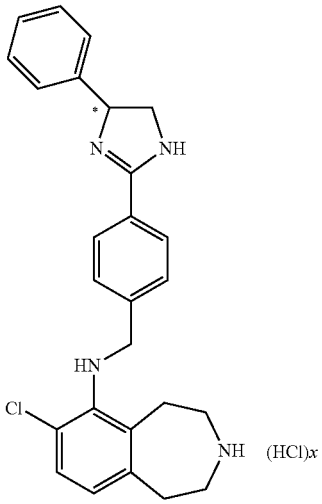

Mix 7-chloro-6-(4-cyanobenzylamino)-3-(2,2,2-trifluoroacetyl)-2,3,4,5-tetrahydro-1H-benzo[d]azepine (200 mg, 0.49 mmol, 1.0 equiv.), 1-(R)-phenyl-ethane-1,2-diamine (600 mg, 4.4 mmol, prepared as described in *J. Org. Chem.* 1997, 62, 3586) and p-toluenesulfonic acid monohydrate (102 mg, 0.53 mmol) in a sealed tube equipped with a magnetic stirrer. Heat the mixture to 200° C. for 16 h. Cool the mixture to ambient temperature. Dilute with DCM (50 mL) and wash with saturated aqueous $NaHCO_3$ (10 mL). Collect the organic fraction and concentrate in vacuo. Purify by chromatography on silica gel eluting with DCM/2M ammonia in methanol (98:2 to 80:20).

Use a method similar to the General Procedure 2-3 to give title compound as the hydrochloride. Use reverse phase HPLC [Column: Symmetry C18, 10×300 mm, flow 25 mL/min, water with 0.1% TFA/Acetonitrile (9:1 to 2:3)] followed by SCX chromatography to obtain the free base of the title compound. Use a method similar to the General Procedure 2-3 to obtain the title compound (38 mg, 16%). MS (ES+) m/z: 431 (M+H)$^+$. $[\alpha]^{20}_D$ −20° (c 0.5, MeOH).

EXAMPLE 151

7-Chloro-6-[4-(1-methyl-1H-imidazol-2-yl)-benzylamino]-2,3,4,5-tetrahydro-1H-benzo[d]azepine Succinate

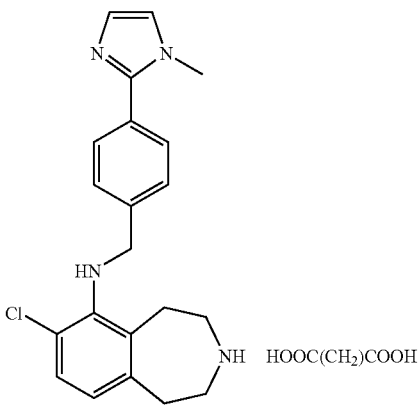

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (455 mg, 1.1 mmol) with 4-(1-methyl-1H-imidazol-2-yl)-benzylamine (240 mg, 1.3 mmol) in toluene (8 mL). Purify by chromatography on silica gel eluting with hexane/EtOAc (10:1, 5:1 and 3:1) followed by SCX chromatography [pre-wash column with methanol followed by DCM, load material dissolved in DCM, then elute with DCM/2M ammonia in methanol (1:1) and concentrate in vacuo] to obtain 7-chloro-6-[4-(1-methyl-1H-imidazol-2-yl)-benzylamino]-3-(2,2,2-trifluoroacetyl)-2,3,4,5-tetrahydro-1H-benzo[d]azepine (429 mg, 93%). MS (ES+) m/z: 463 (4+H)$^+$.

Use a method similar to the General Procedure 1-3 to deprotect 7-chloro-6-[4-(1-methyl-1H-imidazol-2-yl)-benzylamino]-3-(2,2,2-trifluoroacetyl)-2,3,4,5-tetrahydro-1H-benzo[d]azepine. Purify by chromatography on silica gel eluting with DCM/2M ammonia in methanol (99:1 to 90:10) to give the free base of the title compound. Use a method similar to the General Procedure 2-1 to give the title compound (350 mg, 73%). MS (ES+) m/z: 367 (M+H)$^+$.

EXAMPLE 152

7-Chloro-6-(4-ethanesulfonyl-benzylamino)-2,3,4,5-tetrahydro-1H-benzo[d]azepine Hydrochloride

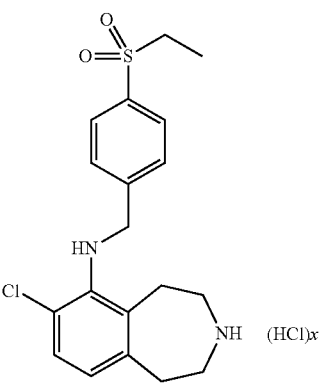

Use a method similar to the General Procedure 5-2, using 7-chloro-3-(2,2,2-trifluoroacetyl)-6-trifluoromethanesulfonyloxy-2,3,4,5-tetrahydro-1H-benzo[d]azepine (0.2 g, 0.35 mmol) and 4-ethanesulfonyl-benzylamine (0.2 g, 1.06 mmol) to give 7-chloro-6-(4-ethanesulfonyl-benzylamino)-3-(2,2-trifluoroacetyl)-2,3,4,5-tetrahydro-1H-benzo[d]azepine as a colorless oil.

Use a method similar to the General Procedure 1-1 to obtain the free base of the title compound as a yellow oil. Use a method similar to the General Procedure 2-2 to form the hydrochloride salt. Purify by reverse phase preparative HPLC (Zorbax SB-Phenyl 21.2×250 mm, 5 micron, 22 mL/min of 0.1% HCl in water/acetonitrile (9:1 to 1:1) over 30 min, detector at 230 nm) to obtain the title compound as a white solid (57 mg, 36%).

MS (ES+) m/z: 379 (M+H)$^+$.

EXAMPLE 153

7-Chloro-6-[4-(2-propanesulfonyl)-benzylamino]-2,3,4,5-tetrahydro-1H-benzo[d]azepine Hydrochloride

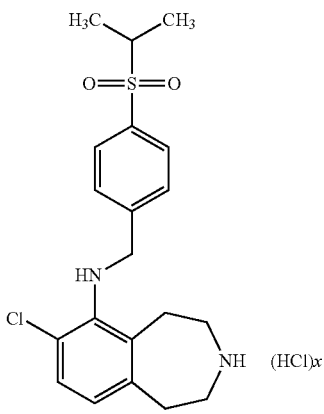

The title compound may be prepared essentially as described in Example 152, using 7-chloro-3-(2,2,2-trifluoroacetyl)-6-trifluoromethanesulfonyloxy-2,3,4,5-tetrahydro-1H-benzo[d]azepine and 4-(2-propanesulfonyl)-benzylamine (11% yield, MS (ES+) m/z 393 (M+H)$^+$).

EXAMPLE 154

7-Chloro-6-(4-methoxycarbonyl-benzylamino)-2,3,4,5-tetrahydro-1H-benzo[d]azepine Succinate

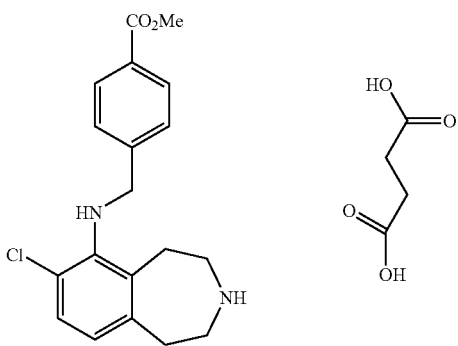

Treat 4-aminomethyl-benzoic acid methyl ester hydrochloride (0.2 g, 0.71 mmol) with $K_2CO_3$ (1.0 g, 0.71 mmol) in a mixture of toluene/water (1:1, 2 mL). Separate the organic layer, dry over anhydrous $Na_2SO_4$ and use as a toluene solution for the next step. Use a method similar to the General Procedure 5-2, using 7-chloro-3-(2,2,2-trifluoroacetyl)-6-trifluoromethanesulfonyloxy-2,3,4,5-tetrahydro-1H-benzo[d]azepine (0.1 g, 0.24 mmol) and 4-aminomethyl-benzoic acid methyl ester (0.2 g, 0.71 mmol) to give 7-chloro-6-(4-methoxycarbonyl-benzylamino)-3-(2,2,2-trifluoroacetyl)-2,3,4,5-tetrahydro-1H-benzo[d]azepine as a colorless oil.

Use a method similar to the General Procedure 1-1 to obtain the free base of the title compound as a yellow oil. Use a method similar to the General Procedure 2-1 to obtain the title compound as a white solid (20 mg, 18%). MS (ES+) m/z: 345 (M+H)$^+$.

EXAMPLE 155

6-(4-Carboxy-benzylamino)-7-chloro-2,3,4,5-tetrahydro-1H-benzo[d]azepine Hydrochloride

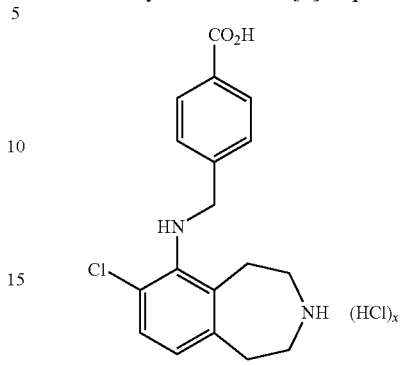

Combine 7-chloro-6-(4-methoxycarbonyl-benzylamino)-3-(2,2,2-trifluoroacetyl)-2,3,4,5-tetrahydro-1H-benzo[d]azepine (70 mg, 0.16 mmol), potassium carbonate (0.87 g, 6.3 mmol), methanol (2 mL), water (2 mL) and heat at 50° C. for 3 h. Purify by SCX chromatography to obtain 6-(4-carboxy-benzylamino)-7-chloro-2,3,4,5-tetrahydro-1H-benzo[d]azepine as a yellow oil.

Use a method similar to the General Procedure 2-2 to form the hydrochloride salt. Purify by reverse phase preparative HPLC [Zorbax SB-Phenyl 21.2×250 mm, 5 micron, 22 mL/min of 0.1% HCl in water/acetonitrile (9:1 to 1:1) over 30 min, detector at 230 nm] to obtain the title compound as a white solid (30 mg, 46%). MS (ES+) m/z: 331 (M+H)$^+$.

EXAMPLE 156

7-Chloro-6-(4-methylcarbamoyl-benzylamino)-2,3,4,5-tetrahydro-1H-benzo[d]azepine Hydrochloride

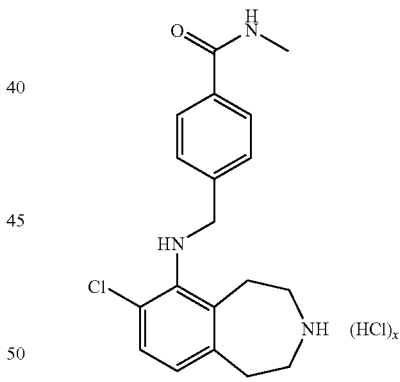

Combine 3-(tert-butoxycarbonyl)-6-(4-carboxy-benzylamino)-7-chloro-2,3,4,5-tetrahydro-1H-benzo[d]azepine (0.1 g, 0.3 mmol), methylamine hydrochloride (31 mg, 0.46 mmol), triethylamine (0.1 g, 0.9 mmol), HATU (0.2 g, 0.5 mmol), anhydrous DMF (3 mL) and stir at ambient temperature for 17 h. Partition the reaction mixture between brine (5 mL) and diethyl ether (5 mL), separate the organic layer and dry over anhydrous $Na_2SO_4$. Evaporate the solvent to obtain 3-(tert-butoxycarbonyl)-7-chloro-6-(4-methylcarbamoyl-benzylamino)-2,3,4,5-tetrahydro-1H-benzo[d]azepine as a yellow oil (0.1 g, 93%). MS (ES+) m/z: 344 (M+H–Boc)$^+$.

Use a method similar to the General Procedure 1-5 and purify the residue by SCX chromatography to obtain the free base of the title compound as a yellow oil. Use a method similar to the General Procedure 2-2 to form the hydrochloride salt. Purify by reverse phase preparative HPLC [Zorbax SB-Phenyl 21.2×250 mm, 5 micron, 22 mL/min of 0.1% HCl in water/acetonitrile (9:1 to 1:1) over 30 min, detector at 230 nm] to obtain the title compound as a white solid (0.9 g, 65%). MS (ES+) m/z: 344 (M+H)⁺.

Examples 157-158 may be prepared essentially as described in Example 156 by using 3-(tert-butoxycarbonyl)-6-(4-carboxy-benzylamino)-7-chloro-2,3,4,5-tetrahydro-1H-benzo[d]azepine and the appropriate amine. Overall yields and MS (ES+) data are shown in the Table below.

| Ex. | R | R' | Compound | Yield (%) | MS (ES+) m/z |
|---|---|---|---|---|---|
| 157 | Me | Me | 7-Chloro-6-(4-dimethylcarbamoyl-benzylamino)-2,3,4,5-tetrahydro-1H-benzo[d]azepine Hydrochloride | 51 | 358 (M + H)⁺ |
| 158 | i-Pr | H | 7-Chloro-6-(4-isopropylcarbamoyl-benzylamino)-2,3,4,5-tetrahydro-1H-benzo[d]azepine Hydrochloride | 56 | 372 (M + H)⁺ |

EXAMPLE 159

6-(4-tert-Butylcarbamoyl-benzylamino)-7-chloro-2,3,4,5-tetrahydro-1H-benzo[d]azepine Hydrochloride

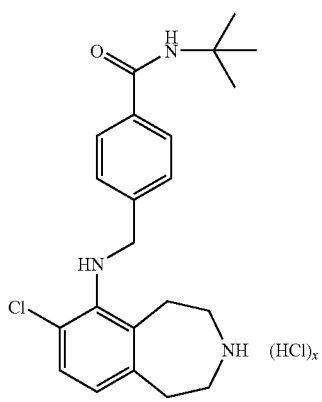

Use a method similar to the General Procedure 5-2, using 7-chloro-3-(2,2,2-trifluoroacetyl)-6-trifluoromethanesulfonyloxy-2,3,4,5-tetrahydro-1H-benzo[d]azepine (0.2 g, 0.35 mmol) and 4-aminomethyl-N-tert-butyl-benzamide (0.2 g, 1.06 mmol), to give 6-(4-tert-butylcarbamoyl-benzylamino)-7-chloro-3-(2,2,2-trifluoroacetyl)-2,3,4,5-tetrahydro-1H-benzo[d]azepine as a colorless oil.

Use a method similar to the General Procedure 1-1 to obtain the free base of the title compound as a yellow oil. Use a method similar to the General Procedure 2-2 to form the hydrochloride salt and purify by reverse phase preparative HPLC [Zorbax SB-Phenyl 21.2×250 mm, 5 micron, 22 mL/min of 0.1% HCl in water/acetonitrile (9:1 to 1:1) over 30 min, detector at 230 nm] to obtain the title compound as a white solid (65 mg, 41%). MS (ES+) m/z: 386 (M+H)⁺.

Examples 160-161 may be prepared essentially as described in Example 159 by using 7-chloro-3-(2,2,2-trifluoroacetyl)-6-trifluoromethanesulfonyloxy-2,3,4,5-tetrahydro-1H-benzo[d]azepine and the appropriate amine. Overall yields and MS (ES+) data are shown in the Table below.

| Ex. | R | R' | Compound | Yield (%) | MS (ES+) m/z |
|---|---|---|---|---|---|
| 160 | t-Bu | Me | 6-(4-tert-Butylcarbamoyl-3-fluoro-benzylamino)-7-chloro-2,3,4,5-tetrahydro-1H-benzo[d]azepine Hydrochloride | 48 | 404 (M + H)⁺ |
| 161 | n-Pr | Me | 7-Chloro-6-[3-fluoro-4-(N-methyl-N-propyl-carbamoyl)-benzyl-amino]-2,3,4,5-tetrahydro-1H-benzo[d]azepine Hydrochloride | 48 | 404 (M + H)⁺ |

EXAMPLE 162

7-Chloro-6-[4-(cyclohexylaminocarbonyl-)-3-fluoro-benzylamino]-2,3,4,5-tetrahydro-1H-benzo[d]azepine Succinate

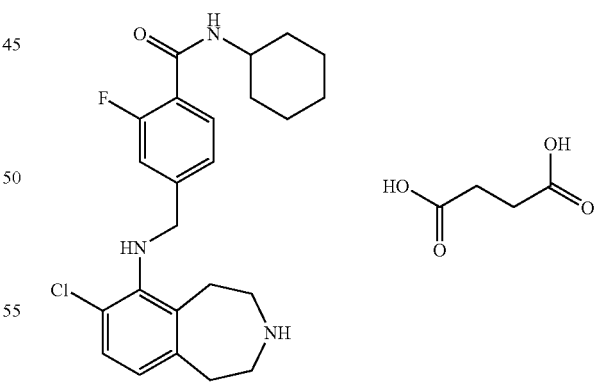

Use a method similar to the General Procedure 5-2 to react 7-chloro-3-(2,2,2-trifluoroacetyl)-6-trifluoromethanesulfonyloxy-2,3,4,5-tetrahydro-1H-benzo[d]azepine (500 mg, 1.17 mmol) with 4-aminomethyl-N-cyclohexyl-2-fluoro-benzamide (441 mg, 1.76 mmol). Purify by chromatography on silica gel eluting with hexane/EtOAc (20:1, 10:1, 7:1 and 5:1) to give 7-chloro-6-[4-(cyclohexylaminocarbonyl-)3-fluoro-benzylamino]-3-(2,2,2-trifluoroacetyl)-2,3,4,5-tetrahydro-1H-benzo[d]azepine as an oil.

Use a method similar to the General Procedure 1-3 and purify by chromatography on silica gel eluting with DCM/ 2M ammonia in methanol (1:0, 20:1. 10:1 and 7:1) followed by reverse phase semi-prep HPLC [SymmetryPrep C18, 7 ☐m, 19×300 mm column eluting with acetonitrile/0.1% trifluoroacetic acid in water (1:9 to 8:2) at 20 mL/min] and SCX chromatography to give the free base of the title compound.

Use a method similar to the General Procedure 2-1 to give the title compound as a yellow solid (97 mg, 15%). MS (ES+) m/z: 430 (M+H)$^+$.

EXAMPLE 163

7-Chloro-6-[4-(2,2,2-trifluoroethylaminocarbonyl)-benzylamino]-2,3,4,5-tetrahydro-1H-benzo[d]azepine Succinate

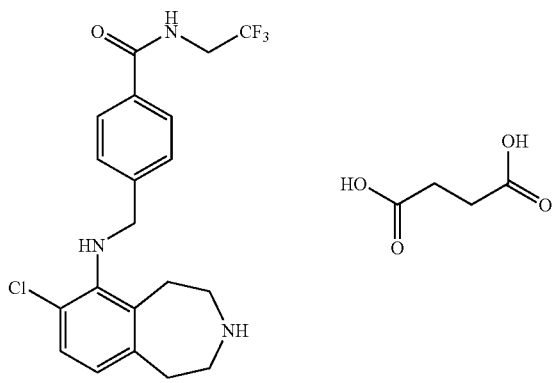

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (250 mg, 0.59 mmol) with 4-aminomethyl-N-(2,2,2-trifluoroethyl)-benzamide (273 mg, 1.17 mmol). Purify by chromatography on silica gel eluting with hexane/EtOAc (20: 1, 10:1, 7:1 and 5:1) to give 7-chloro-3-(2,2,2-trifluoroacetyl)-6-[4-(2,2,2-trifluoroethyl-aminocarbonyl)-benzylamino]-2,3,4,5-tetrahydro-1H-benzo[d]azepine as an oil.

Use a method similar to the General Procedure 1-3 and purify by chromatography on silica gel eluting with DCM/ 2M ammonia in methanol (1:0, 20:1. 10:1 and 7:1) to give the free base of the title compound. Use a method similar to the General Procedure 2-1 to give the title compound as a white solid (191 mg, 61%). MS (ES+) m/z: 412 (M+H)$^+$.

Examples 164-177 may be prepared essentially as described in Example 163 by using 7-chloro-3-(2,2,2-trifluoroacetyl)-6-trifluoromethanesulfonyloxy-2,3,4,5-tetrahydro-1H-benzo[d]azepine and the appropriate amine. Overall yields and MS (ES+) data are shown in the Table below.

| Ex. | NH—R | Compound | Yield (%) | MS (ES+) m/z |
|---|---|---|---|---|
| 164 | NH~~CF$_3$ | 7-Chloro-6-[4-(3,3,3-trifluoro-propylaminocarbonyl)-benzylamino]-2,3,4,5-tetrahydro-1H-benzo[d]azepine Succinate | 38 | 426 (M + H)$^+$ |
| 165 | NH~~C(F)(F)CF$_3$ | 7-Chloro-6-[4-(2,2,3,3,3-pentafluoro-propylaminocarbonyl)-benzylamino]-2,3,4,5-tetrahydro-1H-benzo[d]azepine Succinate | 41 | 462 (M + H)$^+$ |
| 166 | NH~~CH(CH$_3$)CF$_3$ | (±)-7-Chloro-6-[4-(2,2,2-trifluoro-1-methyl-ethylaminocarbonyl)-benzylamino]-2,3,4,5-tetrahydro-1H-benzo[d]azepine Succinate | 46 | 426 (M + H)$^+$ |

-continued

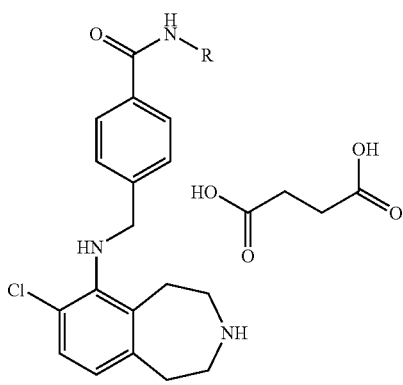

| Ex. | NH—R | Compound | Yield (%) | MS (ES+) m/z |
|---|---|---|---|---|
| 167 | NH-CH(CH₃)-CH₂-CF₃ | (±)-7-Chloro-6-[4-(1-methyl-3,3,3-trifluoro-propylaminocarbonyl)-benzylamino]-2,3,4,5-tetrahydro-1H-benzo[d]azepine Succinate | 28 | 440 (M + H)⁺ |
| 168 | NH-cyclopentyl | 7-Chloro-6-[4-(cyclopentylaminocarbonyl)-benzylamino]-2,3,4,5-tetrahydro-1H-benzo[d]azepine Succinate | 55 | 398 (M + H)⁺ |
| 169 | NH-cyclohexyl | 7-Chloro-6-[4-(cyclohexylaminocarbonyl)-benzylamino]-2,3,4,5-tetrahydro-1H-benzo[d]azepine Succinate | 82 | 412 (M + H)⁺ |
| 170 | NH-cycloheptyl | 7-Chloro-6-[4-(cycloheptylcarbamoyl)-benzylamino]-2,3,4,5-tetrahydro-1H-benzo[d]azepine Succinate | 65 | 426 (M + H)⁺ |
| 171 | NH-CH₂-Ph | 6-[4-(Benzylaminocarbonyl)-benzylamino]-7-chloro-2,3,4,5-tetrahydro-1H-benzo[d]azepine Succinate | 33 | 420 (M + H)⁺ |
| 172 | NH-CH₂-(3,4-diF-Ph) | 7-Chloro-6-[4-(3,4-difluoro-benzylaminocarbonyl)-benzylamino]-2,3,4,5-tetrahydro-1H-benzo[d]azepine Succinate | 55 | 456 (M + H)⁺ |
| 173 | NH-C(CH₃)₂-Ph | 7-Chloro-6-[4-(1-methyl-1-phenyl-ethylaminocarbonyl)-benzylamino]-2,3,4,5-tetrahydro-1H-benzo[d]azepine Succinate | 12 | 448 (M + H)⁺ |
| 174 | NH-CH(CH₃)-CH₂-Ph | (±)-7-Chloro-6-[4-(1-methyl-2-phenyl-ethylaminocarbonyl)-benzylamino]-2,3,4,5-tetrahydro-1H-benzo[d]azepine Succinate | 36 | 448 (M + H)⁺ |
| 175 | NH-(4-tolyl) | 7-Chloro-6-[4-(p-tolylaminocarbonyl)-benzylamino]-2,3,4,5-tetrahydro-1H-benzo[d]azepine Succinate | 60 | 420 (M + H)⁺ |

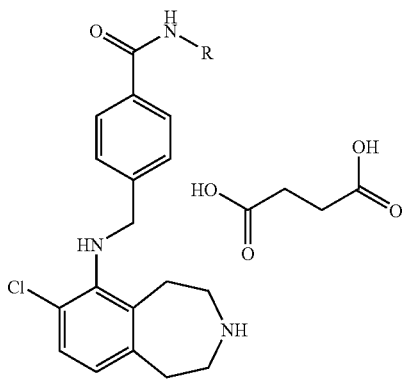

| Ex. | NH—R | Compound | Yield (%) | MS (ES+) m/z |
|---|---|---|---|---|
| 176 | NH-(4-chlorophenyl) | 7-Chloro-6-[4-(4-chloro-phenylaminocarbonyl)-benzylamino]-2,3,4,5-tetrahydro-1H-benzo[d]azepine Succinate | 28 | 440 (M + H)+ |
| 177 | NH-(tetrahydropyran-4-yl) | 7-Chloro-6-[4-(tetrahydro-pyran-4-yl-aminocarbonyl)-benzylamino]-2,3,4,5-tetrahydro-1H-benzo[d]azepine Succinate | 13 | 414 (M + H)+ |

EXAMPLES 178 AND 179

(−)-7-Chloro-6-[4-(2,2,2-trifluoro-1-methyl-ethylaminocarbonyl)-benzylamino]-2,3,4,5-tetrahydro-1H-benzo[d]azepine Succinate and (+)-7-Chloro-6-[4-(2,2,2-trifluoro-1-methyl-ethylaminocarbonyl)-benzylamino]-2,3,4,5-tetrahydro-1H-benzo[d]azepine Succinate

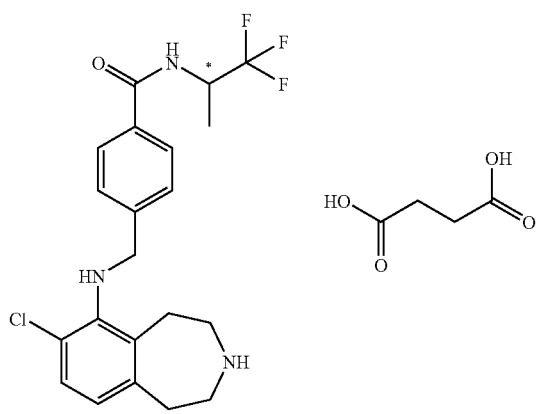

Dissolve (±)-7-chloro-6-[4-(2,2,2-trifluoro-1-methylethylaminocarbonyl)-benzylamino]-2,3,4,5-tetrahydro-1H-benzo[d]azepine (472 mg, 1.11 mmol) in DCM (50 mL) and add di-tert-butyl-dicarbonate (300 mg, 1.34 mmol) and a solution of sodium carbonate (2 g) in water (50 mL). Stir the reaction at room temperature for 2 h then dilute with DCM, wash with water, dry over $Na_2SO_4$, filter and concentrate. Purify by chromatography on silica gel eluting with hexane/EtOAc (10:1, 5:1 and 3:1) to give (±)-3-tert-butoxycarbonyl-7-chloro-6-[4-(2,2,2-trifluoro-1-methyl-ethylaminocarbonyl)-benzylamino]-2,3,4,5-tetrahydro-benzo[d]azepine (330 mg, 57%).

Separate the two enantiomers by chiral HPLC [Chiralpak AD column, 8×30 cm, eluting with 0.2% DMEA in heptane/isopropanol (9:1)].

Use a method similar to the General Procedure 1-5 to deprotect the first eluting compound and purify by SCX chromatography to give (−)-7-chloro-6-[4-(2,2,2-trifluoro-1-methyl-ethylaminocarbonyl)-benzylamino]-2,3,4,5-tetrahydro-1H-benzo[d]azepine. Use a method similar to the General Procedure 2-1 to give (−)-7-chloro-6-[4-(2,2,2-trifluoro-1-methyl-ethylaminocarbonyl)-benzylamino]-2,3,4,5-tetrahydro-1H-benzo[d]azepine succinate as a white solid (50 mg, 15%). MS (ES+) m/z: 426 (M+H)+; $[\alpha]^{20}_D$ −3.3° (c 0.5, $CH_3OH$).

Use a method similar to the General Procedure 1-5 to deprotect the second eluting compound and purify by SCX chromatography to give (+)-7-chloro-6-[4-(2,2,2-trifluoro-1-methyl-ethylaminocarbonyl)-benzylamino]-2,3,4,5-tetrahydro-1H-benzo[d]azepine. Use a method similar to the General Procedure 2-1 to give (+)-7-chloro-6-[4-(2,2,2-trifluoro-1-methyl-ethylaminocarbonyl)-benzylamino]-2,3,4,5-tetrahydro-1H-benzo[d]azepine succinate as a white solid (55 mg, 16%). MS (ES+) m/z: 426 (M+H)+; $[\alpha]^{20}_D$ +4.4° (c 0.5, $CH_3OH$).

EXAMPLES 180 AND 181

(+)-7-Chloro-6-[4-(1-methyl-3,3,3-trifluoro-propylaminocarbonyl)-benzylamino]-2,3,4,5-tetrahydro-1H-benzo[d]azepine Succinate and (−)-7-Chloro-6-[4-(1-methyl-3,3,3-trifluoro-propylaminocarbonyl)-benzylamino]-2,3,4,5-tetrahydro-1H-benzo[d]azepine Succinate

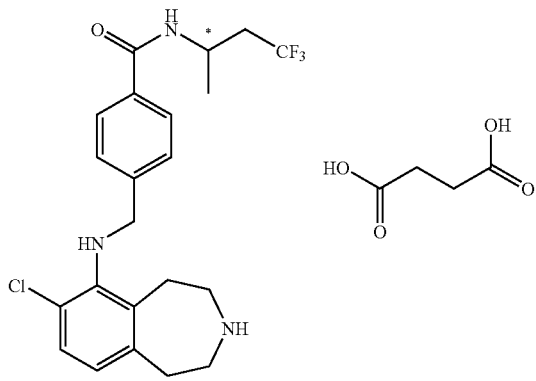

Dissolve (±)-7-chloro-3-(2,2,2-trifluoroacetyl)-6-[4-(1-methyl-3,3,3-trifluoro-propylaminocarbonyl)-benzylamino]-2,3,4,5-tetrahydro-1H-benzo[d]azepine (985 mg, 2.24 mmol) in DCM (50 mL) and add di-tert-butyl-dicarbonate (605 mg, 3.36 mmol) and a solution of sodium carbonate (2 g) in water (50 mL). Stir the mixture at room temperature for 1 h then dilute with DCM, wash with water, dry over Na$_2$SO$_4$, filter and concentrate. Purify by chromatography on silica gel eluting with hexane/EtOAc (10:1, 5:1 and 3:1) to give (±)-3-tert-butoxycarbonyl-7-chloro-6-[4-(1-methyl-3,3,3-trifluoro-propylaminocarbonyl)-benzylamino]-2,3,4,5-tetrahydro-benzo[d]azepine.

Separate the two enantiomers by chiral HPLC [Chiralpak AD column, 8×30 cm, eluting with heptane/isopropanol/0.2% DMEA in methanol (90:5:5)].

Use a method similar to the General Procedure 1-5 to deprotect the first eluting compound and purify by SCX chromatography to give (+)-7-chloro-6-[4-(1-methyl-3,3,3-trifluoro-propylaminocarbonyl)-benzylamino]-2,3,4,5-tetrahydro-1H-benzo[d]azepine.

Use a method similar to the General Procedure 2-1 to give (+)-7-chloro-6-[4-(1-methyl-3,3,3-trifluoro-propylaminocarbonyl)-benzylamino]-2,3,4,5-tetrahydro-1H-benzo[d]azepine succinate as a white solid (186 mg, 15%). MS (ES+) m/z: 440 (M+H)$^+$; [α]$^{20}_D$ +6.5° (c 0.5, CH$_3$OH).

Use a method similar to the General Procedure 1-5 to deprotect the second eluting compound and purify by SCX chromatography to give (−)-7-chloro-6-[4-(1-methyl-3,3,3-trifluoro-propylaminocarbonyl)-benzylamino]-2,3,4,5-tetrahydro-1H-benzo[d]azepine. Use a method similar to the General Procedure 2-1 to give (−)-7-chloro-6-[4-(1-methyl-3,3,3-trifluoro-propylaminocarbonyl)-benzylamino]-2,3,4,5-tetrahydro-1H-benzo[d]azepine succinate as a white solid (191 mg, 15%). MS (ES+) m/z: 440 (M+E)$^+$; [α]$^{20}_D$ −5.2° (c 0.5, CH$_3$OH).

EXAMPLE 182

(R-(+)-7-Chloro-6-[4-(1-phenyl-ethylaminocarbonyl)-benzylamino]-2,3,4,5-tetrahydro-1H-benzo[d]azepine Succinate

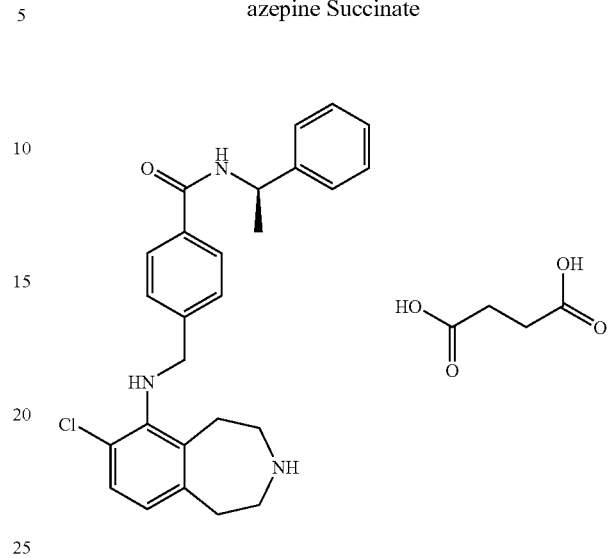

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (250 mg, 0.59 mmol) with (R)-4-aminomethyl-N-(1-phenyl-ethyl)-benzamide (298 mg, 1.17 mmol) in toluene (15 mL). Purify by chromatography on silica gel eluting with hexane/EtOAc (20:1, 10:1, 7:1 and 5:1) to give (R)-(+)-7-chloro-6-[4-(1-phenyl-ethylcaminocarbonyl)-benzylamino]-3-(2,2,2-trifluoroacetyl)-2,3,4,5-tetrahydro-1H-benzo[d]azepine as an oil.

Use a method similar to the General Procedure 1-3 and purify by chromatography on silica gel eluting with DCM/2M ammonia in methanol (1:0, 20:1. 10:1 and 7:1) to give the free base of the title compound. Use a method similar to the General Procedure 2-1 to give the title compound as a yellow solid (158 mg, 49%). MS (ES+) m/z: 434 (m+H)$^+$; [α]$^{20}_D$ +18.7° (c 0.5, CH$_3$OH).

EXAMPLE 183

(S)-(−)-7-Chloro-6-[4-(1-phenyl-ethylaminocarbonyl)-benzylamino]-2,3,4,5-tetrahydro-1H-benzo[d]azepine Succinate

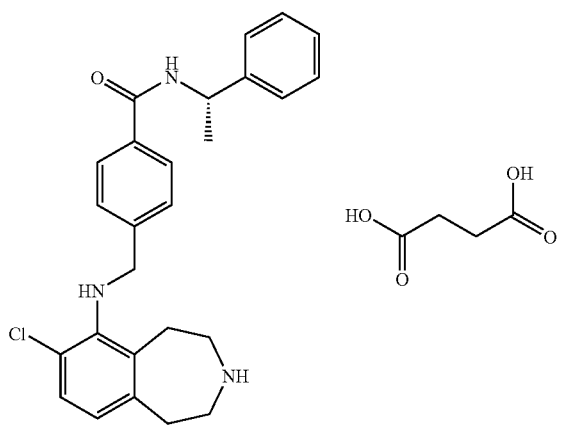

Use a method similar to the Example 182, using 7-chloro-3-(2,2,2-trifluoroacetyl)-6-trifluoromethanesulfonyloxy-2,3,4,5-tetrahydro-1H-benzo[d]azepine (250 mg, 0.59 mmol) and (S)-4-aminomethyl-N-(1-phenyl-ethyl)-benzamide (298 mg, 1.17 mmol) to give the title compound as a white solid (95 mg, 29%). MS (ES+) m/z: 434 (M+H)$^+$; $[\alpha]^{20}_D$ –20.1° (c 0.5, CH$_3$OH).

EXAMPLE 184

7-Chloro-6-{4-[(2-thiophen-2-yl-ethyl)-carbamoyl]-benzylamino}-2,3,4,5-tetrahydro-1H-benzo[d]azepine Succinate

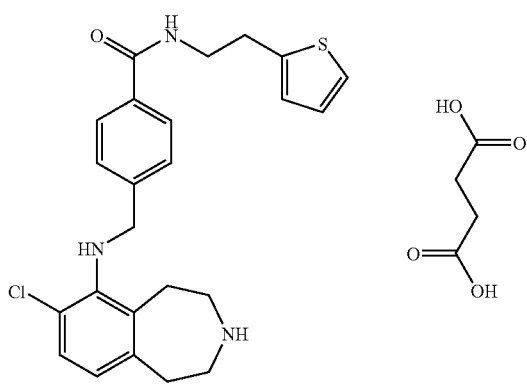

Use a method similar to the General Procedure 5-3, react 7-chloro-3-(2,2,2-trifluoroacetyl)-6-trifluoromethanesulfonyloxy-2,3,4,5-tetrahydro-1H-benzo[d]azepine (250 mg, 0.588 mmol) with 4-aminomethyl-N-(2-thiophen-2-yl-ethyl)-benzamide (306 mg, 1.176 mmol) using palladium(II) acetate (26 mg, 0.118 mmol), tris(dibenzylideneacetone)dipalladium(0) (53 mg, 0.059 mmol), BINAP (220 mg, 0.353 mmol) and cesium carbonate (383 mg, 1.176 mmol) in dioxane (6 mL). Purify by chromatography on silica gel eluting with hexane/EtOAc (1:0, 7:3 and 1:1) to give 7-chloro-6-{4-[(2-thiophen-2-yl-ethyl)-carbamoyl]-benzylamino}-3-(2,2,2-trifluoroacetyl)-2,3,4,5-tetrahydro-1H-benzo[d]azepine as an oil (233 mg, 91%). MS (ES+) m/z: 535 (M+H)$^+$.

Use a method similar to the General Procedure 1-2, using 7-chloro-6-{4-[(2-thiophen-2-yl-ethyl)-carbamoyl]-benzylamino}-3-(2,2,2-trifluoroacetyl)-2,3,4,5-tetrahydro-1H-benzo[d]azepine (223 mg, 0.416 mmol), to give 7-chloro-6-{4-[(2-thiophen-2-yl-ethyl)-carbamoyl]-benzylamino}-2,3,4,5-tetrahydro-1H-benzo[d]azepine as an oil (145 mg, 79%) that was used without any further purification.

Use a method similar to the General Procedure 2-1, using 7-chloro-6-{4-[(2-thiophen-2-yl-ethyl)-carbamoyl]-benzylamino}-2,3,4,5-tetrahydro-1H-benzo[d]azepine (145 mg, 0.330 mmol), to give the title compound as a solid (123 mg, 67%). MS (ES+) m/z: 440 (M+H)$^+$.

Examples 185-194 may be prepared essentially as described in Example 184 by using 7-chloro-3-(2,2,2-trifluoroacetyl)-6-trifluoromethanesulfonyloxy-2,3,4,5-tetrahydro-1H-benzo[d]azepine and the appropriate amine. Overall yields and MS (ES+) data are shown in the Table below.

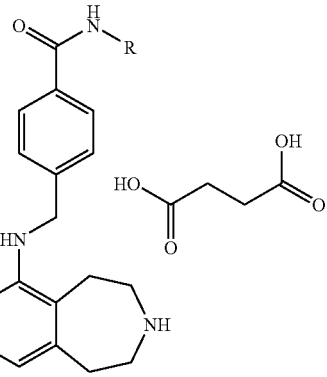

| Ex. | NH—R | Compound | Yield (%) | MS (ES+) m/z |
|---|---|---|---|---|
| 185 | (thiophen-2-ylmethyl, HN-CH$_2$-) | 7-Chloro-6-{4-[(thiophen-2-ylmethyl)-carbamoyl]-benzylamino}-2,3,4,5-tetrahydro-1H-benzo[d]azepine Succinate | 46 | 426 (M + H)$^+$ |
| 186 | (pyridin-2-ylmethyl, HN-CH$_2$-) | 7-Chloro-6-{4-[(pyridin-2-ylmethyl)-carbamoyl]-benzylamino}-2,3,4,5-tetrahydro-1H-benzo[d]azepine Succinate | 49 | 421 (M + H)$^+$ |

-continued

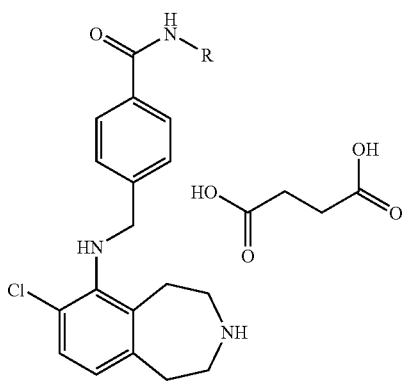

| Ex. | NH—R | Compound | Yield (%) | MS (ES+) m/z |
|---|---|---|---|---|
| 187 | (3-CF3-pyridin-2-ylmethyl)amine | 7-Chloro-6-{4-[(3-trifluoromethyl-pyridin-2-ylmethyl)-carbamoyl]-benzylamino}-2,3,4,5-tetrahydro-1H-benzo[d]azepine Succinate | 39 | 489 (M + H)+ |
| 188 | (4-CF3-pyridin-2-ylmethyl)amine | 7-Chloro-6-{4-[(4-trifluoromethyl-pyridin-2-ylmethyl)-carbamoyl]-benzylamino}-2,3,4,5-tetrahydro-1H-benzo[d]azepine Succinate | 26 | 489 (M + H)+ |
| 189 | (5-CF3-pyridin-2-ylmethyl)amine | 7-Chloro-6-{4-[(5-trifluoromethyl-pyridin-2-ylmethyl)-carbamoyl]-benzylamino}-2,3,4,5-tetrahydro-1H-benzo[d]azepine Succinate | 29 | 489 (M + H)+ |
| 190 | (3-fluoro-pyridin-2-ylmethyl)amine | 7-Chloro-6-{4-[(3-fluoro-pyridin-2-ylmethyl)-carbamoyl]-benzylamino}-2,3,4,5-tetrahydro-1H-benzo[d]azepine Succinate | 37 | 439 (M + H)+ |
| 191 | (5-fluoro-pyridin-2-ylmethyl)amine | 7-Chloro-6-{4-[(5-fluoro-pyridin-2-ylmethyl)-carbamoyl]-benzylamino}-2,3,4,5-tetrahydro-1H-benzo[d]azepine Succinate | 51 | 439 (M + H)+ |
| 192 | (6-fluoro-pyridin-2-ylmethyl)amine | 7-Chloro-6-{4-[(6-fluoro-pyridin-2-ylmethyl)-carbamoyl]-benzylamino}-2,3,4,5-tetrahydro-1H-benzo[d]azepine Succinate | 54 | 439 (M + H)+ |
| 193 | 2-(pyridin-3-yl)ethylamine | 7-Chloro-6-[4-(2-pyridin-3-yl-ethylcarbamoyl)-benzylamino]-2,3,4,5-tetrahydro-1H-benzo[d]azepine Succinate | 46 | 435 (M + H)+ |

-continued

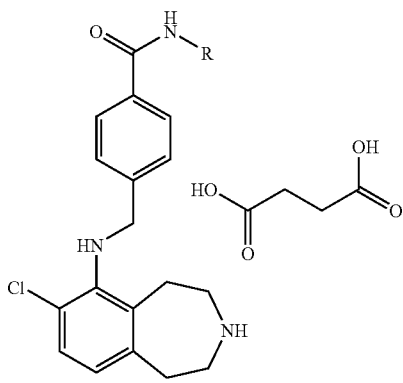

| Ex. | NH—R | Compound | Yield (%) | MS (ES+) m/z |
|---|---|---|---|---|
| 194 | HN–CH₂CH₂-(4-pyridyl) | 7-Chloro-6-[4-(2-pyridin-4-yl-ethylcarbamoyl)-benzylamino]-2,3,4,5-tetrahydro-1H-benzo[d]azepine Succinate | 27 | 435 (M + H)⁺ |

EXAMPLE 195

7-Chloro-6-[4-(2-pyridin-2-yl-ethylcarbamoyl)-benzylamino]-2,3,4,5-tetrahydro-1H-benzo[d]azepine Hydrochloride

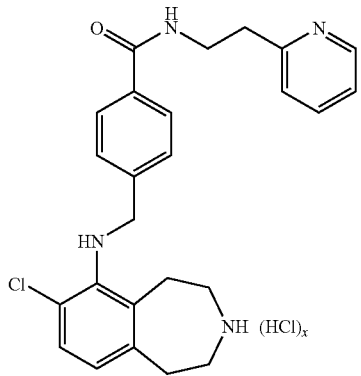

Use a method similar to the General Procedure 5-3 to react 7-chloro-3-(2,2,2-trifluoroacetyl)-6-trifluoromethanesulfonyloxy-2,3,4,5-tetrahydro-1H-benzo[d]azepine (200 mg, 0.471 mmol) and 4-aminomethyl-N-(2-pyridin-2-yl-ethyl)-benzamide (241 mg, 0.942 mmol) using palladium(II) acetate (21 mg, 0.094 mmol), tris(dibenzylideneacetone)dipalladium(0) (43 mg, 0.047 mmol), BINAP (176 mg, 0.283 mmol) and cesium carbonate (307 mg, 0.942 mmol) in dioxane (5 mL). Purify by chromatography on silica gel eluting with hexane and hexane/EtOAc/DCM/methanol (7:1:1:1) to give 7-chloro-6-[4-(2-pyridin-2-yl-ethylcarbamoyl)-benzylamino]-3-(2,2,2-trifluoroacetyl)-2,3,4,5-tetrahydro-1H-benzo[d]azepine as an oil (107 mg, 43%). MS (ES+) m/z: 531 (+H)⁺.

Use a method similar to the General Procedure 1-2, using 7-chloro-6-[4-(2-pyridin-2-yl-ethylcarbamoyl)-benzylamino]-3-(2,2,2-trifluoroacetyl)-2,3,4,5-tetrahydro-1H-benzo[d]azepine (107 mg, 0.202 mmol), to give 7-chloro-6-[4-(2-pyridin-2-yl-ethylcarbamoyl)-benzylamino]-2,3,4,5-tetrahydro-1H-benzo[d]azepine as an oil (85 mg, 97%) that was used without any further purification.

Use a method similar to the General Procedure 2-2, using 7-chloro-6-[4-(2-pyridin-2-yl-ethylcarbamoyl)-benzylamino]-2,3,4,5-tetrahydro-1H-benzo[d]azepine (85 mg, 0.195 mmol), to give the title compound as a solid (103 mg, 97%). MS (ES+) m/z: 435 (M+H)⁺.

EXAMPLE 196

7-Chloro-6-[4-(piperidine-1-carbonyl)-benzylamino]-2,3,4,5-tetrahydro-1H-benzo[d]azepine Succinate

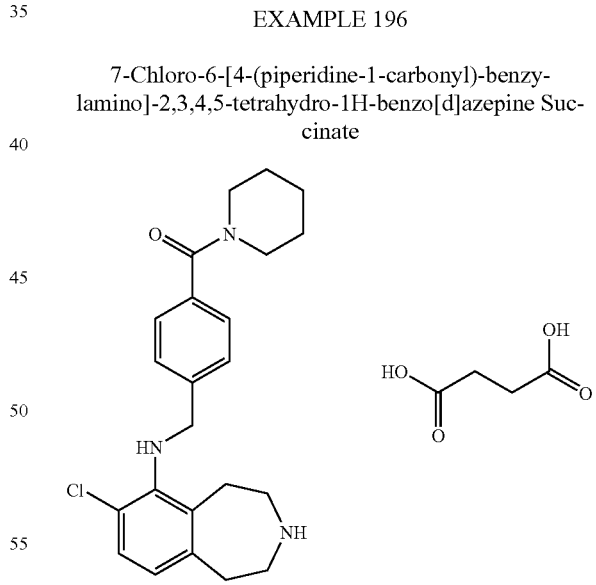

Using a method similar to the General Procedure 5-2, react 7-chloro-3-(2,2,2-trifluoroacetyl)-6-trifluoromethanesulfonyloxy-2,3,4,5-tetrahydro-1H-benzo[d]azepine (500 mg, 1.17 mmol) with 4-(piperidin-1-ylcarbonyl)-benzylamine (308 mg, 1.41 mmol). Purify by chromatography on silica gel eluting with hexane/EtOAc (20:1, 10:1, 7:1 and 5:1) to give 7-chloro-6-[4-(piperidine-1-carbonyl)-benzylamino]-3-(2,2,2-trifluoroacetyl)-2,3,4,5-tetrahydro-1H-benzo[d]azepine as an oil.

Use a method similar to the General Procedure 1-3 and purify by chromatography on silica gel eluting with DCM/2M ammonia in methanol (1:0, 20:1. 10:1 and 7:1) to give the free base of the title compound. Use a method similar to the General Procedure 2-1 to give the title compound as a yellow solid (284 mg, 47%). MS (ES+) m/z: 398 (M+H)+.

EXAMPLE 197

7-Chloro-6-[2-(cyclohexylaminocarbonyl-pyridin-5-ylmethyl)-amino]-2,3,4,5-tetrahydro-1H-benzo[d]azepine Succinate

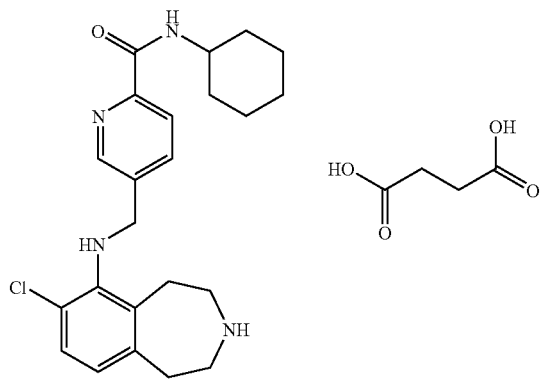

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (348 mg, 0.82 mmol) with 5-aminomethyl-pyridine-2-carboxylic acid cyclohexylamide (200 mg, 0.86 mmol). Purify by chromatography on silica gel eluting with hexane/EtOAc (20:1, 10:1, 7:1 and 5:1) to give 7-chloro-6-[2-(cyclohexylaminocarbonyl-pyridin-5-ylmethyl)-amino]-3-(2,2,2-trifluoroacetyl)-2,3,4,5-tetrahydro-1H-benzo[d]azepine as oil.

Use a method similar to the General Procedure 1-3 and purify by chromatography on silica gel eluting with DCM/2M ammonia in methanol (1:0, 20:1. 10:1 and 7:1) to give the free base of the title compound.

Use a method similar to the General Procedure 2-1 to give the title compound as a yellow solid (147 mg, 34%). MS (ES+) m/z: 413 (M+H)+.

EXAMPLE 198

7-Chloro-6-[2-(4-fluoro-b aminocarbonyl)-pyridin-5-ylmethyl]-amino]-2,3,4,5-tetrahydro-1H-benzo[d]azepine Succinate

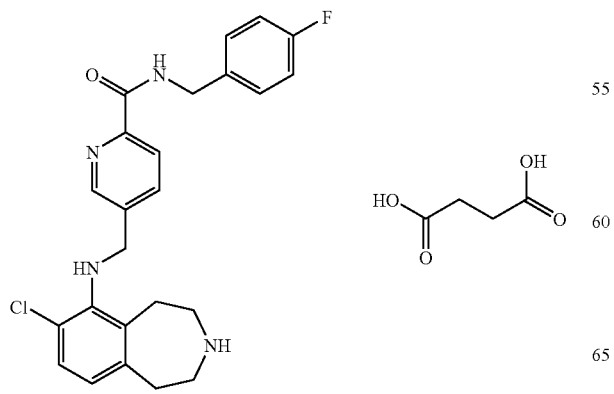

The title compound may be prepared essentially as described in Example 197, using 7-chloro-3-(2,2,2-trifluoroacetyl)-6-trifluoromethanesulfonyloxy-2,3,4,5-tetrahydro-1H-benzo[d]azepine and 5-aminomethyl-pyridine-2-carboxylic acid 4-fluoro-benzylamide (28% yield, MS (ES+) m/z 439).

EXAMPLE 199

7-Chloro-6-(4-tert-butylthiocarbamoyl-benzylamino)-2,3,4,5-tetrahydro-1H-benzo[d]azepine Hydrochloride

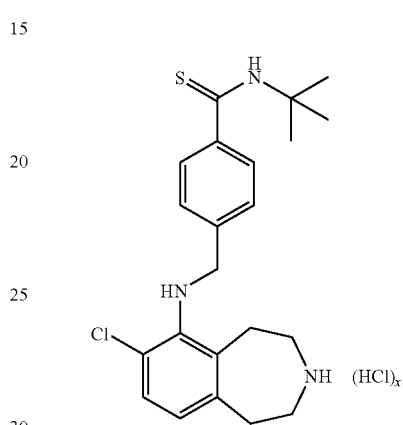

Combine 6-(4-tert-butylcarbamoyl-benzylamino)-7-chloro-2,3,4,5-tetrahydro-1H-benzo-[d]azepine (0.3 g, 0.67 mmol), 2,4-bis(4-methoxyphenyl)-1,3-dithia-2,4-diphosphetane-2,4-disulfide (Lawesson's reagent) (0.3, g, 0.67 mmol) and anhydrous 1,4-dioxane (10 mL) in a sealed tube and heat at 100° C. for 5 h. Cool the reaction mixture to ambient temperature, evaporate the solvent and purify the residue by SCX

EXAMPLE 200

(S)-(−)-7-Chloro-6-[1-(4-fluorophenyl)-ethylamino]-2,3,4,5-tetrahydro-1H-benzo[d]azepine Succinate

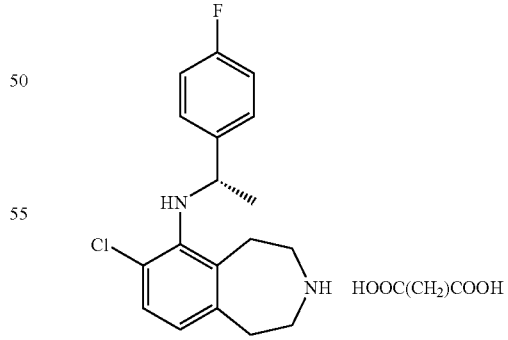

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (7.0 g, 16.4 mmol) with (S)-1-(4-fluorophenyl)ethylamine (6.9 g, 49.3 mmol) in toluene (175 mL). Purify by chromatography on silica gel eluting with hexane/EtOAc (9:1 to 1:1) followed by SCX chromatography [pre-wash column with methanol followed by DCM, load material dissolved in DCM, then elute with DCM/2M ammonia in methanol (1:1) and concentrate in vacuo] to give 7-chloro-6-[1-(S)-(4-fluorophenyl)-ethylamino]-3-(2,2,2-trifluoroacetyl)-2,3,4,5-tetrahydro-1H-benzo[d]azepine (3.96 g, 58%). GC-MS m/z: 414 (M+).

Use a method similar to the General Procedure 1-3 to deprotect 7-chloro-6-[1-(S)-(4-fluorophenyl)-ethylamino]-3-(2,2,2-trifluoroacetyl)-2,3,4,5-tetrahydro-1H-benzo[d]azepine (3.92 g, 9.5 mmol) and purify by chromatography on silica gel eluting with DCM/2M ammonia in methanol (99:1 to 80:20) to give the free base of the title compound. Use a method similar to the General Procedure 2-1 and crystallize the solid from ethanol and methyl-t-butyl ether. Filter and dry the solid in a vacuum oven at 60° C. overnight to obtain the title compound (3.4 g, 83%). MS (ES+) m/z: 319 (M+H)$^+$; $[\alpha]^{20}{}_D$ −102.8° (c 0.5, MeOH).

Examples 201-209 may be prepared essentially as described in Example 200 by using 7-chloro-3-(2,2,2-trifluoroacetyl)-6-trifluoromethanesulfonyloxy-2,3,4,5-tetrahydro-1H-benzo[d]azepine and the appropriate amine. The yields for the Step 1 (General Procedure 5-2), optical rotation and MS (ES+) data are shown in the Table below.

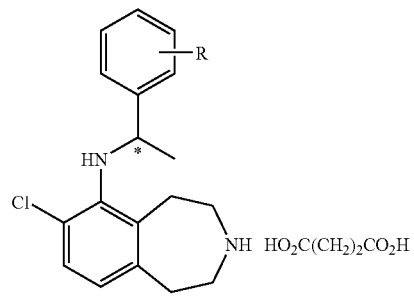

| Ex. | R | Compound | Yield (%) | $[\alpha]^{20}{}_D$ (c, solvent) | MS |
| --- | --- | --- | --- | --- | --- |
| 201 | 4-F | (R)-(+)-7-Chloro-6-[1-(4-fluorophenyl)-ethylamino]-2,3,4,5-tetrahydro-1H-benzo[d]azepine Succinate | 69 | +89.2° (c 0.5, MeOH) | 319 (M + H)$^+$ |
| 202 | 2-F | (+)-7-Chloro-6-[1-(2-fluorophenyl)-ethylamino]-2,3,4,5-tetrahydro-1H-benzo[d]azepine Succinate | 62 | +105° (c 0.5, MeOH) | 319 (M + H)$^+$ |
| 203 | 4-CN | (+)-7-Chloro-6-[1-(4-cyanophenyl)-ethylamino]-2,3,4,5-tetrahydro-1H-benzo[d]azepine Succinate | 60 | +142.1° (c 0.5, MeOH) | 326 (M + H)$^+$ |
| 204 | 4-CN | (−)-7-Chloro-6-[1-(4-cyanophenyl)-ethylamino]-2,3,4,5-tetrahydro-1H-benzo[d]azepine Succinate | 52 | −149.3° (c 0.5, MeOH) | 326 (M + H)$^+$ |
| 205 | 2,3-diF | (+)-7-Chloro-6-[1-(2,3-difluorophenyl)-ethylamino]-2,3,4,5-tetrahydro-1H-benzo[d]azepine Succinate | 14 | +99.3° (c 0.5, MeOH) | 337 (M + H)$^+$ |
| 206 | 2,3-diF | (−)-7-Chloro-6-[1-(2,3-difluorophenyl)-ethylamino]-2,3,4,5-tetrahydro-1H-benzo[d]azepine Succinate | 80 | −107.9° (c 0.5, MeOH) | 337 (M + H)$^+$ |
| 207 | 2,4-diF | (+)-7-Chloro-6-[1-(2,4-difluorophenyl)-ethylamino]-2,3,4,5-tetrahydro-1H-benzo[d]azepine Succinate | 94 | +101.4° (c 0.5, MeOH) | 337 (M + H)$^+$ |
| 208 | 2,4-diF | (−)-7-Chloro-6-[1-(2,4-difluorophenyl)-ethylamino]-2,3,4,5-tetrahydro-1H-benzo[d]azepine Succinate | 96 | −107.9° (c 0.5, MeOH) | 337 (M + H)$^+$ |
| 209 | 3,5-diCF$_3$ | (−)-7-Chloro-6-[1-(3,5-bis-trifluoromethyl-phenyl)-ethylamino]-2,3,4,5-tetrahydro-1H-benzo[d]azepine Succinate | 99 | −93° (c 0.5, MeOH) | 437 (M + H)$^+$ |

EXAMPLE 210

(+)-7-Chloro-6-[(2-trifluoromethoxy-phenyl)-ethylamino]-2,3,4,5-tetrahydro-1H-benzo[d]azepine Oxalate

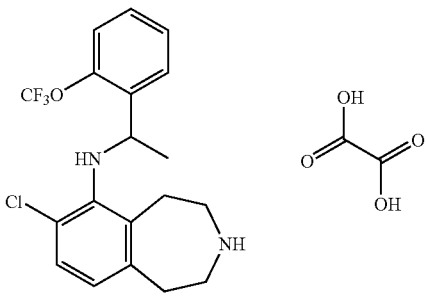

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (0.15 g, 0.35 mmol) with 1-(2-trifluoromethoxyphenyl)-ethylamine Isomer 2 at 90° C. for 15 h. Use a method similar to the General Procedure 1-2 and purify by reverse phase preparative HPLC to give the free base of the title compound. Use a method similar to the General Procedure 2-5 to give the title compound (27 mg, 16%). HPLC $t_R$=4.2 min (Chiralpak AD 4.6×150 mm, 3 micron column, 1.0 mL/min of 94.8/5/0.2 heptane/ethanol/dimethylethylamine isocratic; detector is at 225 nm); HRMS calcd for $C_{19}H_{20}ClF_3N_2O$ 385.1294, found 385.1285; $[\alpha]^{20}_D$ +95.4° (c 0.5, MeOH).

EXAMPLE 211

(±)-7-Chloro-6-[1-(3-fluorophenyl)-ethylamino]-2,3,4,5-tetrahydro-1H-benzo[d]azepine Succinate

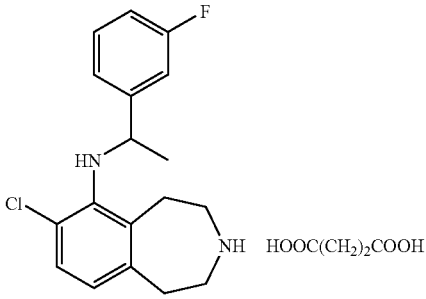

Add palladium(II) acetate (27 mg, 0.12 mmol), BINAP (146 mg, 0.24 mmol), cesium carbonate (270 mg, 0.8 mmol) and (±)-1-(3-fluorophenyl)-ethylamine (230 mg, 1.6 mmol) to a solution of 7-chloro-3-(2,2,2-trifluoroacetyl)-6-trifluoromethanesulfonyloxy-2,3,4,5-tetrahydro-1H-benzo[d]azepine (250 mg, 0.6 mmol) in toluene (9 mL). Degas the slurry and fill with nitrogen. Heat the mixture to 95° C. for 16 h. Add additional palladium(II) acetate (0.1 equiv.) and BINAP (0.2 equiv.) and continue heating the reaction for an additional 24 h. Cool the mixture, dilute with EtOAc (50 mL) then filter through Celite®. Concentrate the filtrate and purify by chromatography on silica gel eluting with hexane/EtOAc (9:1 to 1:1) followed by SCX chromatography to obtain (±)-7-chloro-6-[1-(3-fluorophenyl)-ethylamino]-3-(2,2,2-trifluoroacetyl)-2,3,4,5-tetrahydro-1H-benzo[d]azepine (138 mg, 56%). GC-MS m/z: 414 (M⁺).

Use a method similar to the General Procedure 1-3 to deprotect (±)-7-chloro-6-[1-(3-fluorophenyl)-ethylamino]-3-(2,2,2-trifluoroacetyl)-2,3,4,5-tetrahydro-1H-benzo[d]azepine (132 mg, 0.3 mmol) and purify by chromatography on silica gel eluting with DCM/2M ammonia in methanol (99:1 to 90:10) to give the free base of the title compound. Use a method similar to the General Procedure 2-1 to give the title compound (98 mg, 70%). MS (ES+) m/z: 319 (M+H)⁺.

EXAMPLE 212

(+)-7-Chloro-6-[1-(3-fluorophenyl)-ethylamino]-2,3,4,5-tetrahydro-1H-benzo[d]azepine Succinate

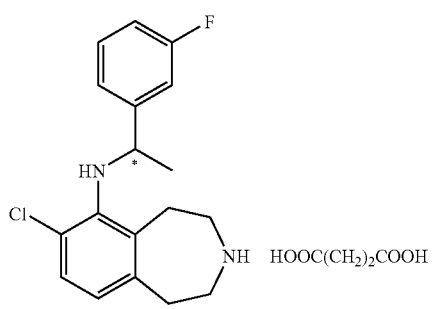

Separate the two enantiomers of (±)-7-chloro-6-[1-(3-fluorophenyl)-ethylamino]-2,3,4,5-tetrahydro-1H-benzo[d]azepine succinate by normal phase chromatography (Chiralpak AD 2×25 cm, elute with 95:5 heptane/isopropanol with 0.2% DMEA).

Use a method similar to the General Procedure 2-1 to obtain the title compound [23 mg, 30% recovery, 99% ee (Chiralpak AD, 4.6×250 mm, eluent: 95:5 heptane/isopropanol, with 0.2% DMEA, 1.0 mL/min)]. MS (ES+) m/z: 319 (M+H)⁺; $[\alpha]^{20}_D$ +64° (c 0.5, MeOH).

EXAMPLE 213

(−)-7-Chloro-6-[1-(3-fluorophenyl)-ethylamino]-2,3,4,5-tetrahydro-1H-benzo[d]azepine Succinate

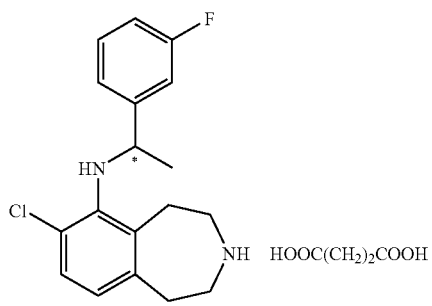

Add tris(dibenzylideneacetone)dipalladium(0) (3.4 g, 3.8 mmol), BINAP (4.7 g, 7.5 mmol), cesium carbonate (8.6 g, 26.3 mmol) and 1-(3-fluorophenyl)-ethylamine Isomer 2 (5.8 g, 41.3 mmol) to a solution of 7-chloro-3-(2,2,2-trifluoroacetyl)-6-trifluoromethanesulfonyloxy-2,3,4,5-tetrahydro-1H-benzo[d]azepine (8.0 g, 18.8 mmol) in toluene (225 mL). Degas the slurry and fill with nitrogen. Heat the mixture to 95° C. for 8 h. Add additional tris(dibenzylideneacetone)dipalladium(0) (0.1 equiv.), and BINAP (0.2 equiv.). Continue heating the reaction for an additional 16 h. Cool the mixture, dilute with EtOAc (200 mL) then filter thru Celite®. Concentrate in vacuo and purify by chromatography on silica gel eluting with hexane/EtOAc (9:1) followed by SCX chromatography to obtain 7-chloro-6-[1-(3-fluorophenyl)-ethylamino]-3-(2,2,2-trifluoroacetyl)-2,3,4,5-tetrahydro-1H-benzo[d]azepine (6.0 g, 78%). GC-MS m/z: 414 (M+).

Use a method similar to the General Procedure 1-3 to deprotect 7-chloro-6-[1-(3-fluorophenyl)-ethylamino]-3-(2,2,2-trifluoroacetyl)-2,3,4,5-tetrahydro-1H-benzo[d]azepine (6.0 g, 14.4 mmol). Purify by chromatography on silica gel eluting with DCM/2M ammonia in methanol (99:1 to 90:10) to give the free base of the title compound. Use a method similar to the General Procedure 2-1 and crystallize the solid from ethanol and methyl-t-butyl ether. Filter and dry the solid under vacuum at 60° C. overnight to obtain the title compound [5.3 g, 84% yield, 99% ee (Chiralpak AD, 4.6×250 mm, eluent: 95:5 heptane/EtOH, with 0.2% DMEA, 1.0 mL/min)]. MS (ES+) m/z: 319 (M+H)+; $[\alpha]^{20}_D$ −90.6° (c 0.5, MeOH).

EXAMPLE 214

(±)-7-Chloro-6-[1-(2-fluorophenyl)-ethylamino]-2,3,4,5-tetrahydro-1H-benzo[d]azepine Succinate

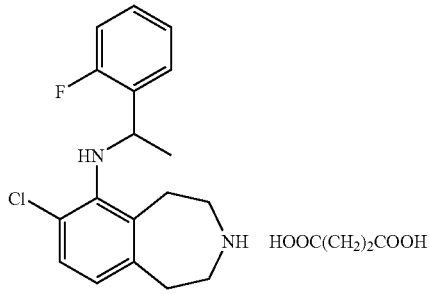

Use a method similar to the General Procedure 5-1 to couple 7-chloro-3-(2,2,2-trifluoroacetyl)-6-trifluoromethanesulfonyloxy-2,3,4,5-tetrahydro-1H-benzo[d]azepine (250 mg, 0.6 mmol) with (±)-1-(2-fluorophenyl)-ethylamine (206 mg, 1.5 mmol) in toluene (5 mL). Purify the residue by chromatography on silica gel eluting with hexane/EtOAc (9:1 to 1:1) followed by SCX chromatography [prewash column with methanol followed by DCM, load material dissolved in DCM, then elute with DCM/2M ammonia in methanol (1:1) and concentrate in vacuo] to obtain (±)-7-chloro-6-[1-(2-fluorophenyl)ethylamino]-3-(2,2,2-trifluoroacetyl)-2,3,4,5-tetrahydro-1H-benzo[d]azepine (86 mg, 35%). GC-MS m/z: 414 (M+).

Use a method similar to the General Procedure 1-3 to deprotect (±)-7-chloro-6-[1-(2-fluorophenyl)-ethylamino]-3-(2,2,2-trifluoroacetyl)-2,3,4,5-tetrahydro-1H-benzo[d]azepine (85 mg, 0.2 mmol) and purify by chromatography on silica gel eluting with DCM/2M ammonia in methanol (99:1 to 90:10) to give the free base of the title compound. Use a method similar to the General Procedure 2-1 to give the title compound (70 mg, 80%). MS (ES+) m/z: 319 (M+H)+.

Examples 215-216 may be prepared essentially as described in Example 214 by using 7-chloro-3-(2,2,2-trifluoroacetyl)-6-trifluoromethanesulfonyloxy-2,3,4,5-tetrahydro-1H-benzo[d]azepine and the appropriate amine. The yields for the Step 1 (General Procedure 5-1), optical rotation and MS (ES+) data are shown in the Table below.

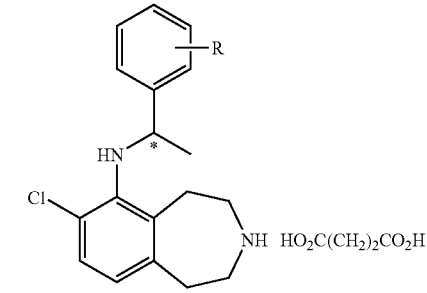

| Ex. | R | Compound | Yield (%) | $[\alpha]^{20}_D$ (c, solvent) | MS (ES+) m/z |
|---|---|---|---|---|---|
| 215 | 3-CN | (+)-7-Chloro-6-[1-(3-cyanophenyl)-ethylamino]-2,3,4,5-tetrahydro-1H-benzo[d]azepine Succinate | 58 | +100.7° (c 0.5, MeOH) | 326 (M + H)+ |
| 216 | 3-CN | (−)-7-Chloro-6-[1-(3-cyanophenyl)-ethylamino]-2,3,4,5-tetrahydro-1H-benzo[d]azepine Succinate | 90 | −109.7° (c 0.5, MeOH) | 326 (M + H)+ |

EXAMPLE 217

(S)-(−)-7-Chloro-6-(1-phenyl-ethylamino)-2,3,4,5-tetrahydro-1H-benzo[d]azepine Succinate

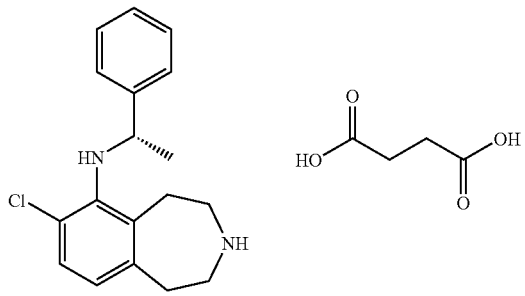

Add palladium(II) acetate (396 mg, 1.8 mmol), BINAP (2.2 g, 3.5 mmol), cesium carbonate (8.0 g, 24.6 mmol), and IS-(−)methylbenzylamine (6.4 g, 52.9 mmol) to a solution of 7-chloro-6-trifluoromethanesulfonyloxy-3-(2,2,2-trifluoroacetyl)-2,3,4,5-tetrahydro-1H-benzo[d]azepine (7.5 g, 17.6 mmol) in toluene (173 ml). Degas the slurry and fill with nitrogen. Heat the mixture to 95° C. for 16 h. GC/MS shows some staring material still present after 16 h, so add additional palladium(II) acetate (0.1 equiv.), BINAP, and IS-(−)-methylbenzylamine (1.0 equiv.). Continue heating the reaction for an additional 24 h. Cool the mixture, dilute with EtOAc (250 ml) then filter through Celite®. Concentrate in vacuo and purify by chromatography on silica gel eluting with hexane/EtOAc/methanol (84:15:1) followed by SCX chromatography to give (S)-7-chloro-6-(1-phenyl-ethylamino)-3-(2,2,2-trifluoroacetyl)-2,3,4,5-tetrahydro-1H-benzo[d]azepine (4.38 g, 63%). GC-MS m/z: 396 (M+).

Use a method similar to the General Procedure 1-1 to deprotect (S)-7-chloro-6-(1-phenyl-ethylamino)-3-(2,2,2-trifluoroacetyl)-2,3,4,5-tetrahydro-1H-benzo[d]azepine (4.3 g, 10.8 mmol). Purify by chromatography on silica gel eluting with DCM/2M ammonia in methanol (99/1 to 80/20) to give the free base of the title compound. Use a method similar to the General Procedure 2-1 and crystallize the solid from ethanol and methyl-t-butyl ether. Filter and dry the solid in a vacuum oven at 70° C. overnight to obtain the title compound (3.6 g, 80%). MS (ES+) m/z: 301 (M+H)+. $[\alpha]^{20}_D$ −95.6° (c 0.5, MeOH).

Examples 218-227 may be prepared essentially as described in Example 217 by using 7-chloro-3-(2,2,2-trifluoroacetyl)-6-trifluoromethanesulfonyloxy-2,3,4,5-tetrahydro-1H-benzo[d]azepine and the appropriate amine. The yields for the Step 1, optical rotation or enantiomeric excess (determined by chiral HPLC) and MS (ES+) data are shown in the Table below.

| Ex. | R | Compound | Yield (%) | $[\alpha]^{20}_D$ (c, solvent) or ee (%) | MS (ES+) m/z |
|---|---|---|---|---|---|
| 218 | H | (R)-(+)-7-Chloro-6-(1-phenyl-ethylamino)-2,3,4,5-tetrahydro-1H-benzo[d]azepine Succinate | 47 | +100.5° (c 0.5, MeOH) | 301 (M + H)+ |
| 219 | 4-CF3 | (+)-7-Chloro-6-[1-(4-trifluoromethyl-phenyl)-ethylamino]-2,3,4,5-tetrahydro-1H-benzo[d]azepine Succinate | 55 | +95.7° (c 0.5, MeOH) | 369 (M + H)+ |
| 220 | 3-CF3 | 7-Chloro-6-[1-(3-trifluoromethyl-phenyl)-ethylamino]-2,3,4,5-tetrahydro-1H-benzo[d]azepine Succinate, Isomer 1 | 90 | 95% ee | 369 (M + H)+ |
| 221 | 3,4-diF | 7-Chloro-6-[1-(3,4-trifluorophenyl)-ethylamino]-2,3,4,5-tetrahydro-1H-benzo[d]azepine Succinate, Isomer 1 | 28 | 94% ee | 337 (M + H)+ |
| 222 | 3,4-diF | (+)-7-Chloro-6-[1-(3,4-trifluorophenyl)-ethylamino]-2,3,4,5-tetrahydro-1H-benzo[d]azepine Succinate | 81 | +89.0° (c 0.5, MeOH) | 337 (M + H)+ |
| 223 | 3,4,5-triF | 7-Chloro-6-[1-(3,4,5-trifluorophenyl)-ethylamino]-2,3,4,5-tetrahydro-1H-benzo[d]azepine Succinate, Isomer 2 | 40 | ND | 355 (M + H)+ |

-continued

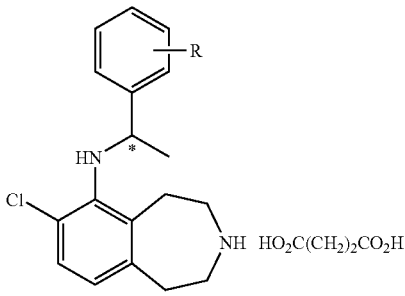

| Ex. | R | Compound | Yield (%) | $[\alpha]^{20}_D$ (c, solvent) or ee (%) | MS (ES+) m/z |
|---|---|---|---|---|---|
| 224 | 3-OCH$_3$ | 7-Chloro-6-[1-(3-methoxy-phenyl)-ethylamino]-2,3,4,5-tetrahydro-1H-benzo[d]azepine Hydrochloride, Isomer 1 | 53 | ND | 331 (M + H)$^+$ |
| 225 | 4-OCH$_3$ | 7-Chloro-6-[1-(4-methoxy-phenyl)-ethylamino]-2,3,4,5-tetrahydro-1H-benzo[d]azepine Hydrochloride, Isomer 1 | 53 | >99% ee | 331 (M + H)$^+$ |
| 226 | 4-OPh | 7-Chloro-6-[1-(4-phenoxyphenyl)-ethylamino]-2,3,4,5-tetrahydro-1H-benzo[d]azepine Succinate, Isomer 1 | 27 | ND | 393 (M + H)$^+$ |
| 227 | 4-OPh | 7-Chloro-6-[1-(4-phenoxyphenyl)-ethylamino]-2,3,4,5-tetrahydro-1H-benzo[d]azepine Succinate, Isomer 2 | 27 | ND | 393 (M + H)$^+$ |

ND = Not determined

EXAMPLE 228

(−)-7-Chloro-6-[1-(3-chloro-4-fluoro-phenyl)-ethylamino]-2,3,4,5-tetrahydro-1H-benzo[d]azepine Succinate

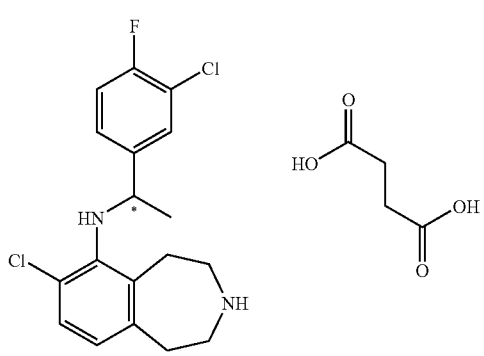

Use a method similar to the General Procedure 5-3 to couple 7-chloro-3-(2,2,2-trifluoroacetyl)-6-trifluoromethanesulfonyloxy-2,3,4,5-tetrahydro-1H-benzo[d]azepine (426 mg, 1.0 mmol) with 1-(3-chloro-4-fluoro-phenyl)-ethylamine Isomer 1 (226 mg, 1.3 mmol). Purify by chromatography on silica gel eluting with EtOAc/hexane (1:7) to give 7-chloro-6-[1-(3-chloro-4-fluoro-phenyl)-ethylamino]-3-(2,2,2-trifluoroacetyl)-2,3,4,5-tetrahydro-1H-benzo[d]azepine as a yellow oil (293 mg, 65%).

Use a method similar to the General Procedure 1-1 to deprotect 7-chloro-6-[1-(3-chloro-4-fluoro-phenyl)-ethylamino]-3-(2,2,2-trifluoroacetyl)-2,3,4,5-tetrahydro-1H-benzo[d]azepine Isomer 1 (293 mg, 0.65 mmol). Purify by chromatography on silica gel eluting with DCM/2M ammonia in methanol (94:6) to give the free base of the title compound as an oil (157 mg, 68%). MS (ES+) m/z: 353 (M+H)$^+$. Use a method similar to preparation E-1 to convert the free base to the title compound. $[\alpha]^{20}_D$ −115.9° (c 0.5, MeOH).

Examples 229-235 may be prepared essentially as described in Example 228 by using 7-chloro-3-(2,2,2-trifluoroacetyl)-6-trifluoromethanesulfonyloxy-2,3,4,5-tetrahydro-1H-benzo[d]azepine and the appropriate amine. The yields for the Step 1 (General Procedure 5-3), optical rotation and MS (ES+) data are shown in the Table below.

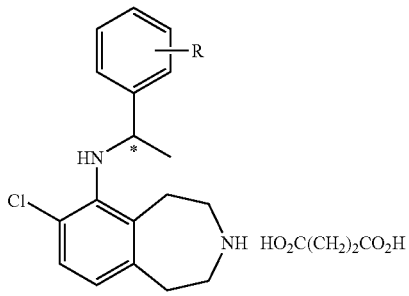

| Ex. | R | Compound | Yield (%) | $[\alpha]^{20}_D$ (c, solvent) | MS |
|---|---|---|---|---|---|
| 229 | 3-Cl | (+)-7-Chloro-6-[1-(3-chlorophenyl)-ethylamino]-2,3,4,5-tetrahydro-1H-benzo[d]azepine Succinate | 17 | +119.6° (c 0.5, CH$_3$OH) | 335 (M + H)$^+$ |
| 230 | 2-Cl | (+)-7-Chloro-6-[1-(2-chlorophenyl)-ethylamino]-2,3,4,5-tetrahydro-1H-benzo[d]azepine Succinate | 30 | +45.0° (c 0.5, CH$_3$OH) | 335 (M + H)$^+$ |
| 231 | 4-CH$_3$ | (R)-(+)-7-Chloro-6-(1-p-tolylethylamino)-2,3,4,5-tetrahydro-1H-benzo[d]azepine Succinate | 57 | +107° (c 0.5, MeOH) | 315 (M + H)$^+$ |
| 232 | 4-CH$_3$ | (S)-(−)-7-Chloro-6-(1-p-tolylethylamino)-2,3,4,5-tetrahydro-1H-benzo[d]azepine Succinate | 54 | −97.2° (c 0.5, MeOH) | 315 (M + H)$^+$ |
| 233 | 3-Cl, 4-F | (+)-7-Chloro-6-[1-(3-chloro-4-fluorophenyl)-ethylamino]-2,3,4,5-tetrahydro-1H-benzo[d]azepine Succinate | 84 | +115.0° (c 0.5, CH$_3$OH) | 353 (M + H)$^+$ |
| 234 | 3,5-diF | (−)-7-Chloro-6-[1-(3,5-difluorophenyl)-ethylamino]-2,3,4,5-tetrahydro-1H-benzo[d]azepine Succinate | 50 | −97.6° (c 0.5, MeOH) | 337 (M + H)$^+$ |
| 235 | 3,5-diF | (+)-7-Chloro-6-[1-(3,5-difluorophenyl)-ethylamino]-2,3,4,5-tetrahydro-1H-benzo[d]azepine Succinate | 41 | +91.0° (c 0.5, MeOH) | 337 (M + H)$^+$ |

EXAMPLE 236

(±)-7-Chloro-6-[1-(4-chlorophenyl)-ethylamino]-2,3,4,5-tetrahydro-1H-benzo[d]azepine Succinate

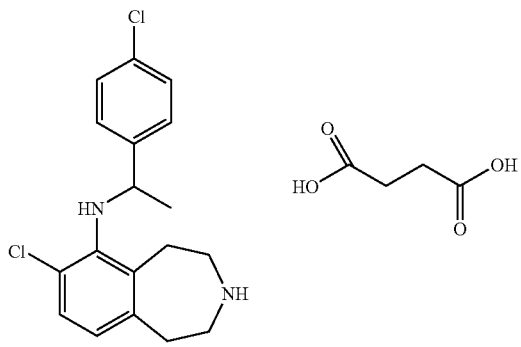

Use a method similar to the General Procedure 5-3 to couple 7-chloro-3-(2,2,2-trifluoroacetyl)-6-trifluoromethanesulfonyloxy-2,3,4,5-tetrahydro-1H-benzo[d]azepine (852 mg, 2.0 mmol) and (±)-4-chloro-(α-methyl)benzylamine (622 mg, 4.0 mmol). Purify by chromatography on silica gel eluting with hexane/EtOAc (1:0 and 9:1) to obtain (±)-7-chloro-6-[1-(4-chlorophenyl)-ethylamino]-3-(2,2,2-trifluoroacetyl)-2,3,4,5-tetrahydro-1H-benzo[d]azepine (326 mg, 38%). MS (ES+) m/z: 431 (M+H)$^+$.

Use a method similar to the General Procedure 1-1 to deprotect (±)-7-chloro-6-[1-(4-chlorophenyl)-ethylamino]-3-(2,2,2-trifluoroacetyl)-2,3,4,5-tetrahydro-1H-benzo[d]azepine. Purify by chromatography on silica gel eluting with DCM/2M ammonia in methanol (95:5) to give the free base of the title compound (61 mg, 100%). MS (ES+) m/z: 335 (M+H)$^+$. Use a method similar to the General Procedure 2-1 to obtain the title compound.

EXAMPLES 237 AND 238

(−)-7-Chloro-6-[1-(4-chlorophenyl)-ethylamino]-2,3,4,5-tetrahydro-1H-benzo[d]azepine Succinate and
(+)-7-Chloro-6-[1-(4-chlorophenyl)-ethylamino]-2,3,4,5-tetrahydro-1H-benzo[d]azepine Succinate

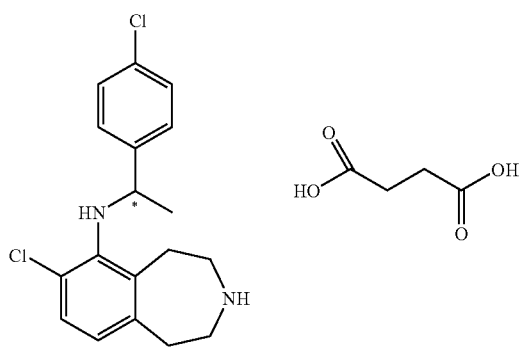

Submit (±)-7-chloro-6-[1-(4-chlorophenyl)-ethylamino]-3-(2,2,2-trifluoroacetyl)-2,3,4,5-tetrahydro-1H-benzo[d]azepine (326 mg, 0.76 mmol) to chiral chromatography (Chiralpak AD, 4.6×150 mm, eluting with heptane/ethanol (9:1) with 0.2% DMEA, 1 mL/min) to provide the two enantiomers: 7-chloro-6-[1-(4-chlorophenyl)ethylamino]-3-(2,2,2-trifluoroacetyl)-2,3,4,5-tetrahydro-1H-benzo[d]azepine Isomer 1 (102 mg, $t_R$=5.25 min) and 7-chloro-6-[1-(4-chlorophenyl)-ethylamino]-3-(2,2,2-trifluoroacetyl)-2,3,4,5-tetrahydro-1H-benzo[d]azepine Isomer 2 (110 mg, $t_R$=6.40 min).

Use a method similar to the General Procedure 1-1 to deprotect 7-chloro-6-[1-(4-chlorophenyl)-ethylamino]-3-(2,2,2-trifluoroacetyl)-2,3,4,5-tetrahydro-1H-benzo[d]azepine Isomer 1. Purify by chromatography on silica gel eluting with DCM/2M ammonia in methanol (95:5) to give 7-chloro-6-[1-(4-chlorophenyl)-ethylamino]-2,3,4,5-tetrahydro-1H-benzo[d]azepine Isomer 1 (Example 237, 82 mg, 100%). MS (ES+) m/z: 335 (M+H)$^+$. Use a method similar to the General Procedure 2-1 to obtain the title compound. $[\alpha]^{20}_D$ −127.7° (c 0.5, CH$_3$OH).

Use a method similar to the General Procedure 1-1 to deprotect 7-chloro-6-[1-(4-chlorophenyl)-ethylamino]-3-(2,2,2-trifluoroacetyl)-2,3,4,5-tetrahydro-1H-benzo[d]azepine Isomer 2. Purify by chromatography on silica gel eluting with DCM/2M ammonia in methanol (95:5) to give 7-chloro-6-[1-(4-chlorophenyl)-ethylamino]-2,3,4,5-tetrahydro-1H-benzo[d]azepine Isomer 2 (Example 238, 68 mg, 78%). MS (ES+) m/z: 335 (M+H)$^+$. Use a method similar to the General Procedure 2-1 to obtain the title compound. $[\alpha]^{20}_D$ +133.6° (c 0.5, CH$_3$OH).

EXAMPLES 239 AND 240

7-Chloro-6-[1-(2,5-difluorophenyl)-ethylamino]-2,3,4,5-tetrahydro-1H-benzo[d]azepine Succinate Isomer 1, and 7-chloro-6-[1-(2,5-difluorophenyl)-ethylamino]-2,3,4,5-tetrahydro-1H-benzo[d]azepine Succinate Isomer 2

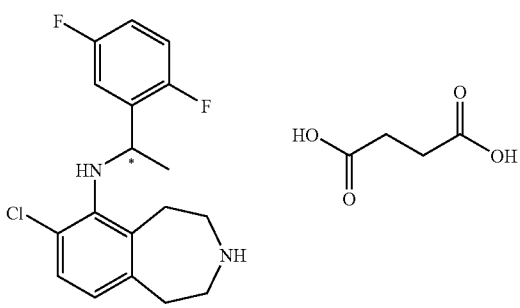

Use a method similar to the General Procedure 5-1 to couple 7-chloro-3-(2,2,2-trifluoroacetyl)-6-trifluoromethanesulfonyloxy-2,3,4,5-tetrahydro-1H-benzo[d]azepine (550 mg, 1.27 mmol) and crude (±)-α-methyl-(2',5'-difluoro)benzylamine (400 mg).

Separate the two enantiomers by chiral chromatography (eluent: 75:20:5 heptane/isopropanol/methanol, 4.6×250 mm Chiralpak AD, 1 mL/min, uv 260 nm) to obtain 7-chloro-6-[1-(2,5-difluorophenyl)-ethylamino]-3-(2,2,2-trifluoroacetyl)-2,3,4,5-tetrahydro-1H-benzo[d]azepine Isomer 1 [150 mg, 29%; chiral HPLC: $t_R$=4.5 min; MS (ES+) m/z: 433 (M+H)$^+$] and 7-chloro-6-[1-(2,5-difluorophenyl)-ethylamino]-3-(2,2,2-trifluoroacetyl)-2,3,4,5-tetrahydro-1H-benzo[d]azepine Isomer 2 [130 mg, 25%; chiral HPLC: $t_R$=5.5 min; MS (ES+) m/z: 433 (M+H)$^+$], both as opaque oils which solidify upon standing to off-white waxy solids.

Use a method similar to the General Procedure 1-1 to deprotect 7-chloro-6-[1-(2,5-difluorophenyl)-ethylamino]-3-(2,2,2-trifluoroacetyl)-2,3,4,5-tetrahydro-1H-benzo[d]azepine Isomer 1 (140 mg, 0.32 mmol). Purify by SCX chromatography to give 7-chloro-6-[1-(2,5-difluorophenyl)-ethylamino]-2,3,4,5-tetrahydro-1H-benzo[d]azepine Isomer 1 (102 mg, 95%) as a yellow oil. Use a method similar to the General Procedure 2-1 to obtain the Isomer 1 of the title compound (130 mg, 95%) as an off-white solid. MS (ES+) m/z: 337 (+H)$^+$.

Use a method similar to the General Procedure 1-1 to deprotect 7-chloro-6-[1-(2,5-difluorophenyl)-ethylamino]-3-(2,2,2-trifluoroacetyl)-2,3,4,5-tetrahydro-1H-benzo[d]azepine Isomer 2 (125 mg, 0.29 mmol). Purify by SCX chromatography to give 7-chloro-6-[1-(2,5-difluorophenyl)-ethylamino]-2,3,4,5-tetrahydro-1H-benzo[d]azepine Isomer 2 (87.7 mg, 90%) as a yellow oil. Use a method similar to the General Procedure 2-1 to obtain the Isomer 2 of the title compound (117 mg, 99%) as an off-white solid. MS (ES+) m/z: 337 (M+H)$^+$.

EXAMPLE 241

(−)-7-Chloro-6-[1-(3,5-difluoro-4-methoxy-phenyl)-ethylamino]-2,3,4,5-tetrahydro-1H-benzo[d]azepine Succinate

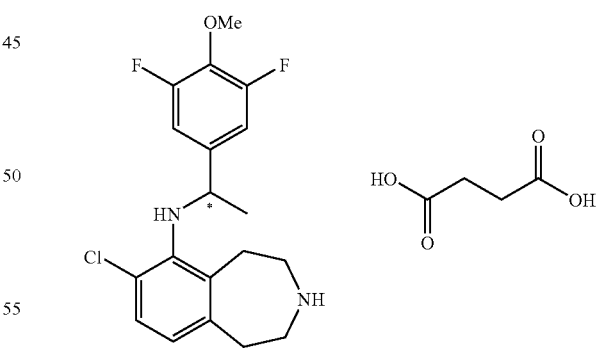

Use a method similar to the General Procedure 5-1 to couple 7-chloro-3-(2,2,2-trifluoroacetyl)-6-trifluoromethanesulfonyloxy-2,3,4,5-tetrahydro-1H-benzo[d]azepine (300 mg, 0.7 mmol) and crude α-methyl-(3',5'-difluoro-4'-methoxy)benzylamine (380 mg). Purify by chromatography on silica gel eluting with hexane/EtOAc (95:5) followed by chiral chromatography [heptane/isopropanol/ dimethylethylamine (90:10:0.2), 4.6×250 mm Chiralpak AD, 1 mL/min, uv 250 nm] to give 7-chloro-6-[1-(3,5-difluoro-4-methoxy-phenyl)-ethylamino]-3-(2,2,2-trifluoroacetyl)-2,3,4,5-tetrahydro-1H-benzo[d]azepine Isomer 1 [59 mg, 18% yield, 99% ee, chiral HPLC: $t_R$=6.0 min; MS (ES−) m/z: 461 (M−H)$^−$] and 7-chloro-6-[1-(3,5-difluoro-4-methoxy-phenyl)-ethylamino]-3-(2,2,2-trifluoroacetyl)-2,3,4,5-tetrahydro-1H-benzo[d]azepine Isomer 2 [50 mg, 15% yield, 99% ee, chiral HPLC: $t_R$=7.7 min; MS (ES−) m/z: 461 (M−H)$^−$]. Use a method similar to the General Procedure 1-1 to deprotect 7-chloro-6-[1-(3,5-difluoro-4-methoxy-phenyl)-ethylamino]-3-(2,2,2-trifluoroacetyl)-2,3,4,5-tetrahydro-1H-benzo[d]azepine Isomer 2 (50 mg, 0.14 mmol). Purify by SCX chromatography to give 7-chloro-6-[1-(3,5-difluoro-4-methoxy-phenyl)-ethylamino]-2,3,4,5-tetrahydro-1H-benzo[d]azepine Isomer 2 (35 mg, 70%) as a yellow oil. Use a method similar to the General Procedure 2-1, using 7-chloro-6-[1-(3,5-difluoro-4-methoxy-phenyl)ethylamino]-2,3,4,5-tetrahydro-1H-benzo[d]azepine Isomer 2 (35 mg, 0.10 mmol), to give the title compound (44 mg, 97%) as an off-white powder. MS (ES+) m/z: 367 (+H)$^+$; $[\alpha]^{20}_D$ −107.0° (c 0.5, $CH_3OH$).

EXAMPLE 242

(+)-7-Chloro-6-[(2-methylphenyl)-ethylamino]-2,3,4,5-tetrahydro-1H-benzo[d]azepine Oxalate

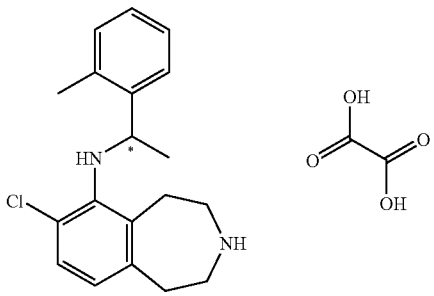

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (0.15 g, 0.35 mmol) with (R)-1-(2-methyl)-ethylamine (162 mg, 1.2 mmol) at 90° C. for 17 h. Deprotect according to the General Procedure 1-2. Purify by reverse phase preparative HPLC and form the oxalate salt according to the General Procedure 2-5 to give the title compound (72 mg, 51%). HPLC $t_R$=4.0 min (Chiralpak AD 4.6×150 mm, 3 micron column, 1.0 mL/min of 89.8:10:0.2 heptane/isopropanol/DMEA, isocratic; detector is at 225 nm); HRMS calcd for $C_{19}H_{23}ClN_2$ 315.1628, found 315.1623. $[\alpha]^{20}_D$ +67.2° (c 0.5, $CH_3OH$).

EXAMPLE 243

(+)-7-Chloro-6-(indan-1-ylamino)-2,3,4,5-tetrahydro-1H-benzo[d]azepine Succinate

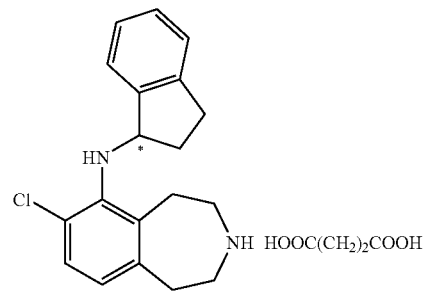

Use a method similar to the General Procedure 5-1 to couple 7-chloro-3-(2,2,2-trifluoroacetyl)-6-trifluoromethanesulfonyloxy-2,3,4,5-tetrahydro-1H-benzo[d]azepine (200 mg, 0.5 mmol) with (R)-1-aminoindan (188 mg, 1.4 mmol) in toluene (5 mL). Purify by chromatography on silica gel eluting with hexane/EtOAc (9:1 to 1:1) followed by SCX chromatography [pre-wash column with methanol followed by DCM, load material dissolved in DCM, then elute with DCM/2M ammonia in methanol (1:1) and concentrate in vacuo] to give 7-chloro-6-(indan-1-ylamino)-3-(2,2,2-trifluoroacetyl)-2,3,4,5-tetrahydro-1H-benzo[d]azepine (129 mg, 67%). GC-MS m/z: 408 (M$^+$).

Use a method similar to the General Procedure 1-1 to deprotect 7-chloro-6-(indan-1-ylamino)-3-(2,2,2-trifluoroacetyl)-2,3,4,5-tetrahydro-1H-benzo[d]azepine (125 mg, 0.3 mmol) and purify by chromatography on silica gel eluting with DCM/2M ammonia in methanol (99:1 to 80:20) to give the free base of the title compound. Use a method similar to the General Procedure 2-1 to give the title compound (104 mg, 78%). MS (ES+) m/z: 313 (M+H)$^+$. $[\alpha]^{20}_D$ +73.9° (c 0.5, MeOH).

EXAMPLE 244

(+)-7-Chloro-6-(5-fluoro-indan-1-ylamino)-2,3,4,5-tetrahydro-1H-benzo[d]azepine Succinate

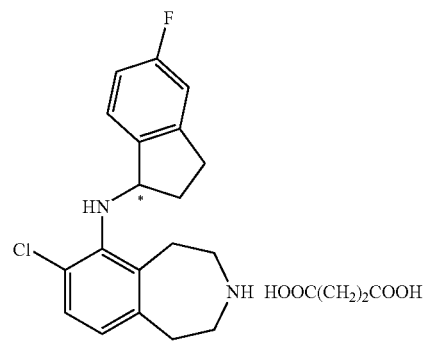

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (210 mg, 0.5 mmol) with 5-fluoro-indan-ylamine Isomer 1 (161 mg, 1.1 mmol) in toluene (10 mL). Purify by chromatography on silica gel eluting with hexane/EtOAc (9:1 to 1:1) followed by SCX chromatography to obtain 7-chloro-6-[1-(3,5-bis-trifluoromethyl-phenyl)-ethylamino]-3-(2,2,2-trifluoroacetyl)-2,3,4,5-tetrahydro-1H-benzo[d]azepine Isomer 1 (616 mg, 99%).

Use a method similar to the General Procedure 1-3 to deprotect 7-chloro-6-(5-fluoro-indan-ylamine)-3-(2,2,2-trifluoroacetyl)-2,3,4,5-tetrahydro-1H-benzo[d]azepine Isomer 1 (200 mg, 0.5 mmol). Purify by chromatography on silica gel eluting with DCM/2M ammonia in methanol (99/1 to 90/10) to give the free base of the title compound. Use Preparation E-1 to give the title compound (140 mg, 66%). MS (ES+) m/z: 331 (M+H)$^+$. $[\alpha]^{20}_D$ +80.0° (C, 0.5, MeOH)

EXAMPLE 245

($\pm$)-7-Chloro-6-(2,3-dihydro-benzofuran-3-ylamino)-2,3,4,5-tetrahydro-1H-benzo[d]azepine Succinate

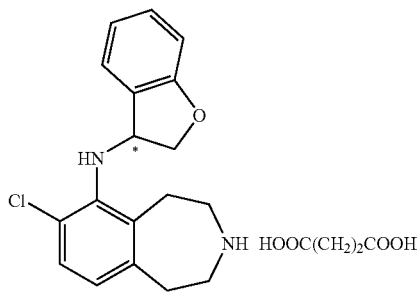

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (0.15 g, 0.35 mmol) with 2,3-dihydro-benzofuran-3-ylamine (prepared as described in WO 0069816) (0.14 g, 1.1 mmol) at 90° C. for 18 h.

Use a method similar to the General Procedure 1-2 and purify by reverse phase preparative HPLC [Zorbax SB-Phenyl 4.6×150 mm, 5 micron column, 1 mL/min of 0.1% TFA in water/ACN (9:1 to 1:9) over 30 min, detector at 230 and 254 nm n].

Use a method similar to the General Procedure 2-1 to give the title compound (4.3 mg, 3%). HRMS calcd for $C_{18}H_{19}ClN_2O$ 315.1264, found 315.1256.

EXAMPLE 246

7-Chloro-6-(indan-2-yl-amino)-2,3,4,5-tetrahydro-1H-benzo[d]azepine Succinate

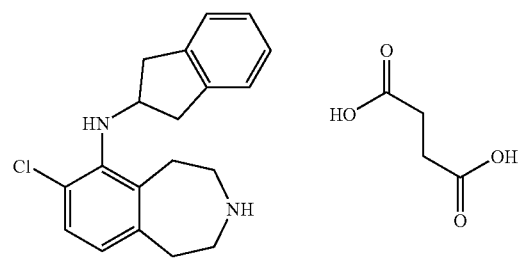

Use a method similar to the General Procedure 5-3, using 7-chloro-3-(2,2,2-trifluoroacetyl)-6-trifluoromethanesulfonyloxy-2,3,4,5-tetrahydro-1H-benzo[d]azepine (426 mg, 1.0 mmol) and 2-aminoindane (400 mg, 3.0 mmol), to give 7-chloro-6-(indan-2-yl-amino)-3-(2,2,2-trifluoroacetyl)-2,3,4,5-tetrahydro-1H-benzo[d]azepine as a slightly yellow oil (354 mg, 86%). MS (ES+) m/z: 409 (M+H)$^+$.

Using a method similar to the General Procedure 1-1, deprotect 7-chloro-6-(indan-2-yl-amino)-3-(2,2,2-trifluoroacetyl)-2,3,4,5-tetrahydro-1H-benzo[d]azepine (354 mg, 0.87 mmol) to obtain 7-chloro-6-(indan-2-yl-amino)-2,3,4,5-tetrahydro-1H-benzo[d]azepine as a pale-yellow oil (166 mg, 61%). MS (ES+) m/z: 313 (M+H)$^+$. Use a method similar to the General Procedure 2-1 to give the title compound.

EXAMPLE 247

(−)-7-Chloro-6-[(N-methyl)-1-phenylethylamino]-2,3,4,5-tetrahydro-1H-benzo[d]azepine Succinate

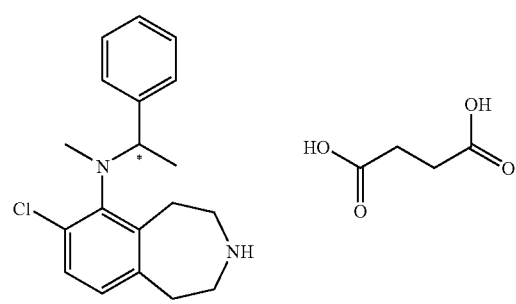

Dissolve (−)-7-chloro-6-(1-phenyl-ethylamine)-3-(2,2,2-trifluoroacetyl)-2,3,4,5-tetrahydro-1H-benzo[d]azepine (192 mg) in DCE (5 mL) and add acetic acid (0.33 mL, 5.8 mmol), formaldehyde (37% solution; 0.5 mL) and sodium triacetoxyborohydride (570 mg, 2.7 mol) and stir the reaction at ambient temperature for 16 h. Dilute the reaction with DCM and wash with 1N aqueous NaOH. Dry the organic layers over $Na_2SO_4$, filter and concentrate. Purify by chromatography on silica gel eluting with hexane/EtOAc (20:1, 10:1 and 5:1) to give (−)-7-chloro-6-(methyl-1-phenylethylamino)-3-(2,2,2-trifluoroacetyl)-2,3,4,5-tetrahydro-1H-benzo[d]azepine as an oil.

Use a method similar to the General Procedure 1-3 to deprotect (−)-7-chloro-6-(methyl-1-phenylethylamino)-3-(2,2,2-trifluoroacetyl)-2,3,4,5-tetrahydro-1H-benzo[d]azepine and purify by SCX chromatography to give the free base of the title compound. Use a method similar to the General Procedure 2-1 to give the title compound as a white solid (176 mg, 85%). MS (ES+) m/z: 315 (M+H)$^+$. $[\alpha]^{20}_D$ −5.4° (c 0.5, $CH_3OH$).

EXAMPLE 248

7-Chloro-6-[(N-methyl)-benzylamino]-2,3,4,5-tetrahydro-1H-benzo[d]azepine Succinate

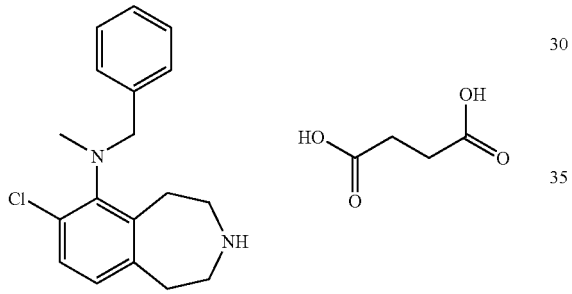

Dissolve 6-benzylamino-7-chloro-2,3,4,5-tetrahydro-1H-benzo[d]azepine (330 mg, 0.86 mmol) in DCM (3 mL) and add triethylamine (250 □L, 1.8 mmol) followed by di-tert-butyl-dicarbonate (260 mg, 1.2 mmol). Stir at ambient temperature for 1 h. Pour the mixture into water (250 mL), extract with DCM (3×25 mL) and concentrate in vacuo to give, after chromatography on silica gel eluting with hexane/EtOAc (9:1), 6-benzylamino-3-tert-butoxycarbonyl-7-chloro-2,3,4,5-tetrahydro-1H-benzo[d]azepine as a colorless oil (260 mg, 78%).

Dissolve 6-benzylamino-3-tert-butoxycarbonyl-7-chloro-2,3,4,5-tetrahydro-1H-benzo[d]azepine (50 mg, 0.11 mmol) in acetonitrile (3 mL) and add a solution of formaldehyde in water (37%, 85 μL, 0.97 mmol) followed by sodium cyanoborohydride (16.5 mg, 0.26 mmol). Heat the solution to reflux 1 h, cool to ambient temperature, add glacial acetic acid (0.25 mL) and stir 72 h. Pour the mixture into water (100 mL) containing methanol (1 mL), extract with DCM (3×20 mL), wash the organic extracts with brine, dry over $MgSO_4$, filter and concentrate in vacuo. Dissolve the resulting residue in DCM (5 mL), and add trifluoroacetic acid (2 mL). Stir for 2 h at ambient temperature and evaporate the solvent. Purify by SCX chromatography. Use a method similar to the General Procedure 2-1 to give the title compound (45 mg, 95%). MS (ES+) m/z: 301 (M+H)$^+$.

EXAMPLE 249

7-Chloro-6-[(N-methyl)-3-fluorobenzylamino]-2,3,4,5-tetrahydro-1H-benzo[d]azepine Succinate

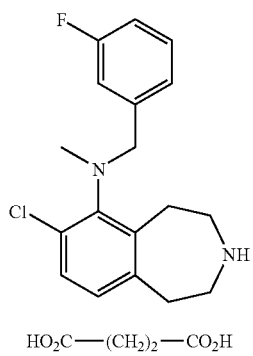

The title compound may be prepared essentially as described in Example 248 by using 7-chloro-6-(3-fluorobenzylamino)-2,3,4,5-tetrahydro-1H-benzo[d]azepine (85% yield and MS (ES+) an/z 319 (M+H)$^+$).

EXAMPLE 250

7-Chloro-6-(1-phenyl-cyclopropylamino)-2,3,4,5-tetrahydro-1H-benzo[d]azepine Succinate

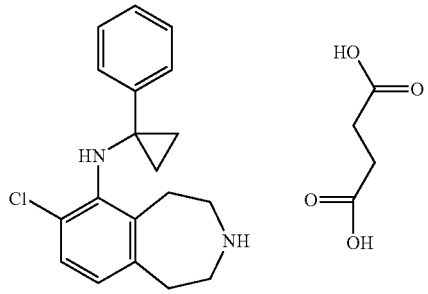

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (0.2 g, 0.47 mmol) with 1-phenyl-cyclopropylamine (0.2 g, 1.41 mmol) using tris(dibenzylideneacetone)dipalladium(0) (43.0 mg, 0.05 mmol), BINAP (0.1 g, 0.15 mmol) and cesium carbonate (0.3 g, 0.97 mmol) at 90° C. for 17 h to obtain 7-chloro-6-(1-phenyl-cyclopropylamino)-3-(2,2,2-trifluoroacetyl)-2,3,4,5-tetrahydro-1H-benzo[d]azepine as a colorless oil.

Use a method similar to the General Procedure 1-1 to obtain the free base of the title compound as a yellow oil. Use a method similar to the General Procedure 2-1 to obtain the title compound as a white solid (85 mg, 33%).

Example 251 may be prepared essentially as described in Example 250 by using 7-chloro-3-(2,2,2-trifluoroacetyl)-6-trifluoromethanesulfonyloxy-2,3,4,5-tetrahydro-1H-benzo[d]azepine and 1-(2,4-dichlorophenyl)-cyclopropylamine. The overall yield (3 steps) is shown in the Table below.

| Ex. | Structure | Compound | Yield (%) |
|---|---|---|---|
| 251 | 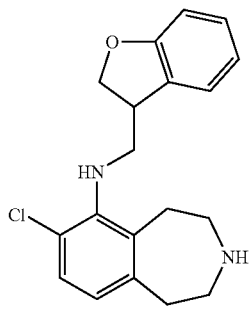 | 7-Chloro-6-[1-(2,4-dichlorophenyl)-cyclopropylamino]-2,3,4,5-tetrahydro-1H-benzo[d]azepine Succinate | 19 |

EXAMPLE 252

(±)-7-Chloro-6-(2,3-dihydro-benzofuran-3-yl-methylamino)-2,3,4,5-tetrahydro-1H-benzo[d]azepine Succinate Use a method similar to the General Procedure 5-2 to couple 2,3-dihydro-benzofuran-3-yl-methylamine (prepared as described in WO 0069816) (0.14 g, 1.1 mmol) with 7-chloro-3-(2,2,2-trifluoroacetyl)-6-trifluoromethanesulfonyloxy-2,3,4,5-tetrahydro-1H-benzo[d]azepine (0.15 g, 0.35 mmol) at 90° C. for 18 h.

Use a method similar to the General Procedure 1-2 to deprotect 7-chloro-3-(2,2,2-trifluoroacetyl)-6-trifluoromethanesulfonyloxy-2,3,4,5-tetrahydro-1H-benzo[d]azepine. Purify by reverse phase preparative HPLC [Zorbax SB-Phenyl 4.6×150 mm 5 micron column, 1 mL/min of 1% TFA in water/ACN (9:1 to 1:9) over 30 min, detector at 230 and 254 nm]. Use a method similar to the General Procedure 2-1 to give the title compound (4.3 mg, 3%).

EXAMPLE 253

7-Chloro-6-[(2,3-dihydrobenzo[b]-5-yl)-methylamino]-2,3,4,5-tetrahydro-1H-benzo[d]azepine Succinate

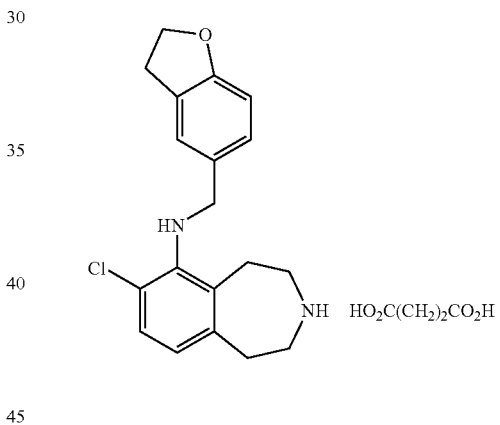

Suspend commercially available 2,3-dihydrobenzo[b]furan-5-yl-methylamine hydrochloride (1.0 g, 5.4 mmol) in DCM (100 mL). Add 1N aqueous NaOH (15 mL) and stir until all solids dissolve. Add two spatulas of NaCl. Stir the mixture and extract twice with DCM. Combine the organic layers, dry over $Na_2SO_4$, and concentrate in vacuo to obtain 2,3-dihydrobenzo[b]furan-5-yl-methylamine (650 mg, 81%). MS (ES+) m/z: 133 $M+H–NH_3)^+$.

Use a method similar to the General Procedure 5-3 to couple 7-chloro-3-(2,2,2-trifluoroacetyl)-6-trifluoromethanesulfonyloxy-2,3,4,5-tetrahydro-1H-benzo[d]azepine (426 mg, 1.0 mmol) with 5-aminomethyl-2,3-dihydrobenzo[b]furane (223 mg, 1.5 mmol). Purify by chromatography on silica gel eluting with hexane/EtOAc (1:0 and 9:1) to obtain 7-chloro-6-[(2,3-dihydrobenzo[b]furan-5-yl)-methylamino]-3-(2,2,2-trifluoroacetyl)-2,3,4,5-tetrahydro-1H-benzo[d]azepine (244 mg, 58%). MS (ES+) m/z: 425 $(M+H)^+$.

Use a method similar to the General Procedure 1-1 to deprotect 7-chloro-6-[(2,3-dihydrobenzo[b]furan-5-yl)-methylamino]-3-(2,2,2-trifluoroacetyl)-2,3,4,5-tetrahydro-1H-benzo[d]azepine. Purify by chromatography on silica gel eluting with DCM/2M ammonia in methanol (95:5) to give the free base of the title compound (105 mg, 32%). MS (ES+) m/z: 329 (M+H)$^+$. Use a method similar to the General Procedure 2-1 to obtain the title compound.

Examples 254-260 may be prepared essentially as described in Example 253 by using 7-chloro-3-(2,2,2-trifluoroacetyl)-6-trifluoromethanesulfonyloxy-2,3,4,5-tetrahydro-1H-benzo[d]azepine and the appropriate amine. The yields for the Step 1 (General Procedure 5-3) and MS (ES+) data are shown in the Table below.

| Ex. | NH—R | Compound | Yield (%) | MS (ES+) m/z |
|---|---|---|---|---|
| 254 | | (±)-7-Chloro-6-[C-(3-methyl-2,3-dihydro-benzofuran-5-yl)-methylamino]-2,3,4,5-tetrahydro-1H-benzo[d]azepine Succinate | 50 | 343 (M + H)$^+$ |
| 255 | | (±)-7-Chloro-6-[C-(3-methyl-2,3-dihydro-benzofuran-6-yl)-methylamino]-2,3,4,5-tetrahydro-1H-benzo[d]azepine Succinate | 66 | 343 (M + H)$^+$ |
| 256 | | 7-Chloro-6-[C-(3,3-dimethyl-2,3-dihydro-benzofuran-6-yl)-methylamino]-2,3,4,5-tetrahydro-1H-benzo[d]azepine Succinate | 57 | 357 (M + H)$^+$ |
| 257 | | 7-Chloro-6-[C-(3,3-dimethyl-2,3-dihydro-benzofuran-5-yl)-methylamino]-2,3,4,5-tetrahydro-1H-benzo[d]azepine Succinate | 64 | 357 (M + H)$^+$ |
| 258 | | 7-Chloro-6-[C-(2,2-dimethyl-3-oxo-2,3-dihydro-benzofuran-5-yl)-methylamino]-2,3,4,5-tetrahydro-1H-benzo[d]azepine Succinate | 47 | 371 (M + H)$^+$ |
| 259 | | 7-Chloro-6-[C-(2,2-dimethyl-3-oxo-2,3-dihydro-benzofuran-6-yl)-methylamino]-2,3,4,5-tetrahydro-1H-benzo[d]azepine Succinate | 67 | 371 (M + H)$^+$ |

-continued

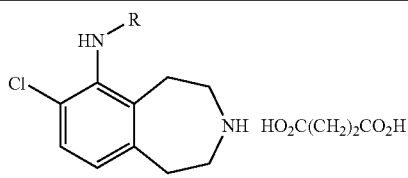

| Ex. | NH—R | Compound | Yield (%) | MS (ES+) m/z |
|---|---|---|---|---|
| 260 | 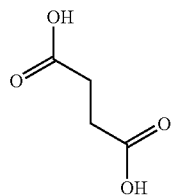 | 7-Chloro-6-[(2,2-dimethyl-chroman-6-yl)-methylamino]-2,3,4,5-tetrahydro-1H-benzo[d]azepine Succinate | 24 | 371 (M + H)+ |

EXAMPLE 261

7-Chloro-6-(naphthalen-2-yl-methylamino)-2,3,4,5-tetrahydro-1H-benzo[d]azepine Succinate

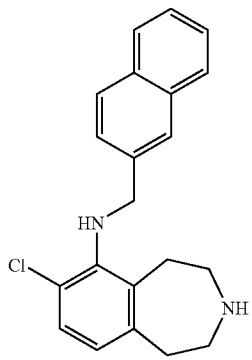

Use a method similar to the General Procedure 5-2 to couple 2-aminomethylnaphthalene (prepared as described in WO 9509159) (0.17 g, 1.1 mmol) with 7-chloro-3-(2,2,2-trifluoroacetyl)-6-trifluoromethanesulfonyloxy-2,3,4,5-tetrahydro-1H-benzo[d]azepine-(0.15 g, 0.35 mmol) at 90° C. for 18 h.

Use a method similar to the General Procedure 1-2 to give the free base of the title compound. HRMS calcd for $C_{21}H_{21}ClN_2$ 337.1471, found 337.1461. Use a method similar to the General Procedure 2-1 to give the title compound (104 mg, 66% overall).

EXAMPLE 262

7-Chloro-6-[(quinolin-6-yl-methyl)-amino]-2,3,4,5-tetrahydro-1H-benzo[d]azepine Hydrochloride

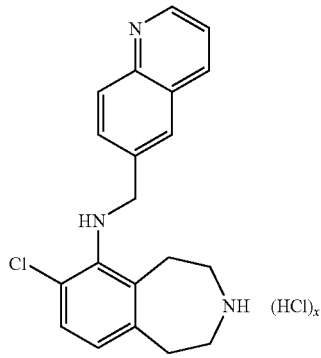

Use a method similar to the General Procedure 5-2, using 7-chloro-3-(2,2,2-trifluoroacetyl)-6-trifluoromethanesulfonyloxy-2,3,4,5-tetrahydro-1H-benzo[d]azepine (0.2 g; 0.35 mmol) and 6-aminomethyl-quinoline (0.2 g, 1.06 mmol) with tris(dibenzylideneacetone)dipalladium(0) (32.0 mg, 0.04 mmol), BINAP (44.0 mg, 0.07 mmol) and cesium carbonate (0.2 g, 0.71 mmol) at 90° C. for 17 h, to obtain 7-chloro-6-[(quinolin-6-yl-methyl)-amino]-3-(2,2,2-trifluoroacetyl)-2,3,4,5-tetrahydro-1H-benzo[d]azepine as a colorless oil.

Use a method similar to the General Procedure 1-1 to obtain the free base of the title compound as a yellow oil. Use a method similar to the General Procedure 2-2 to form the hydrochloride salt and purify by reverse phase preparative HPLC [Zorbax SB-Phenyl 21.2×250 mm, 5 micron column, 22 mL/min of 0.1% HCl in water/acetonitrile (9:1 to 1:1) over 30 min. detector at 230 nm) to obtain the title compound as a white solid (50 mg, 56% overall). MS (ES+) m/z: 338 (M+H)+.

Examples 263-266 may be prepared essentially as described in Example 262 by using 7-chloro-3-(2,2,2-trifluoroacetyl)-6-trifluoromethanesulfonyloxy-2,3,4,5-tetrahydro-1H-benzo[d]azepine and the appropriate amine. Overall yields and MS (ES+) data are shown in the Table below.

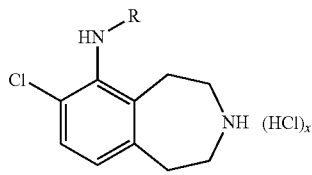

| Ex. | NH—R | Compound | Yield (%) | MS (ES+) m/z |
|---|---|---|---|---|
| 263 | isoquinolin-3-yl-methyl-NH | 7-Chloro-6-[(isoquinolin-3-yl-methyl)-amino]-2,3,4,5-tetrahydro-1H-benzo[d]azepine Hydrochloride | 63 | 338 (M + H)$^+$ |
| 264 | quinolin-3-yl-methyl-NH | 7-Chloro-6-[(quinolin-3-yl-methyl)-amino]-2,3,4,5-tetrahydro-1H-benzo[d]azepine Hydrochloride | 35 | 338 (M + H)$^+$ |
| 265 | quinolin-2-yl-methyl-NH | 7-Chloro-6-[(quinolin-2-yl-methyl)-amino]-2,3,4,5-tetrahydro-1H-benzo[d]azepine Hydrochloride | 20 | 338 (M + H)$^+$ |
| 266 | 2-phenyl-benzoxazol-6-yl-methyl-NH | 7-Chloro-6-[(2-phenyl-benzoxazol-6-yl-methyl)-amino]-2,3,4,5-tetrahydro-1H-benzo[d]azepine Hydrochloride | 15 | 404 (M + H)$^+$ |

EXAMPLE 267

6-[(Benzofuran-6-ylmethyl)-amino]-7-chloro-2,3,4,5-tetrahydro-1H-benzo[d]azepine Succinate

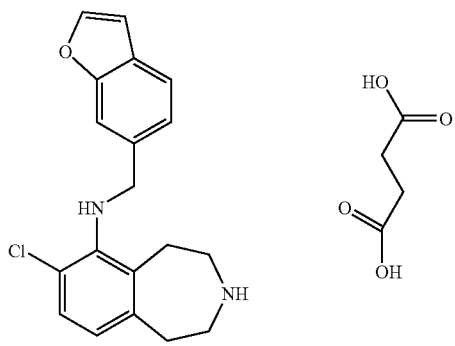

Use a method similar to the General Procedure 5-2, using 7-chloro-3-(2,2,2-trifluoroacetyl)-6-trifluoromethanesulfonyloxy-2,3,4,5-tetrahydro-1H-benzo[d]azepine (0.2 g, 0.35 mmol) and 6-aminomethyl-benzofuran (0.2 g, 1.06 mmol) with tris(dibenzylideneacetone)dipalladium (0) (32.0 mg, 0.04 mmol), BINAP (88.0 mg, 0.11 mmol) and cesium carbonate (0.2 g, 0.71 mmol) at 90° C. for 17 h, to obtain 6-[(benzofuran-6-yl-methyl)-amino]-7-chloro-3-(2,2,2-trifluoroacetyl)-2,3,4,5-tetrahydro-1H-benzo[d]azepine as a colorless oil.

Use a method similar to the General Procedure 1-1 to obtain the free base of the title compound as a yellow oil. Use a method similar to the General Procedure 2-1 to obtain the title compound as a white solid (72 mg, 46% overall). MS (ES+) m/z: 327 (M+H)$^+$.

Examples 268-271 may be prepared essentially as described in Example 267 by using 7-chloro-3-(2,2,2-trifluoroacetyl)-6-trifluoromethanesulfonyloxy-2,3,4,5-tetrahydro-1H-benzo[d]azepine and the appropriate amine. Overall yields and MS (ES+) data are shown in the Table below.

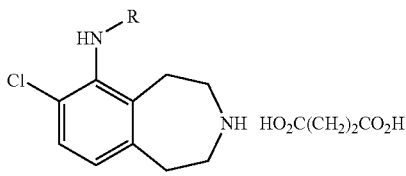

| Ex. | NH—R | Compound | Yield (%) | MS (ES+) m/z |
|---|---|---|---|---|
| 268 | | 6-[(Benzo[1,3]dioxol-4-yl-methyl)-amino]-7-chloro-2,3,4,5-tetrahydro-1H-benzo[d]azepine Succinate | 54 | 331 (M + H)+ |
| 269 | | 6-[(Benzo[1,3]dioxol-5-yl-methyl)-amino]-7-chloro-2,3,4,5-tetrahydro-1H-benzo[d]azepine Succinate | 55 | 331 (M + H)+ |
| 270 | | 6-(Benzo[b]thiophen-4-yl-methylamino)-7-chloro-2,3,4,5-tetrahydro-1H-benzo[d]azepine Succinate | 73 | 343 (M + H)+ |
| 271 | | 6-(Benzo[b]thiophen-6-yl-methylamino)-7-chloro-2,3,4,5-tetrahydro-1H-benzo[d]azepine Succinate | 48 | 343 (M + H)+ |

EXAMPLE 272

6-[(Benzothiazol-6-yl-methyl)-amino]-7-chloro-2,3,4,5-tetrahydro-1H-benzo[d]azepine Oxalate

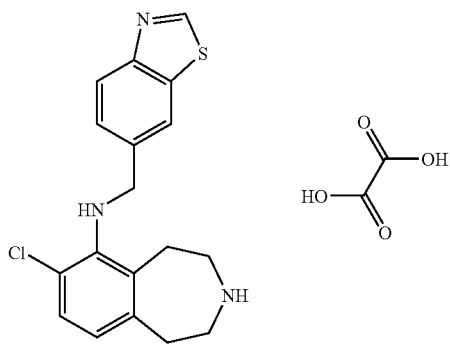

Using a method similar to the General Procedure 5-4, combine 6-amino-7-chloro-3-(2,2,2-trifluoroacetyl)-2,3,4,5-tetrahydro-1H-benzo[d]azepine (0.1 g, 0.35 mmol), 6-bromomethyl-benzothiazole (80 mg, 0.35 mmol), and potassium carbonate (47.0 mg, 0.35 mmol) in anhydrous DMF (1 mL) in a sealed tube. Heat at 150° C. for 3 h to obtain 6-[(benzothiazol-6-yl-methyl)-amino]-7-chloro-3-(2,2,2-trifluoroacetyl)-2,3,4,5-tetrahydro-1H-benzo[d]azepine as a colorless oil.

Use a method similar to the General Procedure 1-1 to obtain the free base of the title compound as a yellow oil. Use a method similar to the General Procedure 2-5 to obtain the title compound as a white solid (25 mg, 16% overall). MS (ES+) m/z: 344 (M+H)+.

EXAMPLE 273

7-Chloro-6-[(quinolin-8-yl-methyl)-amino]-2,3,4,5-tetrahydro-1H-benzo[d]azepine Hydrochloride

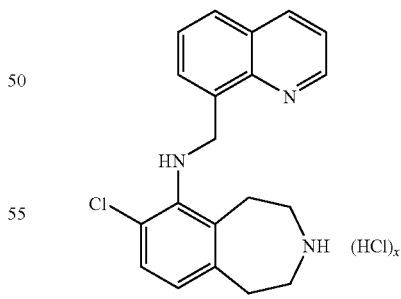

Using a method similar to the General Procedure 5-4, combine 6-amino-7-chloro-3-(2,2,2-trifluoroacetyl)-2,3,4,5-tetrahydro-1H-benzo[d]azepine (0.1 g, 0.35 mmol), 8-bromomethyl-quinoline (83.6 mg, 0.038 mmol), cesium carbonate (0.2 g, 0.68 mmol) and anhydrous acetonitrile (1 mL) in a sealed tube and heat at 50° C. for 12 h to obtain 7-chloro-6-[(quinolin-8-yl-methyl)-amino)-amino]-3-(2,2,2-trifluoroacetyl)-2,3,4,5-tetrahydro-1H-benzo[d]azepine as a colorless oil.

Use a method similar to the General Procedure 1-1 to obtain the free base of the title compound as a yellow oil. Use a method similar to the General Procedure 2-2 to form the hydrochloride salt and purify by reverse phase preparative HPLC [Zorbax SB-Phenyl 21.2×250 mm, 5 micron column, 22 mL/min of 0.1% HCl in water/acetonitrile (9:1 to 1:1) over 30 min, detector at 230 nm) to obtain the title compound as a white solid (13 mg, 8% overall). MS (ES+) m/z: 338 (M+H)$^+$.

EXAMPLE 274

7-Chloro-6-[(2-cyclohexyl-benzothiazol-6-yl-methyl)-amino]-2,3,4,5-tetrahydro-1H-benzo[d]azepine Succinate

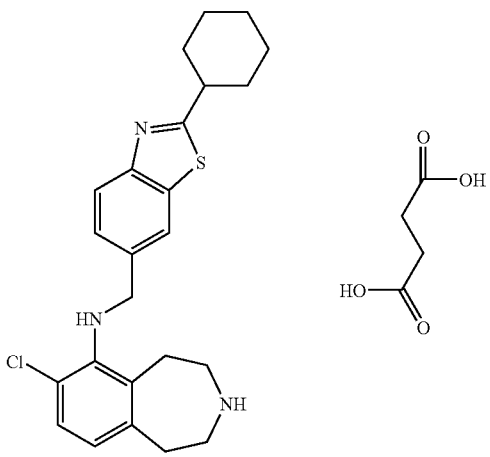

Using a method similar to the General Procedure 5-4, combine 6-amino-7-chloro-3-(2,2,2-trifluoroacetyl)-2,3,4,5-tetrahydro-1H-benzo[d]azepine (60 mg, 0.21 mmol), 6-bromomethyl-2-cyclohexyl-benzothiazole (0.1 g, 0.31 mmol), potassium carbonate (58 mg, 0.42 mmol) and anhydrous toluene (2 mL) in a sealed tube and heat at 100° C. for 72 h to obtain 7-chloro-6-[(2-cyclohexyl-benzothiazol-6-yl-methyl)-amino]-3-(2,2,2-trifluoroacetyl)-2,3,4,5-tetrahydro-1H-benzo[d]azepine as a colorless oil.

Use a method similar to the General Procedure 1-1 to obtain the free base of the title compound as a yellow oil. Use a method similar to the General Procedure 2-1 to obtain the title compound as a white solid (40 mg, 35% overall). MS (ES+) m/z: 427 (M+H)$^+$.

Examples 275-277 may be prepared essentially as described in Example 274 by using 6-amino-7-chloro-3-(2,2,2-trifluoroacetyl)-2,3,4,5-tetrahydro-1H-benzo[d]azepine and the appropriate bromide. Overall yields and MS (ES+) data are shown in the Table below.

| Ex. | NH—R | Compound | Yield (%) | MS (ES+) m/z |
|---|---|---|---|---|
| 275 | | 7-Chloro-6-[(2-phenyl-benzothiazol-6-yl-methyl)-amino]-2,3,4,5-tetrahydro-1H-benzo[d]azepine Succinate | 39 | 420 (M + H)$^+$ |
| 276 | | 6-[(2-Benzyl-benzothiazol-6-yl-methyl)-amino]-7-chloro-2,3,4,5-tetrahydro-1H-benzo[d]azepine Succinate | 36 | 453 (M + H)$^+$ |
| 277 | | 6-[(Benzoxazol-6-yl-methyl)-amino]-7-chloro-2,3,4,5-tetrahydro-1H-benzo[d]azepine Succinate | 7 | 328 (M + H)$^+$ |

EXAMPLE 278

7-Chloro-6-[(1-methyl-indol-4-yl-methyl)-amino]-2,3,4,5-tetrahydro-1H-benzo[d]azepine Succinate

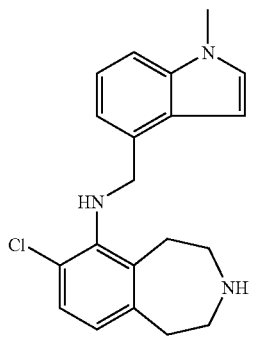 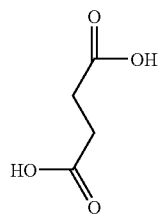

Using a method similar to the General Procedure 5-1, couple 7-chloro-3-(2,2,2-trifluoroacetyl)-6-trifluoromethanesulfonyloxy-2,3,4,5-tetra-hydro-1H-benzo[d]azepine (0.1 g, 0.24 mmol) with 4-aminomethyl-1-methylindole (0.1 g, 0.71 mmol) to obtain 7-chloro-6-[(1-methyl-indol-4-yl-methyl)-amino]-3-(2,2,2-trifluoroacetyl)-2,3,4,5-tetrahydro-1H-benzo[d]azepine as a colorless oil.

Use a method similar to the General Procedure 1-1 to obtain the free base of the title compound as a yellow oil. Use a method similar to the General Procedure 2-1 to obtain the title compound as a white solid (0.1 g, 91% overall). MS (ES+) m/z: 340 (M+H)$^+$.

Examples 279-280 may be prepared essentially as described in Example 278 by using 7-chloro-3-(2,2,2-trifluoroacetyl)-6-trifluoromethanesulfonyloxy-2,3,4,5-tetrahydro-1H-benzo[d]azepine with the appropriate amine. Overall yields and MS (ES+) data are shown in the Table below.

EXAMPLE 281

7-Chloro-6-(pyridin-2-ylmethylamino)-2,3,4,5-tetrahydro-1H-benzo[d]azepine Hydrochloride

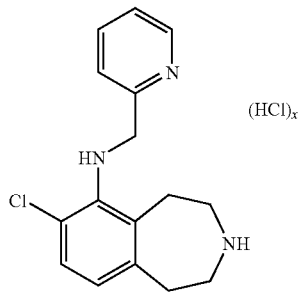

Use a method similar to the General Procedure 5-1 to couple 7-chloro-3-(2,2,2-trifluoroacetyl)-6-trifluoromethanesulfonyloxy-2,3,4,5-tetrahydro-1H-benzo[d]azepine (500 mg, 1.17 mmol) with pyridin-2-ylmethylamine (254 mg, 2 equiv.) using palladium acetate (0.1 equiv.), BINAP (0.3 equiv.) and cesium carbonate (1.4 equiv.) in toluene (5 mL). Purify the residue by chromatography on silica gel eluting with hexane/EtOAc (10:1, 5:1, 3:1, and 1:1) to give 7-chloro-6-(pyridin-2-ylmethylamino)-3-(2,2,2-trifluoroacetyl)-2,3,4,5-tetrahydro-1H-benzo[d]azepine as an oil.

Use a method similar to the General Procedure 1-3 to deprotect 7-chloro-6-(pyridin-2-ylmethylamino)-3-(2,2,2-trifluoroacetyl)-2,3,4,5-tetrahydro-1H-benzo[d]azepine.

Purify by SCX chromatography followed by silica gel chromatography eluting with DCM/2M ammonia in methanol (1:0, 40:1, 20:1 and 10:1) to give the free base of the title compound. Use a method similar to the General Procedure 2-2 to give the title compound as an off white solid (207 mg, 55% overall). MS (ES+) m/z: 288 (M+H)$^+$.

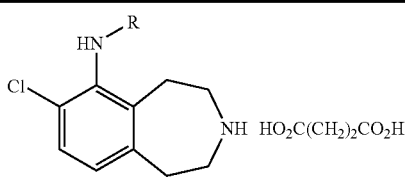

| Ex. | NH—R | Compound | (%) | MS (ES+) m/z |
|---|---|---|---|---|
| 279 | NH, 1-methyl-indol-6-yl-methyl | 7-Chloro-6-[(1-methyl-indol-6-yl-methyl)-amino]-2,3,4,5-tetrahydro-1H-benzo[d]azepine Succinate | 42 | 340 (M + H)$^+$ |
| 280 | NH, benzofuran-6-ylmethyl | 6-[(Benzofuran-6-ylmethyl)-amino]-7-chloro-2,3,4,5-tetrahydro-1H-benzo[d]azepine Succinate | 46 | 327 (M + H)$^+$ |

EXAMPLE 282

7-Chloro-6-(pyridin-4-ylmethylamino)-2,3,4,5-tetrahydro-1H-benzo[d]azepine Hydrochloride

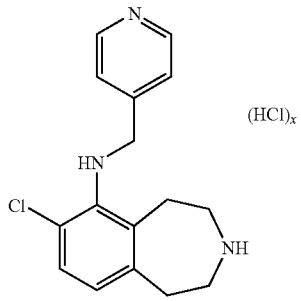

may be prepared essentially as described in Example 281 by using 7-chloro-3-(2,2,2-trifluoroacetyl)-6-trifluoromethanesulfonyloxy-2,3,4,5-tetrahydro-1H-benzo[d]azepine and pyridin-4-ylmethylamine (28% yield, and MS (ES+) 288 (M+H)+).

EXAMPLE 283

(±)-7-Chloro-6-[(1-pyridin-4-yl-ethyl)-amino]-2,3,4,5-tetrahydro-1H-benzo[d]azepine Succinate

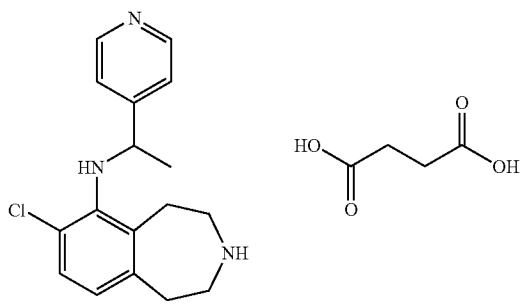

Use a method similar to the General Procedure 5-3 to couple 7-chloro-3-(2,2,2-trifluoroacetyl)-6-trifluoromethanesulfonyloxy-2,3,4,5-tetrahydro-1H-benzo[d]azepine (400 mg, 0.94 mmol) and (±)-1-pyridin-4-yl-ethylamine (prepared as described in *Bull. Kor. Chem. Soc.* 1998, 19 (8), 891-893) (172 mg, 1.41 mmol). Purify by chromatography on silica gel eluting with hexane/EtOAc (1:0, 4:1 and 1:1) to give (±)-7-chloro-6-[(1-pyridin-4-yl-ethyl)-amino]-3-(2,2,2-trifluoroacetyl)-2,3,4,5-tetrahydro-1H-benzo[d]azepine.

Use a method similar to the General Procedure 1-1 to give the free base of the title compound (73 mg, 26%). Use a method similar to the General Procedure 2-1, using (±)-7-chloro-6-[(1-pyridin-4-yl-ethyl)-amino]-2,3,4,5-tetrahydro-1H-benzo[d]azepine (73 mg, 0.243 mmol), to give the title compound (31 mg, 31%). MS (ES+) m/z: 302 (M+H)+.

Examples 284-287 may be prepared essentially as described in Example 283 by using 7-chloro-3-(2,2,2-trifluoroacetyl)-6-trifluoromethanesulfonyloxy-2,3,4,5-tetrahydro-1H-benzo[d]azepine and the appropriate amine. The yields for the Step 1 (General Procedure 5-3) and MS (ES+) data are shown in the Table below.

| Ex. | NH—R | Compound | Yield (%) | MS (ES+) m/z |
|---|---|---|---|---|
| 284 | F-pyridin-3-yl-CH2-NH | 7-Chloro-6-(5-fluoro-pyridin-3-ylmethylamino)-2,3,4,5-tetrahydro-1H-benzo[d]azepine Succinate | 88 | 306 (M + H)+ |
| 285 | CF3-pyridin-3-yl-CH2-NH | 7-Chloro-6-(6-trifluoromethyl-pyridin-3-yl-methylamino)-2,3,4,5-tetrahydro-1H-benzo[d]azepine Succinate | 83 | 356 (M + H)+ |
| 286 | CF3-pyridin-3-yl-CH2-NH | 7-Chloro-6-(4-trifluoromethyl-pyridin-3-yl-methylamino)-2,3,4,5-tetrahydro-1H-benzo[d]azepine Succinate | 60 | 356 (M + H)+ |
| 287 | CF3-pyridin-2-yl-CH2-NH | 7-Chloro-6-[(6-trifluoromethyl-pyridin-2-ylmethyl)-amino]-2,3,4,5-tetrahydro-1H-benzo[d]azepine Succinate | 84 | 356 (M + H)+ |

EXAMPLE 288

7-Chloro-6-[(5-fluoro-pyridin-2-ylmethyl)-amino]-2,3,4,5-tetrahydro-1H-benzo[d]azepine Succinate

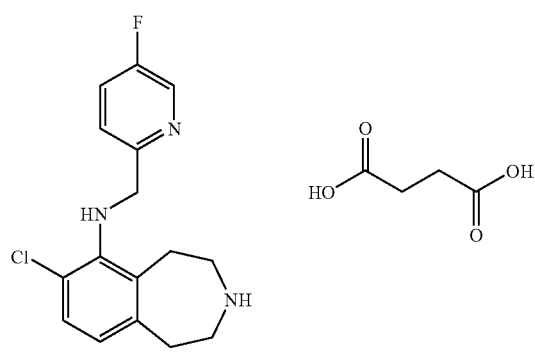

Use a method similar to the General Procedure 5-1 to couple 2-aminomethyl-5-fluoro-pyridine (230 mg, 1.8 mmol) and a solution of 7-chloro-3-(2,2,2-trifluoroacetyl)-6-trifluoromethanesulfonyloxy-2,3,4,5-tetrahydro-1H-benzo[d]azepine (500 mg, 1.2 mmol) in toluene (4 mL). Purify by chromatography on silica gel eluting with hexane/EtOAc (9:1 to 1:1) followed by SCX chromatography to give 7-chloro-6-[(5-fluoro-pyridin-2-ylmethyl)-amino]-3-(2,2,2-trifluoro-acetyl)-2,3,4,5-tetrahydro-1H-benzo[d]azepine (302 mg, 64%). GC-MS m/z: 402 (M+).

Dissolve 7-chloro-6-[(5-fluoro-pyridin-2-ylmethyl)-amino]-3-(2,2,2-trifluoroacetyl)-2,3,4,5-tetrahydro-1H-benzo[d]azepine (297 mg, 0.74 mmol) in ethanol (5 mL). Add 5N aqueous NaOH (10 equiv.) and stir for 1 h at ambient temperature. Concentrate in vacuo and purify by SCX chromatography followed by chromatography on silica gel eluting with DCM/2M ammonia in methanol (99:1 to 9:1) to obtain the free base of the title compound. Use a method similar to the General Procedure 2-1 and crystallize the solid from methanol and diethyl ether. Dry the solid in a vacuum oven at 60° C. overnight to obtain the title compound (181 mg, 58%). MS (ES+) m/z: 306 (M+H)+.

EXAMPLE 289

7-Chloro-6-{[5-(2,2,2-trifluoro-ethoxy)-pyridin-2-ylmethyl]-amino}-2,3,4,5-tetrahydro-1H-benzo[d]azepine Succinate

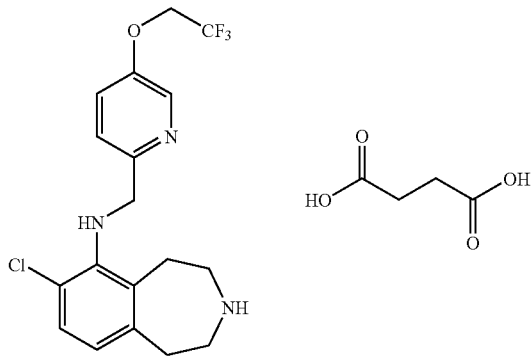

Use a method similar to the General Procedure 5-2 to couple 7-chloro-6-trifluoromethanesulfonyloxy-3-(2,2,2-trifluoroacetyl)-2,3,4,5-tetrahydro-1H-benzo[d]azepine (370 mg, 0.9 mmol) with 2-aminomethyl-5-(2,2,2-trifluoroethoxy)-pyridine (180 mg, 0.9 mmol) in toluene (8 mL). Purify by chromatography on silica gel eluting with hexane/EtOAc (10:1, 5:1 and 3:1) followed by SCX chromatography [prewash column with methanol followed by DCM, load material dissolved in DCM, then elute with DCM/2M ammonia in methanol (1:1) and concentrate in vacuo] to obtain 7-chloro-6-{[5-(2,2,2-trifluoro-ethoxy)-pyridin-2-ylmethyl]-amino}-3-(2,2,2-trifluoroacetyl)-2,3,4,5-tetrahydro-1H-benzo[d]azepine.

Use a method similar to the General Procedure 1-3 to deprotect 7-chloro-6-{[5-(2,2,2-trifluoro-ethoxy)-pyridin-2-ylmethyl]-amino}-3-(2,2,2-trifluoroacetyl)-2,3,4,5-tetrahydro-1H-benzo[d]azepine. Purify by chromatography on silica gel eluting with DCM/2M ammonia in methanol (99/1 to 90/10) to obtain the free base of the title compound. Use a method similar to the General Procedure 2-1 to give the title compound (184 mg, 42%). MS (ES+) m/z: 386 (M+H)+.

Examples 290-291 may be prepared essentially as described in Example 289 by using 7-chloro-3-(2,2,2-trifluoroacetyl)-6-trifluoromethanesulfonyloxy-2,3,4,5-tetrahydro-1H-benzo[d]azepine and the appropriate amine. Overall yields and MS (ES+) data are shown in the Table below.

| Ex. | O—R | Compound | Yield (%) | MS (ES+) m/z |
|---|---|---|---|---|
| 290 | | 7-Chloro-6-{[5(2,2,2-trifluoro-1,1-dimethyl-ethoxy)-pyridin-2-ylmethyl]-amino}-2,3,4,5-tetrahydro-1H-benzo[d]azepine Succinate | 48 | 414 (M + H)+ |
| 291 | | (±)-7-Chloro-6-{[5-(2,2,2-trifluoro-1-methyl-ethoxy)-pyridin-2-ylmethyl]-amino}-2,3,4,5-tetrahydro-1H-benzo[d]azepin Succinate | 49 | 400 (M + H)+ |

EXAMPLES 292 AND 293

(−)-7-Chloro-6-{[5-(2,2,2-trifluoro-1-methyl-ethoxy)-pyridin-2-ylmethyl]-amino}-2,3,4,5-tetrahydro-1H-benzo[d]azepine Succinate and (+)-7-Chloro-6-{[5-(2,2,2-trifluoro-1-methyl-ethoxy)-pyridin-2-ylmethyl]-amino}-2,3,4,5-tetrahydro-1H-benzo[d]azepine Succinate

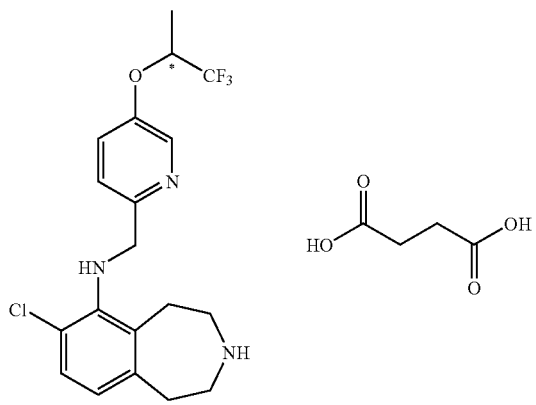

Separate the two enantiomers of (±)-7-chloro-6-{[5-(2,2,2-trifluoro-1-methyl-ethoxy)-pyridin-2-ylmethyl]-amino}-2,3,4,5-tetrahydro-1H-benzo[d]azepine succinate by normal phase chiral HPLC (Chiralcel OD 8×35 cm, elute with 4:1 heptane/3A-ethanol with 0.2% DMEA). Purify each enantiomer by chromatography on silica gel eluting with DCM/2M ammonia in methanol (20:1). Use a method similar to the General Procedure 2-1 to obtain the title compounds: (−)-7-Chloro-6-{[5-(2,2,2-trifluoro-1-methyl-ethoxy)-pyridin-2- ylmethyl]-amino}-2,3,4,5-tetrahydro-1H-benzo[d]azepine succinate (Example 292, 75 mg, 38%), 95% ee [Chiralpak AD, 4.6×150 mm, eluent: 85/15 heptane/3A ethanol with 0.2% DMEA, 0.6 mL/min)]; MS (ES+) m/z: 400 (M+H)⁺. $[\alpha]^{20}_D$ −12.1° (c 0.5, MeOH). (+)-7-Chloro-6-{[5-(2,2,2-trifluoro-1-methyl-ethoxy)-pyridin-2-ylmethyl]-amino}-2,3,4,5-tetrahydro-1H-benzo[d]azepine succinate (Example 293, 72 mg, 37%), 93% ee [Chiralpak AD, 4.6×150 mm, eluent: 85/15 heptane/3A ethanol with 0.2% DMEA, 0.6 mL/min)]. MS (ES+) m/z: 400 (M+H)⁺. $[\alpha]^{20}_D$ +7.4° (c 0.5, MeOH).

EXAMPLE 294

(±)-7-Chloro-6-[(1-thiophen-2-yl-ethyl)-amino]-2,3,4,5-tetrahydro-1H-benzo[d]azepine Succinate

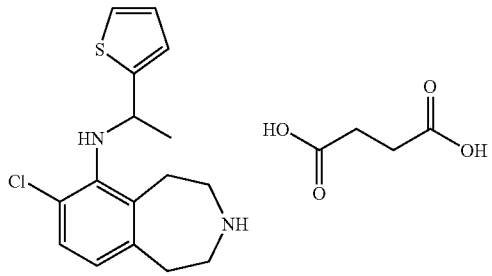

Use a method similar to the General Procedure 5-3 to couple 7-chloro-3-(2,2,2-trifluoroacetyl)-6-trifluoromethanesulfonyloxy-2,3,4,5-tetrahydro-1H-benzo[d]azepine (200 mg, 0.47 mmol) with (±)-1-thiophen-2-yl-ethylamine (prepared as described in *J. Amer. Chem. Soc.* 1942, 64, 477-479) (200 mg, 1.57 mmol). Purify by chromatography on silica gel eluting with hexane/EtOAc (1:0, 9:1 and 4:1) to give (±)-7-chloro-6-[(1-thiophen-2-yl-ethyl)-amino]-3-(2,2,2-trifluoroacetyl)-2,3,4,5-tetrahydro-1H-benzo[d]azepine (126 mg, 67%).

Use a method similar to the General Procedure 1-1, using (±)-7-chloro-6-[(1-thiophen-2-yl-ethyl)-amino]-3-(2,2,2-trifluoroacetyl)-2,3,4,5-tetrahydro-1H-benzo[d]azepine (126 mg, 0.313 mmol), to give the free base of the title compound (73 mg, 77%). Use a method similar to the General Procedure 2-1, using (±)-7-chloro-6-[(1-thiophen-2-yl-ethyl)-amino]-2,3,4,5-tetrahydro-1H-benzo[d]azepine (73 mg, 0.241 mmol) to give the title compound (100 mg, 50% overall). MS (ES+) m/z: 307 (+H)⁺.

EXAMPLE 295

(+)-7-Chloro-6-[(1-thiophen-2-yl-ethyl)-amino]-2,3,4,5-tetrahydro-1H-benzo[d]azepine Succinate, Isomer 1

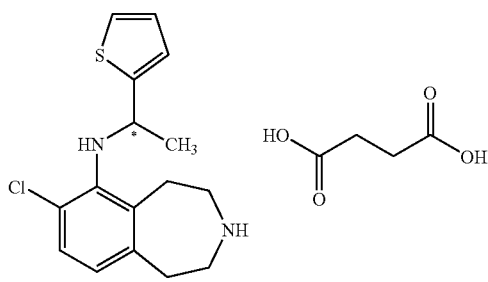

Separate the two enantiomers of (±)-7-chloro-6-[(1-thiophen-2-yl-ethyl)-amino]-3-(2,2,2-trifluoroacetyl)-2,3,4,5-tetrahydro-1H-benzo[d]azepine by chiral preparative HPLC (Chiralpak AD, 8×30 cm; eluent: 9:1 heptane/isopropanol with 0.2% DMEA; flow: 350 mL/min at 240 nm (UV), ~650 mg load] to obtain 7-chloro-6-[(1-thiophen-2-yl-ethyl)-amino]-3-(2,2,2-trifluoroacetyl)-2,3,4,5-tetrahydro-1H-benzo[d]azepine Isomer 1, ee=100% [Analytical Column: Chiralpak AD, 4.6×250 mm; eluent: 9:1 heptane/isopropanol with 0.2% DMEA; flow: 1 mL/min at 250 nm (UV).

Use a method similar to the General Procedure 1-1, using 7-chloro-6-[(1-thiophen-2-yl-ethyl)-amino]-3-(2,2,2-trifluoroacetyl)-2,3,4,5-tetrahydro-1H-benzo[d]azepine Isomer 1, to give 7-chloro-6-[(1-thiophen-2-yl-ethyl)-amino]-2,3,4,5-tetrahydro-1H-benzo[d]azepine Isomer 1. Use a method similar to the General Procedure 2-1, using 7-chloro-6-[(1-thiophen-2-yl-ethyl)-amino]-2,3,4,5-tetrahydro-1H-benzo[d]azepine Isomer 1 (73 mg, 0.241 mmol) to give the title compound (100 mg, 98%). MS (ES+) m/z: 307 (M+H)⁺. $[\alpha]^{20}_D$ +115.0° (c 0.5, MeOH).

EXAMPLE 296

(±)-7-Chloro-6-[1-(5-methylthiophen-2-yl)ethylamino]-2,3,4,5-tetrahydro-1H-benzo[d]azepine Succinate

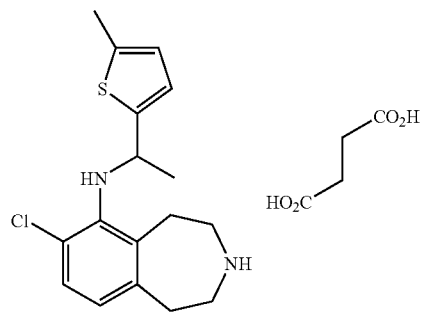

Use a method similar to the General Procedure 5-1 to couple 7-chloro-3-(2,2,2-trifluoroacetyl)-6-trifluoromethanesulfonyloxy-2,3,4,5-tetrahydro-1H-benzo[d]azepine (96 mg, 0.227 mmol) with (±)-2-(1-aminoethyl)-5-methylthiophene (48 mg, 0.34 mmol) using palladium(II) acetate (10 mg, 0.0454 mmol), BINAP (60 mg, 0.0908 mmol) and cesium carbonate (148 mg, 0.454 mmol) in toluene (10 mL). Purify by chromatography on silica gel eluting with hexane/EtOAc (1:0, 19:1) to give (±)-7-chloro-6-[1-(5-methylthiophen-2-yl)ethylamino]-3-(2,2,2-trifluoroacetyl)-2,3,4,5-tetrahydro-1H-benzo[d]azepine as an oil (47 mg, 50%). GC-MS m/z 416 (M⁺).

Use a method similar to the General Procedure 1-2, using (±)-7-chloro-6-[1-(5-methylthiophen-2-yl)ethylamino]-3-(2,2,2-trifluoroacetyl)-2,3,4,5-tetrahydro-1H-benzo[d]azepine (47 mg, 0.113 mmol) to give (±)-7-chloro-6-[1-(5-methylthiophen-2-yl)ethylamino]-2,3,4,5-tetrahydro-1H-benzo[d]azepine as an oil (30 mg, 83%) that was used without further purification. Use a method similar to the General Procedure 2-1 to give the title compound as a white solid (36 mg, 88% j. MS (ES+) m/z: 321 (M+H)⁺.

EXAMPLE 297

(+)-7-Chloro-6-[1-(5-phenyl-thiophen-2-yl)-ethylamino]-2,3,4,5-tetrahydro-1H-benzo[d]azepine Succinate

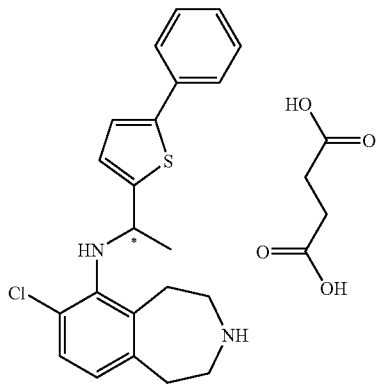

Use a method similar to the General Procedure 5-3 to couple 7-chloro-3-(2,2,2-trifluoroacetyl)-6-trifluoromethanesulfonyloxy-2,3,4,5-tetrahydro-1H-benzo[d]azepine (0.328 g, 0.773 mmol) with 15-phenyl-thiophen-2-yl)ethylamine Isomer 1 (0.236 g, 1.16 mmol) using palladium (II) acetate (69 mg, 0.309 mmol), tris(dibenzylideneacetone)-dipalladium(0) (142 mg, 0.155 mmol), BINAP (578 mg, 0.928 mmol) and cesium carbonate (504 mg, 1.546 mmol) in toluene (10 mL). Purify by chromatography on silica gel eluting with hexane/EtOAc (1:0 and 19:1) to give 7-chloro-6-[1-(5-phenyl-thiophen-2-yl)-ethylamino]-3-(2,2,2-trifluoroacetyl)-2,3,4,5-tetrahydro-1H-benzo[d]azepine Isomer 1 (89 mg, 34%).

Use a method similar to the General Procedure 1-2, using 7-chloro-6-[1-(5-phenyl-thiophen-2-yl)-ethylamino]-3-(2,2,2-trifluoroacetyl)-2,3,4,5-tetrahydro-1H-benzo[d]azepine Isomer 1 (89 mg, 0.186 mmol) to give 7-chloro-6-[1-(5-phenyl-thiophen-2-yl)-ethylamino]-2,3,4,5-tetrahydro-1H-benzo[d]azepine Isomer 1 (65 mg, 92%) as an oil that was used without further purification. Use a method similar to the General Procedure 2-1, using 7-chloro-6-[1-(5-phenyl-thiophen-2-yl)-ethylamino]-2,3,4,5-tetrahydro-1H-benzo[d]azepine Isomer 1 (65 mg, 0.17 mmol), to give the title compound as a white solid (58 mg, 68%). MS (ES+) m/z: 383 (M+H)$^+$; $[\alpha]^{20}_D$ +159.0° (c 0.5, MeOH).

EXAMPLE 298

(−)-7-Chloro-6-[1-(5-phenyl-thiophen-2-yl)-ethylamino]-2,3,4,5-tetrahydro-1H-benzo[d]azepine Succinate

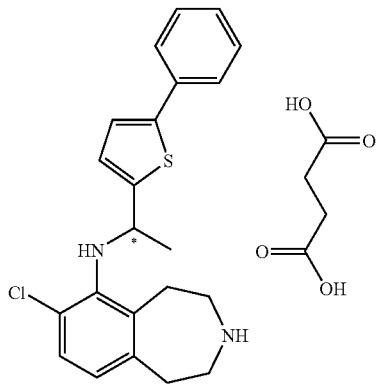

Use a method similar to the General Procedure 5-3 to couple 7-chloro-3-(2,2,2-trifluoroacetyl)-6-trifluoromethanesulfonyloxy-2,3,4,5-tetrahydro-1H-benzo[d]azepine (0.484 g, 1.138 mmol) with 1-(5-phenyl-thiophen-2-yl)ethylamine Isomer 2 (0.347 g, 1.71 mmol) using palladium (II) acetate (102 mg, 0.45 mmol), tris(dibenzylideneacetone)-dipalladium(0) (209 mg, 0.228 mmol), BINAP (851 mg, 1.366 mmol) and cesium carbonate (741 mg, 2.276 mmol) in toluene (12 mL). Purify by chromatography on silica gel eluting with hexane:EtOAc (1:0 and 19:1) to give 7-chloro-6-[1-(5-phenyl-thiophen-2-yl)-ethylamino]-3-(2,2,2-trifluoroacetyl)-2,3,4,5-tetrahydro-1H-benzo[d]azepine Isomer 2 (247 mg, 63%).

Use a method similar to the General Procedure 1-2, using 7-chloro-6-[1-(5-phenyl-thiophen-2-yl)-ethylamino]-3-(2,2,2-trifluoroacetyl)-2,3,4,5-tetrahydro-1H-benzo[d]azepine Isomer 2 (247 mg, 0.516 mmol) to give 7-chloro-6-[1-(5-phenyl-thiophen-2-yl)-ethylamino]-2,3,4,5-tetrahydro-1H-benzo[d]azepine Isomer 2 (184 mg, 93%) as an oil that was used without further purification. Use a method similar to the General Procedure 2-1, using 7-chloro-6-[1-(5-phenyl-thiophen-2-yl)-ethylamino]-2,3,4,5-tetrahydro-1H-benzo[d]azepine Isomer 2 (184 mg, 0.48 mmol) to give the title compound as a white solid (200 mg, 83%). MS (ES+) m/z: 383 (M+H)$^+$; $[\alpha]^{20}_D$ −196.5° (c 0.5, MeOH).

EXAMPLE 299

(±)-7-Chloro-6-[(1-thiophen-3-yl-ethyl)-amino]-2,3,4,5-tetrahydro-1H-benzo[d]azepine Succinate

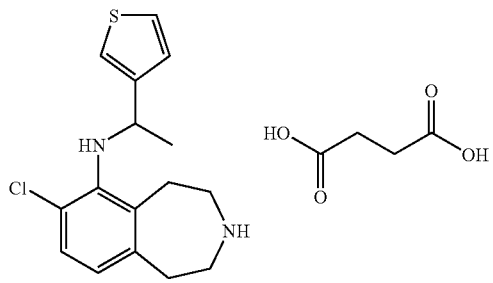

Use a method similar to the General Procedure 5-3 to couple 7-chloro-3-(2,2,2-trifluoroacetyl)-6-trifluoromethanesulfonyloxy-2,3,4,5-tetrahydro-1H-benzo[d]azepine (200 mg, 0.47 mmol) with (±)-1-thiophen-3-yl-ethylamine (prepared as described in *J. Heterocycl. Chem.* 1988, 25, 1571-1581) (90 mg, 0.70 mmol). Purify by chromatography on silica gel eluting with hexane/EtOAc (1:0, 9:1 and 4:1) to give (±)-7-chloro-6-(1-thiophen-3-yl-ethylamino)-3-(2,2,2-trifluoroacetyl)-2,3,4,5-tetrahydro-1H-benzo[d]azepine (100 mg, 53%).

Use a method similar to the General Procedure 1-1, using (±)-7-chloro-6-(1-thiophen-3-yl-ethylamino)-3-(2,2,2-trifluoroacetyl)-2,3,4,5-tetrahydro-1H-benzo[d]azepine (100 mg, 0.248 mmol), to give the free base of the title compound (74 mg, 98%). Use a method similar to the General Procedure 2-1, using (±)-7-chloro-6-(1-thiophen-3-yl-ethylamino)-2,3,4,5-tetrahydro-1H-benzo[d]azepine (74 mg, 0.242 mmol) to give the title compound (108 mg, 54% overall). MS (ES+) m/z: 307 (M+H)$^+$.

EXAMPLE 300

7-Chloro-6-[(5-methylfuran-2-ylmethyl)-amino]-2,3,4,5-tetrahydro-1H-benzo[d]azepine Hydrochloride

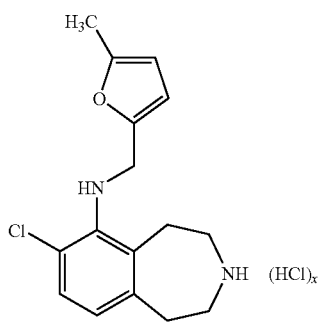

Combine 7-chloro-3-(2,2,2-trifluoroacetyl)-6-trifluoromethanesulfonyloxy-2,3,4,5-tetrahydro-1H-benzo[d]azepine (100 mg, 0.24 mmol), 2-(di-tert-butylphosphino)-biphenyl (6.8 mg, 0.023 mmol), tris(dibenzylideneacetone) dipalladium (11 mg, 0.012 mmol) and potassium phosphate (70 mg, 0.33 mmol) in a pressure tube and degas. Dissolve the mixture in dry toluene (2 mL) and degas. Add a solution of 5-methylfurfurylamine (30 mg, 0.27 mmol) in toluene (1 mL) and degas. Stir at 90° C. for 24 h. Cool to ambient temperature, dilute with ethyl ether and filter through Celite®. Concentrate and purify by chromatography on silica gel eluting with hexane/EtOAc (20:1). Remove the solvent and add 7M ammonia in methanol (4 mL). Stir at ambient temperature for 24 h. Concentrate and purify by SCX chromatography to give the free base of the title compound. Use a method similar to the General Procedure 2-2 to obtain the title compound as a solid (56 mg, 66%). MS (ES+) m/z: 291 (M+H)$^+$.

Examples 301-302 may be prepared essentially as described in Example 300 by using 7-chloro-3-(2,2,2-trifluoroacetyl)-6-trifluoromethanesulfonyloxy-2,3,4,5-tetrahydro-1H-benzo[d]azepine and the appropriate amine. Overall yields and MS (ES+) data are shown in the Table below.

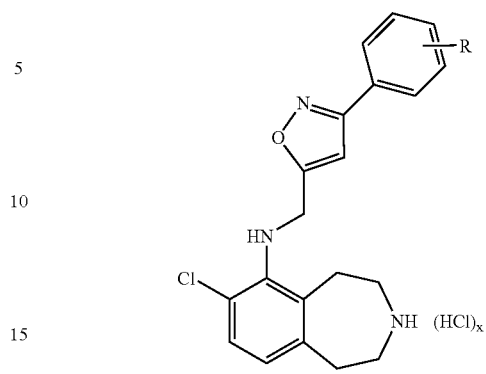

| Ex. | R | Compound | Yield (%) | MS (ES+) m/z |
|---|---|---|---|---|
| 301 | 4-Cl | 7-Chloro-6-{[3-(4-chlorophenyl)-isoxazol-5-ylmethyl]-amino}-2,3,4,5-tetrahydro-1H-benzo[d]azepine Hydrochloride | 30 | 389 (M + H)$^+$ |
| 302 | 4-OMe | 7-Chloro-6-{[3-(4-methoxyphenyl)-isoxazol-5-ylmethyl]-amino}-2,3,4,5-tetrahydro-1H-benzo[d]azepine Hydrochloride | 54 | 384 (M + H)$^+$ |

EXAMPLE 303

7-Chloro-6-(thiazol-5-ylmethyl-amino)-2,3,4,5-tetrahydro-1H-benzo[d]azepine Hydrochloride

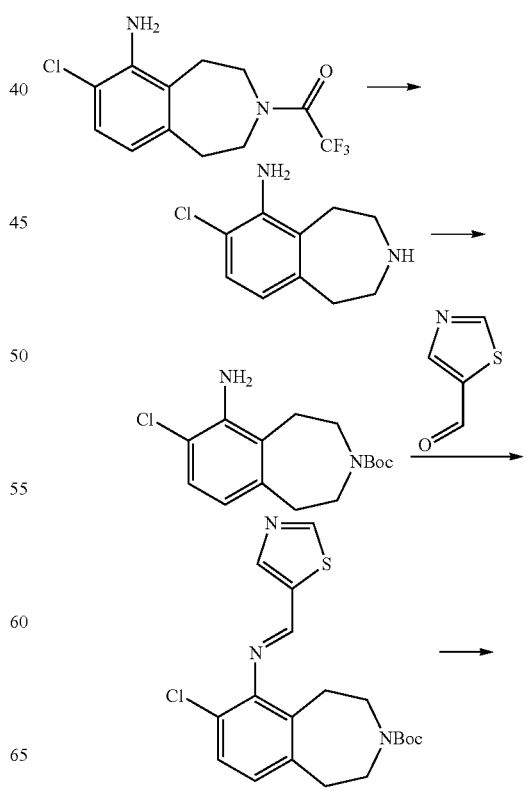

-continued

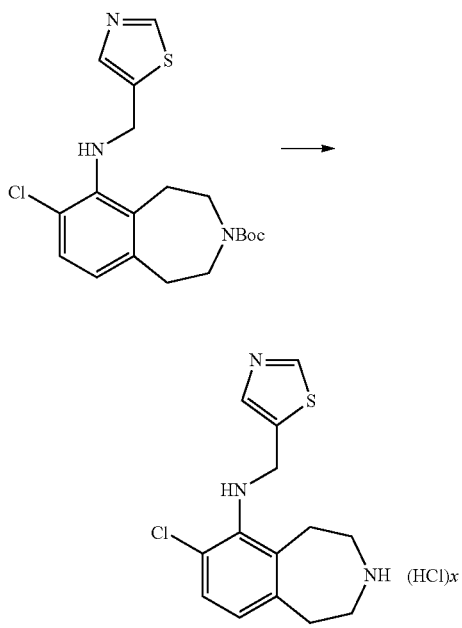

Thiazole-5-carbaldehyde: Add DMSO slowly to a solution of oxalyl chloride (1.6 g, 13 mmol) in anhydrous DCM (30 mL) under nitrogen at −78° C. and stir for 10 min. Add dropwise a solution of 5-hydroxymethylthiazole (1.15 g, 10 mmol) in DCM (10 mL) and stir the mixture for 40 min. Add triethylamine and stir for 5 min and then quench the reaction with water. Extract the mixture three times with ether, combine the organic extracts, wash with brine, dry over $Na_2SO_4$, filter and concentrate in vacuo. Purify by chromatography on silica gel eluting with EtOAc/hexane (2:5) to give thiazole-5-carbaldehyde (337 mg, 29%).

3-(tert-Butoxycarbonyl)-7-chloro-6-(thiazol-5-ylmethyleneamino)-2,3,4,5-tetrahydro-1H-benzo[d]azepine: Dissolve 6-amino-7-chloro-3-(2,2,2-trifluoroacetyl)-2,3,4,5-tetrahydro-1H-benzo[d]azepine (285 mg, 0.97 mmol) in methanol (10 mL). Add 7N ammonia in methanol (10 mL) and stir overnight at ambient temperature. Concentrate in vacuo and dissolve the residue in THF (10 mL). Add saturated aqueous $NaHCO_3$ (5 mL) and di-tert-butyl-dicarbonate (254 mg, 1.16 mmol). Stir the reaction mixture at ambient temperature for 4 h. Dilute the mixture with water, extract three times with EtOAc, combine the organic extracts, dry over $Na_2SO_4$, filter and concentrate in vacuo to give crude material. Mix thiazole-5-carbaldehyde (165 mg, 1.45 mmol) with above crude residue (0.97 mmol, assuming 100% conversion), acetic acid (87 mg, 1.45 mmol) and 1,2-dichloroethane (10 mL). Stir at ambient temperature for 20 min. Add sodium triacetoxyborohydride and stir under nitrogen overnight. Quench the reaction with saturated aqueous $NaHCO_3$, separate the organic layer and extract the aqueous layer three times with DCM. Combine the organic extracts, dry over $Na_2SO_4$, filter and concentrate in vacuo. Purify by chromatography on silica gel eluting with EtOAc/hexane (1:3) to afford the desired intermediate as a yellow oil (228 mg, 60% three steps). MS (ES+) m/z: 392 (M+H)$^+$.

3-(t-Butoxycarbonyl)-7-chloro-6-(thiazol-5-ylmethylamino)-2,3,4,5-tetrahydro-1H-benzo[d]azepine: Dissolve 3-(t-butoxycarbonyl)-7-chloro-6-(thiazol-5-ylmethyleneamino)-2,3,4,5-tetrahydro-1H-benzo[d]azepine (228 mg, 0.58 mmol) in methanol (10 mL), add sodium borohydride (263 mg, 7 mmol) and reflux for 28 h. Cool to ambient temperature, dilute with EtOAc and add slowly water. Separate the organic layer, extract the aqueous layer three times with EtOAc. Combine the organic extracts, dry over $Na_2SO_4$, filter and concentrate in vacuo. Purify by chromatography on silica gel eluting with EtOAc/hexane (1:3) to give the desired intermediate as a colorless oil (134 mg, 58%). MS (ES+) m/z: 394 (M+H)$^+$.

7-Chloro-6-(thiazol-5-ylmethyl-amino)-2,3,4,5-tetrahydro-1H-benzo[d]azepine Hydrochloride: Use a method similar to the General Procedure 1-6 to deprotect 3-(tert-butoxycarbonyl)-7-chloro-6-(thiazol-5-ylmethyl-amino)-2,3,4,5-tetrahydro-1H-benzo[d]azepine (134 mg, 0.34 mmol). Purify by chromatography on silica gel eluting with DCM/2M ammonia in methanol (94:6) to give 7-chloro-6-(thiazol-5-ylmethyl-amino)-2,3,4,5-tetrahydro-1H-benzo[d]azepine as an oil (90 mg, 90%). MS (ES+) m/z: 294 (M+H)$^+$. Use a method similar to the General Procedure 2-2 to obtain the title compound.

EXAMPLE 304

7-Chloro-6-[(3-pyridyl)amino]-2,3,4,5-tetrahydro-1H-benzo[d]azepine Succinate

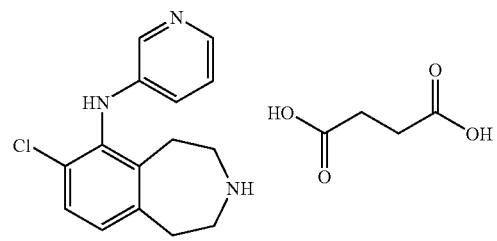

Use a method similar to the General Procedure 5-1 to couple 7-chloro-3-(2,2,2-trifluoroacetyl)-6-trifluoromethanesulfonyloxy-2,3,4,5-tetrahydro-1H-benzo[d]azepine (300 mg, 0.7 mmol) with 3-aminopyridine (75 mg, 0.85 mmol). Purify by chromatography on silica gel eluting with hexane/EtOAc (4:1) to give 7-chloro-6-[(3-pyridyl)amino]-3-(2,2,2-trifluoroacetyl)-2,3,4,5-tetrahydro-1H-benzo[d]azepine as an off-white solid (20 mg, 8%). MS (ES+) m/z: 370 (M+H)$^+$.

Use a method similar to the General Procedure 1-1 to deprotect 7-chloro-6-[(3-pyridyl)amino]-3-(2,2,2-trifluoroacetyl)-2,3,4,5-tetrahydro-1H-benzo[d]azepine (20 mg, 0.05 mmol). Purify by SCX chromatography to give 7-chloro-6-[(3-pyridyl)amino]-2,3,4,5-tetrahydro-1H-benzo[d]azepine as a yellow oil (15 mg, 99%). Use a method similar to the General Procedure 2-1, using 7-chloro-6-[(3-pyridyl)amino]-2,3,4,5-tetrahydro-1H-benzo[d]azepine (15.1 mg, 0.05 mmol), to give the title compound as a light yellow solid (20 mg, 97%). MS (ES+) m/z: 319 (M+H)$^+$.

EXAMPLE 305

7,9-Dichloro-6-(3,4-difluorobenzylamino)-2,3,4,5-tetrahydro-1H-benzo[d]azepine Hydrochloride

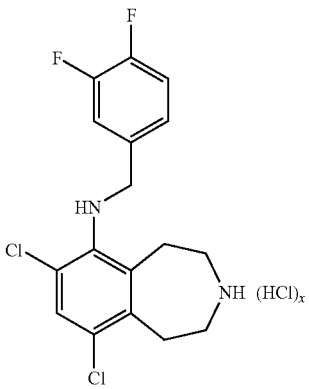

Dissolve 7-dichloro-6-(3,4-difluorobenzylamino)-3-(2,2,2-trifluoroacetyl)-2,3,4,5-tetrahydro-1H-benzo[d]azepine (150 mg, 0.36 mmol) in anhydrous toluene (20 mL). Add N-chlorosuccinimide (140 mg, 1 mmol) and heat at 60° C. for 4 h. Cool to room temperature, pour reaction mixture into water (250 mL) and extract with EtOAc (3×50 mL). Wash combined organic extracts with water, brine, dry over Na$_2$SO$_4$, filter, and concentrate in vacuo. Purify by chromatography on silica gel eluting with hexane/EtOAc (4:1) to give 7,9-dichloro-6-(3,4-difluorobenzylamino)-3-(2,2,2-trifluoroacetyl)-2,3,4,5-tetrahydro-1H-benzo[d]azepine (110 mg, 67%). MS (ES+) m/z: 453 (M+H)$^+$.

Use a method similar to the General Procedure 1-1 to deprotect 7,9-dichloro-6-(3,4-difluorobenzylamino)-3-(2,2,2-trifluoroacetyl)-2,3,4,5-tetrahydro-1H-benzo[d]azepine (120 mg, 0.26 mmol). Purify by SCX chromatography to give 7,9-dichloro-6-(3,4-difluorobenzylamino)-2,3,4,5-tetrahydro-1H-benzo[d]azepine as a yellow oil (81 mg, 88%). Use a method similar to the General Procedure 2-2, using 7,9-dichloro-6-(3,4-difluorobenzylamino)-2,3,4,5-tetrahydro-1H-benzo[d]azepine (75 mg, 0.21 mmol), to give the title compound as a yellow gum (80 mg, 96%). MS (ES+) m/z: 357 (M+H)$^+$.

EXAMPLE 306

7-Chloro-9-fluoro-6-(3-fluorobenzylamino)-2,3,4,5-tetrahydro-1H-benzo[d]azepine Succinate

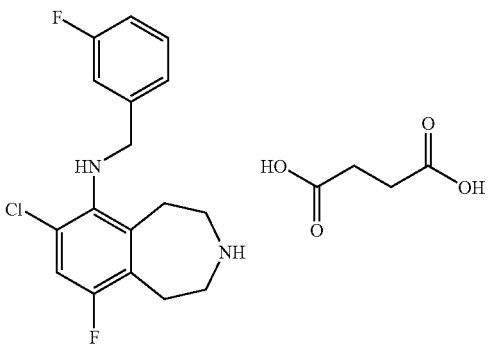

Use a method similar to the General Procedure 5-1 to couple 7-chloro-9-fluoro-3-(2,2,2-trifluoroacetyl)-6-trifluoromethanesulfonyloxy-2,3,4,5-tetrahydro-1H-benzo[d]azepine (130 mg, 0.3 mmol) with 3-fluorobenzylamine (100 □L, 0.89 mmol). Purify by chromatography on silica gel eluting with hexane/EtOAc (9:1 and 4:1) followed by SCX chromatography to give 7-chloro-9-fluoro-6-(3-fluorobenzylamino)-3-(2,2,2-trifluoroacetyl)-2,3,4,5-tetrahydro-1H-benzo[d]azepine as a yellow oil (35 mg, 28%). MS (ES+) m/z: 401 (M+H)$^+$.

Use a method similar to the General Procedure 1-1 to deprotect 7-chloro-9-fluoro-6-(3-fluorobenzylamino)-3-(2,2,2-trifluoroacetyl)-2,3,4,5-tetrahydro-1H-benzo[d]azepine (32 mg, 0.08 mmol). Purify by SCX chromatography to give 7-chloro-9-fluoro-6-(3-fluorobenzylamino)-2,3,4,5-tetrahydro-1H-benzo[d]azepine as a yellow oil (10 mg, 45%). Use a method similar to the General Procedure 2-1, using 7-chloro-9-fluoro-6-(3-fluorobenzylamino)-2,3,4,5-tetrahydro-1H-benzo[d]azepine (10 mg, 0.033 mmol), to give the title compound as a light yellow solid (14 mg, 97%). MS (ES+) m/z: 323 (M+H)$^+$.

EXAMPLE 307

7-Fluoro-6-(4-fluorobenzylamino)-2,3,4,5-tetrahydro-1H-benzo[d]azepine Succinate

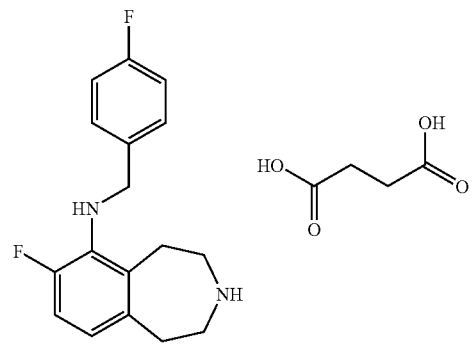

Use a method similar to the General Procedure 5-1 to couple 7-chloro-3-(2,2,2-trifluoroacetyl)-6-trifluoromethanesulfonyloxy-2,3,4,5-tetrahydro-1H-benzo[d]azepine (250 mg, 0.61 mmol) with 4-fluorobenzylamine (92 mg, 1.2 equiv.) using palladium(II) acetate (0.1 equiv.), BINAP (0.3 equiv.) and cesium carbonate (1.4 equiv.) in toluene (5 mL). Purify by chromatography on silica gel eluting with hexane/EtOAc (10:1, 5:1, 3:1 and 1:1) to give 7-fluoro-6-(4-fluorobenzylamino)-3-(2,2,2-trifluoroacetyl)-2,3,4,5-tetrahydro-1H-benzo[d]azepine as an oil.

Use a method similar to the General Procedure 1-3 to deprotect 7-fluoro-6-(4-fluorobenzylamino)-3-(2,2,2-trifluoroacetyl)-2,3,4,5-tetrahydro-1H-benzo[d]azepine. Purify by SCX chromatography to give the free base of the title compound. Use a method similar to the General Procedure 2-1 to give the title compound as an off white solid (14 mg, 6%). MS (ES+) m/z: 289 (M+H)$^+$.

EXAMPLE 308

6-Benzylamino-7-cyano-2,3,4,5-tetrahydro-1H-benzo[d]azepine Succinate

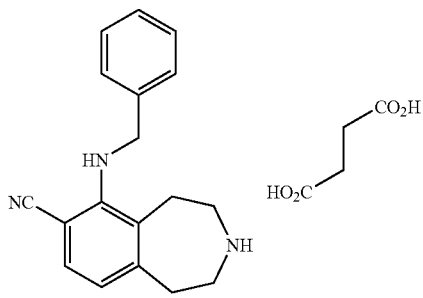

Use a method similar to the General Procedure 5-1 to couple 7-cyano-3-(2,2,2-trifluoroacetyl)-6-trifluoromethanesulfonyloxy-2,3,4,5-tetrahydro-1H-benzo[d]azepine (125 mg, 0.3 mmol) with benzylamine (0.1 mL, 0.9 mmol) using palladium(II) acetate (7 mg, 0.03 mmol), BINAP (37 mg, 0.06 mmol) and cesium carbonate (137 mg, 0.4 mmol) in toluene (3 mL). Purify by chromatography on silica gel eluting with heptane/EtOAc (4:1 to 1:1) to give 6-benzylamino-7-cyano-3-(2,2,2-trifluoroacetyl)-2,3,4,5-tetrahydro-1H-benzo[d]azepine as a clear oil (60 mg, 54%). ES (ES+) m/z: 374 (M+H)+.

Use a method similar to the General Procedure 1-2, using 6-benzylamino-7-cyano-3-(2,2,2-trifluoroacetyl)-2,3,4,5-tetrahydro-1H-benzo[d]azepine (56 mg, 0.15 mmol), to give 6-benzylamino-7-cyano-2,3,4,5-tetrahydro-1H-benzo[d]azepine as a clear oil (38 mg, 93%). MS (ES+) m/z: 278 (M+H)+. Use a method similar to the General Procedure 2-1 to give the title compound as a white powder (39 mg, 71%). MS (ES+) m/z: 278 (M+H)+.

Examples 309-310 may be prepared essentially as described in Example 308 by using 7-cyano-3-(2,2,2-trifluoroacetyl)-6-trifluoromethanesulfonyloxy-2,3,4,5-tetrahydro-1H-benzo[d]azepine and the appropriate amine. Overall yields and MS (ES+) data are shown in the Table below.

| Ex. | R | Compound | Yield (%) | MS (ES+) m/z |
|---|---|---|---|---|
| 309 | 4-F | 7-Cyano-6-(4-fluorobenzyl]amino)-2,3,4,5-tetrahydro-1H- | 46 | 296 (M + H)+ |
| 310 | 2-F | 7-Cyano-6-(2-fluorobenzy]amino)-2,3,4,5-tetrahydro-1H-benzo[d]azepine Succinate | 43 | 296 (M + H)+ |

EXAMPLE 311

6-(3-Fluorobenzylamino)-7-trifluoromethyl-2,3,4,5-tetrahydro-1H-benzo[d]azepine Succinate

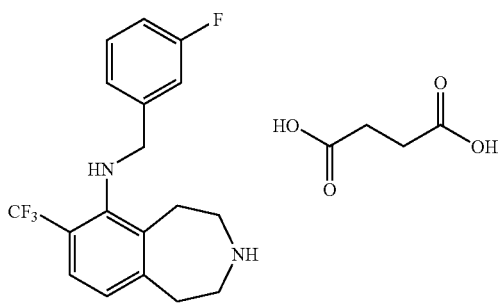

Use a method similar to the General Procedure 5-1 to couple 3-(2,2,2-trifluoroacetyl)-6-trifluoromethanesulfonyloxy-7-trifluoromethyl-2,3,4,5-tetrahydro-1H-benzo[d]azepine (110 mg, 0.24 mmol) and 3-fluorobenzyl amine (90 µL, 0.7 mmol). Purify by chromatography on silica gel eluting with hexane/EtOAc (95:5) followed by SCX chromatography to give 6-(3-fluorobenzylamino)-3-(2,2,2-trifluoroacetyl)-7-trifluoromethyl-2,3,4,5-tetrahydro-1H-benzo[d]azepine as a yellow oil (55 mg, 53%). MS (ES+) m/z: 435 (M+H)+.

Use a method similar to the General Procedure 1-1 to deprotect 6-(3-fluorobenzylamino)-3-(2,2,2-trifluoroacetyl)-7-trifluoromethyl-2,3,4,5-tetrahydro-1H-benzo[d]azepine (55 mg, 0.13 mmol). Purify by SCX chromatography to give 6-(3-fluorobenzylamino)-7-trifluoromethyl-2,3,4,5-tetrahydro-1H-benzo[d]azepine as a yellow oil (34 mg, 81%). Use a method similar to the General Procedure 2-1 to give the title compound as an off-white solid (33 mg, 72%). MS (ES+) m/z: 339 (M+H)+.

EXAMPLE 312

(S)-(−)-6-[1-(4-Fluorophenyl)-ethylamino]-7-trifluoromethyl-2,3,4,5-tetrahydro-1H-benzo[d]azepine Succinate

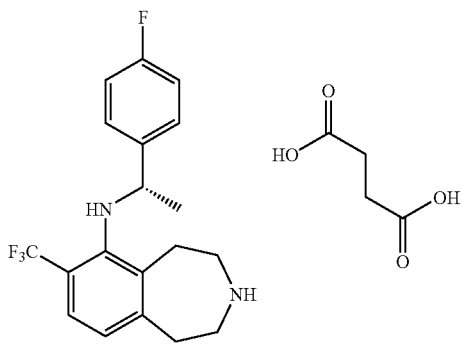

Use a method similar to the General Procedure 5-3 to couple 3-(2,2,2-trifluoroacetyl)-6-trifluoromethanesulfonyloxy-7-trifluoromethyl-2,3,4,5-tetrahydro-1H-benzo[d]azepine (430 mg, 0.94 mmol) with (S)-1-(4-fluorophenyl)ethylamine (195 mg, 1.40 mmol). Purify by chromatography on silica gel eluting with EtOAc/hexane (1:8) to give (S)-6-[1-(4-fluorophenyl)-ethylamino]-3-(2,2,2-trifluoroacetyl)-7-trifluoromethyl-2,3,4,5-tetrahydro-1H-benzo[d]azepine (279 mg, 65%). MS (ES+) m/z: 449 (M+H)+.

Use a method similar to the General Procedure 1-1 to deprotect (S)-6-[1-(4-fluorophenyl)-ethylamino]-3-(2,2,2-trifluoroacetyl)-7-trifluoromethyl-2,3,4,5-tetrahydro-1H-benzo[d]azepine (279 mg, 0.62 mmol). Purify by chromatography on silica gel eluting with DCM/2M ammonia in methanol (94:6) to obtain (S)-6-[1-(4-fluorophenyl)-ethylamino]-7-trifluoromethyl-2,3,4,5-tetrahydro-1H-benzo[d]azepine as a colorless oil (190 mg, 87%). MS (ES+) m/z: 353 (M+H)+. Use a method similar to the General Procedure 2-1 to give the title compound. $[\alpha]^{20}_D$ −96.7° (c 0.5, MeOH).

EXAMPLE 313

(S)-7-Ethyl-6-[1-(4-fluorophenyl)-ethylamino]-2,3,4,5-tetrahydro-1H-benzo[d]azepine Succinate

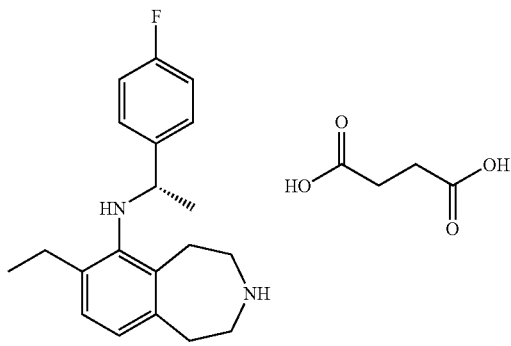

Use a method similar to the General Procedure 5-3 to couple 7-ethyl-3-(2,2,2-trifluoroacetyl)-6-trifluoromethanesulfonyloxy-2,3,4,5-tetrahydro-1H-benzo[d]azepine (335 mg, 0.8 mmol) and (S)-1-(4-fluorophenol)ethyl amine (557 mg, 4.0 mmol). Purify by chromatography on silica gel eluting with hexane/EtOAc (1:0, 9:1 and 17:3) to give (S)-7-ethyl-6-[1-(4-fluorophenyl)-ethylamino]-3-(2,2,2-trifluoroacetyl)-2,3,4,5-tetrahydro-1H-benzo[d]azepine (127 mg, 39%). MS (ES+) m/z: 409 (M+H)+.

Use a method similar to the General Procedure 1-1 to deprotect (S)-7-ethyl-6-[1-(4-fluorophenyl)-ethylamino]-3-(2,2,2-trifluoroacetyl)-2,3,4,5-tetrahydro-1H-benzo[d]azepine. Purify by chromatography on silica gel eluting with DCM/2M ammonia in methanol (93:7) to give (S)-7-ethyl-6-[1-(4-fluorophenyl)-ethylamino]-2,3,4,5-tetrahydro-1H-benzo[d]azepine (70 mg, 72%). MS (ES+) m/z: 313 (M+H)+. Use a method similar to the General Procedure 2-1 to obtain the title compound.

EXAMPLE 314

7-Propyl-6-[(2-thienyl)methylamino]-2,3,4,5-tetrahydro-1H-benzo[d]azepine Hydrochloride

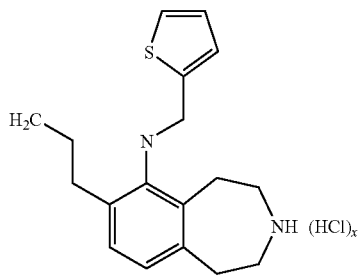

Use a method similar to the General Procedure 5-1 to couple 7-propyl-3-(2,2,2-trifluoroacetyl)-6-trifluoromethanesulfonyloxy-2,3,4,5-tetrahydro-1H-benzo[d]azepine and 2-(aminomethyl)-thiophene. Purify by chromatography on silica gel eluting with hexane/EtOAc (9:1 and 4:1) to give 7-propyl-6-[(2-thienyl)methylamino]-3-(2,2,2-trifluoroacetyl)-2,3,4,5-tetrahydro-1H-benzo[d]azepine as a yellow solid. MS (ES+) m/z: 397 (M+H)+.

Use a method similar to the General Procedure 1-1 to deprotect 7-propyl-6-[(2-thienyl)methylamino]-3-(2,2,2-trifluoroacetyl)-2,3,4,5-tetrahydro-1H-benzo[d]azepine. Purify by SCX chromatography to give the free base of the title compound as a yellow oil. Use a method similar to the General Procedure 2-2 to give the title compound as a light yellow solid. MS (ES+) m/z: 301 (M+H)+.

General Procedure 7

Dissolve the appropriate substituted 3-tert-butoxycarbonyl-6-dimethylcarbamoyl-thio-2,3,4,5-tetrahydro-1H-benzo[d]azepine (1.0 equiv) in methanol (0.1-0.2 M solution). Add potassium hydroxide (32 equiv.) and heat the mixture at 50° C. for 2-8 h. Cool the reaction to ambient temperature and add the appropriate halide (1.0-5.0 equiv.). Stir the mixture at ambient temperature for 0.5-16 h. Remove the solvent in vacuo and partition the residue between DCM and water. Extract the aqueous phase with DCM, combine the organic extracts, dry over $Na_2SO_4$, filter and concentrate. Purify by chromatography in silica gel eluting with hexane/EtOAc mixtures to obtain the desired compound.

Preparation 172

3-tert-Butoxycarbonyl-7-chloro-6-dimethylcarbamoylthio-2,3,4,5-tetrahydro-1H-benzo[d]azepine

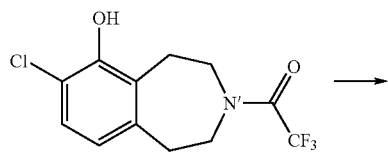

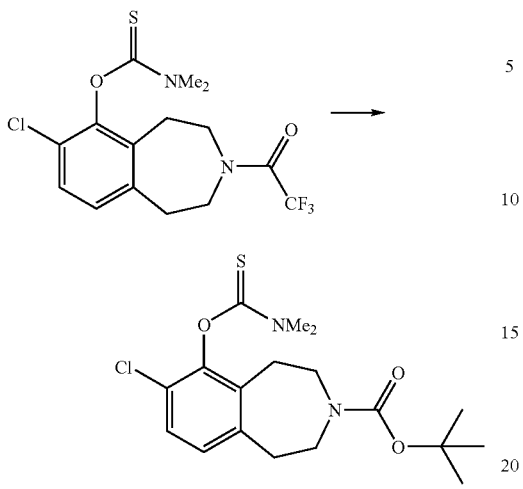

7-Chloro-6-dimethylthiocarbamoyloxy-3-(2,2,2-trifluoroacetyl)-2,3,4,5-tetrahydro-1H-benzo[d]azepine: Place 7-chloro-6-hydroxy-3-(2,2,2-trifluoroacetyl)-2,3,4,5-tetrahydro-1H-benzo[d]azepine (64.3 g, 219 mmol) in acetone (450 mL) and water (200 mL) with $K_2CO_3$ (91.8 g, 664 mmol) and dimethylthiocarbamoyl chloride (31.5 g, 255 mmol). Stir at ambient temperature for 1.25 h. Add additional dimethylthiocarbamoyl chloride (3 g, 24 mmol) and stir for an additional 1.75 h at ambient temperature. Add more dimethylthiocarbamoyl chloride (0.7 g, 5.7 mmol) and water (150 mL) to the mixture and stir for 0.5 h at ambient temperature. Slowly add water (500 mL) to the reaction over 2 h to promote crystallization and stir the resulting slurry at ambient temperature for 1.5 h. Collect the solid by filtration to give the desired intermediate (76 g, 91%).

3-tert-Butoxycarbonyl-7-chloro-6-dimethylcarbamoylthio-2,3,4,5-tetrahydro-1H-benzo[d]azepine: Dissolve 7-chloro-6-dimethylthiocarbamoyloxy-3-(2,2,2-trifluoroacetyl)-2,3,4,5-tetrahydro-1H-benzo[d]azepine (55 g, 407 mmol) in diphenyl ether (1500 mL) and heat to 250° C. for 2.5 h. Cool the reaction and dilute with methanol (308 mL). Add 1N aqueous NaOH (616 mL) and stir at 60° C. for 4 h Cool the reaction to ambient temperature and extract between DCM (3×500 mL) and water (500 mL). Combine the organic extracts and add to 1N aqueous HCl (1 L). Stir the reaction at ambient temperature for 0.25 h then wash with hexane (5×400 mL). Adjust the pH of the aqueous layer to 7.0 with 5N aqueous NaOH and mix the aqueous solution with DCM (2.5 L). Cool the mixture in an ice bath and add $K_2CO_3$ (169 g, 1221 mmol) and di-t-butyl dicarbonate (67.5 g, 390 mmol) and stir the reaction at ambient temperature for 0.5 h. Add di-t-butyl dicarbonate (16.35 g, 75 mmol) and stir for 0.3 h at ambient temperature. Add di-t-butyl dicarbonate (0.1 g, 0.46 mmol) and stir for 0.25 h at ambient temperature. Concentrate the mixture in vacuo to remove the volatiles and warm to 45° C. Seed the mixture with a small amount of the title compound and stir for 1 h at 45° C. Cool the reaction in an ice bath and stir for an additional 2 h. Collect the resultant solid by filtration and rinse with cold hexane (100 mL). Concentrate the filtrate in vacuo, recrystallize from DCM/heptane, and isolate the solids by filtration. Combine the solids and dry in vacuo to give the title compound as a white crystalline solid (142 g, 91%). MS (ES+) m/z 385 (M+H)+.

Preparation 173

3-tert-Butoxycarbonyl-7-chloro-6-diethylcarbamoylthio-2,3,4,5-tetrahydro-1H-benzo[d]azepine and 3-tert-butoxycarbonyl-7,9-dichloro-6-dimethylcarbamoylthio-2,3,4,5-tetrahydro-1H-benzo[d]azepine

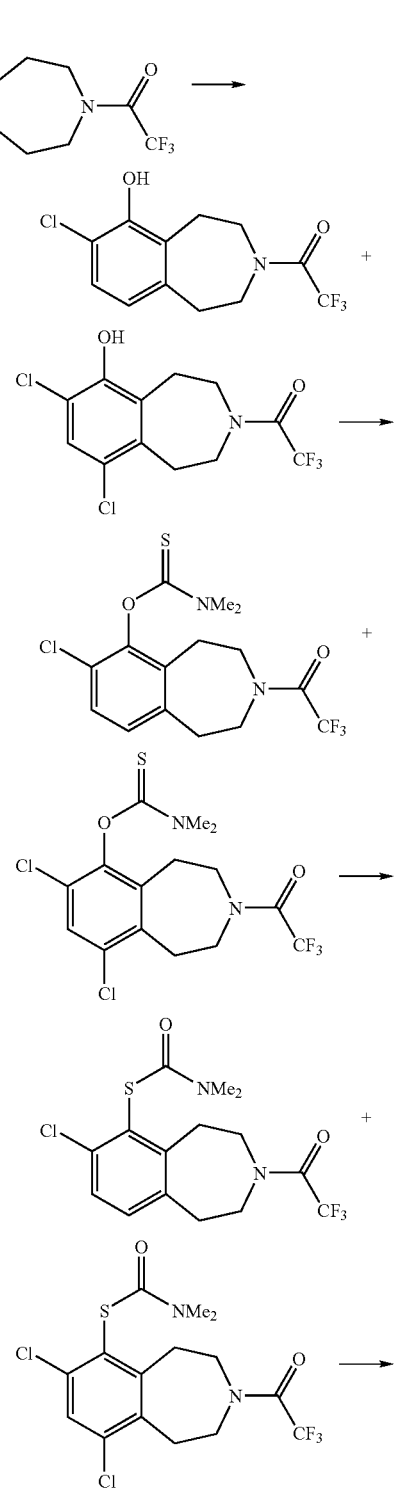

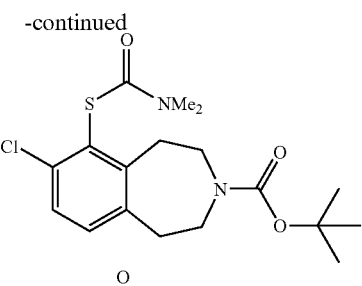

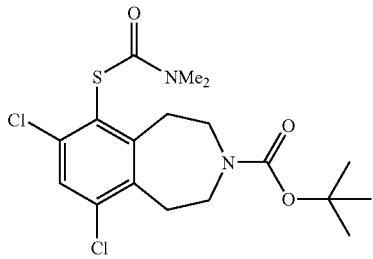

7-Chloro-6-hydroxy-3-(2,2,2-trifluoroacetyl)-2,4,5-tetrahydro-1H-benzo[d]azepine and 7,9-dichloro-6-hydroxy-3-(2,2,2-trifluoroacetyl)-2,3,4,5-tetrahydro-1H-benzo[d]azepine:

To a solution of 6-hydroxy-3-(2,2,2-trifluoroacetyl)-2,3,4,5-tetrahydro-1H-benzo[d]azepine (0.961 g, 3.71 mmol) in toluene (30 mL) at 70° C., add diisobutylamine (52 μL, 0.30 mmol) followed by slow addition of neat sulfuryl chloride (343 μL, 4.27 mmol). Stir for 1 h at 70° C. and concentrate in vacuo. Dilute the residue with water, extract three times with EtOAc, dry over anhydrous Na$_2$SO$_4$ and concentrate in vacuo to afford a 4:1 mixture of 7-chloro-6-hydroxy-3-(2,2,2-trifluoroacetyl)-2,3,4,5-tetrahydro-1H-benzo[d]azepine and 7,9-dichloro-6-hydroxy-3-(2,2,2-trifluoroacetyl)-2,3,4,5-tetrahydro-1H-benzo[d]azepine as a white solid (1.07 g, 98%).

7-Chloro-6-dimethylthiocarbamoyloxy-3-(2,2,2-trifluoroacetyl)-2,3,4,5-tetrahydro-1H-benzo[d]azepine and 7,9-dichloro-6-dimethylthiocarbamoyloxy-3-(2,2,2-trifluoroacetyl)-2,3,4,5-tetrahydro-1H-benzo[d]azepine: To a mixture of 4:1 7-chloro-6-hydroxy-3-(2,2,2-trifluoroacetyl)-2,3,4,5-tetrahydro-1H-benzo[d]azepine and 7,9-dichloro-6-hydroxy-3-(2,2,2-trifluoroacetyl)-2,3,4,5-tetrahydro-1H-benzo[d]azepine (0.513 g, 1.75 mmol) in anhydrous dioxane (10 mL) under nitrogen, add dimethyl thiocarbamoyl chloride (0.432 g, 3.50 mmol), 4-dimethylaminopyridine (21 mg, 0.18 mmol) and triethylamine (731 μL, 5.24 mmol) and heat under reflux overnight. Cool the reaction mixture to ambient temperature and dilute with water, extract three times with EtOAc, dry over anhydrous Na$_2$SO$_4$ and concentrate in vacuo. Purify by chromatography on silica gel eluting with hexane/EtOAc (17:1) to afford a mixture of 4:1 7-chloro-6-dimethylthiocarbamoyloxy-3-(2,2,2-trifluoroacetyl)-2,3,4,5-tetrahydro-1H-benzo[d]azepine and 7,9-dichloro-6-dimethylthiocarbamoyloxy-3-(2,2,2-trifluoroacetyl)-2,3,4,5-tetrahydro-1H-benzo[d]azepine as a yellow oil (0.64 g, 95%)

7-Chloro-6-dimethylcarbamoylthio-3-(2,2,2-trifluoroacetyl)-2,3,4,5-tetrahydro-1H-benzo[d]azepine and 7,9-dichloro-6-dimethylcarbamoylthio-3-(2,2,2-trifluoroacetyl)-2,3,4,5-tetrahydro-1H-benzoazepine: Heat the mixture of 4:1 7-chloro-6-dimethylthiocarbamoyloxy-3-(2,2,2-trifluoroacetyl)-2,3,4,5-tetrahydro-1H-benzo[d]azepine and 7,9-dichloro-6-dimethylthiocarbamoyloxy-3-(2,2,2-trifluoroacetyl)-2,3,4,5-tetrahydro-1H-benzo[d]azepine (0.630 g, 1.66 mmol) in diphenyl ether (4.5 mL) at 250° C. for 4 h under nitrogen. Cool to ambient temperature. Purify by chromatography on silica gel eluting with hexane/EtOAc (7:3) to give a mixture of 4:1 7-chloro-6-dimethylcarbamoylthio-3-(2,2,2-trifluoroacetyl)-2,3,4,5-tetrahydro-1H-benzo[d]azepine and 7,9-dichloro-6-dimethylcarbamoylthio-3-(2,2,2-trifluoroacetyl)-2,3,4,5-tetrahydro-1H-benzo[d]azepine as a yellow oil (0.54 g, 85%).

3-tert-Butoxycarbonyl-7-chloro-6-dimethylcarbamoylthio-2,3,4,5-tetrahydro-1H-benzo[d]azepine and 3-tert-butoxycarbonyl-7,9-dichloro-6-dimethylcarbamoylthio-2,3,4,5-tetrahydro-1H-benzo[d]azepine: To the mixture of 4:1 7-chloro-6-dimethylcarbamoylthio-3-(2,2,2-trifluoroacetyl)-2,3,4,5-tetrahydro-1H-benzo[d]azepine and 7,9-dichloro-6-dimethylcarbamoylthio-3-(2,2,2-trifluoroacetyl)-2,3,4,5-tetrahydro-1H-benzo[d]azepine (0.536 g, 1.47 mmol) in methanol (7 mL), add aqueous potassium carbonate (0.812 g, 5.88 mmol in 1.5 mL of water). Stir for 5 h at ambient temperature; add di-tert-butyl dicarbonate (418 mg, 1.91 mmol) and stir for an additional 30 min. Dilute with EtOAc and water. Separate the layers and extract the aqueous layer three times with EtOAc. Dry over anhydrous Na$_2$SO$_4$, and concentrate in vacuo. Purify by chromatography on silica gel eluting with hexane/EtOAc (7:3) to give a mixture of 4:1 3-tert-butoxycarbonyl-7-chloro-6-dimethylcarbamoylthio-2,3,4,5-tetrahydro-1H-benzo[d]azepine and 3-tert-butoxycarbonyl-7,9-dichloro-6-dimethylcarbamoylthio-2,3,4,5-tetrahydro-1H-benzo[d]azepine as a white solid (0.52 g, 96%).

Preparation 174

7-Bromo-3-tert-butoxycarbonyl-6-dimethylcarbamoylthio-2,3,4,5-tetrahydro-1H-benzo[d]azepine

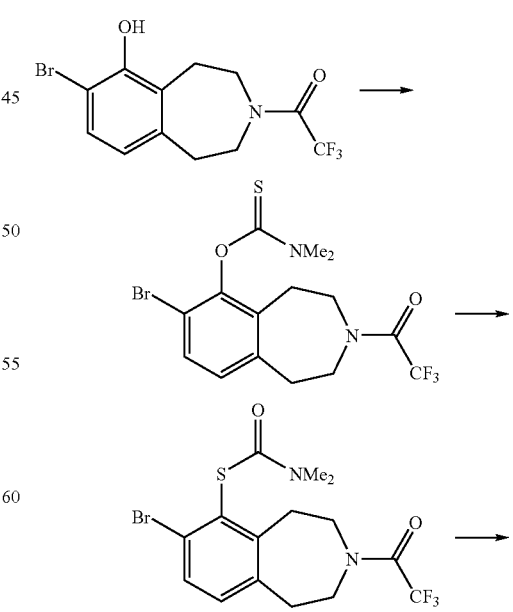

253
-continued

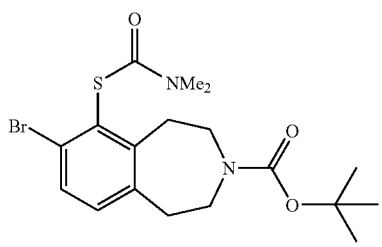

Use a method similar to the Preparation 172, using 7-bromo-6-hydroxy-3-(2,2,2-trifluoroacetyl)-2,3,4,5-tetrahydro-1H-benzo[d]azepine to give the title compound.

Preparation 175

3-tert-Butoxycarbonyl-6-dimethylcarbamoylthio-7-methyl-2,3,4,5-tetrahydro-1H-benzo[a]azepine

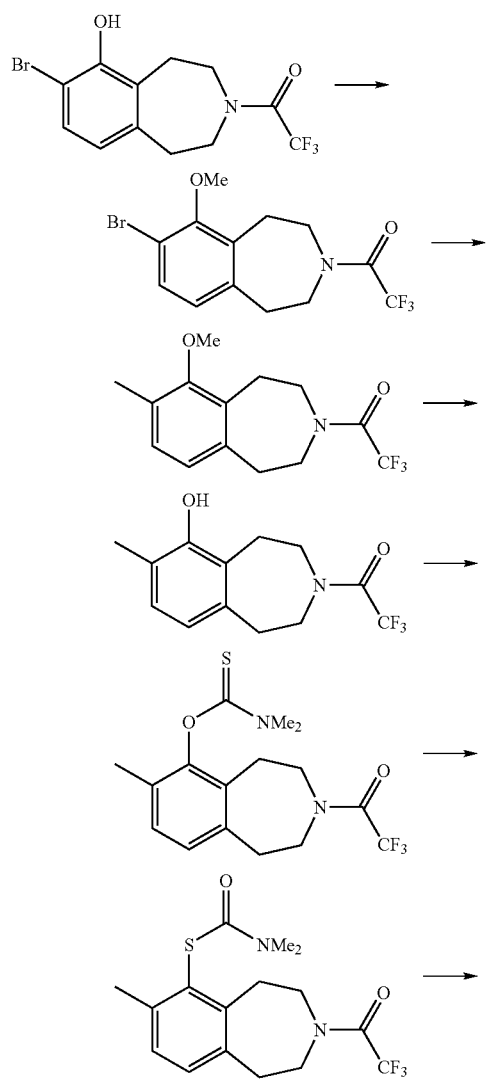

254
-continued

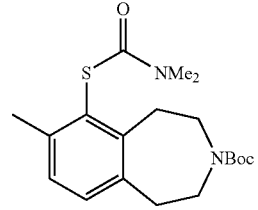

7-Bromo-6-methoxy-3-(2,2,2-trifluoroacetyl)-2,3,4,5-tetrahydro-1H-benzo[d]azepine: Add potassium carbonate (10.214 g, 73.9 mmol) to a solution of 7-bromo-6-hydroxy-3-(2,2,2-trifluoroacetyl)-2,3,4,5-tetrahydro-1H-benzo[d]azepine (5.0 g, 14.8 mmol) in acetone (50 mL) and stir for 10 min. Add methyl iodide (4.2 g, 1.5 mL, 29.6 mmol) and stir the mixture overnight at room temperature. Remove the solvent in vacuo and partition the residue between water and DCM. Extract the aqueous phase twice with DCM. Combine the organic extracts, dry over $Na_2SO_4$, filter and concentrate in vacuo to obtain the desired intermediate as a solid (5.15 g, 99%). MS (ES+) m/z: 352 (M+H)$^+$.

6-Methoxy-7-methyl-3-(2,2,2-trifluoroacetyl)-2,3,4,5-tetrahydro-1H-benzo[d]azepine: Add potassium carbonate (5.65 g, 40.91 mmol), tetrakis(triphenylphosphine)palladium (1.576 g, 1.363 mmol) and trimethylboroxine (2.053 g, 2.3 mL, 16.35 mmol) to a solution of 7-bromo-6-methoxy-3-(2,2,2-trifluoroacetyl)-2,3,4,5-tetrahydro-1H-benzo[d]azepine (4.8 g, 13.63 mmol) in dimethylformamide (40 mL) under nitrogen. Heat the mixture to 115° C. for 6 h. Add water and extract the aqueous phase twice with EtOAc. Combine the organic extracts, dry over $Na_2SO_4$, filter and concentrate in vacuo. Purify by chromatography on silica gel eluting with hexane/EtOAc (1:0 and 19:1) to obtain the desired intermediate as a solid (3.23 g, 83%). GC-MS m/z 287 (M$^+$).

6-Hydroxy-7-methyl-3-(2,2,2-trifluoroacetyl)-2,3,4,5-tetrahydro-1H-benzo[d]azepine: Add borontribromide (21.6 mL, 1.0 M solution in DCM) to a solution of 6-methoxy-7-methyl-3-(2,2,2-trifluoroacetyl)-2,3,4,5-tetrahydro-1H-benzo[d]azepine (3.1 g, 10.8 mmol) in DCM (200 mL) at 0° C. under nitrogen. Warm to room temperature and stir overnight. Dilute with DCM and wash with water. Dry the organic layer over $Na_2SO_4$, filter and concentrate in vacuo. Purify by chromatography on silica gel eluting with hexane/EtOAc (1:0 and 9:1) to obtain the desired intermediate as a solid (2.74 g, 93%). MS (ES+) m/z: 274 (M+H)$^+$.

6-Dimethylthiocarbamoyloxy-7-methyl-3-(2,2,2-trifluoroacetyl)-2,3,4,5-tetrahydro-1H-benzo[d]azepine: Dissolve 6-hydroxy-7-methyl-3-(2,2,2-trifluoroacetyl)-2,3,4,5-tetrahydro-1H-benzo[d]azepine (1.0 g, 3.66 mmol) in acetone (50 mL). Add potassium carbonate (1.517 g, 10.98 mmol) and dimethylthiocarbamoyl chloride (0.904 g, 7.32 mmol). Heat the mixture at reflux overnight. Remove the solvent in vacuo and partition the residue between water and DCM. Dry the organic phase over $Na_2SO_4$, filter and concentrate. Purify by chromatography on silica gel eluting with hexane/EtOAc (1:0 and 9:1) to obtain the desired intermediate as a solid (1.18 g, 90%). MS (ES+) m/z: 361 (M+H)$^+$.

6-Dimethylcarbamoylthio-7-methyl-3-(2,2,2-trifluoroacetyl)-2,3,4,5-tetrahydro-1H-benzo[d]azepine: Dissolve 6-dimethylthiocarbamoyloxy-7-methyl-3-(2,2,2-trifluoroacetyl)-2,3,4,5-tetrahydro-1H-benzo[d]azepine (1.15 g, 3.19 mmol) in diphenyl ether (20 mL) and heat to 265° C. for 3 h in a sealed tube. Cool the reaction to room temperature. Purify by chromatography on silica gel eluting with hexane/EtOAc (4:1 and 7:3) to obtain the desired intermediate as a solid (1.10 g, 96%). MS (ES+) m/z: 361 (M+H)+.

3-tert-Butoxycarbonyl-6-dimethylcarbamoylthio-7-methyl-2,3,4,5-tetrahydro-1H-benzo[d]azepine: Dissolve 6-dimethylcarbamoylthio-7-methyl-3-(2,2,2-trifluoroacetyl)-2,3,4,5-tetrahydro-1H-benzo[d]azepine (1.048 g, 2.9 mmol) in methanol (40 mL). Add a solution of potassium carbonate (1.6 g, 11.6 mmol) in water (10 mL). Stir at room temperature overnight. Remove the solvent and partition the residue between water and DCM. Extract the aqueous phase twice with DCM. Combine the organic extracts, dry over $Na_2SO_4$, filter and concentrate. Dissolve the residue (0.756 g, 2.86 mmol) in DCM (50 mL). Add triethylamine (0.579 g, 0.8 mL, 2.0 equiv) and di-tert-butyl dicarbonate (0.624 g, 2.86 mmol) and stir at room temperature overnight. Dilute with DCM and wash with water. Dry the organic phase over $Na_2SO_4$, filter and concentrate to obtain the title compound as foam (1.038 g, 99%). MS (ES+) m/z: 264 (M+H−Boc)+.

Preparation 176

3-tert-Butoxycarbonyl-7-cyano-6-dimethylcarbamoylsulfanyl-2,3,4,5-tetrahydro-1H-benzo[d]azepine

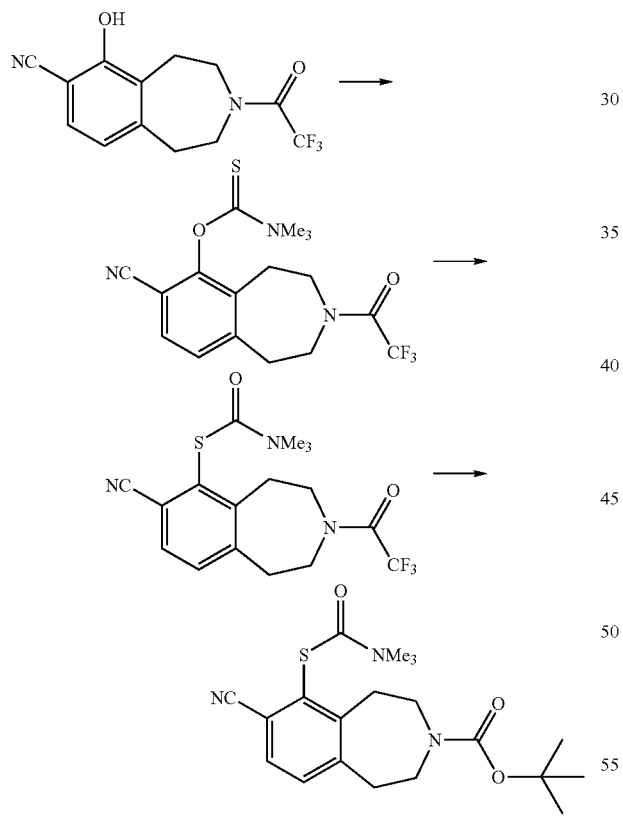

7-Cyano-6-dimethylthiocarbamoyloxy-3-(2,2,2-trifluoroacetyl)-2,3,4,5-tetrahydro-1H-benzo[d]azepine: Add dimethylthiocarbamoyl chloride (197 mg, 1.58 mmol) to a stirred solution of 7-cyano-6-hydroxy-3-(2,2,2-trifluoroacetyl)-2,3,4,5-tetrahydro-1H-benzo[d]azepine (150 mg, 0.53 mmol), DMAP (6 mg, 0.05 mmol) and dry triethylamine (300 µL) in dry 1,4-dioxane (5 mL) under an atmosphere of nitrogen and heat at 120° C. for 6 h. Cool and continue stirring for 2 days at ambient temperature. Dilute with EtOAc, wash with 1N aqueous HCl, water, saturated aqueous $Na_2CO_3$ and brine. Dry over $MgSO_4$ then concentrate in vacuo. Purify by chromatography on silica gel eluting with EtOAc:heptane (0:1 to 3:10) to give the desired intermediate as a white solid (158 mg, 81%).

7-Cyano-6-dimethylcarbamoylsulfanyl-3-(2,2,2-trifluoroacetyl)-2,3,4,5-tetrahydro-1H-benzo[d]azepine: Heat a round bottom flask containing a solution of 7-cyano-6-dimethylthiocarbamoyloxy-3-(2,2,2-trifluoroacetyl)-2,3,4,5-tetrahydro-1H-benzo[d]azepine (786 mg, 2.12 mmol) in diphenyl ether (21 mL) in a preheated oil bath at 230° C. for 2 h. Cool and purify by chromatography on silica gel eluting with EtOAc:heptane (0:1 to 1:1) to give the desired intermediate as a yellow foam (740 mg, 94%). $^1$H NMR (300 MHz, $CDCl_3$) δ 7.60-7.56 (d, 1H), 7.36-7.30 (d, 1H), 3.88-3.68 (m, 4H), 3.34-3.03 (m, 10H).

3-tert-Butoxycarbonyl-7-cyano-6-dimethylcarbamoylsulfanyl-2,3,4,5-tetrahydro-1H-benzo[d]azepine: Add potassium carbonate (4.13 g, 30 mmol) to a stirred solution of 7-cyano-6-dimethylcarbamoylsulfanyl-3-(2,2,2-trifluoroacetyl)-2,3,4,5-tetrahydro-1H-benzo[d]azepine (740 mg, 2.0 mmol) in methanol (40 mL)/water (15 mL) and stir for 1.5 h. Add DCM (10 mL), di-tert-butyl dicarbonate (480 mg, 2.2 mmol) and stir at ambient temperature for 3 days. Concentrate in vacuo and dilute with DCM, wash with water and extract with DCM. Combine the organic layers, wash with brine, dry over $MgSO_4$ and concentrate in vacuo. Purify by chromatography on silica gel eluting with EtOAc:heptane (0:1 to 1:1) to give the title compound as a colourless foam (370 mg, 50%). $^1$H NMR (300 MHz, $CDCl_3$) δ 7.52 (d, J=8 Hz, 1H), 7.29 (d, J=8 Hz, 1H), 3.69-3.48 (m, 4H), 3.26-3.02 (m, 10H), 1.45 (s, 9H).

Preparation 177

(S)-3-tert-Butoxycarbonyl-7-chloro-6-(5-oxo-tetrahydro-furan-2-ylmethylthio)-2,3,4,5-tetrahydro-1H-benzo[d]azepine

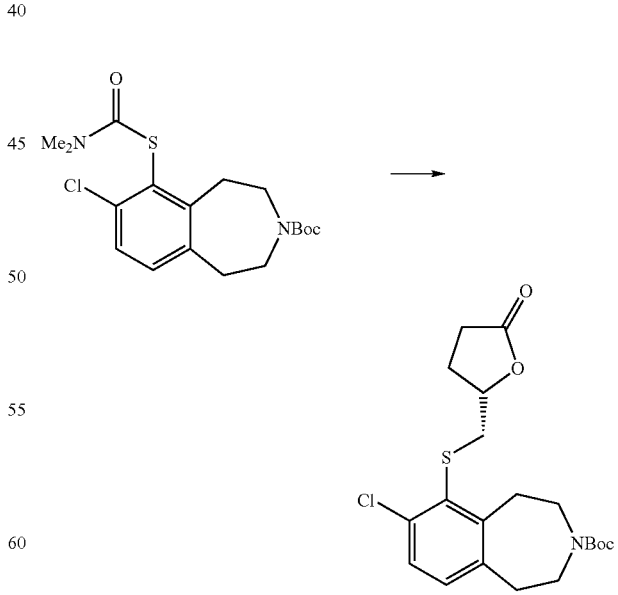

To a solution of 3-tert-butoxycarbonyl-7-chloro-6-dimethylcarbamoylthio-2,3,4,5-tetrahydro-benzo[d]azepine (137 mg, 0.356 mmol) in methanol (2 mL) add potassium hydroxide pellets (640 mg, 11.4 mmol) and heat for 3 h at 50° C. Cool to ambient temperature, add saturated aqueous NH₄Cl, extract three times with EtOAc, dry over anhydrous Na₂SO₄, and concentrate in vacuo. Dissolve the crude thiophenol thus obtained in dry DMF (2 mL), and add with stirring sodium hydride (18 mg, 0.713 mmol, 95% dispersion), followed by (S)-(+)-dihydro-5-(p-tolylsulfonyloxymethyl)-2-(3H)-furanone (144 mg, 0.533 mmol). Continue stirring overnight at ambient temperature, then dilute cautiously with EtOAc and cold saturated aqueous NH₄Cl. Extract three times with EtOAc, dry over anhydrous Na₂SO₄, and concentrate in vacuo. Purify by chromatography on silica gel eluting with hexane/EtOAc (7:3) to give the title compound as a colorless oil.

Preparation 178

5-Chloromethyl-3-methyl-[1,2,4]oxadiazole

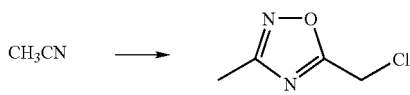

Add with stirring hydroxylamine (50% in water, 25.0 mL, 0.380 mol) to a solution of acetonitrile (5.0 mL, 95.0 mmol) and ethanol (500 mL). Heat at 70° C. for 18 h. Concentrate in vacuo to provide crude N-hydroxyacetamidine (7.0 g, 100%). Add slowly with stirring vinyl chloroacetate (2.1 mL) to N-hydroxyacetamidine (*J. Org. Chem.* 1971, 36, 1306-1307) (1.00 g, 13.5 mmol) and heat at 90° C. for 5 h. Cool to ambient temperature, dilute with DCM, wash with aqueous 1N aqueous NaOH, dry over anhydrous Na₂SO₄ and concentrate in vacuo to give the title compound (904 mg, 50%).

The compounds of Preparation 179-182 were prepared essentially as described in Preparation 178.

| Prep. | Structure | Compound |
|---|---|---|
| 179 | 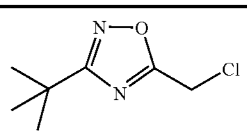 | 3-tert-Butyl-5-chloromethyl-[1,2,4]oxadiazole |
| 180 | 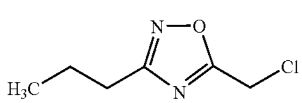 | 5-Chloromethyl-3-propyl-[1,2,4]oxadiazole |
| 181 | 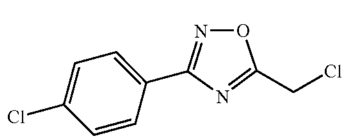 | 5-Chloromethyl-3-(4-chlorophenyl)-[1,2,4]oxadiazole |
| 182 | 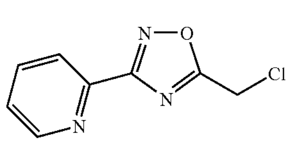 | 2-(5-Chloromethyl-[1,2,4]oxadiazol-3-yl)-pyridine |

Preparation 183

2-Bromomethyl-6-chloropyridine


Heat a mixture of 2-chloro-6-methylpyridine (5.46 g, 42.8 mmol), NBS (8.38 g, 47.08 mmol), and benzoyl peroxide (500 mg, 2.06 mmol) in carbon tetrachloride (80 mL) for 20 h at 85° C. Cool to ambient temperature, filter, and concentrate in vacuo. Purify by chromatography on silica gel eluting with hexane/toluene (4:3) to provide the title compound as a white solid (3.64 g, 41%).

Preparation 184

3-Bromo-2-bromomethyl-pyridine

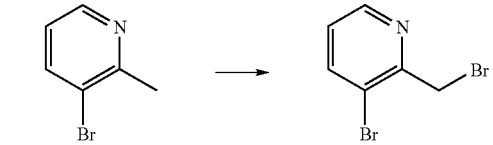

Heat a mixture of 3-bromo-2-methylpyridine (*J. Med. Chem.* 1987, 30, 871-880) (2.7 g, 15.8 mmol), NBS (3.10 g, 17.42 mmol), and benzoyl peroxide (190 mg, 0.78 mmol) in carbon tetrachloride (50 mL) overnight at 85° C. Cool to ambient temperature, filter, and concentrate in vacuo. Purify by chromatography on silica gel eluting with toluene to provide the title compound as a white solid (1.81 g, 45%).

Preparation 185

2-Bromo-6-bromomethyl-pyridine

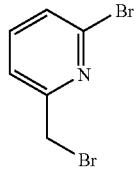

Use a method similar to the Preparation 184, using 2-bromo-6-methylpyridine, to give the title compound.

Preparation 186

5-Bromo-2-bromomethylpyridine

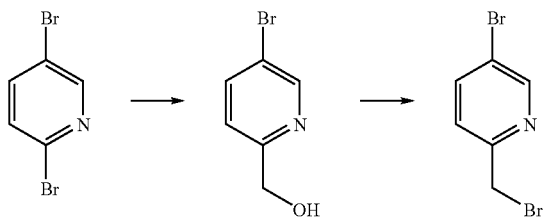

2-Hydroxymethyl-5-bromopyridine: Dissolve 2,5-dibromopyridine (10 g, 42 mmol) in toluene (500 mL) and cool to −78° C. Add 2.5M n-butyllithium in hexane (20.3 mL, 50.6 mmol) and stir the mixture for 7 h at the same temperature. Add DMF (4.2 mL, 54.87 mmol) and stir for 1 h. Warm the solution to 0° C. and add sodium borohydride (3.2 g, 84.42 mmol). Stir the mixture at ambient temperature for 3 h. Dilute with EtOAc and saturated aqueous NH$_4$Cl. Separate the layers and extract the aqueous layer three times with EtOAc. Dry over anhydrous Na$_2$SO$_4$, filter and concentrate in vacuo. Recrystallization from hexane/EtOAc (9:1) gives the desired intermediate as a white solid (5.3 g, 66%).

5-Bromo-2-bromomethyl-pyridine: Dissolve 2-hydroxymethyl-5-bromopyridine (5.21 g, 27.7 mmol) in 48% aqueous hydrobromic acid (20 mL). Heat the mixture at 150° C. for 2 h. Cool to ambient temperature and remove excess hydrobromic acid under vacuum. Dilute with water, add cautiously saturated aqueous NaHCO$_3$ and extract three times with EtOAc. Dry over anhydrous Na$_2$SO$_4$, filter and concentrate in vacuo. Purify by chromatography on silica gel eluting with hexane/EtOAc (9:1) to give the title compound as pink oil (6.0 g, 87%) that crystallizes in the freezer.

Preparation 187

2-Chloromethyl-3-methylpyridine Hydrochloride

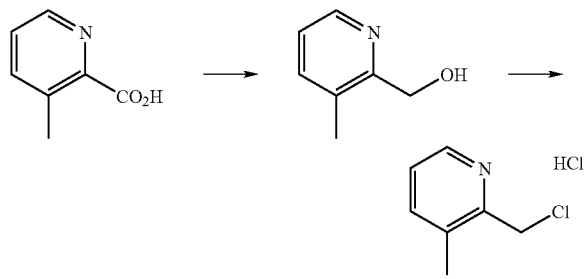

2-Hydroxymethyl-3-methylpyridine: Heat a mixture of 3-methylpicolinic acid (1.0 g, 7.3 mmol), potassium carbonate (4.1 g, 29.7 mmol), and iodomethane (4.4 g, 31.0 mmol) in acetone (35 mL) overnight under reflux. Filter, wash the residue with EtOAc, and concentrate in vacuo. Pass through a short plug of silica gel eluting with hexane/EtOAc (1:1) to provide 2-methoxycarbonyl-3-methylpyridine as a pale yellow liquid (630 mg, 57%). To a solution of 2-methoxycarbonyl-3-methylpyridine in anhydrous THF (10 mL) at 0° C., add with stirring a solution of 1M lithium aluminum hydride in THF (5 mL, 5 mmol), and continue stirring for 30 min at 0° C. Allow the mixture to warm to ambient temperature and quench cautiously with 0.5M aqueous NaOH. Heat the mixture at 60° C. for 40 min, cool to ambient temperature, extract with EtOAc, dry over anhydrous Na$_2$SO$_4$ and concentrate in vacuo. Purify by chromatography on silica gel eluting with hexane/EtOAc (4:3) to give the desired intermediate (90 mg, 18%).

2-Chloromethyl-3-methylpyridine hydrochloride: To 2-hydroxymethyl-3-methylpyridine (90 mg, 0.73 mmol) in dry DCM (10 mL) at ambient temperature, add with stirring thionyl chloride (0.53 mL, 7.3 mmol). Continue stirring overnight, concentrate in vacuo, and azeotrope three times with chloroform. Triturate the residue with dry ether, filter, and dry under vacuum to obtain the title compound as a beige solid (130 mg, 100%).

Preparation 188

2-Chloromethyl-6-Methylpyridine

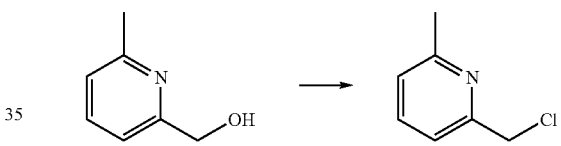

Add with stirring a solution of thionyl chloride (0.77 mL, 10.6 mmol) in dry DCM (20 mL) to 2-hydroxymethyl-6-methylpyridine (1.0 g, 8.12 mmol) in dry DCM (20 mL) at 0° C. Continue stirring at 0° C. for 1.25 h. Quench with isopropanol and concentrate in vacuo. Dissolve the residue in DCM, wash with saturated aqueous NaHCO$_3$, dry over anhydrous Na$_2$SO$_4$, and concentrate in vacuo to give the title compound. MS (ES+) m/z 142 (M+H)$^+$.

Preparation 189

5-Butyl-2-chloromethylpyridine Hydrochloride

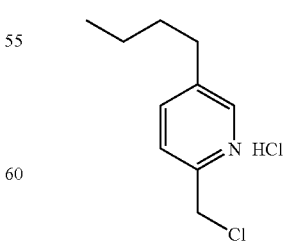

Use a method similar to the Preparation 187, using fusaric acid, to give the title compound. MS (APCI+) m/z 184 (M+H)$^+$.

Preparation 190

6-Bromomethylnicotinonitrile

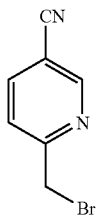

Use a method similar to the Preparation 184, using 5-cyano-2-methylpyridine, to give the title compound.

Preparation 191

5-Bromomethyl-pyridine-2-carbonitrile

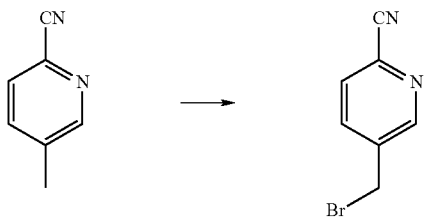

Use a method similar to the Preparation 184, using 5-methyl-picolinonitrile (*J. Chem. Soc.* 1962, 2637-2658), to give the title compound.

Preparation 192

2-Chloromethyl-3-trifluoromethylpyridine Hydrochloride

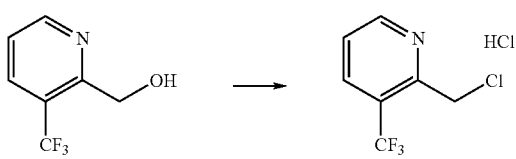

Use the chlorination method described in Preparation 187, using 2-hydroxymethyl-3-trifluoromethylpyridine, to give the title compound. MS (APCI+) m/z 196 (M+H)$^+$.

Preparation 193

2-Chloromethyl-3-methoxypyridine

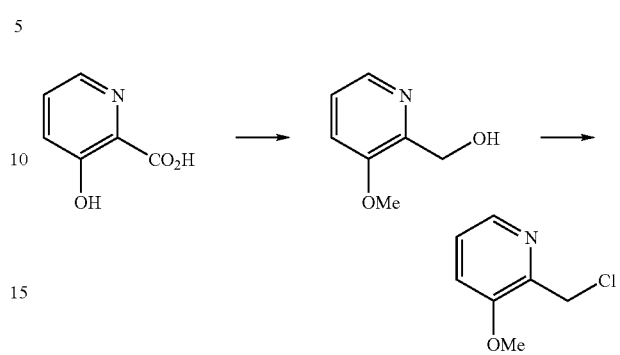

2-Hydroxymethyl-3-methoxypyridine: Heat a mixture of 3-hydroxypicolinic acid (5.3 g, 38 mmol), potassium carbonate (15.8 g, 114 mmol), and iodomethane (9.6 mL, 153 mmol) in acetone (100 mL) and DMF (10 mL) overnight at 60° C. Cool the reaction mixture to ambient temperature, pour into brine, extract three times with ethyl ether, dry over anhydrous MgSO$_4$ and concentrate in vacuo. Pass through a short plug of silica gel eluting with ether to provide 3-methoxy-2-methoxycarbonylpyridine as a pale yellow liquid (6.3 g, 100%). To a solution of 3-methoxy-2-methoxycarbonyl-pyridine (2.34 g, 14.0 mmol) in dry THF (25 mL) add slowly with stirring a solution of 1M lithium aluminum hydride in THF (10 mL, 10 mmol) and continue stirring overnight at ambient temperature. Quench cautiously with sodium sulfate decahydrate, filter under suction and rinse the solids with additional THF. Concentrate in vacuo. Purify by chromatography on silica gel eluting with hexane/EtOAc (3:1) to provide the desired intermediate as a white solid (350 mg, 18%).

2-Chloromethyl-3-methoxypyridine: Use a method similar to the Preparation 188, using 2-hydroxymethyl-3-methoxypyridine, to give the title compound. MS (APCI+) m/z 158 (M+H)$^+$.

Preparation 194

2-Chloromethyl-6-methoxypyridine Hydrochloride

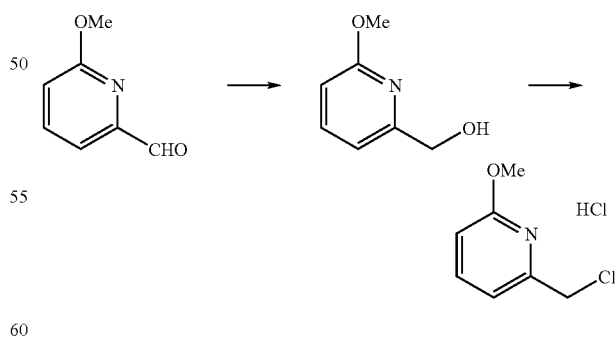

2-Hydroxymethyl-6-methoxypyridine: To 6-methoxy-pyridine-2-carbaldehyde (*J. Org. Chem.* 1990, 55, 69-73) (11.0 g, 80.3 mmol) in wet THF (200 mL) add portion wise with stirring sodium borohydride (3.0 g, 79 mmol) and continue stirring for 1 h at ambient temperature. Add brine, extract the reaction mixture twice with EtOAc, dry the organic layer over anhydrous Na$_2$SO$_4$ and concentrate in vacuo. Pass the residue

Preparation 195

3-Bromomethyl-6-chloro-pyridazine

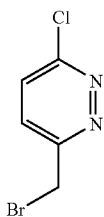

Use a method similar to the Preparation 184, using 3-chloro-6-methylpyridazine, to give the title compound as a red-orange liquid that darkens on standing.

2-Chloromethyl-6-methoxypyridine hydrochloride: Use the chlorination method described in Preparation 187, using 2-hydroxymethyl-6-methoxypyridine, to give the title compound as a pale yellow solid. MS (APCI+) m/z 158 $(M+H)^+$.

through a small plug of silica gel eluting with hexane/EtOAc (3:1) to provide the desired intermediate as a clear liquid (9.0 g, 81%).

Preparation 196

(±)-2-(1-Chloroethyl)-3-cyanothiophene

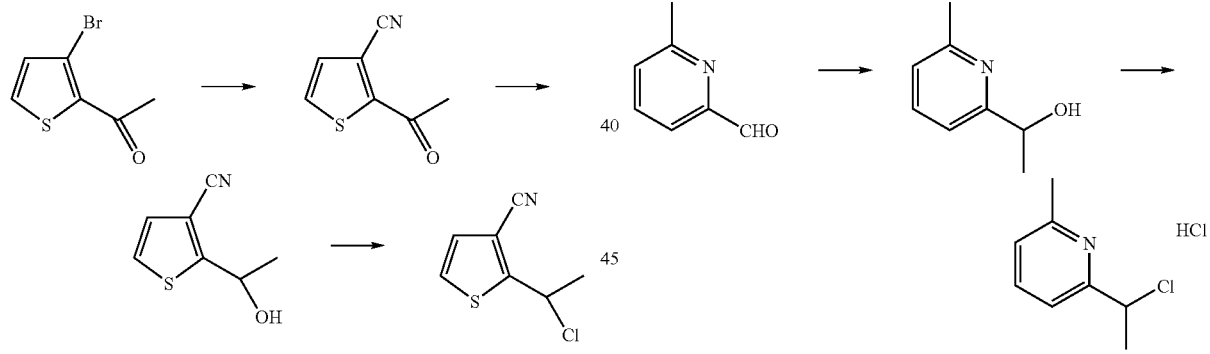

2-Acetyl-3-cyanothiophene: Heat a stirred solution of 2-acetyl-3-bromothiophene (1.49 g, 7.29 mmol) (*Chem. Pharm. Bull.* 2000, 48, 1558-1566) in dry NMP (72 mL) for 10 h at 150° C. in the presence of copper cyanide (3.26 g, 36.5 mmol). Dilute the mixture with water, extract three times with diethyl ether, dry over anhydrous $Na_2SO_4$ and concentrate in vacuo. Purify by chromatography on silica gel eluting with hexane/EtOAc (10:1) to give the desired intermediate as a dark oil (1.1 g, 99%).

(±)-2-(1-Hydroxyethyl)-3-cyanothiophene: Use a method similar to the reduction procedure described in Preparation 194, using 2-acetyl-3-cyanothiophene, to give the desired intermediate as dark oil.

(±)-2-(1-Chloroethyl)-3-cyanothiophene: Use a method similar to the Preparation 188, using (±)-2-(1-hydroxyethyl)-3-cyanothiophene, to give the title compound as dark oil. Use the crude material without further purification.

Preparation 197

(±)-2-(1-Bromoethyl)-pyridine

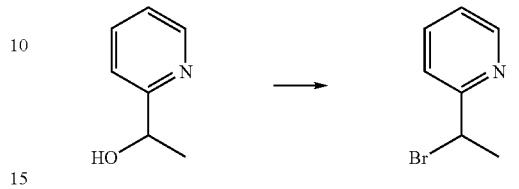

To (±)-2-(1-hydroxyethyl)-pyridine (*Bull. Chem. Soc. Jpn.* 1990, 63, 461-465) (10.0 g, 81.3 mmol) in DCM (120 mL) at 0° C., add with stirring triphenylphosphine (22.39 g, 85.365 mmol) followed by NBS (15.2 g, 85.4 mmol) in portions. Warm the reaction mixture to ambient temperature and continue stirring for 3 h. Concentrate in vacuo and purify by chromatography on silica gel eluting with hexane/EtOAc (19:1) to give the title compound.

Preparation 198

(±)-2-(1-Chloroethyl)-6-methylpyridine Hydrochloride

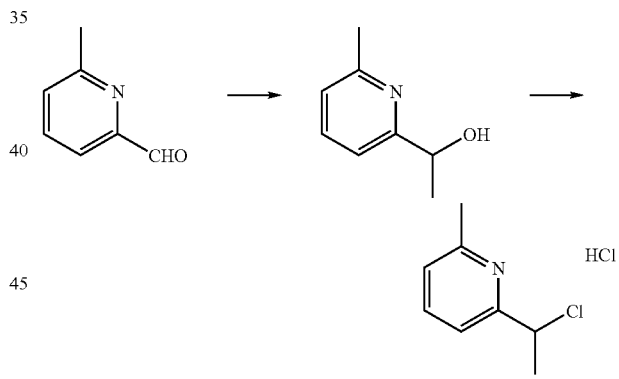

(±)-2-(1-Hydroxyethyl)-6-methylpyridine: To 6-methylpyridine-2-carboxaldehyde (2.0 g, 16.5 mmol) in dry THF (55 mL) at 0° C. under nitrogen, add a solution of 3M methyl magnesium bromide in ether (6.0 mL, 18.0 mmol) dropwise with stirring. After 1 h at 0° C., quench with saturated aqueous $NH_4Cl$, extract three times with EtOAc, dry over anhydrous $Na_2SO_4$ and concentrate in vacuo to give the desired intermediate (crude, 2.3 g).

(±)-2-(1-Chloroethyl)-6-methylpyridine hydrochloride: To the crude 2-(1-hydroxyethyl)-6-methylpyridine (1.6 g, 11.7 mmol) in dry DCM (15 mL) add with stirring thionyl chloride (2.0 mL, 27 mmol) and continue stirring overnight Concentrate in vacuo, azeotrope three times with dry chloroform and dry under high vacuum to provide the title compound as a tan solid (1.9 g, 85%). MS (APCI+) m/z 156 $(M+H)^+$.

Preparation 199

(R)-Methanesulfonic acid 1-(6-methyl-pyridin-2-yl)-ethyl ester

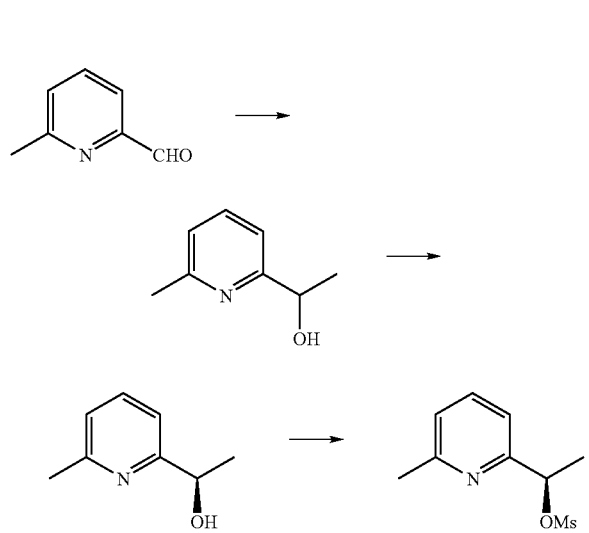

(±)-1-(6-Methyl-pyridin-2-yl)-ethanol: Use a method similar to the Preparation 198 (Step 1), using 6-methyl-2-pyridinecarboxaldehyde and methylmagnesium bromide, to give the desired intermediate.

(R)-1-(6-Methyl-pyridin-2-yl)-ethanol: Stir a mixture of 1-(6-methyl-pyridin-2-yl)-ethanol (2.9 g, 21 mmol), 4 A molecular sieves powder (3 g), vinyl acetate (6 mL) and lipase Candida Antarctica acrylic resin (0.87 g) in i-Pr$_2$O (40 mL) at ambient temperature overnight (J. Org. Chem. 1998, 63, 2481-2487; Synlett 1999, 41-44). Remove the solid residue by filtration. Evaporate the volatile substances and purify by chromatography eluting with hexane/EtOAc (7:3 to 1:1) to give the faster eluting (R)-acetic acid 1-(6-methyl-pyridin-2-yl)-ethyl ester as colorless oil (1.9 g, 50%), and the slower eluting (S)-alcohol as light yellow oil (1.258 g, 43%). Dissolve (R)-acetic acid 1-(6-methyl-pyridin-2-yl)-ethyl ester (1.72 g, 9.62 mmol) in methanol (50 mL) and add potassium carbonate (5.3 g, 38.5 mmol) in water (10 mL). Stir the mixture at ambient temperature for 4 h. Dilute with brine, extract three times with EtOAc, dry over anhydrous Na$_2$SO$_4$, filter through a short pad of silica gel and concentrate in vacuo to give the desired intermediate as a colorless oil (1.17 g, 89%).

(R)-Methanesulfonic acid 1-(6-methyl-pyridin-2-yl)-ethyl ester: To a stirred solution of (R)-1-(6-methyl-pyridin-2-yl)-ethanol (175 mg, 1.28 mmol) and triethylamine (355 µl, 2.56 mmol) in DCM (5 mL) at 0° C. add methanesulfonyl chloride (148 µl, 1.92 mmol). Stir at 0° C. for 30 min and quench the reaction mixture with saturated aqueous NaHCO$_3$ at the same temperature. Extract the mixture three times with EtOAc, dry over anhydrous Na$_2$SO$_4$, and concentrate in vacuo. Purify by chromatography on silica gel eluting with hexane/EtOAc (8:2) to give the title compound as a colorless oil (274 mg, 100%).

Preparation 200

(±)-2-(1-Bromoethyl)-3-methyl-pyridine

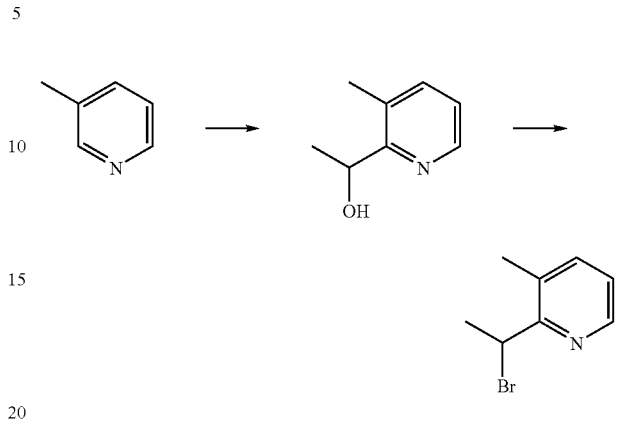

(±)-1-(3-Methyl-pyridin-2-yl)ethanol: Dissolve N,N-dimethylethanolamine (70.45 mmol) in hexane (90 mL) at 0° C., add 2.5M n-butyl lithium in hexane (140.9 mmol,) and stir for 30 min at this temperature. Add a solution of 3-picoline (35.23 mmol) in hexane (10 mL) and continue stirring at 0° C. for 1 h. Cool the resulting mixture to −78° C., add acetaldehyde (70.45 mmol) and continue stirring at −78° C. for 1 h. Dilute with water, warm to ambient temperature, extract three times with EtOAc, dry over anhydrous Na$_2$SO$_4$, and concentrate in vacuo. Purify by chromatography eluting with hexane/EtOAc (85:15) to give the desired intermediate as a light yellow oil.

(±)-2-(1-Bromoethyl)-3-methyl-pyridine: Use a method similar to the Preparation 197, using 1-(3-fluoro-pyridin-2-yl)-ethanol, to give the title compound.

Preparation 201

(±)-2-[1-Methanesulfonyloxy-(2,2,2-trifluoroethyl)]pyridine

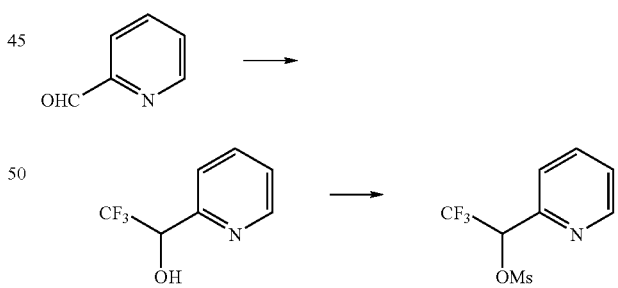

(±)-2-[1-Hydroxy-(2,2,2-trifluoroethyl)]-pyridine: To a stirred solution of 2-pyridine carboxaldehyde (2.09 g, 19.5 mmol) and (trifluoromethyl)trimethylsilane (3.33 g, 23.4 mmol) in THF (30 mL) at 0° C. add 1M tetrabutylammonium fluoride in THF (956 µl, 0.956 mmol). Continue stirring for 30 min at 0° C. and then at ambient temperature for 2 h. Add 1M aqueous HCl (20 mL) and stir 2 h at ambient temperature. Dilute with aqueous 1M aqueous NaOH to pH 8, extract the mixture three times with EtOAc, dry over anhydrous Na$_2$SO$_4$, and concentrate in vacuo. Purify by chromatography eluting with hexane/EtOAc (8:2) to give the desired intermediate as a yellow oil (3.22 g, 93%).

(±)-2-[1-Methanesulfonyloxy-(2,2,2-trifluoroethyl)]pyridine: Use a method similar to the Preparation 199 (Step 3), using (±)-2-[1-hydroxy-(2,2,2-trifluoroethyl)]pyridine, to give the title compound.

Preparation 202

(±)-2-(1-Bromopropyl)pyridine

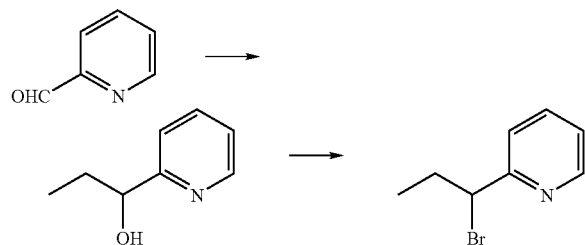

(±)-1-Pyridin-2-yl-propan-1-ol: To a stirred solution of 2-pyridine carboxaldehyde (4.0 g, 37.34 mmol) in THF (50 mL) at 0° C., add 3M ethyl magnesium bromide in ether (18.7 mL, 56.0 mmol), continue stirring for 30 min at 0° C. and then at ambient temperature for 2 h. Add water (200 mL), extract three times with EtOAc, dry over anhydrous Na$_2$SO$_4$, filter through a short pad of silica gel and concentrate in vacuo to give the desired intermediate as a yellow oil (3.39 g, 66%).

(±)-2-(1-Bromopropyl)pyridine: Use a method similar to the Preparation 197, using 1-pyridin-2-yl-propan-1-ol, to give the title compound.

Preparation 203

(±)-1-Pyridazin-3-yl-ethanol

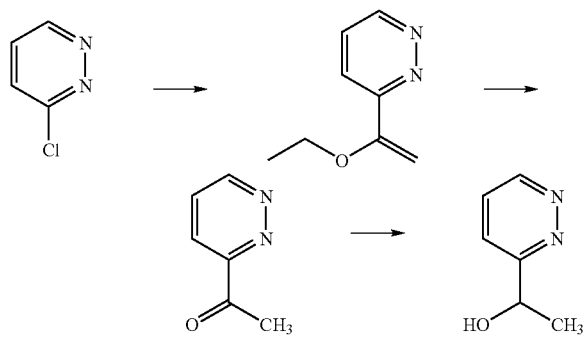

3-(1-Ethoxyvinyl)pyridazine: Heat pyridazine-3-chloride (WO 0107416) (2 g, 17.5 mmol) with tributyl-(1-ethoxyvinyl)tin (7.1 mL, 21.1 mmol) and dichlorobis(triphenylphosphine)palladium(II) (1.1 g, 1.6 mmol) in DMF (18 mL) at 110° C. for 13 h. Cool the mixture, dilute with ether (175 mL) and add a solution of potassium fluoride (5.43 g, 94 mmol) in water (10 mL). After 1 h, filter the mixture through Celite®, and wash the filtrate with brine. Dry the combined organic extracts over Na$_2$SO$_4$ and evaporate. Purify by chromatography on silica gel eluting with EtOAc:hexane (0:1 to 6:4) to obtain the desired intermediate (1.7 g, 65%). HPLC t$_R$=3.7 min (Zorbax Eclipse XBD-C8 4.6×150 mm 5 micron column, 1.5 mL/min of 90/10 to 10/90 0.1% TFA in water/acetonitrile over 10 min. Detector is at 230 and 254 nm.).

1-Pyridazin-3-yl-ethanone: Stir 3-(1-ethoxyvinyl)pyridazine (1.7 g, 11.3 mmol) in acetone (6.3 mL) and 2.5N aqueous HCl (3.1 mL) for 2 h at ambient temperature and evaporate. Dissolve the residue in DCM and wash the organic layer with saturated aqueous NaHCO$_3$, dry the organic layer over Na$_2$SO$_4$ and evaporate to obtain the desired intermediate (1.4 g, 99%). HPLC t$_R$=1.9 min (Zorbax Eclipse XBD-C8 4.6×150 mm 5 micron column, 1.5 mL/min of 90/10 to 10/90 0.1% TFA in water/acetonitrile over 10 min. Detector is at 230 and 254 nm.).

(±)-1-Pyridazin-3-yl-ethanol: To 1-pyridazin-3-yl-ethanone (1.4 g, 11.2 mmol) in methanol (112 mL) add sodium borohydride (0.85 g, 22.5 mmol) at 0° C. and stir for 1 h at ambient temperature. Evaporate the mixture and purify by chromatography on silica gel eluting with EtOAc:hexane (1:1 to 1:0) and methanol:EtOAc (0:1 to 1:9) to obtain the title compound (1.3 g, 93%).

Preparation 204

(R)-(−)-1-(2-Pyridin-2-yl)ethanol methanesulfonate ester

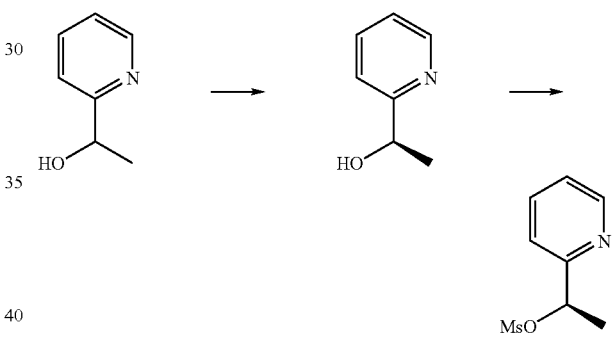

(R)-1-(Pyridin-2-yl)-ethanol: Stir a mixture of (±)-1-(pyridin-2-yl)-ethanol (21.2 mmol), 4 A molecular sieves powder (3 g), vinyl acetate (6 mL) and lipase *Candida Antarctica* acrylic resin (0.87 g) in i-Pr$_2$O (40 mL) at ambient temperature overnight-(*J. Org. Chem.* 1998, 63, 2481-2487; Synlett 1999, 41-44). Remove the solid residue by filtration. Evaporate the volatile substances and purify by chromatography eluting with hexane/EtOAc (7:3 to 1:1) to give the faster eluting (R)acetic acid 1-(pyridin-2-yl)-ethyl ester as colorless oil (50%) and the slower eluting (S)-alcohol as light yellow oil (43%). Dissolve (R)-acetic acid 1-(pyridin-2-yl)-ethyl ester (9.620 mmol) in methanol (50 mL) and add potassium carbonate (38.48 mmol) in water (10 mL). Stir the mixture at ambient temperature for 4 h. Dilute with brine, extract three times with EtOAc, dry over anhydrous Na$_2$SO$_4$, filter through a short pad of silica gel and concentrate in vacuo to give the desired intermediate as a colorless oil (89%).

(R)-(−)-1-(2-Pyridinyl)ethanol methanesulfonate ester: To a stirred solution of (R)-1-(pyridin-2-yl)-ethanol (1.28 mmol) and triethylamine (2.56 mmol) in DCM (5 mL) at 0° C. add methanesulfonyl chloride (1.92 mmol). Stir at 0° C. for 30 min and quench the reaction mixture with saturated aqueous NaHCO$_3$ at the same temperature. Extract three times with EtOAc, dry over anhydrous Na$_2$SO$_4$, and concentrate in vacuo. Purify by chromatography on silica gel eluting with hexane/EtOAc (4:1) to give the title compound as a colorless oil (100%). MS (APCI+) m/z 202 (M+H)+; $[\alpha]_D^{25}=-73.5°$ (c 1, CHCl$_3$).

Preparation 205

(±)-1-(4-Fluorophenyl)ethyl bromide

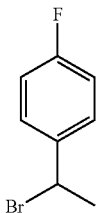

Method A: Add carbon tetrabromide (646 mg, 1.95 mmol) to a solution of triphenylphosphine (511 mg, 1.95 mmol) and (±)-4-fluoro-α-methylbenzyl alcohol (260 mg, 1.86 mol) in dry DMF (20 mL) at 0° C. under nitrogen. Stir the reaction for 2 h to give the title compound. No further purification required.

Method B: Add HBr (460 µL of 48% W/W in water, 4.28 mmol) to a solution of (±)-4-fluoro-α-methylbenzyl alcohol (300 mg, 2.14 mmol) in dry DCM (10 mL) at ambient temperature under an atmosphere of nitrogen. Stir for 2.5 h. Reduce volume in vacuo to give the title compound. Dilute with DCM (1 mL) and use without further purification.

Preparation 206

(±)-2-(1-Bromoethyl)benzonitrile

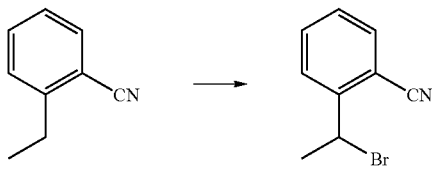

Use a method similar to the Preparation 184, using 2-ethylbenzonitrile, to give the title compound as a clear liquid.

Preparation 207

1-(4-Bromomethylphenyl)-3,3-dimethylbutan-1-one

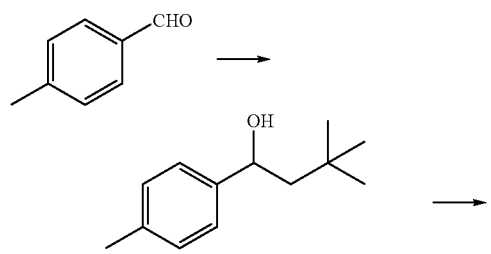

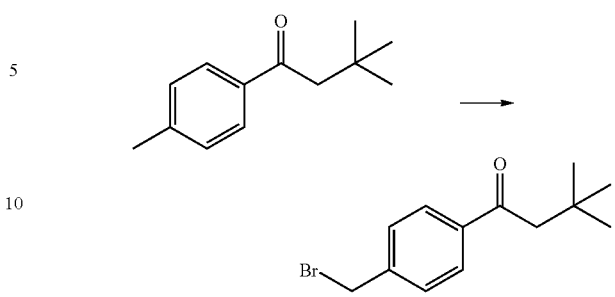

(±)-3,3-Dimethyl-1-p-tolylbutan-1-ol: To a stirred solution of 4-methylbenzaldehyde (1.51 g, 12.6 mmol) in THF (30 mL) at 0° C., add neopentyl magnesium chloride (33.0 mL, 16.34 mmol, 0.5-1M in ether) and continue stirring at 0° C. for 1 h. Dilute with saturated aqueous NH$_4$Cl, extract three times with EtOAc, dry over anhydrous Na$_2$SO$_4$, and concentrate in vacuo. Purify by chromatography on silica gel eluting with hexane/EtOAc (95:5) to give the desired intermediate as a colorless oil (2.15 g, 89%).

3,3-Dimethyl-1-p-tolyl-butan-1-one: To a stirred solution of (±)-3,3-dimethyl-1-p-tolyl-butan-1-ol (2.15 g, 11.3 mmol) in hexane (30 mL) add manganese dioxide (2.94 g, 33.8 mmol) and heat the mixture overnight at 65° C. Cool to ambient temperature, filter the manganese salts, and concentrate in vacuo to give the desired intermediate as a colorless oil (2.2 g, 100%).

1-(4-Bromomethylphenyl)-3,3-dimethylbutan-1-one: Use a method similar to the Preparation 184, using 3,3-dimethyl-1-p-tolylbutan-1-one, to give the title compound.

Preparation 208

1-(Bromomethylphenoxy)-3,3-dimethylbutan-2-one

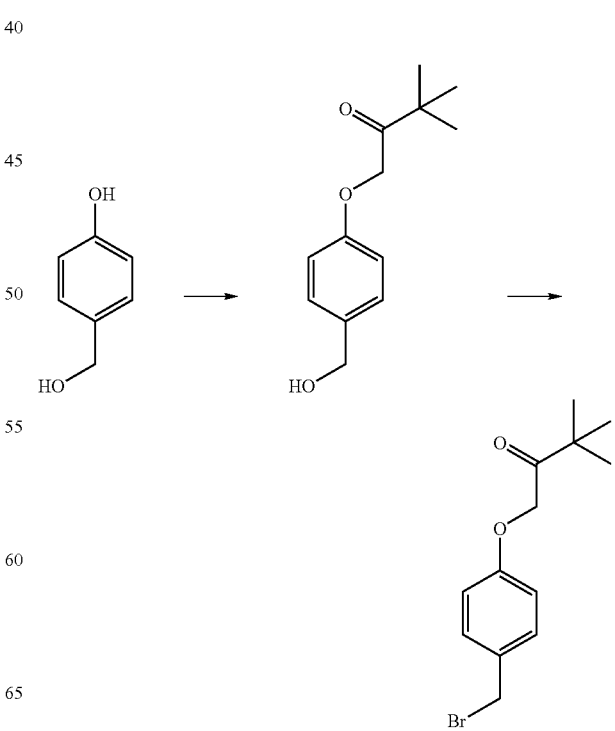

1-(4-Hydroxymethylphenoxy)-3,3-dimethylbutan-2-one:
Mix potassium carbonate (2.764 g, 20 mmol), 4-hydroxybenzyl alcohol (1.49 g, 12 mmol) in absolute ethanol (100 mL), add 1-bromopinacolone (1.791 g, 10 mmol) dropwise. Heat the mixture under reflux for 12 h. Add water to dissolve the solid, and remove most of the ethanol in vacuo. Extract the mixture with EtOAc three times. Combine the organic layers, wash with brine, dry over Na$_2$SO$_4$, filter and concentrate. Purify the residue by chromatography on silica gel eluting with EtOAc:hexane (1:2) to provide the desired intermediate as a colorless oil (1.08 g, 48%). MS (ES+) m/z: 205 M+H−H$_2$O)$^+$.

1-(4-Bromomethylphenoxy)-3,3-dimethylbutan-2-one:
Add phosphorous tribromide (1.45 g, 5.34 mmol) slowly to a solution of 1-(4-hydroxymethyl-phenoxy)-3,3-dimethylbutan-2-one (1.08 g, 4.85 mmol) in anhydrous THF under nitrogen at 0° C. Stir at 0° C. for 1 h and then raise to ambient temperature. Stir overnight. Dilute with EtOAc, wash with saturated aqueous NaHCO$_3$, brine, dry over Na$_2$SO$_4$, filter and concentrate. Purify the residue by chromatography on silica gel eluting with EtOAc:hexane (1:6) to provide the title compound (1.152 g, 83%). MS (ES+) m/z: 205 (M-Br)$^+$.

Preparation 209

1-(4-Bromomethyl-3-chlorophenoxy)-3,3-dimethylbutan-2-one

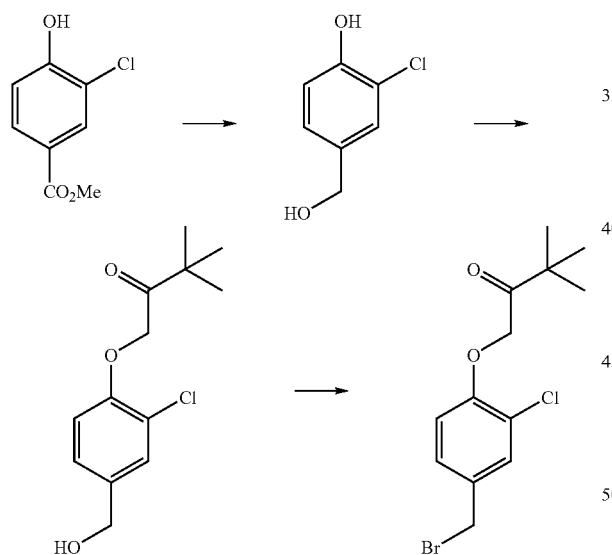

3-Chloro-4-hydroxybenzyl alcohol: Add a solution of DIBAL-H in toluene (1.0 M, 35 mL) to a solution of methyl 3-chloro-4-hydroxybenzoate (1.9 g, 10 mmol) at 0° C. under nitrogen. Stir the reaction at 0° C. and gradually warm to ambient temperature overnight. Quench the reaction with slow addition of 0.1N aqueous HCl, add more acid to break the gel-like solid to two clear layers. Separate the organic layer, and extract the aqueous layer with EtOAc three times. Combine the organic layers, wash with brine, dry over Na$_2$SO$_4$, filter and concentrate to give a white solid. MS (ES−) m/z 157 (M−H)$^−$.

1-(4-Bromomethyl-3-chlorophenoxy)-3,3-dimethyl-butan-2-one: Use a method similar to the Preparation 208 to convert 3-chloro-4-hydroxy-benzyl alcohol to the title compound (1.144 g, 64% two steps). MS (ES+) m/z 319.0 (M+H)$^+$.

Preparation 210

1-Bromomethyl-4-(2,2-dimethyl-propoxy)-benzene

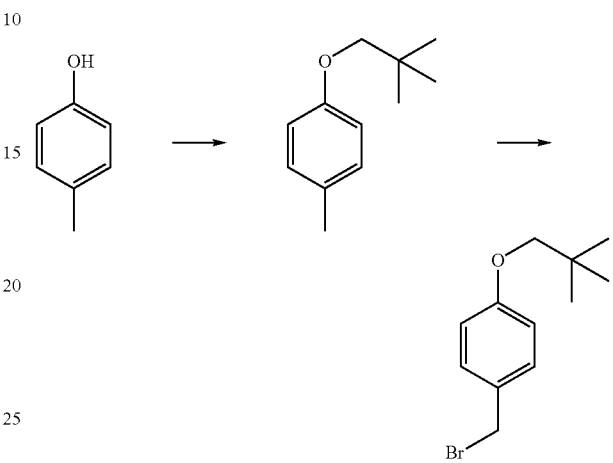

1-(2,2-Dimethyl-propoxy)-4-methyl-benzene: To a solution of p-cresol (526 mg, 4.87 mmol) in THF (50 mL), add with stirring diisopropyl azodicarboxylate (2.16 mL, 10.7 mmol) followed by triphenylphosphine (306 mg, 11.7 mmol) and neopentyl alcohol (5.15 g, 58.4 mmol). Heat at 60° C. for 3 h, cool to ambient temperature and concentrate in vacuo. Purify by chromatography on silica gel eluting with hexane/EtOAc to give the desired intermediate as a colorless oil.

1-Bromomethyl-4-(2,2-dimethyl-propoxy)-benzene: Use a method similar to the Preparation 184, using 1-(2,2-dimethyl-propoxy)-4-methylbenzene, to give the title compound.

Preparation 211

1-Bromomethyl-2-methanesulfonylbenzene

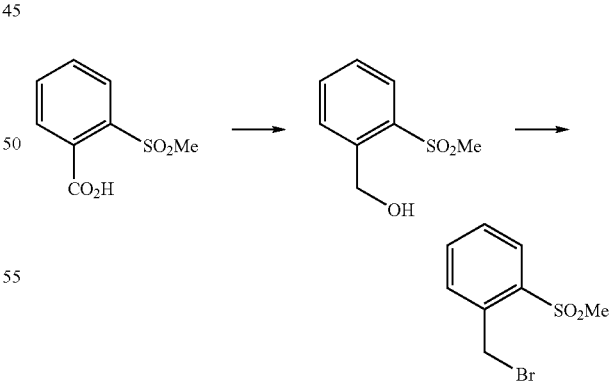

(2-Methanesulfonylphenyl)methanol: To a stirred solution of 2-methanesulfonyl-benzoic acid (2.7 g, 13.5 mmol) in dry THF (60 mL) at 0° C., add a solution of borane in THF (27.0 mL, 0.5 M, 13.5 mmol). Allow the mixture to warm to ambient temperature and continue stirring for 2 days. Quench the excess borane by slow addition of methanol, add brine, extract three times with EtOAc, dry over anhydrous Na$_2$SO$_4$ and concentrate in vacuo to provide the crude desired intermediate as a clear, thick oil (2.4 g, 97%).

1-Bromomethyl-2-methanesulfonylbenzene: To a stirred solution of (2-methanesulfonyl-phenyl)methanol (735 mg, 3.99 mmol) in dry DCM (2 mL) at 0° C., add a solution of 1M phosphorous tribromide in DCM (6.0 mL, 6.0 mmol) and continue stirring for 1 h. Dilute with saturated aqueous NaHCO$_3$, extract three times with ethyl ether, dry over anhydrous MgSO$_4$ and concentrate in vacuo. Purify by chromatography on silica gel eluting with hexane/EtOAc (12:1) to provide the title compound as a white solid (950 mg, 97%).

Preparation 212

1-Bromomethyl-4-(3,3,3-trifluoro-2-methyl-2-trifluoromethylpropylthio)benzene

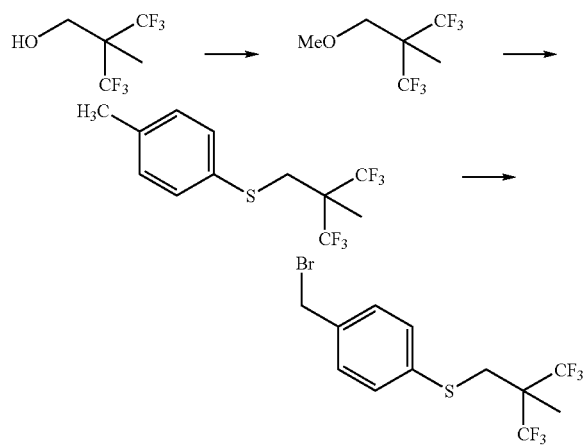

Methanesulfonic acid 3,3,3-trifluoro-2-methyl-2-trifluoromethyl-propyl ester: To 2,2-bis(trifluoromethyl)propanol (4.34 g, 22.1 mmol) in DCM (100 mL) at 0° C. add with stirring triethylamine (6.2 mL, 44 mmol) followed by methanesulfonyl chloride (2.6 mL, 33 mmol). After 15 min at 0° C. dilute with water and extract three times with EtOAc. Dry over anhydrous Na$_2$SO$_4$ and concentrate in vacuo to give the crude desired intermediate as a yellow oil (6.16 g, 100%).

1-Methyl-4-(3,3,3-trifluoro-2-methyl-2-trifluoromethylpropylthio)benzene: In a sealed tube dissolve 4-methylbenzenethiol (4.13 g, 33.2 mmol) in DMF (20 mL) at ambient temperature. Add portionwise with stirring sodium hydride (899 mg, 37.5 mmol) followed by tetrabutylammonium iodide (82 mg, 0.22 mmol) and a solution of methanesulfonic acid 3,3,3-trifluoro-2-methyl-2-trifluoromethylpropyl ester (6.16 g, 22.5 mmol) in DMF (10 mL). Stir at 150° C. overnight, cool the mixture to ambient temperature and dilute cautiously with water. Extract three times with EtOAc, dry over anhydrous Na$_2$SO$_4$, and concentrate in vacuo. Purify by chromatography on silica gel eluting with hexane to give the desired intermediate as a yellow oil (4.5 g, 62%).

1-Bromomethyl-4-(3,3,3-trifluoro-2-meth-yl-2-trifluoromethylpropylthio)benzene: Use a method similar to the Preparation 184, using 1-methyl-4-(3,3,3-trifluoro-2-methyl-2-trifluoromethylpropylthio)benzene, to give the title compound.

Preparation 213

1-Bromomethyl-4-(3,3,3-trifluoro-2-methyl-2-trifluoromethylpropane-1-sulfinyl)-benzene

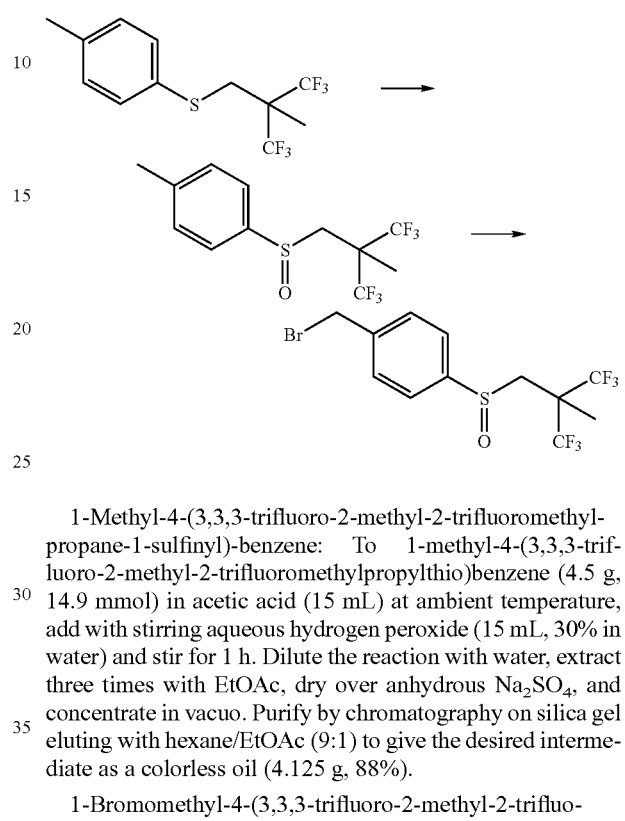

1-Methyl-4-(3,3,3-trifluoro-2-methyl-2-trifluoromethylpropane-1-sulfinyl)-benzene: To 1-methyl-4-(3,3,3-trifluoro-2-methyl-2-trifluoromethylpropylthio)benzene (4.5 g, 14.9 mmol) in acetic acid (15 mL) at ambient temperature, add with stirring aqueous hydrogen peroxide (15 mL, 30% in water) and stir for 1 h. Dilute the reaction with water, extract three times with EtOAc, dry over anhydrous Na$_2$SO$_4$, and concentrate in vacuo. Purify by chromatography on silica gel eluting with hexane/EtOAc (9:1) to give the desired intermediate as a colorless oil (4.125 g, 88%).

1-Bromomethyl-4-(3,3,3-trifluoro-2-methyl-2-trifluoromethylpropane-1-sulfinyl)-benzene: To 1-methyl-4-(3,3,3-trifluoro-2-methyl-2-trifluoromethylpropane-1-sulfinyl)-benzene (4.13 g, 13.0 mmol) in carbon tetrachloride (50 mL) add NBS (2.31 g, 13.0 mmol), benzoyl peroxide (314 mg, 1.30 mmol) and stir overnight at reflux. Cool to ambient temperature, dilute with water and extract three times with EtOAc. Dry over anhydrous Na$_2$SO$_4$ and concentrate in vacuo. Purify by chromatography on silica gel eluting with hexane/EtOAc (9:1) to give the title compound as colorless oil (2.3 g, 55%).

Preparation 214

1-Bromomethyl-4-(2,2-dimethylpropane-1-sulfonyl)benzene

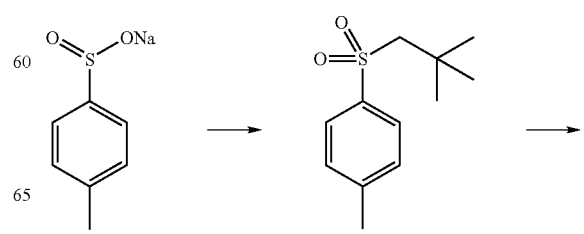

-continued

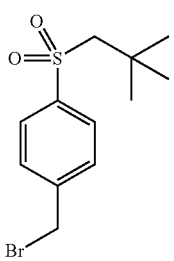

1-(2,2-Dimethyl-propane-1-sulfonyl)-4-methyl-benzene: In a sealed tube, dissolve p-toluenesulfinic acid sodium salt (5.71 g, 32.1 mmol) in DMF (20 mL) and water (10 mL). Add neo-pentyl bromide (6.3 mL, 48 mmol) and tetrabutylammonium iodide (592 mg, 1.60 mmol) and heat the mixture at 145° C. overnight. Cool the reaction to ambient temperature, dilute with water and extract 3 times with EtOAc. Dry over anhydrous $Na_2SO_4$ and concentrate in vacuo. Purify by chromatography on silica gel eluting with hexane/EtOAc (9:1) to give the desired intermediate as a colorless oil (3.3 g, 45%).

1-Bromomethyl-4-(2,2-dimethylpropane-1-sulfonyl)benzene: Use a method similar to the Preparation 213 (Step 2), using 1-(2,2-dimethylpropane-1-sulfonyl)-4-methyl-benzene, to give the title compound.

Preparation 215

1-Bromomethyl-4-(3,3,3-trifluoro-2-methyl-2-trifluoromethylpropane-1-sulfonyl)-benzene

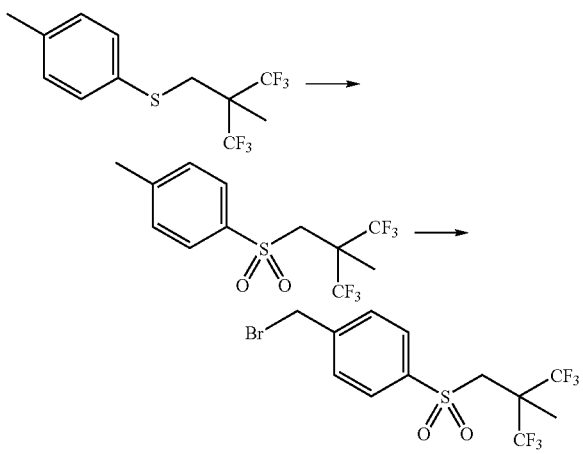

1-Methyl-4-(3,3,3-trifluoro-2-methyl-2-trifluoromethylpropane-1-sulfonyl)benzene: To 1-methyl-4-(3,3,3-trifluoro-2-methyl-2-trifluoromethylpropylthio)benzene (3.47 g, 11.49 mmol) in trifluoroacetic acid (15 mL) at ambient temperature add with stirring aqueous hydrogen peroxide (15 mL, 30% in water) and stir for 1 h. After removing trifluoroacetic acid in vacuo, dilute with saturated aqueous $NaHCO_3$. Extract three times with EtOAc, dry over anhydrous $Na_2SO_4$, and concentrate in vacuo. Purify by chromatography on silica gel eluting with hexane/EtOAc (9:1) to give the desired intermediate as a colorless oil (2.8 g, 74%).

1-Bromomethyl-4-(3,3,3-trifluoro-2-methyl-2-trifluoromethylpropane-1-sulfonyl)benzene: Use a method similar to the Preparation 213 (Step 2), using 1-methyl-4-(3,3,3-trifluoro-2-methyl-2-trifluoromethylpropane-1-sulfonyl)benzene, to give the title compound.

Preparation 216

1-Bromomethyl-4-(4'-trifluoromethyl)-phenylsulfonylbenzene

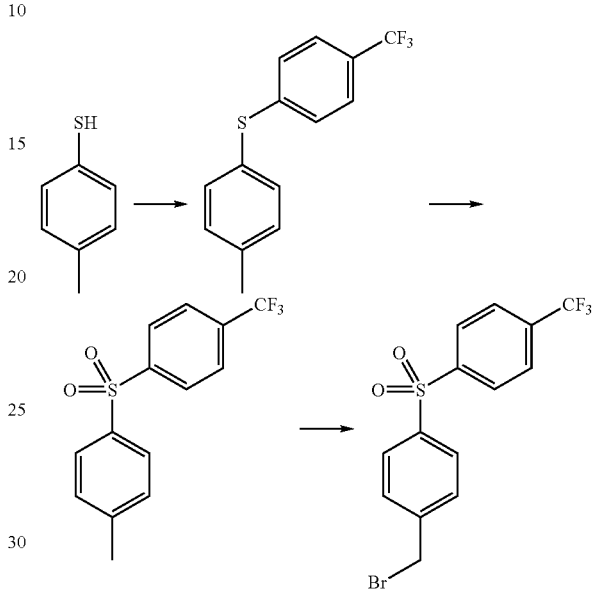

1-Methyl-4-(4-trifluoromethyl)-phenylthio-benzene: Heat a mixture of 4-methylbenzenethiol (7.67 g, 61.8 mmol), 1-bromo-4-trifluoromethyl-benzene (4.63 g, 20.6 mmol), 2,2,6,6-tetramethyl-3,5-heptanedione (379 mg, 2.06 mmol), cesium carbonate (20.1 g, 61.8 mmol) and CuCl (102 mg, 1.03 mmol) in NMP (30 mL) at 150° C. for 3 h. Cool the mixture to ambient temperature, dilute with water, extract three times with EtOAc, dry the organic layer over anhydrous $Na_2SO_4$, and concentrate in vacuo. Recrystallize the residue from hexane/EtOAc to give the desired intermediate as a white solid (3.87 g, 70%).

1-Bromomethyl-4-(4-trifluoromethyl)-phenylsulfonylbenzene: Use a method similar to the Preparation 215, using 1-methyl-4-(4-trifluoromethyl)-phenylthiobenzene, to give the title compound.

Preparation 217

1-(4-Bromomethylbenzenesulfonylmethyl)-2,4-difluorobenzene

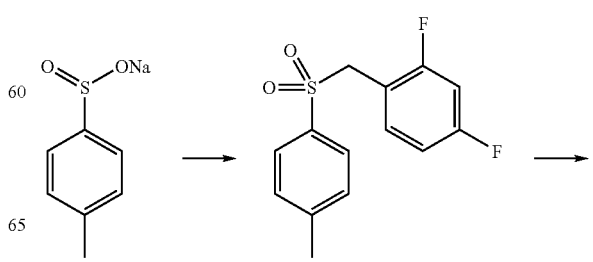

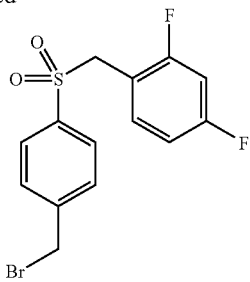

Use a method similar to the Preparation 214, using 2,4-difluorobenzyl bromide, to give the title compound.

Preparation 218

1-Bromomethyl-4-cyclohexylmethanesulfonyl-benzene

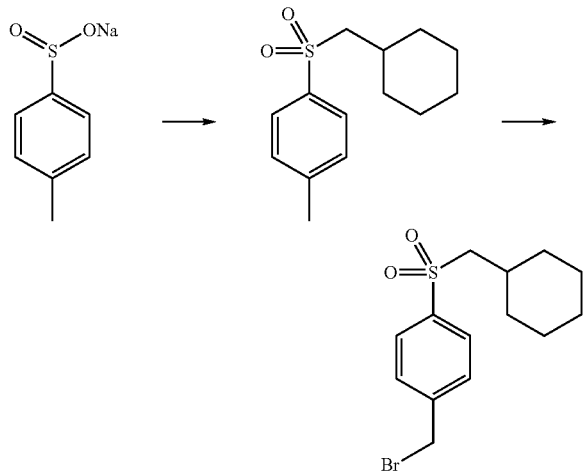

Use a method similar to the Preparation 214, using cyclohexylmethyl bromide, to give the title compound.

Preparation 219

Methyl 4-bromomethyl-2-fluorobenzoate

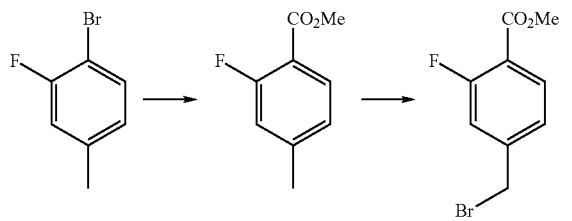

Methyl 2-fluoro-4-methyl-benzoate: Mix 1-bromo-2-fluoro-4-methylbenzene (15 g, 79.4 mmol), palladium acetate (712 mg, 3.17 mmol), 1,3-bis(diphenylphosphino)-propane (2.94 g, 7.14 mmol), triethylamine (16.1 g, 159 mmol) in methanol (150 mL) and DMF (100 mL). Degas the mixture under vacuo and pressurize to 65 psi with carbon monoxide. Stir the reaction at 110° C. for 2 days. Remove methanol in vacuo, dilute the mixture with water, and extract three times with EtOAc. Dry over anhydrous $Na_2SO_4$ and concentrate in vacuo. Purify by chromatography on silica gel eluting with hexane/EtOAc (9:1) to give the desired intermediate as a white solid (7.40 g, 55%). Methyl 4-bromomethyl-2-fluoro-benzoate: Use a method similar to the Preparation 184, using methyl 2-fluoro-4-methylbenzoate, to give the title compound as a white solid.

Preparation 220

4-Chloromethyl-N-cyclohexylbenzamide

To 4-chloromethylbenzoyl chloride (1.03 g, 5.47 mmol) in DCM (20 mL) at 0° C., add with stirring triethylamine (0.839 mL, 6.02 mmol) followed by cyclohexylamine (0.688 mL, 6.02 mmol), and continue stirring for 15 min. Dilute the reaction mixture with aqueous 1M hydrochloric acid, extract three times with EtOAc, wash with water and saturated aqueous $NaHCO_3$. Dry the combined organic extracts over anhydrous $Na_2SO_4$ and concentrate in vacuo to give the title compound as a white solid (1.31 g, 95%).

The compounds of Preparations 221-235 may be prepared essentially as described in Preparation 220 by using 4-chloromethylbenzoyl chloride and the appropriate amine.

| Prep. | NH—R | Compound |
|---|---|---|
| 221 | HN—CH₂C(CH₃)₃ | 4-Chloromethyl-N-(2,2-dimethyl-propyl)-benzamide |
| 222 | HN—C(CH₃)₃ | N-tert-Butyl-4-chloromethyl-benzamide |
| 223 | HN—CH₂-cyclohexyl | 4-Chloromethyl-N-cyclohexylmethyl-benzamide |

-continued

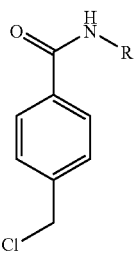

| Prep. | NH—R | Compound |
|---|---|---|
| 224 | (4-CF3-benzyl) | 4-Chloromethyl-N-(4-trifluoromethyl-benzyl)-benzamide |
| 225 | (2,3,4-trifluoro-benzyl) | 4-Chloromethyl-N-(2,3,4-trifluoro-benzyl)-benzamide |
| 226 | (3,4-difluoro-benzyl) | 4-Chloromethyl-N-(3,4-difluoro-benzyl)-benzamide |
| 227 | (2-fluoro-4-CF3-benzyl) | 4-Chloromethyl-N-(2-fluoro-4-trifluoromethyl-benzyl)-benzamide |
| 228 | (3,5-bis-CF3-benzyl) | N-(3,5-Bis-trifluoromethyl-benzyl)-4-chloromethyl-benzamide |
| 229 | (4-fluoro-2-CF3-benzyl) | 4-Chloromethyl-N-(4-fluoro-2-trifluoromethyl-benzyl)-benzamide |
| 230 | (S)-1-cyclohexyl-ethyl | (S)-4-Chloromethyl-N-(1-cyclohexyl-ethyl)-benzamide |
| 231 | (R)-1-cyclohexyl-ethyl | (R)-4-Chloromethyl-N-(1-cyclohexyl-ethyl)-benzamide |

-continued

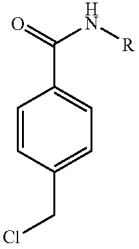

| Prep. | NH—R | Compound |
|---|---|---|
| 232 | (S)-1-(4-F-phenyl)-ethyl | (S)-4-Chloromethyl-N-[1-(4-fluoro-phenyl)-ethyl]-benzamide |
| 233 | (R)-1-(4-F-phenyl)-ethyl | (R)-4-Chloromethyl-N-[1-(4-fluoro-phenyl)-ethyl]-benzamide |
| 234 | (S)-1-(4-Cl-phenyl)-ethyl | (S)-4-Chloromethyl-N-[1-(4-chloro-phenyl)-ethyl]-benzamide |
| 235 | (R)-1-(4-Cl-phenyl)-ethyl | (R)-4-Chloromethyl-N-[1-(4-chlorophenyl)-ethyl]-benzamide |

Preparation 236

2-(2-Iodoethoxy)propane

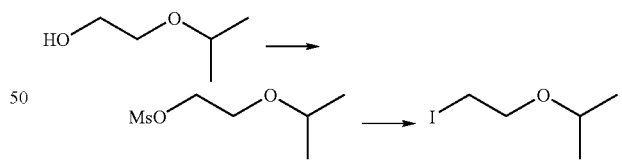

Methanesulfonic acid 2-isopropoxyethyl ester: To a stirred solution of 2-isopropoxyethanol (2.0 mL, 17.37 mmol) in DCM (100 mL) at ambient temperature add methanesulfonyl chloride (1.48 mL, 18.08 mmol). Add triethylamine (2.70 mL, 19.37 mmol) slowly followed by DMAP (catalytic). Continue stirring overnight and concentrate in vacuo. Add diethyl ether and filter. Wash the filtrate with aqueous 1N aqueous HCl, brine, and saturated aqueous NaHCO$_3$. Dry over anhydrous MgSO$_4$ and concentrate in vacuo to give the desired intermediate (2.97 g, 94%).

2-(2-Iodoethoxy)propane: To a stirred solution of methanesulfonic acid 2-isopropoxy-ethyl ester (2.95 g, 16.2 mmol) in acetone (200 mL) at ambient temperature add sodium iodide (7.28 g, 19.4 mmol) and continue stirring overnight. Concentrate in vacuo, add diethyl ether and filter, and concentrate in vacuo to give the title compound as a pale yellow liquid (3.12 g, 90%).

Preparation 237

(R)-Toluene-4-sulfonic Acid Tetrahydrofuran-3-yl Ester

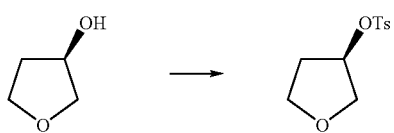

To (R)-tetrahydro-furan-3-ol (2.0 g, 22.7 mmol), triethylamine (3.8 mL, 27.3 mmol), DMAP (277 mg, 2.26 mmol), and silver oxide (5.26 g, 22.7 mmol) in dry DCM (30 mL) at 0° C. under nitrogen, add portion wise with stirring p-toluenesulfonyl chloride (4.76 g, 25.0 mmol). Warm to ambient temperature overnight, filter from silver salts, and concentrate in vacuo. Purify by chromatography on silica gel eluting with hexane/EtOAc (7:1) to give the title compound as a clear liquid (4.7 g, 85%).

Preparation 238

(S)-Toluene-4-sulfonic Acid Tetrahydrofuran-3-yl Ester

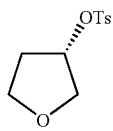

Use a method similar to the Preparation 237, using (S)-tetrahydro-furan-3-ol, to give the title compound as a clear liquid.

Preparation 239

2-(2-Bromoethyl)-pyridine Hydrobromide

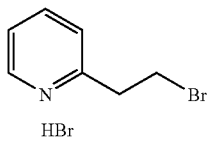

Use a method similar to the bromination procedure described in Preparation 186 (Step 2), using 2-pyridineethanol, to give the title compound. Recrystallize from 2-propanol to give a light brown solid.

Preparation 240

5-(3-Bromopropyl)-3-tert-butyl-[1,2,4]oxadiazole

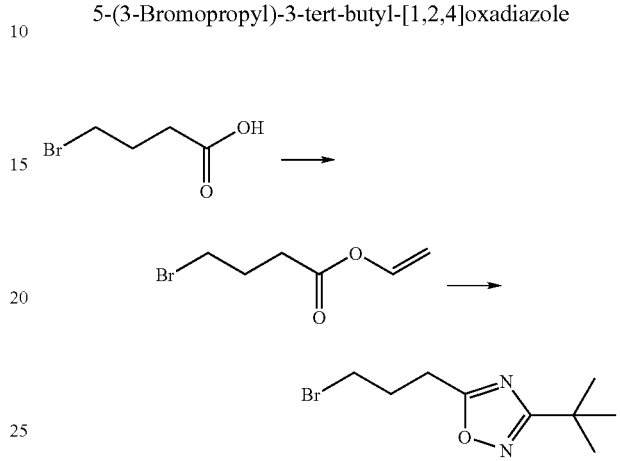

4-Bromobutyric acid vinyl ester: To 4-bromobutyric acid (1.0 g, 6.0 mmol) in vinyl acetate (54 mL) add with stirring palladium(II) acetate (188 mg, 0.84 mmol) and continue stirring overnight at ambient temperature. Filter and concentrate in vacuo to provide the crude desired intermediate.

5-(3-Bromopropyl)-3-tert-butyl[1,2,4]oxadiazole: Use a method similar to the Preparation 178, using 4-bromobutyric acid vinyl ester, to give the title compound.

Preparation 241

1-Bromomethyl-2-fluoro-4-phenoxybenzene

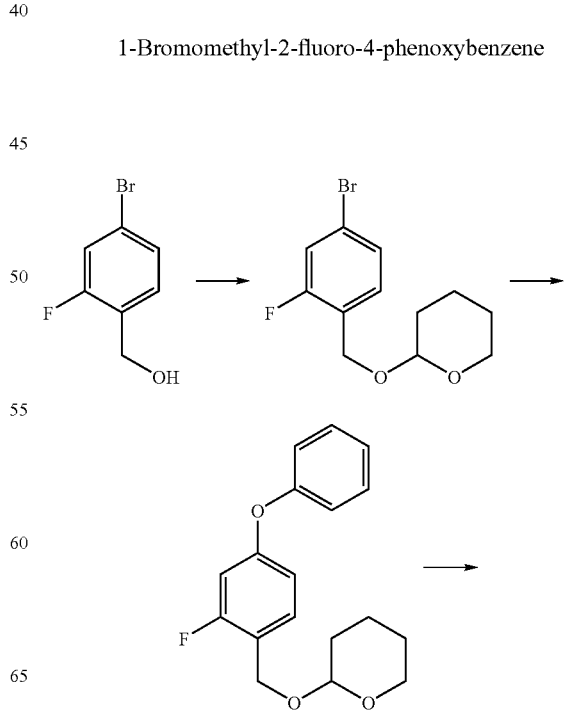

-continued

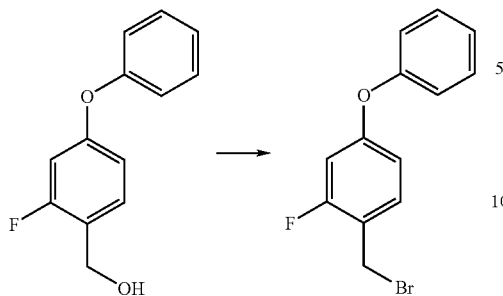

2-(4-Bromo-2-fluoro-benzyloxy)-tetrahydro-pyran: Mix under nitrogen atmosphere 4-bromo-2-fluorobenzyl alcohol, (4.1 g, 20 mmol), dihydropyran (2 g, 24 mmol), p-toluenesulfonic acid monohydrate (100 mg, 0.52 mmol), and anhydrous DCM (70 mL). Stir for 16 h at ambient temperature. Dilute with DCM, wash sequentially with saturated aqueous NaHCO$_3$ then brine. Separate the organic layer, dry over Na$_2$SO$_4$ and concentrate in vacuo. Purify by chromatography on silica gel eluting with hexane/EtOAc (1:0 and 9:1) to obtain the desired intermediate as a clear oil (4.36 g, 75%). MS (ES+) m/z: 312 (M+Na)$^+$.

2-(2-Fluoro-4-phenoxy-benzyloxy)-tetrahydro-pyran: Mix under argon atmosphere 2-(4-bromo-2-fluorobenzyloxy)-tetrahydropyran (2.9 g, 10 mmol), phenol (1.9 g, 20 mmol), 2,2,6,6-tetramethylheptane-3,5-dione (184.3 mg, 1.0 mmol), cesium carbonate (6.5 g, 20 mmol) and anhydrous NMP (20 mL). Degas the flask and fill with argon. Add copper(I) chloride (495 mg, 5 mmol) quickly. Degas the flask three times then fill with argon. Heat at 120° C. for 3 h. Cool to ambient temperature. Dilute with EtOAc and filter. Concentrate in vacuo and purify by chromatography on silica gel to obtain the desired intermediate (2.05 g, 68%). MS (ES+) m/z: 325 (M+Na)$^+$.

(2-Fluoro-4-phenoxy-phenyl)-methanol: Mix under nitrogen atmosphere 2-(2-fluoro-4-phenoxy-benzyloxy)-tetrahydro-pyran (2.05 g, 6.8 mmol), methanol (60 mL) and p-toluenesulfonic acid monohydrate (260 mg, 1.35 mmol). Stir at ambient temperature for 16 h. Dilute with EtOAc. Wash with saturated aqueous NaHCO$_3$. Separate the organic layer, dry over Na$_2$SO$_4$ and concentrate in vacuo to give the desired intermediate (1.41 g, 95%). MS (ES+) m/z: 201 (M–OH)$^+$.

1-Bromomethyl-2-fluoro-4-phenoxy-benzene: Dissolve under nitrogen atmosphere (2-fluoro-4-phenoxyphenyl)-methanol (1.41 g, 6.5 mmol) in anhydrous THF (60 mL). Cool to 0° C. in an ice bath. Add phosphorous tribromide (2.11 g, 7.8 mmol). Stir at cold for 1 h, then remove the ice bath and stir at ambient temperature for 16 h. Quench the reaction with saturated aqueous NaHCO$_3$. Extract aqueous phase three times with EtOAc. Combine organic fractions, wash with brine, dry over Na$_2$SO$_4$ and concentrate in vacuo. Purify by chromatography on silica gel eluting with hexane/EtOAc (9:1). Evaporate the solvent to obtain the title compound (1.31 g, 72%).

Preparation 242

3-tert-Butoxycarbonyl-7-chloro-6-(4-hydroxymethyl-benzylthio)-2,3,4,5-tetrahydro-1H-benzo[d]azepine

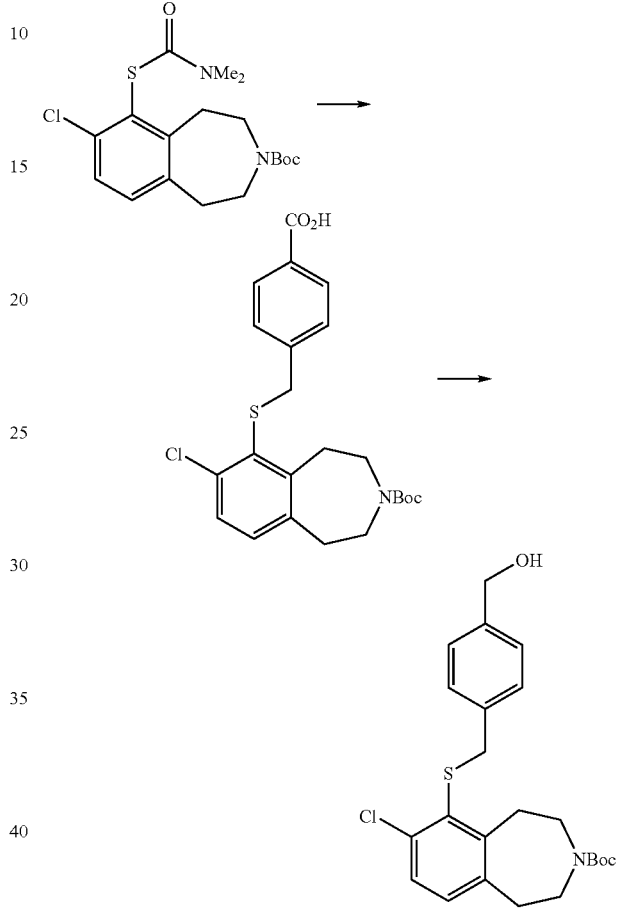

3-tert-Butoxycarbonyl-6-(4-carboxy-benzylthio)-7-chloro-2,3,4,5-tetrahydro-1H-benzo[d]azepine: To a solution of 3-tert-butoxycarbonyl-7-chloro-6-dimethylcarbamoylthio-2,3,4,5-tetrahydro-1H-benzo[d]azepine (1.0 g, 2.6 mmol) in methanol (15 mL) under nitrogen, add with stirring potassium hydroxide (4.5 g, 80.3 mmol) at ambient temperature. Heat at 55-60° C. for 2 h, cool to ambient temperature, and add methyl 4-bromomethylbenzoate (1.2 g, 5.2 mmol). TLC after 20 min shows formation of product; however, after 4 h at ambient temperature both TLC and LC/MS indicate complete hydrolysis of the ester and the carbamate. Dilute with saturated aqueous NH$_4$Cl, extract three times with EtOAc, dry over anhydrous MgSO$_4$, and concentrate in vacuo. Dissolve the crude material in THF (10 mL), treat with di-tert-butyl-dicarbonate (2 equiv) and saturated aqueous NaHCO$_3$ (10 mL), and stir overnight. Extract three times with EtOAc, dry over anhydrous MgSO$_4$ and concentrate in vacuo to give the desired intermediate as an oil that was used without purification [2.32 g, 50% purity with (Boc)$_2$O]. MS (ES+) m/z 348 (M+H–Boc)$^+$.

3-tert-Butoxycarbonyl-7-chloro-6-(4-hydroxymethyl-benzylthio)-2,3,4,5-tetrahydro-1H-benzo[d]azepine: To a solution of 3-tert-butoxycarbonyl-6-(4-carboxybenzylthio)-

7-chloro-2,3,4,5-tetrahydro-1H-benzo[d]azepine (1.85 g, 50% purity, 2.06 mmol) in anhydrous THF (40 mL) under nitrogen, add with stirring 1M borane in THF (4.2 mL) at 0° C. Warm to ambient temperature and stir 2-3 h. Quench by the careful addition of water (3 mL), dilute with saturated aqueous NaHCO₃, extract three times with ethyl ether, dry over anhydrous MgSO₄, and concentrate in vacuo. Purify by chromatography on silica gel eluting with hexane/EtOAc (5:1) to provide the title compound as a white solid (485 mg, 54%).

Preparation 243

3-tert-Butoxycarbonyl-7-chloro-6-(4-methanesulfonylmethylbenzylthio)-2,3,4,5-tetrahydro-1H-benzo[d]azepine

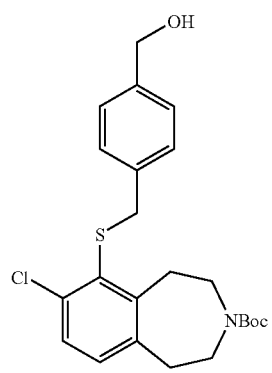
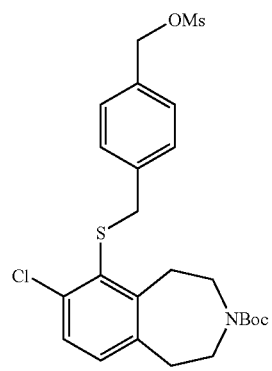
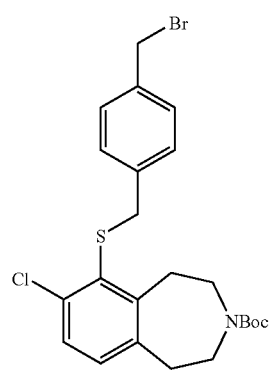
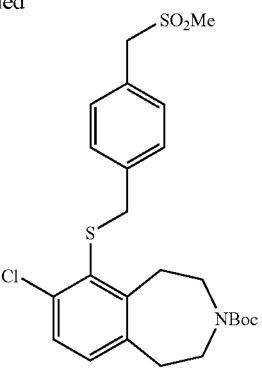

3-tert-Butoxycarbonyl-7-chloro-6-(4-methanesulfonyloxymethyl-benzylthio)-2,3,4,5-tetrahydro-1H-benzo[d]azepine: To a stirred solution of 3-tert-butoxycarbonyl-7-chloro-6-(4-hydroxymethyl-benzylthio)-2,3,4,5-tetrahydro-1H-benzo[d]azepine (170 mg, 0.391 mmol) in anhydrous DCM under nitrogen, add methanesulfonyl chloride (33 µL, 0.426 mmol) and triethylamine (61 µL, 0.44 mmol) and continue stirring for 2 h. Dilute with water (5 mL) and extract three times with DCM. Wash the combined organic extracts with brine, dry over anhydrous Na₂SO₄, and concentrate in vacuo to obtain the desired intermediate that was used without purification.

3-tert-Butoxycarbonyl-6-(4-bromomethyl-benzylthio)-7-chloro-2,3,4,5-tetrahydro-1H-benzo[d]azepine: Dissolve the crude 3-tert-butoxycarbonyl-7-chloro-6-(4-methanesulfonyloxymethyl-benzylthio)-2,3,4,5-tetrahydro-1H-benzo[d]azepine in anhydrous acetone (3 mL), treat with anhydrous lithium bromide (335 mg, 3.89 mmol) and continue stirring overnight. Add water, extract the reaction mixture three times with ethyl ether, wash with brine, dry over anhydrous MgSO₄, and concentrate in vacuo to obtain the desired intermediate that was used without purification.

3-tert-Butoxycarbonyl-7-chloro-6-(4-methanesulfonylmethyl-benzylthio)-2,3,4,5-tetrahydro-1H-benzo[d]azepine: To the crude 3-tert-butoxycarbonyl-6-(4-bromomethyl-benzylthio)-7-chloro-2,3,4,5-tetrahydro-1H-benzo[d]azepine in anhydrous DMF (1 mL) under nitrogen, add with string sodium methanesulfinate (400 mg, 3.9 mmol), and continue stirring for 30 min at ambient temperature followed by 2 h at 40° C. Add water, extract three times with EtOAc, wash with brine, dry over anhydrous MgSO₄, and concentrate in vacuo. Purify by chromatography on silica gel eluting with hexane/EtOAc (3:1) to give a clear oil that solidifies on standing to a white solid (118 mg, 61%).

Preparation 244

6-(4-Bromo-3-fluorobenzylthio)-3-tert-butoxycarbonyl-7-chloro-2,3,4,5-tetrahydro-1H-benzo[d]azepine

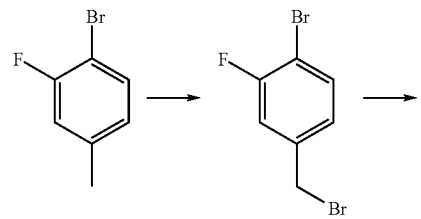

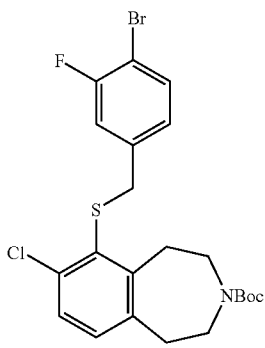

1-Bromo-4-bromomethyl-2-fluorobenzene: Use a method similar to the Preparation 184, using 4-bromo-3-fluorotoluene, to give the desired intermediate as a white solid.

6-(4-Bromo-3-fluorobenzylthio)-3-tert-butoxycarbonyl-7-chloro-2,3,4,5-tetrahydro-1H-benzo[d]azepine: Use a method similar to the Preparation 177, using 3-tert-butoxycarbonyl-7-chloro-6-dimethylcarbamoylthio-2,3,4,5-tetrahydro-1H-benzo[d]azepine and 1-bromo-4-bromomethyl-2-fluorobenzene, to give the title compound as a white solid.

Preparation 245

(±)-3-tert-Butoxycarbonyl-7-chloro-6-(1-methoxycarbonyl-1-phenyl-methylthio)-2,3,4,5-tetrahydro-1H-benzo[d]azepine

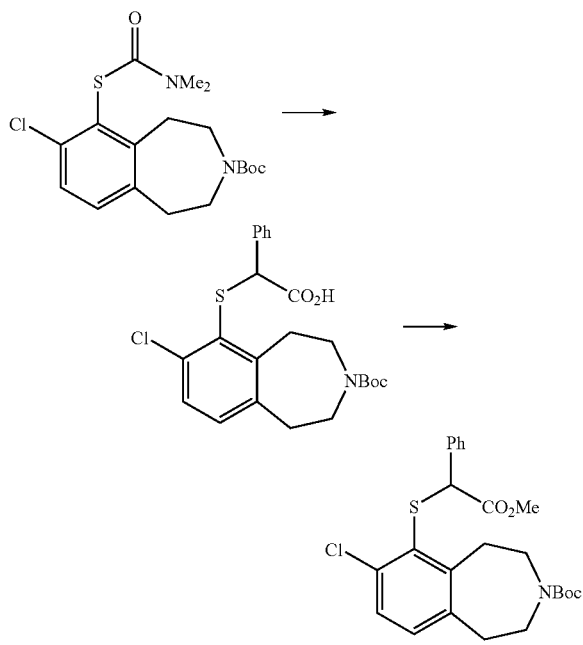

(±)-3-tert-Butoxycarbonyl-6-(1-carboxy-1-phenyl-methylthio)-7-chloro-2,3,4,5-tetrahydro-1H-benzo[d]azepine: To a solution of 3-tert-butoxycarbonyl-7-chloro-6-dimethylcarbamoylthio-2,3,4,5-tetrahydro-1H-benzo[d]azepine (1.23 g, 3.2 mmol) in methanol (20 mL) under nitrogen, add with stirring potassium hydroxide (5.36 g, 95.5 mmol) at ambient temperature. Heat at 55-60° C. for 2 h, cool to ambient temperature, and add methyl α-bromophenylacetate (600 μL, 3.81 mmol). After 30 min, dilute with saturated aqueous $NH_4Cl$, extract three times with EtOAc, dry over anhydrous $MgSO_4$, and concentrate in vacuo. Dissolve the crude material in THF (10 mL), treat with di-tert-butyl-dicarbonate (2 equiv) and saturated aqueous $NaHCO_3$ (10 mL), and stir overnight. Extract three times with EtOAc, dry over anhydrous $MgSO_4$ and concentrate in vacuo to give the desired intermediate as an oil that is used without purification (1.1 g, 77%).

(±)-3-tert-Butoxycarbonyl-6-(1-methoxycarbonyl-1-phenyl-methylthio)-7-chloro-2,3,4,5-tetrahydro-1H-benzo[d]azepine: Treat a solution of 3-tert-butoxycarbonyl-6-(1-carboxy-1-phenyl-methylthio)-7-chloro-2,3,4,5-tetrahydrobenzo[d]azepine (200 mg, 0.447 mmol) in anhydrous DMF (2 mL) with methyl iodide (317 mg, 2.237 mmol) and potassium carbonate (310 mg, 2.237 mmol) for 1.5 h at ambient temperature. Add water and extract the aqueous phase three times with EtOAc. Dry the organic phase over $MgSO_4$ and concentrate to obtain the title compound that was used without purification.

Preparation 246

6-(3-Bromo-4-chloro-benzylthio)-3-tert-butoxycarbonyl-7-chloro-2,3,4,5-tetrahydro-1H-benzo[d]azepine

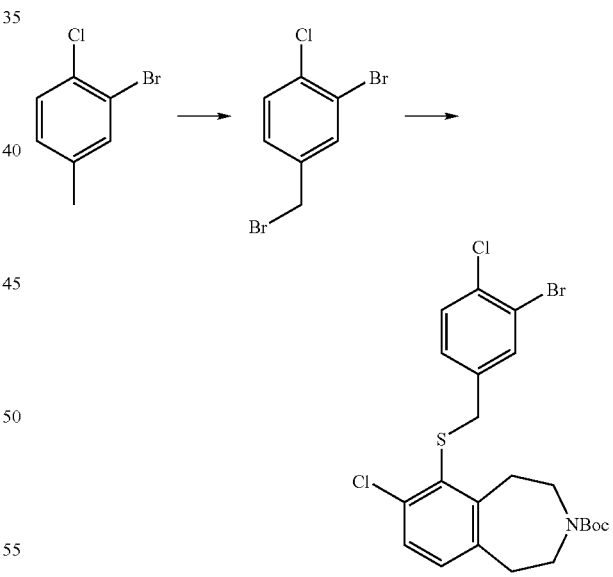

2-Bromo-4-bromomethyl-1-chloro-benzene: Use a method similar to the Preparation 184, using 3-bromo-4-chlorotoluene, to give the desired intermediate.

6-(3-Bromo-4-chloro-benzylthio)-3-tert-butoxycarbonyl-7-chloro-2,3,4,5-tetrahydro-1H-benzo[d]azepine: Use a method similar to the Preparation 177, using 3-tert-butoxycarbonyl-7-chloro-6-dimethylcarbamoylsulfanyl-2,3,4,5-tetrahydro-1H-benzo[d]azepine and 2-bromo-4-bromomethyl-1-chloro-benzene, to give the title compound.

Preparation 247

3-tert-Butoxycarbonyl-6-(5-carboxy-pyridin-2-ylmethylthio)-7-chloro-2,3,4,5-tetrahydro-1H-benzo[d]azepine

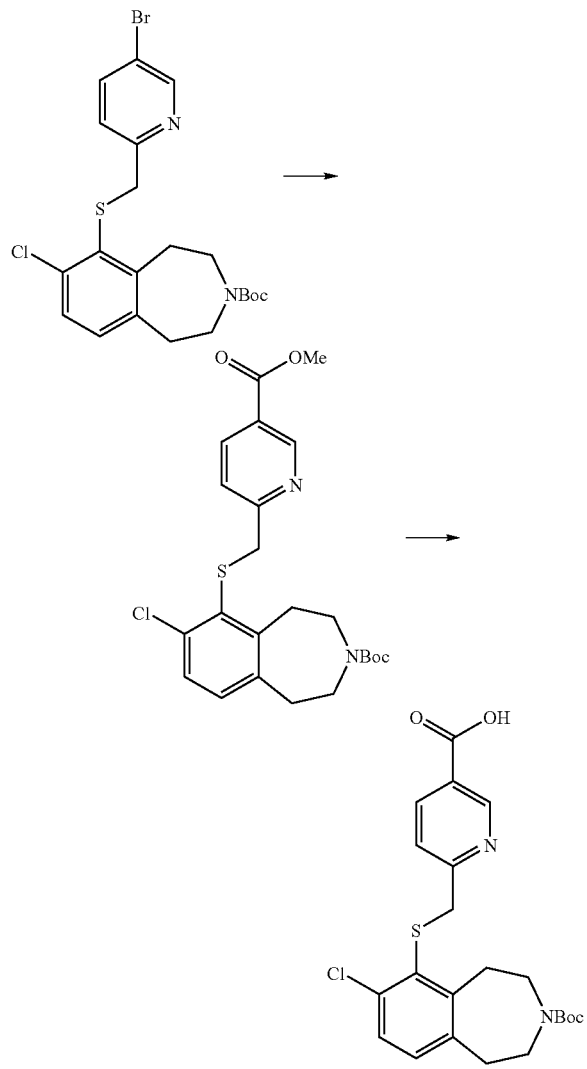

3-tert-Butoxycarbonyl-4-chloro-6-(5-methoxycarbonyl-pyridin-2-ylmethylthio)-2,3,4,5-tetrahydro-1H-benzo[d]azepine: Dissolve 3-tert-butoxycarbonyl-6-(5-bromopyridin-2-ylmethylthio)-7-chloro-2,3,4,5-tetrahydro-1H-benzo[d]azepine (2.13 g, 4.40 mmol), palladium acetate (35 mg, 0.156 mmol), 1,1'-bis(diphenylphosphino)ferrocene (150 mg, 0.271 mmol) and triethylamine (1.30 mL) in methanol (10 mL) and DMF (5 mL). Degas and then heat under a balloon filled with carbon monoxide at 75° C. for 10 h. Remove methanol in vacuo, and dilute the mixture with water. Extract three times with EtOAc, dry over anhydrous Na$_2$SO$_4$, and concentrated in vacuo. Purify by chromatography on silica gel eluting with hexane/EtOAc (7:1) to give the desired intermediate as a clear oil (1.86 g, 91%). MS (APCI+) m/z 463 (M+H)$^+$, 363 (M+H–Boc)$^+$.

3-tert-Butoxycarbonyl-6-(5-carboxy-pyridin-2-ylmethylthio)-7-chloro-2,3,4,5-tetrahydro-1H-benzo[d]azepine: Dissolve 3-tert-butoxycarbonyl-6-(5-methoxycarbonyl-pyridin-2-ylmethylthio)-chloro-2,3,4,5-tetrahydro-1H-benzo[d]azepine (1.86 g, 4.03 mmol) in methanol (25 mL). Add 1M aqueous lithium hydroxide (12 mL) and stir at ambient temperature overnight. Remove methanol in vacuo, and dilute the mixture with cold 0.5M aqueous HCl to pH 4. Add brine and extract three times with EtOAc. Dry over anhydrous Na$_2$SO$_4$, and concentrate in vacuo to give the title compound as an off-white solid (1.78 g, 95%). MS (APCI+) m/z 449 (M+H)$^+$, 349 (M+H–Boc)$^+$.

Preparation 248

6-(4-Bromo-thiophen-2-ylmethylthio)-3-tert-butoxycarbonyl-7-chloro-2,3,4,5-tetrahydro-1H-benzo[d]azepine

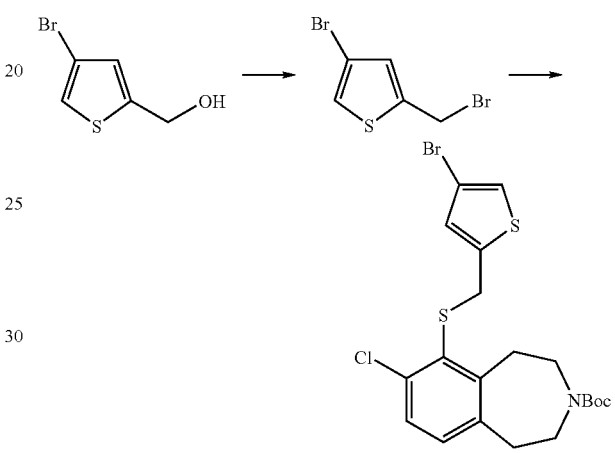

3-Bromo-5-bromomethyl-thiophene: Use the bromination procedure described in Preparation 211 (Step 2), using (3-bromothiophen-2-yl)methanol (Synthesis 1983, 1, 73-75), to give the desired intermediate as a light brown liquid.

6-(4-Bromo-thiophen-2-ylmethylthio)-3-tert-butoxycarbonyl-7-chloro-2,3,4,5-tetrahydro-1H-benzo[d]azepine: Use a method similar to the Preparation 177, using 3-tert-butoxycarbonyl-7-chloro-6-dimethylcarbamoylthio-2,3,4,5-tetrahydro-1H-benzo[a]azepine and 3-bromo-5-bromomethyl-thiophene, to give the title compound as a gum.

EXAMPLE 315

7-Chloro-6-(2-isopropoxyethylthio)-2,3,4,5-tetrahydro-1H-benzo[d]azepine Hydrochloride

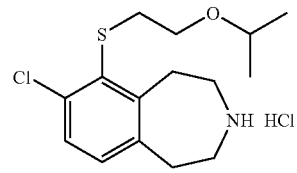

To a 4:1 mixture of 3-tert-butoxycarbonyl-7-chloro-6-dimethylcarbamoylthio-2,3,4,5-tetrahydro-1H-benzo[d]azepine and 3-tert-butoxycarbonyl-7,9-dichloro-6-dimethylcarbamoylthio-2,3,4,5-tetrahydro-1H-benzo[d]azepine (200 mg, 0.52 mmol) in methanol (5 mL) under nitrogen, add potassium hydroxide (0.9 g, 16.1 mmol) at ambient temperature.

When the mixture becomes homogenous, heat at 55-60° C. for 2-3 h, until TLC shows the disappearance of starting material. Cool to ambient temperature, add aqueous saturated ammonium chloride, extract three times with diethyl ether, dry over anhydrous MgSO$_4$, and concentrate in vacuo. Dissolve the crude 3-tert-butoxycarbonyl-7-chloro-6-mercapto-2,3,4,5-tetrahydro-1H-benzo[d]azepine in anhydrous THF (5 mL) under nitrogen and add with stirring 1.0 M potassium t-butoxide in THF (1.0 mL) at ambient temperature. After 10 min, add 2-(2-iodoethoxy)propane (223 mg, 1.04 mmol), and allow the reaction to continue overnight. Dilute with aqueous saturated ammonium chloride, extract the mixture three times with diethyl ether, dry over anhydrous MgSO$_4$, and concentrate in vacuo. Purify by chromatography on silica gel eluting with hexane/EtOAc (12:1) to provide 3-tert-butoxycarbonyl-7-chloro-6-(2-isopropoxy-ethylthio)-2,3,4,5-tetrahydro-1H-benzo[d]azepine as a clear oil (127 mg, 63%). Use a method similar to the General Procedure 1-4 to give the title compound as a white solid. MS (ES+) m/z: 300 (M+H)$^+$.

EXAMPLE 316

(±)-7-Chloro-6-(1-pyridin-2-yl-ethylthio)-2,3,4,5-tetrahydro-1H-benzo[d]azepine Hydrochloride

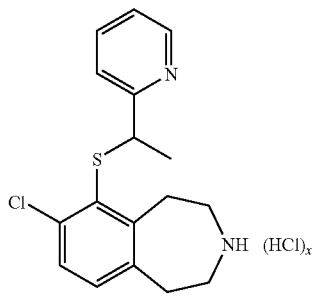

Use a method similar to the General Procedure 7, using 3-tert-butoxycarbonyl-7-chloro-6-dimethylcarbamoylthio-2,3,4,5-tetrahydro-1H-benzo[d]azepine and (±)-2-(1-bromoethyl)-pyridine to give, after deprotection by a method similar to the General Procedure 1-4, the title compound as a white solid. MS (APCI+) m/z: 319 (M+H)$^+$.

EXAMPLE 317

(−)-7-Chloro-6-(1-pyridin-2-yl-ethylthio)-2,3,4,5-tetrahydro-1H-benzo[d]azepine Succinate

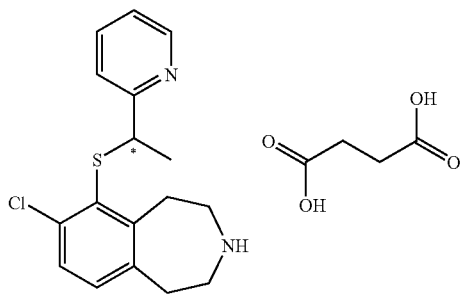

Separate the enantiomers of (±)-7-chloro-6-(1-pyridin-2-yl-ethylthio)-2,3,4,5-tetrahydro-1H-benzo[d]azepine by chiral normal phase chromatography (Chiralpak AD 8×30 cm column, eluting with 0.2% DMEA in methanol). Take the second eluting isomer and purify by chromatography on silica gel eluting with DCM/2M ammonia in methanol (100:1 to 80:20).

Use the General Procedure 2-1 to give the title compound as a white solid (4.27 g, 33%). MS (ES+) m/z: 319 (M+H)$^+$; ee=99.4%; $[\alpha]^{20}_D$ −179° (c 0.5, CH$_3$OH).

EXAMPLE 318

(−)-7-Chloro-6-(1-pyridin-2-yl-ethylthio)-2,3,4,5-tetrahydro-1H-benzo[d]azepine Hydrochloride

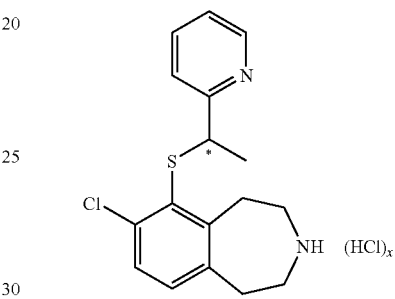

Use a method similar to the General Procedure 7, except that the alkylation is conducted at 0° C., to react 3-tert-butoxycarbonyl-7-chloro-6-dimethylcarbamoylthio-2;3,4,5-tetrahydro-1H-benzo[d]azepine with (R)-(−)-1-(2-pyridinyl)ethanol methanesulfonate ester. Use a method similar to the General Procedure 1-4 to give the title compound as a white solid. MS (APCI+) m/z: 319 (M+H)$^+$; ee=98.6% [Chiral HPLC: Chiralpak AD-H 0.46×15 cm column, eluting with 15:85 ethanol/heptane].

EXAMPLE 319

(±)-7-Chloro-6-[1-(6-methylpyridin-2-yl)-ethylthio]-2,3,4,5-tetrahydro-1H-benzo[d]azepine Hydrochloride

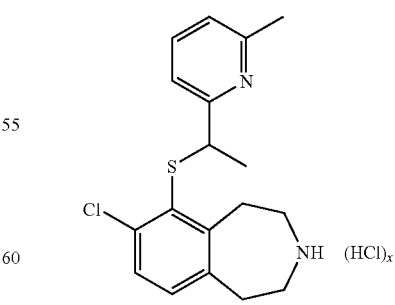

Use a method similar to the Example 315, using 3-tert-butoxycarbonyl-7-chloro-6-dimethylcarbamoylthio-2,3,4,5-tetrahydro-1H-benzo[d]azepine and (±)-2-(1-chloroethyl)-6-methylpyridine hydrochloride to give, after deprotection by a method similar to the General Procedure 1-4, the title compound as a tan solid. MS (ES+) m/z: 333 (M+H)$^+$.

EXAMPLE 320

7-Chloro-6-[1-(6-methylpyridin-2-yl)-ethylthio]-2,3,4,5-tetrahydro-1H-benzo[d]azepine Hydrochloride, Isomer 1

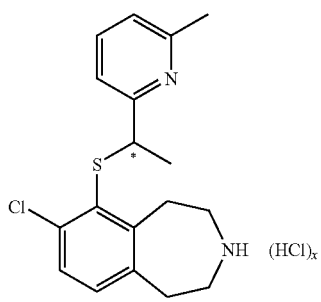

Use a method similar to the Preparation 177, except that the alkylation is conducted at 0° C., to react 3-tert-butoxycarbonyl-7-chloro-6-dimethylcarbamoylthio-2,3,4,5-tetrahydro-1H-benzo[d]azepine with (R)-methanesulfonic acid 1-(6-methyl-pyridin-2-yl)-ethyl ester. Use a method similar to the General Procedure 1-5, basic workup, and a method similar to the General Procedure 2-2 to give the title compound as a white solid. MS (APCI+) m/z: 333 (M+H)$^+$; ee >97%, $t_R$=6.53 min. (Chiral HPLC: Chiralpak OJ 120 Å 4.6×250 mm, 45° C.; eluent: 20% isopropanol with 0.05% triethylamine in SFC, flow rate 2 mL/min, LTV detector at 234 nm).

EXAMPLE 321

(±)-7-Chloro-6-[1-(3-methylpyridin-2-yl)-ethylthio]-2,3,4,5-tetrahydro-1H-benzo[d]azepine Hydrochloride

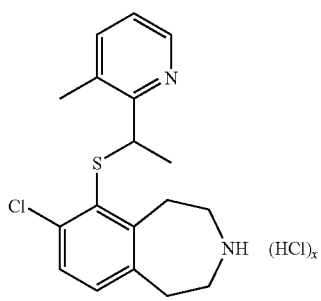

Use a method similar to the Preparation 177 to react 3-tert-butoxycarbonyl-7-chloro-6-dimethylcarbamoylthio-2,3,4,5-tetrahydro-1H-benzo[d]azepine with (±)-2-(1-bromoethyl)-3-methyl-pyridine. Use a method similar to the General Procedure 1-5, basic workup, and a method similar to the General Procedure 2-2 to give the title compound as a white solid. MS (APCI+) m/z: 333 (M+H)$^+$.

EXAMPLE 322

(−)-7-Chloro-6-[1-(3-methylpyridin-2-yl)-ethylthio]-2,3,4,5-tetrahydro-1H-benzo[d]azepine Hydrochloride

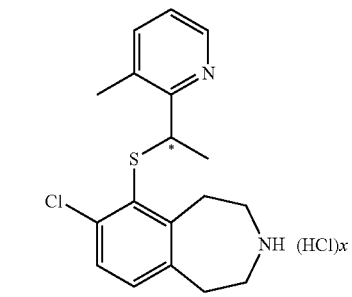

Separate the enantiomers of (±)-7-chloro-[1-(3-methyl-pyridin-2-yl)-ethylthio]-2,3,4,5-tetrahydro-1H-benzo[d]azepine by chiral normal phase chromatography (Chiralpak AD 8×30 cm column, eluting with 85:15 heptane:0.2% DMEA in ethanol). Take the second eluting isomer and purify by SCX column chromatography.

Use the General Procedure 2-2 to give the title compound as a white solid (60 mg, 43%). MS (ES+) m/z: 333 (M+H)$^+$; $[\alpha]^{20}_D$ −232° (c 0.5, CH$_3$OH).

EXAMPLE 323

(±)-7-Chloro-6-(2,2,2-trifluoro-1-pyridin-2-yl-ethylthio)-2,3,4,5-tetrahydro-1H-benzo[d]azepine Hydrochloride

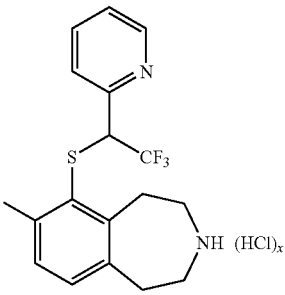

Use a method similar to the Preparation 177 to react 3-tert-butoxycarbonyl-7-chloro-6-dimethylcarbamoylthio-2,3,4,5-tetrahydro-1H-benzo[d]azepine with (±)-2-[1-methanesulfonyloxy-(2,2,2-trifluoroethyl)]-pyridine. Use a method similar to the General Procedure 1-5, basic workup, and a method similar to the General Procedure 2-2 to give the title compound as a white solid. MS (APCI+) m/z: 373 (M+H)$^+$.

EXAMPLE 324

(±)-7-Chloro-6-(1-pyridin-2-yl-propylthio)-2,3,4,5-tetrahydro-1H-benzo[d]azepine Hydrochloride

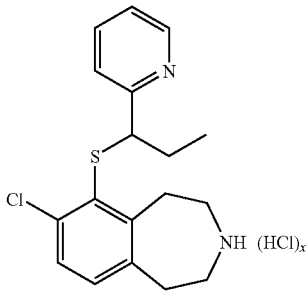

Use method similar to the Preparation 177 to react 3-tert-butoxycarbonyl-7-chloro-6-dimethylcarbamoylthio-2,3,4,5-tetrahydro-1H-benzo[d]azepine with (±)-2-(1-bromopropyl)pyridine. Use a method similar to the General Procedure 1-5, basic workup, and a method similar to the General Procedure 2-2 to give the title compound as a white solid. MS (APCI+) m/z: 333 (M+H)$^+$.

EXAMPLE 325

(±)-7-Chloro-6-[1-(pyridazin-3-yl)-ethylthio]-2,3,4,5-tetrahydro-1H-benzo[d]azepine Oxalate

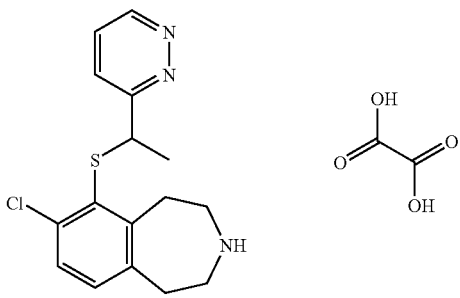

Dissolve (±)-1-pyridazin-3-yl-ethanol (38 mg, 0.31 mmol) in thionyl chloride (0.14 mL) at 0° C. and stir for 1 h at ambient temperature. Evaporate the mixture, add toluene and evaporate again. Treat this residue with the thiolate prepared from 7-chloro-6-dimethylcarbamoylthio-2,3,4,5-tetrahydro-1H-benzo[d]azepine-3-carboxylic acid tert-butyl ether (0.1 g, 0.25 mmol) according to the General Procedure 7 in the presence of potassium carbonate (0.3 g, 2.25 mmol) in DMF (3 mL) at 80° C. for 16 h.

Use a method similar to the General Procedure 1-5, basic work-up, and a method similar to the General Procedure 2-5 to give the title compound (38 mg, 37%). HRMS calcd for $C_{16}H_{19}ClN_3S$ 320.0988, found 320.0970.

EXAMPLE 326

(+)-7-Chloro-6-[1-(pyridazin-3-yl)-ethylthio]-2,3,4,5-tetrahydro-1H-benzo[d]azepine Oxalate

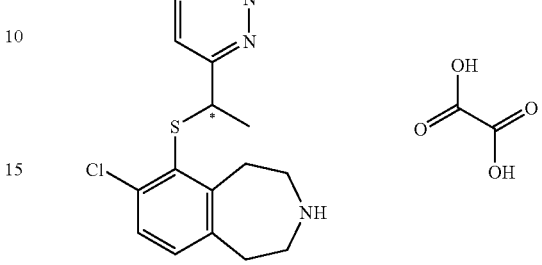

Dissolve (±)-1-pyridazin-3-yl-ethanol (0.29 g, 2.35 mmol) in thionyl chloride (1.0 mL) at 0° C. and stir for 1 h at ambient temperature. Evaporate the mixture, add toluene and evaporate again. Treat this residue with the thiolate prepared from 7-chloro-6-dimethylcarbamoylthio-2,3,4,5-tetrahydro-1H-benzo[d]azepine-3-carboxylic acid tert-butyl ether (0.72 g, 1.88 mmol) according to the General Procedure 7 in the presence of potassium carbonate (2.60 g, 18.8 mmol) and tetrabutylammonium iodide (7 mg, 0.02 mmol) in DMF (20 mL) at 80° C. for 28 h. Separate the enantiomers by preparative HPLC (Waters Symmetry C18 4.6×150 mm 3.5 micron column, 1 mL/min of 90:10 to 50:50:0.1% TFA in water:ACN over 25 min. Detector is at 254 nm) to obtain 3-tert-butoxycarbonyl-7-chloro-6-[1-(pyridazin-3-yl)-ethylthio]-2,3,4,5-tetrahydro-1H-benzo[d]azepine, isomer 1.

Use a method similar to the General Procedure 1-5, basic work-up, and a method similar to the General Procedure 2-5 to give the title compound (56 mg, 7%). HPLC $t_R$=3.0 min (Chiralpak AD-H 4.6×150 mm, 3 micron column, 1.0 mL/min of 99.8:0.2 methanol/dimethylethylamine isocratic; detector at 225 nm); HRMS calc'd for $C_{16}H_{19}ClN_3S$ 320.0988, found 320.1001. $[\alpha]^{20}_D$ +160° (c 0.5, $CH_3OH$).

EXAMPLE 327

7-Chloro-6-(pyridazin-3-ylmethylthio)-2,3,4,5-tetrahydro-1H-benzo[d]azepine Hydrochloride

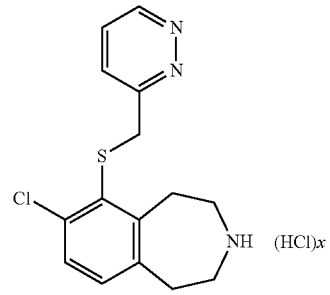

React 3-chloromethyl-pyridazine (prepared as described in WO 99/54333, WO 98/49166) (1.8 g, 11.0 mmol) with 3-tert-butoxycarbonyl-7-chloro-6-dimethylcarbamoylthio-2,3,4,5-tetrahydro-1H-benzo[d]azepine (2.2 g, 5.7 mmol) according to the General Procedure 7 in the presence of tetrabutylammonium iodide (0.1 g, 0.27 mmol) at ambient temperature for 3 h.

Use a method similar to the General Procedure 14 to give the title compound as a tan powder (1.9 g, 98%): HRMS calcd for $C_{15}H_{16}ClN_3S$ 306.0832, found 306.0829.

EXAMPLE 328

7-Chloro-6-(6-chloro-pyridazin-3-ylmethylthio)-2,3,4,5-tetrahydro-1H-benzo[d]azepine Hydrochloride

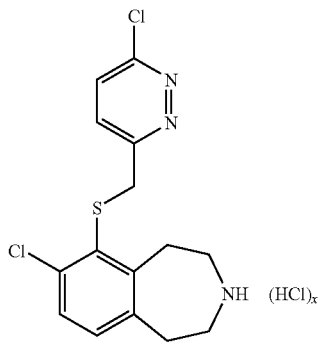

Use a method similar to the Preparation 177, using 3-tert-butoxycarbonyl-7-chloro-6-dimethylcarbamoylthio-2,3,4,5-tetrahydro-1H-benzo[d]azepine and 3-bromomethyl-6-chloropyridazine to give 3-tert-butoxycarbonyl-7-chloro-6-(6-chloro-pyridazin-3-ylmethylthio)-2,3,4,5-tetrahydro)-1H-benzo[d]azepine. Use a method similar to the General Procedure 14 to give the title compound as an off-white powder. MS (APCI+) m/z: 340 (M+H)$^+$.

EXAMPLE 329

7-Chloro-6-[6-(2,2-dimethylpropoxy)-pyridazin-3-ylmethylthio]-2,3,4,5-tetrahydro-1H-benzo[d]azepine Hydrochloride

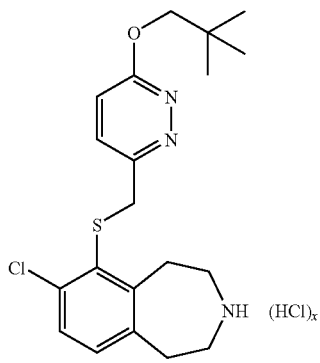

To a stirred solution of neopentyl alcohol (105 mg, 1.19 mmol) in THF (5 mL) at ambient temperature add sodium hydride (31 mg, 95%, 1.19 mmol) and continue stirring for 3 h at ambient temperature. Add a solution of 3-tert-butoxycarbonyl-7-chloro-6-(6-chloro-pyridazin-3-ylmethylthio)-2,3,4,5-tetrahydro-1H-benzo[d]azepine (315 mg, 0.59 mmol) in THF (1 mL) and continue stirring overnight at ambient temperature and then at 60° C. for 1 h. Dilute with water, extract the reaction mixture three times with EtOAc, dry over anhydrous $Na_2SO_4$, and concentrate in vacuo. Purify by chromatography on silica gel eluting with hexane/EtOAc (6:1) to give 3-tert-butoxycarbonyl-7-chloro-6-[6-(2,2-dimethylpropoxy)-pyridazin-3-ylmethylthio]-2,3,4,5-tetrahydro-1H-benzo[d]azepine as a clear oil (81 mg, 28%). MS (APCI+) m/z: 492 (M+H)$^+$, 392 (M+H–Boc)$^+$. Use a method similar to the General Procedure 1-4 to give the title compound as a white powder. MS (APCI+) m/z: 392 (M+H)$^+$, m/z: 322 M+H–$C_5H_{11}$)$^+$.

EXAMPLE 330

7-Chloro-6-(thiophen-2-ylmethylthio)-2,3,4,5-tetrahydro-1H-benzo[d]azepine Hydrochloride

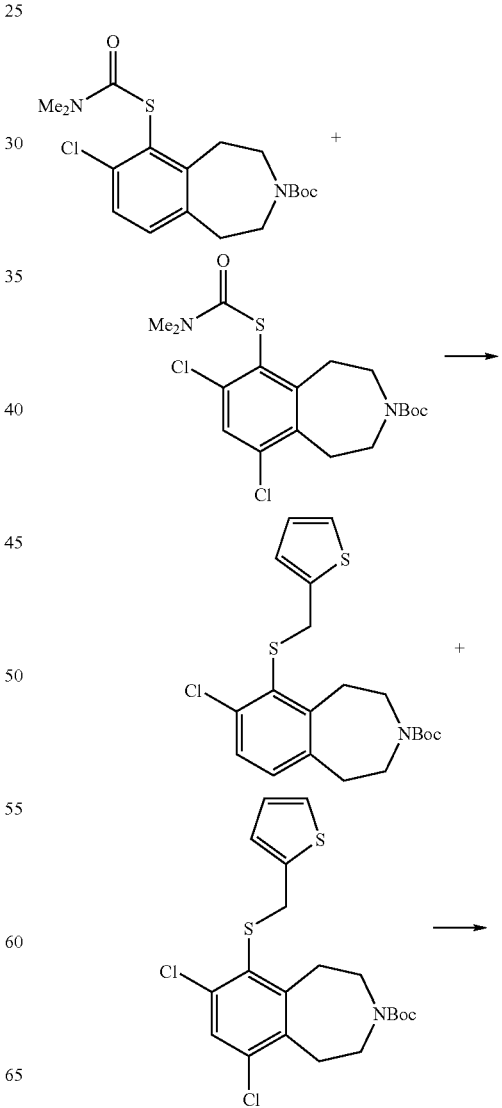

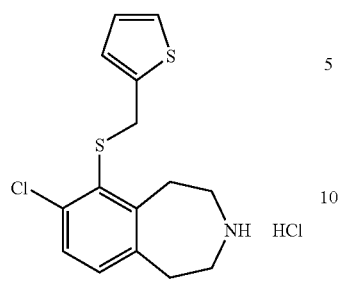

To a 4:1 mixture of 3-tert-butoxycarbonyl-7-chloro-6-dimethylcarbamoylthio-2,3,4,5-tetrahydro-1H-benzo[d]azepine and 3-tert-butoxycarbonyl-7,9-dichloro-6-dimethylcarbamoylthio-2,3,4,5-tetrahydro-benzo[d]azepine (108 mg, 0.281 mmol) in methanol (3 ml), add potassium hydroxide pellets (504 mg, 9.0 mmol) and heat the mixture 2 h at 50° C. Cool the reaction to ambient temperature, add 2-chloromethylthiophene (186 µL, 1.406 mmol), and continue stirring for 30 min. Dilute with EtOAc and water. Separate the layers and extract the aqueous layer three times with EtOAc, dry over anhydrous Na$_2$SO$_4$, and concentrate in vacuo. Purify by chromatography on silica gel eluting with hexane/EtOAc (19:1) to give 3-tert-butoxycarbonyl-7-chloro-6-(thiophen-2-ylmethylthio)-2,3,4,5-tetrahydro-benzo[d]azepine as a colorless oil (36 mg, 31%).

Use a method similar to the General Procedure 1-5, using 3-tert-butoxycarbonyl-7-chloro-6-(thiophen-2-ylmethylthio)-2,3,4,5-tetrahydro-benzo[d]azepine to give, after basic workup and a method similar to the General Procedure 2-2, the title compound as a white solid. MS (ES+) m/z: 310 (M+H)$^+$.

EXAMPLE 331

(±)-7-Chloro-6-(3-cyanothiophen-2-ylmethylthio)-2,3,4,5-tetrahydro-1H-benzo[d]azepine Trifluoroacetate

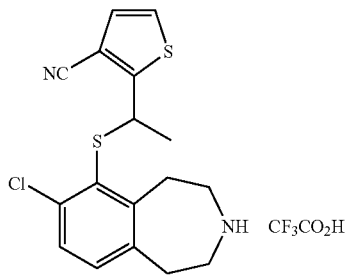

Use a method similar to the Preparation 177, using 3-tert-butoxycarbonyl-7-chloro-6 dimethylcarbamoylthio-2,3,4,5-tetrahydro-1H-benzo[d]azepine and (±)-2-(1-chloroethyl)-3-cyanothiophene to give, after deprotection using a method similar to the General Procedure 1-5, the title compound as a white solid. MS (APCI+) m/z: 349 (M+H)$^+$.

EXAMPLE 332

7-Chloro-6-(5-methylisoxazol-3-ylmethylthio)-2,3,4,5-tetrahydro-1H-benzo[d]azepine Hydrochloride

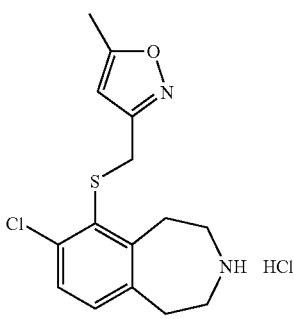

To a 4:1 mixture of 3-tert-butoxycarbonyl-7-chloro-6-dimethylcarbamoylthio-2,3,4,5-tetrahydro-1H-benzo[d]azepine and 3-tert-butoxycarbonyl-7,9-dichloro-6-dimethylcarbamoylthio-2,3,4,5-tetrahydro-1H-benzo[d]azepine (200 mg, 0.521 mmol) in methanol (3.3 mL) under nitrogen add potassium hydroxide (0.9 g, 16.1 mmol) at ambient temperature. When the mixture becomes homogenous, heat at 55-60° C. for 2-3 h, until TLC shows the disappearance of starting material. Cool to ambient temperature, add 3-(chloromethyl)-5-methylisoxazole (82 mg, 0.62 mmol) and continue stirring for 30 min. Add aqueous saturated ammonium chloride, extract the mixture three times with diethyl ether, dry over anhydrous MgSO$_4$, and concentrate in vacuo. Treat a solution of the crude material so obtained in DCM (2 mL) with 2M hydrogen chloride in ether (excess) and continue stirring until TLC shows consumption of the starting material. Concentrate in vacuo, purify by preparative TLC eluting with 19:1 DCM/saturated ammonia in methanol, and convert to the hydrochloride by following a method similar to the General Procedure 2-2 to give the title compound as a white solid. MS (APCI+) m/z: 309 (M+H)$^+$.

EXAMPLE 333

7,9-Dichloro-6-(5-methylisoxazol-3-ylmethylthio)-2,3,4,5-tetrahydro-1H-benzo[d]azepine Hydrochloride

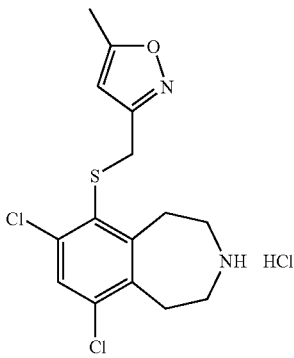

Obtain the free base of the title compound as a minor product from Example 332, after preparative TLC eluting with 19:1 DCM/saturated ammonia in methanol. Use a method similar to the General Procedure 2-2 to give the title compound as a white solid. MS (APCI+) m/z: 343 (M+H)+.

EXAMPLE 334

7-Chloro-6-(2-methylthiazol-4-ylmethylthio)-2,3,4,5-tetrahydro-1H-benzo[d]azepine Hydrochloride

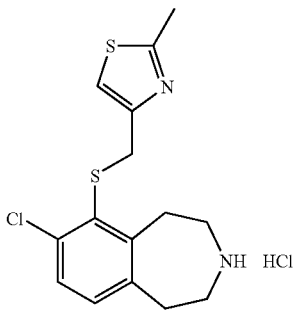

Use a method similar to the Example 332, using 3-tert-butoxycarbonyl-7-chloro-6-dimethylcarbamoylthio-2,3,4,5-tetrahydro-1H-benzo[d]azepine and 4-chloromethyl-2-methylthiazole hydrochloride to give, after deprotection by the General Procedure 1-4, the title compound as a white solid. MS (APCI+) m/z: 325 (M+H)+.

EXAMPLE 335

6-(4-Bromothiophen-2-ylmethylthio)-7-chloro-2,3,4,5-tetrahydro-1H-benzo[d]azepine Hydrochloride

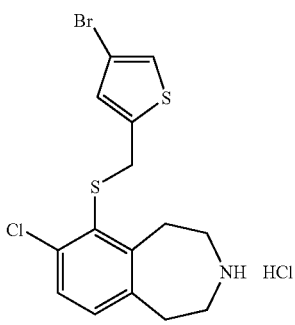

Use a method similar to the General Procedure 14, using 6-(4-bromothiophen-2-ylmethylthio)-3-tert-butoxycarbonyl-7-chloro-2,3,4,5-tetrahydro-1H-benzo[d]azepine to give the title compound as a white solid. MS (APCI+) m/z: 390 (M+H)+.

EXAMPLE 336

7-Chloro-6-(4-cyanothiophen-2-ylmethylthio)-2,3,4,5-tetrahydro-1H-benzo[d]azepine Hydrochloride

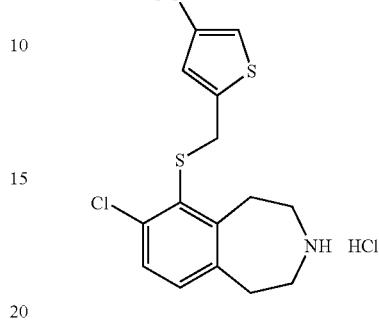

Degas a stirred solution of 6-(4-bromothiophen-2-ylmethylthio)-3-tert-butoxycarbonyl-7-chloro-2,3,4,5-tetrahydro-1H-benzo[d]azepine (183 mg, 0.37 mmol), zinc cyanide (50 mg, 0.42 mmol) and tetrakistriphenylphosphine palladium(0) (30 mg, 0.026 mmol) in dry DMF. Purge with dry nitrogen, and heat at 120° C. for 6 h. Dilute with water, extract three times with EtOAc, dry over anhydrous MgSO4 and concentrate in vacuo. Purify by chromatography on silica gel eluting with hexane/EtOAc (10:1) to give 3-tert-butoxycarbonyl-7-chloro-6-(4-cyanothiophen-2-ylmethylthio)-2,3,4,5-tetrahydro-1H-benzo[d]azepine as an oil (85 mg, 52%). MS (APCI+) m/z: 335 (M+H−Boc)+. Use a method similar to the General Procedure 1-4 to give the title compound as a white solid. MS (APCI+) m/z: 335 (M+H)+.

EXAMPLE 337

7-Chloro-6-([1,2,4]-oxadiazol-3-ylmethylthio)-2,3,4,5-tetrahydro-1H-benzo[d]azepine Hydrochloride

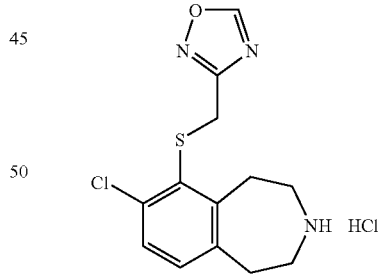

Use a method similar to the Preparation 177, using 3-tert-butoxycarbonyl-7-chloro-6-dimethylcarbamoylthio-2,3,4,5-tetrahydro-1H-benzo[d]azepine and 3-chloromethyl-1,2,4-oxadiazole to give, after deprotection using a method similar to the General Procedure 1-4, the title compound as a white solid. MS (ES+) m/z 296 (M+H)+.

Examples 338-343 may be prepared essentially as described in Example 337 using 3-tert-butoxycarbonyl-7-chloro-6-dimethylcarbamoylthio-2,3,4,5-tetrahydro-1H-benzo[d]azepine and the appropriately substituted 5-chloromethyl-1,2,4-oxadiazole or 4 chloromethyl-thiazole. MS (ES+) data are included in the Table below.

| Ex. | SR | Compound | MS (ES+) m/z |
|---|---|---|---|
| 338 | 3-methyl-[1,2,4]oxadiazol-5-ylmethyl | 7-Chloro-6-(3-methyl-[1,2,4]oxadiazol-5-ylmethylthio)-2,3,4,5-tetrahydro-1H-benzo[d]azepine Hydrochloride | 310 (M + H)+ |
| 339 | 3-tert-butyl-[1,2,4]oxadiazol-5-ylmethyl | 6-(3-tert-Butyl-[1,2,4]oxadiazol-5-ylmethylthio)-7-chloro-2,3,4,5-tetrahydro-1H-benzo[d]azepine Hydrochloride | 352 (M + H)+ |
| 340 | 3-propyl-[1,2,4]oxadiazol-5-ylmethyl | 7-Chloro-6-(3-propyl-[1,2,4]oxadiazol-5-ylmethylthio)-2,3,4,5-tetrahydro-1H-benzo[d]azepine Hydrochloride | 338 (M + H)+ |
| 341 | 3-(4-chlorophenyl)-[1,2,4]oxadiazol-5-ylmethyl | 7-Chloro-6-[3-(4-chlorophenyl)-[1,2,4]oxadiazol-5-ylmethylthio]-2,3,4,5-tetrahydro-1H-benzo[d]azepine Hydrochloride | 406 (M + H)+ |
| 342 | 3-(pyridin-2-yl)-[1,2,4]oxadiazol-5-ylmethyl | 7-Chloro-6-(3-pyridin-2-yl-[1,2,4]oxadiazol-5-ylmethylthio)-2,3,4,5-tetrahydro-1H-benzo[d]azepine Hydrochloride | 373 (M + H)+ |
| 343 | 2-(4-trifluoromethylphenyl)-thiazol-4-ylmethyl | 7-Chloro-6-[2-(4-trifluoromethyl-phenyl)-thiazol-4-ylmethylthio)-2,3,4,5-tetrahydro-1H-benzo[d]azepine Hydrochloride | 455 (M + H)+ |

EXAMPLE 344

7-Chloro-6-(pyridin-2-ylmethylthio)-2,3,4,5-tetrahydro-1H-benzo[d]azepine Hydrochloride

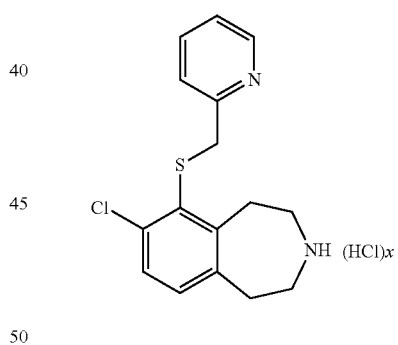

Using a method similar to the General Procedure 7, react 3-tert-butoxycarbonyl-7-chloro-6-dimethylaminocarbonylthio-2,3,4,5-tetrahydro-1H-benzo[d]azepine (8 g, 20.8 mmol) with 2-picolyl chloride hydrochloride (3.41 g, 20.8 mmol). Dilute the reaction mixture with diethyl ether and filter the precipitate. Concentrate the filtrate in vacuo, dissolve the residue in diethyl ether (100 mL) and add 1N aqueous HCl (100 mL). Stir the mixture for 16 h at ambient temperature. Separate, wash the aqueous layer with diethyl ether, adjust the pH of the aqueous layer to 12 with sodium hydroxide and extract with diethyl ether. Dry over $Na_2SO_4$ and concentrate in vacuo to give the free base of the title compound. Use the General Procedure 2-2 to give the title compound as a white solid (4.91 g, 78%). MS (ES+) m/z: 305 (M+H)+.

EXAMPLE 345

7-Chloro-6-(pyridin-2-ylmethylthio)-2,3,4,5-tetrahydro-1H-benzo[d]azepine Succinate

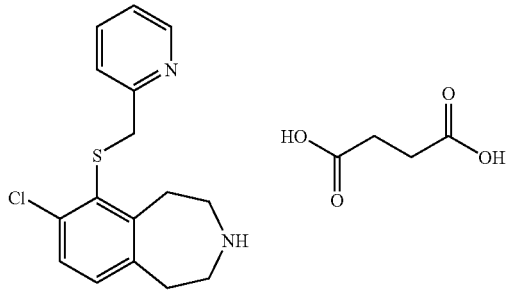

Dissolve 3-tert-butoxycarbonyl-7-chloro-6-dimethylcarbamoylthio-2,3,4,5-tetrahydro-1H-benzo[d]azepine (1 equiv.) in methanol (0.1-0.4 M) and add potassium hydroxide (8-20 equiv.). Stir at 60° C. for 4-24 h. Cool the reaction mixture in an ice bath, add picolyl chloride hydrochloride (1-3 equiv.) and stir the mixture at ambient temperature for 16-24 h. Add a volume of toluene approximately equal to the volume of the reaction mixture and concentrate the resulting mixture to approximately ½ the resulting total volume and repeat this process once more. Add water until all solids dissolve and separate the layers. Dry the organic layer over $Na_2SO_4$ and filter. Heat the solution (containing about 0.25-0.40 M of free base of the title compound) to 50-75° C. and then optionally seed with previously formed crystals of the title compound. Add succinic acid (1-1.3 equivalents) in isopropyl alcohol (0.25-0.40M solution) to the solution over 545 min. Cool the solution to 20-25° C. over 1-3 h and filter, rinsing with a solution of toluene/isopropyl alcohol (1:1). Dry the resulting solid under vacuum at 50-70° C./5 Torr to give the title compound as a white solid, mp 159-160° C. Anal. Calc'd for $C_{20}H_{23}ClN_2O_4S$: C, 56.80; H, 5.48; N, 6.62. Found: C, 56.56; H, 5.41; N, 6.57.

EXAMPLE 346

7,9-Dichloro-6-(pyridin-2-ylmethylthio)-2,3,4,5-tetrahydro-1H-benzo[d]azepine Hydrochloride

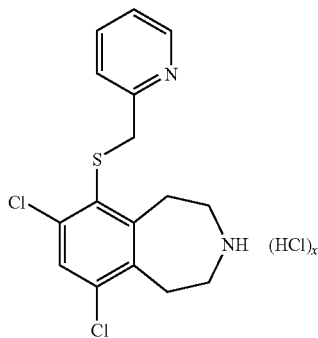

Obtain as minor product from the reaction of the 4:1 mixture of 3-tert-butoxycarbonyl-7-chloro-6-dimethylcarbamoylthio-2,3,4,5-tetrahydro-1H-benzo[d]azepine and 3-tert-butoxycarbonyl-7,9-dichloro-6-dimethylcarbamoylthio-2,3,4,5-tetrahydro-benzo[d]azepine with 2-bromomethylpyridine hydrobromide, using a method similar to the General Procedure 7. Treat a solution of the crude mixture in DCM with 4M hydrogen chloride in dioxane (excess) overnight Concentrate in vacuo and purify by preparative TLC eluting with 19:1 DCM/saturated ammonia in methanol. Use a method similar to the General Procedure 2-2 to give the title compound as an off-white solid. MS (APCI+) m/z: 339 (M+H)⁺.

EXAMPLE 347

7-Chloro-6-(2-fluorobenzylthio)-2,3,4,5-tetrahydro-1H-benzo[d]azepine Hydrochloride

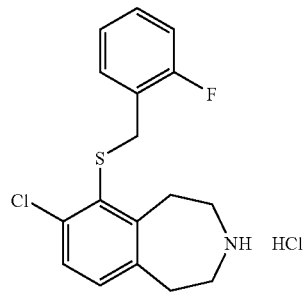

To a mixture of 3-tert-butoxycarbonyl-7-chloro-6-dimethylcarbamoylthio-2,3,4,5-tetrahydro-1H-benzo[d]azepine and 3-tert-butoxycarbonyl-7,9-dichloro-6-dimethylcarbamoylthio-2,3,4,5-tetrahydro-benzo[d]azepine (102 mg, 0.267 mmol) in methanol (2 ml), add potassium hydroxide pellets (450 mg, 8.02 mmol) and heat the mixture 3 h at 60° C. Cool to ambient temperature, add aqueous saturated ammonium chloride solution, extract three times with EtOAc, dry over anhydrous $Na_2SO_4$, and concentrate in vacuo. Dissolve the crude thiophenol thus obtained in dry DCM (2 mL) under nitrogen, and add DBU (80 □L, 0.54 mmol) and 2-fluorobenzyl bromide (65 □L, 0.54 mmol) with stirring. Stir overnight at ambient temperature, dilute with water, extract three times with EtOAc, dry over anhydrous $Na_2SO_4$, and concentrate in vacuo. Purify by chromatography on silica gel eluting with hexane/EtOAc (9:1) to give 3-tert-butoxycarbonyl-7-chloro-6-(2-fluorobenzylthio)-2,3,4,5-tetrahydro-1H-benzo[d]azepine as a yellow oil (31 mg, 25%). Use a method similar to the General Procedure 1-4 to give the title compound as a white solid. MS (ES+) m/z: 322 (M+H)⁺.

EXAMPLE 348

7-Chloro-6-(pyridin-3-ylmethylthio)-2,3,4,5-tetrahydro-1H-benzo[d]azepine Hydrochloride

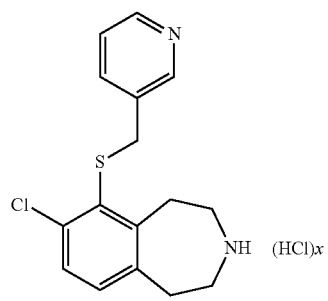

Use a method similar to the Example 347, using 3-tert-butoxycarbonyl-7-chloro-6-dimethylcarbamoylthio-2,3,4,5-tetrahydro-1H-benzo[d]azepine and 3-(bromomethyl)pyridine hydrobromide to give, after deprotection by a method similar to the General Procedure 1-4, the title compound as a white solid. MS (ES+) m/z: 305 (M+H)+.

EXAMPLE 349

7-Chloro-6-(5-fluoropyridin-2-ylmethylthio)-2,3,4,5-tetrahydro-1H-benzo[d]azepine Succinate

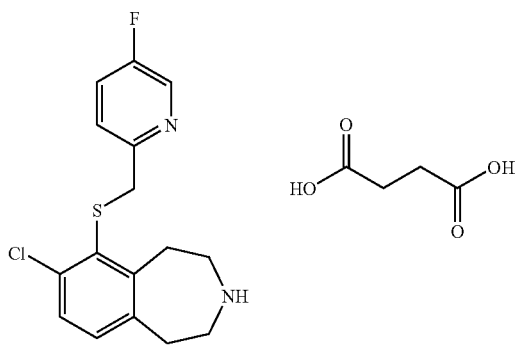

Dissolve 3-tert-butoxycarbonyl-7-chloro-6-dimethylcarbamoylthio-2,3,4,5-tetrahydro-1H-benzo[d]azepine (527 mg, 1.4 mmol) and potassium hydroxide (1.1 g, 20.5 mmol) in methanol (10 mL) and heat the solution to reflux for 2 h. Cool the reaction mixture to ambient temperature and remove the solvent in vacuo. Slurry the residue with EtOAc (50 ml), and wash the slurry with a saturated NH₄Cl. Collect and dry the organic phase over Na₂SO₄, remove the solvent under reduced pressure to obtain the intermediate thiophenol as an oil. Dissolve the oil in DMSO (10 ml), add triethylamine (1.1 ml, 8.2 mmol) and methanesulfonic acid 5-fluoro-pyridin-2-ylmethyl ester (500 mg, 2.4 mmol). Heat the reaction mixture to 60° C. for 1 h. Monitor the reaction by HPLC and TLC. Cool the reaction to ambient temperature, add 1:1 hexane/EtOAc (80 ml) and wash the organic layer with a 5% NaCl (3×30 ml). Collect the organic layer, concentrate, and purify by chromatography on silica gel eluting with hexane/EtOAc (9:1 to 1:1) to obtain 3-tert-butoxycarbonyl-7-chloro-6-(5-fluoro-pyridin-2-ylmethylthio)-2,3,4,5-tetrahydro-1H-benzo[d]azepine (519 mg, 89%). MS (ES+) m/z: 423 (M+H)+.

Use the General Procedure 1-4 to deprotect 3-tert-butoxycarbonyl-7-chloro-6-(5-fluoro-pyridin-2-ylmethylthio)-2,3,4,5-tetrahydro-1H-benzo[d]azepine (510 mg, 1.2 mmol). Purify by SCX chromatography followed by chromatography on silica gel eluting with DCM/2M ammonia in methanol (99:1 to 90:10). Use the General Procedure 2-1 to give the title compound (370 mg, 70%). MS (ES+) m/z: 323 (M+H)+.

EXAMPLE 350

7-Chloro-6-(6-chloropyridin-2-ylmethylthio)-2,3,4,5-tetrahydro-1H-benzo[d]azepine Hydrochloride

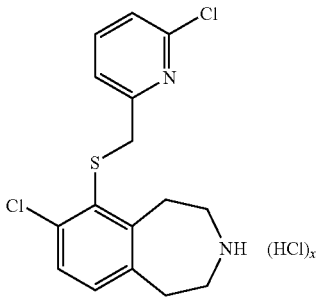

Use a method similar to the Preparation 177, using 3-tert-butoxycarbonyl-7-chloro-6-dimethylcarbamoylthio-2,3,4,5-tetrahydro-1H-benzo[d]azepine and 2-bromomethyl-6-chloropyridine hydrochloride to give, after deprotection by a method similar to the General Procedure 1-4, the title compound as an off-white solid. MS (APCI+) m/z: 339 (M+H)+.

Examples 351-360 may be prepared essentially as described in Example 350 by using 3-tert-butoxycarbonyl-7-chloro-6-dimethylcarbamoylthio-2,3,4,5-tetrahydro-1H-benzo[d]azepine and the appropriately substituted chloromethylpyridine, bromomethylpyridine or chloromethylquinoline. MS (ES+) data are included in the Table below.

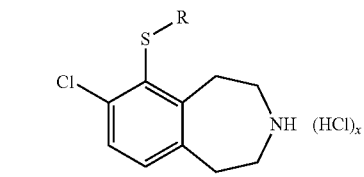

| Ex. | SR | Compound | MS (ES+ or APCI+) |
|---|---|---|---|
| 351 | 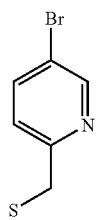 Cl | 7-Chloro-6-(6-chloro-pyridin-3-ylmethylthio)-2,3,4,5-tetrahydro-1H-benzo[d]azepine Hydrochloride | 339 (M + H)+ |
| 352 | Br | 6-(5-Bromo-pyridin-2-ylmethylthio)-7-chloro-2,3,4,5-tetrahydro-1H-benzo[d]azepine Hydrochloride | 385 (M + H)+ |

309
-continued

| Ex. | SR | Compound | MS (ES+ or APCI+) |
|---|---|---|---|
| 353 | 3-Bromo-pyridin-2-ylmethylthio | 6-(3-Bromo-pyridin-2-ylmethylthio)-7-chloro-2,3,4,5-tetrahydro-1H-benzo[d]azepine Hydrochloride | 385 (M + H)⁺ |
| 354 | 6-Bromo-pyridin-2-ylmethylthio | 6-(6-Bromo-pyridin-2-ylmethylthio)-7-chloro-2,3,4,5-tetrahydro-1H-benzo[d]azepine Hydrochioride | 385 (M + H)⁺ |
| 355 | 3-methyl-pyridin-2-ylmethylthio | 7-Chloro-6-(3-methyl-pyridin-2-ylmethylthio)-2,3,4,5-tetrahydro-1H-benzo[d]azepine Hydrochloride | 319 (M + H)⁺ |
| 356 | 5-cyano-pyridin-2-ylmethylthio | 7-Chloro-6-(5-cyano-pyridin-2-ylmethylthio)-2,3,4,5-tetrahydro-1H-benzo[d]azepine Hydrochloride | 330 (M + H)⁺ |
| 357 | 6-cyano-pyridin-3-ylmethylthio | 7-Chloro-6-(6-cyano-pyridin-3-ylmethylthio)-2,3,4,5-tetrahydro-1H-benzo[d]azepine Hydrochloride | 330 (M + H)⁺ |
| 358 | 6-trifluoromethyl-pyridin-2-ylmethylthio | 7-Chloro-6-(6-trifluoromethyl-pyridin-2-ylmethylthio)-2,3,4,5-tetrahydro-1H-benzo[d]azepine Hydrochloride | 373 (M + H)⁺ |
| 359 | 3-trifluoromethyl-pyridin-2-ylmethylthio | 7-Chloro-6-(3-trifluoromethyl-pyridin-2-ylmethylthio)-2,3,4,5-tetrahydro-1H-benzo[d]azepine Hydrochloride | 373 (M + H)⁺ |

310
-continued

| Ex. | SR | Compound | MS (ES+ or APCI+) |
|---|---|---|---|
| 360 | quinolin-2-ylmethylthio | 7-Chloro-6-(quinolin-2-ylmethylthio)-2,3,4,5-tetrahydro-1H-benzo[d]azepine Hydrochloride | 355 (M + H)⁺ |

EXAMPLE 361

7-Chloro-6-(3-methoxypyridin-2-ylmethylthio)-2,3,4,5-tetrahydro-1H-benzo[d]azepine Hydrochloride Use a method similar to the Example 315, using 3-tert-butoxycarbonyl-7-chloro-6-dimethylcarbamoylthio-2,3,4,5-tetrahydro-1H-benzo[d]azepine and 2-chloromethyl-3-methoxypyridine to give, after deprotection by a method similar to the General Procedure 1-4, the title compound as a white solid (71 mg). MS (APCI+) m/z: 335 (M+H)⁺.

EXAMPLE 362

7-Chloro-6-(6-methoxypyridin-2-ylmethylthio)-2,3,4,5-tetrahydro-1H-benzo[d]azepine Hydrochloride Use a method similar to the Example 330, using 3-tert-butoxycarbonyl-7-chloro-6-dimethylcarbamoylthio-2,3,4,5-tetrahydro-1H-benzo[d]azepine and 2-chloromethyl-6-methoxypyridine hydrochloride to give, after deprotection by a method similar to the General Procedure 14, the title compound as a white solid (120 mg). MS (APCI+) m/z: 335 (M+H)$^+$.

EXAMPLE 363

6-(5-Butylpyridin-2-ylmethylthio)-7-chloro-2,3,4,5-tetrahydro-1H-benzo[d]azepine Hydrochloride

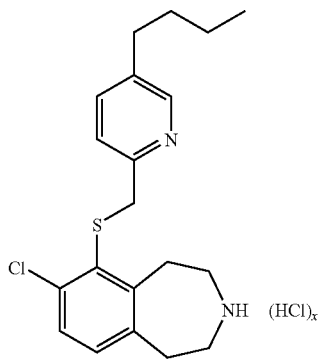

Use a method similar to the Example 315, using 3-tert-butoxycarbonyl-7-chloro-6-dimethylcarbamoylthio-2,3,4,5-tetrahydro-1H-benzo[d]azepine and 5-butyl-2-chloromethylpyridine hydrochloride to give the title compound as a white solid. MS (APCI+) m/z: 330 (M+H)$^+$.

EXAMPLE 364

7-Chloro-6-[5-(3-methylbutyl)-pyridin-2-ylmethylthio]-2,3,4,5-tetrahydro-1H-benzo[d]azepine Hydrochloride

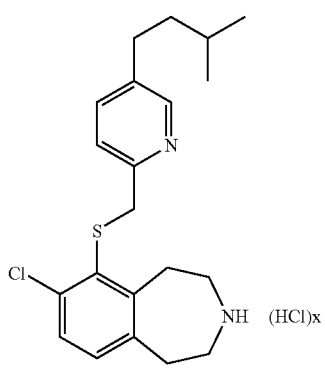

To 6-(5-bromo-pyridin-2-ylmethylthio)-3-tert-butoxycarbonyl-7-chloro-2,3,4,5-tetrahydro-1H-benzo[d]azepine (219 mg, 0.452 mmol) and dichloro[1,1'-bis(diphenylphosphino)ferrocene]palladium(II) dichloromethane adduct (18 mg, 0.022 mmol) under dry nitrogen add with stirring a solution of 0.5M 3-methylbutylzinc bromide in TIE (4.6 mL, 2.3 mmol). Degas, purge with dry nitrogen, and stir overnight at ambient temperature. Dilute with EtOAc, wash with water, dry over anhydrous MgSO$_4$ and concentrate in vacuo. Purify by chromatography on silica gel eluting with hexane/EtOAc (5:1) to give 3-tert-butoxycarbonyl-7-chloro-6-[5-(3-methyl-butyl)-pyridin-2-ylmethylthio]-2,3,4,5-tetrahydro-1H-benzo[d]azepine as an oil (160 mg, 75%). MS (APCI+) m/z: 475 (M+H)$^+$. Use a method similar to the General Procedure 1-4 to give the title compound as a tan solid. MS (APCI+) m/z: 375 (M+M)$^+$.

EXAMPLE 365

7-Chloro-6-[5-(2,2-dimethylpropyl)-pyridin-2-ylmethylthio]-2,3,4,5-tetrahydro-1H-benzo[d]azepine Hydrochloride

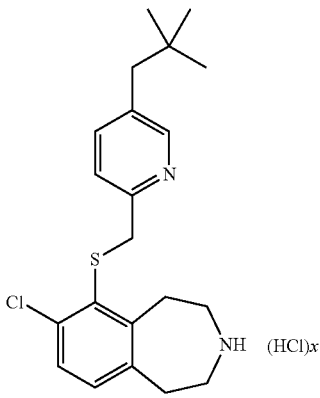

To a stirred solution of 1.0 M neopentyl magnesium chloride in diethyl ether (50 mL, 50 mmol) at −78° C. under nitrogen, add via syringe a solution of 0.5 M zinc chloride in THF (100 mL, 50 mmol). Warm gradually to ambient temperature and transfer via syringe of this solution (25 mL, ~8.33 mmol) to a stirred solution of 3-tert-butoxycarbonyl-6-(5-bromo-pyridin-2-ylmethylthio)-7-chloro-2,3,4,5-tetrahydro-1H-benzo[d]azepine (300 mg, 0.62 mmol) in THF (2 mL) at ambient temperature. Add dichloro[1,1'-bis(diphenylphosphino)ferrocene]palladium(II) dichloromethane adduct (50 mg, 0.061 mmol) and heat at 65° C. for 6 h. Cool to ambient temperature, dilute with EtOAc, wash with water, dry over anhydrous MgSO$_4$ and concentrate in vacuo. Purify by chromatography on silica gel eluting with hexane/EtOAc (6:1) to give 3-tert-butoxycarbonyl-7-chloro-6-[5-(2,2-dimethyl-propyl)-pyridin-2-ylmethylthio]-2,3,4,5-tetrahydro-1H-benzo[d]azepine as an oil (69 mg, 24%). MS (APCI+) m/z: 501 (M+H)$^+$. Use a method similar to the General Procedure 1-4 to give the title compound as a white powder. MS (APCI+) m/z: 375 (M+H)$^+$.

EXAMPLE 366

7-Chloro-6-(5-cyclohexylpyridin-2-ylmethylthio)-2,3,4,5-tetrahydro-1H-benzo[d]azepine Hydrochloride

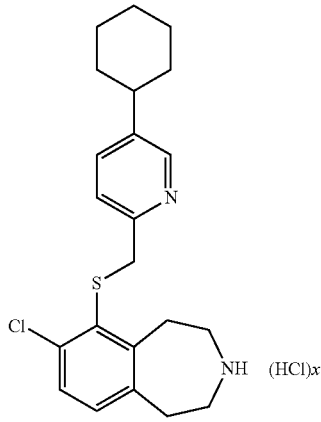

To a mixture of 6-(5-bromopyridin-2-ylmethylthio)-3-tert-butoxycarbonyl-7-chloro-2,3,4,5-tetrahydro-1H-benzo[d]azepine (146 mg, 0.30 mmol) and dichloro[1,1'-bis(diphenylphosphino)ferrocene]palladium(II) dichloromethane adduct (12 mg, 0.015 mmol) under dry nitrogen add with stirring a solution of 0.5 M cyclohexylzinc bromide in THF (3.0 mL, 1.5 mmol). Degas, purge with dry nitrogen, and stir overnight at 60° C. Cool to ambient temperature, dilute with EtOAc, wash with water, dry over anhydrous MgSO$_4$ and concentrate in vacuo. Purify by chromatography on silica gel eluting with hexane/EtOAc (5:1) to give 3-tert-butoxycarbonyl-7-chloro-6-(5-cyclohexyl-pyridin-2-ylmethylthio)-2,3,4,5-tetrahydro-1H-benzo[d]azepine as an oil (46 mg, 32%). MS (APCI+) m/z: 487 (M+H)$^+$. Use a method similar to the General Procedure 14 to give the title compound as a white solid. MS (APCI+) m/z: 387 (M+H)$^+$.

EXAMPLE 367

7-Chloro-6-(5-cyclopentylpyridin-2-ylmethylthio)-2,3,4,5-tetrahydro-1H-benzo[d]azepine Succinate

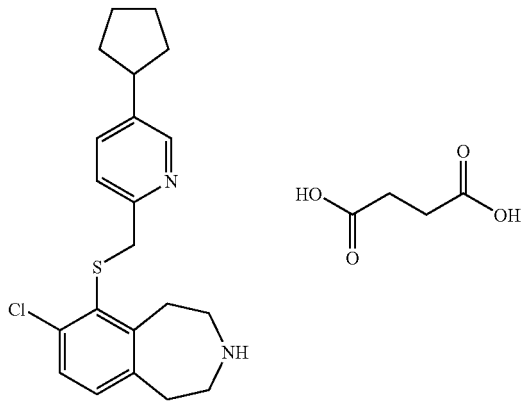

Use a method similar to the Example 366 to react 6-(5-bromo-pyridin-2-ylmethylthio)-3-tert-butoxycarbonyl-7-chloro-2,3,4,5-tetrahydro-1H-benzo[d]azepine with a solution of cyclopentylzinc bromide in THF. Use a method similar to the General Procedure 1-4, basic workup, and a method similar to the General Procedure 2-1 to give the title compound as a tan solid. MS (APCI+) m/z: 373 (M+H)$^+$.

EXAMPLE 368

7-Chloro-6-(5-cyclohexylmethylpyridin-2-ylmethylthio)-2,3,4,5-tetrahydro-1H-benzo[d]azepine Hydrochloride

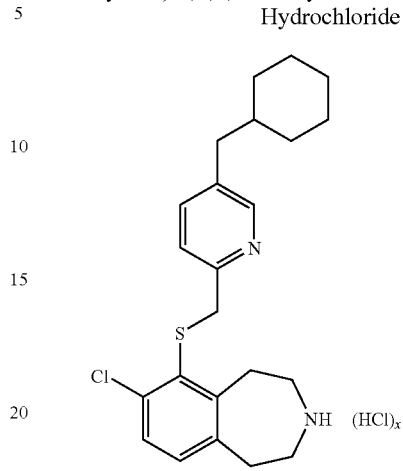

Use a method similar to the Example 366 to react 6-(5-bromo-pyridin-2-ylmethylthio)-3-tert-butoxycarbonyl-7-chloro-2,3,4,5-tetrahydro-1H-benzo[d]azepine with cyclohexylmethylzinc bromide. Use a method similar to the General Procedure 1-5, basic workup, and a method similar to the General Procedure 2-2 to give the title compound as a white solid. MS (APCI+) m/z: 401 (M+H)$^+$.

EXAMPLE 369

7-Chloro-6-(3,4,5,6-tetrahydro-2H-[1,3']bipyridinyl-6'-ylmethylthio)-2,3,4,5-tetrahydro-1H-benzo[d]azepine Hydrochloride

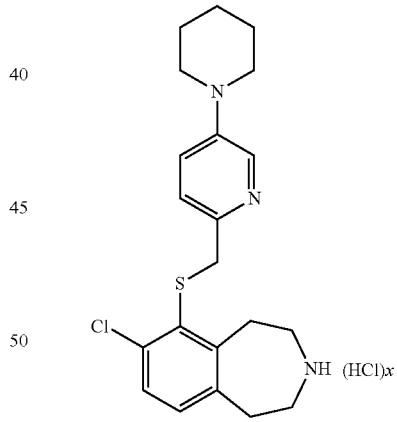

In a sealed tube, add tris(dibenzylideneacetone)dipalladium(0) (3.44 mg, 0.00376 mmol) and 2,2'-bis(diphenylphosphino)-1,1'-binaphthyl (4.98 mg, 0.00752 mmol) to a mixture of 6-(5-bromopyridin-2-ylmethylthio)-3-tert-butoxycarbonyl-7-chloro-2,3,4,5-tetrahydro-1H-benzo[d]azepine (242 mg, 0.501 mmol), sodium tert-butoxide (96 mg, 1.0 mmol), 18-crown-6 (13 mg, 0.050 mmol) and piperidine (496 µL, 5.01 mmol) in toluene (3 mL). Flush the mixture with nitrogen and heat overnight. Cool to ambient temperature, dilute with water and extract three times with EtOAc. Dry over anhydrous Na$_2$SO$_4$ and concentrate in vacuo. Purify by chromatography on silica gel eluting with hexane/EtOAc (9:1) to give 3-tert-butoxycarbonyl-7-chloro-6-(3,4,5,6-tetrahydro-2H-[1,3']bipyridinyl-6'-ylmethylthio)-2,3,4,5-tetrahydro-1H-benzo[d]azepine as a yellow oil (179 mg, 73%).

Use a method similar to the General Procedure 1-5, using 3-tert-butoxycarbonyl-7-chloro-6-(3,4,5,6-tetrahydro-2H-[1,3']bipyridinyl-6'-ylmethylthio)-2,3,4,5-tetrahydro-1H-benzo[d]azepine to give, after basic workup and a method similar to the General Procedure 2-2, the title compound as a yellow solid. MS (ES+) m/z: 388 (M+H)$^+$.

EXAMPLE 370

7-Chloro-6-(5-pyrrolidin-1-yl-pyridin-2-ylmethylthio)-2,3,4,5-tetrahydro-1H-benzo[d]azepine Hydrochloride

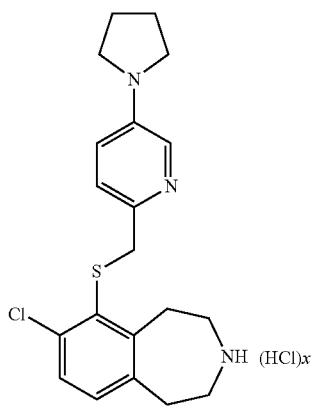

Use a method similar to the Example 369, using 6-(5-bromopyridin-2-ylmethylthio)-3-tert-butoxycarbonyl-7-chloro-2,3,4,5-tetrahydro-1H-benzo[d]azepine and pyrrolidine to give the title compound as a pale yellow solid. MS (ES+) m/z: 374 (M+H)$^+$.

EXAMPLE 371

6-(5-Azepan-1-yl-pyridin-2-ylmethylthio)-7-chloro-2,3,4,5-tetrahydro-1H-benzo[d]azepine Hydrochloride

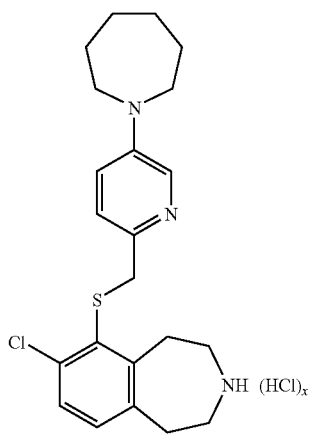

Use a method similar to the Example 369, using 6-(5-bromopyridin-2-ylmethylthio)-3-tert-butoxycarbonyl-7-chloro-2,3,4,5-tetrahydro-1H benzo[d]azepine and homopiperidine to give the title compound as a yellow solid. MS (ES+) m/z 402 (M+H)$^+$.

EXAMPLE 372

7-Chloro-6-(3,4,5,6-tetrahydro-2H-[1,2']bipyridinyl-5'-ylmethylthio)-2,3,4,5-tetrahydro-1H-benzo[d]azepine Hydrochloride

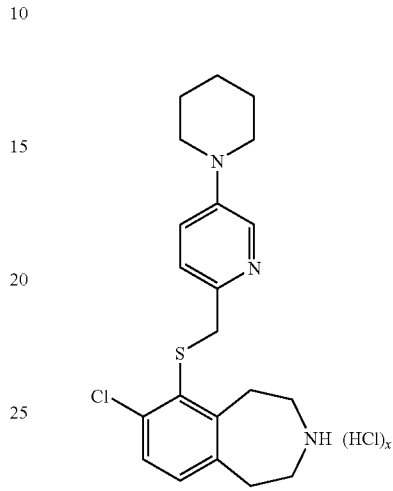

Use a method similar to the Example 369, using 3-tert-butoxycarbonyl-7-chloro-6-(6-chloropyridin-3-ylmethylthio)-2,3,4,5-tetrahydro-1H-benzo[d]azepine and piperidine, to give the title compound as a white solid. MS (ES+) m/z: 388 (M+H)$^+$.

EXAMPLE 373

7-Chloro-6-[5-(4-fluorophenylethynyl)-pyridin-2-ylmethylthio]-2,3,4,5-tetrahydro-1H-benzo[d]azepine Hydrochloride

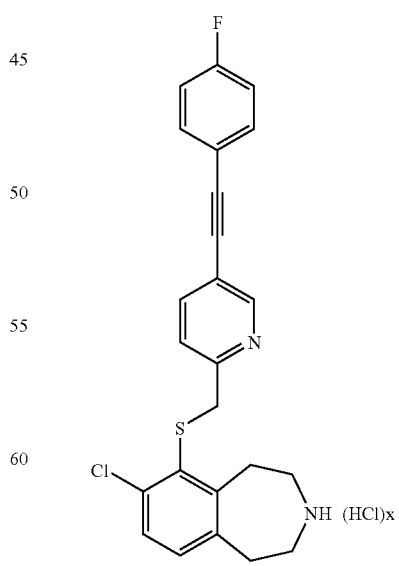

Dissolve 3-tert-butoxycarbonyl-6-(5-bromopyridin-2-ylmethylthio)-7-chloro-2,3,4,5-tetrahydro-1H-benzo[d]

azepine (1.0 g, 2.07 mmol), tetrakistriphenylphosphine palladium(0) (120 mg, 0.104 mmol), cuprous iodide-(20 mg, 0.105 mmol), triethylamine (2.60 mL) and 1-ethynyl-4-fluorobenzene (500 mg, 4.16 mmol) in DMF (8 mL). Degas the mixture, purge with nitrogen, and heat at 65° C. for 3 days. Dilute the mixture with water, extract three times with EtOAc, dry over anhydrous Na$_2$SO$_4$, and concentrate in vacuo. Purify by chromatography on silica gel eluting with hexane/EtOAc (50:1) to give 3-tert-butoxycarbonyl-7-chloro-6-[5-(4-fluorophenylethynyl)-pyridin-2-ylmethylthio]-2,3,4,5-tetrahydro-1H-benzo[d]azepine as a tan foam (1.02 g, 95%). MS (APCI+) m/z: 523 (M+H)$^+$, 423 (M+H– Boc)$^+$. Use a method similar to the General Procedure 14 to give the title compound as a tan powder. MS (APCI+) m/z: 423 (M+H)$^+$.

EXAMPLE 374

(Z)-7-Chloro-6-{5-[2-(4-fluorophenyl)vinyl]-pyridin-2-ylmethylthio}-2,3,4,5-tetrahydro-1H-benzo[d]azepine Hydrochloride

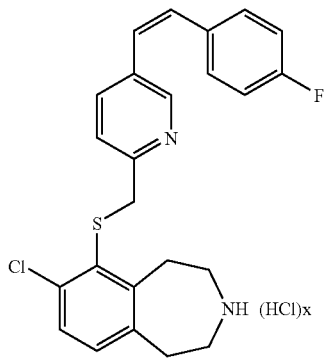

Dissolve 3-tert-butoxycarbonyl-7-chloro-6-[5-(4-fluorophenylethynyl)-pyridin-2-ylmethylthio]-2,3,4,5-tetrahydro-1H-benzo[d]azepine (1.0 g, 1.9 mmol), Lindlar catalyst (240 mg), and quinoline (0.8 mL) in methanol (30 mL). Degas, purge with nitrogen, and stir under a balloon of hydrogen for 36 h. Filter the mixture and wash the catalyst with additional methanol. Concentrate the filtrate in vacuo. Purify by chromatography on silica gel eluting with hexane/EtOAc (8:1) to give (Z)-3-tert-butoxycarbonyl-7-chloro-6-{5-[2-(4-fluoro-phenyl)-vinyl]-pyridin-2-ylmethylthio}-2,3,4,5-tetrahydro-1H-benzo[d]azepine as a clear oil (630 mg, 63%). MS (APCI+) m/z: 525 (M+H), 425 (M+H–Boc)$^+$. Use a method similar to the General Procedure 1-4 to give the title compound as a pale yellow solid. MS (APCI+) m/z: 425 (M+H)$^+$.

EXAMPLE 375

7-Chloro-6-[5-(2-fluoro-4-trifluoromethylbenzylcarbamoyl)-pyridin-2-ylmethylthio]-2,3,4,5-tetrahydro-1H-benzo[d]azepine Succinate

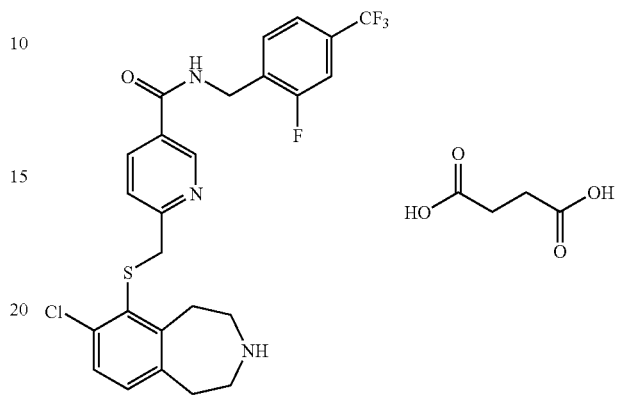

Dissolve 3-tert-butoxycarbonyl-6-(5-carboxypyridin-2-ylmethylthio)-7-chloro-2,3,4,5-tetrahydro-1H-benzo[d]azepine (300 mg, 0.67 mmol) in DMF (5.0 mL). Treat successively with HATU (305 mg, 0.802 mmol), N,N-diisopropylethylamine (140 µL, 0.804 mmol) and 2-fluoro-4-(trifluoromethyl)benzylamine (260 mg, 1.34 mmol). Stir overnight at 40° C. Dilute the mixture with water, extract three times with EtOAc, dry over anhydrous Na$_2$SO$_4$, and concentrate in vacuo. Purify by chromatography on silica gel eluting with hexane/EtOAc (3:1) to give 3-tert-butoxycarbonyl-7-chloro-6-[5-(2-fluoro-4-trifluoromethyl-benzylcarbamoyl)-pyridin-2-ylmethylthio]-2,3,4,5-tetrahydro-1H-benzo[d]azepine as a foam (409 g, 98%). Use a method similar to the General Procedure 1-4 to give, after basic work-up and a method similar to the General Procedure 2-1, the title compound as an off-white solid. MS (APCI+) m/z: 524 (M+H)$^+$.

EXAMPLE 376

7-Chloro-6-[5-(2,2-dimethylpropylcarbamoyl)-pyridin-2-ylmethylthio]-2,3,4,5-tetrahydro-1H-benzo[d]azepine Succinate

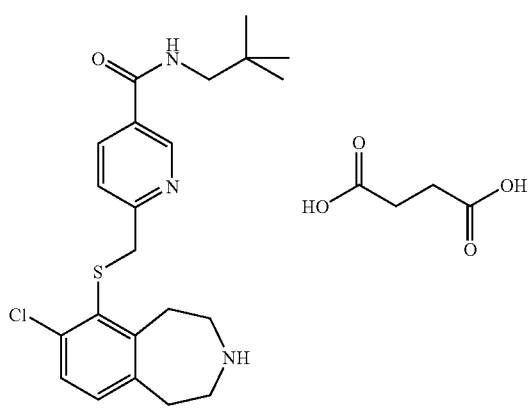

Use a method similar to the Example 375, using 3-tert-butoxycarbonyl-6-(5-carboxy-pyridin-2-ylmethylthio)-7-chloro-2,3,4,5-tetrahydro-1H-benzo[d]azepine and neopentylamine, to give the title compound as an off-white solid. MS (APCI+) m/z: 418 (M+H)⁺.

EXAMPLE 377

7-Chloro-6-[5-(4-fluoro-benzylcarbamoyl)-pyridin-2-ylmethylthio]-2,3,4,5-tetrahydro-1H-benzo[d]azepine Succinate

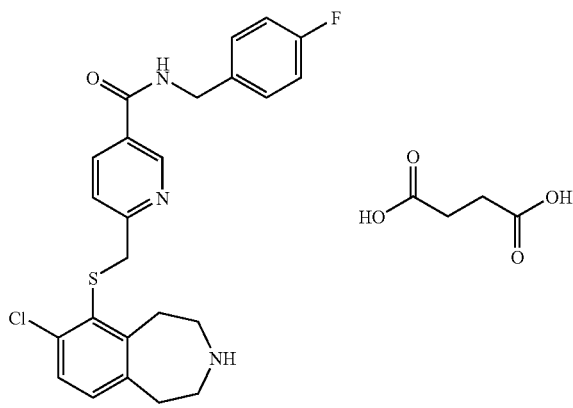

Use a method similar to the Example 375, using 3-tert-butoxycarbonyl-6-(5-carboxy-pyridin-2-ylmethylthio)-7-chloro-2,3,4,5-tetrahydro-1H-benzo[d]azepine and 4-fluorobenzylamine, to give the title compound as an off-white solid. MS (APCI+) m/z: 456 (M+H)⁺.

EXAMPLE 378

7-Chloro-6-[5-(cyclohexylmethylcarbamoyl)-pyridin-2-ylmethylthio]-2,3,4,5-tetrahydro-1H-benzo[d]azepine Hydrochloride

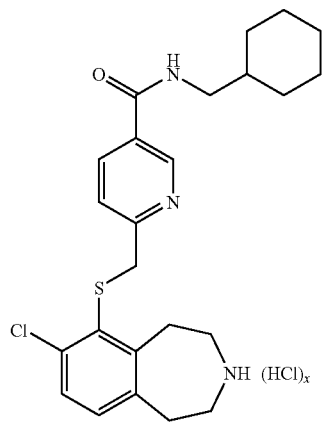

Use a method similar to the Example 375, using 3-tert-butoxycarbonyl-6-(5-carboxy-pyridin-2-ylmethylthio)-7-chloro-2,3,4,5-tetrahydro-1H-benzo[d]azepine and aminomethylcyclohexane to give, after deprotection by the General Procedure 1-4, the title compound as a white solid. MS (APCI+) m/z: 444 (M+H)⁺.

EXAMPLE 379

6-(5-tert-Butylcarbamoyl-pyridin-2-ylmethylthio)-7-chloro-2,3,4,5-tetrahydro-1H-benzo[d]azepine Hydrochloride

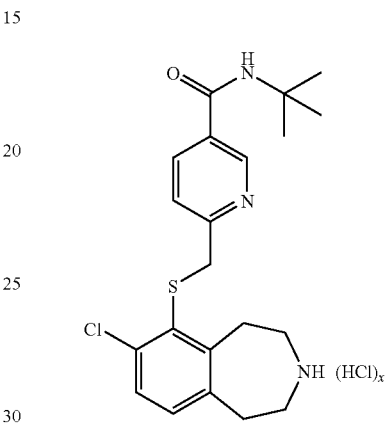

Use a method similar to the Example 375, using 3-tert-butoxycarbonyl-6-(5-carboxy-pyridin-2-ylmethylthio)-7-chloro-2,3,4,5-tetrahydro-1H-benzo[d]azepine and tert-butylamine to give, after deprotection by the General Procedure 14, the title compound as an off-white solid. MS (APCI+) m/z: 404 (M+H)⁺.

EXAMPLE 380

7-Chloro-6-(4-trifluoromethoxybenzylthio)-2,3,4,5-tetrahydro-1H-benzo[d]azepine Hydrochloride

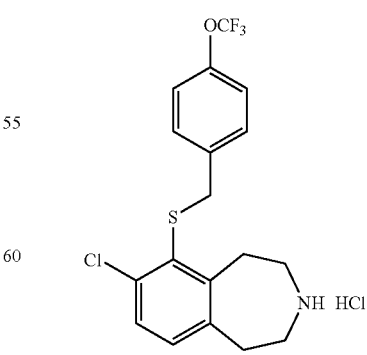

To a 4:1 mixture of 3-tert-butoxycarbonyl-7-chloro-6-dimethylcarbamoylthio-2,3,4,5-tetrahydro-1H-benzo[d]azepine and 3-tert-butoxycarbonyl-7,9-dichloro-6-dimethylcarbamoylthio-2,3,4,5-tetrahydro-1H-benzo[d]azepine (102 mg, 0.27 mmol) in methanol (1.7 mL) under nitrogen, add potassium hydroxide (0.9 g, 16.1 mmol) at ambient temperature. When the mixture becomes homogenous, heat at 55-60° C. for 2-3 h, until TLC shows the disappearance of starting material. Cool to ambient temperature, add aqueous saturated ammonium chloride solution, extract three times with diethyl ether, dry over anhydrous $MgSO_4$, and concentrate in vacuo. Dissolve the crude 3-tert-butoxycarbonyl-7-chloro-6-mercapto-2,3,4,5-tetrahydro-1H-benzo[d]azepine in anhydrous DCM (2 mL) under nitrogen. Add with stirring DBU (80 μL, 0.532 mmol) and 4-(trifluoromethoxy)benzyl bromide (77 μL, 0.53 mmol) at ambient temperature and allow the reaction to continue overnight. Dilute with aqueous saturated ammonium chloride solution, extract three times with diethyl ether, dry over anhydrous $MgSO_4$, and concentrate in vacuo. Treat a solution of the crude 3-tert-butoxycarbonyl-7-chloro-6-(4-trifluoromethoxy-benzylthio)-2,3,4,5-tetrahydro-1H-benzo[d]azepine in DCM (2 mL) with 2M hydrogen chloride in ether (excess) and continue stirring until TLC shows consumption of starting material. Concentrate in vacuo and triturate the obtained solid with ether/pentane (10:90). Purify by preparative TLC eluting with 19:1 DCM/saturated ammonia in methanol and convert to the hydrochloride by following a method similar to the General Procedure 2-2 to give the title compound as a white solid (48 mg, 43%). MS (APCI+) m/z: 388 (M+H)+.

Examples 381-383 may be prepared essentially as described in Example 380 by using 3-tert-butoxycarbonyl-7-chloro-6-dimethylcarbamoylthio-2,3,4,5-tetrahydro-1H-benzo[d]azepine and the appropriately substituted benzyl bromide. Example 382 may be purified after deprotection by preparative reverse phase HPLC [Column: YMC ODS-AQ 120 Å 20×250 mm [S10-20 μm], eluent: gradient from 95:5 to 5:95 A/B, flow rate: 15 mL/min; solvent A: water, 0.1% TFA, 1% isopropanol; solvent B: acetonitrile, 0.05% TFA, 1% isopropanol]. MS (ES+) data are included in the Table below.

EXAMPLE 384

7-Chloro-6-(4-fluoro-benzylthio)-2,3,4,5-tetrahydro-1H-benzo[d]azepine Trifluoroacetate

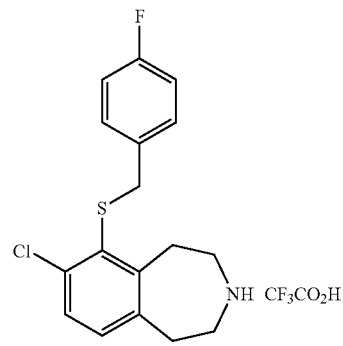

Use a method similar to the Example 380 to react 3-tert-butoxylcarbonyl-7-chloro-6-dimethylcarbamoylthio-2,3,4,5-tetrahydro-1H-benzo[d]-azepine with 4 fluorobenzyl bromide. Purify by preparative reverse phase HPLC [Column: YMC ODS-AQ 120 Å 20×250 mm [S10-20 μm], eluent: gradient from 95:5 to 5:95 A/B, flow rate: 15 mL/min; solvent A: water, 0.1% TFA, 1% isopropanol; solvent B: acetonitrile, 0.05% TFA, 1% isopropanol] to give the title compound as a white solid. MS (ES+) m/z: 322 (M+H)+.

Examples 385-386 may be prepared essentially as described in Example 384 by using 3-tert-butoxycarbonyl-7-chloro-6-dimethylcarbamoylthio-2,3,4,5-tetrahydro-1H-benzo[d]azepine and the appropriately substituted benzyl bromide. MS (ES+) data are included in the Table below.

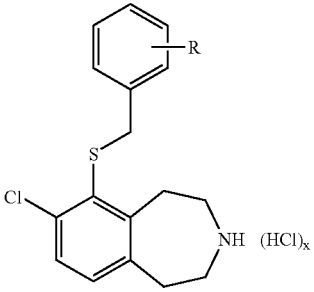

| Ex. | R | Compound | MS (ES+) m/z |
|---|---|---|---|
| 381 | 2-Cl | 7-Chloro-6-(2-chloro-benzylthio)-2,3,4,5-tetrahydro-1H-benzo[d]azepine Hydrochloride | 338 (M + H)+ |
| 382 | 2-CN | 7-Chloro-6-(2-cyano-benzylthio)-2,3,4,5-tetrahydro-1H-benzo[d]azepine Hydrochloride | 329 (M + H)+ |
| 383 | 4-Ph | 7-Chloro-6-(4-phenyl-benzylthio)-2,3,4,5-tetrahydro-1H-benzo[d]azepine Hydrochloride | 380 (M + H)+ |

| Ex. | R | Compound | MS (ES+) m/z |
|---|---|---|---|
| 385 | 4-Cl | 7-Chloro-6-(4-chloro-benzylthio)-2,3,4,5-tetrahydro-1H-benzo[d]azepine Trifluoroacetate | 338 (M + H)+ |
| 386 | 4-CN | 7-Chloro-6-(4-cyano-benzylthio)-2,3,4,5-tetrahydro-1H-benzo[d]azepine Trifluoroacetate | 329 (M + H)+ |

EXAMPLE 387

7-Chloro-6-(3,4-dichlorobenzylthio)-2,3,4,5-tetrahydro-1H-benzo[d]azepine Trifluoroacetate

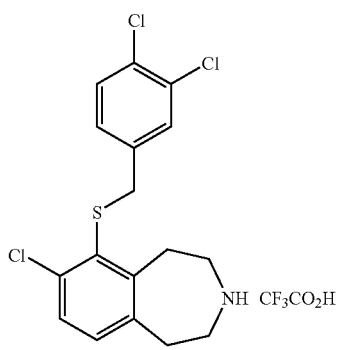

To a 4:1 mixture of 3-tert-butoxycarbonyl-7-chloro-6-dimethylcarbamoylthio-2,3,4,5-tetrahydro-1H-benzo[d]azepine and 3-tert-butoxycarbonyl-7,9-dichloro-6-dimethylcarbamoylthio-2,3,4,5-tetrahydro-1H-benzo[d]azepine (200 mg, 0.521 mmol) in methanol (3.3 mL) under nitrogen add potassium hydroxide (0.9 g, 16.07 mmol) at ambient temperature. When the mixture becomes homogenous, heat at 55-60° C. for 2-3 h, until TLC shows the disappearance of starting material. Cool to ambient temperature, add aqueous saturated ammonium chloride solution, extract three times with diethyl ether, dry over anhydrous $MgSO_4$, and concentrate in vacuo. Dissolve the crude 3-tert-butoxycarbonyl-7-chloro-6-mercapto-2,3,4,5-tetrahydro-1H-benzo[d]azepine in anhydrous DCM (5 mL) under nitrogen. Add PS-DIEA (Argonaut, 3.83 mmol/g, 410 mg, 1.57 mmol) and 3,4-dichlorobenzyl bromide (100 µL, 0.586 mmol) at ambient temperature and allow the reaction to continue overnight. Filter the reaction mixture from the resin and rinse with DCM (2 mL), methanol (2 mL), DCM (2 mL), and methanol (2 mL). Concentrate in vacuo. Treat a solution of the crude 3-tert-butoxycarbonyl-7-chloro-6-(3,4-dichloro-benzylthio)-2,3,4,5-tetrahydro-1H-benzo[d]azepine in DCM (2 mL) with a 2M hydrogen chloride in ether (excess) and continue stirring until TLC shows consumption of starting material. Concentrate in vacuo and triturate the obtained solid with ether:pentane (10:90). Purify by preparative reverse phase HPLC (Column: Xterra Prep RP18 19×250 mm; Solvent A: 10 mM aqueous ammonium carbonate, Solvent B: acetonitrile; 30-100% B over 20 minutes; flow rate 25 mL/min) to give the title compound as a white solid (97 mg, 38%). MS (APCI+) m/z: 374 (M+H)+.

Examples 388-393 may be prepared essentially as described in Example 387 by using 3-tert-butoxycarbonyl-7-chloro-6-dimethylcarbamoylthio-2,3,4,5-tetrahydro-1H-benzo[d]azepine and the appropriately substituted benzyl bromide. MS (ES+) data are included in the Table below.

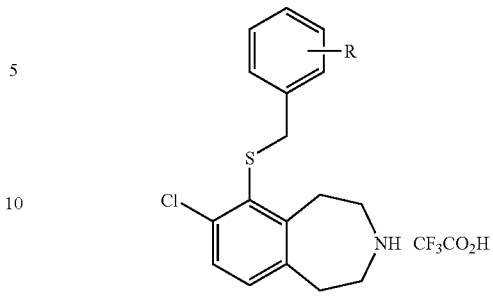

| Ex. | R | Compound | MS (ES+ or APCI+) |
|---|---|---|---|
| 388 | 3-Cl | 7-Chloro-6-(3-chloro-benzylthio)-2,3,4,5-tetrahydro-1H-benzo[d]azepine Trifluoroacetate | 338 (M + H)+ |
| 389 | 3-F | 7-Chloro-6-(3-fluoro-benzylthio)-2,3,4,5-tetrahydro-1H-benzo[d]azepine Trifluoroacetate | 322 (M + H)+ |
| 390 | 3,4-diF | 7-Chloro-6-(3,4-difluoro-benzylthio)-2,3,4,5-tetrahydro-1H-benzo[d]azepine Trifluoroacetate | 340 (M + H)+ |
| 391 | 3,5-diF | 7-Chloro-6-(3,5-difluoro-benzylthio)-2,3,4,5-tetrahydro-1H-benzo[d]azepine Trifluoroacetate | 340 (M + H)+ |
| 392 | 3,4,5-triF | 7-Chloro-6-(3,4,5-trifluoro-benzylthio)-2,3,4,5-tetrahydro-1H-benzo[d]azepine Trifluoroacetate | 358 (M + H)+ |
| 393 | 3-OCF3 | 7-Chloro-6-(3-trifluoromethoxybenzylthio)-2,3,4,5-tetrahydro-1H-benzo[d]azepine Trifluoroacetate | 388 (M + H)+ |

EXAMPLE 394

7,9-Dichloro-6-(3-fluorobenzylthio)-2,3,4,5-tetrahydro-1H-benzo[d]azepine Trifluoroacetate

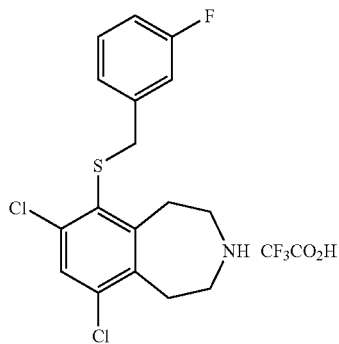

Obtain as minor product from the reaction of the 4:1 mixture of 3-tert-butoxycarbonyl-7-chloro-6-dimethylcarbamoylthio-2,3,4,5-tetrahydro-1H-benzo[d]azepine and 3-tert-butoxycarbonyl-7,9-dichloro-6-dimethylcarbamoylthio-2,3,4,5-tetrahydro-benzo[d]azepine with 3-fluorobenzyl bromide, using a method similar to the Example 387. Depro-

EXAMPLE 395

7,9-Dichloro-6-(3,4,5-trifluorobenzylthio)-2,3,4,5-tetrahydro-1H-benzo[d]azepine Trifluoroacetate

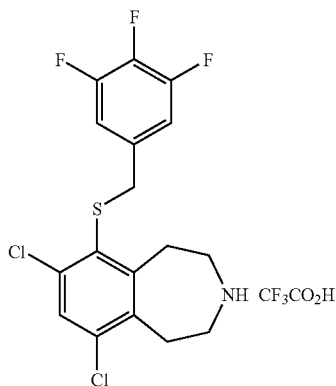

Obtain as minor product from the reaction of the 4:1 mixture of 3-tert-butoxycarbonyl-7-chloro-6-dimethylcarbamoylthio-2,3,4,5-tetrahydro-1H-benzo[d]azepine and 3-tert-butoxycarbonyl-7,9-dichloro-6-dimethylcarbamoylthio-2,3,4,5-tetrahydro-benzo[d]azepine with 3,4,5-trifluorobenzyl bromide, using a method similar to the Example 387. Deprotect and isolate the title compound as a white solid after preparative reverse phase HPLC. MS (APCI+) m/z: 392 (+H)+.

EXAMPLE 396

7-Chloro-6-(2-nitro-benzylthio)-2,3,4,5-tetrahydro-1H-benzo[d]azepine Hydrochloride

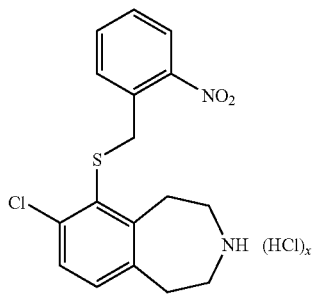

Use a method similar to the Example 387, using 3-tert-butoxylcarbonyl-7-chloro-6-dimethylcarbamoylthio-2,3,4,5-tetrahydro-1H-benzo[d]-azepine and 2-nitrobenzyl bromide to give, after chromatography eluting with hexane/EtOAc (10:1) and deprotection by the General Procedure 1-4, the title compound as an off-white powder. MS (APCI+) m/z: 349 (M+H)+.

Examples 397-399 may be prepared essentially as described in Example 396 by using 3-tert-butoxycarbonyl-7-chloro-6-dimethylcarbamoylthio-2,3,4,5-tetrahydro-1H-benzo[d]azepine and the appropriately substituted benzyl bromide. MS (ES+) data are included in the Table below.

![structure with R substituent]

| Ex. | R | Compound | MS (ES+ or APCI+) |
|---|---|---|---|
| 397 | 2-OCF$_3$ | 7-Chloro-6-(2-trifluoromethoxybenzylthio)-2,3,4,5-tetrahydro-1H-benzo[d]azepine Hydrochloride | 388 (M + H)+ |
| 398 | 3-OPh | 7-Chloro-6-(3-phenoxybenzylthio)-2,3,4,5-tetrahydro-1H-benzo[d]azepine Hydrochloride | 396 (M + H)+ |
| 399 | 3,5-diCF$_3$ | 7-Chloro-6-(3,5-bistrifluoromethylbenzylthio)-2,3,4,5-tetrahydro-1H-benzo[d]azepine Hydrochloride | 440 (M + H)+ |

EXAMPLE 400

7,9-Dichloro-6-(3,5-bis-trifluoromethylbenzylthio)-2,3,4,5-tetrahydro-1H-benzo[d]azepine Hydrochloride (2148393)

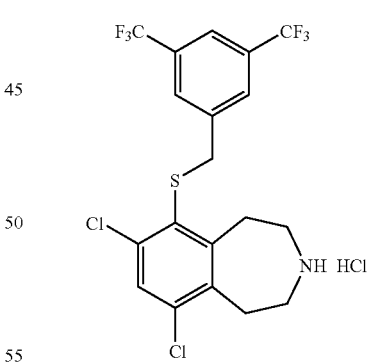

Obtain as minor product from the reaction of the 4:1 mixture of 3-tert-butoxycarbonyl-7-chloro-6-dimethylcarbamoylthio-2,3,4,5-tetrahydro-1H-benzo[d]azepine and 3-tert-butoxycarbonyl-7,9-dichloro-6-dimethylcarbamoylthio-2,3,4,5-tetrahydro-benzo[d]azepine with 3,5-bis-trifluoromethylbenzyl bromide, using a method similar to the Example 396. Deprotect the crude mixture and purify by preparative reverse phase HPLC (Column: Xterra Prep RP18 19×250 mm; solvent A: 10 mM aqueous ammonium carbonate; solvent B: acetonitrile; 30-100% B over 20 minutes; flow rate 25 mL/min). Use a method similar to the General Procedure 2-2 to give the title compound as a white solid. MS (APCI+) m/z: 474 (M+H)+.

EXAMPLE 401

7-Chloro-6-(2,6-difluorobenzylthio-)2,3,4,5-tetrahydro-1H-benzo[d]azepine Hydrochloride

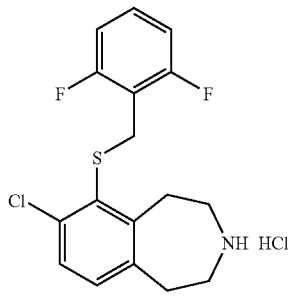

Use a method similar to the Example 330, using 3-tert-butoxycarbonyl-7-chloro-6-dimethylcarbamoylthio-2,3,4,5-tetrahydro-1H-benzo[d]azepine and 2,6-difluorobenzyl bromide to give, after deprotection by the General Procedure 1-4, the title compound.

EXAMPLE 402

7-Chloro-6-(2-trifluoromethylbenzylthio)-2,3,4,5-tetrahydro-1H-benzo[d]azepine Hydrochloride

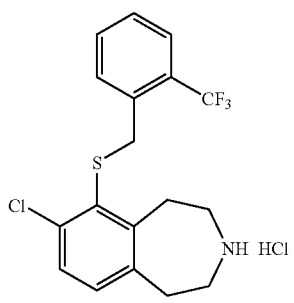

Use a method similar to the Example 347 to react 3-tert-butoxycarbonyl-7-chloro-6-dimethylcarbamoylthio-2,3,4,5-tetrahydro-1H-benzo[d]azepine with 2-trifluoromethylbenzyl bromide. Use a method similar to the General Procedure 1-4 to give the title compound as a waxy tan solid. MS (APCI+) m/z: 372 (M+H)+.

EXAMPLE 403

7-Chloro-6-(4-methoxycarbonylbenzylthio)-2,3,4,5-tetrahydro-benzo[d]azepine Hydrochloride

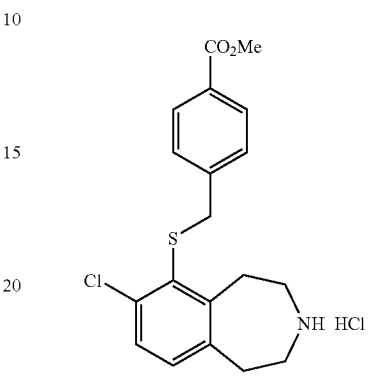

Use a method similar to the Preparation 177, using 3-tert-butoxycarbonyl-7-chloro-6-dimethylcarbamoylthio-2,3,4,5-tetrahydro-1H-benzo[d]azepine and methyl 4-(bromomethyl)benzoate to give, after deprotection by the General Procedure 14, the title compound as a white solid. MS (ES+) m/z: 362 (M+H)+.

EXAMPLE 404

7-Chloro-6-(3-methoxycarbonylbenzylthio)-2,3,4,5-tetrahydro-1H-benzo[d]azepine Hydrochloride

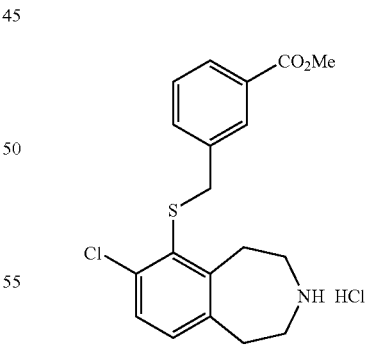

Use a method similar to the Example 347 to react 3-tert-butoxycarbonyl-7-chloro-6-dimethylcarbamoylthio-2,3,4,5-tetrahydro-1H-benzo[d]azepine with methyl 3-(bromomethyl)benzoate. Use a method similar to the General Procedure 1-5, basic workup, and a method similar to the General Procedure 2-2 to give the title compound. MS (APCI+) m/z: 362 (M+H)+.

EXAMPLE 405

7-Chloro-6-(2-methoxycarbonylbenzylthio)-2,3,4,5-tetrahydro-1H-benzo[d]azepine Hydrochloride

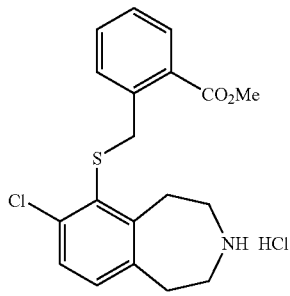

Use a method similar to the Example 347, using the 4:1 mixture of 3-tert-butoxycarbonyl-7-chloro-6-dimethylcarbamoylthio-2,3,4,5-tetrahydro-1H-benzo[d]azepine and 3-tert-butoxycarbonyl-7,9-dichloro-6-dimethylcarbamoylthio-2,3,4,5-tetrahydro-benzo[d]azepine with methyl 2-(bromomethyl)benzoate. Use a method similar to the General Procedure 1-4 and purify by preparative reverse phase HPLC (Column: Xterra Prep RP18 19×250 mm; solvent A: 10 mM aqueous ammonium carbonate, solvent B: acetonitrile; 30-100% B over 20 minutes; flow rate 25 mL/min). Use a method similar to the General Procedure 2-2, to give the title compound as a white solid. MS (ES+) m/z: 362 (M+H)$^+$.

EXAMPLE 406

7,9-Dichloro-6-(2-methoxycarbonylbenzylthio)-2,3,4,5-tetrahydro-1H-benzo[d]azepine Hydrochloride

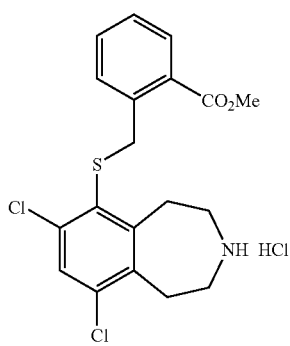

Obtain the free base of the title compound as a minor product from Example 405, after preparative reverse phase HPLC (Column: Xterra Prep RP18 19×250 mm; solvent A: 10 mM aqueous ammonium carbonate; solvent B: acetonitrile; 30-100% B over 20 minutes; flow rate 25 mL/min). Use a method similar to the General Procedure 2-2 to give the title compound as a white solid MS (ES+) m/z: 396 (M+H)$^+$.

EXAMPLE 407

6-(4-Benzoylbenzylthio)-7-chloro-2,3,4,5-tetrahydro-1H-benzo[d]azepine Hydrochloride

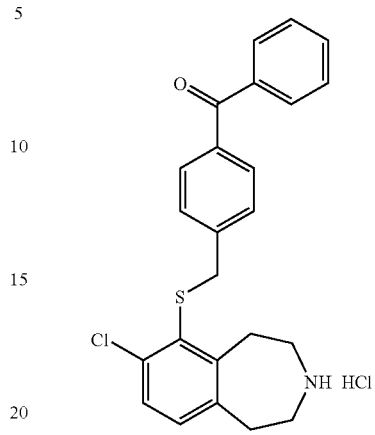

Use a method similar to the Example 380 to react 3-tert-butoxycarbonyl-7-chloro-6-dimethylcarbamoylthio-2,3,4,5-tetrahydro-1H-benzo[d]azepine with 4-(bromomethyl)benzophenone. Purify by preparative reverse phase HPLC (Column: Xterra Prep RP18 19×250 mm; Solvent A: 10 mM aqueous ammonium carbonate, Solvent B: acetonitrile; 30-100% B over 20 minutes; flow rate 25 mL/ruin). Use a method similar to the General Procedure 2-2 to give the title compound as a white solid. MS (ES+) m/z: 408 (M+H)$^+$.

EXAMPLE 408

7-Chloro-6-[4-(3,3-dimethyl-2-oxo-butoxy)-benzylthio]-2,3,4,5-tetrahydro-1H-benzo[d]azepine Succinate

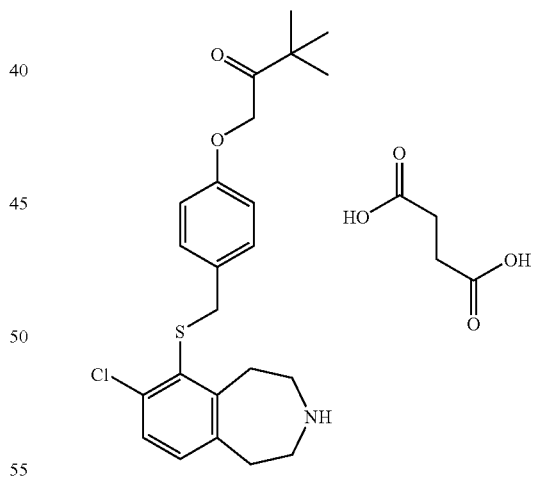

Use a method similar to the General Procedure 7, using 3-tert-butoxycarbonyl-7-chloro-6-dimethylcarbamoylthio-2,3,4,5-tetrahydro-1H-benzo[d]azepine (577 mg, 1.5 mmol) and 1-(4-bromomethylphenoxy)-3,3-dimethylbutan-2-one (556 mg, 1.95 mmol) to give, after chromatography on silica gel eluting with EtOAc/hexane (1:5), 3-tert-butoxycarbonyl-7-chloro-6-[4-(3,3-dimethyl-2-oxo-butoxy)-benzylthio]-2,3,4,5-tetrahydro-1H-benzo[d]azepine as a colorless oil (669 mg, 86%). MS (ES+) m/z: 518 (M+H)$^+$.

Use a method similar to the General Procedure 1-5 to deprotect 3-tert-butoxycarbonyl-7-chloro-6-[4-(3,3-dimethyl-2-oxo-butoxy)-benzylthio]-2,3,4,5-tetrahydro-1H-benzo[d]azepine (669 mg, 1.29 mmol). Purify by chromatography on silica gel eluting with DCM/2M ammonia in methanol (92:8) to give the free base of the title compound as a colorless oil (349 mg, 64%). MS (ES+) m/z: 418 (M+H)+. Use a method similar to the General Procedure 2-1 to give the title compound.

EXAMPLE 409

7-Chloro-6-[3-chloro-4-(3,3-dimethyl-2-oxo-butoxy)-benzylthio]-2,3,4,5-tetrahydro-1H-benzo[d]azepine Succinate

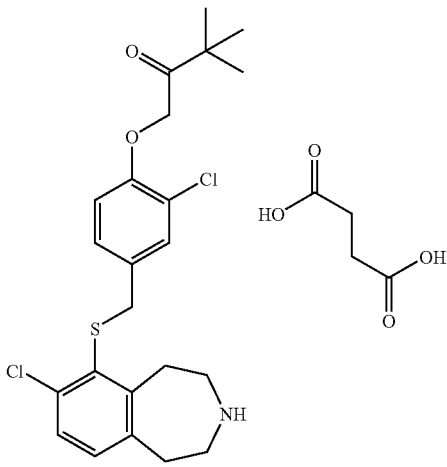

Use a method similar to the Example 408, using 3-tert-butoxycarbonyl-7-chloro-6-dimethylcarbamoylthio-2,3,4,5-tetrahydro-1H-benzo[d]azepine and 1-(4-bromomethyl-3-chlorophenoxy)-3,3-dimethylbutan-2-one to give the title compound. MS (ES+) m/z: 452 (M+H)+.

EXAMPLE 410

7-Chloro-6-(4-methanesulfonylmethyl-benzylthio)-2,3,4,5-tetrahydro-1H-benzo[d]azepine Hydrochloride

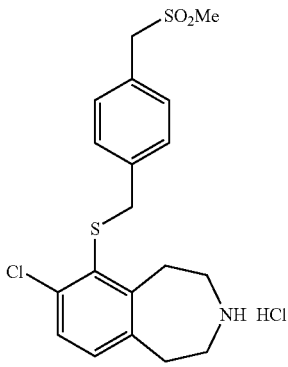

Use a method similar to the General Procedure 1-4, using 3-tert-butoxycarbonyl-7-chloro-6-(4-methanesulfonylm-ethyl-benzylthio)-2,3,4,5-tetrahydro-1H-benzo[d]azepine to give the title compound as a white solid. MS (ES+) m/z: 396 (M+H)+.

EXAMPLE 411

7-Chloro-6-(5-chloro-thiophen-2-ylmethylthio)-2,3,4,5-tetrahydro-1H-benzo[d]azepine Hydrochloride

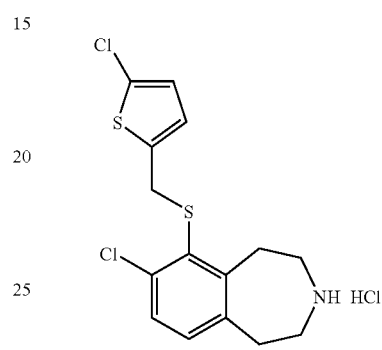

Use a method similar to the Example 387, using 3-tert-butoxycarbonyl-7-chloro-6-dimethylcarbamoylthio-2,3,4,5-tetrahydro-1H-benzo[d]azepine and 2-chloro-5-(chloromethyl)thiophene to give, after hydrochloride formation by the General Procedure 2-2, the title compound as a brown solid. MS (APCI+) m/z: 344 (M+H)+.

EXAMPLE 412

7-Chloro-6-(pyridin-4-ylmethylthio)-2,3,4,5-tetrahydro-1H-benzo[d]azepine Hydrochloride

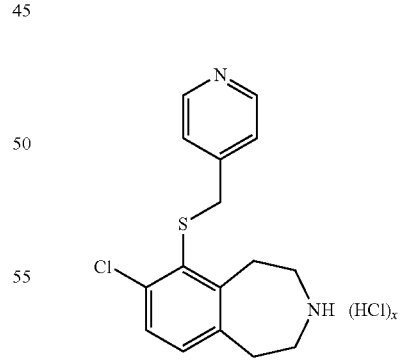

Use a method similar to the Example 387, using 3-tert-butoxycarbonyl-7-chloro-6-dimethylcarbamoylthio-2,3,4,5-tetrahydro-1H-benzo[d]azepine and 4-bromomethylpyridine hydrobromide to give, after hydrochloride formation by the General Procedure 2-2, the title compound as a white solid. MS (APCI+) m/z: 305 (M+H)+.

EXAMPLE 413

7-Chloro-6-(6-methyl-pyridin-2-ylmethylthio)-2,3,4,5-tetrahydro-1H-benzo[d]azepine Hydrochloride

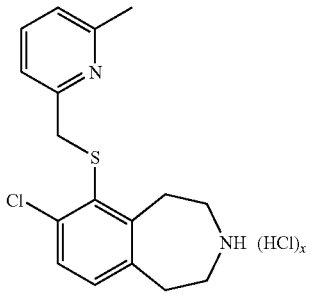

Use a method similar to the Example 387, using 3-tert-butoxycarbonyl-7-chloro-6-dimethylcarbamoylthio-2,3,4,5-tetrahydro-1H-benzo[d]azepine and 2-chloromethyl-6-methylpyridine to give, after chromatography on silica gel eluting with hexane/EtOAc (4:1) and deprotection by the General Procedure 1-4, the title compound as a white solid. MS (ES+) m/z: 319 (M+H)$^+$.

EXAMPLE 414

7-Chloro-6-[3-fluoro-4-(3-methylbutyl)-benzylthio]-2,3,4,5-tetrahydro-1H-benzo[d]azepine Hydrochloride

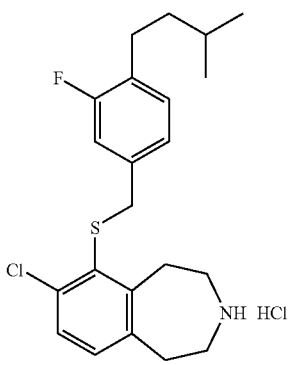

To 6-(4-bromo-3-fluorobenzylthio)-3-tert-butoxycarbonyl-7-chloro-2,3,4,5-tetrahydro-1H-benzo[d]azepine (0.210 mg, 0.42 mmol) and dichloro[1,1'-bis(diphenylphosphino)-ferrocene]palladium(II) dichloromethane adduct (17 mg, 0.021 mmol) add 0.5 M 3-methylbutylzinc bromide in THF (4.2 mL, 2.10 mmol). Degas, purge with dry nitrogen, and stir overnight at 80° C. Cool to ambient temperature, dilute with EtOAc, wash with water, dry over anhydrous MgSO$_4$ and concentrate in vacuo. Purify by chromatography on silica gel eluting with hexane/EtOAc (9:1) to give 3-tert-butoxycarbonyl-7-chloro-6-[3-fluoro-4-(3-methylbutyl)-benzylthio]-2,3,4,5-tetrahydro-1H-benzo[d]azepine as a yellow oil (85 mg, 42%). Use a method similar to the General Procedure 1-4 to give the title compound as a white solid. MS (ES+) m/z: 392 (M+H)$^+$.

EXAMPLE 415

7-Chloro-6-(4-cyclohexylmethyl-3-fluorobenzylthio)-2,3,4,5-tetrahydro-1H-benzo[d]azepine Succinate

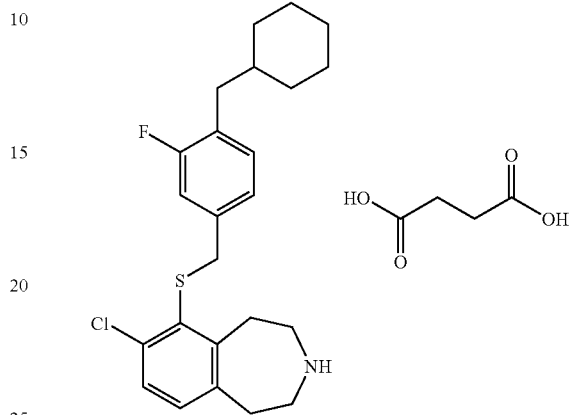

Use a method similar to the Example 414 to react 6-(4-bromo-3-fluorobenzylthio)-3-tert-butoxycarbonyl-7-chloro-2,3,4,5-tetrahydro-1H-benzo[d]azepine with (cyclohexyl)methylzinc bromide. Use a method similar to the General Procedure 1-4, basic work-up, and a method similar to the General Procedure 2-1, to give the title compound as a white solid. MS (ES+) m/z: 418 (M+H)$^+$.

EXAMPLE 416

7-Chloro-6-(4-cyclohexyl-3-fluorobenzylthio)-2,3,4,5-tetrahydro-1H-benzo[d]azepine Hydrochloride

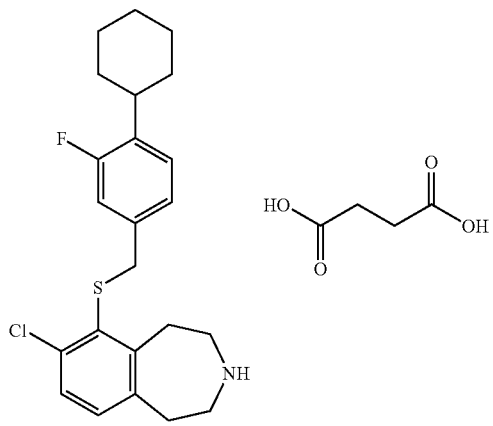

Use a method similar to the Example 414, using 6-(4-bromo-3-fluorobenzylthio)-3-tert-butoxycarbonyl-7-chloro-2,3,4,5-tetrahydro-1H-benzo[d]azepine and cyclohexylzinc bromide. Use a method similar to the General Procedure 1-4, basic work-up, and a method similar to the General Procedure 2-1, to give the title compound as a white solid. MS (ES+) m/z: 404 (M+H)$^+$.

EXAMPLE 417

7-Chloro-6-(2,5'-difluoro-2'-methoxybiphenyl-4-ylmethylthio)-2,3,4,5-tetrahydro-1H-benzo[d]azepine Hydrochloride

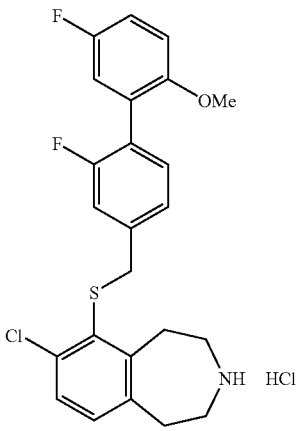

Degas a stirred mixture of 6-(4-bromo-3-fluorobenzylthio)-3-tert-butoxycarbonyl-7-chloro-2,3,4,5-tetrahydro-1H-benzo[d]azepine (212 mg, 0.424 mmol), 5-fluoro-2-methoxybenzene boronic acid (108 mg, 0.636 mmol), potassium carbonate (292 mg, 2.12 mmol), triphenylphosphine (11 mg, 0.0424 mmol) and bis(triphenylphosphine)palladium(II) chloride (15 mg, 0.0212 mmol) in dioxane (3 mL) and water (1 mL). Purge with dry nitrogen and heat at 100° C. for 5 h. Cool to ambient temperature, add water, extract three times with EtOAc, dry over anhydrous $Na_2SO_4$ and concentrate in vacuo. Purify by chromatography on silica gel eluting with hexane/EtOAc (9:1) to give 3-tert-butoxycarbonyl-7-chloro-6-(2,5'-difluoro-2'-methoxy-biphenyl-4-ylmethylthio)-2,3,4,5-tetrahydro-1H-benzo[d]azepine as yellow oil (216 mg, 93%). Use a method similar to the General Procedure 1-4 to give the title compound as a yellow foam. MS (ES+) m/z: 446 (M+H)+.

EXAMPLE 418

7-Chloro-6-(2'-chloro-2-fluorobiphenyl-4-ylmethylthio)-2,3,4,5-tetrahydro-1H-benzo[d]azepine Hydrochloride

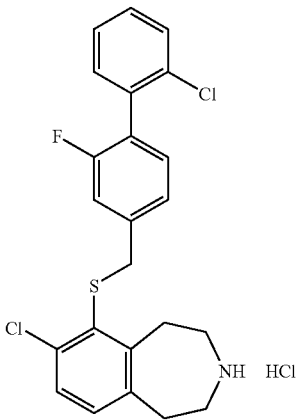

Use a method similar to the Example 417, using 2-chlorophenylboronic acid to give, after deprotection by the General Procedure 1-4, the title compound as a white solid. MS (ES+) m/z: 432 (M+H)+.

EXAMPLE 419

7-Chloro-6-(3-fluoro-4-piperidin-1-yl-benzylthio)-2,3,4,5-tetrahydro-1H-benzo[d]azepine Hydrochloride

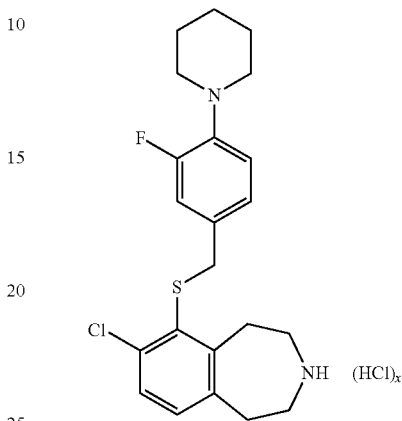

In a sealed tube, add tris(dibenzylideneacetone)dipalladium (13 mg, 0.014 mmol) and 2,2'-bis(diphenylphosphino)-1,1'-binaphthyl (19 mg, 0.029 mmol) to a mixture of 6-(4-bromo-3-fluorobenzylthio)-3-tert-butoxycarbonyl-7-chloro-2,3,4,5-tetrahydro-1H-benzo[d]azepine (957 mg, 1.91 mmol), sodium tert-butoxide (367 mg, 3.83 mmol), 18-crown-6 (50 mg, 0.191 mmol) and piperidine (944 µl, 9.57 mmol) in toluene (10 mL). Flush the mixture with nitrogen and heat overnight. Cool to ambient temperature, dilute with water and extract three times with EtOAc. Dry over anhydrous $Na_2SO_4$ and concentrate in vacuo. Purify by chromatography on silica gel eluting with hexane/EtOAc (9:1) to give 3-tert-butoxycarbonyl-7-chloro-6-(3-fluoro-4-piperidin-1-yl-benzylthio)-2,3,4,5-tetrahydro-1H-benzo[d]azepine as a yellow oil (511 mg, 33%). Use a method similar to the General Procedure 1-4 to give the title compound as a white solid. MS (ES+) m/z: 405 (M+H)+.

EXAMPLE 420

7-Chloro-6-(3-fluoro-4-pyrrolidin-1-yl-benzylthio)-2,3,4,5-tetrahydro-1H-benzo[d]azepine Hydrochloride

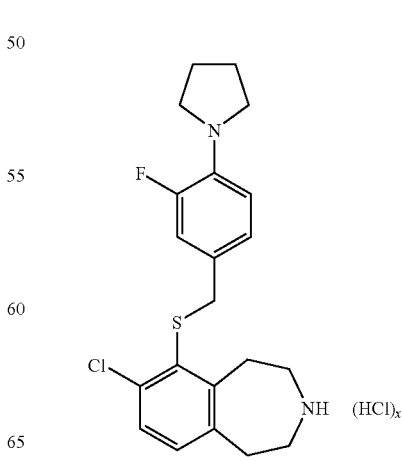

Use a method similar to the Example 419 to react 6-(4-bromo-3-fluorobenzylthio)-3-tert-butoxycarbonyl-7-chloro-2,3,4,5-tetrahydro-1H-benzo[d]azepine with pyrrolidine. Use a method similar to the General Procedure 1-4 to give the title compound as a white solid. MS (ES+) m/z: 391 (M+H)+.

EXAMPLE 421

6-(4-Azepan-1-yl-3-fluorobenzylthio)-7-chloro-2,3,4,5-tetrahydro-1H-benzo[d]azepine Hydrochloride

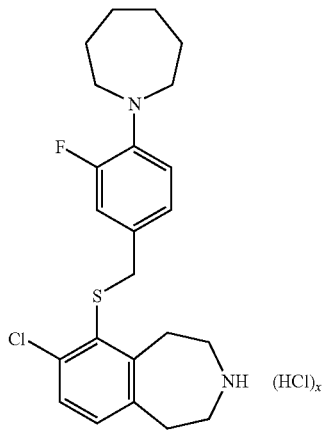

Use a method similar to the Example 419 to react 6-(4-bromo-3-fluorobenzylthio)-3-tert-butoxycarbonyl-7-chloro-2,3,4,5-tetrahydro-1H-benzo[d]azepine with homopiperidine. Use a method similar to the General Procedure 14 to give the title compound as a white solid. MS (ES+) m/z: 419 (M+H)+.

EXAMPLE 422

7-Chloro-6-(4-chloro-3-pyrrolidin-1-yl-benzylthio)-2,3,4,5-tetrahydro-1H-benzo[d]azepine hydrochloride

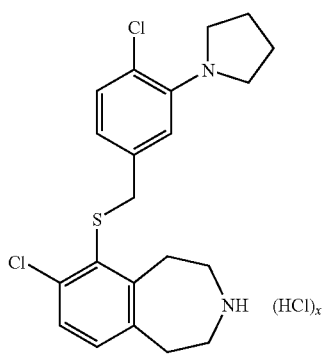

Use a method similar to the Example 419, using 6-(3-bromo-4-chloro-benzylthio)-3-tert-butoxycarbonyl-7-chloro-2,3,4,5-tetrahydro-1H-benzo[d]azepine and pyrrolidine to give, after deprotection using a method similar to the General Procedure 1-4, the title compound as a white solid. MS (ES+) m/z: 407 (M+H)+.

EXAMPLE 423

7-Chloro-6-(4-cyclohexylmethoxybenzylthio)-3-tert-butoxycarbonyl-2,3,4,5-tetrahydro-1H-benzo[d]azepine Hydrochloride

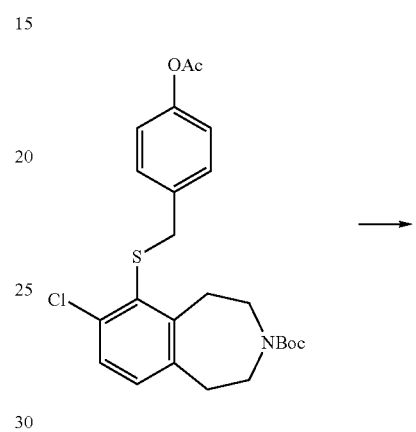

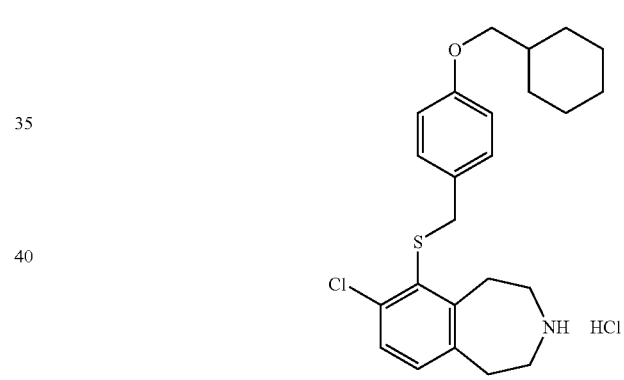

Use a method similar to the Preparation 177, using 3-tert-butoxycarbonyl-7-chloro-6-dimethylcarbamoylthio-2,3,4,5-tetrahydro-1H-benzo[d]azepine and 4-(chloromethyl)phenyl acetate to give 6-(4-acetoxybenzylthio)-3-tert-butoxycarbonyl-7-chloro-2,3,4,5-tetrahydro-1H-benzo[d]azepine as a white solid.

To 6-(4-acetoxybenzylthio)-3-tert-butoxycarbonyl-7-chloro-2,3,4,5-tetrahydro-1H-benzo[d]azepine (532 mg, 1.15 mmol) in methanol (8 mL) at ambient temperature add with stirring a solution of potassium carbonate (796 mg, 5.77 mmol) in water (4 mL) and stir the mixture for 2 h. Dilute with water, extract three times with EtOAc, dry over anhydrous $Na_2SO_4$, and concentrate in vacuo. To a portion of the crude phenol thus obtained (204 mg, 0.487 mmol) in THF (5 mL), add with stirring diisopropyl azodicarboxylate (216 µl, 1.71 mmol) followed by triphenylphosphine (306 mg, 1.17 mmol) and cyclohexylmethanol (619 mg, 5.42 mmol). Heat at 60° C. for 3 h, cool to ambient temperature and concentrate in vacuo. Purify by chromatography on silica gel eluting with hexane/

EtOAc (9:1) to give 3-tert-butoxycarbonyl-7-chloro-6-(4-cyclohexylmethoxy-benzylthio)-2,3,4,5-tetrahydro-1H-benzo[d]azepine as a colorless oil (176 mg, 70%). Use a method similar to the General Procedure 1-4 to give the title compound as a white solid. MS (ES+) m/z: 416 (M+H)+.

EXAMPLE 424

7-Chloro-6-(4-cycloheptyloxybenzylthio)-2,3,4,5-tetrahydro-1H-benzo[d]azepine Hydrochloride

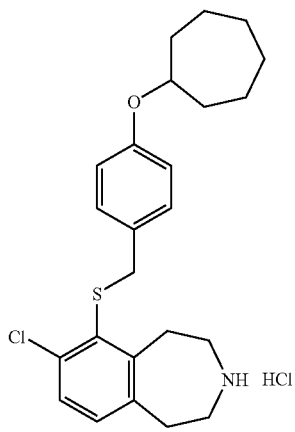

Use a method similar to the Example 423 to react 6-(4-acetoxybenzylthio)-3-tert-butoxycarbonyl-7-chloro-2,3,4,5-tetrahydro-1H-benzo[d]azepine with cycloheptanol. Use a method similar to the General Procedure 1-4 to give the title compound as a white solid. MS (ES+) m/z: 416 (M+H)+.

EXAMPLE 425

7-Chloro-6-[4-(2,2-dimethylpropoxy)-benzylthio]-2,3,4,5-tetrahydro-1H-benzo[d]azepine Hydrochloride

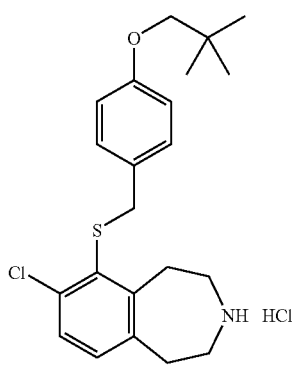

Use a method similar to the Preparation 177 to react 3-tert-butoxycarbonyl-7-chloro-6-dimethylcarbamoylthio-2,3,4,5-tetrahydro-1H-benzo[d]azepine and 1-bromomethyl-4-(2,2-dimethylpropoxy)-benzene. Use a method similar to the General Procedure 1-4 to give the title compound as a white solid. MS (ES+) m/z: 390 (M+H)+.

EXAMPLE 426

7-Chloro-6-(2-methanesulfonylbenzylthio)-2,3,4,5-tetrahydro-1H-benzo[d]azepine Hydrochloride

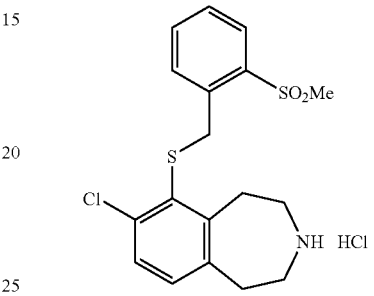

Use a method similar to the Preparation 177, using 3-tert-butoxycarbonyl-7-chloro-6-dimethylcarbamoylthio-2,3,4,5-tetrahydro-1H-benzo[d]azepine and 1-bromomethyl-2-methanesulfonyl-benzene to give, after deprotection by the General Procedure 1-4, the title compound and as a white solid. MS (APCI+) m/z: 382 (M+H)+.

EXAMPLE 427

7-Chloro-6-(4-methanesulfonylbenzylthio)-2,3,4,5-tetrahydro-1H-benzo[d]azepine Hydrochloride

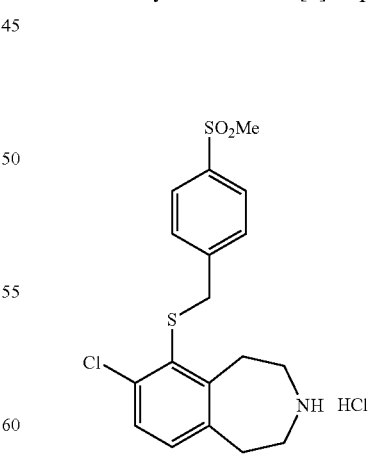

Use a method similar to the Example 380, using 3-tert-butoxycarbonyl-7-chloro-6-dimethylcarbamoylthio-2,3,4,5- tetrahydro-1H-benzo[d]azepine and 4 methylsulfonylbenzyl bromide to give, after hydrochloride formation by the General Procedure 2-2, the title compound as a white solid. MS (ES+) m/z: 382 (M+H)⁺.

EXAMPLE 428

7-Chloro-6-[4-(3,3,3-trifluoro-2-methyl-2-trifluoromethylpropane-1-sulfinyl)-benzylthio]-2,3,4,5-tetrahydro-1H-benzo[d]azepine Hydrochloride

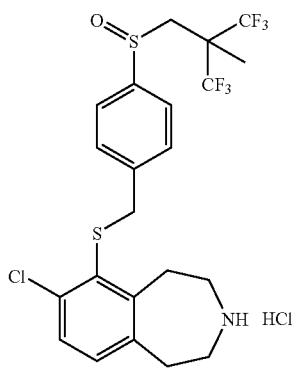

To 3-tert-butoxycarbonyl-7-chloro-6-dimethylcarbamoylthio-2,3,4,5-tetrahydro-1H-benzo[d]azepine (723 mg, 1.88 mmol) in methanol (10 mL) add potassium hydroxide pellets (3.34 g, 60.2 mmol) and stir mixture at 50° C. for 2 h. Cool to ambient temperature, add aqueous saturated ammonium chloride, extract three times with EtOAc, dry over anhydrous Na₂SO₄, and concentrate in vacuo to give the crude 3-tert-butoxycarbonyl-7-chloro-6-mercapto-2,3,4,5-tetrahydro-1H-benzo[d]azepine. Dissolve the compound in DMF (5 mL), add cesium carbonate (920 mg, 2.82 mmol) and 1-bromomethyl-4-(3,3,3-trifluoro-2-methyl-2-trifluoromethyl-propane-1-sulfinyl)-benzene (824 mg, 2.071 mmol) and stir 2 h at ambient temperature. Dilute with water, extract three times with EtOAc, dry over anhydrous Na₂SO₄, and concentrate in vacuo. Purify by chromatography on silica gel eluting with hexane/EtOAc (9:1) to give 3-tert-butoxycarbonyl-7-chloro-6-[4-(3,3,3-trifluoro-2-methyl-2-trifluoromethyl-propane-1-sulfinyl)-benzylthio]-2,3,4,5-tetrahydro-1H-benzo[d]azepine as a yellow oil (986 mg, 83%). Use a method similar to the General Procedure 14 to give the title compound as a white foam. MS (ES+) m/z: 530 (M+H)⁺.

Examples 429-432 may be prepared essentially as described in Example 428 by using 3-tert-butoxycarbonyl-7-chloro-6-dimethylcarbamoylthio-2,3,4,5-tetrahydro-1H-benzo[d]azepine with the appropriately substituted benzyl bromide. MS (ES+) data are included in the Table below.

| Ex. | SO₂R | Compound | MS (ES+ or APCI+) |
|---|---|---|---|
| 429 | SO₂-CH₂-C(CH₃)₃ | 7-Chloro-6-[4-(2,2-dimethyl-propane-1-sulfonyl)-benzylthio]-2,3,4,5-tetrahydro-1H-benzo[d]azepine Hydrochloride | 438 (M + H)⁺ |
| 430 | SO₂-CH₂-C(CF₃)₂CH₃ | 7-Chloro-6-[4-(3,3,3-trifluoro-2-methyl-2-trifluoromethyl-propane-1-sulfonyl)-benzylthio]-2,3,4,5-tetrahydro-1H-benzo[d]azepine Hydrochloride | 546 (M + H)⁺ |
| 431 | SO₂-C₆H₄-CF₃ | 7-Chloro-6-[4-(4-trifluoromethyl-benzenesulfonyl)-benzylthio]-1,2,4,5-tetrahydro-benzo[d]azepine Hydrochloride | 512 (M + H)⁺ |
| 432 | SO₂-CH₂-cyclohexyl | 7-Chloro-6-(4-cyclohexyl-methanesulfonyl-benzylthio)-2,3,4,5-tetrahydro-1H-benzo[d]azepine Hydrochloride | 464 (M + H)⁺ |

EXAMPLE 433

7-Chloro-6-[4-(2,4-difluoro-phenylmethanesulfonyl)-benzylthio]-2,3,4,5-tetrahydro-1H-benzo[d]azepine Succinate

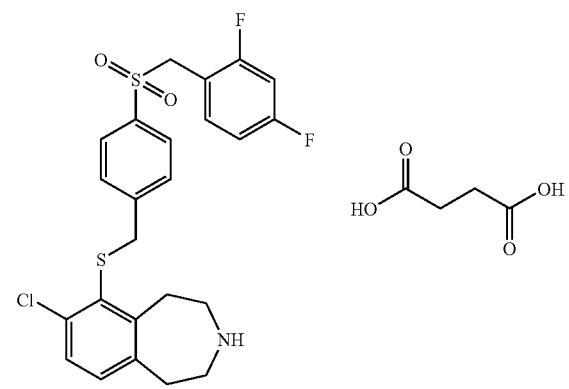

Use a method similar to the Example 428 to react 3-tert-butoxycarbonyl-7-chloro-6-dimethylcarbamoylthio-2,3,4,5-tetrahydro-1H-benzo[d]azepine with 1-(4-bromomethyl-benzenesulfonylmethyl)-2,4-difluoro-benzene. Use a method similar to the General Procedure 1-4, basic work-up, and a method similar to the General Procedure 2-1, to give the title compound as a white solid. MS (ES+) m/z: 494 (M+H)$^+$.

EXAMPLE 434

7-Chloro-6-[4-(3,3,3-trifluoro-2-methyl-2-trifluoromethylpropylthio)-benzylthio]-2,3,4,5-tetrahydro-1H-benzo[d]azepine Succinate

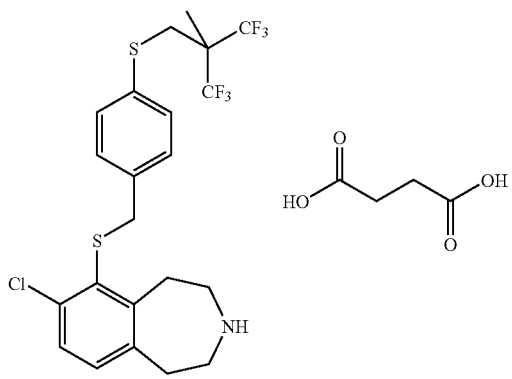

Use a method similar to the Example 428 to react 3-tert-butoxycarbonyl-7-chloro-6-dimethylcarbamoylthio-2,3,4,5-tetrahydro-1H-benzo[d]azepine with 1-bromomethyl-4-(3,3,3-trifluoro-2-methyl-2-trifluoromethyl-propylthio)benzene. Use a method similar to the General Procedure 1-5, basic workup, and a method similar to the General Procedure 2-1, to give the title compound as a white solid. MS (APCI+) m/z: 514 (M+H)$^+$.

EXAMPLE 435

7-Chloro-6-[4-(3,3-dimethylbutyryl)-benzylthio]-1,2,4,5-tetrahydro-benzo[d]azepine Hydrochloride

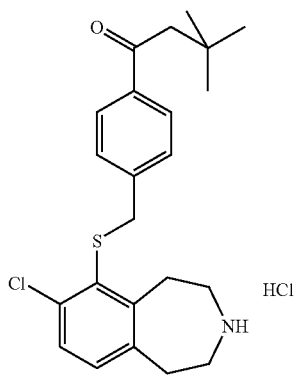

Use a method similar to the Example 428 to react 3-tert-butoxycarbonyl-7-chloro-6-dimethylcarbamoylthio-2,3,4,5-tetrahydro-1H-benzo[d]azepine with 1-(4-bromomethylphenyl)-3,3-dimethylbutan-1-one. Use a method similar to the General Procedure 1-4, basic workup, and a method similar to the General Procedure 2-2 to give the title compound as a white solid. MS (APCI+) m/z: 402 (M+H)$^+$.

EXAMPLE 436

(±)-7-Chloro-6-[1-(2-cyanophenyl)-ethylthio]-2,3,4,5-tetrahydro-1H-benzo[d]azepine Hydrochloride

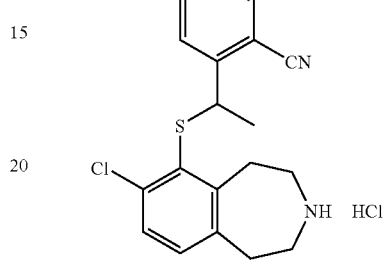

Use a method similar to the Preparation 177, using 3-tert-butoxycarbonyl-7-chloro-6-dimethylcarbamoylthio-2,3,4,5-tetrahydro-1H-benzo[d]azepine and (±)-2-(1-bromoethyl)benzonitrile to give, after deprotection by the General Procedure 1-4, the title compound as a white solid. MS (APCI+) m/z: 343 (M+H)$^+$.

EXAMPLE 437

(−)-7-Chloro-6-[1-(2-cyanophenyl)-ethylthio]-2,3,4,5-tetrahydro-1H-benzo[d]azepine Hydrochloride

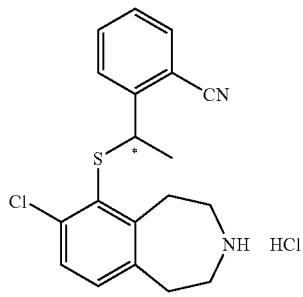

Dissolve (±)-7-chloro-6-[1-(2-cyanophenyl)-ethylthio]-2,3,4,5-tetrahydro-1H-benzo[d]azepine succinate (326 mg, 1.0 mmol) in DCM (5 mL) and pyridine (0.4 mL, 5 mmol). Add di-tert-butyl-dicarbonate (270 mg, 1.2 mmol) and stir the mixture for 16 h at ambient temperature. Wash the mixture with 5N aqueous NaOH and saturated aqueous NaHCO$_3$ successively. Collect the organic layer and concentrate in vacuo. Purify the residue by chromatography on silica gel eluting with hexane/EtOAc (1:1) to obtain (±)-3-tert-butoxycarbonyl-7-chloro-6-[1-(2-cyanophenyl)-ethylthio]-2,3,4,5-tetrahydro-1H-benzo[d]azepine (393 mg, 93%). Separate the enantiomers of (±) 3-tert-butoxycarbonyl-7-chloro-6-[1-(2-cyanophenyl)-ethylthio]-2,3,4,5-tetrahydro-1H-benzo[d]azepine by chiral normal phase chromatography (Chiralpak AD 8×30 cm column, eluting with heptane/isopropylamine, 95:5).

Take the second eluting isomer and deprotect using the General Procedure 1-5. Purify with SCX chromatography. Use a method similar to the General Procedure 2-2 to obtain the title compound (125 mg, 37%). MS (ES+) m/z: 343 (M+H)$^+$. [α]$^{20}_D$ –112° (c 0.5, CH$_3$OH).

EXAMPLES 438 AND 439

6-[4-(2-Butyl-2H-pyrazol-3-yl)-benzylthio]-7-chloro-2,3,4,5-tetrahydro-1H-benzo[d]azepine Hydrochloride and 6-[4-(1-Butyl-1H-pyrazol-3-yl)-benzylthio]-7-chloro-2,3,4,5-tetrahydro-1H-benzo[d]azepine Hydrochloride

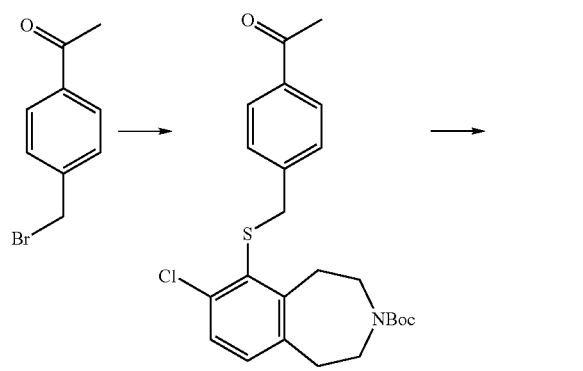

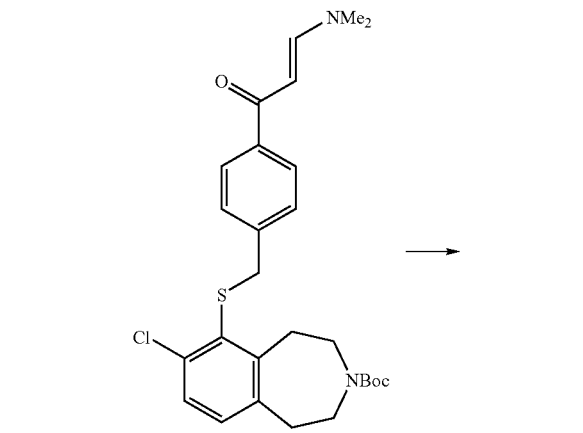

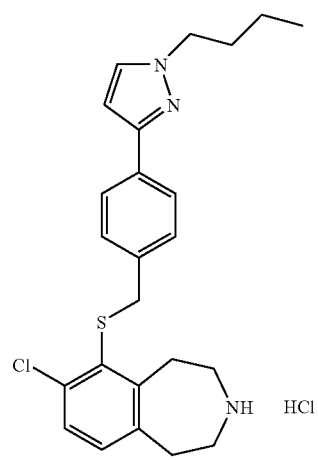

4-Acetylbenzyl bromide: Use a method similar to the Preparation 184, using 4-methylacetophenone, to give the desired intermediate as a white solid.

6-(4-Acetylbenzylthio)-3-tert-butoxycarbonyl-7-chloro-2,3,4,5-tetrahydro-1H-benzo[d]azepine: Use a method similar to the Example 380, using 3-tert-butoxycarbonyl-7-chloro-6-dimethylcarbamoylthio-2,3,4,5-tetrahydro-1H-benzo[d]azepine and 4-acetylbenzyl bromide to give, after chromatography eluting with hexane/EtOAc (15:1), the desired intermediate as a white solid. MS (APCI+) m/z 346 (M+H–Boc)$^+$.

3-tert-Butoxycarbonyl-7-chloro-6-[4-(3-dimethylaminoacryloyl)-benzylthio]-2,3,4,5-tetrahydro-1H-benzo[d]azepine: Heat a solution of 6-(4-acetylbenzylthio)-3-tert-butoxycarbonyl-7-chloro-2,3,4,5-tetrahydro-1H-benzo[d]azepine (1.0 g, 2.2 mmol) in toluene (10 mL) at 110° C. overnight in the presence of tert-butoxy-bis(dimethylamino)-methane (1.0 mL, 4.84 mmol). Concentrate in vacuo to provide the desired intermediate as a dark oil (1.2 g, 100%). MS (APCI+) m/z 401 (M+H–Boc)$^+$.

6-[4-(1-Butyl-1H-pyrazol-3-yl)-benzylthio]-7-chloro-2,3,4,5-tetrahydro-1H-benzo[d]azepine Hydrochloride: To a stirred mixture of 3-tert-butoxycarbonyl-7-chloro-6-[4-(3-dimethylaminoacryloyl)-benzylthio]-2,3,4,5-tetrahydro-1H-benzo[d]azepine (240 mg, 0.475 mmol), butylhydrazine oxalate (102 mg, 0.574 mmol), sodium carbonate (55 mg, 0.444 mmol) in water (8 mL) and methanol (10 mL) add acetic acid (ca. 3-6 drops) to pH 5. Heat overnight at 70° C. Concentrate in vacuo. Purify by chromatography on silica gel eluting with hexane/EtOAc (10:1) to give a mixture of the desired intermediates, 3-tert-butoxycarbonyl-6-[4-(2-butyl-2H-pyrazol-3-yl)-benzylthio]-7-chloro-2,3,4,5-tetrahydro-1H-benzo[d]azepine (65 mg, 32%), MS (APCI+) m/z: 426 (M+H–Boc)$^+$ and 3-tert-butoxycarbonyl-6-[4-(1-butyl-1H-pyrazol-3-yl)-benzylthio]-7-chloro-2,3,4,5-tetrahydro-1H-benzo[d]azepine (100 mg, 50%), MS (APCI+) m/z: 426 (M+H–Boc)$^+$.

Use a method similar to the General Procedure 1-4, using 3-tert-butoxycarbonyl-6-[4-(2-butyl-2H-pyrazol-3-yl)-benzylthio]-7-chloro-2,3,4,5-tetrahydro-1H-benzo[d]azepine, to give 6-[4-(2-butyl-2H-pyrazol-3-yl)-benzylthio]-7-chloro-2,3,4,5-tetrahydro-1H-benzo[d]azepine (Example 438) as a white solid. MS (APCI+) m/z: 426 (M+H)⁺.

Use a method similar to the General Procedure 1-4, using 3-tert-butoxycarbonyl-6-[4-(1-butyl-1H-pyrazol-3-yl)-benzylthio]-7-chloro-2,3,4,5-tetrahydro-1H-benzo[d]azepine, to give 6-[4-(1-butyl-1H-pyrazol-3-yl)-benzylthio]-7-chloro-2,3,4,5-tetrahydro-1H-benzo[d]azepine (Example 439) as a white solid. MS (APCI+) m/z: 426 (M+H)⁺.

EXAMPLE 440

6-(4 tert-Butylcarbamoyl-3-fluorobenzylthio)-7-chloro-2,3,4,5-tetrahydro-1H-benzo[d]azepine Hydrochloride

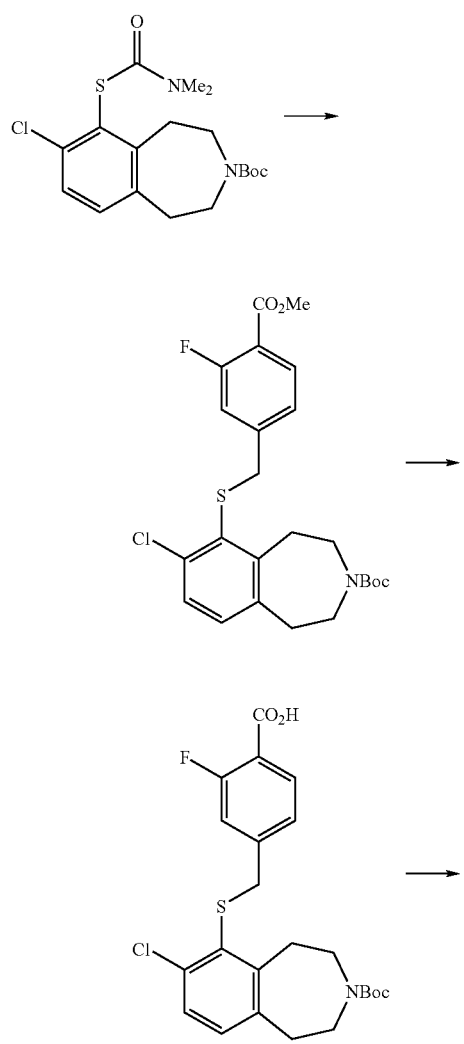

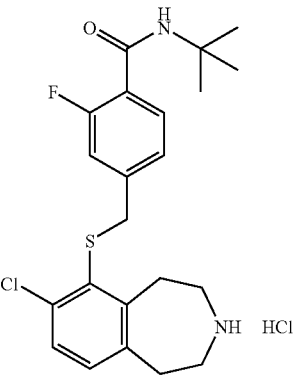

3-tert-Butoxycarbonyl-7-chloro-6-(3-fluoro-4-methoxycarbonylbenzylthio)-2,3,4,5-tetrahydro-1H-benzo[d]azepine: Use a method similar to the Example 428, using 3-tert-butoxycarbonyl-7-chloro-6-dimethylcarbamoylthio-2,3,4,5-tetrahydro-1H-benzo[d]azepine and methyl 4-bromomethyl-2-fluorobenzoate, to give the desired intermediate as a white solid.

3-tert-Butoxycarbonyl-6-(4-carboxy-3-fluorobenzylthio)-7-chloro-2,3,4,5-tetrahydro-1H-benzo[d]azepine: Heat a stirred solution of 3-tert-butoxycarbonyl-7-chloro-6-(3-fluoro-4-methoxycarbonylbenzylthio)-2,3,4,5-tetrahydro-1H-benzo[d]azepine (3.56 g, 7.44 mmol) in THF (50 mL) and water (40 mL) overnight at 65° C. in the presence of potassium hydroxide (8.30 g, 148.77 mmol). Cool the mixture to 0° C., add slowly a 1N solution of hydrochloric acid until pH 5. Extract three times with EtOAc, dry over anhydrous Na₂SO₄ and concentrate in vacuo to provide the desired intermediate as a white solid (3.5 g, 99%).

6-(4-tert-Butylcarbamoyl-3-fluorobenzylthio)-7-chloro-2,3,4,5-tetrahydro-1H-benzo[d]azepine Hydrochloride: To a solution of 3-tert-butoxycarbonyl-6-(4-carboxy-3-fluorobenzylthio)-7-chloro-2,3,4,5-tetrahydro-1H-benzo[d]azepine (1.1 g, 2.36 mmol) in DMF (7 mL), add tert-butylamine (12.05 g, 165.2 mmol), EDC (1.81 g, 9.44 mmol) and HOBt (1.44 g, 10.62 mmol) and stir in a sealed tube at 70° C. overnight. Dilute with EtOAc, wash with water, dry over anhydrous MgSO₄ and concentrate in vacuo. Purify by chromatography on silica gel eluting with hexane/EtOAc (9:1) to give 3-tert-butoxycarbonyl-6-(4-tert-butylcarbamoyl-3-fluorobenzylthio)-7-chloro-2,3,4,5-tetrahydro-1H-benzo[d]azepine as a clear oil. MS (APCI+) m/z: 421 (M+H)⁺. Use a method similar to the General Procedure 1-4 to give the title compound as a white powder. MS (APCI+) m/z: 421 (M+H)⁺.

Examples 441-447 may be prepared essentially as described in Example 440 by reacting 3-tert-butoxycarbonyl-6-(4-carboxy-3-fluorobenzylthio)-7-chloro-2,3,4,5-tetrahydro-1H-benzo[d]azepine with the appropriate amine. MS (ES+) data are included in the Table below.

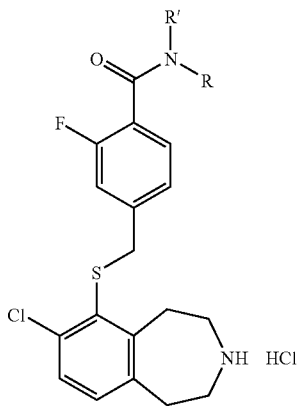

| Ex. | N—R | R' | Compound | MS (ES+ or APCI+) |
|---|---|---|---|---|
| 441 | N-(n-Pr) | H | 7-Chloro-6-(3-fluoro-4-n-propylcarbamoyl-benzylthio)-2,3,4,5-tetrahydro-1H-benzo[d]azepine Hydrochloride | 407 (M + H)+ |
| 442 | N-(i-Bu) | H | 6-(4-iso-Butylcarbamoyl-3-fluoro-benzylthio)-7-chloro-2,3,4,5-tetrahydro-1H-benzo[d]azepine Hydrochloride | 421 (M + H)+ |
| 443 | N-(n-Pr) | n-Pr | 7-Chloro-6-(4-dipropylcarbamoyl-3-fluoro-benzylthio)-2,3,4,5-tetrahydro-1H-benzo-[d]azepine Hydrochloride | 449 (M + H)+ |
| 444 | 4-fluorobenzyl-N | H | 7-Chloro-6-[3-fluoro-4-(4-fluoro-benzylcarbamoyl)-benzylthio]-2,3,4,5-tetrahydro-1H-benzo[d]azepine Hydrochloride | 473 (M + H)+ |
| 445 | cyclohexyl-N | H | 7-Chloro-6-(4-cyclohexylcarbamoyl-3-fluoro-benzylthio)-2,3,4,5-tetrahydro-1H-benzo[d]azepine Hydrochloride | 447 (M + H)+ |
| 446 | 2-isobutyl-pyrrolidine | | 7-Chloro-6-[3-fluoro-4-(2-isobutyl-pyrrolidine-1-carbonyl)-benzylthio]-2,3,4,5-tetrahydro-1H-benzo[d]azepine Hydrochloride | 475 (M + H)+ |
| 447 | 3-(4-fluorophenyl)-pyrrolidine | | 7-Chloro-6-{3-fluoro-4-[3-(4-fluoro-phenyl)-pyrrolidine-1-carbonyl]-benzylthio}-2,3,4,5-tetrahydro-1H-benzo[d]azepine-Hydrochloride | 513 (M + H)+ |

EXAMPLE 448

(S)-(+)-6-(4-sec-Butylcarbamoyl-3-fluorobenzylthio)-7-chloro-2,3,4,5-tetrahydro-1H-benzo[d]azepine Hydrochloride

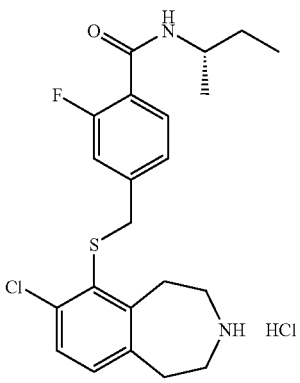

3-tert-Butoxycarbonyl-7-chloro-6-(4-chlorocarbonyl-3-fluorobenzylthio)-2,3,4,5-tetrahydro-1H-benzo[d]azepine: To a solution of 3-tert-butoxycarbonyl-6-(4-carboxy-3-fluoro-benzylthio)-7-chloro-2,3,4,5-tetrahydro-1H-benzo[d]azepine (1.95 g, 4.21 mmol) in DCM (20 mL) at 0° C. under nitrogen, add three drops of DMF and oxalyl chloride (1.06 g, 8.41 mmol). Stir for 2 h and concentrate in vacuo to afford the desired intermediate as a yellow oil (1.93 g, 95%).

(S)-3-tert-Butoxycarbonyl-6-(4-sec-butylcarbamoyl-3-fluorobenzylthio)-7-chloro-2,3,4,5-tetrahydro-1H-benzo[d]azepine: To a solution of 3-tert-butoxycarbonyl-7-chloro-6-(4-chlorocarbonyl-3-fluoro-benzylthio)-2,3,4,5-tetrahydro-1H-benzo[d]azepine (415 mg, 0.860 mmol) in DCM (10 mL), add (S)-(+)-sec-butylamine (1.0 g, 13.7 mmol) and stir at ambient temperature for 30 min. Concentrate in vacuo and purify by chromatography on silica gel eluting with hexane/EtOAc (4:1) to give the desired intermediate as a pale oil (352 mg, 79%). MS (APCI+) m/z: 421 (M+H−Boc)+.

(S)-(+)-(4-sec-Butylcarbamoyl-3-fluorobenzylthio)-7-chloro-2,3,4,5-tetrahydro-1H-benzo[d]azepine Hydrochloride: Use a method similar to the General Procedure 1-4, using (+)-3-tert-butoxycarbonyl-6-(4-sec-butylcarbamoyl-3-fluoro-benzylthio)-7-chloro-2,3,4,5-tetrahydro-1H-benzo[d]azepine, to give the title compound as a pale solid. MS (APCI+) m/z: 421 (M+H)+. [α]$^{20}_D$ +8.7° (c 0.5, CH$_3$OH).

Examples 449-454 may be prepared essentially as described in Example 448 by reacting 3-tert-butoxycarbonyl-6-(4-carboxy-3-fluoro-benzylthio)-7-chloro-2,3,4,5-tetrahydro-1H-benzo[d]azepine with the appropriate amine. Optical rotation and MS (ES+) data are included in the Table below.

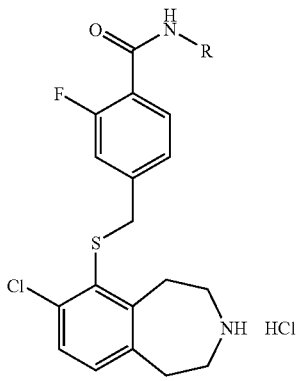

| Ex. | NH—R | Compound | [α]$^{20}_D$ (c, solvent) | MS (ES+) m/z |
|---|---|---|---|---|
| 449 | ![HN-propyl] | (R)-(−)-6-(4-sec-Butylcarbamoyl-3-fluoro-benzylthio)-7-chloro-2,3,4,5-tetrahydro-1H-benzo[d]azepine Hydrochloride | −7.0° (c 0.5, CH$_3$OH). | 421 (M + H)+ |
| 450 | ![HN-CH2-2-Cl-phenyl] | 7-Chloro-6-[4-(2-chloro-benzylcarbamoyl)-3-fluoro-benzylthio]-2,3,4,5-tetrahydro-1H-benzo[d]azepine Hydrochloride | — | 489 (M + H)+ |
| 451 | ![HN-CH2-2-CF3-phenyl] | 7-Chloro-6-[3-fluoro-4-(2-trifluoromethyl-benzylcarbamoyl)-benzylthio]-2,3,4,5-tetrahydro-1H-benzo[d]azepine Hydrochloride | — | 523 (M + H)+ |

-continued

| Ex. | NH—R | Compound | $[\alpha]^{20}_D$ (c, solvent) | MS (ES+) m/z |
|---|---|---|---|---|
| 452 | 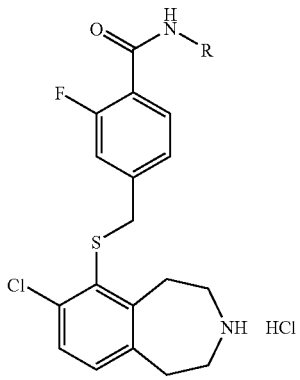 | 7-Chloro-6-[3-fluoro-4-(2-fluoro-4-trifluoromethyl-benzyl-carbamoyl)-benzylthio]-2,3,4,5-tetrahydro-1H-benzo[d]aze-pine Hydrochloride | — | 541 (M + H)⁺ |
| 453 | | (S)-(−)-7-Chloro-6-{3-fluoro-4-[1-(4-fluoro-phenyl)-ethyl-carbamoyl]-benzylthio}-2,3,4,5-tetrahydro-1H-benzo-[d]azepine Hydrochloride | −25.8° (c 0.5, CH₃OH) | 487 (M + H)⁺ |
| 454 | | (R)-(+)-7-Chloro-6-{3-fluoro-4-[1-(4-fluoro-phenyl)-ethyl-carbamoyl]-benzylthio}-2,3,4,5-tetrahydro-1H-benzo-[d]azepine Hydrochloride | +24.9° (c 0.5, CH₃OH) | 487 (M + H)⁺ |

EXAMPLE 455

7-Chloro-6-(3-fluoro-4-isobutylcarbamoyl-benzylthio)-2,3,4,5-tetrahydro-1H-benzo[d]azepine Succinate

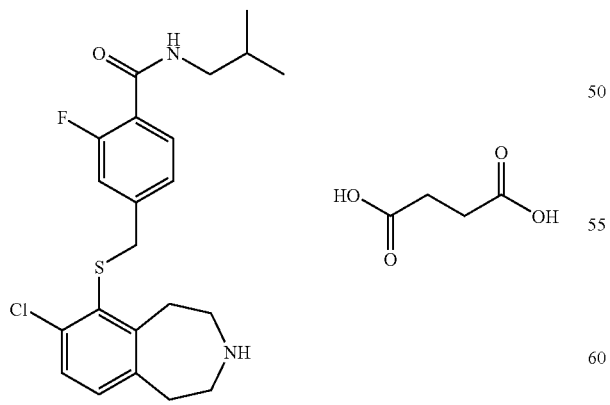

Use a method similar to the Example 448 to react 3-tert-butoxycarbonyl-6-(4-carboxy-3-fluoro-benzylthio)-7-chloro-2,3,4,5-tetrahydro-1H-benzo[d]azepine with isobutylamine. Use a method similar to the General Procedure 14, basic work-up, and a method similar to the General Procedure 2-1 to give the title compound as a white solid. MS (ES+) m/z: 403 (M+H)⁺.

EXAMPLE 456

7-Chloro-6-(4-cyclohexylcarbamoylbenzylthio)-2,3,4,5-tetrahydro-1H-benzo[d]azepine Succinate

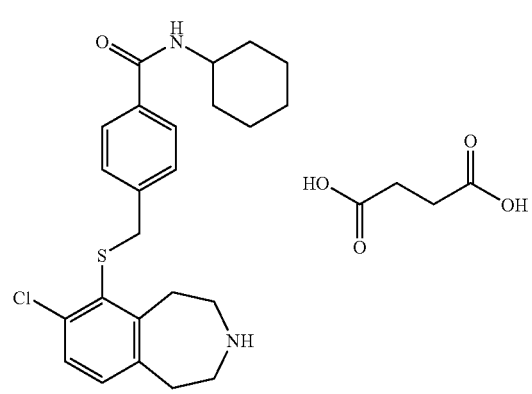

Use a method similar to the Preparation 177 to react 3-tert-butoxycarbonyl-7-chloro-6-dimethylcarbamoylthio-2,3,4,5-tetrahydro-1H-benzo[d]azepine with 4-chloromethyl-N-cyclohexylbenzamide. Use a method similar to the General Procedure 1-5, basic workup, and a method similar to the General Procedure 2-1 to give the title compound as a white solid MS (ES+) m/z: 429 (M+H)$^+$.

Examples 457-465 may be prepared essentially as described in Example 456 by using 3-tert-butoxycarbonyl-7-chloro-6-diethylcarbamoylthio-2,3,4,5-tetrahydro-1H-benzo[d]azepine and the appropriately substituted benzyl chloride. Optical rotation and MS (ES+) data are included in the Table below.

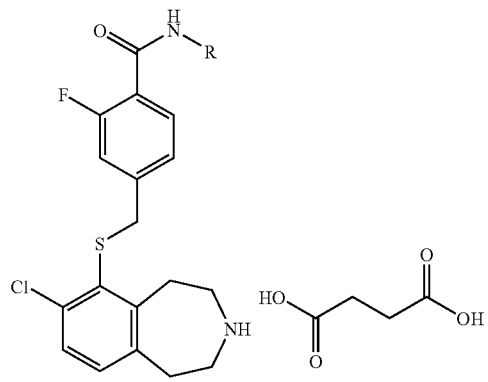

| Ex. | NH—R | Compound | $[\alpha]^{20}_D$ (c, solvent) | MS (ES+ or (APCI+) |
|---|---|---|---|---|
| 457 | ![] | 7-Chloro-6-[4-(2-fluoro-4-trifluoromethyl-benzylcarbamoyl)-benzylthio]-2,3,4,5-tetrahydro-1H-benzo[d]azepine Succinate | — | 523 (M + H)$^+$ |
| 458 | ![] | [4-(3,5-Bis-trifluoromethyl-benzylcarbamoyl)-benzylthio]-7-chloro-2,3,4,5-tetrahydro-1H-1H-benzo[d]azepine Succinate | — | 573 (M + H)$^+$ |
| 459 | ![] | 7-Chloro-6-[4-(4-fluoro-2-trifluoromethyl-benzylcarbamoyl)-benzylthio]-2,3,4,5-tetrahydro-1H-benzo[d]azepine Succinate | — | 523 (M + H)$^+$ |
| 460 | ![] | (S)-(+)-7-Chloro-6-[4-(1-cyclohexyl-ethylcarbamoyl)-benzylthio]-2,3,4,5-tetrahydro-1H-benzo[d]azepine Succinate | +11.2° (c 0.5, CH$_3$OH) | 457 (M + H)$^+$ |
| 461 | ![] | (R)-(−)-7-Chloro-6-[4-(1-cyclohexyl-ethylcarbamoyl)-benzylthio]-2,3,4,5-tetrahydro-1H-benzo[d]azepine Succinate | +11.3° (c 0.5, CH$_3$OH). | 457 (M + H)$^+$ |
| 462 | ![] | (R)-(+)-7-Chloro-6-{4-[1-(4-fluoro-phenyl)-ethylcarbamoyl]-benzylthio}-2,3,4,5-tetrahydro-1H-benzo[d]azepine Succinate | +2.2° (c 0.5, CH$_3$OH) | 469 (M + H)$^+$ |

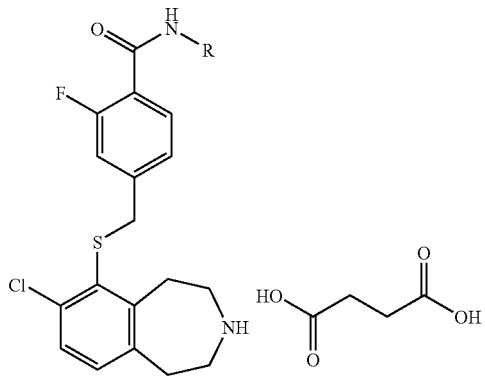

| Ex. | NH—R | Compound | $[\alpha]^{20}_D$ (c, solvent) | MS (ES+ or APCI+) |
|---|---|---|---|---|
| 463 | (4-F-phenyl)-CH(CH₃)-NH, (S) | (S)-(−)-7-Chloro-6-{4-[1-(4-fluoro-phenyl)-ethylcarbamoyl]-benzylthio}-2,3,4,5-tetrahydro-1H-benzo[d]azepine Succinate | +1.6° (c 0.5, CH₃OH) | 469 (M + H)⁺ |
| 464 | (4-Cl-phenyl)-CH(CH₃)-NH, (R) | (R)-(−)-7-Chloro-6-{4-[1-(4-chloro-phenyl)-ethylcarbamoyl]-benzylthio}-2,3,4,5-tetrahydro-1H-benzo[d]azepine Succinate | −5.8° (c 0.5, CH₃OH) | 485 (M + H)⁺ |
| 465 | (4-Cl-phenyl)-CH(CH₃)-NH, (S) | (S)-(+)-7-Chloro-6-{4-[1-(4-chloro-phenyl)-ethylcarbamoyl]-benzylthio}-2,3,4,5-tetrahydro-1H-benzo[d]azepine Succinate | +5.5° (c 0.5, CH₃OH) | 485 (M + H)⁺ |

EXAMPLE 466

7-Chloro-6-[4-(2,2-dimethyl-propylcarbamoyl)-benzylthio]-2,3,4,5-tetrahydro-1H-benzo[d]azepine Hydrochloride

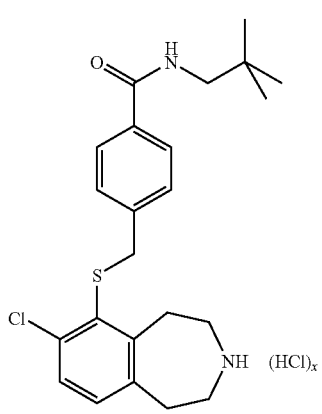

Use a method similar to the Example 456, using 3-tert-butoxycarbonyl-7-chloro-6-dimethylcarbamoylthio-2,3,4,5-tetrahydro-1H-benzo[d]azepine and 4-chloromethyl-N-(2,2-dimethyl-propyl)-benzamide to give, after deprotection by a method similar to the General Procedure 14, the title compound as a white solid. MS (ES+) m/z: 417 (M+H)⁺.

Examples 467-471 may be prepared essentially as described in Example 466 by using 3-tert-butoxycarbonyl-7-chloro-6-dimethylcarbamoylthio-2,3,4,5-tetrahydro-1H-benzo[d]azepine and the appropriately substituted benzyl chloride. MS (ES+) data are included in the Table below.

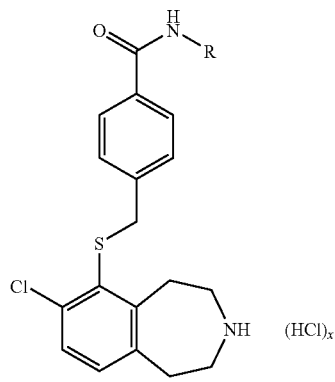

| Ex. | NH—R | Compound | MS (ES+) m/z |
|---|---|---|---|
| 467 | NH—C(CH₃)₃ | 6-(4-tert-Butylcarbamoyl-benzylthio)-7-chloro-2,3,4,5-tetrahydro-1H-benzo[d]azepine Hydrochloride | 403 (M + H)⁺ |
| 468 | NH—CH₂-cyclohexyl | 7-Chloro-6-[4-(cyclohexylmethyl-carbamoyl)-benzylthio]-2,3,4,5-tetrahydro-1H-benzo[d]azepine Hydrochloride | 443 (M + H)⁺ |
| 469 | 4-CF₃-benzyl-NH | 7-Chloro-6-[4-(4-trifluoromethyl-benzylcarbamoyl)-benzylthio]-2,3,4,5-tetrahydro-1H-benzo[d]azepine Hydrochloride | 505 (M + H)⁺ |
| 470 | 3,4-difluoro-benzyl-NH | 7-Chloro-6-[4-(3,4-difluoro-benzylcarbamoyl)-benzylthio]-2,3,4,5-tetrahydro-1H-benzo[d]azepine Hydrochloride | 473 (M + H)⁺ |
| 471 | 2,3,4-trifluoro-benzyl-NH | 7-Chloro-6-[4-(2,3,4-trifluoro-benzylcarbamoyl)-benzylthio]-2,3,4,5-tetrahydro-1H-benzo[d]azepine Hydrochloride | 491 (M + H)⁺ |

EXAMPLE 472

(±)-7-Chloro-6-(1-methoxycarbonyl-1-phenyl-methyllthio)-2,3,4,5-tetrahydro-1H-benzo[d]azepine Hydrochloride

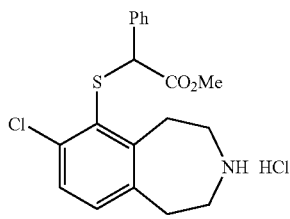

Use a method similar to the General Procedure 1-4, using (±)-3-tert-butoxycarbonyl-7-chloro-6-(1-methoxycarbonyl-1-phenyl-methyllthio)-2,3,4,5-tetrahydro-1H-benzo[d]azepine, to give the title compound as a white solid. MS (ES+) m/z 362 (M+H)⁺.

EXAMPLE 473

(±)-7-Chloro-6-(2-hydroxy-1-phenyl-ethylthio)-2,3,4,5-tetrahydro-1H-benzo[d]azepine Hydrochloride

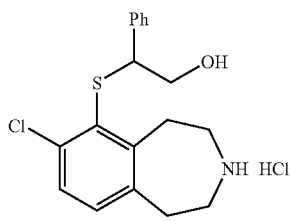

To a stirred solution of (±)-3-tert-butoxycarbonyl-6-(1-carboxy-1-phenyl-methyllthio)-7-chloro-2,3,4,5-tetrahydro-1H-benzo[d]azepine (220 mg, 0.447 mmol) in THF (10 mL) at 0° C., add a solution of 1M borane in THF (1.4 mL, 1.4 mmol). Continue stirring for 2 h at 0° C. and then overnight at ambient temperature. Quench by slow addition of methanol, stir 1 h at ambient temperature and concentrate in vacuo. Add aqueous saturated ammonium chloride, extract three times with EtOAc, dry over anhydrous MgSO₄, and concentrate in vacuo. Purify by chromatography on silica gel eluting with 19:1 DCM/saturated ammonia in methanol. Use a method similar to the General Procedure 1-4 to give the title compound as a white solid. MS (ES+) m/z: 334 (M+H)⁺.

EXAMPLE 474

7,9-Dichloro-6-methoxycarbonylmethylthio-2,3,4,5-tetrahydro-1H-benzo[d]azepine Hydrochloride

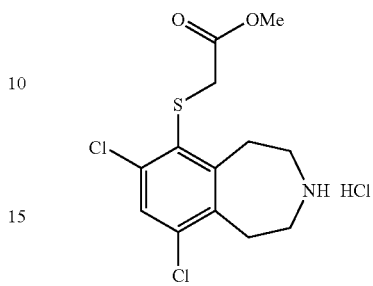

Obtain as minor product from the reaction of the 4:1 mixture of 3-tert-butoxycarbonyl-7-chloro-6-dimethylcarbamoylthio-2,3,4,5-tetrahydro-1H-benzo[d]azepine and 3-tert-butoxycarbonyl-7,9-dichloro-6-dimethylcarbamoylthio-2,3,4,5-tetrahydro-benzo[d]azepine with methyl bromoacetate, using a method similar to the Example 347. Use a method similar to the General Procedure 1-4 to give the title compound as a white solid. MS (ES+) m/z: 320 (M+H)⁺.

EXAMPLE 475

6-(4-Benzyloxybenzylthio)-7-chloro-2,3,4,5-tetrahydro-1H-benzo[d]azepine Succinate

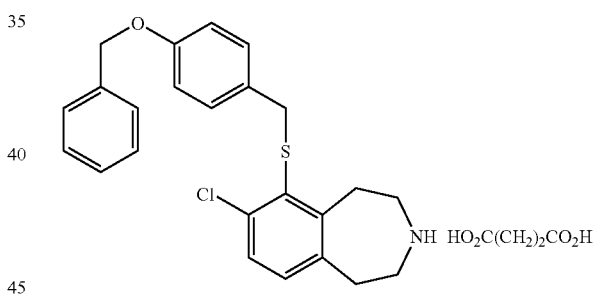

Dissolve 3-tert-butoxycarbonyl-7-chloro-6-dimethylcarbamoylthio-2,3,4,5-tetrahydro-1H-benzo[d]azepine (706 mg, 1.84 mmol) in methanol (20 mL). Add potassium hydroxide (3.5 g, 55 mmol) and heat the mixture at reflux for 3h. Cool to ambient temperature. Pour reaction in saturated aqueous NH₄Cl solution. Extract three times with EtOAc. Combine organic extracts, dry over Na₂SO₄ and concentrate in vacuo to obtain crude 3-tert-butoxycarbonyl-7-chloro-6-mercapto-2,3,4,5-tetrahydro-1H-benzo[d]azepine (602 mg, 100%). Dissolve 3-tert-butoxycarbonyl-7-chloro-6mercapto-2,3,4,5-tetrahydro-1H-benzo[d]azepine (282 mg, 0.9 mmol) in acetone (30 mL). Add 4-benzyloxybenzyl chloride (251 mg, 1.08 mmol), potassium carbonate (powder) (373 mg, 2.7 mmol) and potassium iodide (powder) (15 mg, 0.1 mmol) and reflux for 16 h. Cool the reaction to ambient temperature, dilute with acetone, filter and concentrate in vacuo. Purify by chromatography on silica gel eluting with hexane/EtOAc (1:0 and 17:3) to give 6-(4-benzyloxybenzylthio)-3-tert-butoxycarbonyl-7-chloro-2,3,4,5-tetrahydro-1H-benzo[d]azepine (309 mg, 67%). MS (ES+) m/z: 510 (M+H)⁺.

Use a method similar to the General Procedure 1-4 and purify by chromatography on silica gel eluting with DCM/ 2M ammonia in methanol (95:5) to obtain the free base of the title compound (230 mg, 92%). MS (ES+) m/z: 410 (M+H)+. Use a method similar to the General Procedure 2-1 to obtain the title compound.

EXAMPLE 476

7-Chloro-6-[(2-fluoro-4-phenoxy)benzylthio]-2,3,4, 5-tetrahydro-1H-benzo[d]azepine Succinate

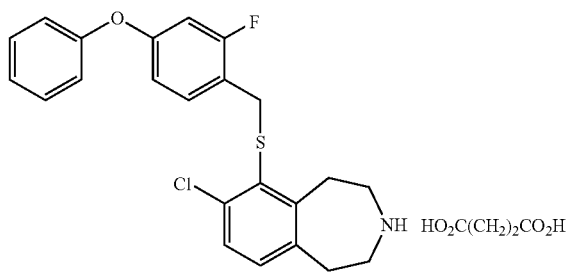

Use a method similar to the Example 475, using 3-tert-butoxycarbonyl-7-chloro-6-dimethylcarbamoylthio-2,3,4,5-tetrahydro-1H-benzo[d]azepine and 1-bromomethyl-2-fluoro-4-phenoxybenzene to provide, after chromatography on silica gel eluting with hexane/EtOAc (85:15), 3-tert-butoxycarbonyl-7-chloro-6-[(2-fluoro-4-phenoxy)-benzylthio]-2,3,4,5-tetrahydro-1H-benzo[d]azepine (384 mg, 83%). MS (ES+) m/z: 414 (N-Boc+2H)+.

Use a method similar to the General Procedure 1-4 and purify by chromatography on silica gel eluting with DCM/ 2M ammonia in methanol (95:5) to obtain the free base of the title compound (203 mg, 65%). MS (ES+) m/z: 414 (M+H)+. Use a method similar to the General Procedure 2-1 to obtain the title compound.

EXAMPLE 477

7-Chloro-6-[2-(4-fluorophenyl)-2-oxo-ethylthio]-2,3, 4,5-tetrahydro-1H-benzo[d]azepine Hydrochloride

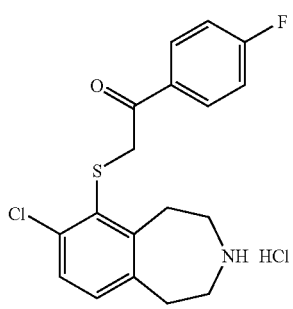

Use a method similar to the Example 475, using crude 3-tert-butoxycarbonyl-7-chloro-6-mercapto-2,3,4,5-tetrahydro-1H-benzo[d]azepine and 2-bromo-4'-fluoroacetophenone (239 mg, 1.1 mmol) to provide, after stirring at ambient temperature for 16 h and purification by chromatography on silica gel eluting with hexane/EtOAc (4:1), 3-tert-butoxycarbonyl-7-chloro-6-[2-(4-fluorophenyl)-2-oxo-ethylthio]-2,3, 4,5-tetrahydro-1H-benzo[d]azepine (38 mg, 9%).

Use a method similar to the General Procedure 1-5 and purify by chromatography on silica gel eluting with DCM/ 2M ammonia in methanol (95:5) to obtain the free base of the title compound (23 mg, 78%). MS (ES+) m/z: 350 (M+H)+. Use a method similar to the General Procedure 2-2 to obtain the title compound.

EXAMPLE 478

7-Chloro-6-(2-hydroxyethylthio)-2,3,4,5-tetrahydro-1H-benzo[d]azepine Hydrochloride

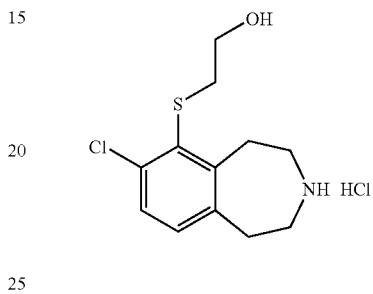

Use a method similar to the Example 347, using 3-tert-butoxycarbonyl-7-chloro-6-dimethylcarbamoylthio-2,3,4,5-tetrahydro-1H-benzo[d]azepine and methyl bromoacetate to give 3-tert-butoxycarbonyl-7-chloro-6-methoxycarbonylmethylthio-2,3,4,5-tetrahydro-1H-benzo[d]azepine.

To a solution of 3-tert-butoxycarbonyl-7-chloro-6-methoxycarbonylmethylthio-2,3,4,5-tetrahydro-1H-benzo[d] azepine (750 mg, 1.94 mmol) in THF (25 mL) at −78° C. under nitrogen, add 1M DIBAL in toluene (5.0 mL, 5.0 mmol) dropwise with stirring. Warm to −30° C. over 1 h and quench carefully with water. Extract with EtOAc, dry over anhydrous MgSO4, and concentrate in vacuo. Purify by chromatography on silica gel eluting with hexane/EtOAc (4:1) to give 3-tert-butoxycarbonyl-7-chloro-6-(2-hydroxy-ethylthio)-2,3,4,5-tetrahydro-1H-benzo[d]azepine (651 mg, 94%).

Use a method similar to the General Procedure 1-4, using 3-tert-butoxycarbonyl-7-chloro-6-(2-hydroxyethylthio)-2,3, 4,5-tetrahydro-1H-benzo[d]azepine (190 mg, 0.531 mmol) to give the title compound as a white solid (105 mg, 67%). MS (ES+) m/z: 258 (M+H)+.

EXAMPLE 479

7-Chloro-6-(3-methoxycarbonylpropylthio)-2,3,4,5-tetrahydro-1H-benzo[d]azepine Hydrochloride

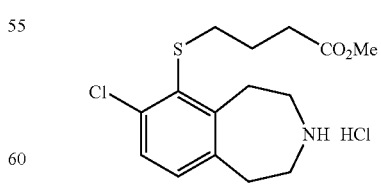

Use a method similar to the Example 347, using 3-tert-butoxycarbonyl-7-chloro-6-dimethylcarbamoylthio-2,3,4,5-tetrahydro-1H-benzo[d]azepine and methyl 4-bromobutyrate to give, after deprotection by the General Procedure 1-4, the title compound as a white solid. MS (ES+) m/z: 314 (M+H)+.

EXAMPLE 480

7-Chloro-6-(4-methoxycarbonyl-butylthio)-2,3,4,5-tetrahydro-1H-benzo[d]azepine Hydrochloride

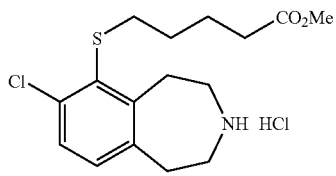

Use a method similar to the Example 387 to react 3-tert-butoxycarbonyl-7-chloro-6-dimethylcarbamoylthio-2,3,4,5-tetrahydro-1H-benzo[d]azepine with methyl-5-bromovalerate. Purify by preparative TLC eluting with 19:1 DCM/saturated ammonia in methanol. Use a method similar to the General Procedure 2-2 to give the title compound as a white solid. MS (APCI+) m/z: 328 (M+H)+.

EXAMPLE 481

7,9-Dichloro-6-(4-methoxycarbonylbutylthio)-2,3,4,5-tetrahydro-1H-benzo[d]azepine Hydrochloride

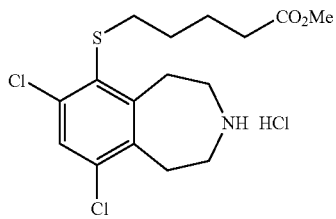

Obtain the free base of the title compound as a minor product from Example 480, after preparative TLC eluting with 19:1 DCM/saturated ammonia in methanol. Use a method similar to the General Procedure 2-2 to obtain the title compound as a pale yellow solid. MS (APCI+) m/z: 362 (M+H)+.

EXAMPLE 482

7-Chloro-6-cyanomethylthio-2,3,4,5-tetrahydro-1H-benzo[d]azepine Trifluoroacetate

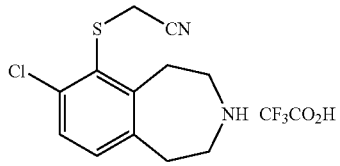

Use a method similar to the Example 387 to react 3-tert-butoxycarbonyl-7-chloro-6-dimethylcarbamoylthio-2,3,4,5-tetrahydro-1H-benzo[d]azepine with bromoacetonitrile. Purify by preparative reverse phase HPLC (Column: Xterra Prep RP18 19×250 mm; Solvent A: 10 mM aqueous ammonium carbonate, Solvent B: acetonitrile; 30-100% B over 20 minutes; flow rate 25 mL/min) to give the title compound as a white solid. MS (APCI+) m/z: 253 (M+H)+.

EXAMPLE 483

6-Cyanomethylthio-7,9-dichloro-2,3,4,5-tetrahydro-1H-benzo[d]azepine Trifluoroacetate

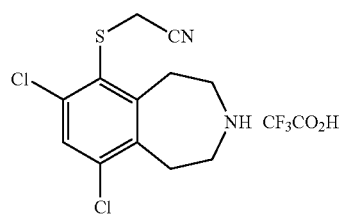

Obtain the title compound as a minor product from Example 482, after preparative reverse phase HPLC (Column: Xterra Prep RP18 19×250 mm; solvent A: 10 mM aqueous ammonium carbonate, solvent B: acetonitrile; 30-100% B over 20 minutes; flow rate 25 mL/min). MS (APCI+) m/z: 287 (M+H)+.

EXAMPLE 484

(±)-7-Chloro-6-(1-cyanoethylthio)-2,3,4,5-tetrahydro-1H-benzo[d]azepine Hydrochloride

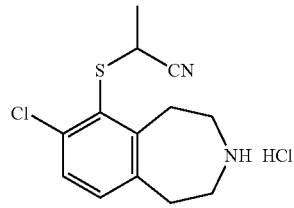

Use a method similar to the Preparation 177, using 3-tert-butoxycarbonyl-7-chloro-6-dimethylcarbamoylthio-2,3,4,5-tetrahydro-1H-benzo[d]azepine and 2-bromopropionitrile to give, after deprotection using a method similar to the General Procedure 1-4, the title compound as a white solid. MS (ES+) m/z: 267 (M+H)+.

EXAMPLE 485

(±)-7-Chloro-6-(1-cyanopropylthio)-2,3,4,5-tetrahydro-1H-benzo[d]azepine Hydrochloride

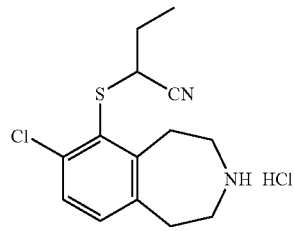

To a stirred solution of 1.5M lithium diisopropylamide in cyclohexane (1.37 mL, 2.05 mmol) in dry THF (5 mL) at −78° C. under dry nitrogen, add a solution of 3-tert-butoxycarbonyl-7-chloro-6-cyanomethylthio-2,3,4,5-tetrahydro-1H-benzo[d]-azepine (600 mg, 1.70 mmol) in THF (5 mL) and continue stirring for 2 h. Rapidly transfer the above solution via cannula to a solution of ethyl iodide (13.2 g, 84.9 mmol) in THF (5 mL) and continue stirring for 1 h. Quench with aqueous saturated ammonium chloride solution, extract three times with EtOAc, dry over anhydrous Na$_2$SO$_4$, and concentrate in vacuo. Purify by chromatography on silica gel eluting with hexane/EtOAc (9:1) to give (±)-3-tert-butoxycarbonyl-7-chloro-6-(1-cyanopropylthio)-2,3,4,5-tetrahydro-1H-benzo[d]azepine as a pale oil (350 mg, 68%). Use a method similar to the General Procedure 1-4 to give the title compound as an off-white solid. MS (ES+) m/z: 281 (M+H)$^+$.

EXAMPLE 486

7-chloro-6-(1-cyano-1-methylethylthio)-2,3,4,5-tetrahydro-1H-benzo[d]azepine Hydrochloride

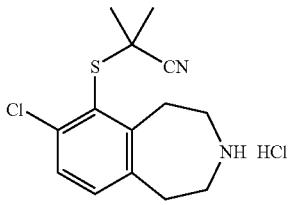

To a stirred solution of 3-tert-butoxycarbonyl-7-chloro-6-cyanomethylthio-2,3,4,5-tetrahydro-1H-benzo[d]-azepine (300 mg, 0.85 mmol) in THF (5 mL) at 0° C., add potassium tert-butoxide (480 mg, 4.26 mmol) at ambient temperature. After 15 min, add methyl iodide (3.02 g, 21.31 mmol) and continue stirring overnight at ambient temperature. Concentrate in vacuo and purify by chromatography on silica gel eluting with hexane/EtOAc (9:1) to give 3-tert-butoxycarbonyl-7-chloro-6-(1-cyano-1-methyl-ethylthio)-2,3,4,5-tetrahydro-1H-benzo[d]azepine (177 mg, 55%). MS (ES+) m/z: 282 (M+H−Boc)$^+$. Use a method similar to the General Procedure 1-4 to give the title compound as an off-white solid. MS (ES+) m/z: 282 (M+H)$^+$.

EXAMPLE 487

7-Chloro-6-(4-cyanobutylthio)-2,3,4,5-tetrahydro-1H-benzo[d]azepine Hydrochloride

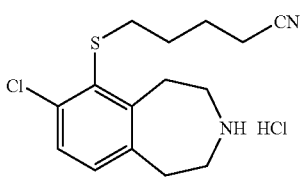

Use a method similar to the Example 387 to react 3-tert-butoxycarbonyl-7-chloro-6-dimethylcarbamoylthio-2,3,4,5-tetrahydro-1H-benzo[d]azepine with 5-bromovaleronitrile. Purify by preparative reverse phase HPLC (Column: Xterra Prep RP18 19×250 mm; Solvent A: 10 mM aqueous ammonium carbonate, Solvent B: acetonitrile; 30-100% B over 20 minutes; flow rate 25 mL/min). Use a method similar to the General Procedure 2-2 to give the title compound as an off-white solid. MS (APCI+) m/z: 295 (M+H)$^+$.

EXAMPLE 488

7,9-Dichloro-6-(4-cyanobutylthio)-2,3,4,5-tetrahydro-1H-benzo[d]azepine Hydrochloride

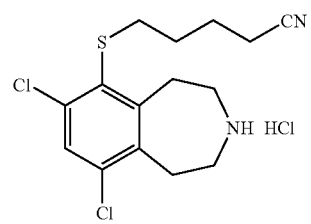

Obtain the free base of the title compound as a minor product from Example 487, after preparative reverse phase HPLC (Column: Xterra Prep RP18 19×250 mm; Solvent A: 10 mM aqueous ammonium carbonate, Solvent B: acetonitrile; 30-100% B over 20 minutes; flow rate 25 mL/min). Use a method similar to the General Procedure 2-2 to obtain the title compound as a tan solid. MS (ES+) m/z: 329 (M+H)$^+$.

EXAMPLE 489

7-Chloro-6-(2-pyridin-2-yl-ethylthio)-2,3,4,5-tetrahydro-1H-benzo[d]azepine Hydrochloride

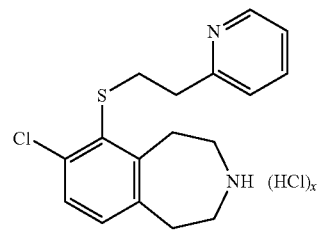

Use a method similar to the Preparation 177, using 3-tert-butoxycarbonyl-7-chloro-6-dimethylcarbamoylthio-2,3,4,5-tetrahydro-1H-benzo[d]azepine and 2-(2-bromoethyl)-pyridine hydrobromide to give, after deprotection using a method similar to the General Procedure 1-4, the title compound. MS (ES+) m/z 319 (M+H)$^+$.

EXAMPLE 490

6-[3-(3-tert-Butyl-[1,2,4]oxadiazol-5-yl)-propylthio]-7-chloro-2,3,4,5-tetrahydro-1H-benzo[d]azepine Hydrochloride

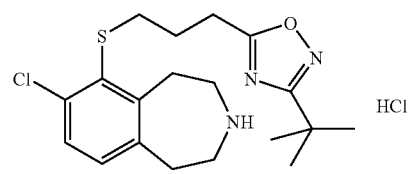

Use a method similar to the Example 387, using 3-tert-butoxycarbonyl-7-chloro-6-dimethylcarbamoylthio-2,3,4,5-tetrahydro-1H-benzo[d]azepine and 5-(3-bromopropyl)-3-tert-butyl-[1,2,4]oxadiazole to give, after deprotection using a method similar to the General Procedure 1-4, the title compound as a white solid. MS (APCI+) m/z 380 (M+H)+.

EXAMPLE 491

(−)-7-Chloro-6-(tetrahydrofuran-3-ylthio)-2,3,4,5-tetrahydro-1H-benzo[d]azepine Hydrochloride

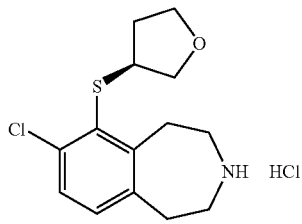

Use a method similar to the Example 332, using 3-tert-butoxycarbonyl-7-chloro-6-dimethylcarbamoylthio-2,3,4,5-tetrahydro-1H-benzo[d]azepine and (S)-toluene-4-sulfonic acid tetrahydrofuran-3-yl ester to give, after deprotection using a method similar to the General Procedure 1-4, the title compound as an off-white solid. MS (APCI+) m/z: 284 (M+H)+; $[\alpha]^{20}_D$ −28.01 (c 0.5, CH$_3$OH). ee=97.8% [Chiral HPLC: Column: YMC ODS-AQ 120 Å 4.6×50 mm [S-3 µm]; eluent: gradient from 95:5 to 5:95 A/B; solvent A: water, 0.01% HFBA, 1% isopropanol; solvent B: acetonitrile, 0.01% HFBA, 1% isopropanol; flow rate 2 mL/min].

EXAMPLE 492

(+)-7-Chloro-6-(tetrahydrofuran-3-ylthio)-2,3,4,5-tetrahydro-1H-benzo[d]azepine Hydrochloride

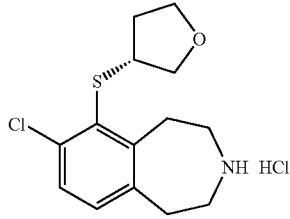

Use a method similar to the Example 332, using 3-tert-butoxycarbonyl-7-chloro-6-dimethylcarbamoylthio-2,3,4,5-tetrahydro-1H-benzo[d]azepine and (R)-toluene-4-sulfonic acid tetrahydro-furan-3-yl ester to give, after deprotection using a method similar to the General Procedure 1-4, the title compound as an off-white solid. MS (APCI+) m/z: 284 (M+H); $[\alpha]^{20}_D$ +32.5° (c 0.5, CH$_3$OH); ee=95.7% [Chiral HPLC: Column: YMC ODS-AQ 120 Å 4.6×50 mm [S-3 µm]; eluent: gradient from 95:5 to 5:95 A/B; solvent A: water, 0.01% HFBA, 10% isopropanol; solvent B: acetonitrile, 0.01% HFBA, 1% isopropanol; flow rate 2 mL/min].

EXAMPLE 493

(±)-7-Chloro-6-(tetrahydrofuran-2-ylmethylthio)-2,3,4,5-tetrahydro-1H-benzo[d]azepine Hydrochloride

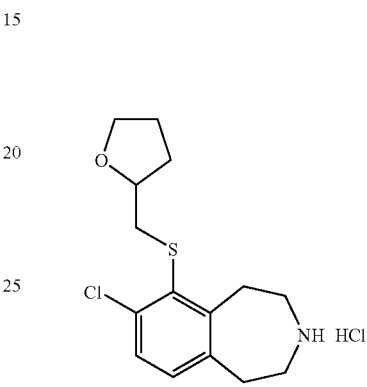

Use a method similar to the Example 330, using 3-tert-butoxycarbonyl-7-chloro-6-dimethylcarbamoylthio-2,3,4,5-tetrahydro-1H-benzo[d]azepine and 2-(bromomethyl)tetrahydrofuran to give, after deprotection by the General Procedure 1-4, the title compound as white crystals. MS (APCI+) m/z: 298 (M+H)+.

EXAMPLE 494

(±)-7-Chloro-6-(tetrahydropyran-2-ylmethylthio)-2,3,4,5-tetrahydro-1H-benzo[d]azepine Hydrochloride

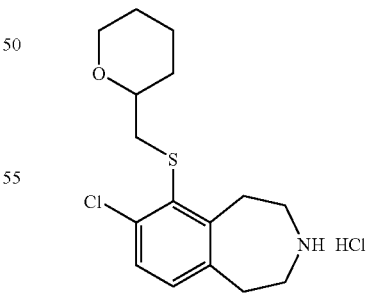

Use a method similar to the Example 330, using 3-tert-butoxycarbonyl-7-chloro-6-dimethylcarbamoylthio-2,3,4,5-tetrahydro-1H-benzo[d]azepine and 2-(bromomethyl)tetrahydropyran to give, after deprotection by the General Procedure 1-4, the title compound as a white solid. MS (APCI+) m/z: 312 (M+H)+.

EXAMPLE 495

(S)-(+)-7-Chloro-6-(5-oxo-tetrahydrofuran-2-ylm-ethylthio)-2,3,4,5-tetrahydro-1H-benzo[d]azepine Hydrochloride

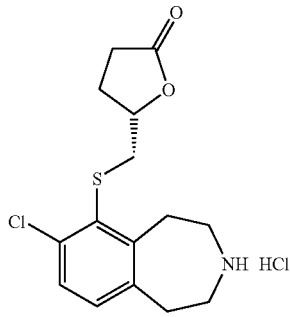

Use a method similar to the General Procedure 1-4, using (S)-3-tert-butoxycarbonyl-7-chloro-6-(5-oxo-tetrahydrofuran-2-ylmethylthio)-2,3,4,5-tetrahydro-1H-benzo[d]azepine to give the title compound as a white solid. MS (ES+) m/z: 312 (M+H)$^+$. $[\alpha]^{20}_D$ +78° (c 0.5, CH$_3$OH).

EXAMPLE 496

7-Chloro-6-(3-dimethylcarbamoylpropylthio)-2,3,4,5-tetrahydro-1H-benzo[d]azepine Hydrochloride

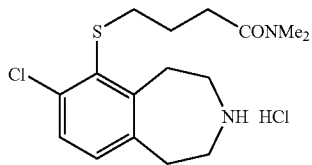

Treat a solution of 3-tert-butoxycarbonyl-7-chloro-6-(3-methoxycarbonyl-propylthio)-2,3,4,5-tetrahydro-1H-benzo[d]azepine (385 mg, 0.90 mmol) in dioxane/water (1:1, 3.5 mL) with lithium hydroxide (43.0 mg, 1.01 mmol) at 80° C. for 1.5 h. Cool to ambient temperature, add aqueous saturated ammonium chloride and brine, extract three times with ethyl ether, dry over anhydrous MgSO$_4$, and concentrate in vacuo. Dissolve the residue in DCM (3.5 mL) and add EDC (162 mg, 0.84 mmol), 1-hydroxybenzotriazole (91.0 mg, 0.67 mmol), triethylamine (0.20 mL, 1.35 mmol), and dimethylamine (0.700 mL, 1.35 mmol). Stir overnight at ambient temperature. Dilute with water, extract with ethyl ether, dry over anhydrous MgSO$_4$; and concentrate in vacuo. Purify by chromatography on silica gel eluting with hexane/EtOAc/methanol 60:40:1 to give 3-tert-butoxycarbonyl-7-chloro-6-(3-dimethylcarbamoyl-propylthio)-2,3,4,5-tetrahydro-1H-benzo[d]azepine.

Dissolve 3-tert-butoxycarbonyl-7-chloro-6-(3-dimethylcarbamoyl-propylthio)-2,3,4,5-tetrahydro-1H-benzo[d]azepine in DCM (1 mL) at ambient temperature and add 4M hydrogen chloride in dioxane (200 μL, 0.8 mmol). Continue stirring until TLC shows consumption of starting material. Concentrate in vacuo, triturate the obtained solid with dry diethyl ether and dry at 50° C. under high vacuum overnight to give the title compound as a hygroscopic white solid (45.0 mg, 57%). MS (ES+) m/z: 327 (M+H)$^+$.

EXAMPLE 497

7-Chloro-6-[3-(1,3-dioxo-1,3-dihydroisoindol-2-yl)-propylthio]-2,3,4,5-tetrahydro-1H-benzo[d]azepine Trifluoroacetate

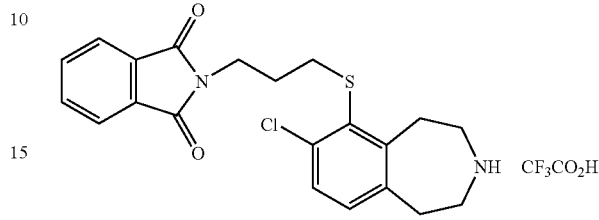

Dissolve 3-tert-butoxycarbonyl-7-chloro-6-dimethylcarbamoylthio-2,3,4,5-tetrahydro-1H-benzo[d]azepine (2.0 g, 5.20 mmol) in methanol (58 mL) and add potassium hydroxide (9.36 g, 167 mmol). Heat at 50° C. for 2 h. Cool to ambient temperature, add aqueous saturated ammonium chloride and water, extract three times with EtOAc, dry over anhydrous Na$_2$SO$_4$, and concentrate in vacuo to give 3-tert-butoxycarbonyl-7-chloro-6-mercapto-2,3,4,5-tetrahydro-1H-benzo[d]azepine (1.62 g, 5.20 mmol). Dissolve the crude 3-tert-butoxycarbonyl-7-chloro-6-mercapto-2,3,4,5-tetrahydro-1H-benzo[d]azepine (1.40 g, 4.46 mmol) in dry DMF (49.8 mL) and add DBU (0.80 mL, 5.35 mmol) and 3-bromopropyl phthalimide (1.55 g, 5.80 mmol). Stir at ambient temperature for 3 h. Add aqueous saturated ammonium chloride and water. Extract twice with EtOAc, dry over anhydrous Na$_2$SO$_4$, and concentrate in vacuo. Purify by chromatography on silica gel eluting with hexane/EtOAc (6:1) to give the free base of title compound (1.64 g, 74%).

Use a method similar to the General Procedure 1-5, to deprotect 3-tert-butoxycarbonyl-7-chloro-6-[3-(1,3-dioxo-1,3-dihydro-isoindol-2-yl)-propylthio]-2,3,4,5-tetrahydro-1H-benzo[d]azepine and purify by preparative reverse phase HPLC to give the title compound. MS (APCI+) m/z 401 (M+H)$^+$.

EXAMPLE 498

6-(3-Benzoylaminopropylthio)-7-chloro-2,3,4,5-tetrahydro-1H-benzo[d]azepine Trifluoroacetate

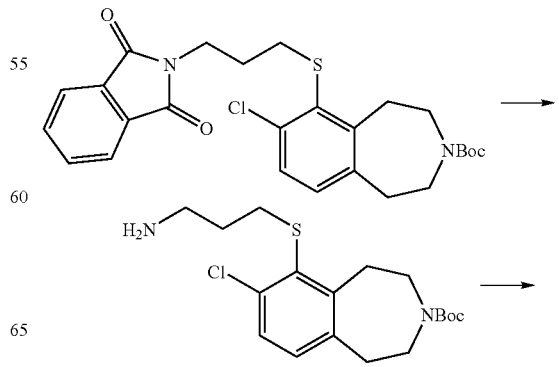

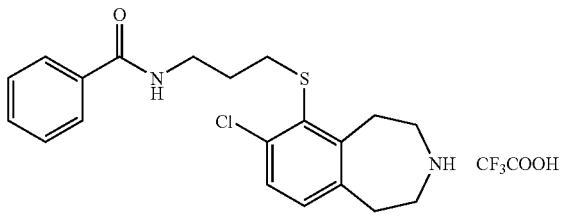

Suspend 3-tert-butoxycarbonyl-7-chloro-6-[3-(1,3-dioxo-1,3-dihydroisoindol-2-yl)-propylthio]-2,3,4,5-tetrahydro-1H-benzo[d]azepine (1.20 g, 2.39 mmol) in ethanol (53.2 mL), add hydrazine (0.150 mL, 4.78 mmol) and heat at 65° C. for 2 h. Cool to ambient temperature, filter from precipitate, and concentrate in vacuo to provide the 6-(3-aminopropylthio)-3-tert-butoxycarbonyl-7-chloro-2,3,4,5-tetrahydro-1H-benzo[d]azepine (861 mg, 97%). MS (APCI+) m/z: 371 (M+H)+.

To a solution of 6-(3-aminopropylthio)-3-tert-butoxycarbonyl-7-chloro-2,3,4,5-tetrahydro-1H-benzo[d]azepine (46.7 mg, 0.126 mmol) in dry DCM (0.5 mL) at ambient temperature under nitrogen, add triethylamine (19.3 µL, 0.139 mmol) and benzoyl chloride (16.1 µL, 0.139 mmol). Stir at ambient temperature for 2.5 h. Add aqueous saturated ammonium chloride and water, extract three times with EtOAc, dry over anhydrous Na$_2$SO$_4$, and concentrate in vacuo. Dissolve the residue in DCM (0.16 mL), add trifluoroacetic acid (44.6 µL, 0.58 mmol) and stir for 18 h at ambient temperature. Concentrate in vacuo and purify by preparative HPLC [Column: YMC ODS-AQ 120 Å 20×250 mm [S10-20 µm]; eluent: 95:5 to 5:95 A/B; solvent A: water, 0.1% TFA, 1% isopropanol; solvent B: acetonitrile, 0.05% TFA, 1% isopropanol; flow rate 20 mL/min] to give the title compound (7.0 mg, 12%). MS (APCI+) m/z 375 (M+H)+.

EXAMPLE 499

6-[3-(3-Phenylureido)-propylthio]-7-chloro-2,3,4,5-tetrahydro-1H-benzo[d]azepine Trifluoroacetate

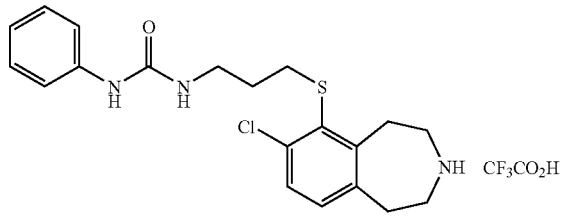

Use a method similar to the Example 498, using phenyl isocyanate, to give the title compound. MS (APCI+) m/z 390 (M+H)+.

EXAMPLE 500

7-Chloro-6-[3-(4-trifluoromethylbenzoylamino)-propylthio]-2,3,4,5-tetrahydro-1H-benzo[d]azepine Trifluoroacetate

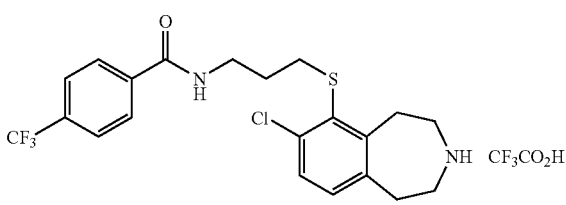

To a stirred solution of 4-trifluoromethylbenzoic acid (60.0 mg, 0.316 mmol) in anhydrous DMF (1.2 mL) at ambient temperature under nitrogen, add EDC (63.6 mg, 0.332 mmol), 1-hydroxybenzotriazole (44.8 mg, 0.332 mmol), 4-dimethylaminopyridine (40.5 mg, 0.332 mmol) and a solution of 6-(3-aminopropylthio)-3-tert-butoxycarbonyl-7-chloro-2,3,4,5-tetrahydro-1H-benzo[d]azepine (123 mg, 0.332 mmol) in DCM (2 mL). Stir for 18 h at ambient temperature. Add water, extract twice with EtOAc, dry over anhydrous Na$_2$SO$_4$, and concentrate in vacuo. Treat the residue with trifluoroacetic acid (0.272 mL, 0.640 mmol) in DCM (0.451 mL) at ambient temperature for 18 h. Concentrate in vacuo and purify by preparative reverse phase HPLC [Column: YMC ODS-AQ 120 Å 20×250 mm [S10-20 µm]; eluent: 95:5 to 5:95 A/B; solvent A: water, 0.1% TFA, 1% isopropanol; solvent B: acetonitrile, 0.05% TFA, 1% isopropanol; flow rate 20 mL/min] to give the title compound as a white solid (31.0 mg, 18%). MS (APCI+) m/z 443 (M+H)+.

EXAMPLE 501

7-Chloro-6-[3-(4-tert-butylbenzoylamino)-propylthio]-2,3,4,5-tetrahydro-1H-benzo[d]azepine Trifluoroacetate

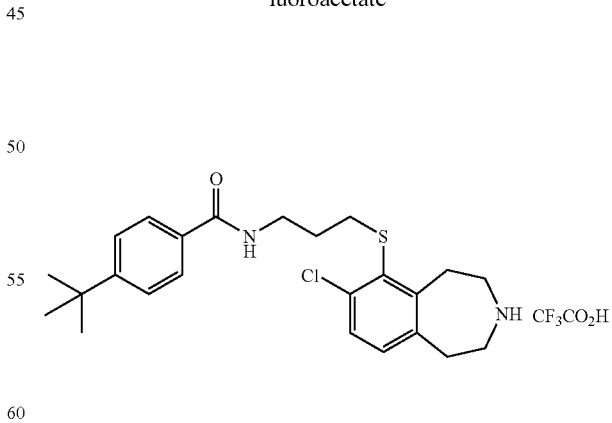

Use a method similar to the Example 500, using 6-(3-aminopropylthio)-3-tert-butoxycarbonyl-7-chloro-2,3,4,5-tetrahydro-1H-benzo[d]azepine and 4-tert-butyl benzoic acid to give the title compound as a white solid. MS (APCI+) m/z 431 (M+H)+.

EXAMPLE 502

7-Chloro-6-(2-ethoxycarbonylamino-ethylthio)-2,3,4,5-tetrahydro-1H-benzo[d]azepine Trifluoroacetate

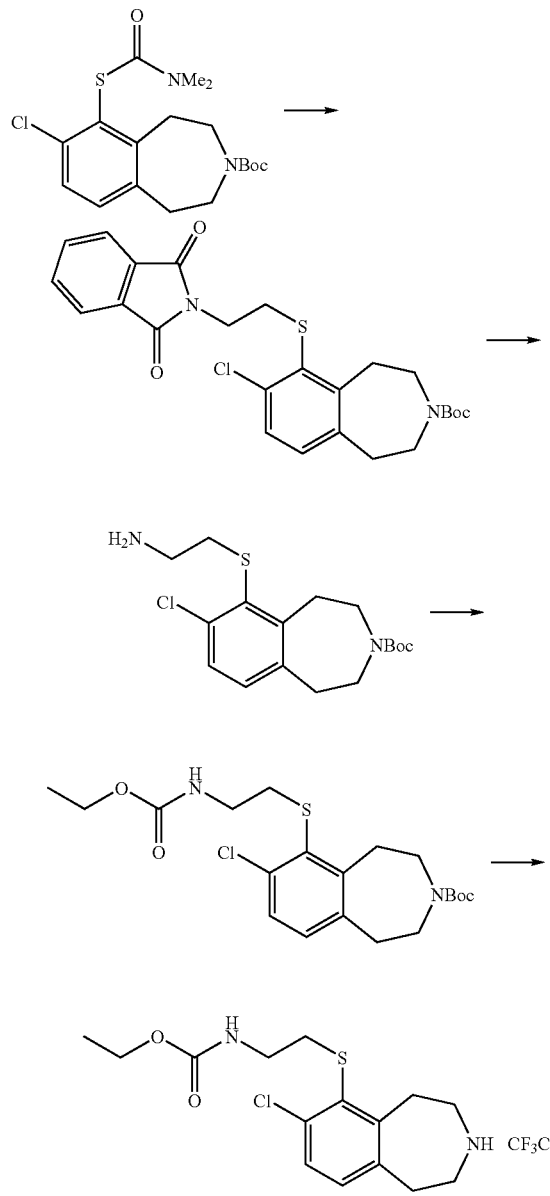

Use a method similar to the Example 497, using 3-tert-butoxycarbonyl-7-chloro-6-dimethylcarbamoylthio-2,3,4,5-tetrahydro-1H-benzo[d]azepine and 3-bromoethyl phthalimide to give 6-(3-aminoethylthio)-3-tert-butoxycarbonyl-7-chloro-2,3,4,5-tetrahydro-1H-benzo[d]azepine. MS (ES+) m/z 357 (M+H)+.

Use a method similar to the Example 498, using 6-(3-aminoethylthio)-3-tert-butoxycarbonyl-7-chloro-2,3,4,5-tetrahydro-1H-benzo[d]azepine and ethyl chloroformate to give, after deprotection using a method similar to the General Procedure 1-5, the title compound as a white solid. MS (APCI+) m/z: 329 (M+H)+.

EXAMPLE 503

7-Chloro-6-{2-[(pyridine-4-carbonyl)amino]-ethylthio}-2,3,4,5-tetrahydro-1H-benzo[d]azepine Trifluoroacetate

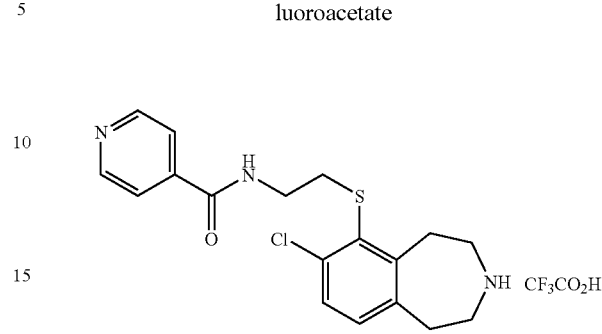

Use a method similar to the Example 500, using 6-(3-aminoethylthio)-3-tert-butoxycarbonyl-7-chloro-2,3,4,5-tetrahydro-1H-benzo[d]azepine and isonicotinic acid to give the title compound. MS (ES+) m/z: 362 (M+H)+.

EXAMPLE 504

7-Chloro-6-[2-(cyclopropanecarbonylamino)-ethylthio]-2,3,4,5-tetrahydro-1H-benzo[d]azepine Trifluoroacetate

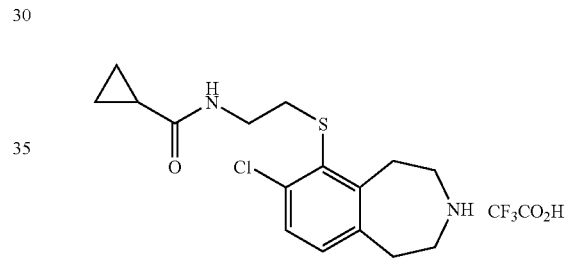

Use a method similar to the Example 498, using 6-(3-aminoethylthio)-3-tert-butoxycarbonyl-7-chloro-2,3,4,5-tetrahydro-1H-benzo[d]azepine and cyclopropanecarbonyl chloride to give, after deprotection using a method similar to the General Procedure 1-5, the title compound. MS (ES+) m/z: 325 (M+H)+.

EXAMPLE 505

6-(2-Benzenesulfonylamino-ethylthio)-7-chloro-2,3,4,5-tetrahydro-1H-benzo[d]azepine Trifluoroacetate

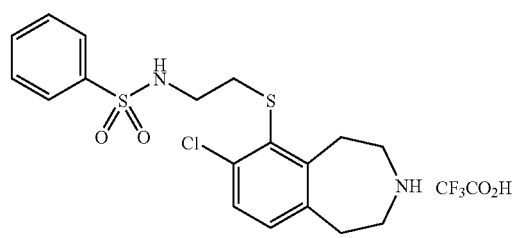

Use a method similar to the Example 498, using 6-(3-amino-ethylthio)-3-tert-butoxycarbonyl-7-chloro-2,3,4,5-tetrahydro-1H-benzo[d]azepine and benzenesulfonyl chlo-

EXAMPLE 506

7-Chloro-6-(3-pyrrol-1-yl-propylthio)-2,3,4,5-tetrahydro-1H-benzo[d]azepine Trifluoroacetate

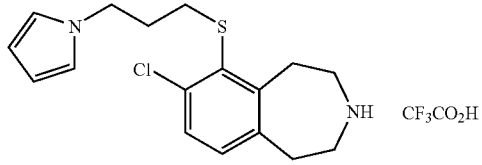

Use a method similar to the Example 497, using 3-tert-butoxycarbonyl-7-chloro-6-dimethylcarbamoylthio-2,3,4,5-tetrahydro-1H-benzo[d]azepine and N-(3-bromopropyl)pyrrole to give, after deprotection using a method similar to the General Procedure 1-5, the title compound as a white solid. MS (ES+) m/z: 321 (M+H)$^+$.

EXAMPLE 507

7-Chloro-6-[2-(2,2-dimethylpropionyloxy)-ethylthio]-2,3,4,5-tetrahydro-1H-benzo[d]azepine Hydrochloride

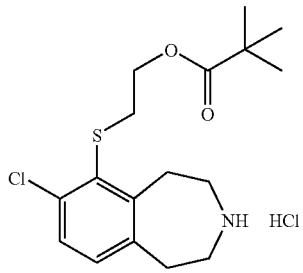

To a stirred solution of 3-tert-butoxycarbonyl-7-chloro-6-(2-hydroxyethylthio)-2,3,4,5-tetrahydrobenzo[d]azepine (85 mg, 0.238 mmol) in DCM (3 ml) at 0° C., add triethylamine (331 µl, 2.381 mmol) followed by trimethylacetyl chloride (147 µl, 1.190 mmol). Continue stirring for 15 min, dilute with water, extract three times with EtOAc, dry over anhydrous Na$_2$SO$_4$, and concentrate in vacuo. Deprotection by the General Procedure 1-5, basic workup, and by the General Procedure 2-2 give the title compound. MS (ES+) m/z 342 (M+H).

ride to give, after deprotection using a method similar to the General Procedure 1-5, the title compound as a white solid. MS (APCI+) m/z: 397 (M+H)$^+$.

EXAMPLE 508

7-Chloro-6-(2-cyclohexanecarbonyloxy-ethylthio)-2,3,4,5-tetrahydro-1H-benzo[d]azepine Hydrochloride

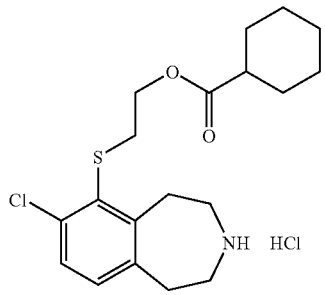

Use a method similar to the Example 507, using cyclohexanecarbonyl chloride, to give the title compound. MS (ES+) m/z 368 (M+H).

EXAMPLE 509

7-Chloro-6-(3-hydroxymethylbenzylthio)-2,3,4,5-tetrahydro-1H-benzo[d]azepine Hydrochloride

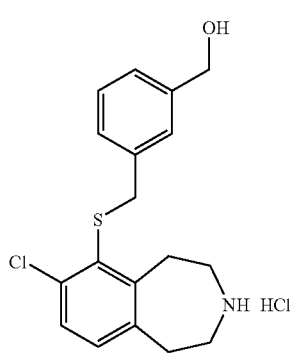

Use a method similar to the Preparation 242, using 3-tert-butoxycarbonyl-7-chloro-6-(3-hydroxymethylbenzylthio)-2,3,4,5-tetrahydro-1H-benzo[d]azepine to give, after deprotection by the General Procedure 1-4, the title compound as a white solid. MS (ES+) m/z: 334 (M+H)$^+$.

EXAMPLE 510

7-Chloro-6-(2-hydroxymethylbenzylthio)-2,3,4,5-tetrahydro-1H-benzo[d]azepine Hydrochloride

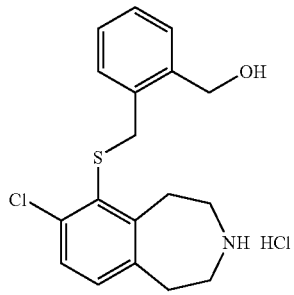

Use a method similar to the Preparation 242, using 3-tert-butoxycarbonyl-7-chloro-6-(2-hydroxymethylbenzylthio)-2,3,4,5-tetrahydro-1H-benzo[d]azepine to give, after deprotection by the General Procedure 1-4, the title compound as a white solid. MS (ES+) m/z: 334 (M+H)⁺.

EXAMPLE 511

7-Chloro-6-(4-hydroxymethylbenzylthio)-2,3,4,5-tetrahydro-1H-benzo[d]azepine Hydrochloride

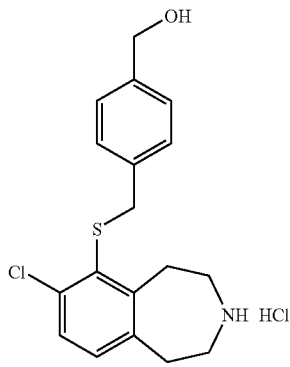

Use a method similar to the General Procedure 1-4, using 3-tert-butoxycarbonyl-7-chloro-6-(4-hydroxymethylbenzylthio)-2,3,4,5-tetrahydro-1H-benzo[d]azepine, to give the title compound as a white solid. MS (ES+) m/z: 334 (M+H)⁺.

EXAMPLE 512

7-Chloro-6-(4-methoxymethylbenzylthio)-2,3,4,5-tetrahydro-1H-benzo[d]azepine Hydrochloride

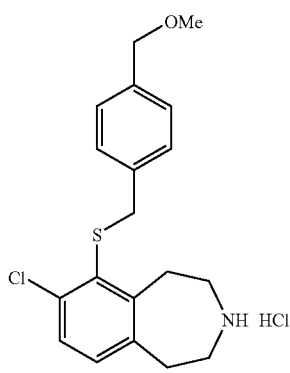

To a stirred solution of 3-tert-butoxycarbonyl-7-chloro-6-(4-hydroxymethyl-benzylthio)-2,3,4,5-tetrahydro-1H-benzo[d]azepine (133 mg, 0.306 mmol) in anhydrous DMF (2 mL) under nitrogen, add sodium hydride (60% dispersion, 13-15 mg, 0.375 mmol) at ambient temperature and continue sting for 30 min. Add methyl iodide (80 □L, 1.28 mmol). After 15 min, dilute with water, extract three times with EtOAc, dry over anhydrous MgSO₄ and concentrate in vacuo. Purify by chromatography on silica gel eluting with hexane/EtOAc (15:1) to give 3-tert-butoxycarbonyl-7-chloro-6-(4-methoxymethyl-benzylthio)-2,3,4,5-tetrahydro-1H-benzo[d]azepine as a clear oil, which crystallizes on standing to a white solid (87 mg, 63%), along with recovered starting material (22 mg, 17%). Use a method similar to the General Procedure 1-4 to give the title compound as a white solid. MS (ES+) m/z: 348 (M+H−Boc)⁺.

EXAMPLE 513

7-Chloro-6-(3-methoxymethylbenzylthio)-2,3,4,5-tetrahydro-1H-benzo[d]azepine Hydrochloride

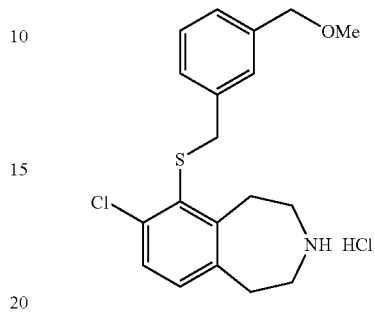

Use a method similar to the Example 512, using 3-tert-butoxycarbonyl-7-chloro-6-(3-hydroxymethylbenzylthio)-2,3,4,5-tetrahydro-1H-benzo[d]azepine to give the title compound as a white solid. MS (ES+) m/z: 348 (M+H).

EXAMPLE 514

7-Chloro-6-(2-methoxymethylbenzylthio)-2,3,4,5-tetrahydro-1H-benzo[d]azepine Hydrochloride

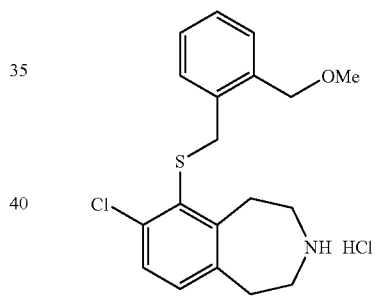

Use a method similar to the Example 512, using 3-tert-butoxycarbonyl-7-chloro-6-(2-hydroxymethylbenzylthio)-2,3,4,5-tetrahydro-1H-benzo[d]azepine to give the title compound as a white solid. MS (ES+) m/z: 348 (M+H).

EXAMPLE 515

7-Chloro-6-(2-methoxyethylthio)-2,3,4,5-tetrahydro-1H-benzo[d]azepine hydrochloride

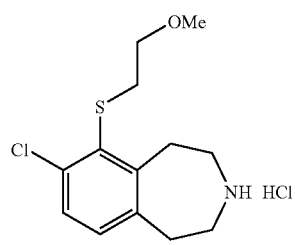

Use a method similar to the Example 512, using 3-tert-butoxycarbonyl-7-chloro-6-(2-hydroxy-ethylthio)-2,3,4,5-tetrahydro-1H-benzo[d]azepine, to give the title compound as a white solid. MS (ES+) m/z: 272 (M+H).

EXAMPLE 516

7-Chloro-6-(4-methoxybutylthio)-2,3,4,5-tetrahydro-1H-benzo[d]azepine hydrochloride

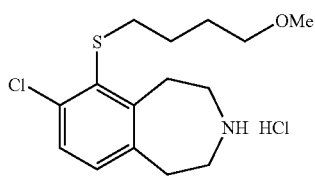

Use a method similar to the Example 478, using 3-tert-butoxycarbonyl-7-chloro-6-(3-methoxycarbonyl-propylthio)-2,3,4,5-tetrahydro-1H-benzo[d]azepine to give 3-tert-butoxycabonyl-7-chloro-6-(4-hydroxybutylthio)-2,3,4,5-tetrahydro-1H-benzo[d]azepine. Use a method similar to the Example 512, using 3-tert-butoxycarbonyl-7-chloro-6-(4-hydroxybutylthio)-2,3,4,5-tetrahydro-1H-benzo[d]azepine to give the title compound as a white solid. MS (ES+) m/z: 300 (M+H)$^+$.

EXAMPLE 517

(±)-7-Chloro-6-(2-methoxy-1-phenylethylthio)-2,3,4,5-tetrahydro-1H-benzo[d]azepine Hydrochloride

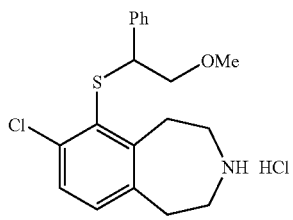

Use a method similar to the Example 512, using (±)-3-tert-butoxycarbonyl-7-chloro-6-(2-hydroxy-1-phenylethylthio)-2,3,4,5-tetrahydro-1H-benzo[d]azepine to give, after deprotection by a method similar to the General Procedure 14, the title compound as an off-white solid. MS (ES+) m/z: 348 (M+H)$^+$.

EXAMPLE 518

(−)-7-Chloro-6-(2-methoxy-1-phenylethylthio)-2,3,4,5-tetrahydro-1H-benzo[d]azepine Hydrochloride

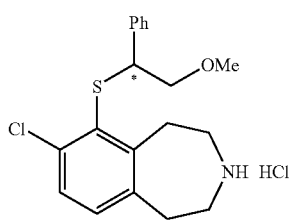

Separate the enantiomers of (±)-7-chloro-6-(2-methoxy-1-phenyl-ethylthio)-2,3,4,5-tetrahydro-1H-benzo[d]azepine by chiral normal phase chromatography (Chiralcel OJ 8×33 cm column, eluting with 0.2% DMEA in ethanol/heptane, 40:60). Collect the second eluting isomer and use the General Procedure 2-2 to give the title compound as a white solid (76 mg, 29%). MS (ES+) m/z: 349 (M+H)$^+$. [α]$^{20}_D$ −176° (c 0.5, CH$_3$OH).

EXAMPLE 519

6-(4-Fluorobenzylthio)-7-methyl-2,3,4,5-tetrahydro-1H-benzo[d]azepine Hydrochloride

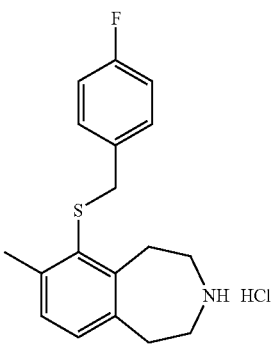

Use a method similar to the General Procedure 7, using 3-tert-butoxycarbonyl-6-dimethylcarbamoylthio-7-methyl-2,3,4,5-tetrahydro-1H-benzo[d]azepine (75 mg, 0.206 mmol) and 4-fluorobenzyl bromide (195 mg, 1.03 mmol) to give, after chromatography on silica gel eluting with hexane/EtOAc (1:0, 9:1 and 4:1), 3-tert-butoxycarbonyl-6-(4-fluorobenzylthio)-7-methyl-2,3,4,5-tetrahydro-1H-benzo[d]azepine as an oil (59 mg, 71%). MS (ES+) m/z: 302 (M+H−Boc)$^+$.

Use a method similar to the General Procedure 1-4, using 3-tert-butoxycarbonyl-6-(4-fluoro-benzylthio)-7-methyl-2,3,4,5-tetrahydro-1H-benzo[d]azepine (55 mg, 0.137 mmol) to give the title compound as a white solid (42 mg, 91%). MS (ES+) m/z: 285 (M+H)$^+$.

EXAMPLE 520

7-Cyano-6-(4-fluorobenzylthio)-2,3,4,5-tetrahydro-1H-benzo[d]azepine Succinate

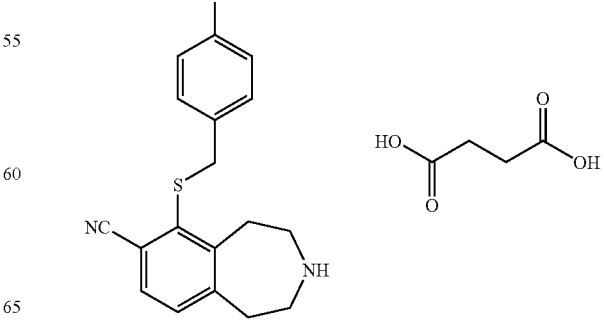

Use a method similar to the General Procedure 7, using 3-tert-butoxycarbonyl-7-cyano-6-dimethylcarbamoylthio-2,3,4,5-tetrahydro-1H-benzo[d]azepine (123 mg, 0.33 mmol) and 4-fluorobenzyl bromide (204 mg, 1.64 mmol), to give 3-tert-butoxycarbonyl-7-cyano-6-(4-fluoro-benzylthio)-2,3,4,5-tetrahydro-1H-benzo[d]azepine as a colorless oil (118 mg, 87%).

Use a method similar to the General Procedure 14, using 3-tert-butoxycarbonyl-7-cyano-6-(4-fluoro-benzylthio)-2,3,4,5-tetrahydro-1H-benzo[d]azepine (118 mg, 0.286 mmol) to give, after basic work-up, the free base of the title compound (89 mg, 100%). MS (ES+) m/z 313 (M+H)$^+$. Use a method similar to the General Procedure 2-1 to give the title compound (123 mg, 100%). MS (ES+) m/z 313 (M+H)$^+$.

EXAMPLE 521

(±)-7-Cyano-6-[1-(4-fluorophenyl)ethylthio]-2,3,4,5-tetrahydro-1H-benzo[d]azepine Succinate

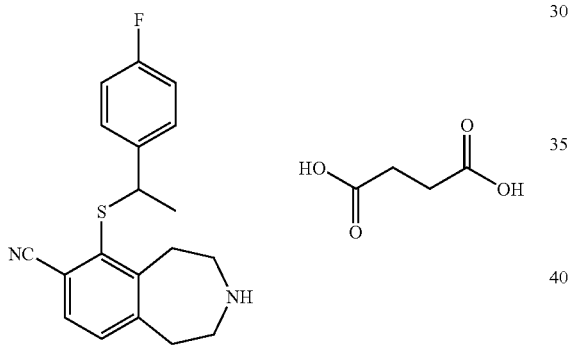

Use a method similar to the General Procedure 7, using 3-tert-butoxycarbonyl-7-cyano-6-dimethylcarbamoylthio-2,3,4,5-tetrahydro-1H-benzo[d]azepine (171 mg, 0.46 mmol) and (±)-1-(4-fluorophenyl)ethyl bromide (377 mg, 1.85 mmol) to give, after purification by chromatography on silica gel, (±)-3-tert-butoxycarbonyl-7-cyano-6-[1-(4-fluorophenyl)-ethylthio]-2,3,4,5-tetrahydro-1H-benzo[d]azepine as a colorless oil (10.3 mg, 5.3%). MS (ES+) m/z 449 (M+Na)$^+$, 465 (M+K)$^+$.

Use a method similar to the General Procedure 1-5, using (±)-3-tert-butoxycarbonyl-7-cyano-6-[1-(4-fluorophenyl)ethylthio]-2,3,4,5-tetrahydro-1H-benzo[d]azepine (10.3 mg, 0.024 mmol) to give, after basic work-up, the free base of the title compound (6.8 mg, 87%). MS (ES+) m/z 327 (M+H)$^+$. Use a method similar to the General Procedure 2-1 to give the title compound as a white solid (9.3 mg, 87%). MS (ES+) m/z 327 (M+H)$^+$.

EXAMPLE 522

7-Cyano-6-[1-(4-fluorophenyl)ethylthio]-2,3,4,5-tetrahydro-1H-benzo[d]azepine Succinate, Isomer 1

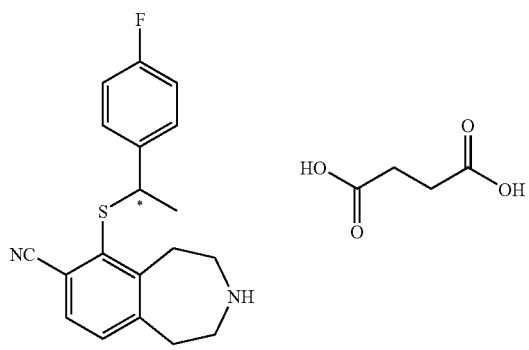

Separate the two enantiomers of (±)-7-cyano-6-[1-(4-fluorophenyl)ethylthio]-2,3,4,5-tetrahydro-1H-benzo[d]azepine by chiral HPLC (Chiralpak AD-H 15 cm×4.6 mm column with a 5 μm packing size. Elute with heptane/ethanol (95:5) containing 0.2% DEA at 0.5 mL/min with an injection volume of 10.00 μL).

Subject the first eluting isomer ($t_R$=17.2 min, ee >99%) to the General Procedure 2-1 to afford the title compound as a white solid. MS (ES+) m/z 327 (M+H)$^+$.

EXAMPLE 523

7-Bromo-6-(3-ethoxycarbonylpropylthio)-2,3,4,5-tetrahydro-1H-benzo[d]azepine Hydrochloride

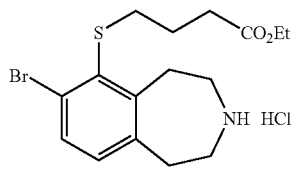

Use a method similar to the Preparation 177, using 3-tert-butoxycarbonyl-7-bromo-6-dimethylcarbamoylthio-2,3,4,5-tetrahydro-1H-benzo[d]azepine and ethyl 4-bromobutyrate to give, after deprotection by a method similar to the General Procedure 1-4, the title compound. MS (ES+) m/z: 374 (M+H)$^+$.

EXAMPLE 524

7-Bromo-6-(3-dimethylcarbamoylpropylthio)-2,3,4,5-tetrahydro-1H-benzo[d]azepine Hydrochloride

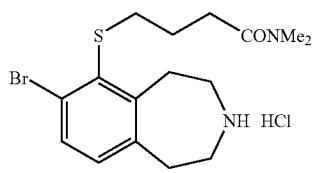

Use a method similar to the Example 523, using 7-bromo-3-tert-butoxycarbonyl-6-(3-ethoxycarbonylpropylthio)-2,3,4,5-tetrahydro-1H-benzo[d]azepine, to give the title compound as a white solid. MS (ES+) m/z: 373 (M+H)⁺.

EXAMPLE 525

7-Bromo-6-(4-oxo-4-pyrrolidin-1-yl-butylthio)-2,3,4,5-tetrahydro-1H-benzo[d]azepine Hydrochloride

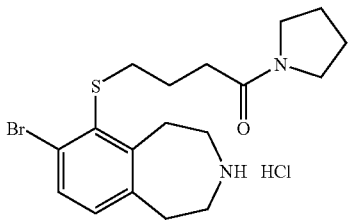

Use a method similar to the Example 523, using 7-bromo-3-tert-butoxycarbonyl-6-(3-ethoxycarbonylpropylthio)-2,3,4,5-tetrahydro-1H-benzo[d]azepine and pyrrolidine to give the title compound. MS (ES+) m/z: 397 (M+H)⁺.

EXAMPLE 526

7-Bromo-6-[3-(1,3-dioxo-1,3-dihydroisoindol-2-yl)-propylthio]-2,3,4,5-tetrahydro-1H-benzo[d]azepine Hydrochloride

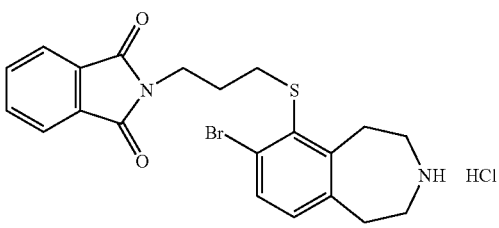

Use a method similar to the Example 497 to react 7-bromo-3-tert-butoxycarbonyl-6-dimethylcarbamoylthio-2,3,4,5-tetrahydro-1H-benzo[d]azepine with 3-bromopropyl phthalimide. Use a method similar to the General Procedure 1-4 to give the title compound as a white solid. MS (ES+) m/z 445 (+H)⁺.

EXAMPLE 527

6-[2-(2,2-Dimethylpropionyloxy)-ethylthio]-7-trifluoromethyl-2,3,4,5-tetrahydro-1H-benzo[d]azepine Hydrochloride

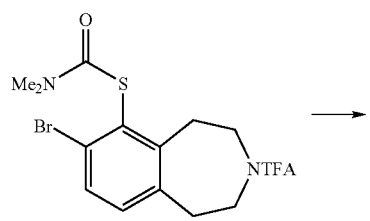

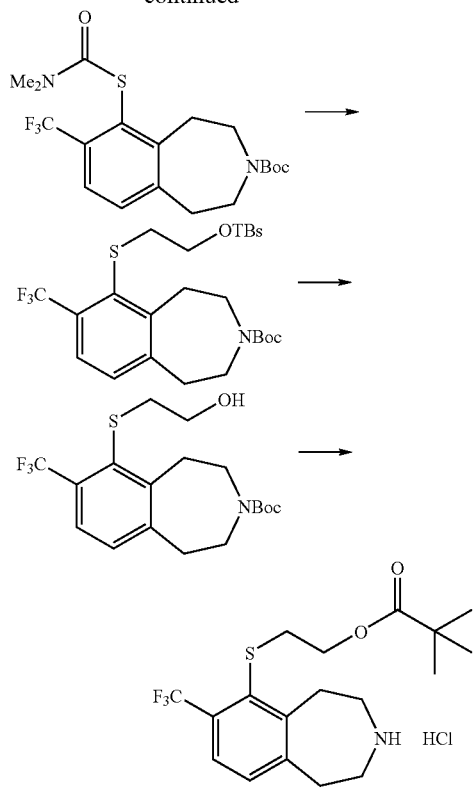

3-tert-Butoxycarbonyl-6-dimethylcarbamoylthio-7-trifluoromethyl-2,3,4,5-tetrahydro-benzo[d]azepine: To a stirred solution of 7-bromo-6-dimethylcarbamoylthio-3-(2,2,2-trifluoroacetyl)-2,3,4,5-tetrahydro-1H-benzo[d]azepine (1.383 g, 3.254 mmol), in NMP (40 ml) add sodium trifluoromethyl acetate (3.54 g, 26.03 mmol), copper(I) iodide (2.47 g, 13.0 mmol) and heat the mixture at 180° C. for 4 h. Cool to ambient temperature. Dilute with EtOAc, water and remove the copper solid residue by filtration. Separate the layers of filtrate and extract the aqueous layer three times with EtOAc. Dry over anhydrous Na₂SO₄, and concentrate in vacuo. Purify by chromatography on silica gel eluting with hexane/EtOAc (6:1) to give the desired intermediate as a yellow oil (882 mg, 74%).

3-tert-Butoxycarbonyl-6-[2-(tert-butyl-dimethylsilanyloxy)ethylthio]-7-trifluoromethyl-2,3,4,5-tetrahydro-1H-benzo[d]azepine: Use a method similar to the Preparation 177, using 3-tert-butoxycarbonyl-6-dimethylcarbamoylthio-7-trifluoromethyl-2,3,4,5-tetrahydro-benzo[d]azepine and (2-bromoethoxy)-tert-butyldimethylsilane to give the desired intermediate.

3-tert-Butoxycarbonyl-6-(2-hydroxyethylthio)-7-trifluoromethyl-2,3,4,5-tetrahydro-1H-benzo[d]azepine: Dissolve 6-[2-(tert-butyl-dimethyl-silanyloxy)-ethylthio]-7-trifluoromethyl-2,3,4,5-tetrahydro-1H-benzo[d]azepine (153 mg, 0.303 mmol) in THF (3 mL). Add 1.0 M tetrabutylammonium fluoride in THF (600 µL, 0.606 mmol,) and stir overnight. Dilute with water, extract three times with EtOAc, dry over anhydrous Na₂SO₄, and concentrate in vacuo. Purify by chromatography on silica gel eluting with hexane/EtOAc (85:15) to give the desired intermediate.

6-[2-(2,2-Dimethylpropionyloxy)-ethylthio]-7-trifluoromethyl-2,3,4,5-tetrahydro-1H-benzo[d]azepine hydrochloride: Use a method similar to the Example 507, using 3-tert-butoxycarbonyl-6-(2-hydroxyethylthio)-7-trifluoromethyl-2,3,4,5-tetrahydro-1H-benzo[d]azepine to give, after deprotection using a method similar to the General Procedure 1-4, the title compound as a white solid. MS (ES+) m/z: 376 (M+H)⁺.

General Procedure 8

Dissolve the appropriate bromide (2 equiv.) in isopropylamine (300-400 equiv.) at room temperature, under nitrogen, then add palladium(I) bis(benzonitrile) dichloride (0.2 equiv.), triphenylphoshine (0.4 equiv.) and copper(I) iodide (0.2 equiv.). Degas the solution and purge with nitrogen, then add the appropriate alkyne (1.0 equiv.). Seal the reaction vessel, stir at room temperature for 30 min, then at 75° C. for 3-4 h. Remove most of the solvent in vacuo, add diethyl ether and 2M aqueous HCl. Dry the organic layer over MgSO₄, filter and concentrate in vacuo. Purify by chromatography on silica gel eluting with isohexane/EtOAc or hexane/EtOAc mixtures.

Preparation 249

2-Ethynyl-thiophene

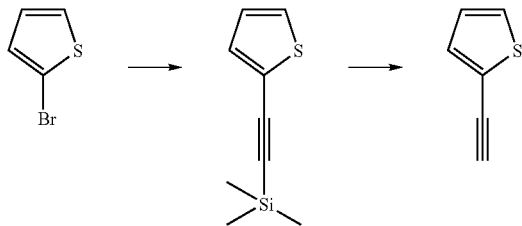

Trimethyl-thiophen-2-ylethynyl-silane: Use a method similar to the General Procedure 8 to couple 2-bromothiophene (0.97 nm, 10 mmol) with ethynyl-trimethylsilane (2.82 mL, 20 mmol). Purify by chromatography on silica gel eluting with isohexane to give the desired intermediate (1.46 g, 81%). GC-MS m/z 180 (M⁺).

2-Ethynyl-thiophene: Add a saturated solution of potassium carbonate in methanol (7.5 mL) to trimethyl-thiophen-2-ylethynyl-silane (540 mg, 3 mmol) in deoxygenated methanol (100 mL) at room temperature under nitrogen. Stir the reaction for 3.5 h, then dilute with dichloromethane (100 mL) and wash with water (3×100 mL). Remove the organic layer, dry using an ISCO® phase separator and then concentrate in vacuo to give the title compound (302 mg, 93%).

Preparation 250

3-tert-Butoxycarbonyl-7-chloro-6-ethynyl-2,3,4,5-tetrahydro-1H-benzo[d]azepine

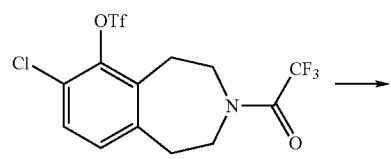

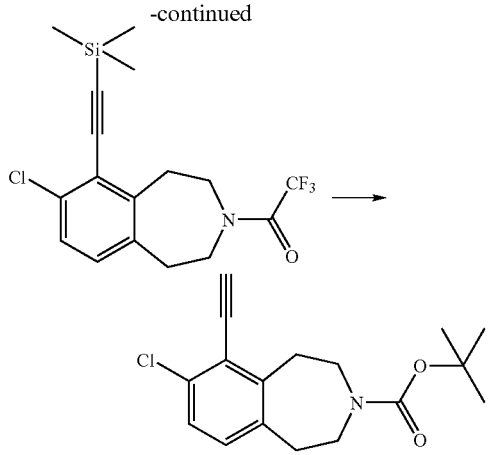

7-Chloro-3-(2,2,2-trifluoroacetyl)-6-trimethylsilanylethynyl-2,3,4,5-tetrahydro-1H-benzo[d]azepine: Use a method similar to the General Procedure 3 to couple 7-chloro-3-(2,2,2-trifluoroacetyl)-6-trifluoromethanesulfonyloxy-2,3,4,5-tetrahydro-1H-benzo[d]azepine (425 mg, 1 mmol) with 2-trimethylsilylacetylene (0.28 mL, 2 mmol). Purify by chromatography on silica gel eluting with isohexane/EtOAc (100:0 to 85:15 gradient over 40 min) to give the desired intermediate (247 mg, 81%). MS (ES+) m/z: 306 (M+H)⁺.

3-tert-Butoxycarbonyl-7-chloro-6-ethynyl-2,3,4,5-tetrahydro-1H-benzo[d]azepine: Add a solution of potassium carbonate (999 mg, 7.2 mmol) in water (5 mL) to 7-chloro-3-(2,2,2-trifluoroacetyl)-6-trimethylsilanylethynyl-2,3,4,5-tetrahydro-1H-benzo[d]azepine (180 mg, 0.48 mmol) in methanol (10 mL) and stir at room temperature, under nitrogen for 1.5 h. Add di-tert-butyl-dicarbonate (115 mg, 0.53 mmol) in dichloromethane (8 mL) and stir for 3 days. Add another solution of di-tert-butyl-dicarbonate (115 mg, 0.53 mmol) in dichloromethane (5 mL) and stir for 2 h. Add water (10 mL) and dichloromethane (10 mL) and separate the organic layer. Extract the aqueous layer with dichloromethane (3×10 mL) and combine the organic layers. Dry using an ISCO® phase separator and concentrate. Purify by chromatography on silica gel eluting with isohexane/EtOAc (1:0 to 4:1 gradient over 30 min) to give the title compound as a solid (150 mg, 100%). MS (ES+) m/z: 328 (M+Na)⁺.

Preparation 251

2-Chloro-pyridazine

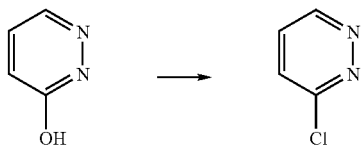

Add 3(2H)-pyridazinone (2 g, 22 mmol) to neat phosphorus oxychloride (4 mL) in a sealed tube and heat the mixture at 80° C. with stirring for 2 h. Add cautiously water (10 mL), saturated aqueous NaHCO₃ (50 mL) and solid Na₂CO₃ until pH=9. Extract the mixture with dichloromethane (4×50 mL). Dry the organic layer over Na₂SO₄, filtrate and concentrate in vacuo to give the title compound as brown oil (2 g, 84%).

Preparation 252

1-tert-Butyl-3-prop-2-ynyl-imidazolidin-2-one

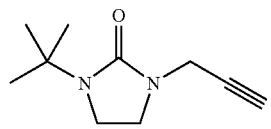

Dissolve 1-tert-butyl-imidazolidin-2-one (2 g, 14 mmol) in anhydrous THF (60 mL) and cool at −78° C. Slowly add n-butyllithium (6.8 mL, 17 mmol, 2.5 M solution in hexanes). Stir the solution for 30 min. Rapidly add propargyl bromide (3.2 mL, 28.2 mmol, 80% solution in toluene). Warm the solution to room temperature while stirring overnight Concentrate the reaction mixture in vacuo and filter the residue on a short pad of silica gel eluting with dichloromethane/diethyl ether (1:1) to give the title compound as a yellow oil that solidifies on standing (1.77 g, 70%). GC-MS m/z (%) 180 (M+, 7), 165 (100), 123 (12), 84 (17).

EXAMPLE 528

7-Chloro-6-pyridin-2-ylethynyl-2,3,4,5-tetrahydro-1H-benzo[d]azepine Succinate

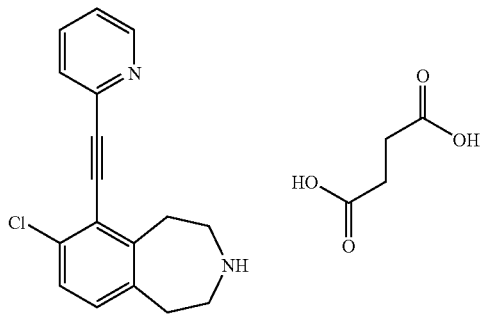

Use a method similar to the General Procedure 3 to couple 7-chloro-3-(2,2,2-trifluoroacetyl)-6-trifluoromethanesulfonyloxy-2,3,4,5-tetrahydro-1H-benzo[d]azepine (425 mg, 1 mmol) with 2-ethynyl-pyridine (0.20 mL, 2 mmol). Purify by chromatography on silica gel eluting with isohexane/EtOAc (1:0 to 1:1 gradient over 40 min) to give 7-chloro-6-pyridin-2-ylethynyl-3-(2,2,2-trifluoroacetyl)-2,3,4,5-tetrahydro-1H-benzo[d]azepine (342 mg, 90%). MS (ES+) m/z: 379 (M+H)$^+$.

Use a method similar to the General Procedure 1-2 to deprotect 7-chloro-6-pyridin-2-ylethynyl-3-(2,2,2-trifluoroacetyl)-2,3,4,5-tetrahydro-1H-benzo[d]azepine (60 mg, 0.159 mmol). Purify by SCX chromatography to give the free base of the title compound (33 mg, 73%). MS (ES+) m/z: 283 (M+H)$^+$. Use a method similar to the General Procedure 2-1 to give the title compound as a light brown solid (45 mg, 95%). MS (ES+) m/z: 283 (M+H)$^+$.

EXAMPLES 529-531

Examples 529-531 may be prepared essentially as described in Example 528 by using 7-chloro-3-(2,2,2-trifluoroacetyl)-6-trifluoromethanesulfonyloxy-2,3,4,5-tetrahydro-1H-benzo[d]azepine and the appropriate alkyne. Overall yields and MS (ES+) data are shown in the Table below.

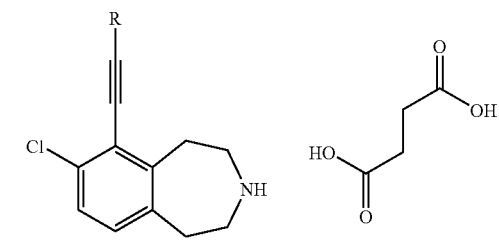

| Ex. | R | Compound | Yield (%) | MS (ES+) m/z |
|---|---|---|---|---|
| 529 | 3-Pyridyl | 7-Chloro-6-pyridin-3-ylethynyl-2,3,4,5-tetrahydro-1H-benzo[d]azepine Succinate | 78 | 283 (M + H)$^+$ |
| 530 | 4-Pyridyl | 7-Chloro-6-pyridin-4-ylethynyl-2,3,4,5-tetrahydro-1H-benzo[d]azepine Succinate | 84 | 283 (M + H)$^+$ |
| 531 | 2-Thiophenyl | 7-Chloro-6-thiophen-2-ylethynyl-2,3,4,5-tetrahydro-1H-benzo[d]azepine Succinate | 95 | 288 (M + H)$^+$ |

EXAMPLE 532

7-Chloro-6-thiazol-2-ylethynyl-2,3,4,5-tetrahydro-1H-benzo[d]azepine Succinate

EXAMPLE 533

7-Chloro-6-pyridazin-3-ylethynyl-2,3,4,5-tetrahydro-1H-benzo[d]azepine (L)-Tartrate

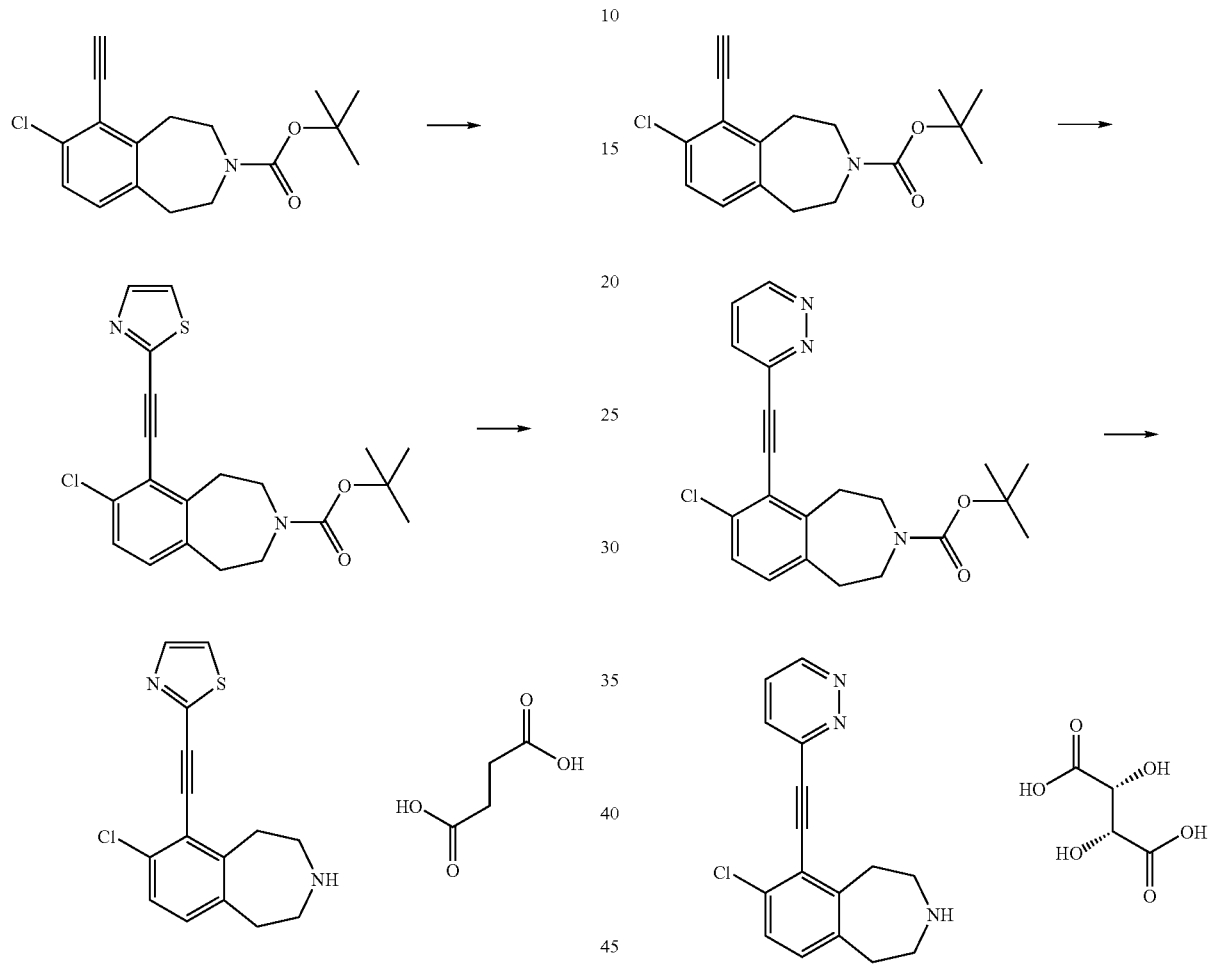

3-tert-Butoxycarbonyl-7-chloro-6-(thiazol-2-ylethynyl)-2,3,4,5-tetrahydro-1H-benzo[d]azepine: Use a method similar to the General Procedure 8 to couple 2-bromo-thiazole (0.09 mL, 0.96 mmol) with 3-tert-butoxycarbonyl-7-chloro-6-ethynyl-2,3,4,5-tetrahydro-1H-benzo[d]azepine (148 mg, 0.48 mmol). Purify by chromatography on silica gel eluting with isohexane/EtOAc (1:0 to 4:1 gradient over 30 min) to give the desired intermediate (165 mg, 89%). MS (ES+) m/z: 389 (M+H)+.

7-Chloro-6-(thiazol-2-ylethynyl)-2,3,4,5-tetrahydro-1H-benzo[d]azepine Succinate: Use a method similar to the General Procedure 1-5 to deprotect 3-tert-butoxycarbonyl-7-chloro-6-(thiazol-2-ylethynyl)-2,3,4,5-tetrahydro-1H-benzo[d]azepine (140 mg, 0.36 mmol). Elute through SCX column to give the free base of the title compound (89 mg, 86%). MS (ES+) m/z: 289 (M+H)+. Use a method similar to the General Procedure 2-1 to give the title compound as a light yellow solid (125 mg, 86%). MS (ES+) m/z: 289 (M+H)+.

3-tert-Butoxycarbonyl-7-chloro-6-pyridazin-3-ylethynyl-2,3,4,5-tetrahydro-1H-benzo[d]azepine: Use a method similar to the General Procedure 8 to couple 2-chloro-pyridazine (98 mg, 0.86 mmol) with 3-tert-butoxycarbonyl-7-chloro-6-ethynyl-2,3,4,5-tetrahydro-1H-benzo[d]azepine (104 mg, 0.34 mmol). Purify by chromatography on silica gel eluting with isohexane/EtOAc (1:0 to 4:1 gradient over 30 min) to give 3-tert-butoxycarbonyl-7-chloro-6-pyridazin-2-ylethynyl-2,3,4,5-tetrahydro-1H-benzo[d]azepine (26 mg, 10%). MS (ES+) m/z: 384 (M+H)+.

7-Chloro-6-pyridazin-3-ylethynyl-2,3,4,5-tetrahydro-1H-benzo[d]azepine (L)-tartrate: Use a method similar to the General Procedure 1-5 to deprotect 3-tert-butoxycarbonyl-7-chloro-6-pyridazin-2-ylethynyl-2,3,4,5-tetrahydro-1H-benzo[d]azepine. Use a method similar to the General Procedure 2-6 to give the title compound as a solid (15 mg, 51%). MS (ES+) m/z: 284 (M+H)+.

EXAMPLE 534

7-Chloro-6-(3-fluoro-phenylethynyl)-2,3,4,5-tetrahydro-1H-benzo[d]azepine (L)-Tartrate

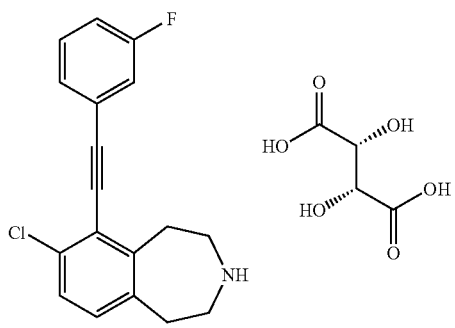

Use a method similar to the General Procedure 3 to couple 7-chloro-3-(2,2,2-trifluoroacetyl)-6-trifluoromethanesulfonyloxy-2,3,4,5-tetrahydro-1H-benzo[d]azepine (425 mg, 1 mmol) with (3-fluorophenyl)-ethyne (241 mg, 2 mmol). Purify by chromatography on silica gel eluting with isohexane/EtOAc (1:0 to 1:1 gradient over 40 min) to give 7-chloro-6-(3-fluoro-phenylethynyl)-3-(2,2,2-trifluoroacetyl)-2,3,4,5-tetrahydro-1H-benzo[d]azepine (247 mg, 64%). MS (ES+) m/z: 396 (M+H)+.

Use a method similar to the General Procedure 1-1 to deprotect 7-chloro-6-(3-fluoro-phenylethynyl)-3-(2,2,2-trifluoroacetyl)-2,3,4,5-tetrahydro-1H-benzo[d]azepine (68 mg, 0.18 mmol). Purify by SCX chromatography to give the free base of the title compound (46 mg, 85%). MS (ES+) m/z: 300 (M+H)+. Use a method similar to the General Procedure 2-6 to give the title compound as a white solid (61 mg, 94%). MS (ES+) m/z: 300 (M+H)+.

EXAMPLE 535

7-Chloro-6-(2-fluoro-phenylethynyl)-2,3,4,5-tetrahydro-1H-benzo[d]azepine Succinate

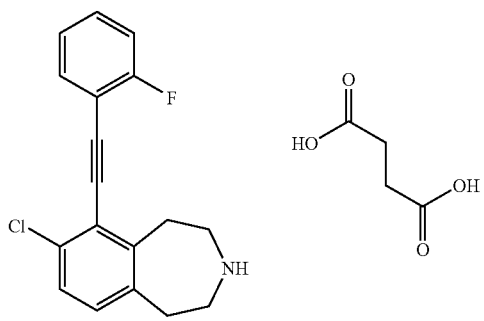

Use a method similar to the General Procedure 3 to couple 7-chloro-3-(2,2,2-trifluoroacetyl)-6-trifluoromethanesulfonyloxy-2,3,4,5-tetrahydro-1H-benzo[d]azepine (425 mg, 1 mmol) with (2-fluorophenyl)-ethyne (241 mg, 2 mmol). Purify by chromatography on silica gel eluting with isohexane/EtOAc (1:0 to 1:1 gradient over 40 min) to give 7-chloro-6-(2-fluoro-phenylethynyl)-3-(2,2,2-trifluoroacetyl)-2,3,4,5-tetrahydro-1H-benzo[d]azepine (262 mg, 68%). MS (ES+) m/z: 396 (M+H)+.

Use methods similar to the General Procedures 1-1 and 2-1 to give the title compound as a white solid (93%). MS (ES+) m/z: 300 (M+H)+.

EXAMPLE 536

6-[3-(3-tert-Butyl-2-oxo-imidazolidin-1-yl)-prop-1-ynyl]-7-chloro-2,3,4,5-tetrahydro-1H-benzo[d]azepine (L)-Tartrate

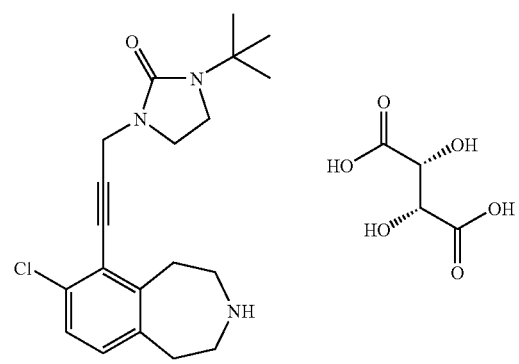

Use a method similar to the General Procedure 3 to couple 7-chloro-3-(2,2,2-trifluoroacetyl)-6-trifluoromethanesulfonyloxy-2,3,4,5-tetrahydro-1H-benzo[d]azepine (425 mg, 1 mmol) with 1-tert-butyl-3-prop-2-ynyl-imidazolidin-2-one (360 mg, 2 mmol). Purify by chromatography on silica gel eluting with isohexane/EtOAc (19:1 to 3:2 gradient) to give 6-[3-(3-tert-butyl-2-oxo-imidazolidin-1-yl)-prop-1-ynyl]-7-chloro-3-(2,2,2-trifluoroacetyl)-2,3,4,5-tetrahydro-1H-benzo[d]azepine (380 mg, 83%) as a yellow oil. LC-MS (ES+) m/z: 478 (M+Na)+, 456 (M+H)+, $t_R$=4.43 min.

Use a method similar to the General Procedure 1-1, but adding water (10 mL) to the ammonia/methanol solution (20 mL, 7N solution), to deprotect 6-[3-(3-tert-butyl-2-oxo-imidazolidin-1-yl)-prop-1-ynyl]-7-chloro-3-(2,2,2-trifluoroacetyl)-2,3,4,5-tetrahydro-1H-benzo[d]azepine (329 mg, 0.72 mmol) and give the free base of the title compound (217 mg, 84%). Use a method similar to the General Procedure 2-6 to give the title compound as a solid (211 mg, 58% overall yield). LC-MS (ES+) m/z: 360 (M+H)+, $t_R$=4.54 min.

Preparation 253

2,2-Difluoro-2-phenyl-ethylamine

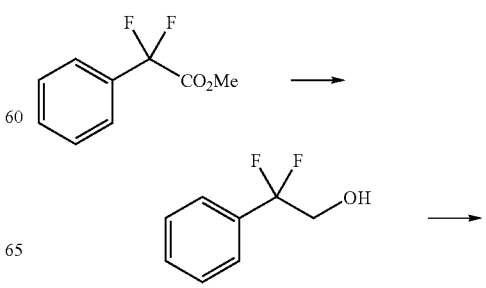

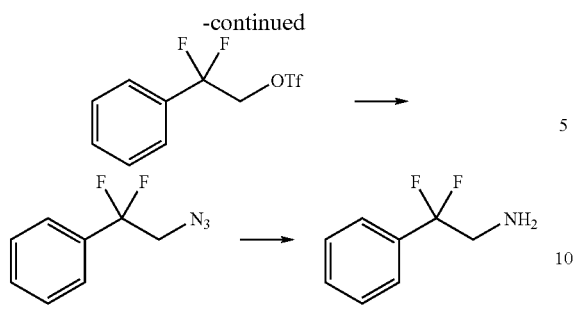

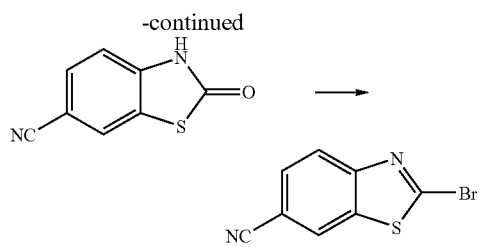

2,2-Difluoro-2-phenyl-ethanol: Add lithium aluminum hydride (5.18 mL, 5.18 mmol, 1M solution in THF) to a solution of methyl difluorophenylethanoate (0.964 g, 5.18 mmol, prepared by following the procedure described in *J. Org. Chem.* 1995, 60, 5174-5179) in anhydrous THF (10 mL) at 0° C. Stir the mixture at room temperature for 45 min. Cool to 0° C. and quench with EtOAc and then water. Separate the organic phase and extract twice the aqueous phase with EtOAc. Dry the combined organic extracts over Na₂SO₄, filter and concentrate in vacuo to provide the desired intermediate (0.8 g, 98%) that was used without any further purification.

2,2-Difluoro-2-phenyl-ethyl trifluoromethanesulfonate: Add triflic anhydride (1.28 mL, 2.14 g) dropwise to a stirred solution of 2,2-difluoro-2-phenyl-ethanol (0.8 g, 5.06 mmol) and 2,6-di-tert-butyl-4-methylpyridine (1.556 g, 7.59 mmol) in anhydrous dichloromethane (25 mL) at −78° C. Stir the reaction overnight while the temperature warms up. Dilute the mixture with pentane and filter the precipitate over Celite®b. Concentrate the filtrate in vacuo and purify the crude mixture by chromatography on silica gel eluting with hexane and hexane/EtOAc (95:5) to provide the title compound (946 mg, 64%).

(2-Azido-1,1-difluoro-ethyl)-benzene: Heat at 60° C. a solution of 2,2-difluoro-2-phenyl-ethyl trifluoromethanesulfonate (759 mg, 2.617 mmol) and sodium azide (357 mg, 5.496 mmol) in anhydrous DMF (10 mL) under nitrogen for 3 h. Cool the reaction mixture to room temperature. Dilute with water and extract the aqueous phase twice with diethyl ether. Wash the combined organic extracts twice with ice-cold water, dry over Na₂SO₄, filter and concentrate in vacuo to provide the desired intermediate as an oil (475 mg, 99%) that was used without any further purification.

2,2-Difluoro-2-phenyl-ethylamine: Dissolve (2-azido-1,1-difluoro-ethyl)-benzene (475 mg, 2.59 mmol) in EtOAc (30 mL). Add 10% Pd/C and submit the mixture to hydrogenation under atmospheric pressure (balloon) for 1 h. Filter the catalyst through Celite® and concentrate the filtrate in vacuo to provide the title compound as an oil (400 mg, 98%) that was used without any further purification.

Preparation 254

2-Bromo-benzothiazole-6-carbonitrile

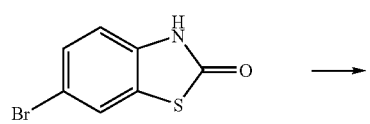

2-Oxo-2,3-dihydro-benzothiazole-6-carbonitrile: Combine 6-bromobenzothiazolinone (2 g, 8.69 mmol), copper cyanide (1.3 g, 1.48 mmol), anhydrous DMF (5 mL) and heat at reflux for 15 h. Add water (20 mL) and sodium cyanide (1.4 g, 27.7 mmol) at 100° C. Cool the reaction mixture to room temperature and stir for 2 h. Extract the reaction mixture with EtOAc (5×30 mL) at 70° C. Combine the organic layers, wash with water (3×40 mL) and dry over anhydrous Na₂SO₄. Concentrate in vacuo to obtain the desired intermediate as a yellow solid (2 g, 87%). GC-MS m/z: 176 (M⁺).

2-Bromo-benzothiazole-6-carbonitrile: Combine 2-oxo-2,3-dihydro-benzothiazole-6-carbonitrile (1.1 g, 6.24 mmol), tetrabutylammonium bromide (3 g, 9.36 mmol), phosphorus pentoxide (2.7 g, 18.7 mmol), anhydrous toluene (40 mL) and heat at reflux for 2.5 h. Cool the reaction mixture to room temperature. Decant the toluene layer and wash with saturated aqueous NaHCO₃ (3×10 mL). Concentrate the organic phase in vacuo and purify the residue by chromatography on silica gel eluting with hexane/EtOAc (1:0 to 4:1 gradient) to obtain the title compound as a colorless oil (0.9 g, 61%). GC-MS m/z: 239 (M⁺).

Preparation 255

6-Aminomethyl-2-cyclohexylmethyl-benzothiazole

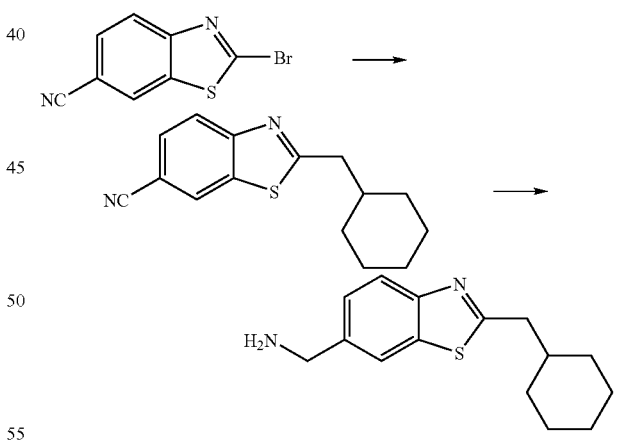

2-Cyclohexylmethyl-benzothiazole-6-carbonitrile: Place 2-bromo-benzothiazole-6-carbonitrile (0.2 g, 0.96 mmol), anhydrous THF (3 mL), 1-methyl-2-pyrrolidinone (3 mL), tetrabutylammonium iodide (1.1 g, 2.89 mmol), tris(dibenzylideneacetone)dipalladium(0) (18 mg, 0.09 mmol) and [1,1'-bis(diphenylphosphino)ferrocine]dichloropalladium (II) (11 mg, 0.09 mmol) in a flask. Add 0.5M cyclohexylmethylzinc bromide in THF (3.8 mL, 1.92 mmol) to the mixture, degas 3 times by partially evacuating the atmosphere and flushing with nitrogen and stir the reaction mixture at 80° C. for 2 h. Cool the reaction mixture to room temperature, dilute with EtOAc (10 mL) and wash with brine (10 mL). Dry the organic layer over anhydrous Na$_2$SO$_4$, filter and concentrate in vacuo. Purity the residue by chromatography on silica gel eluting sequentially with hexane/EtOAc (1:0 to 4:1 gradient) to obtain the desired intermediate as a yellow solid (140 mg, 57%). GC-MS m/z: 256 (M$^+$).

6-Aminomethyl-2-cyclohexylmethyl-benzothiazole: Dissolve 2-cyclohexylmethyl-benzothiazole-6-carbonitrile (0.2 g, 0.55 mmol) in anhydrous THF (2 mL) and add slowly 1M lithium aluminum hydride in THF (0.82 mL, 0.82 mmol) at room temperature. Stir the reaction mixture at room temperature for 0.5 h. Quench the reaction mixture with water until a granular precipitate starts to form and filter through a pad of Celite®. Evaporate the solvent and purify the residue by SCX chromatography to obtain the title compound as a yellow oil (0.1 g, 92%). MS (ES+) m/z: 260 (M+H)$^+$.

Preparation 256

6-Aminomethyl-2-phenyl-benzothiazole

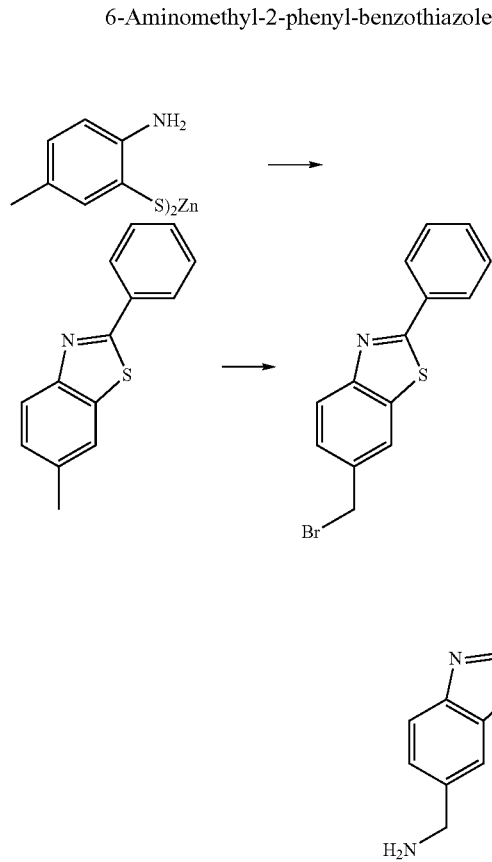

6-Methyl-2-phenyl-benzothiazole: Heat at reflux a mixture of 2-amino-5-methyl-benzenethiol zinc salt (13.5 g, 24.9 mmol, prepared by following the procedure described in *Helv. Chim. Acta* 1974, 57, 2664) and ethyl benzimidate hydrochloride (9.23 g, 49.7 mmol) in methanol (240 mL) for 9 h. Filter the mixture, evaporate the filtrate and purify the residue by chromatography on silica gel eluting with hexane/EtOAc (100:0 to 85:15 gradient) to obtain the desired intermediate (5.7 g, 51%). MS (EI) m/z: 225 (M$^+$).

6-Bromomethyl-2-phenyl-benzothiazole: Heat 5-methyl-2-phenyl-benzothiazole (5.7 g, 25.3 mmol) and NBS (4.73 g, 26.6 mmol) in carbon tetrachloride (140 mL) at 80° C. for 3 h. Cool the mixture, double the volume with dichloromethane, filter and concentrate in vacuo. Purify the crude mixture by chromatography on silica gel eluting with hexane/EtOAc (1:0 to 7:3 gradient) to obtain the desired intermediate (3.1 g, 40%). MS (FI) m/z: 303, 305 (M$^+$).

6-Aminomethyl-2-phenyl-benzothiazole: Add 6-bromomethyl-2-phenyl-benzothiazole (2 g, 6.57 mmol) as a suspension in methanol (100 mL) to 7M ammonia in methanol (400 mL) at 0° C. over 10 min and then stir for 3 h at room temperature. Concentrate in vacuo and purify the crude mixture by chromatography on silica gel eluting with dichloromethane/methanol (1:0 to 3:1) to obtain the title compound (1.2 g, 76%). MS (ES+) m/z: 241 (M+H$^+$).

Preparation 257

5-Aminomethyl-2-isobutyl-benzothiazole

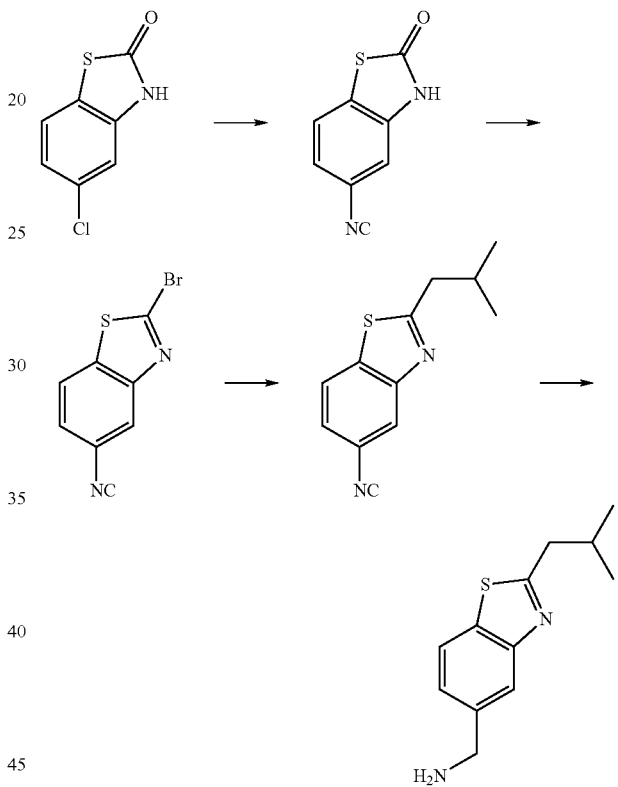

2-Oxo-2,3-dihydro-benzothiazole-5-carbonitrile: Heat a mixture of 5-chloro-3H-benzothiazol-2-one (9.3 g, 50 mmol), nickel(II) bromide (10.9 g, 50 mmol) and sodium cyanide (4.91 g, 100 mmol) in 1-methyl-pyrrolidinone (100 mL) in a microwave reactor 5 to 200° C. over 15 min and hold 1 h. Filter the cooled mixture through a glass frit, add diethyl ether and brine and filter again. Wash the organic phase with brine three times and concentrate in vacuo. Pass the residue through a plug of silica gel eluting with hexane/EtOAc (2:1) and then dichloromethane/methanol (9:1) to obtain the desired intermediate (3.2 g, 36%). MS (ES+) m/z: 177 (M+H)$^+$.

2-Bromo-benzothiazole-5-carbonitrile: Heat 2-oxo-2,3-dihydro-benzothiazole-5-carbonitrile (3.2 g, 18.2 mmol) in toluene (120 mL) with tetrabutylammonium bromide (8.78 g, 27.2 mmol) and phosphorus pentoxide (7.73 g, 54.5 mmol) for 3 h at reflux. Cool the mixture, decant the solution from the reaction residue and partition between diethyl ether and brine. Add water and dichloromethane to the reaction residue and reflux for 20 min. Wash the dichloromethane layer with saturated aqueous NaHCO₃ and brine, and combine with the ether washing. Dry the organic mixture over Na₂SO₄ and concentrate in vacuo. Purify the crude mixture by chromatography on silica gel eluting with hexane/EtOAc (1:0 to 3:7 gradient) to give the desired intermediate (0.85 g, 20%). MS (EI) m/z: 238, 240 (M⁺).

2-Isobuty-benzothiazole-5-carbonitrile: Heat 2-bromo-benzothiazole-5-carbonitrile (0.3 g, 1.26 mmol) in 1-methyl-pyrrolidinone (4.2 mL) with 2-methylpropylzinc bromide (5 mL, 2.5 mmol, 0.5M solution in THF), N-methylimidazole (0.15 g, 1.88 mmol) and [1,1'-bis(diphenylphosphino)ferrocene]dichloropalladium(II) complex with dichloromethane (1:1) (20.5 mg, 0.025 mmol) at 80° C. for 3 h. Cool the mixture and partition between diethyl ether and brine. Dry the organic layer over Na₂SO₄ and concentrate in vacuo. Purify the crude mixture by chromatography on silica gel eluting with hexane/EtOAc (1:0 to 1:1 gradient) to give the desired intermediate (113 mg, 42%). MS (EI) m/z: 216 (M⁺).

5-Aminomethyl-2-isobutyl-benzothiazole: Add lithium aluminum hydride (0.78 mL, 0.78 mmol, 1M solution in THF) to 2-isobutyl-benzothiazole-5-carbonitrile (113 mg, 0.52 mmol) in THF (5 mL) and stir for 4 h at room temperature. Add water (0.27 mL), 2N sodium hydroxide (0.27 mL) and water (0.37 mL). Filter the precipitate and wash the filtrate with brine. Dry over Na₂SO₄ and concentrate in vacuo. Purify the crude mixture by chromatography on silica gel eluting with hexane/EtOAc (1:1) and then 1M ammonia in methanol/dichloromethane (1:9). Purify the polar fraction by SCX chromatography to give the title compound (63 mg, 55%). MS (ES+) m/z: 221 (M+HE).

Preparation 258

6-Aminomethyl-benzo[1,2,3]thiadiazole

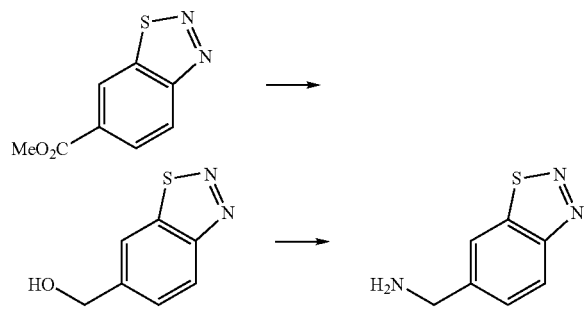

6-Hydroxymethyl-benzo[1,2,3]thiadiazole: Add sodium borohydride (1.35 g, 36 mmol) in five portions over 4 h to a solution of benzo[1,2,3]thiadiazole-6-carboxylic acid methyl ester (0.35 g, 1.8 mmol, prepared by following the procedure described in *J. Heterocyclic Chem.* 1972, 1149) in methanol (18 mL) at 0° C. Add acetone to quench and evaporate the mixture onto silica gel. Purify the residue by chromatography on silica gel eluting with hexane/EtOAc (1:0 to 2:3 gradient) to give the desired intermediate (133 mg, 45%). MS (GCMS) m/z: 166 M⁺.

6-Aminomethyl-benzo[1,2,3]thiadiazole: Stir 6-hydroxymethyl-benzo[1,2,3]thiadiazole (133 mg, 0.8 mmol) in thionylchloride (5 mL) for 3 h at room temperature. Evaporate the mixture then add 7M ammonia in methanol (10 mL) and stir at room temperature in a sealed tube for 48 h. Evaporate the mixture and purify the residue by SCX chromatography to give the title compound (115 mg, 87%). MS (ES+) m/z: 166 (M+H)⁺.

Preparation 259

6-Aminomethyl-3-phenyl-benzothiophene

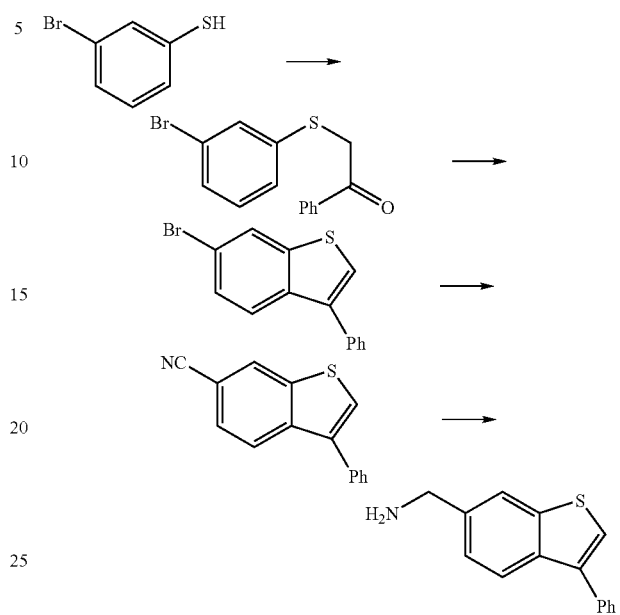

2-(3-Bromo-phenylthio)-1-phenyl-ethanone: Add potassium hydroxide (4.89 g, 87.3 mmol) and 2-bromoacetophenone (15.8 g, 79.3 mmol) to a solution of 3-bromobenzenethiol (15 g, 79.3 mmol) in ethanol (200 mL, 70% in water) at 0° C. After stirring 16 h, add water to precipitate a yellow solid. Filter to obtain the desired intermediate (24.6 g, 100%).

6-Bromo-3-phenylbenzothiophene: Heat 2-(3-bromo-phenylthio)-1-phenyl-ethanone (4 g, 13 mmol) in polyphosphoric acid (4 g) at 80° C. for 4 h. Add EtOAc and water to the mixture and wash with saturated aqueous NaHCO₃ and brine. Dry the organic layer over Na₂SO₄, filter and concentrate in vacuo. Slurry the residue in hexane and purify by chromatography on silica gel eluting with hexane to give the desired intermediate that is used without further purification (2.7 g, 72%). MS (GCMS) m/z: 289 M⁺.

6-Cyano-3-phenylbenzothiophene: Combine 6-bromo-3-phenylbenzothiophene (0.5 g, 1.73 mmol) and copper cyanide (0.56 g, 6.23 mmol) and reflux 3 h in 1-methyl-2-pyrrolidinone (1.73 mL). Add ferric chloride (2.11 g, 7.79 mmol) in concentrated HCl (1.73 mL) and stir 1.5 h. Cool the mixture and partition between diethyl ether and brine. Dry the organic layer over Na₂SO₄, filter and evaporate onto silica gel. Purify the residue by chromatography on silica gel eluting with hexane/EtOAc (1:0 to 3:2 gradient) to give the desired intermediate that is used without further-purification (0.27 g, 67%). MS (GCMS) m/z: 235 M⁺.

6-Aminomethyl-3-phenyl-benzothiophene: Dissolve 6-cyano-3-phenylbenzothiophene (0.27 g, 1.16 mmol) in anhydrous THF (6 mL) and add lithium aluminum hydride (3.45 mL, 1M solution in THF) at 0° C. After 2 h, add water (0.86 mL), 2N aqueous NaOH (0.86 mL) and water (1.24 mL). Filter off the solids and evaporate the residue. Purify by prep HPLC (Zorbax SB-Phenyl column 21.2×250 mm, 5% to 50% acetonitrile in 0.1% TFA-water solution) and obtain the free base by SCX chromatography to give the title compound that is used without further purification (187 mg, 68%). MS (ES+) m/z: 223 (M-NH₂)⁺.

Preparation 260

4-(Difluoro-phenyl-methyl)-benzylamine

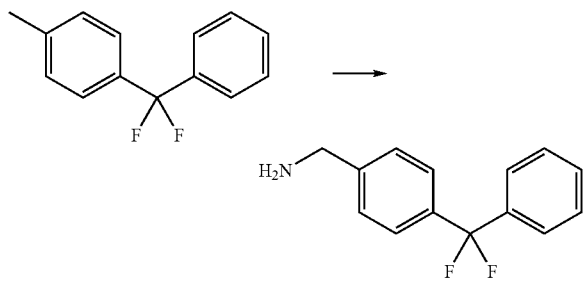

Combine 4-(difluoro-phenyl-methyl)-toluene (0.29 g, 1.35 mmol, prepared by following the procedure described in *Tetrahedron* 1996, 52, 9), NBS (0.26 g, 1.48 mmol), and AIBN (6 mg, 0.03 mmol) in carbon tetrachloride (8 mL) and heat at 80° C. for 16 h. Evaporate the mixture and pass the residue through a pad of silica gel washing with hexane and evaporate the filtrate. Dissolve the residue in methanol and add dropwise to 7M ammonia in methanol (100 mL) at 0° C. After 4.5 h, evaporate the mixture and isolate the amine by SCX chromatography (0.1 g, 32%). MS (ES+) m/z: 234 (M+H)$^+$.

Preparation 261

4-(3,3-Dimethyl-butyryl)-benzylamine

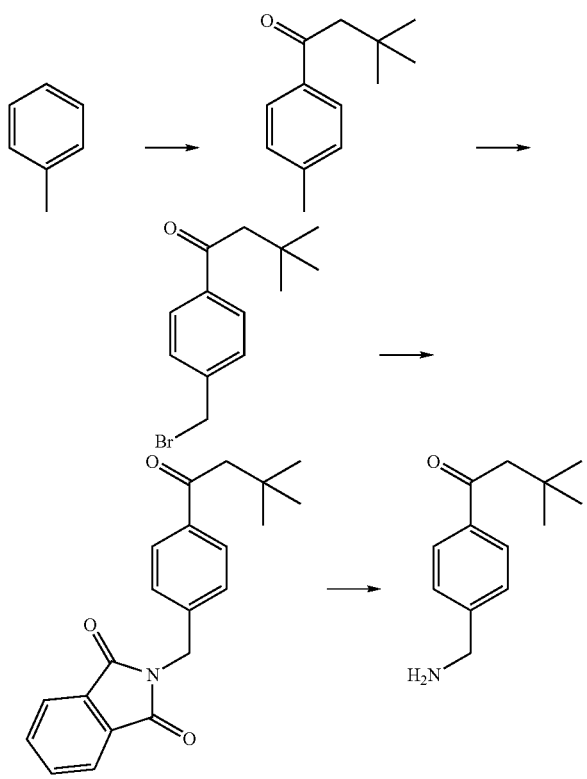

3,3,4'-Trimethylbutyrophenone: Add slowly tert-butylacetyl chloride (2 g, 14.858 mmol) to an ice-cold stirred solution of aluminum trichloride (2.972 g, 22.28 mmol) in anhydrous toluene (40 mL). Stir the reaction mixture at ambient temperature overnight. Add slowly ice-cold water and extract the mixture twice with EtOAc. Dry the combined organic extracts over Na$_2$SO$_4$, filter and concentrate in vacuo to give the desired intermediate (2.82 g, 100%) that was used without any further purification. GC-MS m/z: 190 (M$^+$).

4-(3,3-Dimethyl-butyryl)-benzyl bromide: Heat a mixture of 3,3,4'-trimethylbutyrophenone (2 g, 10.52 mmol), NBS (2.061 g, 11.57 mmol), and AIBN (43 mg, 0.263 mmol) in carbon tetrachloride (60 mL) for 14 h at reflux. Cool the reaction, mixture to ambient temperature and wash sequentially with water, 1M aqueous HCl, 5% aqueous NaHCO$_3$ and brine. Concentrate the organic layer in vacuo to provide the desired intermediate as oil (2.54 g, 90%) that was used without any further purification.

2-[4-(3,3-Dimethyl-butyryl)-benzyl]-isoindole-1,3-dione: Add 4-(3,3-dimethyl-butyryl)-benzyl bromide (1 g, 3.731 mmol) to a stirred suspension of potassium phthalimide (0.705 g, 3.805 mmol) in anhydrous DMF (20 mL). Stir the mixture overnight at room temperature. Dilute with EtOAc and wash twice with ice-cold water. Dry the organic layer over Na$_2$SO$_4$, filter and concentrate in vacuo. Purify the crude mixture by chromatography on silica gel eluting sequentially with hexane and hexane/EtOAc (19:1, 4:1) to provide the desired intermediate as oil (1.24 g, 100%).

4-(3,3-Dimethyl-butyryl)-benzylamine: Add hydrazine hydrate (0.189 mL, 3.913 mmol) to a stirred suspension of 2-[4-(3,3-dimethyl-butyryl)-benzyl]-isoindole-1,3-dione (875 mg, 2.609 mmol) in methanol (15 mL). Heat the mixture to reflux overnight. Cool the mixture to room temperature and concentrate in vacuo. Partition the residue between EtOAc and 5N aqueous HCl and wash the acidic aqueous phase again with 5N aqueous HCl. Basify with 5N aqueous NaOH to pH 12. Extract the basic aqueous solution three times with chloroform. Dry the combined organic extracts over Na$_2$SO$_4$, filter and concentrate in vacuo to give the title compound as a yellow oil (411 mg, 77%) that was used without any further purification.

Preparation 262

4-(3,3-Dimethyl-butyryl)-3-fluoro-benzylamine

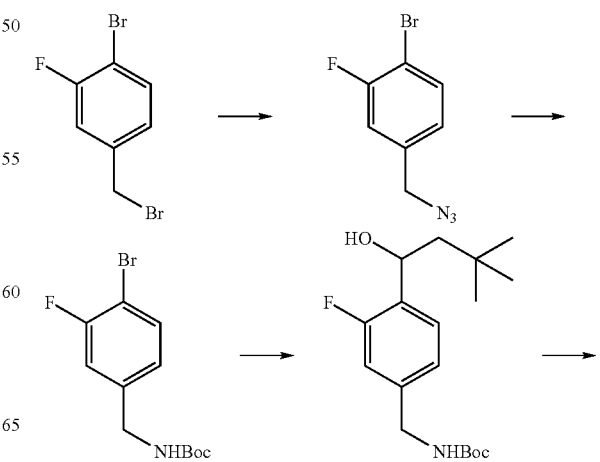

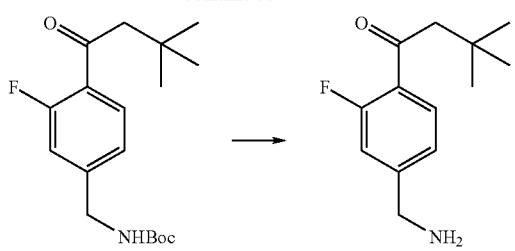

4-Azidomethyl-1-bromo-2-fluoro-benzene: Add sodium azide (2.912 g, 44.8 mmol) to a solution of 4-bromo-3-fluorobenzyl bromide (6 g, 22.4 mmol) in anhydrous DM (127 mL) at room temperature under nitrogen. Heat the mixture at 90° C. for 1 h. Concentrate in vacuo and partition the residue between water and EtOAc. Extract the aqueous phase twice with EtOAc. Wash the combined organics extracts with iced-water. Dry the organic layer over $Na_2SO_4$, filter and concentrate in vacuo to obtain the desired intermediate as a solid (4.92 g, 96%).

4-Bromo-N-(tert-butoxycarbonyl)-3-fluoro-benzylamine: Add 10% Pd/C (492 mg) and di-tert-butyl-dicarbonate (4.668 g, 21.4 mmol) to a solution of 4-azidomethyl-1-bromo-2-fluoro-benzene (4.92 g, 21.4 mmol) in ethanol (90 mL) and submit the mixture to hydrogenation at atmospheric pressure overnight. Filter the reaction mixture over Celite® and concentrate in vacuo. Purify by chromatography on silica gel eluting with hexane/EtOAc (85:15) to obtain the desired intermediate as a solid (1.55 g, 25%).

N-(tert-Butoxycarbonyl)-3-fluoro-4-(1-hydroxy-3,3-dimethyl-butyl)-benzylamine: Add butyllithium (7.3 mL, 11.7 mmol) to a solution of 4-bromo-N-(tert-butoxycarbonyl)-3-fluoro-benzylamine (1.55 g, 5.1 mmol) in diethyl ether (54 mL) at −78° C. under nitrogen and stir for 30 min. Add 3,3-dimethylbutyraldehyde (562 mg, 0.7 mL, 5.6 mmol), stir for 30 min at −78° C. and then warm to room temperature. Add water and extract twice the aqueous phase with EtOAc. Dry the combined organic extracts over $Na_2SO_4$, filter and concentrate in vacuo. Purify by chromatography on silica gel eluting with hexane/EtOAc (85:15) to obtain the desired intermediate as a yellow oil (394 mg, 24%).

N-(tert-Butoxycarbonyl)-4-(3,3-dimethyl-butyryl)-3-fluoro-benzylamine: Add manganese dioxide (1.132 g, 13 mmol) to a solution of N-(tert-butoxycarbonyl)-3-fluoro-4-(1-hydroxy-3,3-dimethyl-butyl)-benzylamine (283 mg, 0.87 mmol) in anhydrous 1,4-dioxane (11.5 mL) at room temperature. Heat the reaction mixture at 70° C. overnight. Filter the reaction mixture over Celite® and concentrate in vacuo. Purify by chromatography on silica gel eluting with hexane/EtOAc (4:1) to obtain the desired intermediate as an oil (216 mg, 77%).

4-(3,3-Dimethyl-butyryl)-3-fluoro-benzylamine: Add 4N hydrogen chloride in dioxane (2.7 mL, 10.8 mmol) to a solution of N-(tert-butoxycarbonyl)-4-(3,3-dimethyl-butyryl)-3-fluoro-benzylamine (296 mg, 0.92 mmol) in dichloromethane (11 mL) and stir for 4 h. Concentrate in vacuo and wash the solid obtained with diethyl ether. Suspend the solid in saturated aqueous $NaHCO_3$ and stir for 30 min. Extract twice with dichloromethane. Dry the combined organic extracts over $Na_2SO_4$, filter and concentrate in vacuo to obtain the title compound as an oil (175 mg, 82%).

Preparation 263

4-(3,3-Dimethyl-butyryl)-2-fluoro-benzylamine

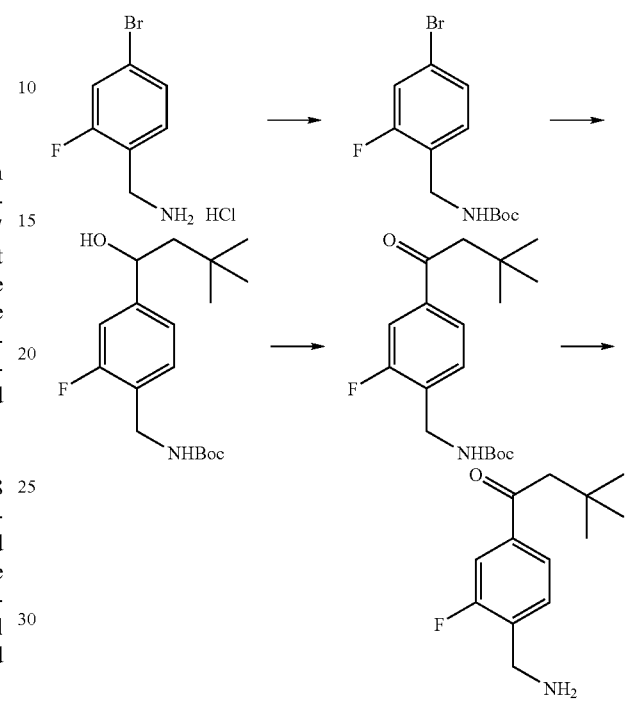

4-Bromo-N-(tert-butoxycarbonyl)-2-fluoro-benzylamine: Add triethylamine (6.334 g, 8.8 mL, 52.6 mmol) and di-tert-butyl-dicarbonate (4.54 g, 20.8 mmol) to a solution of 4-bromo-2-fluoro-benzylamine hydrochloride (5 g, 20.8 mmol) in dichloromethane (254 mL) and stir overnight. Wash the organic layer with water and then extract back the aqueous phase with dichloromethane. Dry the combined organic extracts over $Na_2SO_4$, filter and concentrate in vacuo to obtain the desired intermediate as a white solid (6.11 g, 97%).

N-(tert-Butoxycarbonyl)-2-fluoro-4-(1-hydroxy-3,3-dimethyl-butyl)-benzylamine: Add butyllithium (14.2 mL, 22.7 mmol) to a solution of 4-bromo-N-(tert-butoxycarbonyl)-2-fluoro-benzylamine (3 g, 9.9 mmol) in diethyl ether (105 mL) at −78° C. under nitrogen and stir for 30 min. Add 3,3-dimethylbutyraldehyde (1.086 g, 1.4 mL, 10.8 mmol), stir for 30 min at −78° C. and then warm to room temperature. Add water and extract twice the aqueous phase with EtOAc. Dry the combined organic extracts over $Na_2SO_4$, filter and concentrate in vacuo. Purify by chromatography on silica gel eluting with hexane/EtOAc (85:15) to obtain the desired intermediate as a yellow oil (1.179 g, 37%).

N-(tert-Butoxycarbonyl)-4-(3,3-dimethyl-butyryl)-2-fluoro-benzylamine: Add manganese dioxide (4.4 g, 50.6 mmol) to a solution of N-(tert-butoxycarbonyl)-2-fluoro-4-(1-hydroxy-3,3-dimethyl-butyl)-benzylamine (1.1 g, 3.38 mmol) in anhydrous 1,4-dioxane (45 mL) at room temperature. Heat the reaction mixture at 70° C. overnight. Filter the reaction mixture over Celite® and concentrate in vacuo. Purify by chromatography on silica gel eluting with hexane/EtOAc (9:1) to obtain the desired intermediate as an oil (980 mg, 90%).

4-(3,3-Dimethyl-butyryl)-2-fluoro-benzylamine: Add 4N hydrogen chloride in dioxane (5.5 mL, 22 mmol) to a solution of N-(tert-butoxycarbonyl)-4-(3,3-dimethyl-butyryl)-2-fluoro-benzylamine (600 mg, 1.85 mmol) in dichloromethane (22 mL) and stir for 6.5 h. Concentrate in vacuo and wash the solid obtained with diethyl ether. Suspend the solid into saturated aqueous NaHCO$_3$ and stir for 30 min. Extract the aqueous phase twice with EtOAc. Dry the combined organic extracts over Na$_2$SO$_4$, filter and concentrate in vacuo to obtain the title compound as an oil (420 mg, 99%).

Preparation 264

3-Chloro-4-(3,3,4-dimethyl-butyryl)-benzylamine

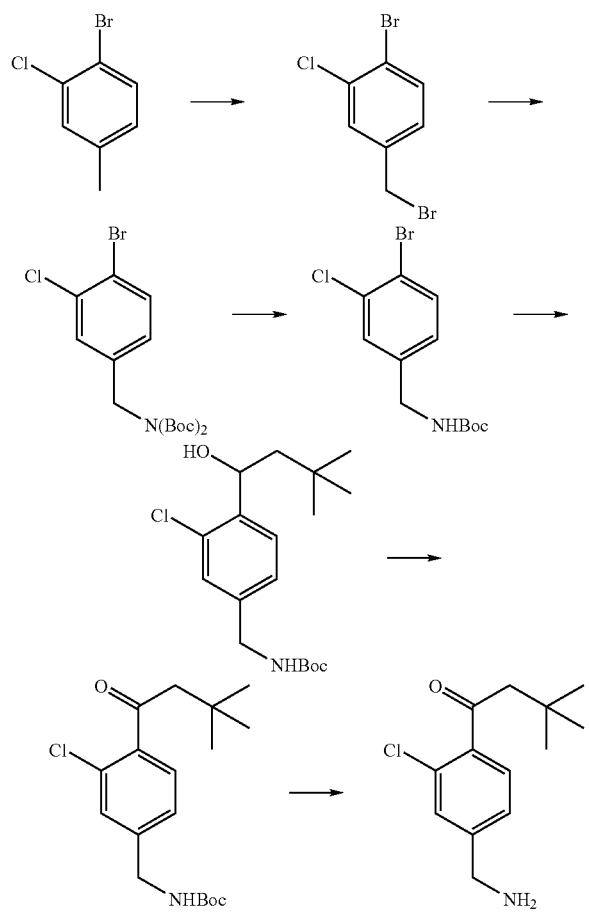

4-Bromo-3-chloro-benzyl bromide: Add NBS (5.266 g, 23.9 mmol) and benzoyl peroxide (49 mg, 0.2 mmol) to a solution of 4-bromo-3-chlorotoluene (4.925 g, 23.9 mmol) in carbon tetrachloride (49 mL) and heat overnight at 90° C. Cool to 0° C. and filter the mixture. Concentrate the filtrate in vacuo to obtain the desired intermediate as a yellow oil (5.807 g, 85%).

4-Bromo-3-chloro-N-(di-tert-butoxycarbonyl)-benzylamine: Add sodium hydride (382 mg, 15.9 mmol) to a solution of di-tert-butyl-iminodicarboxylate (2.533 g, 11.7 mmol) in anhydrous DMF (15 mL) at room temperature under nitrogen and stir for 15 min. Then add a solution of 4-bromo-3-chloro-benzyl bromide (3 g, 10.6 mmol) in anhydrous DMF (5 mL) and stir for 1 h. Add water and extract the aqueous phase twice with EtOAc. Wash the combined organic extracts with iced-water. Dry the organic layer over Na$_2$SO$_4$, filter and concentrate in vacuo. Purify by chromatography on silica gel eluting with hexane/EtOAc (4:1) to obtain the desired intermediate (2.783 g, 62%).

4-Bromo-3-chloro-N-(tert-butoxycarbonyl)-benzylamine: Add a solution of sodium hydroxide (264 mg, 6.6 mmol) in methanol (23.5 mL) to a solution of 4-bromo-3-chloro-N-(di-tert-butoxycarbonyl)-benzylamine (2.783 g, 6.6 mmol) in THF (11.7 mL) and stir overnight Concentrate in vacuo. Add water and filter the precipitate formed to obtain the desired intermediate as a white solid (1.823 g, 86%).

N-(tert-Butoxycarbonyl-3-chloro-4-(1-hydroxy-3,3-dimethyl-butyl)-benzylamine: Add butyllithium (8-2 mL, 13.1 mmol) to a solution of 4-bromo-3-chloro-N-(tert-butoxycarbonyl)-benzylamine (1.823 g, 5.7 mmol) in diethyl ether (46 mL) at −78° C. under nitrogen and stir for 30 min. Add 3,3-dimethylbutyraldehyde (1.427 g, 1.7 mL, 14.3 mmol), stir for 30 min at −78° C. and then warm to room temperature. Add water and extract twice the aqueous phase with EtOAc. Dry the combined organic extracts over Na$_2$SO$_4$, filter and concentrate in vacuo. Purify by chromatography on silica gel eluting with hexane/EtOAc (4:1) to obtain the desired intermediate as a yellow oil (274 mg, 14%).

N-(tert-Butoxycarbonyl)-3-chloro-4-(3,3-dimethyl-butyryl)-benzylamine: Add manganese dioxide (1.096 g, 12.6 mmol) to a solution of N-(tert-butoxycarbonyl)-3-chloro-4-(1-hydroxy-3,3-dimethyl-butyl)-benzylamine (274 mg, 0.8 mmol) in anhydrous 1,4-dioxane (11.5 mL) at room temperature. Heat the mixture at 70° C. overnight. Filter the reaction mixture over Celite® and concentrate in vacuo. Purify by chromatography on silica gel eluting with hexane/EtOAc (4:1) to obtain the desired intermediate as a yellow oil (175 mg, 64%).

3-Chloro-4-(3,3-dimethyl-butyryl)-benzylamine: Add 4N hydrogen chloride in dioxane (0.9 mL, 3.6 mmol) to a solution of N-(tert-butoxycarbonyl)-3-chloro-4-(3,3-dimethyl-butyryl)-benzylamine (100 mg, 0.3 mmol) in dichloromethane (6 mL) and stir overnight. Concentrate in vacuo and wash the solid obtained with diethyl ether. Suspend the solid into saturated aqueous NaHCO$_3$ and stir for 30 min. Extract twice with dichloromethane. Dry the combined organic extracts over Na$_2$SO$_4$, filter and concentrate in vacuo to obtain the title compound as a yellow oil (66 mg, 92%).

Preparation 265

2-Chloro-4-(3,3-dimethyl-butyryl)-benzylamine

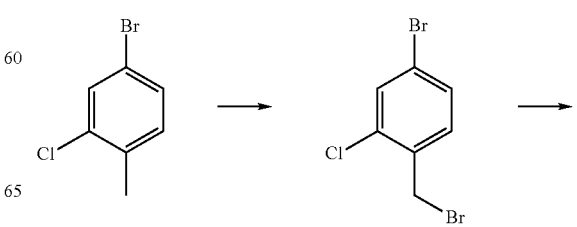

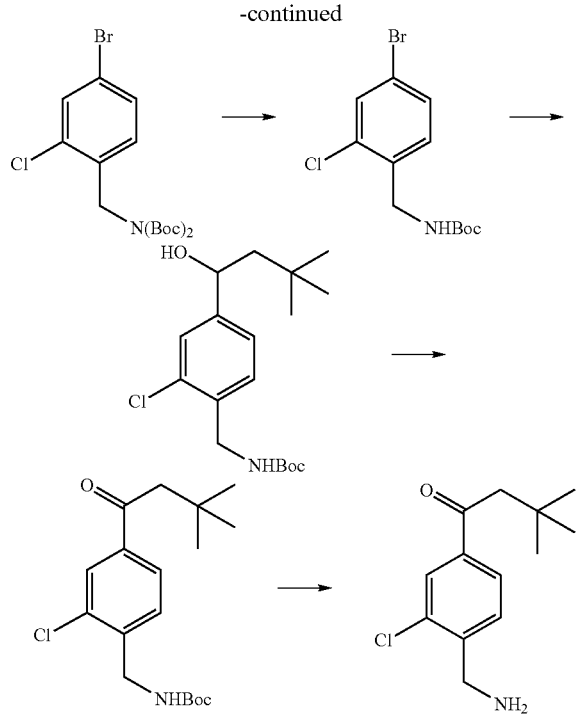

4-Bromo-2-chloro-benzyl bromide: Add NBS (13.171 g, 74 mmol) and benzoyl peroxide (152 mg, 0.63 mmol) to a solution of 4-bromo-2-chlorotoluene (15.2 g, 74 mmol) in carbon tetrachloride (152 mL) and stir for 6 days at 90° C. Cool to 0° C., filter the mixture and concentrate the filtrate in vacuo. Purify by chromatography on silica gel eluting with hexane/EtOAc (99:1) to obtain the desired intermediate as a yellow oil (12.7 g, 61%).

4-Bromo-2-chloro-N-di-(tert-butoxycarbonyl)-benzylamine: Add sodium hydride (382 mg, 15.9 mmol) to a solution of di-tert-butyl-iminodicarboxylate (2.533 g, 11.7 mmol) in anhydrous DMF (15 mL) at room temperature under nitrogen and stir for 15 min. Then add a solution of 4-bromo-2-chloro-benzyl bromide (3 g, 10.6 mmol) in anhydrous DMF (5 mL) and stir for 1 h. Add water and extract the aqueous phase twice with EtOAc. Wash the combined organic extracts with iced-water. Dry the organic layer over $Na_2SO_4$, filter and concentrate in vacuo. Purify by chromatography on silica gel eluting sequentially with hexane and hexane/EtOAc (4:1) to obtain the desired intermediate (4.2 g, 94%).

4-Bromo-N-(tert-butoxycarbonyl)-2-chloro-benzylamine: Add a solution of sodium hydroxide (399 mg, 9.98 mmol) in methanol (35.5 mL) to a solution of 4-bromo-2-chloro-N-di-(tert-butoxycarbonyl)-benzylamine (4.2 g, 9.98 mmol) in THF (17.7 mL) and stir overnight Concentrate in vacuo and partition the residue between water and EtOAc. Extract the aqueous phase twice with EtOAc. Dry the combined organic extracts over $Na_2SO_4$, filter and concentrate in vacuo. Purify by chromatography on silica gel eluting with hexane/EtOAc (4:1) to obtain the desired intermediate (2.625 g, 82%).

N-(tert-Butoxycarbonyl)-2-chloro-4-(1-hydroxy-3,3-dimethyl-butyl)-benzylamine: Add butyllithium (11.7 mL, 18.65 mmol) to a solution of 4-bromo-N-(tert-butoxycarbonyl)-2-chloro-benzylamine (2.601 g, 8.11 mmol) in diethyl ether (86 mL) at −78° C. under nitrogen and stir for 2 h. Add 3,3-dimethylbutyraldehyde (1.868 g, 2.3 mL, 18.65 mmol), stir for 30 min at −78° C. and then warm to room temperature. Add water and extract twice the aqueous phase with EtOAc. Dry the combined organic extracts over $Na_2SO_4$, filter and concentrate in vacuo. Purify by chromatography on silica gel eluting hexane/EtOAc (85:15) to obtain the desired intermediate as a yellow oil (1.825 mg, 66%).

N-(tert-Butoxycarbonyl)-2-chloro-4-(3,3-dimethyl-butyryl)-benzylamine: Add manganese dioxide (7.276 g, 83.7 mmol) to a solution of N-(tert-butoxycarbonyl)-2-chloro-4-(1-hydroxy-3,3-dimethyl-butyl)-benzylamine (1.819 g, 5.3 mmol) in anhydrous 1,4-dioxane (75 mL) at room temperature. Heat the mixture at 70° C. overnight. Filter the reaction mixture over Celite® and concentrate in vacuo. Purify by chromatography on silica gel eluting with hexane/EtOAc (85:15) to obtain the desired intermediate as a yellow oil (1.362 g, 76%).

2-Chloro-4-(3,3-dimethyl-butyryl)-benzylamine: Add 4N hydrogen chloride in dioxane (6 mL, 24 mmol) to a solution of N-(tert-butoxycarbonyl)-2-chloro-4-(3,3-dimethyl-butyryl)-benzylamine (700 mg, 2.06 mmol) in dichloromethane (25 mL) and stir overnight. Concentrate in vacuo and wash the solid obtained with diethyl ether. Suspend the solid into saturated aqueous $NaHCO_3$ and stir for 30 min. Extract twice with dichloromethane. Dry the combined organic extracts over $Na_2SO_4$, filter and concentrate in vacuo to obtain the title compound as a yellow oil (477 mg, 97%).

Preparation 266

4-[2-(3,3-Dimethyl-butyl)-[1,3]dioxolan-2-yl]-benzylamine

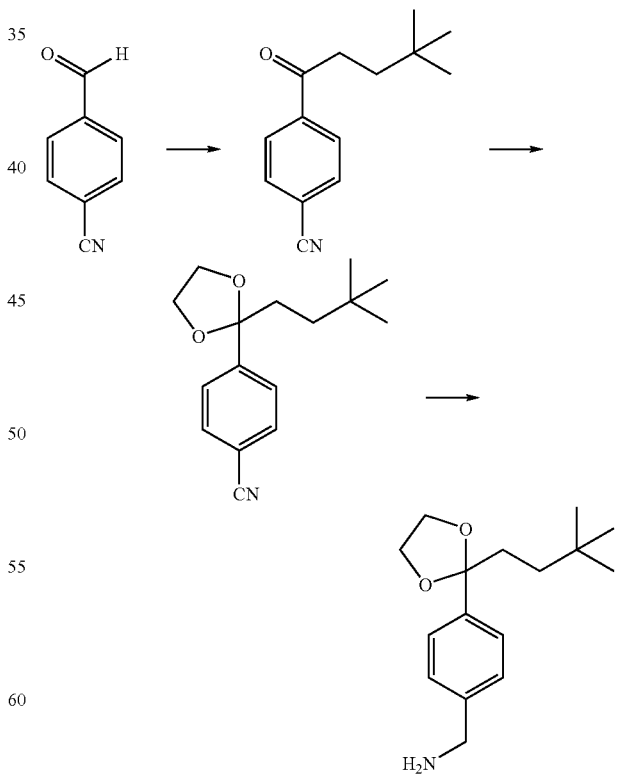

4-(4,4-Dimethyl-pentanoyl)-dibenzonitrile: Keep Mg turnings (402 mg, 15.251 mmol) in vacuo in a two-neck round bottom flask for 2 h. Purge the flask with nitrogen/vacuo several times. Add a couple crystals of iodine, anhydrous THF (60 mL) and 3,3-dimethyl-bromobutane (0.8 mL, 5.59 mmol) slowly (exothermic reaction observed). Add dropwise the remaining 3,3-dimethyl-bromobutane (1.6 mL, 11.18 mmol) and reflux the mixture overnight Add some additional 3,3-dimethyl-bromobutane (0.24 mL, 1.67 mmol) and reflux for 30 min. Cool the mixture to −10° C. and add a solution of 4-cyanobenzaldehyde (4 g, 30.502 mmol) in anhydrous THF (40 mL). Warm the flask gradually to room temperature overnight. Quench the mixture with 0.1M aqueous HCl (100 mL) and extract twice with EtOAc. Dry the combined organic extracts over $Na_2SO_4$, filter and concentrate in vacuo. Purify the crude mixture by chromatography on silica gel eluting with hexane/EtOAc (19:1) to give the desired intermediate as an oil (0.752 g, 23%).

4-[2-(3,3-Dimethyl-butyl)-[1,3]dioxolan-2-yl]-benzonitrile: Dissolve 4-(4,4-dimethyl-pentanoyl)-benzonitrile (275 mg, 1.28 mmol) in toluene (10 mL). Add ethylene glycol (0.35 mL, 6.4 mmol) and p-toluenesulfonic acid monohydrate (24 mg, 0.128 mmol). Heat the mixture at 135° C. in a Dean-Stark for 2 h and then at 120° C. overnight. Cool the mixture to room temperature, dilute with EtOAc and wash with saturated aqueous $NaHCO_3$. Dry the organic phase over $MgSO_4$, filter and concentrate in vacuo. Purify the crude mixture by chromatography on basic alumina eluting with hexane and hexane/EtOAc (19:1) to give the desired intermediate as an oil (0.272 g, 82%).

4-[2-(3,3-Dimethyl-butyl)-[1,3]dioxolan-2-yl]-benzylamine: Dissolve 4-[2-(3,3-dimethyl-butyl)-[1,3]dioxolan-2-yl]-benzonitrile (271 mg, 1.046 mmol) in anhydrous THF (10 mL). Add under nitrogen 1M lithium aluminum hydride in THF (2.1 mL, 2.1 mmol) at 0° C. and stir the mixture at room temperature for 2 h. Cool to 0° C., add water and extract the aqueous phase twice with EtOAc. Dry the combined organic extracts over $MgSO_4$, filter and concentrate in vacuo to obtain the desired intermediate as an oil (0.263 mg) that was used without any further purification.

Preparation 267

4-Cyclohexanecarbonyl-benzylamine

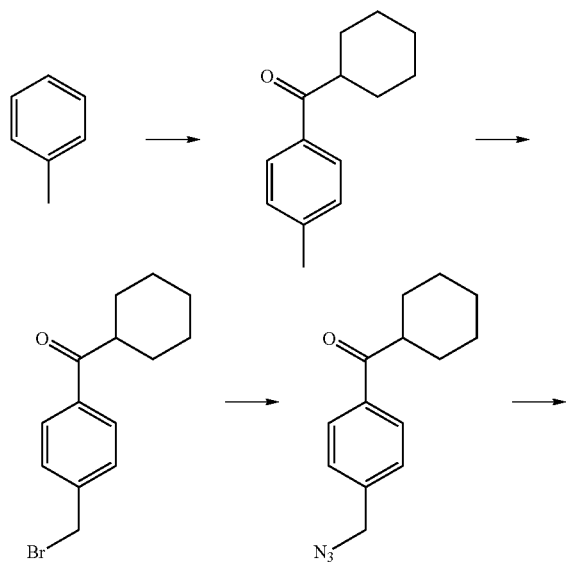

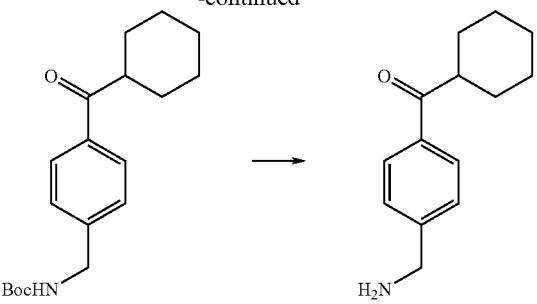

Cyclohexyl-p-tolyl-methanone: Dissolve cyclohexanecarbonyl chloride (2 g, 13.6 mmol) in anhydrous toluene (30 mL). Cool the solution to 0° C., add aluminum trichloride (2.72 g, 20.46 mmol) in three portions and stir the reaction mixture at ambient temperature overnight Cool to 0° C., add slowly water and extract the mixture with EtOAc. Dry the organic layer over $Na_2SO_4$, filter and concentrate in vacuo. Purify the crude mixture by chromatography on silica gel eluting with hexane and hexane/EtOAc (19:1) to give the desired intermediate (2.75 g, 100%).

4-(Cyclohexanecarbonyl)-benzyl bromide: Heat a mixture of cyclohexyl-p-tolyl-methanone (1 g, 4.943 mmol), NBS (1.232 g, 6.92 mmol), and AIBN (41 mg, 0.247 mmol) in carbon tetrachloride (80 mL) for 14 h at reflux. Add additional NBS (264 mg) and AIBN (19 mg) and reflux the mixture for 4 h. Cool the reaction mixture to ambient temperature and filter. Concentrate the filtrate in vacuo to provide the desired intermediate as oil (1.132 g, 81%) that was used without any further purification.

(4-Azidomethyl-phenyl)-cyclohexyl-methanone: Add sodium azide (441 mg, 6.785 mmol) to a stirred solution of 4-(cyclohexanecarbonyl)-benzyl bromide (954 mg, 3.393 mmol) in anhydrous DMF (20 mL) and heat the mixture to 90° C. for 2 h. Cool the mixture to room temperature, add water and extract the aqueous solution with diethyl ether. Dry the combined organic extracts over $Na_2SO_4$, filter and concentrate in vacuo. Purify the crude mixture by chromatography on silica gel eluting with hexane and hexane/EtOAc (19:1) to give the desired intermediate as oil (310 mg, 38%).

N-(tert-Butoxycarbonyl)-4-cyclohexanecarbonyl-benzylamine: Add 10% Pd/C (100 mg) to a solution of (4-azidomethyl-phenyl)-cyclohexyl-methanone (310 mg, 1,274 mmol) and di-tert-butyl-dicarbonate (278 mg, 1274 mmol) in ethanol (5 mL). Submit the mixture to hydrogenation under atmospheric pressure (balloon) for 1 h. Filter the catalyst through Celite® and concentrate the filtrate in vacuo. Purify the crude mixture by chromatography on silica gel eluting with hexane and hexane/EtOAc (92:8) to provide the desired intermediate as a white solid (197 mg, 49%).

4-Cyclohexanecarbonyl-benzylamine: Add 4N hydrogen chloride in dioxane (1 mL) to a stirred solution of N-(tert-butoxycarbonyl)-4-cyclohexanecarbonyl-benzylamine (197 mg, 0.621 mmol) in anhydrous dichloromethane (4 mL) and stir the mixture at ambient temperature for 16 h. Concentrate in vacuo and partition the residue between dichloromethane and saturated aqueous $NaHCO_3$. Extract the aqueous phase twice with dichloromethane. Dry the combined organic extracts over $Na_2SO_4$, filter and concentrate in vacuo to give the title compound (125 mg, 93%) that was used without any further purification. MS (ES+) m/z: 218 (M+H)$^+$.

Preparation 268

4-(2-Cyclopentyl-acetyl)-benzylamine

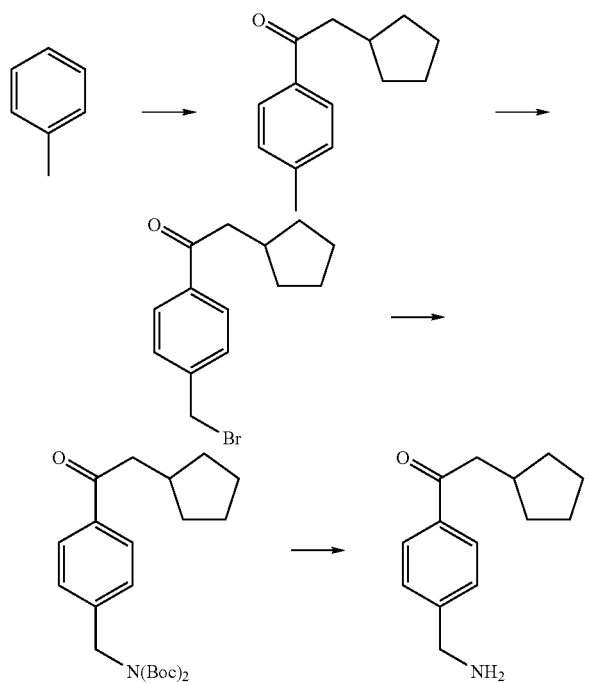

2-Cyclopentyl-1-p-tolyl-ethanone: Add aluminum trichloride (2.719 g, 20.4 mmol) in three portions to a solution of cyclopentylacetyl chloride (2 g, 13.6 mmol) in anhydrous toluene (30 mL) at 0° C. Stir the solution at room temperature overnight. Cool to 0° C., add water and extract the aqueous phase with EtOAc. Dry the organic phase over MgSO$_4$, filter and concentrate in vacuo. Purify the crude mixture by chromatography on silica gel eluting with hexane and hexane/EtOAc (19:1) to give the desired intermediate as an oil (2.5 g, 91%).

1-(4-Bromomethyl-phenyl)-2-cyclopentyl-ethanone: Add NBS (523 mg, 2.94 mmol) and AIBN (44 mg, 0.267 mmol) to a solution of 2-cyclopentyl-1-p-tolyl-ethanone (540 mg, 2.67 mmol) in carbon tetrachloride (80 mL) and heat overnight at 85° C. Add water and extract the aqueous phase with dichloromethane. Dry the organic phase over MgSO$_4$, filter and concentrate in vacuo. Purify the crude mixture by chromatography on silica gel eluting with hexane and hexane/EtOAc (98:2, 95:5) to obtain the desired intermediate as an oil (479 mg, 64%).

N-Di-(tert-butoxycarbonyl)-4-(2-cyclopentyl-acetyl)-benzylamine: Add sodium hydride (42 mg, 1.65 mmol) to a solution of di-tert-butyl-iminodicarboxylate (262 mg, 1.21 mmol) in anhydrous DMF (5 mL) at room temperature under nitrogen and stir for 5 min. Then add a solution of 1-(4-bromomethyl-phenyl)-2-cyclopentyl-ethanone (310 mg, 1.1 mmol) in anhydrous DMF (15 mL) and stir for 1 h. Add water and extract the aqueous phase twice with EtOAc. Wash the combined organic extracts with iced-water. Dry the organic layer over MgSO$_4$, filter and concentrate in vacuo. Purify by chromatography on silica gel eluting with hexane/EtOAc (19:1) to obtain the desired intermediate (360 mg, 78%).

4-(2-Cyclopentyl-acetyl)-benzylamine: Add 4N hydrogen chloride in dioxane (15 mL) to a solution of N-di-(tert-butoxycarbonyl)-4-(2-cyclopentyl-acetyl)-benzylamine (300 mg, 0.72 mmol) in EtOAc (20 mL) and stir overnight. Concentrate in vacuo, suspend the solid obtained in diethyl ether and add hexane. Filter and wash the solid with hexane. Suspend the solid into dichloromethane, add saturated aqueous NaHCO$_3$ and stir until both phases are clear (15 min). Extract the aqueous phase with dichloromethane and EtOAc. Dry the combined organic extracts over MgSO$_4$, filter and concentrate in vacuo to obtain the title compound as an oil that was used without any further purification.

Preparation 268

The compound of Preparation 269 may be prepared essentially as described in Preparation 268 by using cyclohexylacetyl chloride. Overall yield and MS (ES+) data are shown in the Table below.

| Prep. | NH—R | Compound | Yield (%) | MS (ES+) m/z |
|---|---|---|---|---|
| 269 | 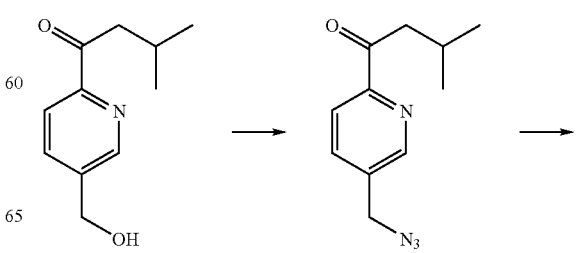 | 4-(2-Cyclohexyl-acetyl)-benzylamine | 40 | 232 (M + H)$^+$ |

Preparation 270

5-Aminomethyl-2-(3-methyl-butyryl)-pyridine

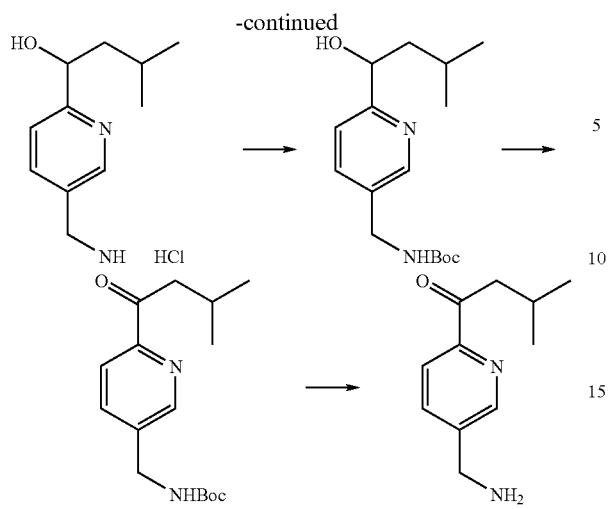

5-Azidomethyl-2-(3-methyl-butyryl)-pyridine: Add DBU (240 mg, 1.55 mmol) to a solution of 5-hydroxymethyl-2-(3-methyl-butyryl)-pyridine (250 mg, 1.29 mmol) and diphenylphosphorylazide (430 mg, 1.55 mmol) in anhydrous toluene (10 mL) at 0° C. Stir at 0° C. for 30 min, warm to room temperature and stir for 4 h. Dilute with EtOAc and water. Extract the aqueous phase twice with EtOAc. Dry the combined organic extracts over Na$_2$SO$_4$, filter and concentrate in vacuo. Purify the crude mixture by chromatography on silica gel eluting with hexane and hexane/EtOAc (9:1) to provide the desired intermediate (300 mg, 99%). MS (ES+) m/z: 219 (M+H)$^+$.

5-Aminomethyl-2-(1-hydroxy-3-methyl-butyl)-pyridine hydrochloride: Add 10% Pd/C (20 mg) to a solution of 5-azidomethyl-2-(3-methyl-butyryl)-pyridine (80 mg, 0.367 mmol) in ethanol (10 mL) containing concentrated HCl (1 mL). Submit the mixture to hydrogenation at atmospheric pressure for 2 h. Filter the reaction mixture over Celite® and concentrate in vacuo to afford the desired intermediate (95 mg, 98%). MS (ES+) m/z: 195 (M+H)$^+$.

5-tert-Butoxycarbonylaminomethyl-2-(1-hydroxy-3-methyl-butyl)-pyridine: Add di-tert-butyl-dicarbonate (78 mg, 0.356 mmol) and triethylamine (0.149 mL, 1.068 mmol) to a solution of 5-aminomethyl-2-(1-hydroxy-3-methyl-butyl)-pyridine hydrochloride (95 mg, 0.356 mmol) in anhydrous dichloromethane (5 mL). Stir the solution at room temperature for 3 h. Dilute the reaction mixture with dichloromethane and wash with water. Extract the aqueous phase with dichloromethane. Dry the combined organic extracts over Na$_2$SO$_4$, filter and concentrate in vacuo. Purify the crude mixture by chromatography on silica gel eluting with hexane/EtOAc (4:1) to afford the desired intermediate (60 mg, 59%).

5-tert-Butoxycarbonylaminomethyl-2-(3-methyl-butyryl) pyridine: Add manganese dioxide (240 mg) to a solution of 5-tert-butoxycarbonylaminomethyl-2-(1-hydroxy-3-methyl-butyl)-pyridine (60 mg, 0.2 mmol) in anhydrous 1,4-dioxane (1 mL) at room temperature. Heat the reaction mixture at 70° C. for 2 h. Filter the reaction mixture over Celite® and concentrate in vacuo to afford the desired intermediate (60 mg, 99%).

5-Aminomethyl-2-(3-methyl-butyryl)-pyridine: Add 4N hydrogen chloride in dioxane (0.5 mL) to a solution of 5-tert-butoxycarbonylaminomethyl-2-(3-methyl-butyryl)-pyridine (60 mg, 0.2 mmol) in anhydrous dichloromethane (2 mL) and stir the solution overnight. Concentrate in vacuo and partition the residue between saturated aqueous NaHCO$_3$ and dichloromethane. Extract the aqueous phase with dichloromethane (2×15 mL) and EtOAc (2×15 mL). Dry the combined organic extracts over Na$_2$SO$_4$, filter and concentrate in vacuo to obtain the title compound (37 mg, 95%) that was used without any further purification.

Preparation 271

2-Bromo-5-tert-butoxycarbonylaminomethyl-pyridine

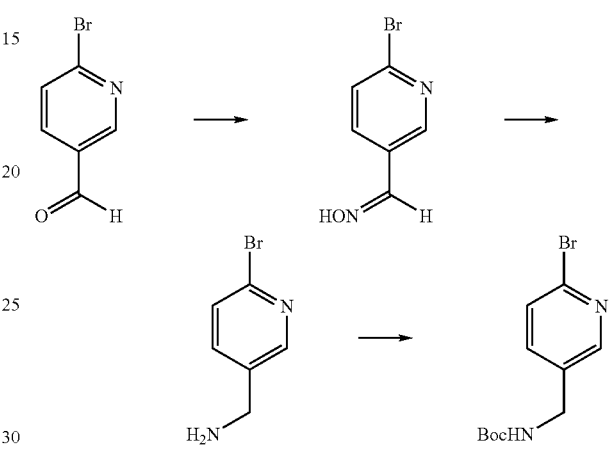

2-Bromo-pyridine-5-carbaldehyde oxime: Add hydroxylamine hydrochloride (1.494 g, 21.504 mmol) and a solution of NaHCO$_3$ (2.71 g, 32.256 mmol) in water (15 mL) to a solution of 2-bromo-5-formyl-pyridine (2 g, 10.752 mmol, prepared by following the procedure described in *J. Org. Chem.* 2004, 69, 250-262) in absolute ethanol (100 mL). Stir the mixture at room temperature for 2 h. Concentrate in vacuo and partition the residue between EtOAc and water. Extract the aqueous phase with EtOAc. Dry the combined organic extracts over Na$_2$SO$_4$, filter and concentrate in vacuo. Purify the crude mixture by chromatography on silica gel eluting with hexane and hexane/EtOAc (9:1, 4:1) to afford the desired intermediate as a solid (1.362 g, 63%).

5-Aminomethyl-2-bromo-pyridine: Add dropwise a solution of 2-bromo-pyridine-5-carbaldehyde oxime (0.5 g, 2.487 mmol) in DME (10 mL) to a solution of titanium(IV) chloride (0.573 mL, 5.223 mmol) and sodium borohydride (395 mg, 10.445 mmol) in DME (20 mL) at 0° C. Allow the mixture to warm to room temperature and stir for 3 h. Add water and remove the solvent in vacuo. Basify the mixture to pH 12 with 1N aqueous NaOH and extract with dichloromethane. Dry the combined organic extracts over Na$_2$SO$_4$, filter and concentrate in vacuo to afford the desired intermediate (340 mg, 73%) that was used without further purification.

2-Bromo-5-tert-butoxycarbonylaminomethyl-pyridine: Add di-tert-butyl-dicarbonate (397 mg, 1.818 mmol) and triethylamine (0.507 mL, 3.636 mmol) to a solution of 5-aminomethyl-2-bromo-pyridine (340 mg, 1.818 mmol) in anhydrous dichloromethane (15 mL). Stir the solution overnight at room temperature. Dilute the reaction mixture with dichloromethane and wash with water. Extract the aqueous phase with dichloromethane. Dry the combined organic extracts over Na$_2$SO$_4$, filter and concentrate in vacuo. Purify the crude mixture by chromatography on silica gel eluting with hexane and hexane/EtOAc (4:1) to afford the title compound as a solid (322 mg, 62%).

Preparation 272

5-Aminomethyl-2-(3,3-dimethyl-butyryl)-pyridine

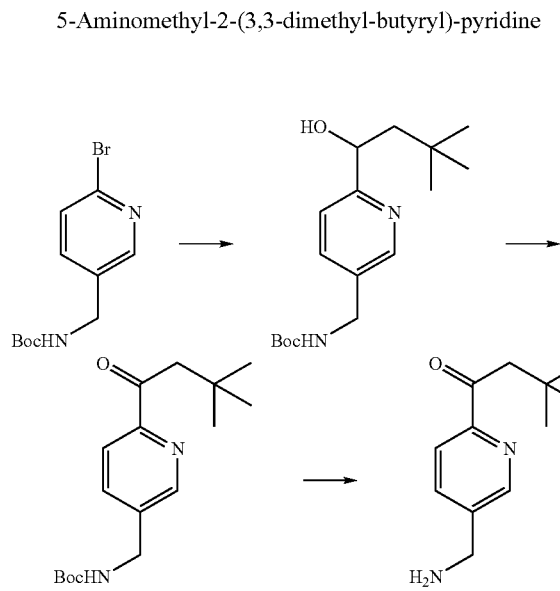

5-tert-Butoxycarbonylaminomethyl-2-(1-hydroxy-3,3-dimethyl-butyl)-pyridine: Add slowly butyllithium (1.088 mL, 1.741 mmol, 1.6M solution in hexane) to a solution of 2-bromo-5-tert-butoxycarbonylaminomethyl-pyridine (200 mg, 0.696 mmol) in anhydrous THF (10 mL) at −78° C. Stir the mixture at this temperature for 35 min. Add 3,3-dimethylbutyraldehyde (0.219 mL, 1.741 mmol) and stir the mixture at −78° C. for 3 h. Quench the reaction mixture at −78° C. with brine. Extract the aqueous phase with EtOAc (3×15 mL). Dry the combined organic extracts over $Na_2SO_4$, filter and concentrate in vacuo. Purify The crude mixture by chromatography on silica gel eluting with hexane and hexane/EtOAc (3:2) to afford the desired intermediate as a colorless oil (118 mg, 55%). MS (ES+) m/z: 309 $(M+H)^+$.

5-tert-Butoxycarbonylaminomethyl-2-(3,3-dimethyl-butyryl)-pyridine: Add manganese dioxide (472 mg, 5.429 mmol) to a solution of 5-tert-butoxycarbonylaminomethyl-2-(1-hydroxy-3,3-diethyl-butyl)-pyridine (118 mg, 0.383 mmol) in anhydrous 1,4-dioxane (5 mL) at room temperature. Heat the reaction mixture at 70° C. overnight. Filter the reaction mixture over Celite® and concentrate in vacuo to obtain the desired intermediate (104 mg, 89%).

5-Aminomethyl-2-(3,3-dimethyl-butyryl)-pyridine: Add 4N hydrogen chloride in dioxane (1 mL) to a solution of 5-tert-butoxycarbonylaminomethyl-2-(3,3-dimethyl-butyryl)-pyridine (104 mg, 0.339 mmol) in anhydrous dichloromethane (4 mL) and stir the solution overnight. Concentrate in vacuo and partition the residue between saturated aqueous $NaHCO_3$ and dichloromethane. Extract the aqueous phase with dichloromethane (2×15 mL) and EtOAc (2×15 mL). Dry the combined organic extracts over $Na_2SO_4$, filter and concentrate in vacuo to obtain the title compound as an oil (62 mg, 88%) that was used without any further purification. MS (ES+) m/z: 207 $(M+H)^+$.

Preparation 273

4-Aminomethyl-N-cycloheptyl-2-fluoro-benzamide

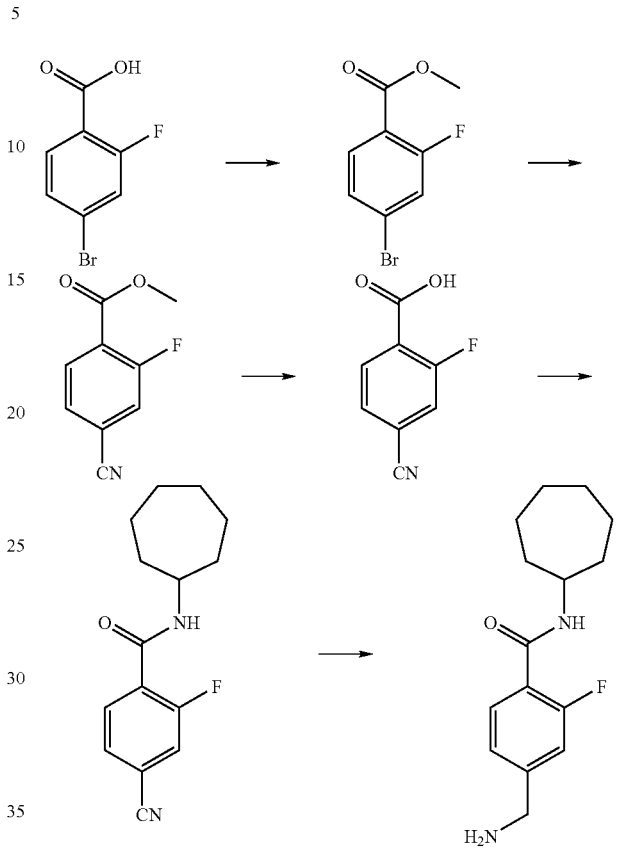

Methyl 4-bromo-2-fluoro-benzoate: Dissolve 4-bromo-2-fluoro-benzoic acid (15 g, 68.5 mmol) in methanol (70 mL). Add concentrated sulfuric acid (500 µl) to the solution and heat the mixture to reflux for 20 h under a nitrogen atmosphere. Cool the mixture to room temperature and concentrate in vacuo. Dissolve the residue in EtOAc (200 mL) and wash successively with saturated aqueous $NaHCO_3$ (50 mL) and water (2×50 mL). Dry the organic layer over $Na_2SO_4$, filter and concentrate in vacuo to obtain the desired intermediate (15.4 g, 96%). GC-MS m/z: 232 $(M^+)$.

Methyl 4-cyano-2-fluoro-benzoate: Slurry methyl 4-bromo-2-fluoro-benzoate (5 g, 21.5 mmol) and copper(I) cyanide (3.8 g, 42.9 mmol) in anhydrous DME (90 mL). Heat the mixture to reflux for 20 h under a nitrogen atmosphere. Cool the mixture to room temperature, dilute with hexane/EtOAc (1:1, 300 mL) and water (150 mL). Filter the mixture through Celite® washing with hexane/EtOAc (1:1) to reduce the emulsion layer. Separate the organic layer and extract the aqueous layer with hexane/EtOAc (1:1, 2×200 mL). Dry the combined organic extracts over $Na_2SO_4$, filter and concentrate in vacuo. Purify the crude mixture by chromatography on silica gel eluting with hexane/EtOAc (9:1 to 1:1 gradient) to obtain the desired intermediate (2.9 g, 76%). GC-MS m/z: 179 $(M^+)$.

4-Cyano-2-fluoro-benzoic acid: Dissolve methyl 4-cyano-2-fluoro-benzoate (2.9 g, 16.2 mmol) in absolute ethanol (100 mL). Add potassium hydroxide (4.5 g, 80.2 mmol) and stir the milky white mixture for 1.5 h. Dilute the mixture with water (125 mL) and wash with diethyl ether (50 mL). Collect the aqueous layer and concentrate in vacuo until solids start to appear in the flask, then adjust the mixture to pH 1 with concentrated HCl. Extract the aqueous mixture with diethyl ether (3×500 mL). Combine the organic extracts and concentrate in vacuo to obtain the desired intermediate as a white solid (2.2 g, 83%).

4-Cyano-N-cycloheptyl-2-fluoro-benzamide: Dissolve 4-cyano-2-fluoro-benzoic acid (1 g, 6.1 mm ol) in anhydrous toluene (25 mL) and thionyl chloride (15 mL). Stir the mixture for 1 h at 90° C. under a nitrogen atmosphere (quench aliquots with methanol and assay by HPLC to determine if starting material has been consumed). Cool the reaction to room temperature and concentrate in vacuo to obtain the acid chloride as a yellow oil (1.25 g). Dissolve the acid chloride (1.25 g) in diethyl ether (75 mL), add triethylamine (0.85 mL, 6.1 mmol) and cycloheptylamine (0.78 mL, 6.1 mmol). Stir the mixture at room temperature for 16 h under a nitrogen atmosphere. Quench the reaction with saturated aqueous Na$_2$CO$_3$ (20 mL). Extract the mixture with EtOAc (30 mL). Dry the organic layer over Na$_2$SO$_4$, filter and concentrate in vacuo to obtain the desired intermediate (1.45 g, 91%). GC-MS m/z: 260 (M$^+$).

4-Aminomethyl-N-cycloheptyl-2-fluoro-benzamide: Add 4-cyano-N-cycloheptyl-2-fluoro-benzamide (1.4 g, 5.4 mmol), 10% Pd/C (Degussa type E101, 415 mg), ethanol (40 mL), water (15 mL) and acetic acid (1.8 mL) to a pressure vessel. Pressurize the vessel to 55 psi with hydrogen, and stir the mixture for 0.5 h (monitor the reaction by TLC). Filter the mixture through Celite® and wash the cake with warm ethanol followed by dichloromethane under a nitrogen atmosphere. Concentrate the filtrate in vacuo to obtain the product as the acetic acid salt. Use SCX chromatography to obtain the title compound (1.36 g, 95%). GC-MS m/z: 264 (M$^+$).

Preparation 274

4-Aminomethyl-N-cycloheptyl-3-fluoro-benzamide

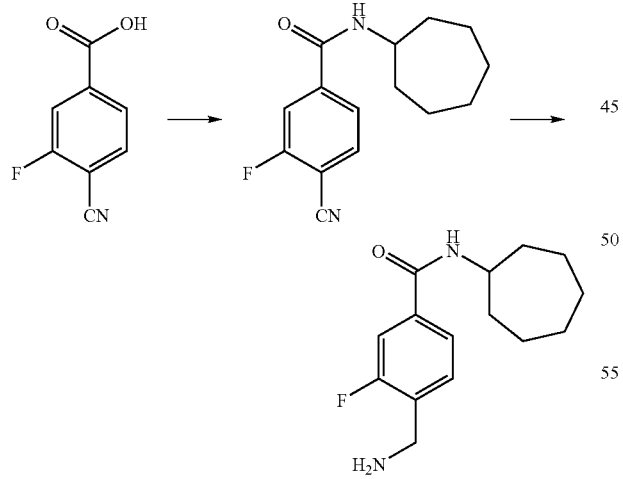

4-Cyano-N-cycloheptyl-3-fluoro-benzamide: Dissolve 4-cyano-3-fluoro-benzoic acid (1 g, 6.1 mmol) in anhydrous toluene (20 mL) and thionyl chloride (10 mL). Stir the mixture for 1.5 h at 90° C. under a nitrogen atmosphere (quench aliquots with methanol and assay by HPLC to determine if staring material has been consumed). Cool the reaction to room temperature and concentrate in vacuo to obtain the acid chloride as a yellow oil. Dissolve the yellow oil in diethyl ether (50 mL), add triethylamine (0.86 mL, 6.1 mmol) and cycloheptylamine (0.79 mL, 6.1 mmol). Stir the mixture at room temperature for 16 h under a nitrogen atmosphere. Quench the reaction with saturated aqueous Na$_2$CO$_3$ (20 mL). Extract the mixture with EtOAc (2×50 mL). Dry the combined organic extracts over Na$_2$SO$_4$, filter and concentrate in vacuo to obtain the desired intermediate (1.24 g, 77%). MS (ES−) m/z: 259.2 (M−H)$^+$.

4-Aminomethyl-N-cycloheptyl-3-fluoro-benzamide: Add 4-cyano-N-cycloheptyl-3-fluoro-benzamide (0.86 g, 3.3 mmol), 10% Pd/C (Degussa type E101, 250 mg), ethanol (25 mL), water (9 mL) and acetic acid (1 mL) to a pressure vessel under a nitrogen atmosphere. Pressurize the vessel to 50 psi with hydrogen, and stir the mixture for 0.5 h. Filter the mixture through Celite® and wash the cake with warm ethanol followed by dichloromethane under a nitrogen atmosphere. Concentrate the filtrate in vacuo to obtain the title compound as the acetic acid salt. Use SCX chromatography to obtain the title compound (805 mg, 92%). MS (ES+) m/z: 265.3 (M+H)$^+$.

Preparation 275

4-Aminomethyl-2-chloro-N-cycloheptyl-benzamide

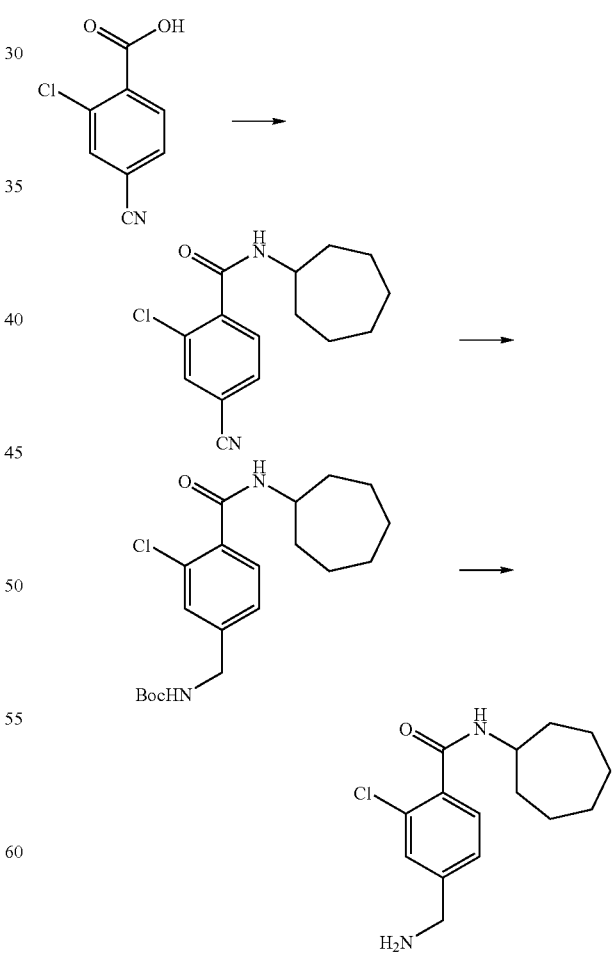

2-Chloro-4-cyano-N-cycloheptyl-benzamide: Dissolve 2-chloro-4-cyano-benzoic acid (1.1 g, 6 mmol) in anhydrous toluene (20 mL) and thionyl chloride (15 mL). Stir the mixture for 1 h at 90° C. under a nitrogen atmosphere (quench aliquots with methanol and assay by HPLC to determine if starting material has been consumed). Cool the reaction to room temperature and concentrate in vacuo to obtain the acid chloride as an oil. Dissolve the oil in diethyl ether (40 mL), add triethylamine (0.84 mL, 6 mmol) and cycloheptylamine (0.77 mL, 6 mmol). Stir the mixture at room temperature for 1 h under a nitrogen atmosphere. Quench the reaction with saturated aqueous $Na_2CO_3$ (20 mL). Extract the mixture with EtOAc (100 mL). Dry the organic layer over $Na_2SO_4$, filter and concentrate in vacuo. Purify the crude mixture by chromatography on silica gel eluting with dichloromethane to obtain the desired intermediate (1.1 g, 66%). MS (ES+) m/z: 277.2 (M+H)$^+$.

4-tert-Butoxycarbonylaminomethyl-2-chloro-N-cycloheptyl-benzamide: Dissolve 2-chloro-4-cyano-N-cycloheptyl-benzamide (460 mg, 1.7 mmol) in methanol (15 mL). Cool the solution to 0° C. under a nitrogen atmosphere and add di-tert-butyl dicarbonate (726 mg, 3.3 mmol) and nickel (II) chloride hexahydrate (40 mg, 0.17 mmol). Add then sodium borohydride (360 mg, 9.5 mmol) portionwise over 30 min. Stir at 0° C. for 1 h then concentrate the mixture in vacuo. Dilute the residue with EtOAc (100 mL), wash with saturated aqueous $NaHCO_3$ (40 mL). Extract the aqueous layer with EtOAc (3×40 mL). Dry the combined organic extracts over $Na_2SO_4$, filter and concentrate in vacuo. Purify the crude mixture by chromatography on silica gel eluting with EtOAc to obtain the desired intermediate (627 mg, 99%). MS (ES+) m/z: 381.3 (M+H)$^+$.

4-Aminomethyl-2-chloro-N-cycloheptyl-benzamide: Dissolve 4-tert-butoxycarbonylaminomethyl-2-chloro-N-cycloheptyl-benzamide (624 mg, 1.6 mmol) in dichloromethane (30 mL) then add trifluoroacetic acid (2 mL). Stir the solution at room temperature under a nitrogen atmosphere for 1 h. Concentrate the mixture in vacuo. Purify the crude mixture by SCX chromatography to obtain the desired intermediate (395 mg, 85%). MS (ES+) m/z: 281.2 (M+H)$^+$.

Preparation 276

4-Aminomethyl-N-cycloheptyl-2-methyl-benzamide

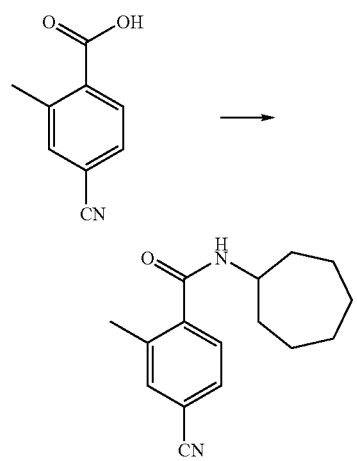

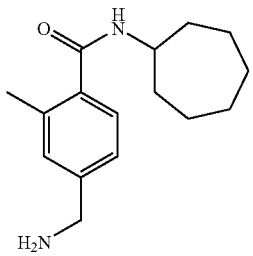

4-Cyano-N-cycloheptyl-2-methyl-benzamide: Add cycloheptylamine (0.83 mL, 6.5 mmol), HOBT (838 mg, 6.2 mmol), EDC (1.2 g, 6.2 mmol) and diisopropylethylamine (3.2 mL, 18.6 mmol) to a solution of 4-cyano-2-methyl-benzoic acid (1 g, 6.2 mmol) in dichloromethane (20 mL) at room temperature under a nitrogen atmosphere. Stir the mixture for 16 h at room temperature. Wash the mixture with water (20 mL), separate and concentrate the organic layer in vacuo. Purify the crude mixture by chromatography on silica gel eluting with hexane/EtOAc (19:1 to 3:2 gradient) to obtain the desired intermediate (830 mg, 52%). MS (ES+) m/z: 257.3 (M+H)$^+$.

4-Aminomethyl-N-cycloheptyl-2-methyl-benzamide: Add 4-cyano-N-cycloheptyl-2-methyl-benzamide (0.82 g, 3.2 mmol), ethanol (23 mL), water (8 mL) and acetic acid (1 mL) to a pressure vessel. Heat vessel to 50° C. to dissolve all solids. Add 10% Pd/C (Degussa type E101, 250 mg) under a nitrogen atmosphere, then pressurize the vessel to 55 psi with hydrogen at ambient temperature. Stir the mixture for 40 min. Filter the mixture through Celite® and wash the cake with warm ethanol (50 mL) followed by dichloromethane (100 mL) under a nitrogen atmosphere. Concentrate the filtrate in vacuo to obtain the title compound as the acetic acid salt. Use SCX chromatography to obtain the title compound (820 mg, 98%). MS (ES+) m/z: 261.3 (M+H)$^+$.

Preparation 277

(R)-4-Aminomethyl-2-fluoro-N-(2,2,2-trifluoro-1-methyl-ethyl)-benzamide

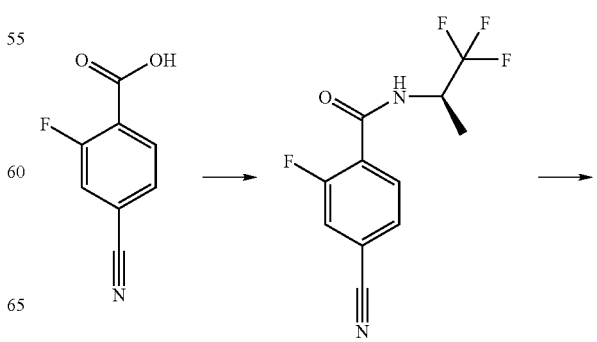

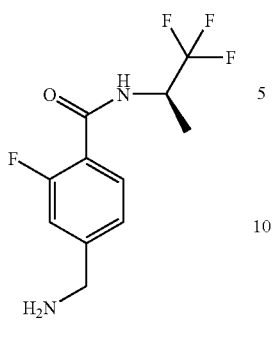

(R)-4-Cyano-2-fluoro-N-(2,2,2-trifluoro-1-methyl-ethyl)-benzamide: Add (R)-(2,2,2-trifluoro-1-methyl)-ethylamine (0.909 g, 6.08 mmol), HOBT (0.82 g, 6.1 mmol), diisopropylethylamine (2.1 mL, 12 mmol) and EDC (1.17 g, 6.08 mmol) to a mixture of 4-cyano-2-fluorobenzoic acid (1.004 g, 6.08 mmol) in anhydrous THF (40 mL) at room temperature. Stir overnight and partition the mixture between EtOAc (250 mL) and saturated aqueous $NaHCO_3$ (100 mL). Dry the organic extract over $Na_2SO_4$, filter and concentrate in vacuo. Purify by chromatography on silica gel eluting with dichloromethane/hexane (1:1 to 1:0 gradient over 71 min; 50 mL/min) to afford the desired intermediate as a white solid (0.985 g, 62%).

(R)-4-Aminomethyl-2-fluoro-N-(2,2,2-trifluoro-1-methyl-ethyl)-benzamide: Combine a solution of (R)-4-cyano-2-fluoro-N-(2,2,2-trifluoro-1-methyl-ethyl)-benzamide (0.904 g, 3.475 mmol) in absolute ethanol (26 mL), water (9.7 mL) and glacial acetic acid (1.2 mL) with 10% Pd/C (Degussa type E101, 0.27 g, 0.13 mmol) under nitrogen. Purge the mixture with nitrogen and then with hydrogen. Stir the slurry at room temperature under hydrogen at 55 psi for 30 min. Purge the reaction mixture with nitrogen and then filter the slurry over Celite®. Wash the filter cake with ethanol (100 mL) and THF (100 mL). Concentrate the filtrate and purify by SCX chromatography eluting with dichloromethane/methanol (1:1) to remove impurities and then with dichloromethane/2M ammonia in methanol (1:1) to elute product. Concentrate to afford the title compound as a colorless oil (0.86 g, 94%).

Preparation 278

3-tert-Butoxycarbonyl-6-(4-carboxy-3-fluoro-benzylamino)-7-chloro-2,3,4,5-tetrahydro-1H-benzo[d]azepine

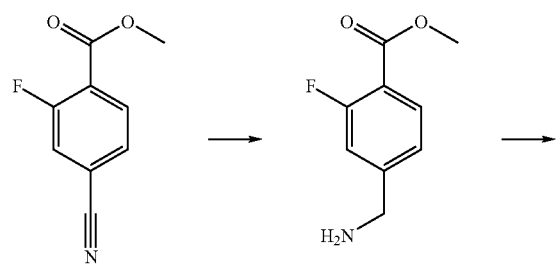

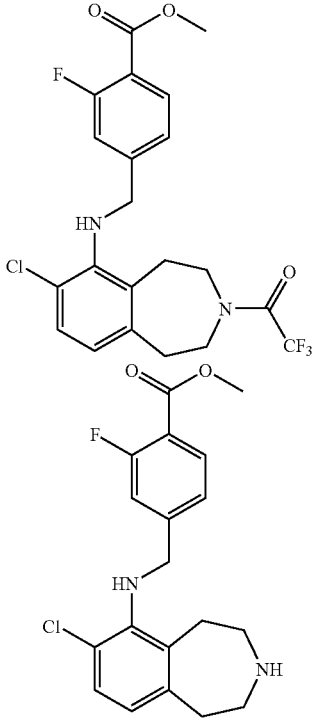

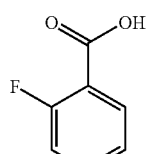

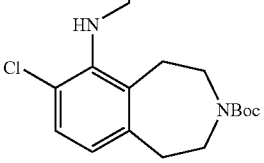

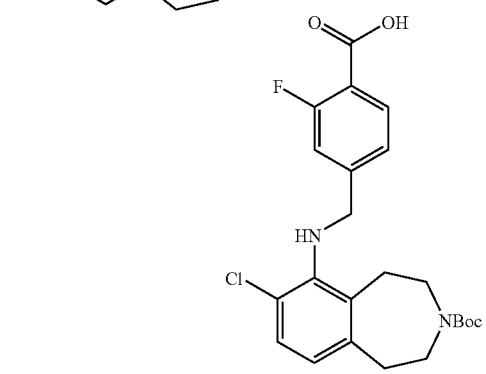

Methyl 4-aminomethyl-2-fluoro-benzoate: Combine a solution of methyl 4-cyano-2-fluoro-benzoate (1 g, 5.58 mmol) in absolute ethanol (42 mL) and acetic acid (1.9 mL) with a mixture of 10% Pd/C (Degussa type E101, 0.17 g, 0.078 mmol) in water (15.6 mL) at room temperature under nitrogen. Purge with nitrogen and then with hydrogen at 55 psi and stir for 1 h. Purge the reaction with nitrogen, filter through Celite® and wash the filter cake with ethanol (100 mL), THF (100 mL) and isopropanol (100 mL). Concentrate in vacuo and purify by SCX chromatography and then chromatography on silica gel (40 g RediSep® column) eluting with dichloromethane/2M ammonia in methanol (99:1 to 9:1 gradient over 30 min; 35 mL/min) to afford the desired intermediate as a white solid (0.602 g, 59%).

7-Chloro-6-(3-fluoro-4-methoxycarbonyl-benzylamino)-3-(2,2,2-trifluoroacetyl)-2,3,4,5-tetrahydro-1H-benzo[d]azepine: Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (1.24 g, 2.91 mmol) with methyl 4-aminomethyl-2-fluoro-benzoate (1.065 g, 5.821 mmol) by using tris(dibenzylideneacetone)dipalladium(0) (0.533 g, 0.582 mmol), BINAP (0.725 g, 1.16 mmol) and cesium carbonate (3.32 g, 10.2 mmol) under nitrogen in anhydrous toluene (20 mL). Purify by chromatography on silica gel eluting with hexane/EtOAc (19:1 to 1:1 gradient over 71 min; 50 mL/min) to afford the desired intermediate as a yellow oil (1.3 g, 100%).

7-Chloro-6-(3-fluoro-4-methoxycarbonyl-benzylamino)-2,3,4,5-tetrahydro-1H-benzo[d]azepine: Add 1M aqueous NaOH (2.8 mL, 2.8 mmol) to a solution of 7-chloro-6-(3-fluoro-4-methoxycarbonyl-benzylamino)-3-(2,2,2-trifluoro-acetyl)-2,3,4,5-tetrahydro-1H-benzo[d]azepine (1.31 g, 2.86 mmol) in 1,4-dioxane (13.3 mL) and water (2.6 mL) at 11° C. Allow mixture to warm to room temperature and stir for 1 h. Concentrate in vacuo and partition the residue between dichloromethane (250 mL) and saturated aqueous NaHCO$_3$ (100 mL). Dry the organic phase over Na$_2$SO$_4$, filter and concentrate in vacuo to afford the desired intermediate that was used without further purification.

3-tert-Butoxycarbonyl-6-(4-carboxy-3-fluoro-benzy-lamino)-7-chloro-2,3,4,5-tetrahydro-1H-benzo[d]azepine: Add 1M aqueous NaOH (5.7 mL, 5.7 mmol) to a mixture of 7-chloro-6-(3-fluoro-4-methoxycarbonyl-benzylamino)-2,3,4,5-tetrahydro-1H-benzo[d]azepine (1.04 g, 2.86 mmol) in 1,4-dioxane (13.3 mL) and water (2.6 mL) at room temperature. Heat the mixture at 50° C. for 2 h. Cool the mixture to 0° C., add a solution of di-tert-butyl-dicarbonate (0.62 g, 2.9 mmol) in 1,4-dioxane (2 mL) and stir at 0° C. for 2 h. Concentrate in vacuo, add EtOAc (50 mL), 1N aqueous KHSO$_4$ (5.7 mL, 5.7 mmol) and water (20 mL) to pH=1. Dry the organic phase over Na$_2$SO$_4$, filter and concentrate in vacuo to afford the title compound as a yellow oil (1.25 g, 98%) that was used without further purification. MS (ES+) m/z: 449.1 (M+H)$^+$.

Preparation 279

5-Aminomethyl-2-cyclohexylamino-pyridine

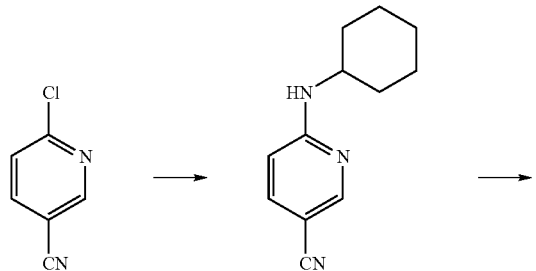

6-Cyclohexylamino-nicotinonitrile: Add cyclohexylamine (7.1 g, 72 mmol) to a mixture of 6-chloronicotinitrile (1 g, 7.2 mmol), potassium carbonate (3 g, 21.7 mmol), and anhydrous DMF (10 mL). Heat the mixture in a sealed flask at 120° C. for 1.5 h. Cool the reaction to ambient temperature, dilute with hexane/EtOAc (1:1, 100 mL) and wash the mixture with aqueous 5% sodium chloride (3×30 mL). Collect the organic layer and concentrate in vacuo to obtain the desired intermediate (1.4 g, 97%). GC-MS m/z: 201 (M$^+$).

5-Aminomethyl-2-cyclohexylamino-pyridine: Charge a solution of 6-cyclohexylamino-nicotinonitrile (1.4 g, 7.1 mmol) in methanol (70 mL) and trifluoroacetic acid (5 mL) to a pressure vessel containing 10% Pd/C (Degussa type E101, 600 mg). Pressurize the vessel to 40 psi with hydrogen and stir for 2 h. Filter the mixture through Celite®, wash with warm ethanol, and dichloromethane. Concentrate the filtrate in vacuo. Purify the crude mixture by chromatography on silica gel eluting with dichloromethane/2M ammonia in methanol (99:1 to 90:10 gradient) to obtain the title compound (920 mg, 54%). MS (ES+) m/z: 206.1 (M+H)$^+$.

Preparation 280

The compound of Preparation 280 may be prepared essentially as described in Preparation 279 using 6-chloronicotinonitrile and cylclohexylmethylamine. Overall yield and MS (ES+) data are shown in the Table below.

| Prep. | Structure | Compound | Yield (%) | MS (ES+) m/z |
|---|---|---|---|---|
| 280 | ![structure] | 5-Aminomethyl-2-cyclohexyl-methylamino-pyridine | 95 | 220.3 (M + H)$^+$ |

Preparation 281

6-Benzylamino-pyridin-3-ylmethylamine

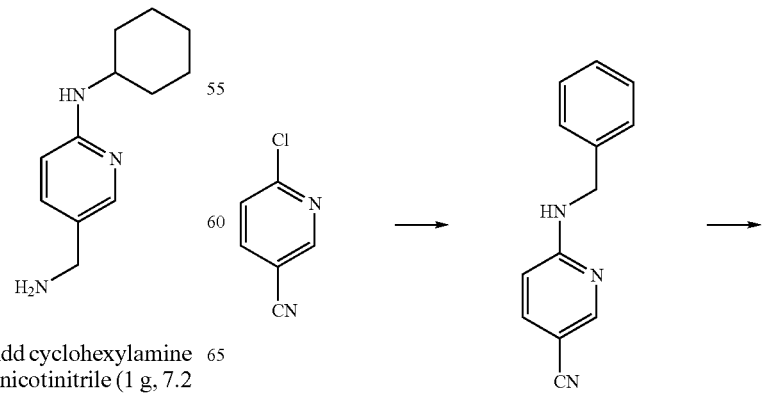

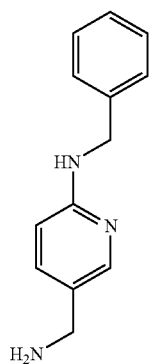

6-Benzylamino-nicotinonitrile: Heat 6-chloroniconitrile (0.58 g, 4.2 mmol) and benzylamine (4.6 mL, 42 mmol) in anhydrous DMF (3 mL) at 120° C. for 4.5 h. Cool at room temperature. Dilute with water and extract with EtOAc. Wash the organic phase with brine, dry over MgSO$_4$, filter, and concentrate in vacuo. Purify by chromatography on silica gel eluting sequentially with hexane/EtOAc (4:1, 2:1, 1:2) to give the desired intermediate as a white solid (840 mg, 96%). MS (ES+) m/z: 210 (4+H)$^+$.

6-Benzylamino-pyridin-3-ylmethylamine: Stir 6-benzylamino-nicotinonitrile (680 mg, 3.3 mmol) and 10% Pd/C (Degussa type E101) vigorously in absolute ethanol (80 mL) under hydrogen at 25 psi for 1 h. Filter the solution through Celite® and concentrate in vacuo. Purify by chromatography on silica gel eluting sequentially with 2M ammonia in methanol/dichloromethane (4:96, 9:91) to give the title compound as a white solid (320 mg, 45%). MS (ES+) m/z: 214 (M+H)$^+$.

Preparation 282

(±)-4-[1-(1,1,2,2,2-Pentafluoroethyl)-ethoxy]-benzylamine

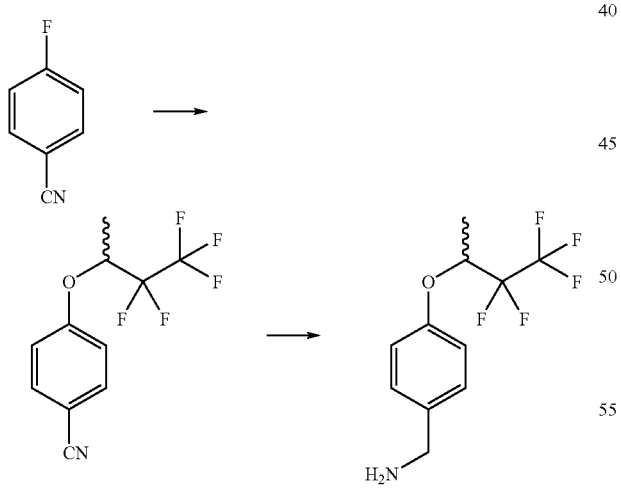

(±)-4-[1-(1,1,2,2,2-Pentafluoroethyl)-ethoxy]-benzonitrile: Add potassium carbonate (27.4 g, 198 mmol) to a mixture of 4-fluorobenzonitrile (8 g, 66 mmol) and (±)-3,3,4,4,4-pentafluoro-2-butanol (17.2 g, 105 mmol) in anhydrous DMF (60 mL). Heat the mixture in a sealed flask for 4 h at 130° C. Cool the reaction to ambient temperature, dilute with hexane/EtOAc (1:1, 350 mL) and wash with aqueous 5% sodium chloride (3×100 mL). Collect the organic layer, dry over Na$_2$SO$_4$, filter and concentrate in vacuo to obtain the desired intermediate (17.1 g, 98%). GC-MS m/z: 432 (M$^+$).

(±)-4-[1-(1,1,2,2,2-Pentafluoroethyl)-ethoxy]-benzylamine: Add (±)-4-[1-(1,1,2,2,2-pentafluoroethyl)-ethoxy]-benzonitrile (1 g, 3.8 mmol) to a slurry of lithium aluminum hydride (400 mg, 10 mmol) in diethyl ether (30 mL) at 0° C. under a nitrogen atmosphere. Stir the mixture at ambient temperature for 2 h, and then quench the reaction sequentially with water (1 mL) and 5N sodium hydroxide (1 mL). Filter the slurry through Celite®, dry the filtrate over Na$_2$SO$_4$, filter and concentrate in vacuo to obtain the title compound (990 mg, 98%). GC-MS m/z: 268 (M$^+$).

Preparation 283

4-[1-(1,1,2,2,2-Pentafluoroethyl)-ethoxy]-benzylamine Isomer

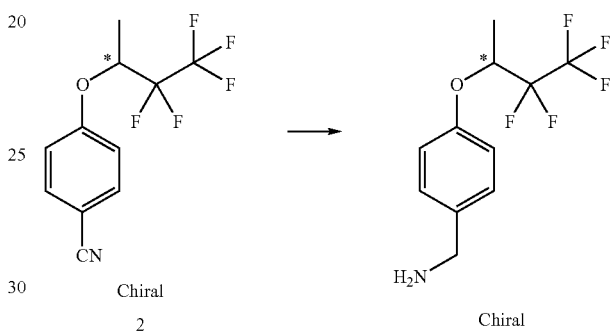

4-[1-(1,1,2,2,2-Pentafluoroethyl)-ethoxy]-benzonitrile Isomer 2: Separate (±)-4-[1-(1,1,2,2,2-pentafluoroethyl)-ethoxy]-benzonitrile by normal phase chiral chromatography (Chiralcel OJ, 8×33 cm, elute with heptane/3A ethanol 97:3, flow rate 375 mL/min). Collect the 2$^{nd}$ eluting isomer as the desired intermediate (11.3 g, 40% recovery, 98.6% ee (Chiralcel OJ, 4.6×250 mm, elute with heptane/3A ethanol 97:3, 1 mL/min). GC-MS m/z: 265 (M$^+$).

4-[1-(1,1,2,2,2-Pentafluoroethyl)-ethoxy]-benzylamine Isomer 2: Reduce 4-[1-(1,1,2,2,2-pentafluoroethyl)-ethoxy]-benzonitrile isomer 2 (11.4 g, 43 mmol) using General Procedure 6-4 to obtain the title compound (11.38 g, 98%). GC-MS m/z: 268

Preparation 284

4-[1-(1,1,2,2,2-Pentafluoroethyl)-ethoxy]-benzylamine Isomer 1

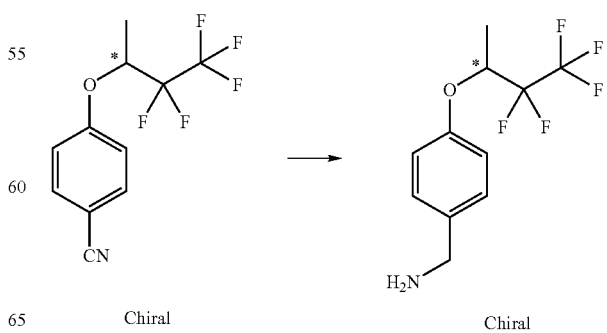

4-[1-(1,1,2,2,2-Pentafluoroethyl)-ethoxy]-benzonitrile Isomer 1: Separate (±)-4-[1-(1,1,2,2,2-pentafluoroethyl)-ethoxy]-benzonitrile by normal phase chiral chromatography (Chiralcel OJ, 8×33 cm, elute with heptane/3A ethanol 97:3, flow rate 375 mL/min). Collect the 1$^{st}$ eluting isomer as the desired intermediate (4.5 g, 33% recovery, 99.3% ee (Chiralcel OJ, 4.6×250 mm, elute with heptane/3A ethanol 97:3, 1 mL/min). GC-MS m/z: 265 (M$^+$).

4-[1-(1,1,2,2,2-Pentafluoroethyl)-ethoxy]-benzylamine Isomer 1: Reduce 4-[1-(1,1,2,2,2-pentafluoroethyl)-ethoxy]-benzonitrile isomer 1 (4.5 g, 17 mmol) using General Procedure 64 to obtain the title compound (4.3 g, 94%). GC-MS m/z: 268 (M$^+$).

Preparation 285

(±)-2-Aminomethyl-5-[1-(1,1,2,2,2-pentafluoroethyl)-ethoxy]-pyridine

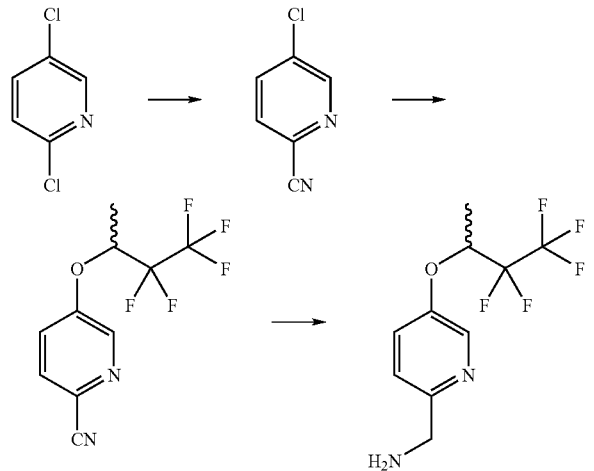

5-Chloro-pyridine-2-carbonitrile: Slurry 2,5-dichloropyridine (6 g, 40.5 mmol), zinc cyanide (2.9 g, 24.7 mmol), zinc (dust) (116 mg, 1.8 mmol) and [1,1'-bis(diphenylphosphino)ferrocene]dichloropalladium(II) complex with dichloromethane (720 mg, 0.98 mmol) in anhydrous DMF (40 mL). Heat the mixture to reflux under a nitrogen atmosphere for 4.5 h. Cool the mixture to room temperature, dilute with EtOAc (300 mL), wash with aqueous 10% sodium chloride (3×75 mL). Collect organic layer, dry over Na$_2$SO$_4$, filter and concentrate in vacuo. Purify by chromatography on silica gel eluting with hexane/EtOAc (9:1 to 1:1 gradient) to obtain the desired intermediate (2.6 g, 46%). GC-MS m/z: 138 (M$^+$).

(±)-4-[1-(1,1,2,2,2-Pentafluoroethyl)-ethoxy]-pyridine-2-carbonitrile: Add (±)-3,3,4,4,4-pentafluoro-2-butanol (710 mg, 4.3 mmol) slowly to a slurry of sodium hydride (104 mg, 1.2 equiv, 60% mineral oil, washed with hexane) in hexamethylphosphoramide (2 mL) under nitrogen at 0° C. Allow the slurry to warm to ambient temperature and stir for 5 min. Add 5-chloro-pyridine-2-carbonitrile (300 mg, 2.2 mmol), then heat the mixture in a sealed flask at 130° C. for 4 h (monitor reaction by GC/MS). Cool the reaction to room temperature, adjust the mixture to pH 9 with saturated aqueous Na$_2$CO$_3$, then extract with diethyl ether (2×50 mL). Dry the combined organic extracts over Na$_2$SO$_4$, filter and concentrate in vacuo. Purify the crude mixture by chromatography on silica gel eluting with hexane/EtOAc (19:1 to 7:3 gradient) to obtain the desired intermediate (380 mg, 66%). GC-MS m/z: 266 (M$^+$).

(±)-2-Aminomethyl-5-[1-(1,2,2,2-pentafluoroethyl)-ethoxy]-pyridine: Add (±)-4-[1-(1,1,2,2,2-pentafluoroethyl)-ethoxy]-pyridine-2-carbonitrile (280 mg, 1 mmol), 10% Pd/C (Degussa type E101, 100 mg), methanol (20 mL) and trifluoroacetic acid (3 mL) to a pressure vessel. Pressurize the vessel to 40 psi with hydrogen, and stir the mixture for 1 h (monitor the reaction by TLC). Filter the mixture through Celite® and wash the cake with warm ethanol followed by dichloromethane under a nitrogen atmosphere. Concentrate the filtrate in vacuo to obtain the crude product as a trifluoroacetic acid salt Prepare the free base using SCX chromatography, then purify by chromatography on silica gel eluting with dichloromethane/2M ammonia in methanol (20:1) to obtain the title compound (172 mg, 61%). GC-MS m/z: 270 (M$^+$).

Preparation 286

4-(1-Methyl-cyclohexylmethoxy)-benzylamine hydrochloride

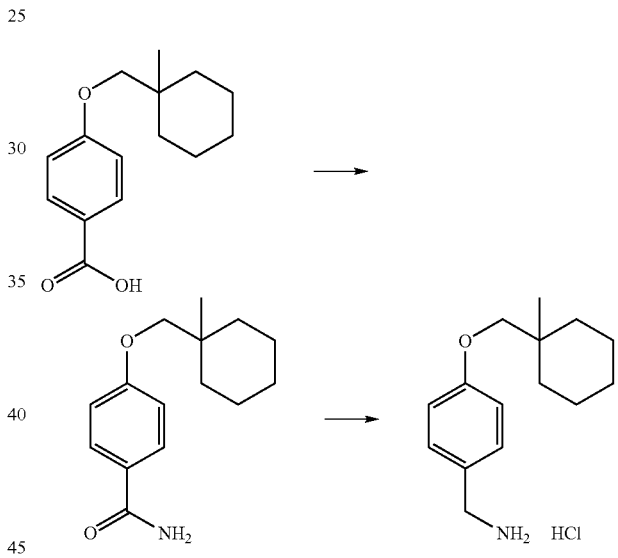

4-(1-Methyl-cyclohexylmethoxy)-benzamide: Add a drop of anhydrous DMF to a mixture of 4-(1-methyl-cyclohexylmethoxy)-benzoic acid (prepared by following the procedure described in Chem. Pharm. Bull. 1982, 30, 3601-3616) (1 g, 4.03 mmol) and thionyl chloride (3.5 mL) at room temperature. Stir the mixture for 1.5 h and then remove the excess of thionyl chloride in vacuo. Take-up the crude acid chloride in anhydrous THF (10 mL) and add the resulting solution to cold concentrated NH$_4$OH (50 mL). Stir for 2.5 h at room temperature and concentrate in vacuo. Collect the solid formed via filtration and dry in vacuo to obtain the desired intermediate (0.94 g, 94%). MS (ES+) m/z: 248 (M+H)$^+$.

4-(1-Methyl-cyclohexylmethoxy)-benzylamine hydrochloride: Add a solution of 4-(1-methyl-cyclohexylmethoxy)-benzamide (6.82 g, 27.6 mmol) in anhydrous THF (75 mL) dropwise over 45 min to a slurry of lithium aluminium hydride (1.57 g, 41.3 mmol) in diethyl ether (100 mL) at room temperature. After the addition is completed, heat the mixture at reflux for 5.5 h. Cool the reaction mixture with an ice bath and quench sequentially with water (1.6 mL), 5N aqueous NaOH (1.6 mL) and water (4.8 mL). Stir the resulting suspension for 1 h and remove the solids formed via filtration through Celite® eluting with THF. Dry the filtrate over Na₂SO₄ and treat the solution with an excess of hydrogen chloride in diethyl ether. Concentrate the mixture in vacuo to obtain the title compound (6.68 g, 90%). MS (ES+) m/z: 233 (M+H)⁺.

Preparation 287

4-Cyclopentyloxy-benzylamine

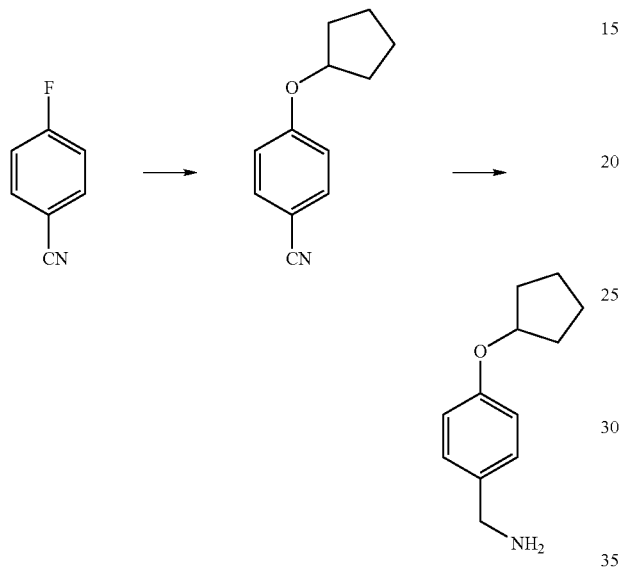

4-Cyclopentyloxy-benzonitrile: Suspend sodium hydride (336 mg, 2.8 mmol, 60% suspension in mineral oil) in anhydrous 1,4-dioxane (10 mL) under nitrogen atmosphere. Add cyclopentanol (620 mg, 7.2 mmol) and stir the resulting solution for 30 min. Add the preformed solution (3.35 mL, 2.4 mmol) to neat 4-fluorobenzonitrile (240 mg, 2 mmol) in a microwave tube and heat the sealed mixture at 100° C. for 30 min. Cool to room temperature and concentrate in vacuo. Purify by chromatography on silica gel eluting with isohexane/EtOAc (95:5 to 1:1 gradient) to obtain the desired intermediate (300 mg, 80%). GC-MS m/z: 187 (M⁺).

4-Cyclopentyloxy-benzylamine: Add a solution of 1M BH₃-THF complex in THF (4.8 mL, 4.8 mmol) to neat 4-cyclopentyloxy-benzonitrile (300 mg, 1.6 mmol) and stir the mixture for 3 h at room temperature and then for 3 h at reflux. Cool to room temperature, pour the reaction into 2N aqueous HCl (10 mL) and stir the mixture for 1 h at room temperature then concentrate in vacuo. Dissolve the crude mixture in methanol and filter through SCX column eluting with methanol followed by 3M ammonia in methanol to obtain the title compound (223 mg, 73%).

Preparations 288-292

The compounds of Preparations 288-292 may be prepared essentially as described in Preparation 287 using the appropriate alcohols. For Preparations 288, 290 and 291, sodium bis(trimethylsilyl)amide (1.2 equiv., 2M solution in THF) was used as base in the first step. Overall yields and MS (EI) data are shown in the Table below.

| Prep. | Structure | Compound | Yield (%) | MS (EI) m/z |
|---|---|---|---|---|
| 288 | 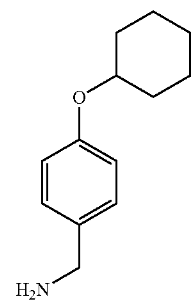 | 4-Cyclohexyloxy-benzylamine | 52 | 205 (M⁺) |
| 289 | 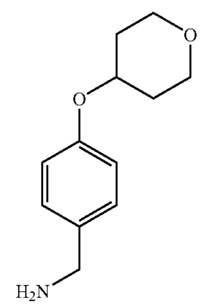 | 4-(Tetrahydro-pyran-4-yloxy)-benzylamine | 42 | 207 (M⁺) |
| 290 | 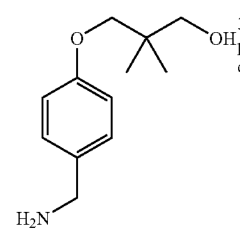 | 3-(4-Aminomethyl-phenoxy)-2,2-dimethyl-propan-1-ol | 38 | 209 (M⁺) |
| 291 | 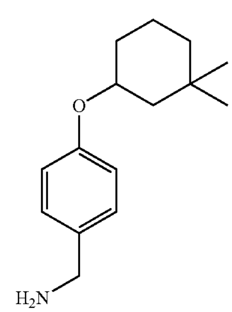 | (±)-4-(3,3-Dimethyl-cyclohexyloxy)-benzylamine | 37 | 233 (M⁺) |
| 292 | 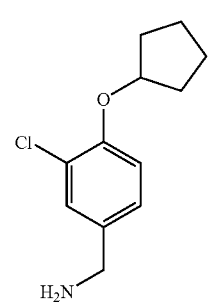 | 3-Chloro-4-cyclopentyloxy-benzylamine | 42 | 225 (M⁺) |

Preparation 293

5-Aminomethyl-2-(3,3-dimethyl-butoxy)-

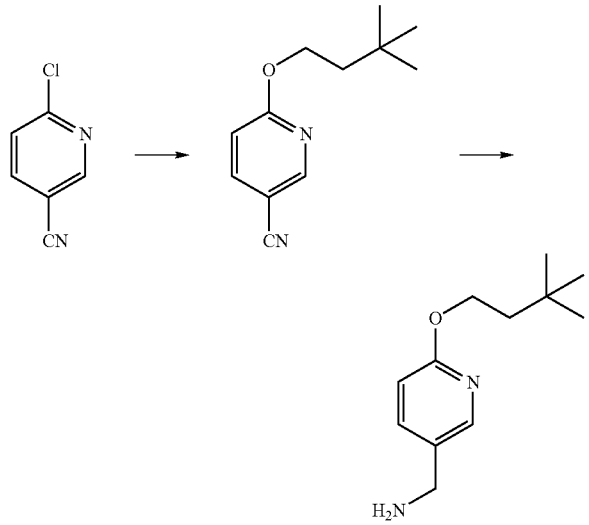

6-(3,3-Dimethyl-butoxy)-nicotinonitrile: Add sodium bis(trimethylsilyl)amide (3.95 mL, 7.9 mmol, 2M solution in THF) to a solution of 3,3-dimethyl-butan-1-ol (960 CL, 7.9 mmol) in anhydrous THF (10 mL). Stir for 30 min at room temperature and then add a solution of 6-chloro-nicotinonitrile (1 g, 7.2 mmol) in anhydrous THF (5 mL). Stir at room temperature overnight and then quench the reaction mixture with saturated aqueous NaHCO₃ (100 mL). Extract the aqueous layer with dichloromethane (3×100 mL) and wash the organic layer with brine (100 mL). Dry the combined organic extracts over MgSO₄ and concentrate in vacuo to give the desired intermediate as a yellow solid (1.4 g, 94%). GC-MS m/z: 204 (Me).

5-Aminomethyl-2-(3,3-dimethyl-butoxy)-pyridine: Dissolve 6-(3,3-dimethyl-butoxy)-nicotinonitrile (1.4 g, 6.86 mmol) in anhydrous THF (10 mL) under nitrogen and add 1M BH₃-THF complex in THF (20.6 mL, 20.6 mmol). Stir the mixture overnight under nitrogen and then pour the reaction carefully into 5N aqueous HCl (20 mL). Stir the resulting suspension for 6 h at room temperature. Then basify by adding 2N aqueous NaOH (50 mL) and extract with dichloromethane (3×100 mL). Dry the combined organic extracts over MgSO₄, filter and concentrate in vacuo. Take-up the resulting oil in methanol and filter it through an SCX column eluting with methanol followed by 3M ammonia in methanol. Concentrate in vacuo to obtain the title compound (754 g, 50%). GC-MS m/z: 208 (M>).

Preparation 294

3,3-Dimethylbutanethiol

Into four separate microwave tubes add thiourea (630 mg, 8.3 mmol) to a solution of 1-chloro-3,3-dimethylbutane (0.5 g, 4.4 mmol) in ethanol (5 mL) and heat in a sealed tube in a microwave reactor at 150 W at 100° C. for 4 h. Cool to room temperature then stand over three days. Combine the reactions and concentrate in vacuo to afford a white solid. Add 2M aqueous NaOH (50 mL) and heat at reflux overnight Cool to room temperature then acidify to pH 2 with 5M aqueous HCl (20 mL). Extract into diethyl ether (50 mL), wash with brine (30 mL) then dry over MgSO₄ and concentrate in vacuo to give the title compound as a clear oil (2 g, 100%).

Preparation 295

5-Aminomethyl-2-tert-butylthio-pyridine

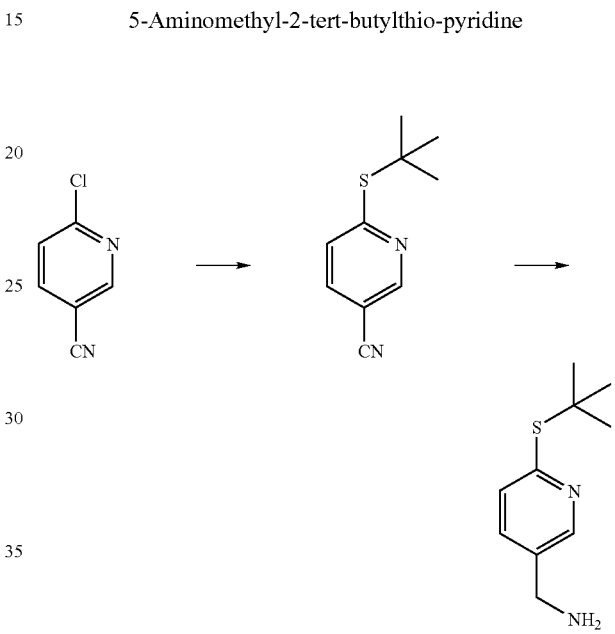

6-(tert-Butylthio)nicotinonitrile: Add sodium ethoxide (12 mL of 21% w/v in ethanol, 36 mmol) to a solution of 2-methyl-2-propanethiol (4.06 mL, 36 mmol) in anhydrous ethanol (90 mL) at 0° C. under nitrogen atmosphere. Stir the solution and allow it to warm to room temperature over 30 min. Add 6-chloronicotinonitrile (5 g, 36 mmol) and then heat the reaction to reflux overnight. Cool to room temperature, add saturated aqueous NaHCO₃ and concentrate in vacuo. Extract into EtOAc or dichloromethane and wash with brine. Dry over MgSO₄ and concentrate in vacuo to give the desired intermediate as orange crystals (6.31 g, 91%). MS (ES+) m/z: 193 (M+H)⁺.

5-Aminomethyl-2-tert-butylthio-pyridine: Use a method similar to the General Procedure 6-5 to react 6-(tert-butylthio)nicotinonitrile (4.4 g, 22.7 mmol) in anhydrous THF (25 mL) with 1M BH₃-THF complex in THF (25 mL, 25 mmol). Add 5M aqueous HCl (10 mL) cautiously and stir the mixture overnight at room temperature. Extract into EtOAc, wash with brine, dry over MgSO₄ and concentrate in vacuo to give an orange solid. Dissolve the crude mixture in methanol and filter through an SCX column eluting with methanol followed by 3M ammonia in methanol to obtain the title compound (2.74 g, 61%). MS (ES+) m/z: 197 (M+H)⁺.

Preparations 296-303

The compounds of Preparations 296-303 may be prepared essentially as described in Preparation 295 using the appropriate thiol and 6-chloronicotinonitrile (Preparations 296-298) or the appropriate aryl fluoride (Preparations 299-303). Overall yields and MS (ES+) data are shown in the Table below.

| Prep. | Structure | Compound | Yield (%) | MS (ES+) m/z |
|---|---|---|---|---|
| 296 | 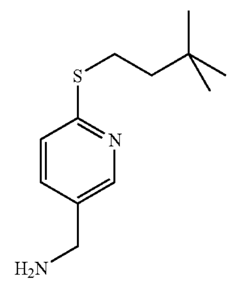 | 5-Aminomethyl-2-(3,3-dimethyl-butylthio)-pyridine | 5 | 225 (M + H)+ |
| 297 | 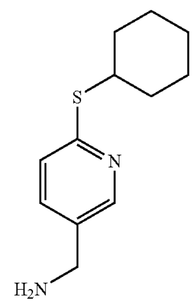 | 5-Aminomethyl-2-cyclohexylthio-pyridine | 47 | 223 (M + H)+ |
| 298 | 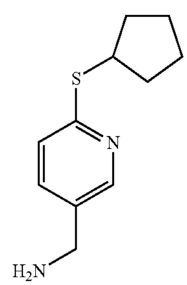 | 5-Aminomethyl-2-cyclopentylthio-pyridine | 63 | 209 (M + H)+ |
| 299 | 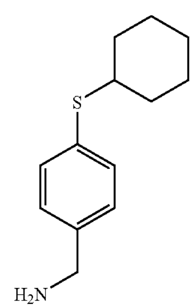 | 4-Cyclohexylthio-benzylamine | 30 | 205 (M + H − NH$_3$)+ |
| 300 | 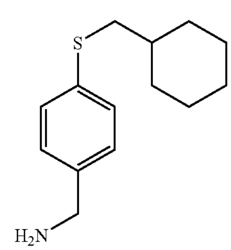 | 4-Cyclohexylmethylthio-benzylamine | 30 | 219 (M + H − NH$_3$)+ |

-continued

| Prep. | Structure | Compound | Yield (%) | MS (ES+) m/z |
|---|---|---|---|---|
| 301 | 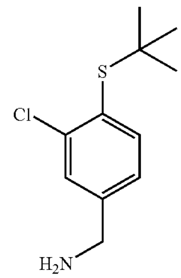 | 4-tert-Butylthio-3-chloro-benzylamine | 52 | 213 $(M + H - NH_3)^+$ |
| 302 | 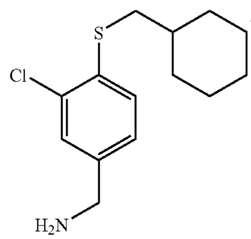 | 4-Cyclohexylmethylthio-3-chloro-benzylamine | 31 | 253 $(M + H - NH_3)^+$ |
| 303 | 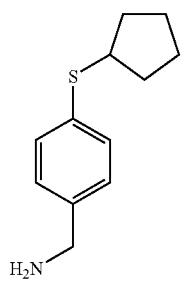 | 4-Cyclopentylthio-benzylamine | 61 | 208 $(M + H - NH_3)^+$ |

Preparation 304

5-Aminomethyl-2-ethoxy-pyridine

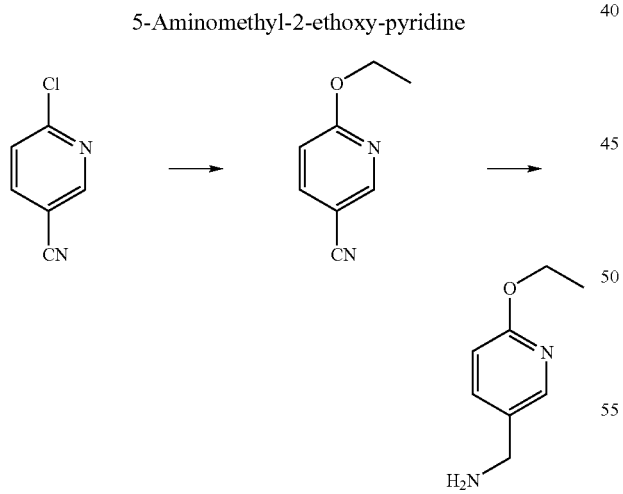

6-(Ethoxy)nicotinonitrile: Add sodium ethoxide (1.6 mL of 21% w/v in ethanol, 4.8 mmol) to a solution of 6-chloronicotinonitrile (612 mg, 4.41 mmol) in anhydrous ethanol (15 mL) and heat the reaction at reflux for 3 h. Cool to room temperature and stir overnight under nitrogen atmosphere. Concentrate in vacuo and dissolve the residue into dichloromethane. Wash with saturated aqueous $NaHCO_3$, dry over $MgSO_4$ and concentrate in vacuo to give the desired intermediate as an off-white solid (545 mg, 83%).

5-Aminomethyl-2-ethoxy-pyridine: Add a solution of 1M $BH_3$-THF complex in THF (7 mL, 7 mmol) to a solution of 6-(ethoxy)nicotinonitrile (911 mg, 4.41 mmol) in anhydrous THF (7 mL) and stir the mixture overnight at reflux. Add a second aliquot of 1M $BH_3$-THF complex in THF (7 mL, 7 mmol) and stir the mixture overnight at reflux. Add 5N aqueous HCl (10 mL) cautiously and stir the mixture overnight at room temperature. Concentrate in vacuo then dissolve the crude mixture in methanol and filter through an SCX column eluting with methanol followed by 3M ammonia in methanol to obtain the title compound (250 mg, 40%). MS (ES+) m/z: 153 $(M+H)^+$.

Preparation 305

4-Ethoxy-3-chloro-benzylamine

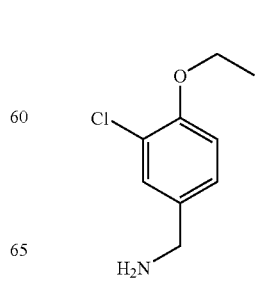

The compound of Preparation 305 may be prepared essentially as described in Preparation 304 using the appropriate aryl fluoride (38% yield, MS (ES+) m/z 169 M+H−NH₃)⁺).

Preparation 306

4-(Tetrahydro-pyran-4-yloxymethyl)-benzylamine

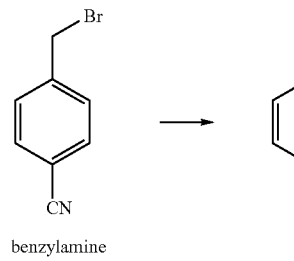
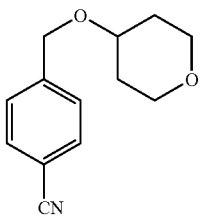

4-(tetrahydro-pyran-4-yloxymethyl)-benzonitrile: Add sodium bis(trimethylsilyl)amide (2.8 mL, 5.61 mmol, 2M solution in THF) to a solution of tetrahydro-pyran-4-ol (572 mg, 5.61 mmol) in anhydrous THF (20 mL) and stir for 30 min. Add a solution of 4-bromomethyl-benzonitrile (1 g, 5.1 mmol) in anhydrous THF (5 mL) and stir the resulting mixture overnight at room temperature. Concentrate in vacuo and purify the crude mixture by chromatography on silica gel eluting with cyclohexane/EtOAc (98:2 to 1:1 gradient) to obtain the desired intermediate as a white solid (845 mg, 76%). GC-MS m/z: 217 (M⁺);

4-(Tetrahydro-pyran-4-yloxymethyl)-benzylamine: Use a method similar to the General Procedure 6-5 to reduce 4-(tetrahydro-pyran-4-yloxymethyl)-benzonitrile (845 mg, 4 mmol). Reflux overnight to obtain the title compound (812 mg, 91%). MS (ES+) m/z: 222.2 (M+H)⁺.

Preparations 307-309

The compounds of Preparations 307-309 may be prepared essentially as described in Preparation 306 using 4-bromomethyl-benzonitrile and the appropriate alcohol. Overall yields and MS (ES+) data are shown in the Table below.

| Prep. | Structure | Compound | Yield (%) | MS (ES+) m/z |
|---|---|---|---|---|
| 307 | 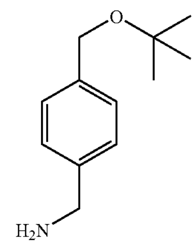 | 4-tert-Butoxymethyl-benzylamine | 22 | 194 (M + H)⁺ |
| 308 | 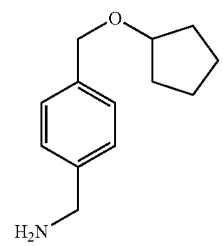 | 4-Cyclo-pentyloxy-methyl-benzylamine | 72 | 206 (M + H)⁺ |
| 309 | 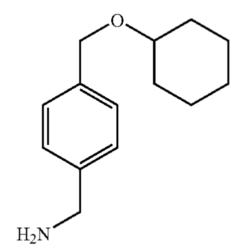 | 4-Cyclo-hexyloxy-methyl-benzylamine | 58 | 220 (M + H)⁺ |

Preparation 310

4-(2,2-Dimethyl-propoxymethyl)-benzylamine

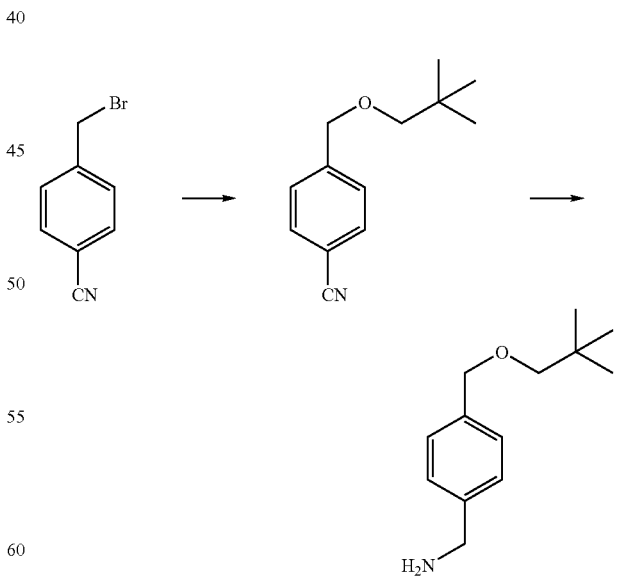

4-(2,2-Dimethyl-propoxymethyl)-benzonitrile: Add sodium bis(trimethylsilyl)amide (3 mL, 6 mmol, 2M solution in THF) to a solution of 2,2-dimethyl-1-propanol (528 mg, 6 mmol) in anhydrous 1,4-dioxane. Stir until the suspension becomes homogenous. Then add a solution of 4-cyanobenzyl bromide (980 mg, 5 mmol) in anhydrous 1,4-dioxane (3 mL). Heat the mixture in a microwave oven at 100° C. for 30 min. Cool to room temperature, add water (50 mL) and extract with EtOAc (3×50 mL). Dry the combined organic extracts over MgSO$_4$, and concentrate in vacuo. Purify the crude mixture by chromatography on silica gel eluting with isohexane/EtOAc (95:5 to 1:1 gradient) to obtain the desired intermediate (811 mg, 80%).

4-(2,2-Dimethyl-propoxymethyl)-benzylamine: Add 1M BH$_3$-THF complex in THF (16 mL, 16 mmol) to neat 4-(2,2-dimethyl-propoxymethyl)-benzonitrile (3.043 g, 15 mmol) and stir the mixture overnight at room temperature. Add methanol and stir until hydrogen evolution stops. Concentrate the solution in vacuo. Dissolve the crude mixture in methanol and filter through an SCX column eluting with methanol followed by 3M ammonia in methanol. Concentrate in vacuo to obtain the title compound (3 g, 96%).

Preparation 311

4-Cycloheptyloxy-benzylamine

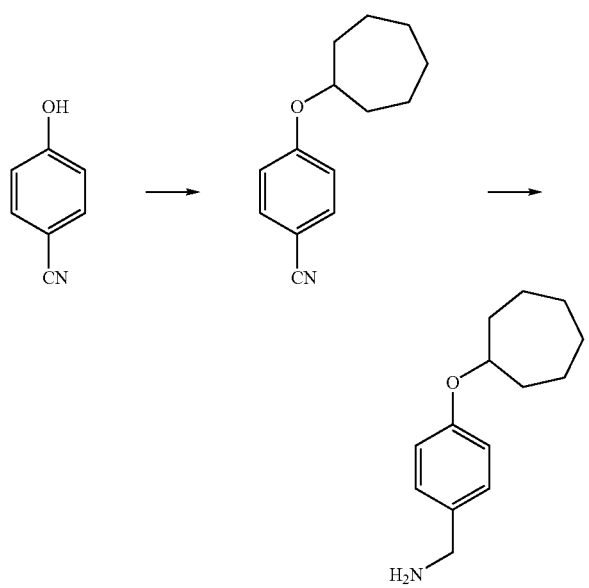

4-Cycloheptyloxy-benzonitrile: Under a nitrogen atmosphere, add 4-hydroxybenzonitrile (4 g, 33.5 mmol), cycloheptanol (2.55 g, 22.3 mmol), tri-n-butylphosphine (8.25 mL, 33.5 mmol), and azodicarboxylate dipiperidine (8.45 g, 33.5 mmol) to anhydrous THF (60 mL) at 0° C. Stir the mixture at 0° C. for 1 h and then at room temperature for 12 h. Dilute with EtOAc (50 mL) and water (50 mL). Separate the layers and extract the aqueous phase with EtOAc (4×30 mL). Wash the combined organic extracts with water (30 mL) and brine (20 mL). Dry over Na$_2$SO$_4$, filter and concentrate in vacuo. Purify the crude mixture by chromatography on silica gel (120 g RediSep column) eluting with hexane/EtOAc (1:0 to 1:1 gradient over 1.25 h; 80 mL/min) to provide the desired intermediate as a colorless oil (2.77 g, 58%). MS (APCI) m/z: 216 (M+H)$^+$.

4-Cycloheptyloxy-benzylamine: Dissolve 4-cycloheptyloxy-benzonitrile (2 g, 9.29 mmol) in anhydrous THF (20 mL) and cool to 0° C. Add borane dimethylsulfide complex (2.8 mL, 27.9 mmol, 10-12 M solution), stir at 0° C. for 0.5 h and then heat at reflux for 1 h. Cool the mixture to 0° C., add methanol (5 mL) and stir for 15 min. Add 2M aqueous HCl (15 mL) and stir for 30 min at room temperature. Concentrate the mixture in vacuo and purify the residue by chromatography on silica gel (45 g RediSep column) eluting with a gradient of dichloromethane in chloroform/methanol/concentrated ammonium hydroxide (80:18:2) over 30 min (80 ml/min) to provide the title compound as a colorless oil (1.87 g, 97%). MS (APCI) m/z: 220 (M+H)$^+$.

Preparation 312

4-Cycloheptylthio-benzylamine

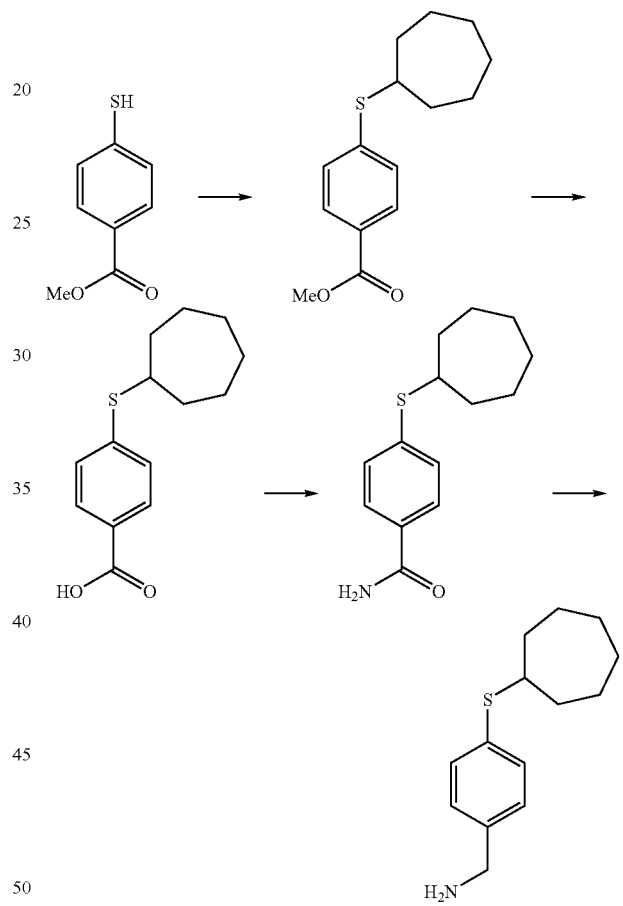

Methyl 4-cycloheptylthio-benzoate: Under a nitrogen atmosphere, add methyl 4-mercaptobenzoate (2.5 g, 15 mmol), cycloheptanol (2.55 g, 22.3 mmol), tri-n-butylphosphine (5.26 g, 26 mmol) and azodicarboxylate dipiperidine (6.56 g, 26 mmol) to anhydrous THF (50 mL) at 0°C. Stir the mixture at 0° C. for 1 h and then at room temperature for 12 h. Dilute with EtOAc (50 mL) and water (50 mL) and extract the aqueous phase with EtOAc (4×30 mL). Wash the combined organic extracts with water (30 mL) and brine (20 mL). Dry the organic phase over Na$_2$SO$_4$, filter and concentrate in vacuo. Purify the crude mixture by chromatography on silica gel (120 g RediSep column) eluting with hexane/EtOAc (1:0 to 1:1 gradient over 1.25 h; 80 mL/min) to provide the desired intermediate as a colorless oil (1.12 g, 40%). MS (APCI) m/z: 265 (M+H)$^+$.

4-Cycloheptylthio-benzoic acid: Add methyl 4-cycloheptylthio-benzoate (1.1 g, 4.16 mmol) and sodium hydroxide (500 mg, 12.5 mmol) to methanol (20 mL) and stir overnight. Add 2M aqueous HCl (20 mL) and extract the aqueous phase with dichloromethane. Wash the combined organic extracts with water (20 mL) and brine (20 mL). Dry the organic solution over $Na_2SO_4$, filter and concentrate in vacuo to provide the desired intermediate as a white solid (984 mg, 94%). MS (APCI) m/z: 251 $(M+H)^+$.

4-Cycloheptylthio-benzamide: Add thionyl chloride (1.35 mL, 18.4 mmol) to a mixture of 4-cycloheptylthio-benzoic acid (984 mg, 3.93 mmol) in dichloromethane (15 mL) at 0° C. Heat the mixture to reflux for 1 h. Cool the mixture to room temperature and concentrate in vacuo. Dissolve the residue in dichloromethane (20 mL) and cool to 0° C. Add triethylamine (1.1 mL, 7.86 mmol) and bubble ammonia gas through the solution Warm the mixture to room temperature and stir for 1 h. Dilute with water (20 mL) and extract the aqueous phase with dichloromethane (3×20 mL). Wash the combined organic extracts with saturated aqueous $NaHCO_3$ (20 mL). Dry the organic solution over $Na_2SO_4$, filter and concentrate in vacuo to provide the desired intermediate as an off-white solid (976 mg, 99%). MS (APCI) m/z: 250 $(M+H)^+$.

4-Cycloheptylthio-benzylamine: Under a nitrogen atmosphere, add 4-cycloheptylthio-benzamide (976 mg, 3.91 mmol) to a slurry of lithium aluminum hydride (0.398 mg, 11.7 mmol) in anhydrous THF (25 mL) at 0° C. Heat the mixture for 1 h. Cool the mixture to 0° C. and add diethyl ether (50 mL). Carefully add water (0.4 mL), 3M aqueous NaOH (0.4 mL) and water (1.2 mL). Filter the solid residue and concentrate the filtrate in vacuo. Purify the crude mixture by chromatography on silica gel (45 g RediSep column) eluting with a gradient of dichloromethane in chloroform/methanol/concentrated ammonium hydroxide (80:18:2) over 45 min (80 mL/min) to give the title compound as a colorless oil (530 mg, 57%). MS (ES+) m/z: 236 $(M+H)^+$.

Preparation 313

4-Cyclohexylmethyl-benzylamine hydrochloride 4-(Cyclohexyl-hydroxy-methyl)-benzonitrile: Dissolve 4-formyl-benzonitrile (5 g, 38.1 mmol) in anhydrous toluene (50 mL). Add chlorodicyclohexylborane (39 mL, 39 mmol, 1M solution in hexane) and 2,6-lutidine (4.25 mL, 39 mmol) and stir the mixture overnight at room temperature. Cool to 0° C., add aqueous hydrogen peroxide (5.4 mL, 48 mmol, 30%) and 3M aqueous NaOH (16 mL, 48 mmol) and stir for 15 min. Add EtOAc and extract the aqueous phase with EtOAc. Wash the combined organic extracts with water and brine. Dry the organic solution over $Na_2SO_4$, filter and concentrate in vacuo. Purify the crude mixture by chromatography on silica gel (45 g RediSep column) eluting with hexane/EtOAc (1:0 to 1:1 gradient over 60 min; 80 mL/min) to provide the desired intermediate as a clear oil (2.3 g, 23%). MS (APCI) z/z: 197 $(M-H_2O)^+$.

4-(Cyclohexyl-methanesulfonyloxy-methyl)-benzonitrile: Dissolve 4-(cyclohexyl-hydroxy-methyl)-benzonitrile (1 g, 4.66 mmol), and triethylamine (1.3 mL, 9.3 mmol) in dichloromethane (20 mL). Cool the mixture to 0° C., add methanesulfonyl chloride (1.49 mL, 5.34 mmol) and stir the solution for 2 h at 0° C. Add water (10 mL) and saturated aqueous $NaHCO_3$ (10 mL). Separate the layers and extract back the aqueous phase with dichloromethane (3×20 mL). Combine the organic layers, wash with water (20 mL), dry over $Na_2SO_4$, filter and concentrate in vacuo to provide the desired intermediate as a yellow oil (1.29 g, 94%). MS (APCI) m/z: 294 $(M+H)^+$.

4-Cyclohexylmethyl-benzylamine hydrochloride: Dissolve 4-(cyclohexyl-methanesulfonyloxy-methyl)-benzonitrile (1.36 g, 4.64 mmol) in diethyl ether (20 mL) and cool the solution to 0° C. Add lithium aluminum hydride (528 mg, 13.9 mmol) and stir the mixture at 0° C. for 2 h and then at room temperature for 3 h. Cool the mixture to 0° C. and carefully add water (0.5 mL), 3M aqueous NaOH (0.55 mL), and water (1.5 mL). Filter the solid residue and concentrate the filtrate in vacuo. Dissolve the crude mixture in diethyl ether and bubble hydrogen chloride to form a white precipitate. Filter and dry the solid in vacuo to provide the title compound as a white solid (420 mg, 44%). MS (APCI) m/z: 204 $(M+H)^+$.

Preparation 314

4-(2-Methyl-butyl)-benzylamine

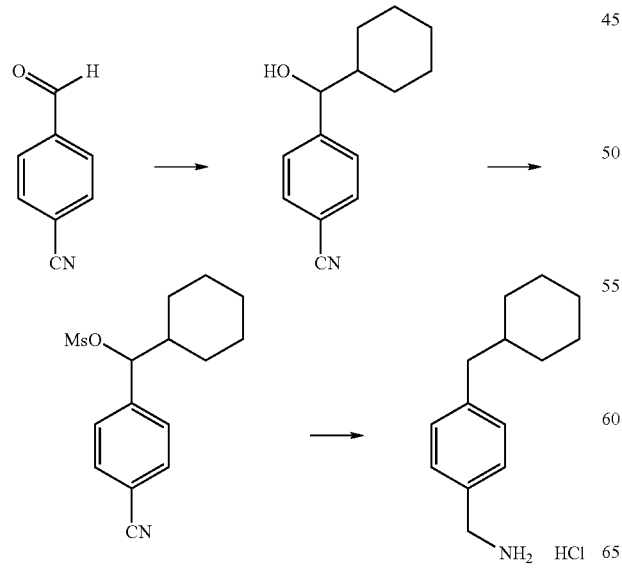

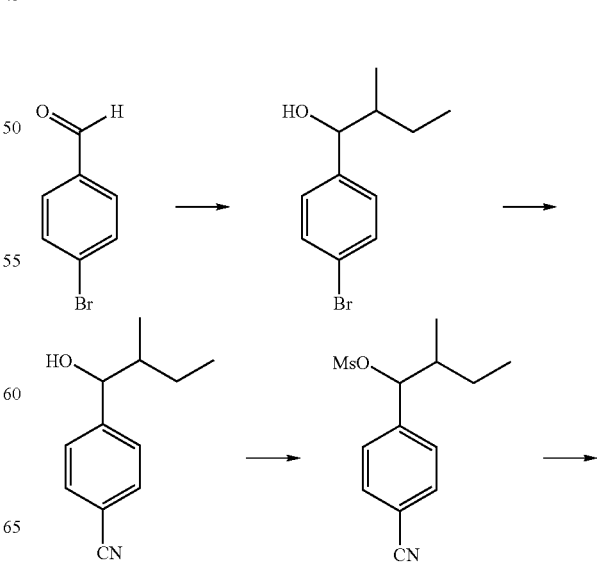

-continued

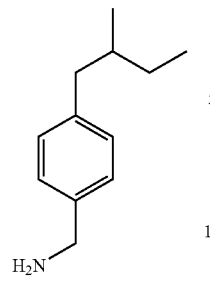

4-(1-Hydroxy-2-methyl-butyl)-1-bromo-benzene: Add slowly a solution of 2-bromo-butane (4.8 g, 35 mmol) in anhydrous THF (20 mL) to a stirring mixture of magnesium (980 mg, 37 mmol) and anhydrous THF (10 mL) under a nitrogen atmosphere. Heat the mixture at reflux for 30 min. Cool the mixture to room temperature and add 4-bromobenzaldehyde (5.36 g, 29 mmol). After stirring for 5 min, cool the mixture in an ice-bath and acidify with 3N aqueous HCl (50 mL). Dilute the mixture with water and extract twice with diethyl ether. Wash the combined organic extracts with water and brine. Dry the organic phase over $Na_2SO_4$, filter and concentrate in vacuo. Purify by chromatography on silica gel eluting with hexane/EtOAc (1:0, 20:1 and 1:1) to provide the desired intermediate as a clear oil (2 g, 28%). MS (APCI) m/z: 243 $(M+H)^+$.

4-(1-Hydroxy-2-methyl-butyl)-benzonitrile: Add 4-(1-hydroxy-2-methyl-butyl)-1-bromo-benzene (1.9 g, 7.8 mmol), zinc cyanide (1.82 g, 15.6 mmol), and tetrakistriphenylphosphine palladium(0) (260 mg, 0.22 mmol) to anhydrous DMF (40 mL) under a nitrogen atmosphere. Heat the mixture at 90° C. for 12 h. Cool the mixture to room temperature, dilute with water and extract the aqueous phase twice with dichloromethane. Wash the combined organic extracts with water and brine. Dry the organic solution over $Na_2SO_4$, filter and concentrate in vacuo. Purify by chromatography on silica gel eluting with hexane/EtOAc (1:0 and 20:1) to provide the desired intermediate (1.2 g, 75%). MS (APCI) m/z: 190 $(M+H)^+$.

4-(1-Methanesulfonyloxy-2-methyl-butyl)-benzonitrile: Add methanesulfonyl chloride (540 mg, 4.72 mmol) to a solution of 4-(1-hydroxy-2-methyl-butyl)-benzonitrile (800 mg, 4.23 mmol) and triethylamine (0.88 mL, 6.35 mmol) in dichloromethane (10 mL) at 0° C. Warm the mixture to room temperature and stir for 1 h. Dilute the mixture with water and dichloromethane. Extract the aqueous layer with dichloromethane. Wash the combined organic extracts with water. Dry the organic solution over $Na_2SO_4$, filter and concentrate in vacuo to provide the desired intermediate as a clear oil (1.38 g) that was used without further purification. MS (APCI) m/z: 268 $(M+H)^+$.

4-(2-Methyl-butyl)-benzylamine: Under a nitrogen atmosphere, add a mixture of 4-(1-methanesulfonyloxy-2-methyl-butyl)-benzonitrile (1.3 g, 4.9 mmol) in diethyl ether (5 mL) to a slurry of lithium aluminum hydride (820 mg, 19.5 mmol) in diethyl ether (25 mL) at 0° C. Heat the mixture under reflux for 1 h. Cool the mixture in an ice-bath and add water (0.9 mL), 15% aqueous NaOH (0.9 mL) and water (2.8 mL). Apply the mixture to a silica gel column eluting with dichloromethane and 5:1 dichloromethane in chloroform/methanol/concentrated ammonium hydroxide (80:18:2) to provide the title compound (450 mg, 52%). MS (ES+) m/z: 178 $(M+H)^+$.

Preparation 315

4-(3,3-Dimethyl-butyl)-benzylamine

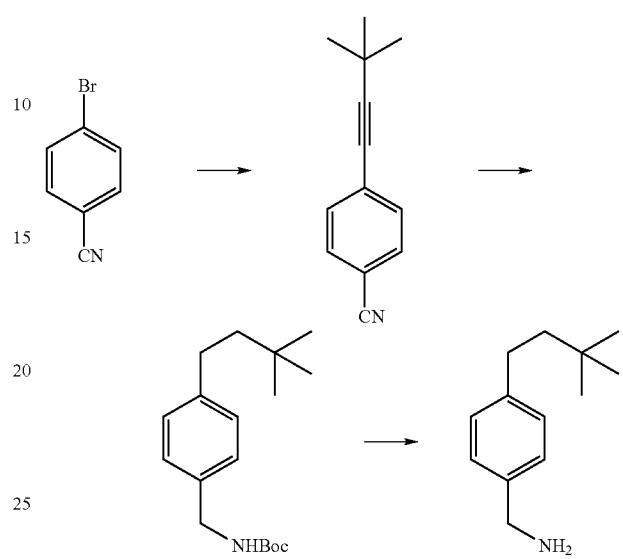

4-(3,3-Dimethyl-but-1-ynyl)-benzonitrile: Dissolve 4-bromobenzonitrile (3 g, 16.48 mmol) in anhydrous DMF (30 mL) in a sealed tube. Degas the solution, purge with nitrogen and add tris(dibenzylideneacetone)dipalladium(0) (453 mg, 0.49 mmol), copper(I) iodide (188 mg, 0.99 mmol), triphenylphosphine (1.08 g, 4.12 mmol), triethylamine (10 mL) and 3,3-dimethylbutyne (6.1 mL, 49.44 mmol). Heat the mixture at 90° C. overnight. Cool to room temperature, add water and extract the aqueous phase twice with EtOAc. Dry the combined organic extracts over $MgSO_4$, filter and concentrate in vacuo. Purify the crude mixture by chromatography on silica gel eluting with hexane and hexane/EtOAc (19:1, 9:1) to give the desired intermediate as a solid (2.75 g, 92%).

N-(tert-Butoxycarbonyl)-4-(3,3-dimethyl-butyl)-benzylamine: Dissolve 4-(3,3-dimethyl-but-1-ynyl)-benzonitrile (0.85 g, 4.64 mmol) in methanol (50 mL). Add 10% Pd/C (Degussa type E101, 0.68 g) and di-tert-butyl-dicarbonate (1.21 g, 5.57 mmol). Submit the mixture to hydrogenation under atmospheric pressure (balloon) for 6 h. Filter the catalyst through Celite® and concentrate the filtrate in vacuo. Purify the crude mixture by chromatography on silica gel eluting with hexane and hexane/EtOAc (9:1, 4:1) to provide the desired intermediate as an oil (1.25 g, 93%). MS (ES+) m/z: 314 $(M+Na)^+$.

4-(3,3-Dimethyl-butyl)-benzylamine: Add 4N hydrogen chloride in dioxane (15 mL) to a stirred solution of N-(tert-butoxycarbonyl)-4-(3,3-dimethyl-butyl)-benzylamine (1.25 g, 4.29 mmol) in methanol (20 mL) and stir at room overnight. Concentrate in vacuo and wash the solid with diethyl ether. Suspend the solid in dichloromethane and saturated aqueous $NaHCO_3$ and stir until both phases are clear (15 min). Extract the aqueous phase twice with dichloromethane. Dry the combined organic extracts over $MgSO_4$, filter and concentrate in vacuo to give the title compound as an oil (0.654 g, 80%) that was used without any further purification. MS (ES+) m/z: 192 $(M+H)^+$.

Preparation 316

3-Aminomethyl-6-(3,3-dimethyl-butyl)-pyridine

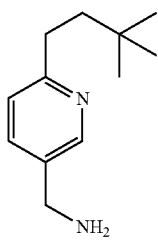

The title compound may be prepared essentially as described in Preparation 315 by using 6-bromonicotinonitrile (45% yield, MS (ES+) m/z 193 (M+H)+).

Preparation 317

3-Aminomethyl-6-cyclohexylmethyl-pyridine

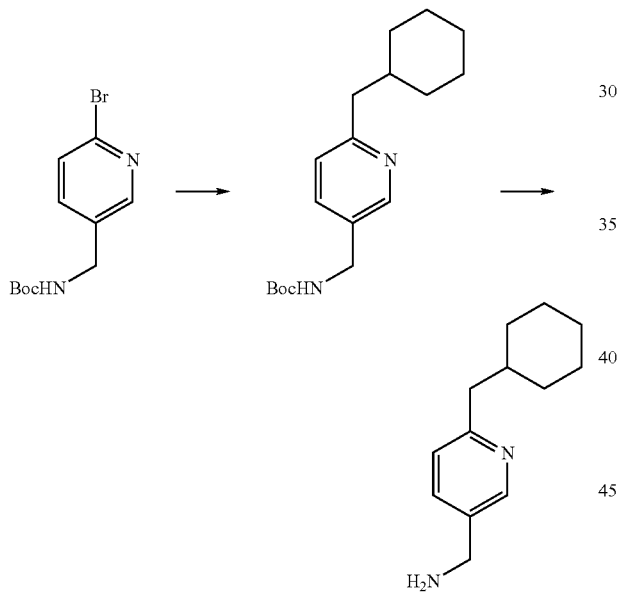

3-tert-Butoxycarbonylaminomethyl-cyclohexylmethyl-pyridine: Dissolve 2-bromo-5-tert-butoxycarbonylaminomethyl-pyridine (500 mg, 1.74 mmol) in anhydrous THF (5 mL) in a sealed tube. Degas the solution, purge with nitrogen and add 1,1'-[bis(diphenylphosphino)ferrocene]dichloropalladium(II) (127 mg, 0.174 mmol) and 0.5M cyclohexylmethylzinc bromide in THF (10.4 mL, 5.22 mmol). Heat the mixture at 60° C. overnight. Cool to room temperature and dilute the reaction mixture with EtOAc. Add water and filter the precipitate over Celite®. Dry the organic phase over MgSO$_4$, filter and concentrate in vacuo. Purify the crude mixture by chromatography on silica gel eluting with hexane and hexane/EtOAc (4:1, 3:2) to give the desired intermediate as an oil (359 mg, 68%). MS (ES+) m/z: 305 (M+H)+.

3-Aminomethyl-6-cyclohexylmethyl-pyridine: Add 4N hydrogen chloride in dioxane (10 mL) to a solution of 3-tert-butoxycarbonylaminomethyl-6-cyclohexylmethyl-pyridine (345 mg, 1.13 mmol) in EtOAc (10 mL) and stir overnight Concentrate in vacuo, suspend the solid obtained in diethyl ether and add hexane. Filter and wash the solid with hexane. Suspend the solid into dichloromethane, add saturated aqueous NaHCO$_3$ and stir until both phases are clear (15 min). Extract the aqueous phase twice with dichloromethane. Dry the combined organic extracts over MgSO$_4$, filter and concentrate in vacuo to obtain the title compound as an oil (205 mg, 97%) that was used without any further purification. MS (ES+) m/z: 205 (M+H)+.

Preparation 318

2-Aminomethyl-5-(3,3-dimethyl-butyl)-pyridine

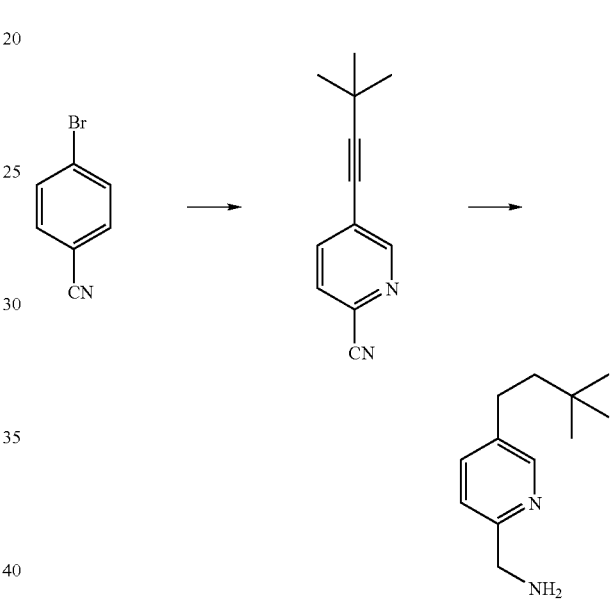

5-(3,3-Dimethyl-but-1-ynyl)-2-cyano-pyridine: Dissolve 5-bromo-2-cyano-pyridine (316 mg, 1.72 mmol) in anhydrous DMF (7 mL) in a sealed tube. Degas the solution, purge with nitrogen and add tris(dibenzylideneacetone)dipalladium (0) (47 mg, 0.05 mmol), copper(I) iodide (20 mg, 0.1 mmol), triphenylphosphine (113 mg, 0.43 mmol), triethylamine (2 mL) and 3,3-dimethylbutyne (0.64 mL, 5.16 mmol). Heat the mixture at 90° C. overnight. Cool to room temperature, add water and extract the aqueous phase twice with EtOAc. Dry the combined organic extracts over MgSO$_4$, filter and concentrate in vacuo. Purify the crude mixture by chromatography on silica gel eluting with hexane and hexane/EtOAc (19:1) to give the desired intermediate as a solid (310 mg, 97%).

2-Aminomethyl-5-(3,3-dimethyl-butyl)-pyridine: Dissolve 5-(3,3-dimethyl-but-1-ynyl)-2-cyano-pyridine (255 mg, 1.5 mmol) in methanol (15 mL). Add 10% Pd/C (Degussa type E101, 230 mg) and submit the mixture to hydrogenation under atmospheric pressure (balloon) overnight. Filter the catalyst through Celite® and concentrate the filtrate in vacuo to provide the title compound as a solid (231 mg, 87%) that was used without any further purification. MS (ES+) m/z: 193 (M+H)+.

Preparation 319

4-(1,3,3-Trimethyl-butyl)-benzylamine

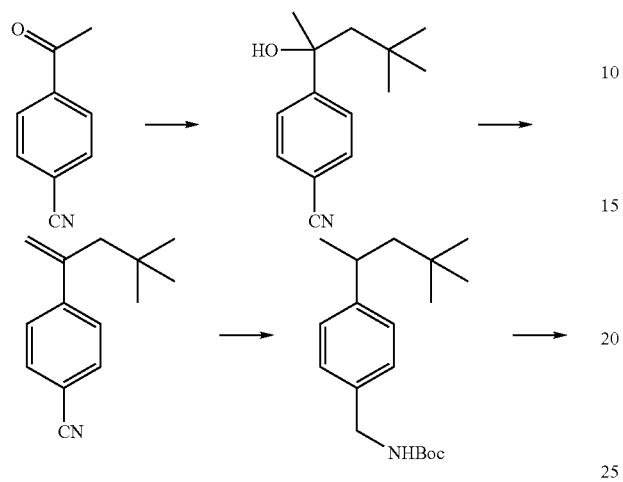

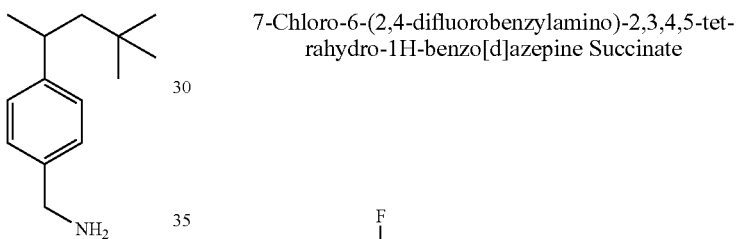

4-(1-Hydroxy-1,3,3-trimethyl-butyl)-benzonitrile: Dissolve 4-acetylbenzonitrile (1 g, 6.88 mmol) in diethyl ether/THF (1:1, 60 mL) and cool the solution to 0° C. Add 1M neopentylmagnesium chloride in diethyl ether (8.3 mL, 8.3 mmol) under nitrogen and stir the mixture at room temperature overnight. Add saturated aqueous NH$_4$Cl and extract the mixture twice with EtOAc. Dry the combined organic extracts over MgSO$_4$, filter and concentrate in vacuo. Purify the crude mixture by chromatography on silica gel eluting with hexane and hexane/EtOAc (19:1, 9:1) to give the desired intermediate (364 mg, 24%).

4-(3,3-Dimethyl-1-methylene-butyl)-benzonitrile: Add p-toluenesulfonic acid monohydrate (308 mg, 1-62 mmol) to a solution of 4-(1-hydroxy-1,3,3-trimethyl-butyl)-benzonitrile (352 mg, 1.62 mmol) in toluene (10 mL). Heat the solution to 100° C. for 30 min. Cool the reaction mixture to room temperature, dilute the reaction mixture with EtOAc and wash the organic phase with saturated aqueous NaHCO$_3$. Dry the organic phase over MgSO$_4$, filter and concentrate in vacuo. Purify the crude mixture by chromatography on silica gel eluting with hexane and hexane/EtOAc (98:2, 19:1) to give the desired intermediate as an oil (200 mg, 62%).

N-(tert-Butoxycarbonyl)-4-(1,3,3-trimethyl-butyl)-benzylamine: Dissolve 4-(3,3-dimethyl-1-methylene-butyl)-benzonitrile (164 mg, 0.82 mmol) in methanol (15 mL). Add 10% Pd/C (Degussa type E101, 130 mg) and di-tert-butyl-dicarbonate (197 mg, 0.902 mmol). Submit the mixture to hydrogenation under atmospheric pressure (balloon) for 3 h. Filter the catalyst through Celite® and concentrate the filtrate in vacuo. Purify the crude mixture by chromatography on silica gel eluting with hexane and hexane/EtOAc (19:1, 9:1) to provide the desired intermediate as an oil (227 mg, 90%). MS (ES+) m/z: 328 (M+Na)$^+$.

4-(1,3,3-Trimethyl-butyl)-benzylamine: Add 4N hydrogen chloride in dioxane (10 mL) to a stirred solution of N-(tert-butoxycarbonyl)-4-(1,3,3-trimethyl-butyl)-benzylamine (225 mg, 0.74 mmol) in EtOAc (15 mL) and stir the mixture at ambient temperature overnight. Concentrate in vacuo and wash the solid with diethyl ether. Suspend the solid in dichloromethane and saturated aqueous NaHCO$_3$ and stir until both phases are clear (15 min). Extract the aqueous phase twice with dichloromethane. Dry the combined organic extracts over MgSO$_4$, filter and concentrate in vacuo to give the title compound as an oil (0.136 g, 90%) that was used without any further purification. MS (ES+) m/z: 206 (M+H)$^+$.

EXAMPLE 537

7-Chloro-6-(2,4-difluorobenzylamino)-2,3,4,5-tetrahydro-1H-benzo[d]azepine Succinate Use a method similar to the General Procedure 5-1 to react 7-chloro-3-(2,2,2-trifluoroacetyl)-6-trifluoromethanesulfonyloxy-2,3,4,5-tetrahydro-1H-benzo[d]azepine (3 g, 7.06 mmol), palladium(II) acetate (0.16 g, 0.71 mmol), BINAP (0.88 g, 1.41 mmol), 2,4-difluorobenzylamine (3.03 g, 21.18 mmol) and cesium carbonate (3.22 g, 9.88 mmol) in degassed toluene (120 mL). Degas the mixture with vacuum/nitrogen purge and heat to 100° C. for 16 h. Cool the mixture to room temperature, dilute with EtOAc, filter through Celite® and concentrate in vacuo to give a brown oil. Purify the crude mixture by chromatography on silica gel eluting with hexane and then hexane/THF (95:5) to obtain 7-chloro-6-(2,4-difluorobenzylamino)-3-(2,2,2-trifluoroacetyl)-2,3,4,5-tetrahydro-1H-benzo[d]azepine as oil (2.25 g, 76%). MS (ES+) m/z: 419 (M+H)$^+$.

Use a method similar to the General Procedure 1-2, using 7-chloro-6-(2,4-difluorobenzylamino)-3-(2,2,2-trifluoroacetyl)-2,3,4,5-tetrahydro-1H-benzo[d]azepine (2.2 g, 5.26 mmol), to give the free base of the title compound as an oil (1.66 g, 98%) that solidified upon standing at room temperature and was used without further purification. MS (ES+) m/z: 323 (M+H)$^+$. Use a method similar to the General Procedure 2-1, using 7-chloro-6-(2,4-difluorobenzylamino)-2,3,4,5-tetrahydro-1H-benzo[d]azepine (1.66 g, 5.14 mmol) to give the title compound as a white solid (2.03 g, 90%). MS (ES+) m/z: 323 (M+H)$^+$.

EXAMPLE 538

7-Chloro-6-(2,5-difluorobenzylamino)-2,3,4,5-tetrahydro-1H-benzo[d]azepine Succinate

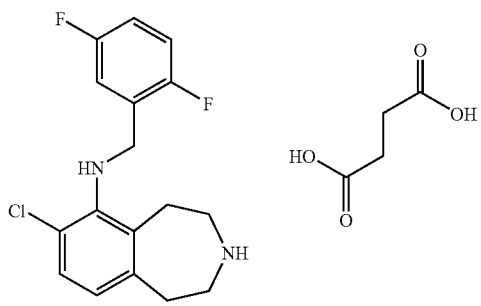

Example 538 may be prepared essentially as described in Example 537 using 7-chloro-3-(2,2,2-trifluoroacetyl)-6-trifluoromethanesulfonyloxy-2,3,4,5-tetrahydro-1H-benzo[d]azepine and 2,5-difluorobenzylamine (680% yield, MS (ES+) m/z 323 (M+H)$^+$).

EXAMPLE 539

7-Chloro-6-(2,2-difluoro-2-phenyl-ethylamino)-2,3,4,5-tetrahydro-1H-benzo[d]azepine Succinate

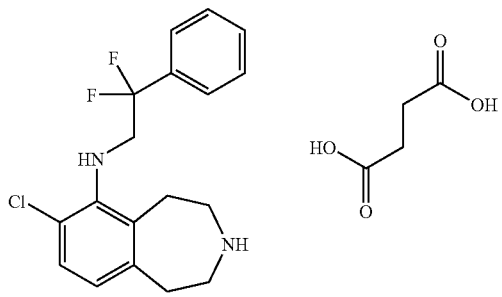

Use a method similar to the General Procedure 5-3 to react 7-chloro-3-(2,2,2-trifluoroacetyl)-6-trifluoromethanesulfonyloxy-2,3,4,5-tetrahydro-1H-benzo[d]azepine (541 mg, 1.274 mmol), palladium(II) acetate (57 mg, 0.225 mmol), tris(dibenzylideneacetone)dipalladium(0) (117 mg, 0.127 mmol), BINAP (0.506 g, 0.764 mmol), 2,2-difluoro-2-phenyl-ethylamine (400 mg, 2.547 mmol) and cesium carbonate (830 mg, 2.548 mmol) in degassed toluene (35 mL). Degas the mixture with vacuum/nitrogen purge and heat to 100° C. for 16 h. Cool the mixture to room temperature, dilute with EtOAc and filter over Celite®. Purify the crude mixture by chromatography on silica gel eluting with hexane and hexane/EtOAc (19:1) to obtain 7-chloro-6-(2,2-difluoro-2-phenyl-ethylamino)-3-(2,2,2-trifluoroacetyl)-2,3,4,5-tetrahydro-1H-benzo[d]azepine as oil (335 mg, 61%). MS (ES+) m/z: 433 (M+H)$^+$.

Use a method similar to the General Procedure 1-2, using 7-chloro-6-(2,2-difluoro-2-phenyl-ethylamino)-3-(2,2,2-trifluoroacetyl)-2,3,4,5-tetrahydro-1H-benzo[d]azepine (317 mg, 0.734 mmol), to give the free base of the title compound as an oil (215 mg, 87%) that was used without further purification. MS (ES+) m/z: 337 (M+H)$^+$. Use a method similar to the General Procedure 2-1, using 7-chloro-6-(2,2-difluoro-2-phenyl-ethylamino)-2,3,4,5-tetrahydro-1H-benzo[d]azepine (215 mg, 0.64 mmol) to give the title compound as a white solid (220 mg, 76%). MS (ES+) m/z: 337 (M+H)$^+$.

EXAMPLE 540

7-Chloro-6-(2,2-difluoro-2-pyridin-2-yl-ethylamino)-2,3,4,5-tetrahydro-1H-benzo[d]azepine Succinate

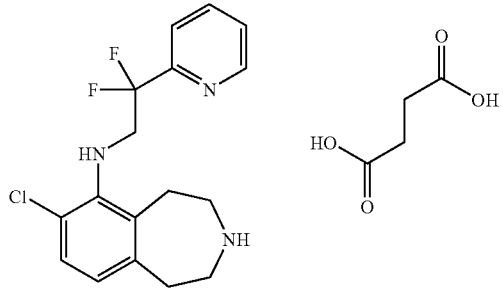

Example 540 may be prepared essentially as described in Example 539 using 7-chloro-3-(2,2,2-trifluoroacetyl)-6-trifluoromethanesulfonyloxy-2,3,4,5-tetrahydro-1H-benzo[d]azepine and 2,2-difluoro-2-pyridin-2-yl-ethylamine (prepared by following the procedure described in *J. Med. Chem.* 2003, 46, 461-473), (37% yield, MS (ES+) m/z 338 (M+H)$^+$).

EXAMPLES 541-544

Examples 541-544 may be prepared essentially as described in Example 262 by using 7-chloro-3-(2,2,2-trifluoroacetyl)-6-trifluoromethanesulfonyloxy-2,3,4,5-tetrahydro-1H-benzo[d]azepine and the appropriate amine. Overall yields and MS (ES+) data are shown in the Table below.

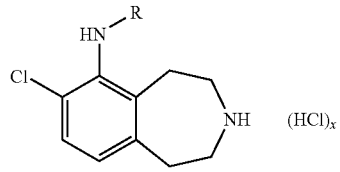

| Ex. | NH—R | Compound | Yield (%) | MS (ES+) m/z |
|---|---|---|---|---|
| 541 | | 7-Chloro-6-(benzo[1,2,3]thiadiazol-6-yl-methylamino)-2,3,4,5-tetrahydro-1H-benzo[d]azepine Hydrochloride | 12 | 345 (M + H)+ |
| 542 | | 7-Chloro-6-(2-cyclohexylmethyl-benzothiazol-6-yl-methylamino)-2,3,4,5-tetrahydro-1H-benzo[d]azepine Hydrochloride | 50 | 441 (M + H)+ |
| 543 | | 7-Chloro-6-[(2-phenyl-benzothiazol-6-yl-methyl)-amino]-2,3,4,5-tetrahydro-1H-benzo[d]azepine Hydrochloride | 27 | 420 (M + H)+ |
| 544 | | 7-Chloro-6-(2-isobutyl-benzothiazol-5-yl-methylamino)-2,3,4,5-tetrahydro-1H-benzo[d]azepine Hydrochloride | 37 | 400 (M + H)+ |

EXAMPLE 545

7-Chloro-6-(3-phenyl-benzothiophen-6-yl-methylamino)-2,3,4,5-tetrahydro-1H-benzo [d]azepine Hydrochloride

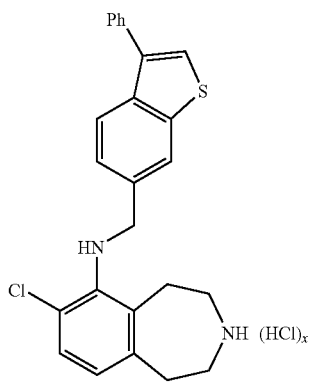

Use a method similar to the General Procedure 5-2, using 7-chloro-3-(2,2,2-trifluoroacetyl)-6-trifluoromethanesulfonyloxy-2,3,4,5-tetrahydro-1H-benzo[d]azepine (0.28 g, 0.66 mmol) and 6-aminomethyl-3-phenyl-benzothiophene (0.19 g, 0.8 mmol) with tris(dibenzylideneacetone)dipalladium(0) (120 mg, 0.13 mmol), BINAP (165 mg, 0.26 mmol) and cesium carbonate (0.3 g, 0.93 mmol) at 90° C. for 17 h, to obtain 7-chloro-6-(3-phenyl-benzothiophen-6-yl-methylamino)-3-(2,2,2-trifluoroacetyl)-2,3,4,5-tetrahydro-1H-benzo[d]azepine that is used without further purification (234 mg, 69%). MS (ES+) m/z: 515 (M+H)+.

Use a procedure similar to General Procedure 1-1 to deprotect 7-chloro-6-(3-phenyl-benzothiophen-6-yl-methylamino)-3-(2,2,2-trifluoroacetyl)-2,3,4,5-tetrahydro-1H-benzo[d]azepine (234 mg, 0.45 mmol) in 7M ammonia in methanol (20 mL). Purify by reverse phase HPLC (Vydac C18 5×25 cm, 30% to 100% acetonitrile in 0.1% TFA-water solution). Recover the free base by SCX chromatography and form the salt according to General Procedure 2-3 to obtain the title compound (38 mg, 17%). HRMS (ES+) m/z: 419.1340 (M+H)+.

EXAMPLE 546

7-Chloro-6-[(difluoro-phenyl-methyl)-benzylamino]-2,3,4,5-tetrahydro-1H-benzo[d]azepine Succinate

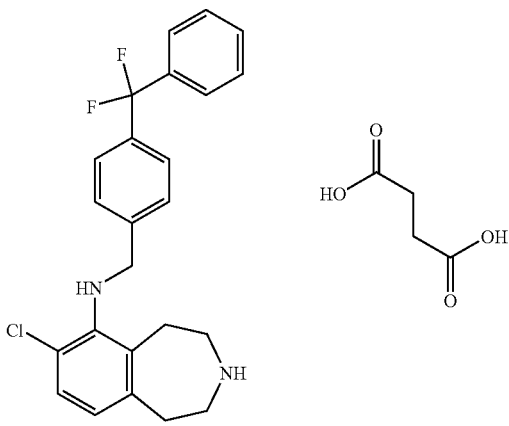

Use a procedure similar to Example 262 using 7-chloro-3-(2,2,2-trifluoroacetyl)-6-trifluoromethanesulfonyloxy-2,3,4,5-tetrahydro-1H-benzo[d]azepine and 4-(difluoro-phenyl-methyl)-benzylamine, followed by deprotection according to General Procedure 1-2 and salt formation according to General Procedure 2-1 to obtain the title compound (175 mg, 77%). MS (ES+) m/z 413 (M+H)+.

EXAMPLE 547

7-Chloro-6-[4-(3,3-dimethyl-butyryl)-benzylamino]-2,3,4,5-tetrahydro-1H-benzo[d]azepine Succinate

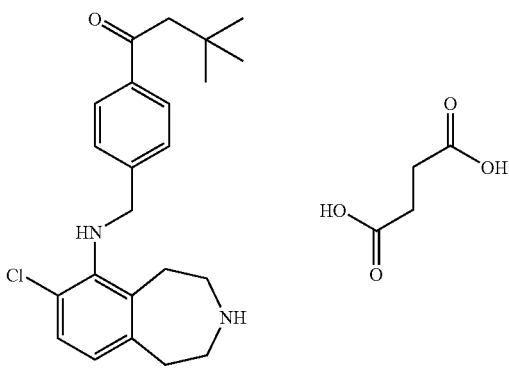

Use a method similar to the General Procedure 5-3 to react 7-chloro-3-(2,2,2-trifluoroacetyl)-6-trifluoromethanesulfonyloxy-2,3,4,5-tetrahydro-1H-benzo[d]azepine (250 mg, 0.588 mmol), palladium(II) acetate (26 mg, 0.118 mmol), tris(dibenzylideneacetone)dipalladium(0) (53 mg, 0.059 mmol), BINAP (0.22 g, 0.353 mmol), 4-(3,3-dimethyl-butyryl)-benzylamine (241 mg, 1.176 mmol) and cesium carbonate (383 mg, 1.176 mmol) in degassed toluene (10 mL). Degas the mixture with vacuum/nitrogen purge and heat to 100° C. for 16 h. Cool the mixture to room temperature, dilute with EtOAc and wash with saturated aqueous NaHCO$_3$. Dry the organic layer over Na$_2$SO$_4$, filter and concentrate in vacuo. Purify the crude mixture by chromatography on silica gel eluting with hexane and then hexane/EtOAc (90:10, 85:15) to obtain 7-chloro-6-[4-(3,3-dimethyl-butyryl)-benzylamino]-3-(2,2,2-trifluoroacetyl)-2,3,4,5-tetrahydro-1H-benzo[d]azepine as oil (185 mg, 65%). MS (ES+) m/z: 481 (M+H)+.

Use a method similar to the General Procedure 1-2, using 7-chloro-6-[4-(3,3-dimethyl-butyryl)-benzylamino]-3-(2,2,2-trifluoroacetyl)-2,3,4,5-tetrahydro-1H-benzo[d]azepine (165 mg, 0.343 mmol), to give the free base of the title compound as an oil (130 mg, 98%) that was used without further purification. MS (ES+) m/z: 385 (M+H)+. Use a method similar to the General Procedure 2-1, using 7-chloro-6-[4-(3,3-dimethyl-butyryl)-benzylamino]-2,3,4,5-tetrahydro-1H-benzo[d]azepine (130 mg, 0.338 mmol) to give the title compound as a white solid (128 mg, 76%). MS (ES+) m/z: 385 (M+H)+.

EXAMPLE 548

7-Chloro-6-[4-(3,3-dimethyl-butyryl)-3-fluoro-benzylamino]-2,3,4,5-tetrahydro-1H-benzo[d]azepine Succinate

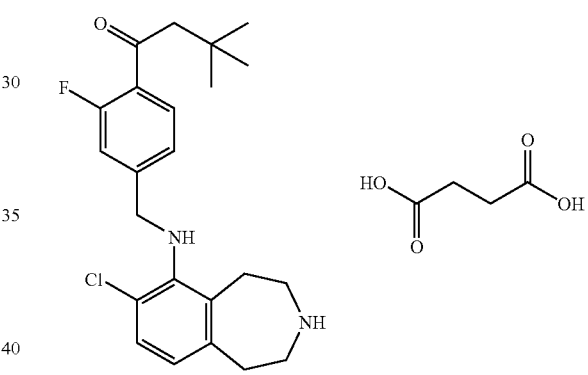

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (96 mg, 0.225 mmol) with 4-(3,3-dimethyl-butyryl)-3-fluoro-benzylamine (105 mg, 0.45 mmol) by using tris(dibenzylideneacetone)dipalladium(0) (41 mg, 0.045 mmol), BINAP (56 mg, 0.09 mmol) and cesium carbonate (103 mg, 0.315 mmol) in anhydrous toluene (15 mL). Purify by chromatography on silica gel eluting with hexane/EtOAc (9:1) to give 7-chloro-6-[4-(3,3-dimethyl-butyryl)-3-fluoro-benzylamino]-3-(2,2,2-trifluoroacetyl)-2,3,4,5-tetrahydro-1H-benzo[d]azepine as a yellow oil (54 mg, 49%). MS (ES+) m/z: 499 (M+H)+.

Use a method similar to the General Procedure 1-2, using 7-chloro-6-[4-(3,3-dimethyl-butyryl)-3-fluoro-benzylamino]-3-(2,2,2-trifluoroacetyl)-2,3,4,5-tetrahydro-1H-benzo[d]azepine (53 mg, 0.11 mmol) to give the free base of the title compound as a yellow oil (42 mg, 96%) that was used without further purification. Use a method similar to the General Procedure 2-1, using 7-chloro-6-[4-(3,3-dimethyl-butyryl)-3-fluoro-benzylamino]-2,3,4,5-tetrahydro-1H-benzo[d]azepine (42 mg, 0.105 mmol) to give the title compound as a white solid (30 mg, 60%). MS (ES+) m/z: 403 (M+H)+.

EXAMPLE 549

7-Chloro-6-[4-(3,3-dimethyl-butyryl)-2-fluoro-benzylamino]-2,3,4,5-tetrahydro-1H-benzo[d]azepine Succinate

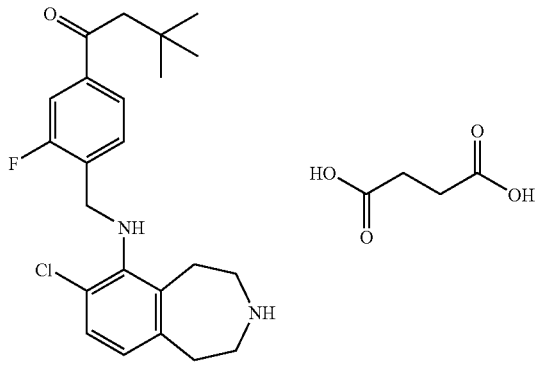

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (127 mg, 0.3 mmol) with 4-(3,3-dimethyl-butyryl)-2-fluoro-benzylamine (120 mg, 0.54 mmol) by using tris(dibenzylideneacetone)dipalladium(0) (27 mg, 0.03 mmol), BINAP (40 mg, 0.06 mmol) and cesium carbonate (137 mg, 0.42 mmol) in anhydrous toluene (20 mL). Purify by chromatography on silica gel eluting with hexane/EtOAc (19:1 and 9:1) followed by reverse phase HPLC [Zorbax Bonus RP, 5 □M 21.2×100 mm, eluting with water/acetonitrile (0.05% TFA in each) (35:65 to 15:85 gradient over 5 min), flow rate 25 mL/min, UV detector (230 nm)] to give 7-chloro-6-[4-(3,3-dimethyl-butyryl)-2-fluoro-benzylamino]-3-(2,2,2-trifluoroacetyl)-2,3,4,5-tetrahydro-1H-benzo[d]azepine as an oil (72 mg, 49%). MS (ES+) m/z: 499 (M+H)$^+$.

Use a method similar to the General Procedure 1-2, using 7-chloro-6-[4-(3,3-dimethyl-butyryl)-2-fluoro-benzylamino]-3-(2,2,2-trifluoroacetyl)-2,3,4,5-tetrahydro-1H-benzo[d]azepine (26 mg, 0.052 mmol) to give the free base of the title compound as a yellow oil (19 mg, 91%) that was used without further purification. Use a method similar to the General Procedure 2-1, using 7-chloro-6-[4-(3,3-dimethyl-butyryl)-2-fluoro-benzylamino]-2,3,4,5-tetrahydro-1H-benzo[d]azepine (18 mg, 0.045 mmol) to give the title compound as a white solid (20 mg, 86%). MS (ES+) m/z: 403 (M+H)$^+$.

EXAMPLE 550

7-Chloro-6-[3-chloro-4-(3,3-dimethyl-butyryl)-benzylamino]-2,3,4,5-tetrahydro-1H-benzo[d]azepine Succinate

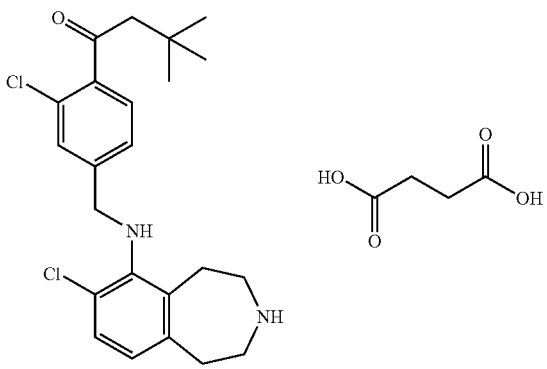

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (90 mg, 0.212 mmol) with 3-chloro-4-(3,3-dimethyl-butyryl)-benzylamine (102 mg, 0.43 mmol) by using tris(dibenzylideneacetone)dipalladium(0) (39 mg, 0.0424 mmol), BINAP (53 mg, 0.0848 mmol) and cesium carbonate (97 mg, 0.297 mmol) in anhydrous toluene (10 mL). Purify by chromatography on silica gel eluting with hexane/EtOAc (9:1) to give 7-chloro-6-[3-chloro-4-(3,3-dimethyl-butyryl)-benzylamino]-3-(2,2,2-trifluoroacetyl)-2,3,4,5-tetrahydro-1H-benzo[d]azepine as an oil (72 mg, 49%). MS (ES+) m/z: 516 (M+H)$^+$.

Use a method similar to the General Procedure 1-2, using 7-chloro-6-[3-chloro-4-(3,3-dimethyl-butyryl)-benzylamino]-3-(2,2,2-trifluoroacetyl)-2,3,4,5-tetrahydro-1H-benzo[d]azepine (70 mg, 0.136 mmol) to give the free base of the title compound as a yellow oil (57 mg, 99%) that was used without further purification. Use a method similar to the General Procedure 2-1, using 7-chloro-6-[3-chloro-4-(3,3-dimethyl-butyryl)-benzylamino]-2,3,4,5-tetrahydro-1H-benzo[d]azepine (57 mg, 0.136 mmol) to give the title compound as a white solid (50 mg, 68%). MS (ES+) m/z: 420 (M+H)$^+$.

EXAMPLE 551

7-Chloro-6-[2-chloro-4-(3,3-dimethyl-butyryl)-benzylamino]-2,3,4,5-tetrahydro-1H-benzo[d]azepine Succinate

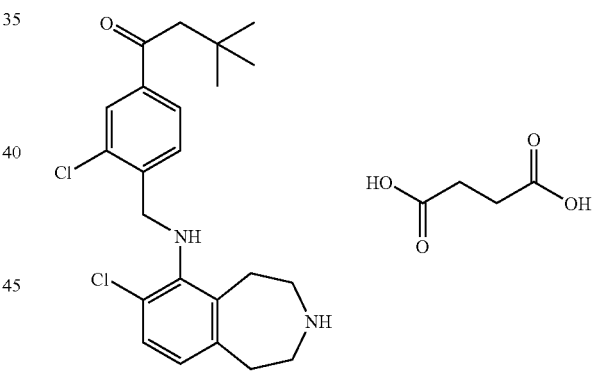

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (300 mg, 0.71 mmol) with 1-(4-aminomethyl-3-chloro-phenyl)-3,3-dimethyl-butan-1-one (338 mg, 1.41 mmol) by using tris(dibenzylideneacetone)dipalladium(0) (130 mg, 9.142 mmol), BINAP (177 mg, 0.284 mmol) and cesium carbonate (324 mg, 0.994 mmol) in anhydrous toluene (31 mL). Purify by chromatography on silica gel eluting with hexane/EtOAc (92:8) followed by reverse phase HPLC [Hichrom Kromasil C18, 5 □M 21.2×100 mm, eluting with water/acetonitrile (0.05% TFA in each) (1:4 to 1:19 gradient over 5 min), flow rate 25 mL/min, UV detector (230 nm)] to give 7-chloro-6-[2-chloro-4-(3,3-dimethyl-butyryl)-benzylamino]-3-(2,2,2-trifluoroacetyl)-2,3,4,5-tetrahydro-1H-benzo[d]azepine as an oil (77 mg, 21%). MS (ES+) m/z: 516 (M+H)$^+$.

Use a method similar to the General Procedure 1-2, using 7-chloro-6-[2-chloro-4-(3,3-dimethyl-butyryl)-benzylamino]-3-(2,2,2-trifluoroacetyl)-2,3,4,5-tetrahydro-1H-benzo[d]azepine (77 mg, 0.15 mmol) to give the free base of the title compound as a yellow oil (93 mg, 99%) that was used without further purification. Use a method similar to the General Procedure 2-1, using 7-chloro-6-[2-chloro-4-(3,3-dimethyl-butyryl)-benzylamino]-2,3,4,5-tetrahydro-1H-benzo[d]azepine (63 mg, 0.15 mmol) to give the title compound as a white solid (52 mg, 65%). MS (ES+) m/z: 420 (M+H)+.

EXAMPLE 552

7-Chloro-6-[4-(4,4-dimethyl-pentanoyl)-benzylamino]-2,3,4,5-tetrahydro-1H-benzo[d]azepine Succinate

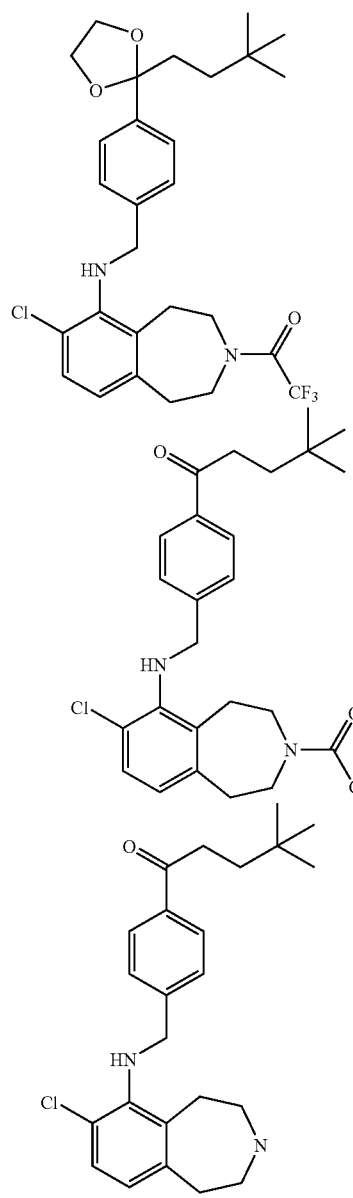

Use a method similar to the General Procedure 5-2 to react 7-chloro-3-(2,2,2-trifluoroacetyl)-6-trifluoromethanesulfonyloxy-2,3,4,5-tetrahydro-1H-benzo[d]azepine (233 mg, 0.55 mmol), tris(dibenzylideneacetone)dipalladium(0) (50 mg, 0.055 mmol), BINAP (73 mg, 0.11 mmol), 4-[2-(3,3-dimethyl-butyl)-[1,3]dioxolan-2-yl]-benzylamine (263 mg, 1 mmol) and cesium carbonate (250 mg, 0.77 mmol) in degassed toluene (20 mL). Degas the mixture with vacuum/nitrogen purge and heat to 100° C. for 14 h. Cool the mixture to room temperature, dilute with EtOAc and filter through Celite®. Purify the crude mixture by chromatography on silica gel eluting with hexane and then hexane/EtOAc (19:1, 9:1 and 4:1) to obtain 7-chloro-6-{4-[2-(3,3-dimethyl-butyl)-[1,3]dioxolan-2-yl]-benzylamine}-3-(2,2,2-trifluoroacetyl)-2,3,4,5-tetrahydro-1H-benzo[d]azepine as oil (185 mg, 63%). MS (ES+) m/z: 539 (M+H)+.

Dissolve 7-chloro-6-{4-[2-(3,3-dimethyl-butyl)-[1,3]dioxolan-2-yl]-benzylamine}-3-(2,2,2-trifluoroacetyl)-2,3,4,5-tetrahydro-1H-benzo[d]azepine (185 mg, 0.34 mmol) in methanol (10 mL) and add 1N aqueous HCl (2 mL). Stir the mixture for 2 h and concentrate in vacuo. Dissolve the residue in dichloromethane and wash with saturated aqueous NaHCO3. Dry the organic phase over MgSO4, filter and concentrate in vacuo to obtain 7-chloro-6-[4-(4,4-dimethyl-pentanoyl)-benzylamino]-3-(2,2,2-trifluoroacetyl)-2,3,4,5-tetrahydro-1H-benzo[d]azepine as an oil (150 mg, 89%).

Use a method similar to the General Procedure 1-2, using 7-chloro-6-[4-(4,4-dimethyl-pentanoyl)-benzylamino]-3-(2,2,2-trifluoroacetyl)-2,3,4,5-tetrahydro-1H-benzo[d]azepine (150 mg, 0.3 mmol), to give the free base of the title compound as an oil (100 mg, 83%) that was used without further purification. Use a method similar to the General Procedure 2-1, using 7-chloro-6-[4-(4,4-dimethyl-pentanoyl)-benzylamino]-2,3,4,5-tetrahydro-1H-benzo[d]azepine (100 mg, 0.25 mmol) to give the title compound as a solid (100 mg, 78%). MS (ES+) m/z: 399 (M+H)+.

EXAMPLE 553

7-Chloro-6-(4-cyclohexanecarbonyl-benzylamino)-2,3,4,5-tetrahydro-1H-benzo[d]azepine Succinate

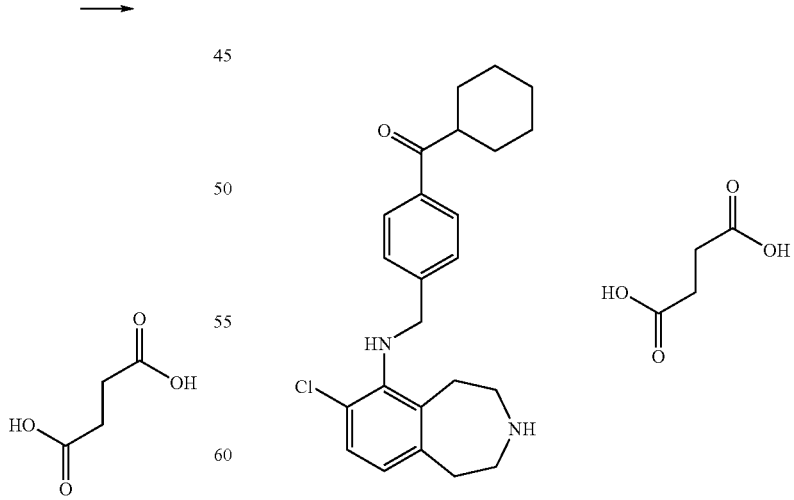

Use a method similar to the General Procedure 5-2 to react 7-chloro-3-(2,2,2-trifluoroacetyl)-6-trifluoromethanesulfonyloxy-2,3,4,5-tetrahydro-1H-benzo[d]azepine (150 mg, 0.353 mmol), tris(dibenzylideneacetone)dipalladium(0) (64 mg, 0.071 mmol), BINAP (88 mg, 0.141 mmol), 4-cyclohexanecarbonyl-benzylamine (125 mg, 0.576 mmol) and cesium carbonate (230 mg, 0.706 mmol) in degassed toluene (10 mL). Degas the mixture with vacuum/nitrogen purge and heat to 100° C. for 6 h. Cool the mixture to room temperature, dilute with EtOAc and filter through Celite®. Purify the crude mixture by chromatography on silica gel eluting with hexane and then hexane/EtOAc (90:10 and 85:15) to obtain 7-chloro-6-(4-cyclohexanecarbonyl-benzylamino)-3-(2,2,2-trifluoro-acetyl)-2,3,4,5-tetrahydro-1H-benzo[d]azepine as oil (130 mg, 75%). MS (ES+) m/z: 493 (M+H)$^+$.

Use a method similar to the General Procedure 1-2, using 7-chloro-6-(4-cyclohexanecarbonyl-benzylamino)-3-(2,2,2-trifluoroacetyl)-2,3,4,5-tetrahydro-1H-benzo[d]azepine (120 mg, 0.243 mmol), to give the free base of the title compound as an oil (86 mg, 89%) that was used without further purification. MS (ES+) m/z: 397 (M+H)$^+$. Use a method similar to the General Procedure 2-1, using 7-chloro-6-(4-cyclohexanecarbonyl-benzylamino)-2,3,4,5-tetrahydro-1H-benzo[d]azepine (86 mg, 0.217 mmol) to give the title compound as a solid (85 mg, 77%). MS (ES+) m/z: 397 (M+H)$^+$.

EXAMPLES 554-557

Examples 554-557 may be prepared essentially as described in Example 553 using 7-chloro-3-(2,2,2-trifluoroacetyl)-6-trifluoromethanesulfonyloxy-2,3,4,5-tetrahydro-1H-benzo[d]azepine and the appropriate amine. Overall yields and MS (ES+) data are shown in the Table below.

| Ex. | Structure | Compound | Yield (%) | MS (ES+) m/z |
|---|---|---|---|---|
| 554 | 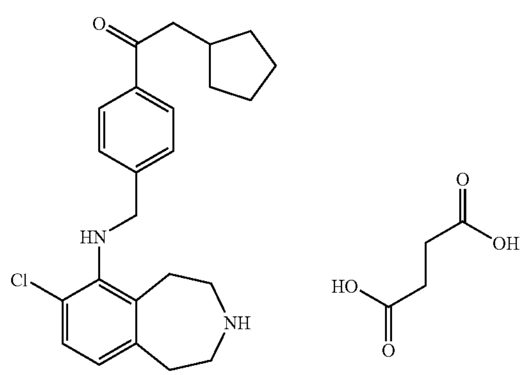 | 7-Chloro-6-[4-(2-cyclopentyl-acetyl)-benzylamino]-2,3,4,5-tetrahydro-1H-benzo[d]azepine Succinate | 64 | 397 (M + H)$^+$ |
| 555 | 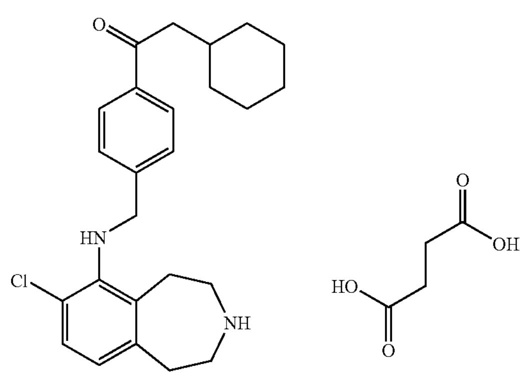 | 7-Chloro-6-[4-(2-cyclohexyl-acetyl)-benzylamino]-2,3,4,5-tetrahydro-1H-benzo[d]azepine Succinate | 30 | 411 (M + H)$^+$ |
| 556 | 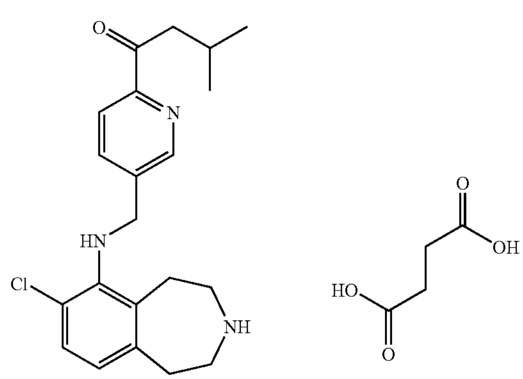 | 7-Chloro-6-[6-(3-methyl-butyryl)-pyridin-3-yl-methylamino]-2,3,4,5-tetrahydro-1H-benzo[d]azepine Succinate | 35 | 372 (M + H)$^+$ |

| Ex. | Structure | Compound | Yield (%) | MS (ES+) m/z |
|---|---|---|---|---|
| 557 | 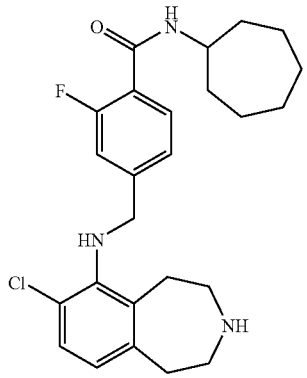 | 7-Chloro-6-[6-(3,3-dimethyl-butyryl)-pyridin-3-yl-methylamino]-2,3,4,5-tetrahydro-1H-benzo[d]azepine Succinate | 30 | 386 (M + H)+ |

EXAMPLE 558

7-Chloro-6-(4-cycloheptylcarbamoyl-3-fluoro-benzylamino)-2,3,4,5-tetrahydro-1H-benzo[d]azepine Succinate

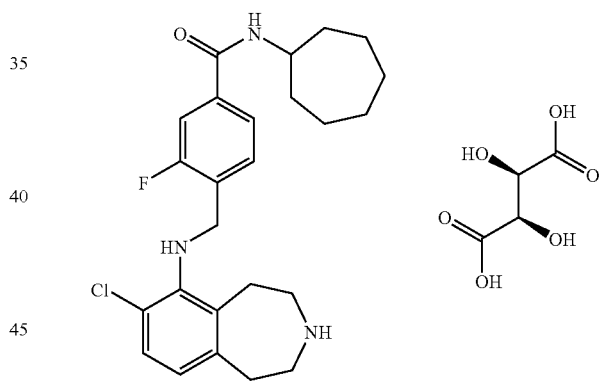

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d] azepine (1.1 g, 2.5 mmol) with 4-aminomethyl-N-cycloheptyl-2-fluoro-benzamide (1.35 g, 5.1 mmol) in anhydrous toluene (25 mL). Purify by chromatography on silica gel eluting with hexane/EtOAc (19:1 to 1:1 gradient) followed by SCX chromatography to obtain 7-chloro-6-[4-cycloheptyl-carbamoyl-3-fluoro-benzylamino]-3-(2,2,2-trifluoroacetyl)-2,3,4,5-tetrahydro-1H-benzo[d]azepine (720 mg, 53%). MS (ES+) m/z: 540.2 (M+H)+.

Use a method similar to the General Procedure 1-2 to deprotect 7-chloro-6-[4-cycloheptylcarbamoyl-3-fluoro-benzylamino]-3-(2,2,2-trifluoroacetyl)-2,3,4,5-tetrahydro-1H-benzo[d]azepine. Purify by chromatography on silica gel eluting with dichloromethane/2M ammonia in methanol (99:1 to 90:10 gradient) to obtain the free base of the title compound. Use a method similar to the General Procedure 2-1 to obtain the title compound (665 mg, 89%). MS (ES+) m/z: 444.2 (M+H)+.

EXAMPLE 559

7-Chloro-6-(4-cycloheptylcarbamoyl-2-fluoro-benzylamino)-2,3,4,5-tetrahydro-1H-benzo[d]azepine (L)-Tartrate Use a method similar to the General Procedure 5-2 to couple 7-chloro-3-(2,2,2-trifluoroacetyl)-6-trifluoromethanesulfonyloxy-2,3,4,5-tetrahydro-1H-benzo[d] azepine (640 mg, 1.5 mmol) with 4-aminomethyl-N-cycloheptyl-3-fluoro-benzamide (795 mg, 3 mmol) in anhydrous toluene (20 mL). Purify the crude mixture by chromatography on silica gel eluting with hexane/EtOAc (19:1 to 3:2 gradient) to obtain 7-chloro-6-(4-cycloheptylcarbamoyl-2-fluoro-benzylamino)-3-(2,2,2-trifluoroacetyl)-2,3,4,5-tetrahydro-1H-benzo[d]azepine (568 mg, 70%). MS (ES+) m/z: 540.2 (M+H)+.

Use a method similar to the General Procedure 1-2 to deprotect 7-chloro-6-(4-cycloheptylcarbamoyl-2-fluoro-benzylamino)-3-(2,2,2-trifluoroacetyl)-2,3,4,5-tetrahydro-1H-benzo[d]azepine. Purify by chromatography on silica gel eluting with dichloromethane/2M ammonia in methanol (99/1 to 93/7 gradient) to give the free base of the title compound. Dissolve the free base (400 mg, 0.9 mmol) and L-tartaric acid (135 mg, 0.9 mmol) in methanol. Concentrate in vacuo to an oil. Triturate oil with dichloromethane and remove solvent in vacuo to obtain the title compound as a solid (460 mg, 74%). MS (ES+) m/z: 444.2 (M+H)+.

EXAMPLE 560

7-Chloro-6-(3-chloro-4-cycloheptylcarbamoyl-benzylamino)-2,3,4,5-tetrahydro-1H-benzo[d]azepine (L)-Tartrate

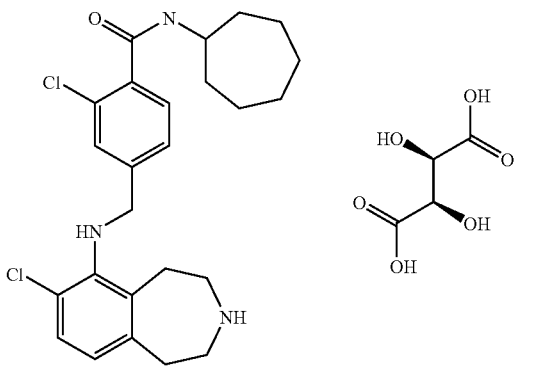

Example 560 may be prepared essentially as described in Example 559 by using 7-chloro-3-(2,2,2-trifluoroacetyl)-6-trifluoromethanesulfonyloxy-2,3,4,5-tetrahydro-1H-benzo[d]azepine and 4-aminomethyl-2-chloro-N-cycloheptyl-benzamide (50% yield, MS (ES+) m/z 460.2 (M+H)+).

EXAMPLE 561

7-Chloro-6-(4-cycloheptylcarbamoyl-3-methyl-benzylamino)-2,3,4,5-tetrahydro-1H-benzo[d]azepine Succinate

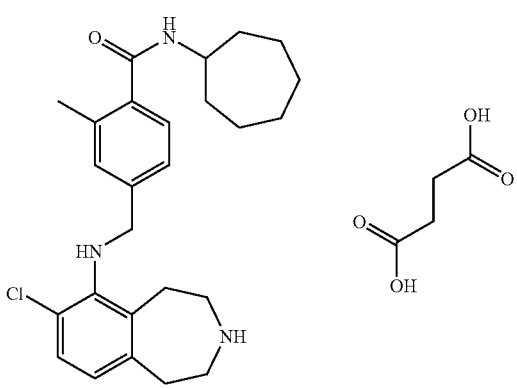

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (660 mg, 1.6 mmol) with 4-aminomethyl-N-cycloheptyl-2-methyl-benzamide (810 mg, 3.1 mmol) in anhydrous toluene (18 mL). Purify the crude mixture by chromatography on silica gel eluting with hexane/THF (19:1 to 7:3 gradient) to obtain 7-chloro-6-(4-cycloheptylcarbamoyl-3-methyl-benzylamino)-3-(2,2,2-trifluoroacetyl)-2,3,4,5-tetrahydro-1H-benzo[d]azepine (690 mg, 83%). MS (ES+) m/z: 536.3 (M+H)+.

Use a method similar to the General Procedure 1-3 to deprotect 7-chloro-6-(4-cycloheptylcarbamoyl-3-methyl-benzylamino)-3-(2,2,2-trifluoroacetyl)-2,3,4,5-tetrahydro-1H-benzo[d]azepine (680 mg, 1.3 mmol). Purify by chromatography on silica gel eluting with dichloromethane/2M ammonia in methanol (99:1 to 97:3 gradient) to give the free base of the title compound. Use a method similar to the General Procedure 2-1 to obtain the title compound (473 mg, 65%). MS (ES+) m/z: 440.3 (M+H)+.

EXAMPLE 562

(R)-7-Chloro-6-[3-fluoro-4-(2,2,2-trifluoro-1-methyl-ethylcarbamoyl)-benzylamino]-2,3,4,5-tetrahydro-1H-benzo[d]azepine Succinate

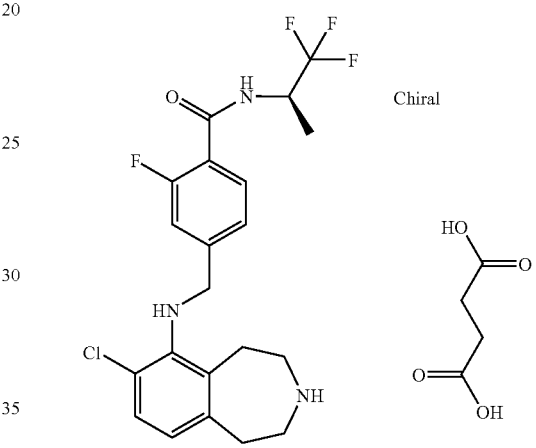

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (0.561 g, 1.319 mmol) with (R)-4-aminomethyl-2-fluoro-N-(2,2,2-trifluoro-1-methyl-ethyl)-benzamide (0.698 g, 2.642 mmol) by using tris(dibenzylideneacetone)dipalladium(0) (0.241 g, 0.264 mmol), BINAP (0.33 g, 0.53 mmol) and cesium carbonate (1.51 g, 4.63 mmol) in anhydrous toluene (13 mL). Purify by chromatography on silica gel (40 g RediSep® column) eluting with hexane/EtOAc (19:1 to 1:1 gradient over 30 min; 35 mL/min) and then by SCX chromatography to afford (R)-7-chloro-6-[3-fluoro-4-(2,2,2-trifluoro-1-methyl-ethylcarbamoyl)-benzylamino]-3-(2,2,2-trifluoroacetyl)-2,3,4,5-tetrahydro-1H-benzo[d]azepine as a colorless oil (0.444 g, 62%). MS (ES+) m/z: 540.1 (M+H)+.

Use a method similar to the General Procedure 1-3 to deprotect (R)-7-chloro-6-[3-fluoro-4-(2,2,2-trifluoro-1-methyl-ethylcarbamoyl)-benzylamino]-3-(2,2,2-trifluoroacetyl)-2,3,4,5-tetrahydro-1H-benzo[d]azepine (0.224 g, 0.415 mmol). Purify by chromatography on silica gel (12 g RediSep® column) eluting with dichloromethane/2M ammonia in methanol (99:1 to 90:10 gradient over 30-min; 35 mL/min) to afford the free base of the title compound as a white foam (0.142 g, 77%). Use a method similar to the General Procedure 2-1, using (R)-7-chloro-6-[3-fluoro-4-(2,2,2-trifluoro-1-methyl-ethylcarbamoyl)-benzylamino]-2,3,4,5-tetrahydro-1H-benzo[d]azepine (0.132 g, 0.299 mmol) to afford the title compound as a white solid (0.135 g, 80%). MS (ES+) m/z: 444.2 (M+H)+.

EXAMPLE 563

7-Chloro-6-(3-fluoro-4-isopropylcarbamoyl-benzylamino)-2,3,4,5-tetrahydro-1H-benzo[d]azepine Succinate

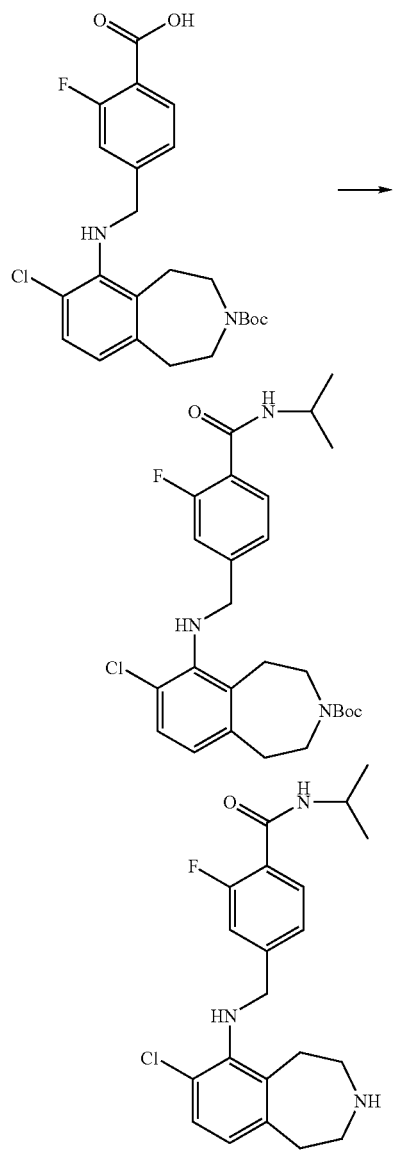

Add isopropylamine (0.15 mL, 1.8 mmol), HOBT (0.24 g, 1.8 mmol), diisopropylethylamine (0.63 mL, 3.6 mmol) and EDC (0.34 g, 1.8 mmol) to a mixture of 3-tert-butoxycarbonyl-6-(4-carboxy-3-fluoro-benzylamino)-7-chloro-2,3,4,5-tetrahydro-1H-benzo[d]azepine (0.403 g, 0.9 mmol) in anhydrous THF (11.8 mL) at room temperature. Stir overnight at room temperature and partition the mixture between EtOAc (250 mL) and saturated aqueous NaHCO$_3$ (100 mL). Dry the organic phase over Na$_2$SO$_4$, filter and concentrate in vacuo. Purify by chromatography on silica gel (40 g RediSep® column) eluting with hexane/EtOAc (19:1 to 1:1 gradient over 30 min; 50 mL/min) to afford 3-tert-butoxycarbonyl-7-chloro-6-(3-fluoro-4-isopropylcarbamoyl-benzylamino)-2,3,4,5-tetrahydro-1H-benzo[d]azepine as a thick colorless oil (0.439 g, 100%). MS (ES+) m/z: 490.2 (M+H)$^+$.

Use a method similar to the General Procedure 14 to deprotect 3-tert-butoxycarbonyl-7-chloro-6-(3-fluoro-4-isopropylcarbamoyl-benzylamino)-2,3,4,5-tetrahydro-1H-benzo[d]azepine (0.406 g, 0.83 mmol) in 1,4-dioxane (12.8 mL). Purify by SCX chromatography eluting with dichloromethane and dichloromethane/2M ammonia in methanol (1:1) followed by chromatography on silica gel (40 g RediSep column) eluting with dichloromethane/2M ammonia in methanol (99:1 to 90:10 over 30 min) and then dichloromethane/2M ammonia in methanol (90:10 over 30 min; 35 mL/min) to afford 7-chloro-6-(3-fluoro-4-isopropylcarbamoyl-benzylamino)-2,3,4,5-tetrahydro-1H-benzo[d]azepine as a colorless oil (0.3237 g). MS (ES+) m/z: 390.1 (M+H)$^+$. Use a method similar to the General Procedure 2-1, using 7-chloro-6-(3-fluoro-4-isopropylcarbamoyl-benzylamino)-2,3,4,5-tetrahydro-1H-benzo[d]azepine (0.301 g, 0.772 mmol) to provide the title compound as a beige solid (0.328 g, 84%). MS (ES+) m/z: 390.1 (M+H)$^+$.

EXAMPLE 564

7-Chloro-6-(3-fluoro-4-propylcarbamoyl-benzylamino)-2,3,4,5-tetrahydro-1H-benzo[d]azepine (L)-Tartrate

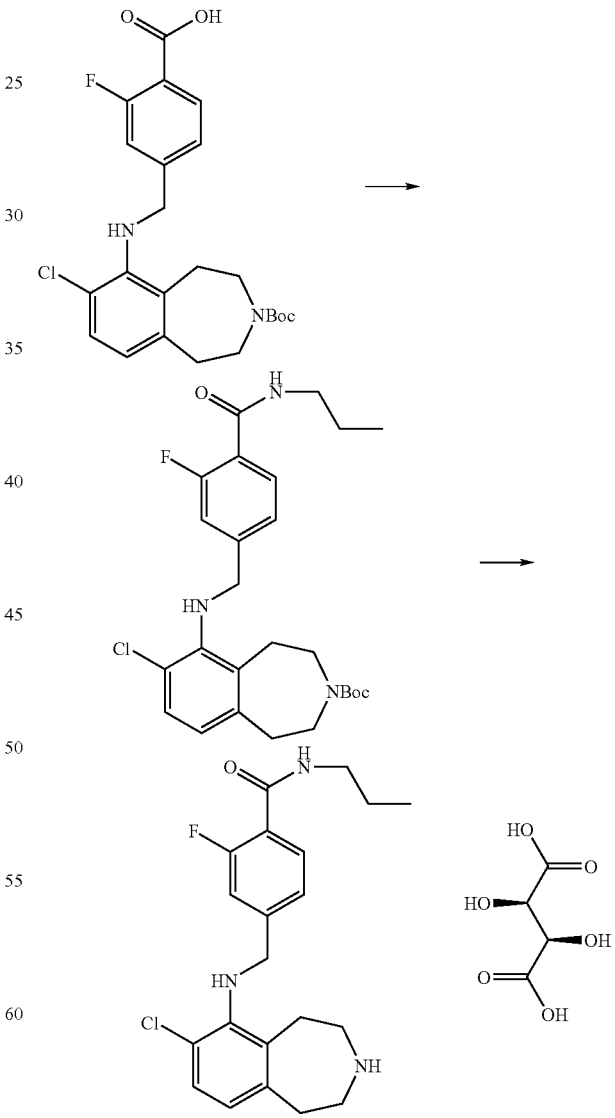

Add a solution of n-propylamine (6.3 mg, 0.11 mmol) in anhydrous THF (0.5 mL), HOBT (14.5 mg, 0.11 mmol), a solution of diisopropylamine (27.7 mg, 0.21 mmol) in anhydrous THF (0.5 mL) and EDC (20.5 mg, 6.11 mmol) to a mixture of 3-tert-butoxycarbonyl-6-(4-carboxy-3-fluoro-benzylamino)-7-chloro-2,3,4,5-tetrahydro-1H-benzo[d]azepine (48.1 mg, 0.11 mmol) in anhydrous THF (1.4 mL) at room temperature. Stir overnight at room temperature and partition the mixture between EtOAc (50 mL) and saturated aqueous NaHCO$_3$ (20 mL). Dry the organic phase over Na$_2$SO$_4$, filter and concentrate in vacuo. Purify by chromatography on silica gel (12 g RediSep® column) eluting with hexane/EtOAc (19:1 to 1:1 gradient over 30 min; 35 mL/min) to afford 3-tert-butoxycarbonyl-7-chloro-6-(3-fluoro-4-propylcarbamoyl-benzylamino)-2,3,4,5-tetrahydro-1H-benzo[d]azepine as a thick colorless oil (37.1 mg, 71%). MS (ES+) m/z: 490.2 (M+H)$^+$.

Use a method similar to the General Procedure 1-4 to deprotect 3-tert-butoxycarbonyl-7-chloro-6-(3-fluoro-4-propylcarbamoyl-benzylamino)-2,3,4,5-tetrahydro-1H-benzo[d]azepine (33.1 mg, 0.83 mmol) in 1,4-dioxane (1 mL). Purify by SCX chromatography eluting with dichloromethane and dichloromethane/2M ammonia in methanol (1:1) to afford 7-Chloro-6-(3-fluoro-4-propylcarbamoyl-benzylamino)-2,3,4,5-tetrahydro-1H-benzo[d]azepine as a colorless oil (25.2 mg, 96%). MS (ES+) m/z: 390.1 (M+H)$^+$. Use a method similar to the General Procedure 2-6, using 7-chloro-6-(3-fluoro-4-propylcarbamoyl-benzylamino)-2,3,4,5-tetrahydro-1H-benzo[d]azepine (25 mg, 0.064 mmol) to provide the title compound as a white foam (31.4 mg, 91%). MS (ES+) m/z: 390.1 (M+H)$^+$.

EXAMPLE 565

7-Chloro-6-[4-(cyclohexylmethylcarbamoyl)-3-fluoro-benzylamino]-2,3,4,5-tetrahydro-1H-benzo[d]azepine (L)-Tartrate

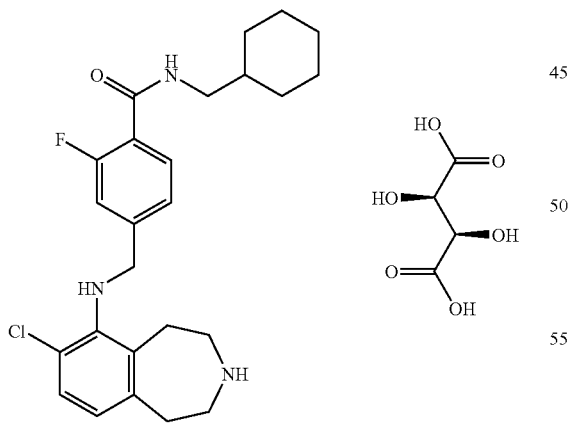

Example 565 may be prepared essentially as described in Example 564 by using 3-tert-butoxycarbonyl-6-(4-carboxy-3-fluoro-benzylamino)-7-chloro-2,3,4,5-tetrahydro-1H-benzo[d]azepine and cyclohexylmethylamine (67% yield, MS (ES+) m/z 444 (M+H)$^+$).

EXAMPLE 566

7-Chloro-6-(6-cyclohexylamino-pyridin-3-ylmethylamino)-2,3,4,5-tetrahydro-1H-benzo[d]azepine Succinate

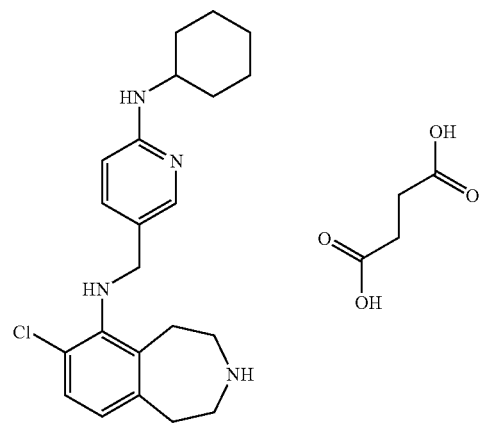

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (800 mg, 1.9 mmol) with 5-aminomethyl-2-cyclohexylamino-pyridine (910 mg, 4.4 mmol) in anhydrous toluene (15 mL). Purify the residue by chromatography on silica gel eluting with hexane/EtOAc (19:1 to 3:2 gradient) to obtain 7-chloro-6-(6-cyclohexylamino-pyridin-3-ylmethylamino)-3-(2,2,2-trifluoroacetyl)-2,3,4,5-tetrahydro-1H-benzo[d]azepine (520 mg, 58%). MS (ES+) m/z: 481.0 (M+H)$^+$.

Use a method similar to the General Procedure 1-3 to deprotect 7-chloro-6-(6-cyclohexylamino-pyridin-3-ylmethylamino)-3-(2,2,2-trifluoroacetyl)-2,3,4,5-tetrahydro-1H-benzo[d]azepine. Purify by chromatography on silica gel eluting with dichloromethane/2M ammonia in methanol (99/1 to 85/15 gradient) to give the free base of the title compound. Use a method similar to the General Procedure 2-1 to obtain the title compound (360 mg, 66%). MS (ES+) m/z: 385.1 (M+H)$^+$.

EXAMPLE 567

7-Chloro-6-(6-cyclohexylmethylamino-pyridin-3-ylmethylamino)-2,3,4,5-tetrahydro-1H-benzo[d]azepine Succinate

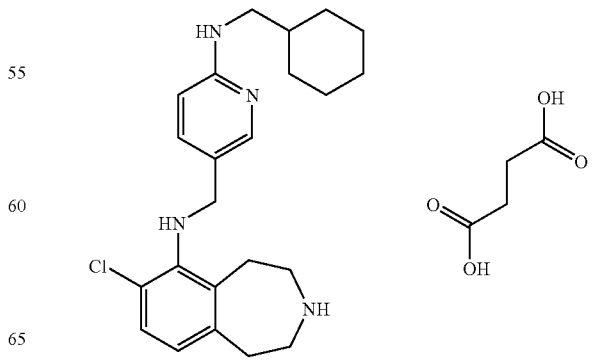

The title compound may be prepared essentially as described in Example 566 by using 7-chloro-3-(2,2,2-trifluoroacetyl)-6-trifluoromethanesulfonyloxy-2,3,4,5-tetrahydro-1H-benzo[d]azepine and 5-aminomethyl-2-cyclohexylmethylamino-pyridine (22% yield, MS (ES+) m/z 399.1 (M+H)+).

EXAMPLE 568

6-[6-(Benzylamino)-pyridin-3-ylmethylamino]-7-chloro-2,3,4,5-tetrahydro-1H-benzo[d]azepine Succinate

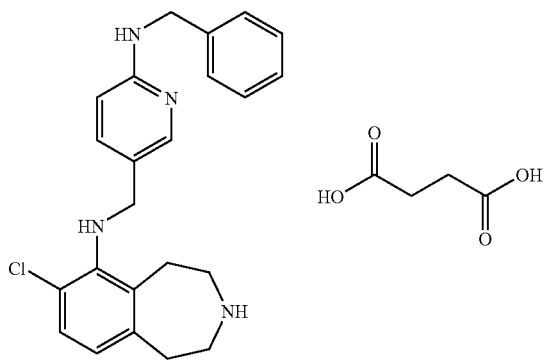

Use a method similar to General Procedure 5-2 to couple 6-benzylamino-pyridin-3-ylmethylamine and 7-chloro-3-(2,2,2-trifluoroacetyl)-6-trifluoromethanesulfonyloxy-2,3,4,5-tetrahydro-1H-benzo[d]azepine to give, after deprotection and salt formation by methods similar to the General Procedures 1-3 and 2-1, the title compound as an off-white solid (45% overall yield). HRMS (ES+) m/z: 393.1836 (M+H)+.

EXAMPLE 569

(±)-7-Chloro-6-{4-[1-(1,1,2,2,2-pentafluoroethyl)-ethoxy]-benzylamino}-2,3,4,5-tetrahydro-1H-benzo[d]azepine Succinate

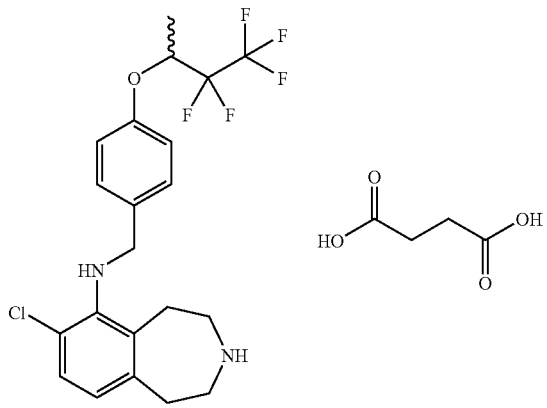

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (751 mg, 1.8 mmol) with (±)-4-[1-(1,1,2,2,2-pentafluoroethyl)-ethoxy]-benzylamine (950 mg, 3.5 mmol) in anhydrous toluene (20 mL). Purify the crude mixture by chromatography on silica gel eluting sequentially with hexane/EtOAc (10:1, 5:1, 3:1) to obtain (±)-7-chloro-6-{4-[1-(1,1,2,2,2-pentafluoroethyl)-ethoxy]-benzylamino}-3-(2,2,2-trifluoroacetyl)-2,3,4,5-tetrahydro-1H-benzo[d]azepine (990 mg, 99%).

Use a method similar to the General Procedure 1-3 to deprotect (±)-7-chloro-6-{4-[1-(1,1,2,2,2-pentafluoroethyl)-ethoxy]-benzylamino}-3-(2,2,2-trifluoroacetyl)-2,3,4,5-tetrahydro-1H-benzo[d]azepine (980 mg, 1.8 mmol). Purify by chromatography on silica gel eluting with dichloromethane/2M ammonia in methanol (99:1 to 90:10 gradient) to give the free base of the title compound. Use a method similar to the General Procedure 2-1 to obtain the title compound (650 mg, 64%). MS (ES+) m/z: 449.1 (M+H)+.

EXAMPLE 570

(−)-7-Chloro-6-{4-[1-(1,1,2,2,2-pentafluoroethyl)-ethoxy]-benzylamino}-2,3,4,5-tetrahydro-1H-benzo[d]azepine Succinate

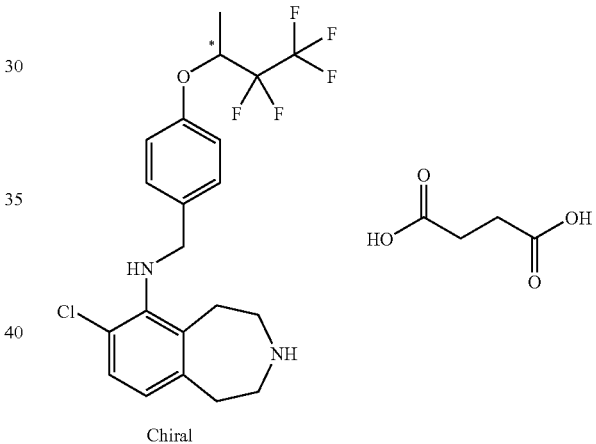

Chiral

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (9 g, 21.1 mmol) with 4-[1-(1,1,2,2,2-pentafluoroethyl)-ethoxy]-benzylamine isomer 2 (11.4 g, 42.3 mmol) in anhydrous toluene (270 mL). Purify the crude mixture by chromatography on silica gel eluting with hexane/EtOAc (19:1 to 4:1 gradient) to obtain 7-chloro-6-{4-[1-(1,1,2,2,2-pentafluoroethyl)-ethoxy]-benzylamino}-3-(2,2,2-trifluoroacetyl)-2,3,4,5-tetrahydro-1H-benzo[d]azepine isomer 2 (9.5 g, 83%).

Use a method similar to the General Procedure 1-3 to deprotect 7-chloro-6-{4-[1-(1,1,2,2,2-pentafluoroethyl)-ethoxy]-benzylamino}-3-(2,2,2-trifluoroacetyl)-2,3,4,5-tetrahydro-1H-benzo[d]azepine isomer 2 (9.5 g, 17.4 mmol). Purify by chromatography on silica gel eluting with dichloromethane/2M ammonia in methanol (99:1 to 90:10 gradient) to give the free base of the title compound. Use a method similar to the General Procedure 2-1 to obtain the title compound (5.9 g, 60%). MS (ES+) m/z: 449.1 (M+H)+. $[\alpha]^{20}_D$ −11.6° (c 0.5, MeOH).

EXAMPLE 571

(+)-7-Chloro-6-{4-[1-(1,1,2,2,2-pentafluoroethyl)-ethoxy]-benzylamino}-2,3,4,5-tetrahydro-1H-benzo[d]azepine Succinate

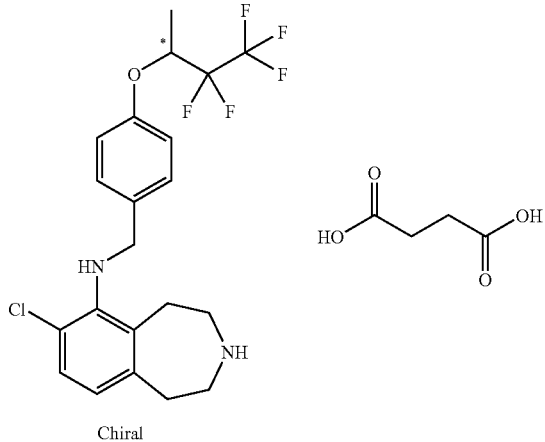

Chiral

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (3.4 g, 8 mmol) with 4-[1-(1,1,2,2,2-pentafluoroethyl)ethoxy]-benzylamine isomer 1 (4.3 g, 16 mmol) in anhydrous toluene (100 mL). Purify the crude mixture by chromatography on silica gel eluting with hexane/EtOAc (19:1 to 3:1 gradient) to obtain 7-chloro-6-{4-[1-(1,1,2,2,2-pentafluoroethyl)-ethoxy]-benzylamino}-3-(2,2,2-trifluoroacetyl)-2,3,4,5-tetrahydro-1H-benzo[c]azepine isomer 1 (3.7 g, 85%).

Use a method similar to the General Procedure 1-3 to deprotect 7-chloro-6-{4-[1-(1,1,2,2,2-pentafluoroethyl)-ethoxy]-benzylamino}-3-(2,2,2-trifluoroacetyl)-2,3,4,5-tetrahydro-1H-benzo[d]azepine isomer 1 (3.7 g, 6.8 mmol). Purify by chromatography on silica gel eluting with dichloromethane/2M ammonia in methanol (99:1 to 97:3 gradient) to give the free base of the title compound. Use a method similar to the General Procedure 2-1 to obtain the title compound (2.8 g, 74%). MS (ES+) m/z: 449.1 (M+H)$^+$. $[\alpha]^{20}_D$ +13.0° (c 0.5, MeOH).

EXAMPLE 572

(±)-7-Chloro-6-{4-[1-(1,1,2,2,2-pentafluoroethyl)-ethoxy]-pyridin-2-ylmethylamino}-2,3,4,5-tetrahydro-1H-benzo[d]azepine Succinate

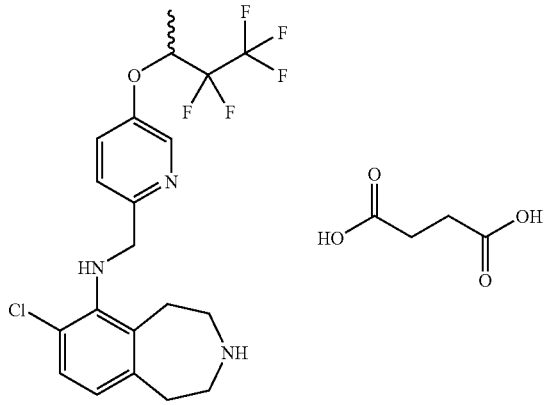

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (268 mg, 0.6 mmol) with (±)-2-aminomethyl-5-[1-(1,1,2,2,2-pentafluoroethyl)-ethoxy]-pyridine (170 mg, 0.6 mmol) in anhydrous toluene (3 mL). Purify the crude mixture by chromatography on silica gel eluting sequentially with hexane/EtOAc (10:1, 5:1, 3:1) to obtain (±)-7-chloro-6-{4-[1-(1,1,2,2,2-pentafluoroethyl)-ethoxy]-pyridin-2-ylmethylamino}-3-(2,2,2-trifluoroacetyl)-2,3,4,5-tetrahydro-1H-benzo[d]azepine (270 mg, 79%). MS (ES+) m/z: 546.1 (M+H)$^+$.

Use a method similar to the General Procedure 1-3 to deprotect (±)-7-chloro-6-{4-[1-(1,1,2,2,2-pentafluoroethyl)-ethoxy]-pyridin-2-ylmethylamino}-3-(2,2,2-trifluoroacetyl)-2,3,4,5-tetrahydro-1H-benzo[d]azepine (265 mg, 0.5 mmol). Purify by chromatography on silica gel eluting with dichloromethane/2M ammonia in methanol (99:1 to 90:10 gradient) to give the free base of the title compound. Use a method similar to the General Procedure 2-1 to obtain the title compound (172 mg, 63%). MS (ES+) m/z: 450.1 (M+H)$^+$.

EXAMPLE 573

(−)-7-Chloro-6-{4-[1-(1,1,2,2,2-pentafluoroethyl)-ethoxy]-pyridin-2-ylmethylamino}-2,3,4,5-tetrahydro-1H-benzo[d]azepine Succinate

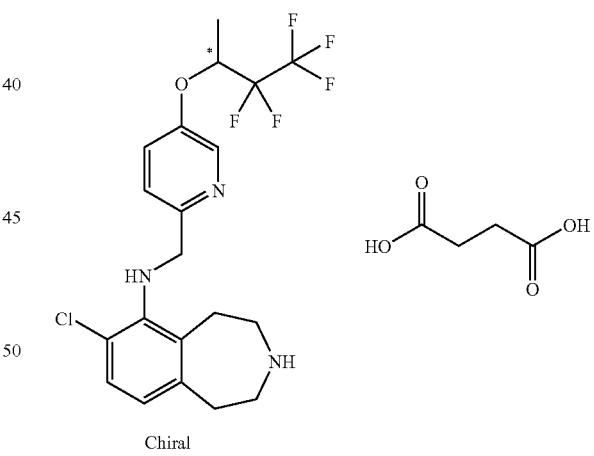

Chiral

Separate (±)-7-chloro-6-{4-[1-(1,1,2,2,2-pentafluoroethyl)-ethoxy]-pyridin-2-ylmethylamino}-2,3,4,5-tetrahydro-1H-benzo[d]azepine succinate (172 mg) by normal phase chiral chromatography (Chiralcel OD, 8×35 cm, eluting with heptane/isopropanol 4:1 with 0.2% DMEA). Collect the 1$^{st}$ eluting isomer, then use a method similar to the General Procedure 2-1 to obtain the title compound [50 mg, 96.3% ee (Chiralcel OD-H, 4.6×150 mm, eluting with heptane/isopropanol 4:1 with 0.2% DMEA, 0.6 mL/min)]. MS (ES+) m/z: 450.1 (M+H)$^+$. $[\alpha]^{20}_D$ −10.5° (c 0.5, MeOH).

EXAMPLE 574

(+)-7-Chloro-6-{4-[1-(1,1,2,2,2-pentafluoroethyl)-ethoxy]-pyridin-2-ylmethylamino}-2,3,4,5-tetrahydro-1H-benzo[d]azepine Succinate

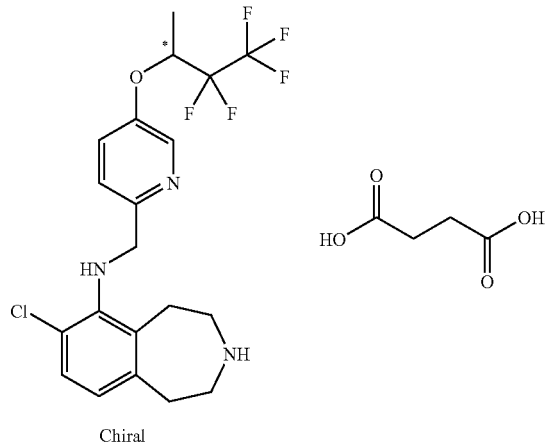

Chiral

Separate (4)-7-chloro-6-{4-[1-(1,1,2,2,2-pentafluoroethyl)-ethoxy]-pyridin-2-ylmethylamino}-2,3,4,5-tetrahydro-1H-benzo[d]azepine succinate (172 mg) by normal phase chiral chromatography (Chiralcel OD, 8×35 cm, eluting with heptane/isopropanol 4:1 with 0.2% DMEA). Collect the 2$^{nd}$ eluting isomer, then use a method similar to the General Procedure 2-1 to obtain the title compound [41 mg, 95.6% ee (Chirialcel OD-H, 4.6×150 mm, eluting with heptane/isopropanol 4:1 with 0.2% DMEA, 0.6 mL/min)]. MS (ES+) m/z: 450.1 (M+H)$^+$. [α]$^{20}{}_D$ +13.1° (c 0.5, MeOH).

EXAMPLE 575

7-Chloro-6-[4-(1-methyl-cyclohexylmethoxy)-benzylamino]-2,3,4,5-tetrahydro-1H-benzo[d]azepine (L)-Tartrate

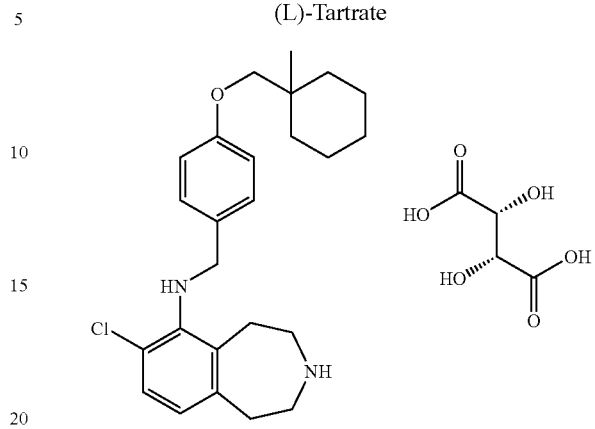

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (200 mg, 0.47 mmol) with 4-(1-methyl-cyclohexylmethoxy)-benzylamine (120 mg, 0.51 mmol) in anhydrous 1,4-dioxane (7 mL). Purify the crude mixture by chromatography on silica gel eluting with isohexane/EtOAc (19:1 to 4:1 gradient) to obtain 7-chloro-6-[4-(1-methyl-cyclohexylmethoxy)-benzylamino]-3-(2,2,2-trifluoroacetyl)-2,3,4,5-tetrahydro-1H-benzo[d]azepine (101 mg, 39%).

Use a method similar to the General Procedure 1-1 to deprotect 7-chloro-6-[4-(1-methyl-cyclohexylmethoxy)-benzylamino]-3-(2,2,2-trifluoroacetyl)-2,3,4,5-tetrahydro-1H-benzo[d]azepine (100 mg, 0.19 mmol). Purify by SCX chromatography eluting with methanol and 3M ammonia in methanol. Use a method similar to the General Procedure 2-6 to obtain the title compound (78 mg, 73%). MS (ES+) m/z: 413.2 (M+H)$^+$.

EXAMPLES 576-580

Examples 576-580 may be prepared essentially as described in Example 575 by using 7-chloro-3-(2,2,2-trifluoroacetyl)-6-trifluoromethanesulfonyloxy-2,3,4,5-tetrahydro-1H-benzo[d]azepine and the appropriate amine. Overall yields and MS (ES+) data are shown in the Table below.

| Ex. | Structure | Compound | Yield (%) | MS (ES+) m/z |
|---|---|---|---|---|
| 576 | 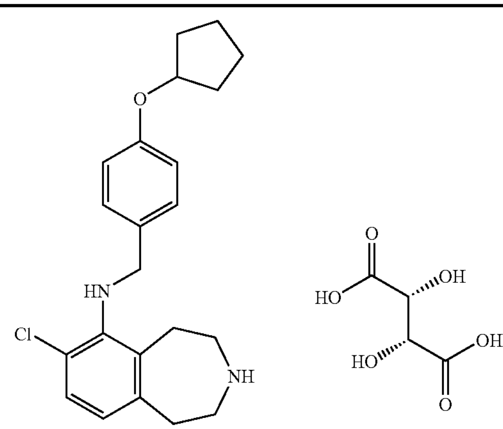 | 7-Chloro-6-(4-cyclopentyloxy-benzylamino)-2,3,4,5,-tetrahydro-1H-benzo[d]azepine (L)-Tartrate | 39 | 371 (M + H)$^+$ |

| Ex. | Structure | Compound | Yield (%) | MS (ES+) m/z |
|---|---|---|---|---|
| 577 | 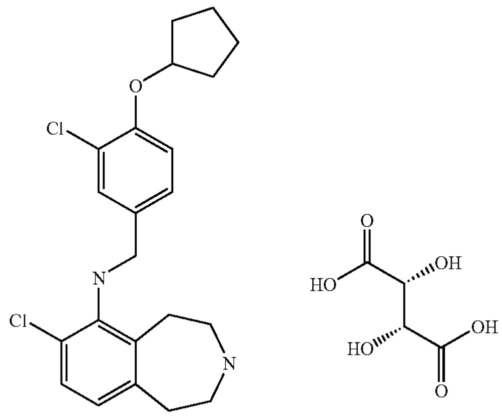 | 7-Chloro-6-(3-chloro-4-cyclopentyloxy-benzylamino)-2,3,4,5,-tetrahydro-1H-benzo[d]azepine (L)-Tartrate | 6 | 405 (M + H)+ |
| 578 | 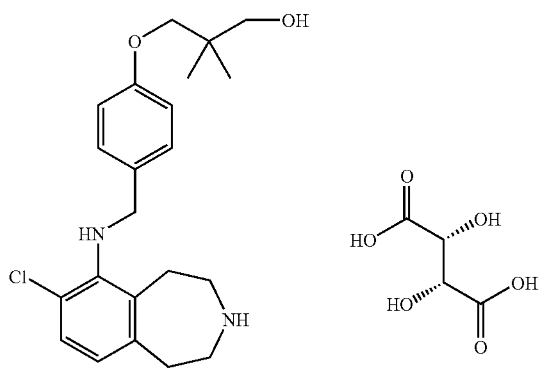 | 7-Chloro-6-[4-(2,2,dimethyl-3-hydroxy-propoxy)-benzylamino)-2,3,4,5,-tetrahydro-1H-benzo[d]azepine (L)-Tartrate | 6 | 389 (M + H)+ |
| 579 | 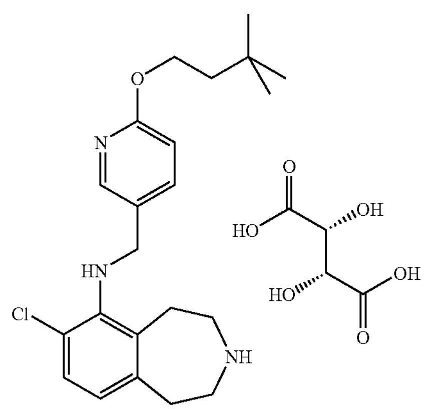 | 7-Chloro-6-[6-(3,3-dimethyl-butoxy)-pyridin-3-ylmethylamino)-2,3,4,5,-tetrahydro-1H-benzo[d]azepine (L)-Tartrate | 50 | 388 (M + H)+ |
| 580 | 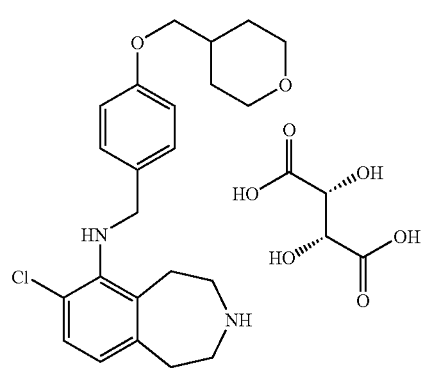 | 7-Chloro-6-[4-(tetrahydro-pyran-4-yloxymethyl)-benzylamino]-2,3,4,5,-tetrahydro-1H-benzo[d]azepine (L)-Tartrate | 37 | 401 (M + H)+ |

EXAMPLE 581

7-Chloro-4-(4-cyclohexyloxy-benzylamino)-2,3,4,5-tetrahydro-1H-benzo[d]azepine (L)-Tartrate

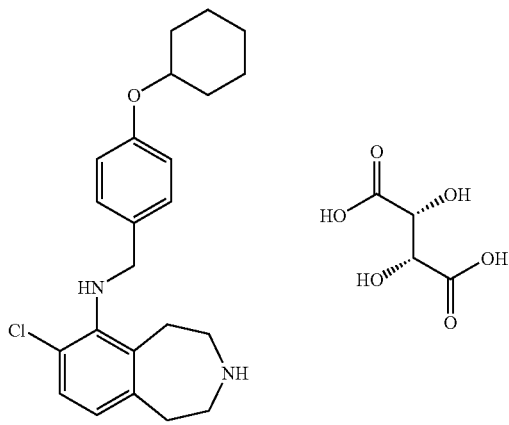

Use a method similar to the General Procedure 5-1 to couple 7-chloro-3-(2,2,2-trifluoroacetyl)-6-trifluoromethanesulfonyloxy-2,3,4,5-tetrahydro-1H-benzo[d]azepine (100 mg, 0.43 mmol) with 4-cyclohexyloxy-benzylamine (58 mg, 0.285 mol) in anhydrous toluene (1 mL). Purify the crude mixture by chromatography on silica gel eluting with cyclohexane/EtOAc (9:1) to give 7-chloro-6-(4-cyclohexyloxy-benzylamino)-3-(2,2,2-trifluoroacetyl)-2,3,4,5-tetrahydro-1H-benzo[d]azepine (78 mg, 69%).

Use a method similar to the General Procedure 1-1 to deprotect 7-chloro-6-(4-cyclohexyloxy-benzylamino)-3-(2,2,2-trifluoroacetyl)-2,3,4,5-tetrahydro-1H-benzo[d]azepine (237 mg, 0.49 mmol) to obtain the free base of the title compound. Use a method similar to the General Procedure 2-6 to obtain the title compound (208 mg, 80%). MS (ES+) m/z: 385.2 (M+H)$^+$.

EXAMPLE 582

7-Chloro-6-[4-(tetrahydro-pyran-4-yloxy)-benzylamino]-2,3,4,5-tetrahydro-1H-benzo[d]azepine (L)-Tartrate

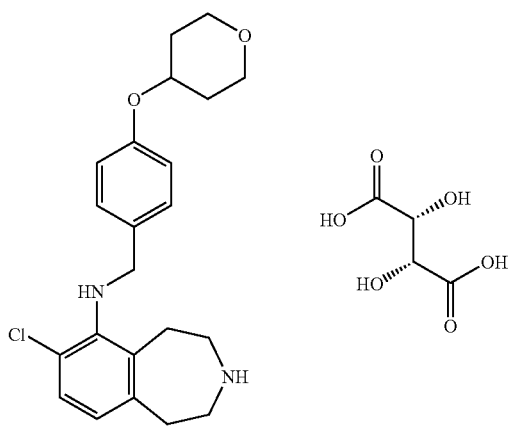

Example 582 may be prepared essentially as described in Example 581 by using 7-chloro-3-(2,2,2-trifluoroacetyl)-6-trifluoromethanesulfonyloxy-2,3,4,5-tetrahydro-1H-benzo[d]azepine and 4-(tetrahydro-pyran-4-yloxy)-benzylamine (4% yield, MS (ES+) m/z 387 (M+H)$^+$).

EXAMPLE 583

(±)-7-Chloro-6-[4-(3,3-dimethyl-cyclohexyloxy)-benzylamino]-2,3,4,5-tetrahydro-1H-benzo[d]azepine Succinate

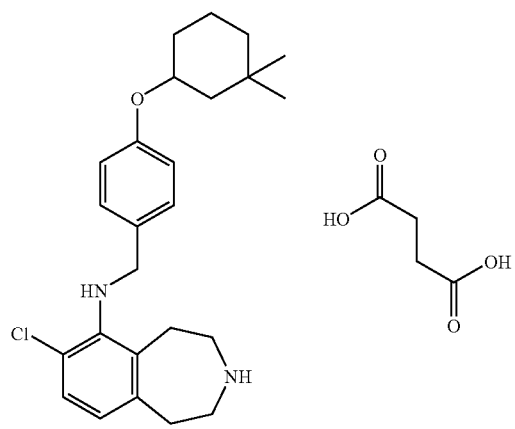

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (387 mg, 0.91 mmol) with (±)-4-(3,3-dimethyl-cyclohexyloxy)-benzylamine (233 mg, 1 mmol) in anhydrous 1,4-dioxane (14 mL). Purify the crude mixture by chromatography on silica gel eluting with cyclohexane/EtOAc (19:1 to 1:1 gradient) to obtain (±)-7-chloro-6-[4-(3,3-dimethyl-cyclohexyloxy)-benzylamino]-3-(2,2,2-trifluoroacetyl)-2,3,4,5-tetrahydro-1H-benzo[d]azepine (227 mg, 50%).

Use a method similar to the General Procedure 1-1 to deprotect (±)-7-chloro-6-[4-(3,3-dimethyl-cyclohexyloxy)-benzylamino]-3-(2,2,2-trifluoroacetyl)-2,3,4,5-tetrahydro-1H-benzo[d]azepine (220 mg, 0.43 mmol). Purify by SCX chromatography eluting with methanol and 3M ammonia in methanol. Further purify the residue by preparative HPLC. Use a method similar to the General Procedure 2-1 to obtain the title compound (65 mg, 13%). MS (ES+) m/z: 413.2 (M+H)$^+$.

EXAMPLE 584

7-Chloro-6-(4-cyclohexylthio-pyridin-3-ylmethylamino)-2,3,4,5-tetrahydro-1H-benzo[d]azepine Succinate

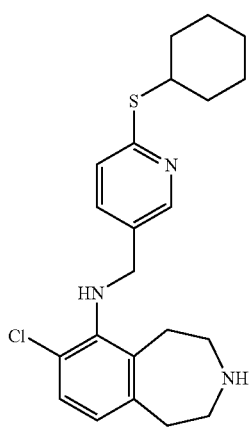
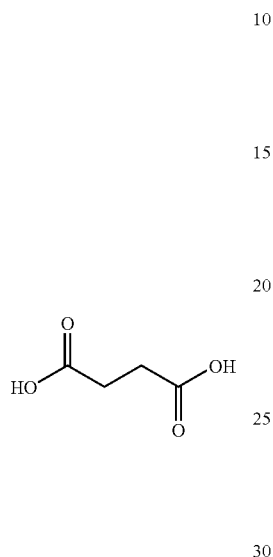

Add cesium carbonate (2.04 g, 6.27 mmol), palladium(II) acetate (46 mg, 0.209 mmol) and BINAP (195.21 mg, 0.313 mmol) to a solution of 7-chloro-3-(2,2,2-trifluoroacetyl)-6-trifluoromethanesulfonyloxy-2,3,4,5-tetrahydro-1H-benzo[d]azepine (1.79 g, 4.18 mmol) and 5-aminomethyl-2-cyclohexylthio-pyridine (1.11 g, 5.02 mmol) in anhydrous toluene (30 mL). Sonicate the resulting suspension for 30 min then heat at 100° C. for 18 h. Cool the reaction to room temperature. Purify the crude mixture by chromatography on silica gel eluting with cyclohexane/EtOAc (98:2 to 60:40 gradient) to give 7-chloro-6-(4-cyclohexylthio-pyridin-3-ylmethylamino)-3-(2,2,2-trifluoroacetyl)-2,3,4,5-tetrahydro-1H-benzo[d]azepine as an oil (1.1 g, 53%).

Use a method similar to the General Procedure 1-1 to deprotect 7-chloro-6-(4-cyclohexylthio-pyridin-3-ylmethylamino)-3-(2,2,2-trifluoroacetyl)-2,3,4,5-tetrahydro-1H-benzo[d]azepine (1.1 g, 2.21 mmol). Purify by SCX chromatography eluting with methanol and 3M ammonia in methanol. Use a method similar to the General Procedure 2-1 to obtain the title compound as a white solid (0.884 g, 77%). MS (ES+) m/z: 402 (M+H)⁺.

EXAMPLE 585

6-(4-tert-Butylthio-pyridin-3-ylmethylamino)-7-chloro-2,3,4,5-tetrahydro-1H-benzo[d]azepine (L)-tartrate

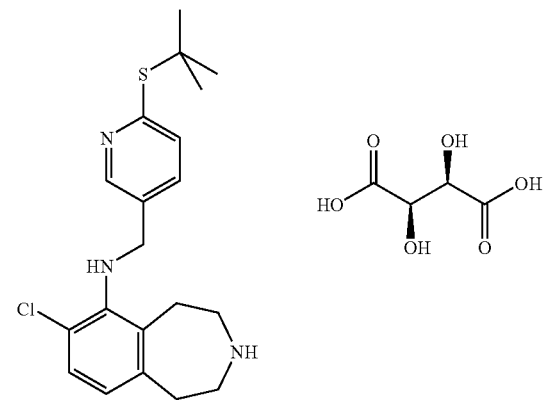

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (990 mg, 2.32 mmol) with 5-aminomethyl-2-tert-butylthio-pyridine (500 mg, 2.55 mmol) in anhydrous toluene (15 mL). Purify the crude mixture by chromatography on silica gel eluting with isohexane/EtOAc (1:0 to 3:1 gradient) to obtain 6-(4-tert-butylthio-pyridin-3-ylmethylamino)-7-chloro-3-(2,2,2-trifluoroacetyl)-2,3,4,5-tetrahydro-1H-benzo[d]azepine (650 mg, 59%). MS (ES+) m/z: 472 (M+H)⁺.

Use a method similar to the General Procedure 1-2 to deprotect 6-(4-tert-butylthio-pyridin-3-ylmethylamino)-7-chloro-3-(2,2,2-trifluoroacetyl)-2,3,4,5-tetrahydro-1H-benzo[d]azepine (650 mg, 1.37 mmol). Purify by SCX chromatography eluting with methanol and 3M ammonia in methanol. Use a method similar to the General Procedure 26 to obtain the title compound (362 mg, 50%). MS (ES+) m/z: 376 (M+H)⁺.

EXAMPLES 586-593

Examples 586-593 may be prepared essentially as described in Example 585 by using 7-chloro-3-(2,2,2-trifluoroacetyl)-6-trifluoromethanesulfonyloxy-2,3,4,5-tetrahydro-1H-benzo[d]azepine and the appropriate amine. Overall yields and MS (ES+) data are shown in the Table below.

| Ex. | Structure | Compound | Yield (%) | MS (ES+) m/z |
|---|---|---|---|---|
| 586 | 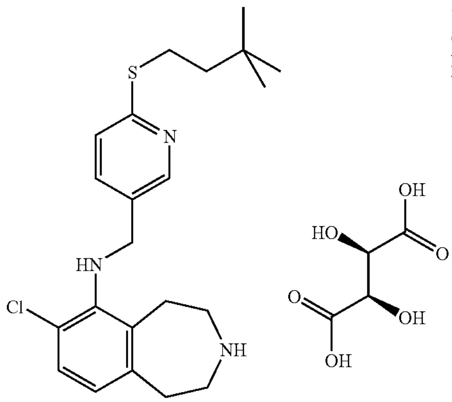 | 7-Chloro-6-[4-(3,3-dimethylbutylthio)-pyridin-3-ylmethylamino]-2,3,4,5-tetrahydro-1H-benzo[d]azepine (L)-Tartrate | 25 | 404 (M + H)+ |
| 587 | 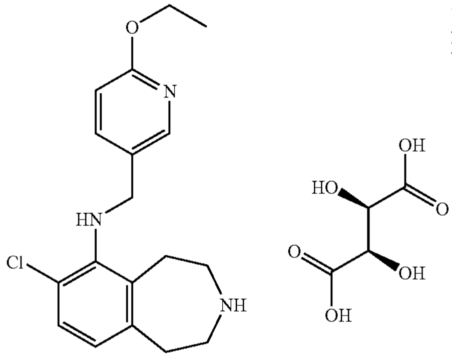 | 7-Chloro-6-(4-ethoxy-pyridin-3-ylmethylamino)-2,3,4,5-tetrahydro-1H-benzo[d]azepine (L)-Tartrate | 30 | 332 (M + H)+ |
| 588 | 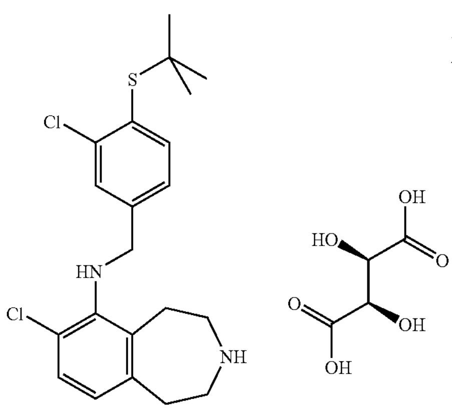 | 6-(4-tert-Butylthio-3-chloro-benzylamino)-7-chloro-2,3,4,5-tetrahydro-1H-benzo[d]azepine (L)-Tartrate | 37 | 409 (M + H)+ |
| 589 | 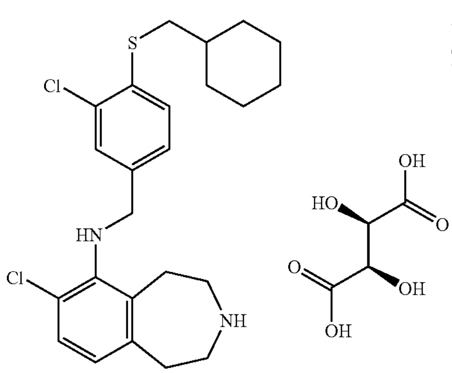 | 7-Chloro-6-(3-chloro-4-cyclohexylmethylthio-benzylamino)-2,3,4,5-tetrahydro-1H-benzo[d]azepine (L)-Tartrate | 27 | 472 (M + Na)+ |

-continued

| Ex. | Structure | Compound | Yield (%) | MS (ES+) m/z |
|---|---|---|---|---|
| 590 | 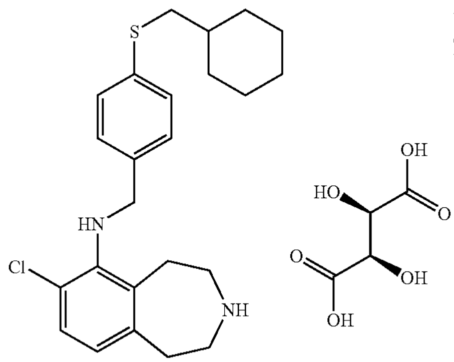 | 7-Chloro-6-(4-cyclohexylmethylthio-benzylamino)-2,3,4,5-tetrahydro-1H-benzo[d]azepine (L)-Tartrate | 13 | 415 (M + H)+ |
| 591 | 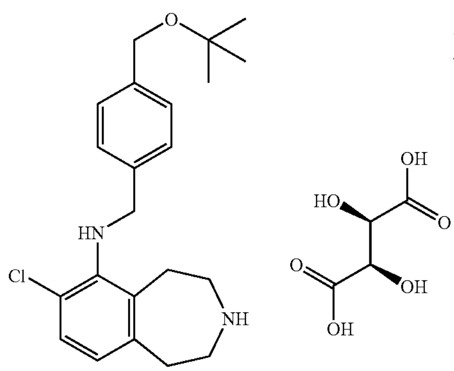 | 6-(4-tert-Butoxymethyl-benzylamino)-7-chloro-2,3,4,5-tetrahydro-1H-benzo[d]azepine (L)-Tartrate | 16 | 373 (M + H)+ |
| 592 | 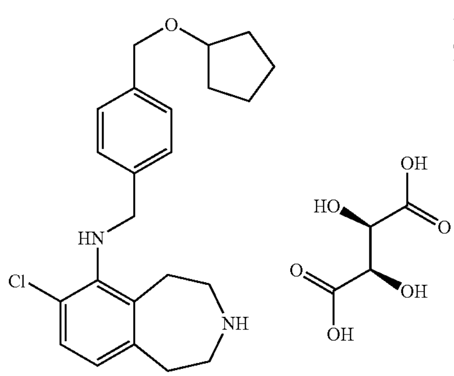 | 7-Chloro-6-(4-cyclopentyloxymethyl-benzylamino)-2,3,4,5-tetrahydro-1H-benzo[d]azepine (L)-Tartrate | 39 | 385 (M + H)+ |
| 593 | 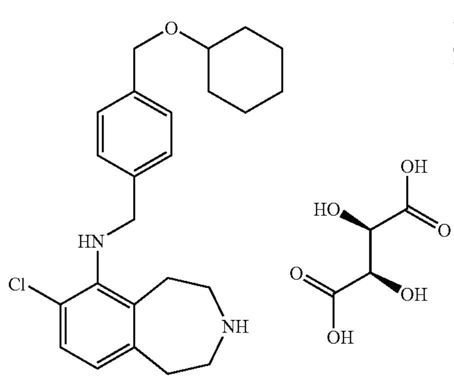 | 7-Chloro-6-(4-cyclohexylmethyl-benzylamino)-2,3,4,5-tetrahydro-1H-benzo[d]azepine (L)-Tartrate | 33 | 399 (M + H)+ |

EXAMPLE 594

7-Chloro-6-[4-(2,2-dimethyl-propoxymethyl)-benzylamino]-2,3,4,5-tetrahydro-1H-benzo[d]azepine (L)-Tartrate

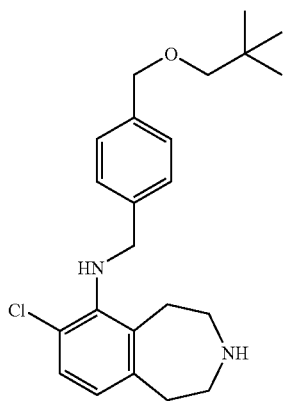

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (426 mg, 1 mmol) with 4-(2,2-dimethyl-propoxymethyl)-benzylamine (230 mg, 1.1 mmol) in anhydrous toluene (20 mL). Purify the crude mixture by chromatography on silica gel eluting with isohexane/EtOAc (1:0 to 4:1 gradient) to obtain 7-chloro-6-[4-(2,2-dimethyl-propoxymethyl)-benzylamino]-3-(2,2,2-trifluoroacetyl)-2,3,4,5-tetrahydro-1H-benzo[d]azepine (380 mg, 79%). MS (ES+) m/z: 483 (M+H)$^+$.

Use a method similar to the General Procedure 1-2 to deprotect 7-chloro-6-[4-(2,2-dimethyl-propoxyethyl)-benzylamino]-3-(2,2,2-trifluoroacetyl)-2,3,4,5-tetrahydro-1H-benzo[d]azepine (380 mg, 0.88 mmol). Purify by SCX chromatography eluting with methanol and 3M ammonia in methanol. Use a method similar to the General Procedure 2-6 to obtain the title compound (319.2 mg, 70%). MS (ES+) m/z: 387 (M+H)$^+$.

EXAMPLE 595

7-Chloro-6-(4-cyclohexylthio-benzylamino)-2,3,4,5-tetrahydro-1H-benzo[d]azepine (L)-Tartrate

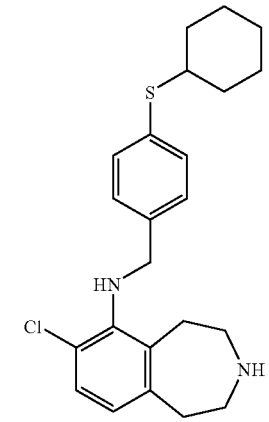 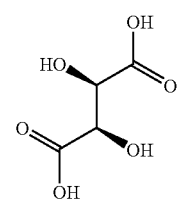

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (167 mg, 0.392 mmol) with 4-cyclohexylthio-benzylamine (95.4 mg, 0.431 mmol) in anhydrous 1,4-dioxane (5 mL). Purify the crude mixture by chromatography on silica gel eluting with isohexane/EtOAc (1:0 to 13:7 gradient) to obtain 7-chloro-6-(4-cyclohexylthio-benzylamino)-3-(2,2,2-trifluoroacetyl)-2,3,4,5-tetrahydro-1H-benzo[d]azepine (155 mg, 79%). MS (ES+) m/z: 519 (M+Na)$^+$.

Use a method similar to the General Procedure 1-2 to deprotect 7-chloro-6-(4-cyclohexylthio-benzylamino)-3-(2,2,2-trifluoroacetyl)-2,3,4,5-tetrahydro-1H-benzo[d]azepine (155 mg, 0.312 mmol). Purify by SCX chromatography eluting with methanol and 3M ammonia in methanol. Use a method similar to the General Procedure 2-6 to obtain the title compound (95 mg, 75%). MS (ES+) m/z: 401 (M+H)$^+$.

EXAMPLES 596-597

Examples 596-597 may be prepared essentially as described in Example 595 by using 7-chloro-3-(2,2,2-trifluoroacetyl)-6-trifluoromethanesulfonyloxy-2,3,4,5-tetrahydro-1H-benzo[d]azepine and the appropriate amine. Overall yields and MS (ES+) data are shown in the Table below.

| Ex. | Structure | Compound | Yield (%) | MS (ES+) m/z |
|-----|-----------|----------|-----------|--------------|
| 596 | 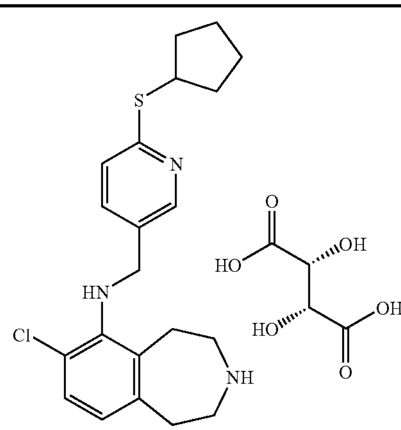          | 7-Chloro-6-(4-cyclopentylthio-pyridin-3-ylmethylamino)-2,3,4,5-tetrahydro-1H-benzo[d]azepine (L)-Tartrate | 58 | 388 (M + H)$^+$ |

-continued

| Ex. | Structure | Compound | Yield (%) | MS (ES+) m/z |
|---|---|---|---|---|
| 597 | 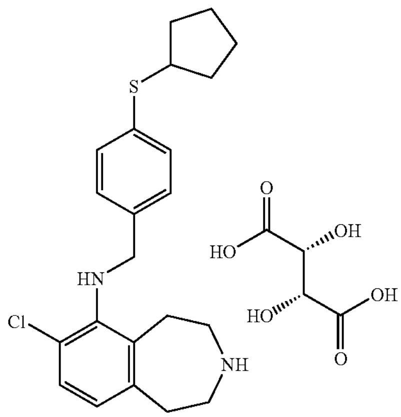 | 7-Chloro-6-(4-cyclopentylthio-benzylamino)-2,3,4,5-tetrahydro-1H-benzo[d]azepine (L)-Tartrate | 66 | 387 (M + H)+ |

EXAMPLE 598

7-Chloro-6-(3-chloro-4-ethoxy-benzylamino)-2,3,4,5-tetrahydro-1H-benzo[d]azepine (L)-Tartrate

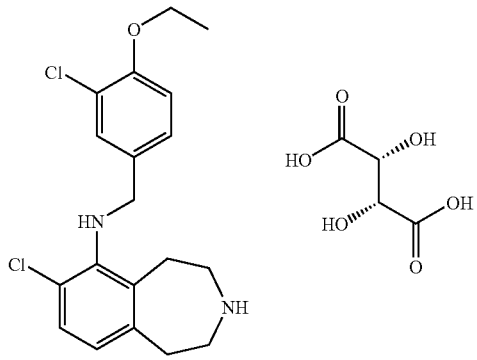

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d]azepine (150 mg, 0.35 mmol) with 4-ethoxy-3-chloro-benzylamine (94.7 mg, 0.51 mmol) in anhydrous 1,4-dioxane (10 mL). Purify the crude mixture by chromatography on silica gel eluting with isohexane/EtOAc (100:0 to 77:23 gradient) to obtain 7-chloro-6-(3-chloro-4-ethoxy-benzylamino)-3-(2,2,2-trifluoroacetyl)-2,3,4,5-tetrahydro-1H-benzo[d]azepine (111.3 mg, 68%). MS (ES+) m/z: 483 (M+Na)+.

Use a method similar to the General Procedure 1-1, but adding water (10 mL) to the 7M ammonia in methanol solution (20 mL), to deprotect 7-chloro-6-(3-chloro-4-ethoxy-benzylamino)-3-(2,2,2-trifluoroacetyl)-2,3,4,5-tetrahydro-1H-benzo[d]azepine (27 mg, 0.072 mmol) to give the free base of the title compound. Use a method similar to the General Procedure 2-6 to give the title compound as a solid (29 mg, 78%). MS (ES+) m/z: 365 (M+H)+.

EXAMPLE 599

7-Chloro-6-(4-cycloheptyloxy-benzylamino)-2,3,4,5-tetrahydro-1H-benzo[d]azepine Succinate

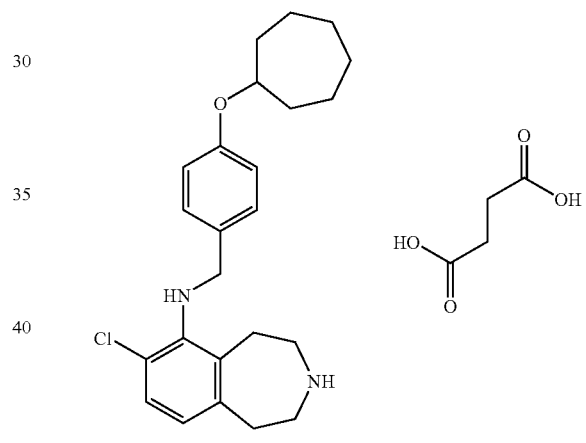

Under a nitrogen atmosphere, add 4-cycloheptyloxy-benzylamine (451 mg, 2.06 mmol), 7-chloro-3-(2,2,2-trifluoroacetyl)-6-trifluoromethanesulfonyloxy-2,3,4,5-tetrahydro-1H-benzo[d]azepine (500 mg, 1.17 mmol), palladium(II) acetate (26 mg, 0.117 mmol), BINAP (110 mg, 0.176 mmol), and cesium carbonate (1.15 g, 3.52 mmol) to toluene (20 mL). Heat the mixture at 90° C. for 12 h. Cool the mixture to room temperature and dilute with EtOAc (25 mL). Filter the solids through cellulose (20 g) and concentrate in vacuo. Purify the crude mixture by chromatography on silica gel (45 g RediSep column) eluting with hexane/EtOAc (1:0 to 4:1 gradient over 1 h; 80 mL/min) to provide 7-chloro-6-(4-cycloheptyloxy-benzylamino)-3-(2,2,2-trifluoroacetyl)-2,3,4,5-tetrahydro-1H-benzo[d]azepine as a colorless oil (384 mg, 61%). MS (APCI) m/z: 495 (M+H)+.

Dissolve 7-chloro-6-(4-cycloheptyloxy-benzylamino)-3-(2,2,2-trifluoroacetyl)-2,3,4,5-tetrahydro-1H-benzo[d]azepine (370 mg, 0.747 mmol) and lithium hydroxide monohydrate (153 mg, 3.73 mmol) in methanol (5 mL) and stir for 6 h. Concentrate the mixture in vacuo and dissolve the residue in water (20 mL). Extract the mixture with EtOAc (3×20 mL). Dry the combined organic extracts over Na2SO4, filter and concentrate in vacuo. Purify the crude mixture by reverse phase HPLC [Phenomonex C18(2) column, 5×25 cm, eluting with a gradient of water/acetonitrile (0.1% TFA in each) (9:1 through 1:9 over 40 min), 118 mL/min] to provide the trifluoroacetate salt of the title compound. Dissolve the residue in methanol and elute through an SCX column with saturated ammonia in methanol to provide the free base of the title compound (197 mg, 65%). Use a method similar to the General Procedure 2-1 to give the title compound as an off-white solid (250 mg, 100%). MS (APCI) m/z: 399 (M+H)⁺.

EXAMPLE 600

7-Chloro-6-(4-cycloheptylthio-benzylamino)-2,3,4,5-tetrahydro-1H-benzo[d]azepine Succinate

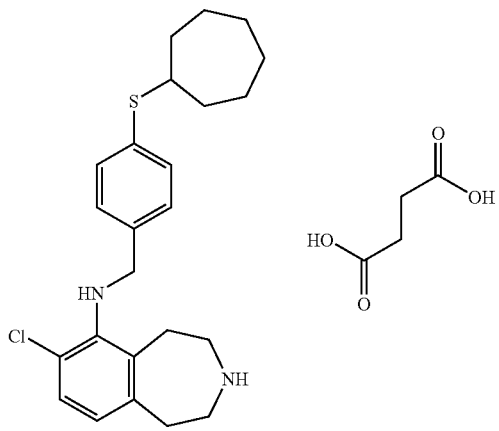

Example 600 may be prepared essentially as described in Example 599 by using 7-chloro-3-(2,2,2-trifluoroacetyl)-6-trifluoromethanesulfonyloxy-2,3,4,5-tetrahydro-1H-benzo[d]azepine and 4-cycloheptylthio-benzylamine (6% yield, MS (ES+) m/z 415 (M+H)⁺).

EXAMPLE 601

7-Chloro-6-(4-cyclohexylmethyl-benzylamino)-2,3,4,5-tetrahydro-1H-benzo[d]azepine Succinate

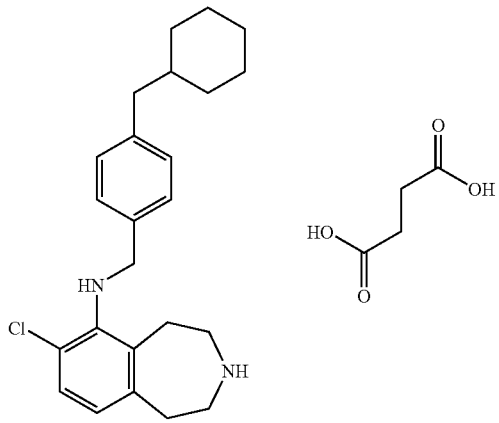

Under a nitrogen atmosphere, add 4-cyclohexylmethylbenzylamine hydrochloride (352 mg, 1.47 mmol), 7-chloro-3-(2,2,2-trifluoroacetyl)-6-trifluoromethanesulfonyloxy-2,3,4,5-tetrahydro-1H-benzo[d]azepine (500 mg, 1.17 mmol), palladium(II) acetate (52.7 mg, 0.235 mmol), BINAP (293 mg, 0.47 mmol) and cesium carbonate (1.53 g, 4.7 mmol) to toluene (20 mL). Heat the mixture at 90° C. for 12 h. Cool the mixture to room temperature and dilute with EtOAc (25 mL). Filter the solids through cellulose (20 g) and concentrate the filtrate in vacuo. Purify the crude mixture by chromatography on silica gel (45 g RediSep column) eluting with hexane/EtOAc (1:0 to 4:1 gradient over 1 h; 80 mL/min) to provide 7-chloro-6-(4-cyclohexylmethyl-benzylamino)-3-(2,2,2-trifluoroacetyl)-2,3,4,5-tetrahydro-1H-benzo[d]azepine as a colorless oil (354 mg, 63%). MS (APCI) m/z: 479 (M+H)⁺.

Dissolve 7-chloro-6-(4-cyclohexylmethyl-benzylamino)-3-(2,2,2-trifluoroacetyl)-2,3,4,5-tetrahydro-1H-benzo[d]azepine (354 mg, 0.739 mmol) and lithium hydroxide monohydrate (100 mg, 2.43 mmol) in methanol (5 mL) and stir overnight. Concentrate the mixture in vacuo and dissolve the residue in water (20 mL). Extract the mixture with EtOAc (3×20 mL). Dry the combined organic extracts over Na₂SO₄, filter, and concentrate in vacuo. Purify the crude mixture by chromatography on silica gel (40 g RediSep column) eluting with a gradient of dichloromethane and chloroform/methanol/concentrated ammonium hydroxide (80:18:2) over 1 h (80 mL/min) followed by reverse phase HPLC [Phenomonex C18(2) column (5×25 cm), eluting with water/acetonitrile (0.1% TFA in each) (9:1 to 1:9 gradient over 40 min), 118 mL/min] to obtain the trifluoroacetate salt of the title compound. Dissolve the residue in methanol and elute through SCX column with saturated ammonia in methanol to provide 7-chloro-6-(4-cyclohexylmethyl-benzylamino)-2,3,4,5-tetrahydro-1H-benzo[d]azepine (184 mg, 64%). Use a method similar to the General Procedure 2-1 to give the title compound as a white solid (240 mg, 100%). MS (ES) m/z: 383 (M+H)

EXAMPLE 602

7-Chloro-6-[4-(2-methyl-butyl)-benzylamino]-2,3,4,5-tetrahydro-1H-benzo[d]azepine Succinate

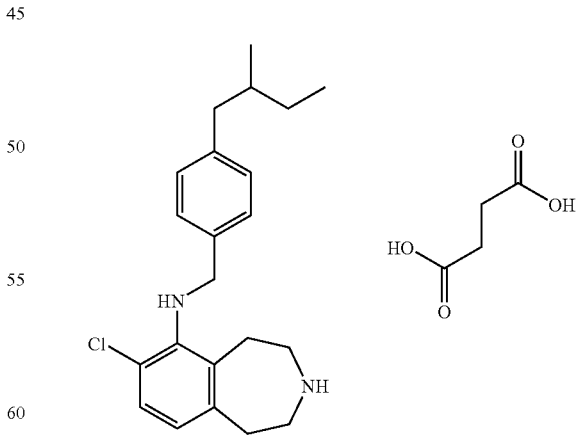

Under a nitrogen atmosphere, add 4-(2-methyl-butyl)-benzylamine (450 mg, 2.54 mmol), 7-chloro-3-(2,2,2-trifluoroacetyl)-6-trifluoromethanesulfonyloxy-2,3,4,5-tetrahydro-1H-benzo[d]azepine (720 mg, 1.7 mmol), palladium(II) acetate (40 mg, 0.17 mmol), BINAP (222 mg, 0.34 mmol) and cesium carbonate (1.4 g, 4.3 mmol) to toluene (20 mL). Heat the mixture at 95° C. for 12 h. Cool the mixture to room temperature and apply the mixture to a silica gel column eluting with hexane/EtOAc (10:1) to provide 7-chloro-6-[4-(2-methyl-butyl)-benzylamino]-3-(2,2,2-trifluoroacetyl)-2,3,4,5-tetrahydro-1H-benzo[d]azepine (450 mg, 59%). MS (ES+) m/z: 453 (M+H)⁺.

Dissolve 7-chloro-6-[4-(2-methyl-butyl)-benzylamino]-3-(2,2,2-trifluoroacetyl)-2,3,4,5-tetrahydro-1H-benzo[d]azepine (450 mg, 1 mmol) and concentrated ammonium hydroxide (5 mL) in methanol (10 mL) and stir overnight. Concentrate the mixture in vacuo. Purify the crude mixture by SCX chromatography eluting with methanol and 3M ammonia in methanol. Concentrate the product in vacuo and purify the residue by reverse phase HPLC [Phenomonex Luna C18 (2), 50 mm×250 mm, eluting with acetonitrile/water with 0.1% TFA (2:3)]. Concentrate in vacuo, basify with potassium carbonate and extract into dichloromethane. Dry the organic solution over Na₂SO₄, filter and concentrate in vacuo to provide the free base of the title compound (205 mg, 57%). Use a method similar to the General Procedure 2-1 to give the title compound as a white solid (280 mg, 59%). MS (APCI) m/z: 357 (M+H)⁺.

EXAMPLE 603

7-Chloro-6-[4-(3,3-dimethyl-butyl)-benzylamino]-2,3,4,5-tetrahydro-1H-benzo[d]azepine Succinate

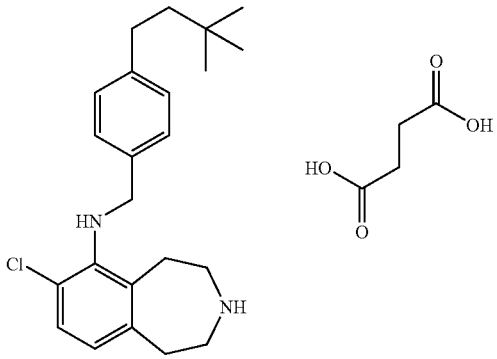

Use a method similar to the General Procedure 5-1 to react 7-chloro-3-(2,2,2-trifluoroacetyl)-6-trifluoromethanesulfonyloxy-2,3,4,5-tetrahydro-1H-benzo[d]azepine (623 mg, 1.46 mmol), palladium(II) acetate (33 mg, 0.146 mmol), BINAP (182 mg, 0.292 mmol), 4-(3,3-dimethyl-butyl)-benzylamine (560 mg, 2.93 mmol) and cesium carbonate (666 mg, 2.04 mmol) in degassed toluene (40 mL). Degas the mixture with vacuum/nitrogen purge and heat to 100° C. for 16 h. Cool the mixture to room temperature, dilute with EtOAc and wash with water. Dry the organic phase over MgSO₄, filter and concentrate in vacuo. Purify the crude mixture by chromatography on silica gel eluting with hexane and then hexane/EtOAc (19:1, 9:1) to obtain 7-chloro-6-[4-(3,3-dimethyl-butyl)-benzylamino]-3-(2,2,2-trifluoroacetyl)-2,3,4,5-tetrahydro-1H-benzo[d]azepine as oil (622 mg, 91%). MS (ES+) m/z: 467 (M+H)⁺.

Use a method similar to the General Procedure 1-2, using 7-chloro-6-[4-(3,3-dimethyl-butyl)-benzylamino]-3-(2,2,2-trifluoroacetyl)-2,3,4,5-tetrahydro-1H-benzo[d]azepine, (448 mg, 0.96 mmol), to give the free base of the title compound as an oil (320 mg, 90%) that was used without further purification. MS (ES+) m/z: 371 (M+H)⁺. Use a method similar to the General Procedure 2-1, using 7-chloro-6-[4-(3,3-dimethyl-butyl)-benzylamino]-2,3,4,5-tetrahydro-1H-benzo[d]azepine (315 mg, 0.85 mmol) to give the title compound as a white solid (340 mg, 82%). MS (ES+) m/z: 371 (M+H)⁺.

EXAMPLE 604

7-Chloro-6-[6-(3,3-dimethyl-butyl)-pyridin-3-yl-methylamino]-2,3,4,5-tetrahydro-1H-benzo[d]azepine Succinate

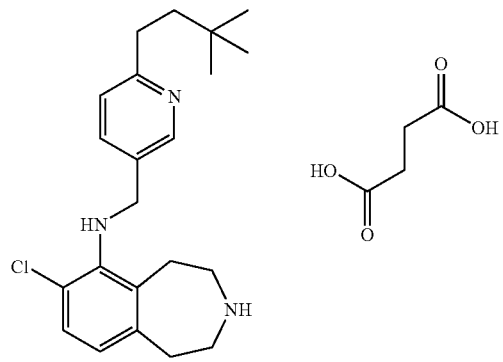

Use a method similar to the General Procedure 5-2 to react 7-chloro-3-(2,2,2-trifluoroacetyl)-6-trifluoromethanesulfonyloxy-2,3,4,5-tetrahydro-1H-benzo[d]azepine (166 mg, 0.39 mmol), tris(dibenzylideneacetone)dipalladium(0) (71 mg, 0.078 mmol), BINAP (103 mg, 0.156 mmol), 3-aminomethyl-6-(3,3-dimethyl-butyl)-pyridine (150 mg, 0.78 mmol) and cesium carbonate (178 mg, 0.546 mmol) in degassed toluene (20 mL). Degas the mixture with vacuum/nitrogen purge and heat to 100° C. for 14 h. Cool the mixture to room temperature, dilute with EtOAc and filter through Celite®. Purify the crude mixture by chromatography on silica gel eluting with hexane and then hexane/EtOAc (19:1, 9:1 and 4:1) to obtain 7-chloro-6-[6-(3,3-dimethyl-butyl)-pyridin-3-yl-methylamino]-3-(2,2,2-trifluoroacetyl)-2,3,4,5-tetrahydro-1H-benzo[d]azepine as oil (149 mg, 82%). MS (ES+) m/z: 468 (M+H)⁺.

Use a method similar to the General Procedure 1-2, using 7-chloro-6-[6-(3,3-dimethyl-butyl)-pyridin-3-yl-methylamino]-3-(2,2,2-trifluoroacetyl)-2,3,4,5-tetrahydro-1H-benzo[d]azepine (140 mg, 0.29 mmol), to give the free base of the title compound as an oil (96 mg, 86%) that was used without further purification. MS (ES+) m/z: 372 (M+H)⁺. Use a method similar to the General Procedure 2-1, using 7-chloro-6-[6-(3,3-dimethyl-butyl)pyridin-3-yl-methylamino]-2,3,4,5-tetrahydro-1H-benzo[d]azepine (96 mg, 0.258 mmol) to give the title compound as a solid (19 mg, 94%). MS (ES+) m/z: 372 (M+H)⁺.

EXAMPLES 605-607

Examples 605-607 may be prepared essentially as described in Example 604 using 7-chloro-3-(2,2,2-trifluoroacetyl)-6-trifluoromethanesulfonyloxy-2,3,4,5-tetrahydro-1H-benzo[d]azepine and the appropriate amine. Overall yields and MS (ES+) data are shown in the Table below.

| Ex. | Structure | Compound | Yield (%) | MS (ES+) m/z |
|---|---|---|---|---|
| 605 | 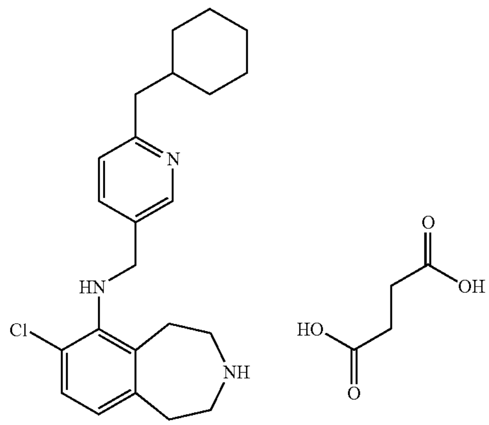 | 7-Chloro-6-(6-cyclohexylmethyl-pyridin-3-yl-methylamino)-2,3,4,5-tetrahydro-1H-benzo[d]azepine Succinate | 42 | 384 (M + H)+ |
| 606 | 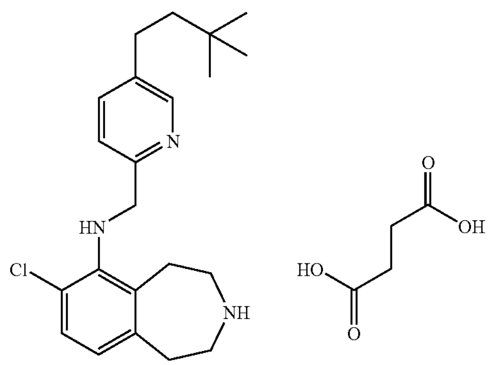 | 7-Chloro-6-[5-(3,3-dimethyl-butyl)-pyridin-2-yl-methylamino]-2,3,4,5-tetrahydro-1H-benzo[d]azepine Succinate | 34 | 372 (M + H)+ |
| 607 | 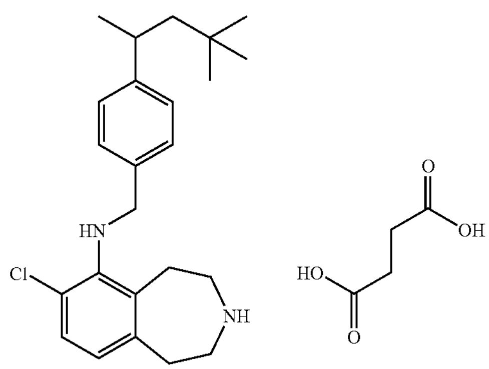 | 7-Chloro-6-[4-(1,3,3-trimethyl-butyl)-benzylamino]-2,3,4,5-tetrahydro-1H-benzo[d]azepine Succinate | 47 | 385 (M + H)+ |

Preparation 320

2-Hydroxymethyl-[1,3,4]-thiadiazole

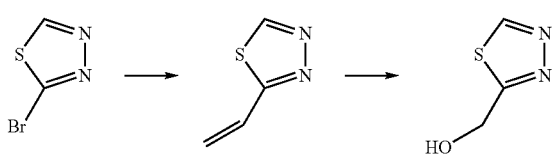

2-Vinyl-[1,3,4]-thiadiazole: Combine 2-bromo-[1,3,4]-thiadiazole (3.5 g±21.2 mmol), tributylvinyltin (6.20 mL, 21.2 mmol) and tetrakis(triphenylphosphine)palladium(0) (735 mg, 0.6 mmol) in anhydrous toluene (141 mL). Heat the mixture at reflux for 18 h. Add methanol and dichloromethane to dissolve the residue and evaporate onto silica gel. Purify the residue by chromatography on silica gel eluting with hexane/EtOAc (1:0 to 1:4 gradient) to give the desired intermediate (0.49 g, 21%). GC-MS m/z: 112 (M+).

2-Hydroxymethyl-[1,3,4]-thiadiazole: At −10° C. bubble ozone through a solution of 2-vinyl-[1,3,4]-thiadiazole (400 mg, 3.57 mmol) in methanol (18 mL). After 20 min the starting material is consumed. Add then sodium borohydride (37 mg, 0.98 mmol) and warm to room temperature. Evaporate the mixture and purify the residue by passage through a pad of silica gel eluting with methanol/dichloromethane (98:2 to 96:4 gradient) to give the title compound (0.24 g, 60%). MS (ES+) m/z: 117 (M+H)+.

Preparation 321

5-Chloromethylthiazole

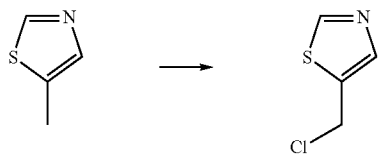

Combine 5-methylthiazole (1.5 g, 15.1 mmol), N-chlorosuccinimide (2.6 g, 19.4 mmol) and AIBN (0.26 g, 1.6 mmol) in carbon tetrachloride (15 mL). Reflux under nitrogen for 3 h. Cool the reaction mixture and concentrate in vacuo. Purify by chromatography on silica gel eluting with hexane/EtOAc (4:1) to give the title compound as a yellow oil (0.38 g, 19%).

Preparation 322

5-Bromomethyl-2-chlorothiazole

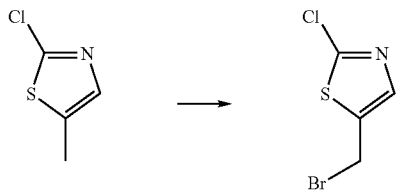

5-Chloromethyl-2-chlorothiazole: Combine 5-methyl-2-chlorothiazole (1.05 g, 7.5 mmol), NBS (1.7 g, 9.6 mmol) and AIBN (0.12 g, 0.73 mmol) in carbon tetrachloride (10 mL). Reflux under nitrogen for 7 h. Cool and concentrate in vacuo. Purify by chromatography on silica gel eluting with hexane/EtOAc (9:1) to give the title compound as a yellow oil (0.82 g, 51%).

Preparation 323

(±)-1-Methanesulfonyloxy-1-thiazol-2-yl-ethyl

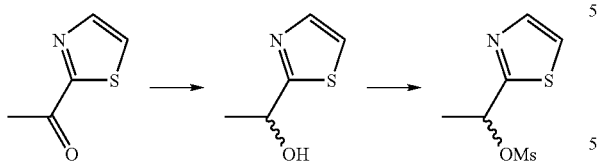

(±)-1-Thiazol-2-yl-ethanol: Add sodium borohydride (357 mg, 9.4 mmol) portionwise, over 5 min, to a solution of 2-acetylthiazole (1.0 g, 7.8 mmol) in methanol (25 mL) at 0° C. under a nitrogen atmosphere. Stir the mixture for 2 h at room temperature. Concentrate the mixture in vacuo, dilute the residue with brine (30 mL) and adjust the mixture to pH 6 with 5N aqueous HCl (10 mL). Extract the mixture with EtOAc (40 mL). Dry the organic layer over $Na_2SO_4$, filter and concentrate in vacuo to obtain the desired intermediate (1.0 g, 99%). GC-MS m/z: 129 ($M^+$).

(±)-1-Methanesulfonyloxy-1-thiazol-2-yl-ethyl: Dissolve 1-thiazol-2-yl-ethanol (1.0 g, 7.7 mmol) in dichloromethane (30 mL) and triethylamine (1.2 mL, 8.5 mmol). Cool the solution to 0° C., then add methanesulphonyl chloride (690 μl, 8.9 mmol) under a nitrogen atmosphere. Stir the solution for 1.5 h at room temperature, then wash with saturated aqueous $NaHCO_3$ (30 mL). Dry the organic layer over $Na_2SO_4$, filter and concentrate in vacuo. Purify the crude mixture by chromatography on silica gel eluting with dichloromethane/hexane/methanol (50:45:5) to obtain the title compound (1.3 g, 81%). GC-MS m/z: 207 ($M^+$).

Preparation 324

(±)-1-(3-Fluorophenyl)ethyl bromide

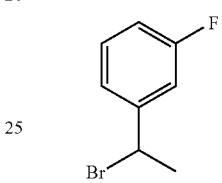

Dissolve (±)-1-(3-fluorophenyl)ethanol (250 mg, 1.786 mmol) in carbon tetrachloride (10 mL). Add phosphorus tribromide (0.1 mL, 1.786 mmol) at 0° C. and stir the solution at room temperature overnight. Dilute the reaction mixture with dichloromethane and wash with brine. Dry the organic phase over $Na_2SO_4$, filter and concentrate in vacuo to obtain the title compound (285 mg) that was used without any further purification.

Preparation 325

(S)-1-[4-(1-Hydroxyethyl)-phenyl]-3,3-dimethylbutan-1-one

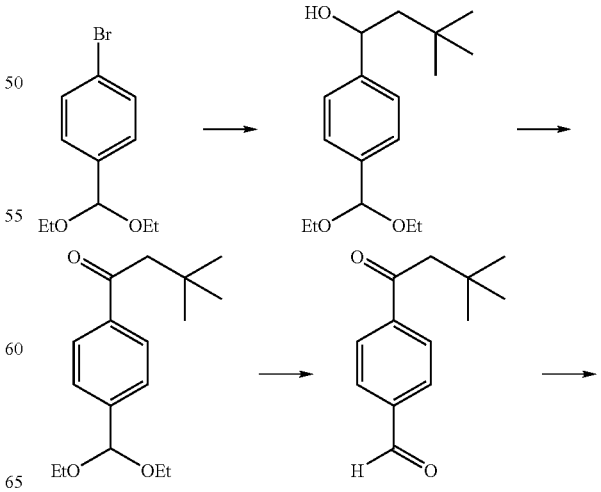

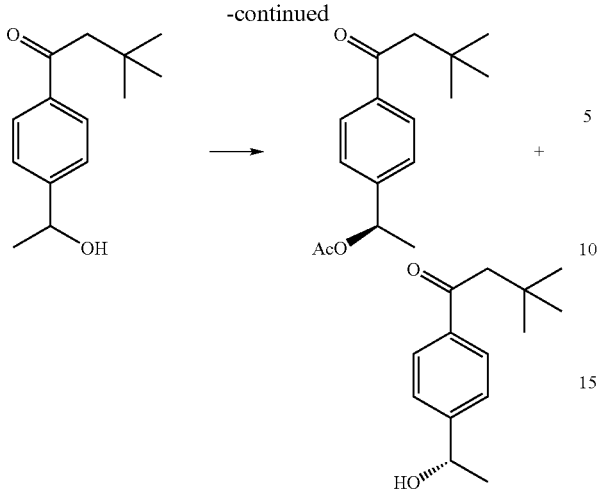

1-[4-(Diethoxymethyl)phenyl]-3,3-dimethylbutan-1-ol: Dissolve 1-bromo-4-(diethoxymethyl)-benzene (6.1 g, 23.55 mmol) in anhydrous THF (150 mL) and cool the solution to −78° C. Add n-butyllithium (11.3 mL, 28.26 mmol, 2.5M solution in hexane) and stir the mixture for 30 min. Add 3,3-dimethylbutyraldehyde (4.7 mL, 35.33 mmol) and stir the mixture for 1 h. Add water and EtOAc. Warm the solution to room temperature and extract the aqueous layer three times with EtOAc. Dry the combined organic extracts with $Na_2SO_4$, filter and concentrate in vacuo. Purify the crude mixture by chromatography on silica gel eluting with hexane/EtOAc (93:7) to give the desired intermediate as a colorless oil (3.8 g, 58%).

1-[4-(Diethoxymethyl)-phenyl]-3,3-dimethylbutan-1-one: Dissolve 1-[4-(diethoxymethyl)-phenyl]-3,3-dimethylbutan-1-ol (3.8 g, 13.57 mmol) in hexane (50 mL). Add manganese dioxide (3.5 g, 40.71 mmol) and stir the mixture at 60° C. overnight. Filter the solid and concentrate the filtrate in vacuo to give the desired intermediate as a colorless oil (3.49 g, 93%).

4-(3,3-Dimethyl-butyryl)-benzaldehyde: Dissolve 1-[4-(diethoxymethyl)-phenyl]-3,3-dimethylbutan-1-one (3.49 g, 12.55 mmol) in acetone (50 mL). Add p-toluenesulfonic acid monohydrate (238 mg, 1.256 mmol). Heat the mixture under reflux for 3 h. Concentrate in vacuo and partition the residue between water and EtOAc. Extract the aqueous phase three times with EtOAc. Dry the combined organic extracts over $Na_2SO_4$, filter and concentrate in vacuo. Purify the crude mixture by chromatography on silica gel eluting with hexane/EtOAc (9:1) to give the desired intermediate as a colorless oil (1.67 g, 65%).

1-[4-(1-Hydroxyethyl)-phenyl]-3,3-dimethylbutan-1-one: Dissolve 4-(3,3-dimethyl-butyryl)-benzaldehyde (1.67 g, 8.186 mmol) in anhydrous THF (20 mL) and cool the solution at −10° C. Add methyl magnesium bromide (2.7 mL, 8.186 mmol, 3M solution in diethyl ether) and stir the mixture for 30 min. Add water at 0° C., dilute with EtOAc and extract the aqueous layer three times with EtOAc. Dry the combined organic extracts over $Na_2SO_4$, filter through a short pad of silica gel and concentrate in vacuo to give the desired intermediate as yellow oil (1.519 g, 84%).

(S)-1-[4-(1-hydroxyethyl)-phenyl]-3,3-dimethylbutan-1-one: Dissolve 1-[4-(1-hydroxyethyl)-phenyl]-3,3-dimethylbutan-1-one (1.519 g, 6.905 mmol) in diisopropyl ether (20 mL). Add 4 Å molecular sieves powder (1.5 g), vinyl acetate (2 mL) and lipase Candida Antarctica acrylic resin (150 mg). Stir the mixture at room temperature overnight. Remove the solid residue by filtration. Concentrate the filtrate in vacuo and purify the crude mixture by chromatography on silica gel eluting with hexane/EtOAc (4:1) to give (R)-1-(1-acetoxy-ethyl)-4-(3,3-dimethyl-butyryl)-benzene as colorless oil (0.661 g, 36%) and (S)-1-[4-(1-hydroxyethyl)-phenyl]-3,3-dimethylbutan-1-one as a light yellow oil (0.737 g, 49%).

Preparation 326

4-Acetyl-benzyl bromide

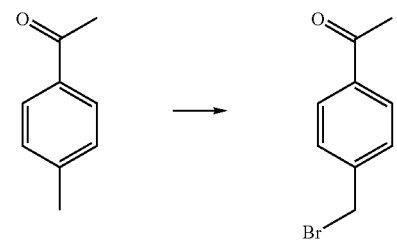

Heat a mixture of 4'-methylacetophenone (5 g, 37.26 mmol), NBS (6.964 g, 39.12 mmol), and AIBN (153 mg, 0.93 mmol) in carbon tetrachloride (120 mL) for 14 h at reflux. Cool to ambient temperature and wash sequentially with water (100 mL), 1M aqueous HCl (100 mL), 5% aqueous $NaHCO_3$ (100 mL) and brine (100 mL). Dry the organic phase over $Na_2SO_4$, filter and concentrate in vacuo. Purify the crude mixture by chromatography on silica gel eluting sequentially with hexane and hexane/EtOAc (19:1, 9:1) to provide the title compound as oil (5.191 g, 65%). GC-MS m/z: 213 ($M^+$).

Preparations 353-354

The compounds of Preparations 353-354 may be prepared essentially as described in Preparation 326 using 4'-methylpropiophenone (Preparation 353) and 4'-methylbutyrophenone (Preparation 354). Yields are shown in the Table below.

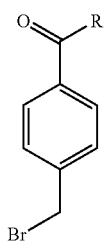

| Prep. | R | Compound | Yield (%) |
|---|---|---|---|
| 353 | Et | 4-Propionyl-benzyl bromide | 92 |
| 354 | n-Pr | 4-Butyryl-benzyl bromide | 42 |

Preparation 329

4-(3-Methyl-butyryl)-benzyl bromide

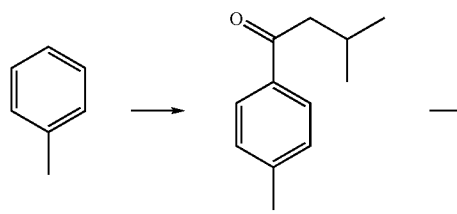

3,4'-Dimethylbutyrophenone: Add slowly isovaleryl chloride (3.0 g, 24.88 mmol) to an ice-cold stirred solution of aluminum trichloride (4.976 g, 37.32 mmol) in anhydrous toluene (60 mL). Stir the reaction mixture at ambient temperature overnight. Add slowly ice-cold water and extract the mixture twice with EtOAc. Dry the combined organic extracts over $Na_2SO_4$, filter and concentrate in vacuo to give the desired intermediate (4.38 g, 100%) that was used without any further purification. GC-MS m/z: 176 ($M^+$).

4-(3-Methyl-butyryl)-benzyl bromide: Heat a mixture of 3,4'-dimethylbutyrophenone (3 g, 17.02 mmol), NBS (3.787 g, 16.18 mmol), and AIBN (70 mg, 0.425 mmol) in carbon tetrachloride (80 mL) for 14 h at reflux. Cool to ambient temperature and filter the mixture. Concentrate the filtrate in vacuo. Purify the crude mixture by chromatography on silica gel eluting sequentially with hexane and hexane/EtOAc (9:1) to provide the title compound as oil (2.802 g, 65%). GC-MS m/z: 255 ($M^+$).

Preparations 356-357

The compounds of Preparations 356-357 may be prepared essentially as described in Preparation 329 using the appropriate acyl chloride. Overall yields and GC-MS data are shown in the Table below.

| Prep. | R | Compound | Yield (%) | GC-MS m/z |
|---|---|---|---|---|
| 330 | i-Propyl | 4-Isobutyryl-benzyl bromide | 32 | 241 ($M^+$) |
| 357 | 2-Pyridyl | 4-(Pyridine-2-carbonyl)-benzyl bromide | 9 | 276 ($M^+$) |

Preparation 332

4 (Pyridine-3-carbonyl)-benzyl methanesulfonate

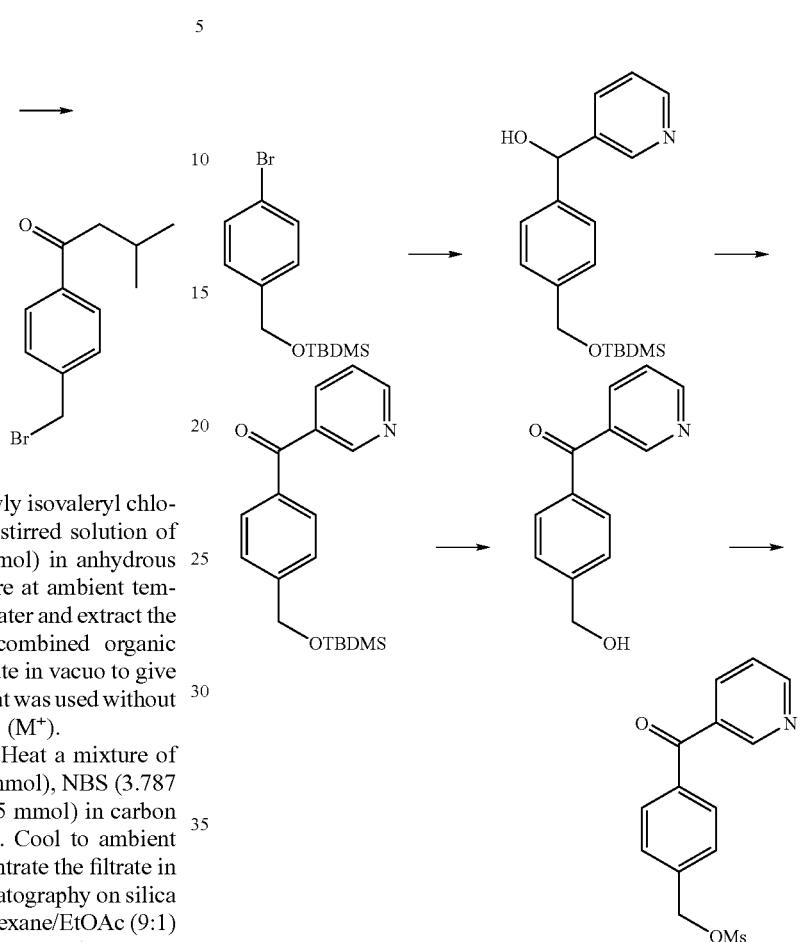

[4-(tert-Butyldimethylsilyloxymethyl)-phenyl]-pyridin-3-yl-methanol: Dissolve 4-(tert-butyldimethylsilyloxymethyl)bromobenzene (1 g, 3.319 mmol, prepared by following the procedure described in *J. Am. Chem. Soc.* 1995, 117, 704-714) in anhydrous THF (20 mL). Cool the solution to −78° C., add n-BuLi (4.149 mL, 6.638 mmol, 1.6M solution in hexane) and stir at this temperature for 1.5 h. Warm to −60° C., stir for an additional 30 min and add 3-pyridine carboxaldehyde. Allow the reaction mixture to warm gradually to room temperature and stir overnight. Add brine and extract with EtOAc. Dry the organic phase over $Na_2SO_4$, filter and concentrate in vacuo. Purify the crude mixture by chromatography on silica gel eluting sequentially with hexane and EtOAc to give the desired intermediate (380 mg, 35%). MS (ES+) m/z: 330 $(M+H)^*$.

[4-(tert-Butyldimethylsilyloxymethyl)-phenyl]-pyridin-3-yl-methanone: Add manganese dioxide (1.44 g) to a stirred solution of [4-(tert-butyldimethylsilyloxymethyl)-phenyl]-pyridin-3-yl-methanol (360 mg, 0.303 mmol) in anhydrous 1,4-dioxane (25 mL). Heat the mixture to 70° C. overnight. Cool the reaction mixture to room temperature, filter through Celite® and wash with EtOAc. Concentrate the filtrate in vacuo. Purify the crude mixture by chromatography on silica gel eluting sequentially with hexane and hexane/EtOAc (1:1) to provide the desired intermediate (233 mg, 65%). GC-MS m/z: 327 ($M^+$).

4-(Pyridine-3-carbonyl)-benzyl alcohol: Add tetrabutylammonium fluoride (1.37 mL, 1.37 mmol, 1M solution in THF) to a solution of [4-(tert-butyldimethylsilyloxymethyl)-phenyl]-pyridin-3-yl-methanone (225 mg, 0.687 mmol) in anhydrous THF (10 mL) at 0° C. and stir at this temperature for 1 h. Concentrate the solvent in vacuo and purify the crude mixture by chromatography on silica gel eluting with EtOAc to provide the desired intermediate (85 mg, 58%). MS (ES+) m/z: 214 (M+H)$^+$.

4-(Pyridine-3-carbonyl)-benzyl methanesulfonate: Dissolve 4-(pyridine-3-carbonyl)-benzyl alcohol (85 mg, 0.399 mmol) in dichloromethane (5 mL). Cool to 0° C. and add triethylamine (0.056 mL, 0.438 mmol) and methanesulfonyl chloride (0.033 mL, 0.438 mmol). Allow the mixture to warm to room temperature and stir for 2 h. Dilute the reaction mixture with dichloromethane and wash with saturated aqueous NaHCO$_3$. Dry the organic phase over Na$_2$SO$_4$, filter and concentrate in vacuo to provide the title compound as oil (115 mg, 100%). GC-MS m/z: 291 (M$^+$).

Preparation 333

4-(Pyridine-4-carbonyl)-benzyl methanesulfonate

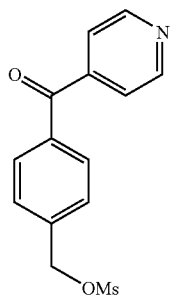

The compound of Preparation 333 may be prepared essentially as described in Preparation 332 using 4-(tert-butyldimethylsilyloxymethyl)bromobenzene and 4-pyridine carboxaldehyde (GC-MS m/z 291 (M)$^+$).

Preparation 334

4-(4-Cyano-benzoyl)-benzyl bromide

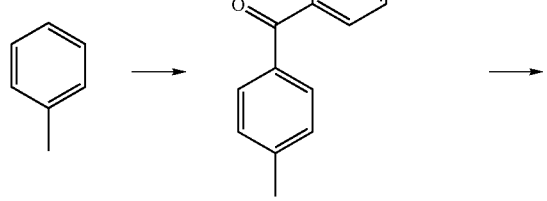

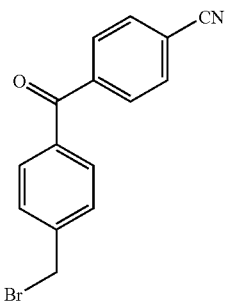

4-(4-Methyl-benzoyl)-benzonitrile: Suspend 4-cyanobenzoyl chloride (2.0 g, 12 mmol) in anhydrous toluene (30 mL). Add aluminum trichloride (2.4 g, 18 mmol) in three portions and stir the reaction mixture at ambient temperature overnight. Cool to 0° C., add carefully water and extract the mixture twice with EtOAc. Dry the combined organic extracts over Na$_2$SO$_4$, filter and concentrate in vacuo to give a solid. Suspend the solid in diethyl ether and filter to obtain the desired intermediate (1.30 g, 49%) that was used without any further purification. GC-MS m/z: 221 (Me).

4-(4-Cyano-benzoyl)-benzyl bromide: Heat a mixture of 4-(4-methyl-benzoyl)-benzonitrile (300 mg, 1.356 mmol), NBS (386 mg, 2.169 mmol), and AIBN (22 mg, 0.136 mmol) in carbon tetrachloride (10 mL) for 14 h at reflux. Add additional NBS (121 mg) and AIBN (11 mg) and reflux the mixture for 3 h. Cool the reaction mixture to ambient temperature and filter the mixture. Concentrate the filtrate in vacuo. Purify the crude mixture by chromatography on silica gel eluting sequentially with hexane and hexane/EtOAc (9:1) to provide the title compound as a solid (286 mg, 70%) GC-MS m/z: 300 (M$^+$).

Preparation 335

4-(3-Cyano-benzoyl)-benzyl bromide

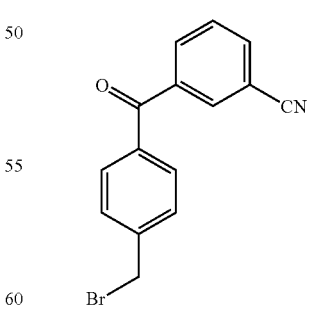

The compound of Preparation 335 may be prepared essentially as described in Preparation 334 using 3-cyanobenzoyl chloride (GC-MS m/z 300 (M$^+$)).

Preparation 336

2-Methanesulfonyloxymethyl-5-(3-methyl-butyryl)-pyridine

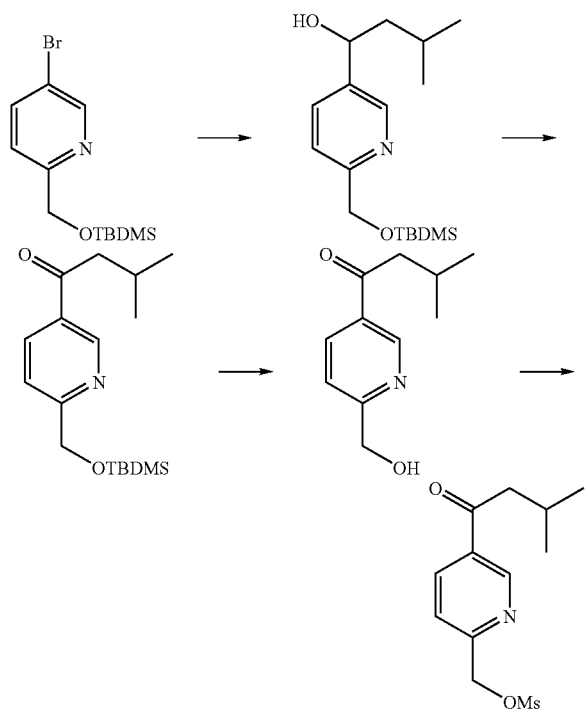

2-(tert-Butyldimethylsilyloxymethyl)-5-(1-hydroxy-3-methyl-butyl)-pyridine: Dissolve 5-bromo-2-(tert-butyldimethylsilyloxymethyl)-pyridine (0.5 g, 1.654 mmol, prepared by following the procedure described in *J. Med. Chem.* 1987, 30, 871-880) in anhydrous THF (12 mL). Cool the solution to −78° C., add n-BuLi (1.14 mL, 1.819 mmol, 1.6M solution in hexane) and stir at this temperature for 40 min. Add slowly isovaleryl aldehyde (0.284 mL, 2.646 mmol) and stir the mixture for 5 h at −78° C. Add additional isovaleryl aldehyde (0.089 mL, 0.827 mmol) and stir the mixture for 1.5 h at −78° C. Add ammonium chloride at −78° C. and warm the mixture to room temperature. Add EtOAc and extract the aqueous layer twice with EtOAc. Dry the combined organic extracts over $Na_2SO_4$, filter and concentrate in vacuo. Purify the crude mixture by chromatography on silica gel eluting with hexane and hexane/EtOAc (4:1) to give the desired intermediate as oil (330 mg, 64%). GC-MS m/z: 309 ($M^+$).

2-(tert-Butyldimethylsilyloxymethyl)-5-(3-methyl-butyryl)-pyridine: Add manganese dioxide (1.32 g) to a stirred solution of 2-(tert-butyldimethylsilyloxymethyl)-5-(1-hydroxy-3-methyl-butyl)-pyridine (330 mg, 1.066 mmol) in anhydrous 1,4-dioxane (30 mL). Heat the mixture to 70° C. overnight. Cool the reaction mixture to room temperature, filter through Celite® and wash with EtOAc. Concentrate the filtrate in vacuo to provide the desired intermediate as oil (327 mg, 100%). GC-MS m/z: 307 (M>).

2-Hydroxymethyl-5-(3-methyl-butyryl)-pyridine: Add tetrabutylammonium fluoride (2.13 mL, 2.13 mmol, 1M solution in THF) to a solution of 2-tert-butyldimethylsilyloxymethyl)-5-(3-methyl-butyryl)-pyridine (330 mg, 1.066 mmol) in anhydrous THY (20 mL) at 0° C. and stir at this temperature for 1 h Concentrate the solvent in vacuo and purify the crude mixture by chromatography on silica gel eluting with EtOAc to provide the desired intermediate (327 mg, 100%).

2-Methanesulfonyloxymethyl-5-(3-methyl-butyryl)-pyridine: Dissolve 2-hydroxymethyl-5-(3-methyl-butyryl)-pyridine (190 mg, 0.98 mmol) in dichloromethane (10 mL). Cool to 0° C. and add triethylamine (0.151 mL, 1.08 mmol) and methanesulfonyl chloride (0.083 mL, 1.08 mmol). Allow the mixture to warm to room temperature and stir for 2 h. Dilute the reaction mixture with dichloromethane and wash with saturated aqueous $NaHCO_3$. Dry the organic phase over $Na_2SO_4$, filter and concentrate in vacuo to provide the title compound as oil (263 mg, 98%).

Preparation 337

5-Methanesulfonyloxymethyl-2-(3-methyl-butyryl)-pyridine

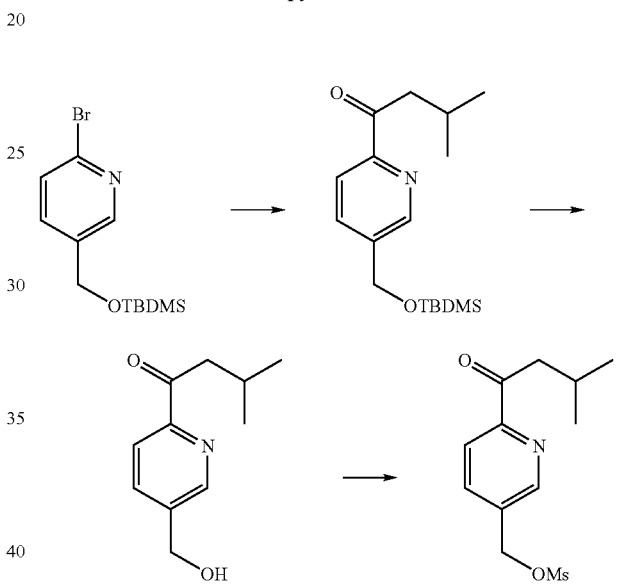

5-(tert-Butyldimethylsilyloxymethyl)-2-(3-methyl-butyryl)-pyridine: Dissolve 2-bromo-5-(tert-butyldimethylsilyloxymethyl)pyridine (1.99 g, 6.583 mmol, prepared by following the procedure described in *J. Org. Chem.* 2004, 69, 250-262) in anhydrous THF (20 mL). Cool the solution to −78° C., add n-BuLi (4.32 mL, 6.912 mmol, 1.6M solution in hexane) and stir at this temperature for 40 min. Add slowly a solution of N-methoxy-N-methyl-3-methyl-butyramide (0.955 g, 6.583 mmol) in anhydrous THF (5 mL). Stir the mixture for 2 h at −78° C. and then allow the mixture to warm to room temperature. Add brine and extract the aqueous layer twice with EtOAc. Dry the combined organic extracts over $Na_2SO_4$, filter and concentrate in vacuo. Purify the crude mixture by chromatography on silica gel eluting with hexane and hexane/EtOAc (19:1) to give the desired intermediate as yellow oil (890 mg, 44%). GC-MS m/z: 307 ($M^+$).

5-Hydroxymethyl-2-(3-methyl-butyryl)-pyridine: Add tetrabutylammonium fluoride (5.853 mL, 5.853 mmol, 1M solution in THF) to a solution of 5-(tert-butyldimethylsilyloxymethyl)-2-(3-methyl-butyryl)-pyridine (900 mg, 2.927 mmol) in anhydrous THF (30 mL) at 0° C. and stir at this temperature for 2 h. Concentrate the solvent in vacuo and purify the crude mixture by chromatography on silica gel eluting with hexane and hexane/EtOAc (3:2) to provide the desired intermediate (478 mg, 84%). MS (ES+) m/z: 194 (M+H)⁺.

5-Methanesulfonyloxymethyl-2-(3-methyl-butyryl)-pyridine: Dissolve 5-hydroxymethyl-2-(3-methyl-butyryl)-pyridine (210 mg, 1.086 mmol) in dichloromethane (5 mL). Cool to 0° C. and add triethylamine (0.167 mL, 1.195 mmol) and methanesulfonyl chloride (0.093 mL, 1.195 mmol). Allow the mixture to warm to room temperature and stir for 2 h. Dilute the reaction mixture with dichloromethane and wash with saturated aqueous NaHCO₃. Dry the organic phase over Na₂SO₄, filter and concentrate in vacuo to provide the title compound (256 mg, 87%). GC-MS m/z: 271

Preparation 338

1-(3-Chloro-propyl)-1,3-dihydro-indol-2-one

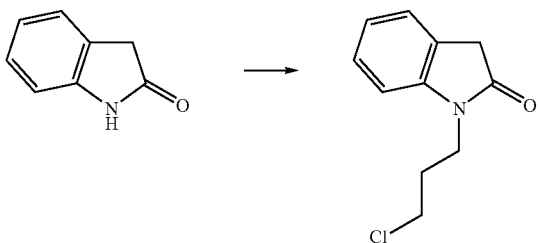

Reflux together oxindole (2.66 g, 20.0 mmol), 1-bromo-3-chloropropane (2.56 mL, 26.0 mmol) and potassium carbonate (5.52 g, 40.0 mmol) in acetonitrile (300 mL) under nitrogen for 16 h. Cool the suspension to room temperature and filter off the precipitate. Concentrate the filtrate in vacuo and purify the crude mixture by chromatography on silica gel eluting with isohexane/EtOAc (1:0 to 3:2 gradient over 40 min) to give the title compound as an orange oil (1.65 g, 39%). MS (ES+) m/z: 210 (M+H)⁺.

Preparation 339

1-(2-Chloro-ethyl)-pyrrolidin-2-one

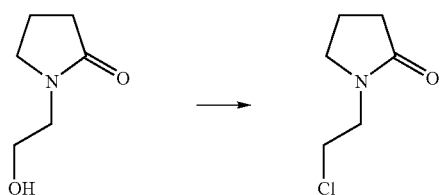

Add thionyl chloride (5 mL) to 1-(2-hydroxy-ethyl)-pyrrolidin-2-one (1.12 mL, 10.0 mmol) dropwise then stir at room temperature for 10 min. Remove solvent in vacuo to give the title compound as an orange oil. MS (ES+) m/z: 148 (M+H)⁺.

Preparation 340

1-(3-Bromo-propyl)-3-methyl-1,3-dihydro-benzoimidazol-2-one

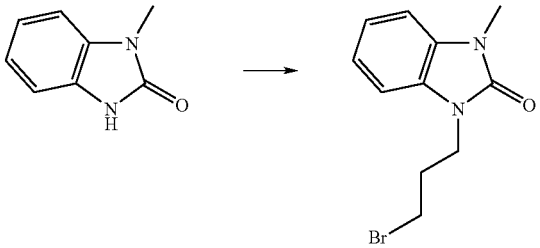

Add portion wise 3-methyl-1,3-dihydro-benzoimidazol-2-one (400 mg, 27.0 mmol) to a suspension of sodium hydride (1.296 g, 32.4 mmol of 60% dispersion in oil) in anhydrous THF (200 mL) under nitrogen over 15 min, then continue to stir for 30 min. Add 1,3-dibromopropane (11.0 mL, 108 mmol) and stir overnight. Then heat at reflux for 3 days. Cool the suspension to room temperature, pour into brine (400 mL), extract with diethyl ether (300 mL), dry over MgSO₄ and concentrate in vacuo. Purify by chromatography on silica gel eluting with isohexane/EtOAc (1:0 to 1:1 gradient over 40 min) to give the title compound as a colourless oil (2.15 g, 30%).

Preparations 341-342

The Compound of Preparation 341 may be prepared essentially as described in Preparation 340 using 3-methyl-1,3-dihydro-benzoimidazol-2-one and 1,4-dibromobutane. The compound of Preparation 342 may be prepared essentially as described in Preparation 340 using 1-tert-butyl-imidazolidin-2-one and 1-bromo-3-chloropropane. Yields are shown in the Table below.

| Prep. | Structure | Compound | Yield (%) |
|---|---|---|---|
| 341 | ![structure] | 1-(4-Bromo-butyl)-3-methyl-1,3-dihydro-benzoimidazol-2-one | 56 |

| Prep. | Structure | Compound | Yield (%) |
|---|---|---|---|
| 342 | 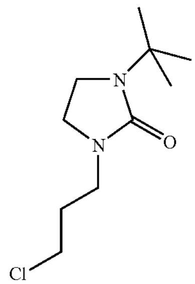 | 1-tert-Butyl-(3-chloro-propyl)-imidazolidin-2-one | 5 |

Preparation 343

1-(3-Bromo-propyl)-3-isopropenyl-1,3-dihydro-benzoimidazol-2-one

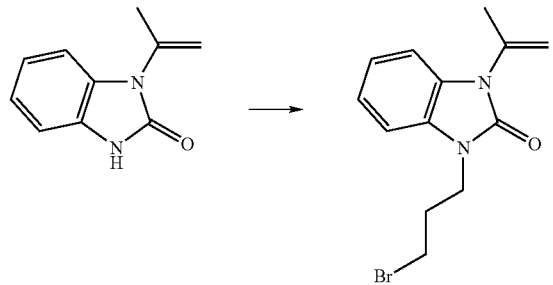

Add sodium hydride (600 mg, 16.5 mmol of 60% dispersion in oil) to a solution of 1-isopropenyl-1,3-dihydro-benzoimidazol-2-one (1.311 g, 7.53 mmol) in anhydrous DMF (10 mL) under nitrogen at room temperature and stir for 2 h. Add 1-bromo-3-chloropropane (900 µL, 9.03 mmol) and stir for 3 days. Pour the suspension into water (100 mL), extract with diethyl ether (2×50 mL). Wash the organic extract with brine (100 mL), dry over MgSO₄ and concentrate in vacuo to give the title compound impurified with 1-(3-chloro-propyl)-3-isopropenyl-1,3-dihydro-benzoimidazol-2-one (2.03 g, 1:1 mixture). MS (ES+) m/z: 251 (M+H)⁺, 293 (M+H)⁺.

Preparation 344

5-(3-Chloropropyl)-3,3-dimethyl-1,3-dihydro-indol-2-one

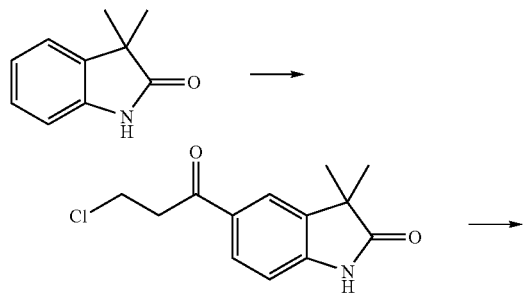

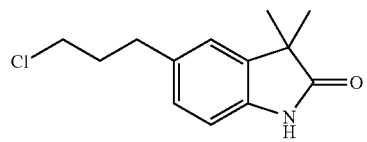

5-(3-Chloropropionyl)-3,3-dimethyl-1,3-dihydro-indol-2-one: Under nitrogen atmosphere, add chloropropionyl chloride (1.54 mL, 16.13 mmol) to a mixture of 3,3-dimethyl-1,3-dihydro-indol-2-one (2.0 g, 12.41 mmol) and aluminium trichloride (10.26 g, 76.92 mmol) in carbon disulphide (70 mL). Heat under reflux for 3 h then allow to cool. Decant off the solvent and replace it carefully with ice/water (200 mL). Allow the resultant suspension to stir for 20 min before filtering off the product and washing with water (80 mL). Dry in vacuo to obtain the desired intermediate as a pale brown solid (3.08 g, 99%).

5-(3-Chloropropyl)-3,3-dimethyl-1,3-dihydro-indol-2-one: Under nitrogen atmosphere, add 5-(3-chloropropyl)-3,3-diethyl-1,3-dihydro-indol-2-one (3.08 g, 12.24 mmol) to trifluoroacetic acid (9.4 mL, 122.4 mmol). Cool the resulting suspension to 0° C. and then add triethylsilane (4.5 mL, 28.2 mmol) dropwise over 2 min. Heat at 45° C. for 30 min then stir at ambient temperature overnight. Pour the reaction mixture onto ice/water (100 mL) and extract with EtOAc (2×100 mL). Dry the combined extracts over MgSO₄, filter and concentrate in vacuo. Purify the crude mixture by chromatography on silica gel eluting with hexane/EtOAc (1:0 to 4:1 gradient), to give the title compound as a yellow-orange solid (2.12 g, 73%).

Preparation 345

3-tert-Butoxycarbonyl-7-chloro-6-dimethylcarbamoylthio-9-fluoro-2,3,4,5-tetrahydro-1H-benzo[d]azepine

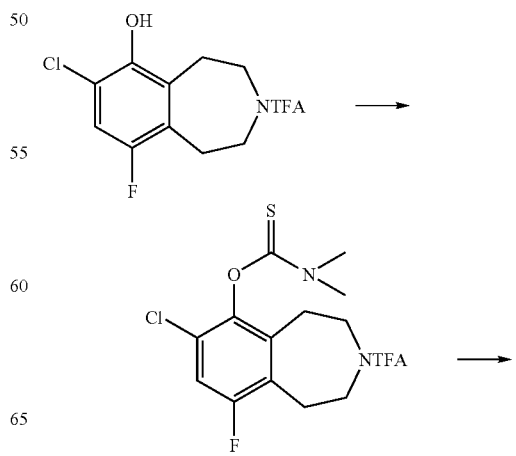

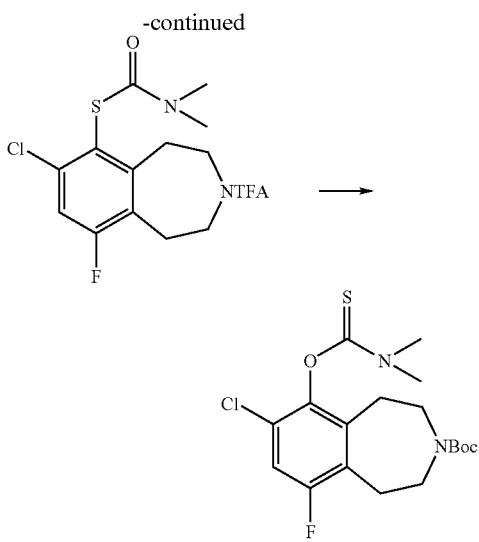

7-Chloro-6-(O-dimethylthiocarbamoyl)-9-fluoro-3-(2,2,2-trifluoroacetyl)-2,3,4,5-tetrahydro-1H-benzo[d]azepine: Heat 7-chloro-9-fluoro-6-hydroxy-3-(2,2,2-trifluoroacetyl)-2,3,4,5-tetrahydro-1H-benzo[d]azepine (0.56 g, 1.8 mmol) at reflux in anhydrous 1,4-dioxane (18 mL) with triethylamine (1.01 mL, 7.2 mmol), N,N-dimethyl-4-aminopyridine (22 mg, 0.18 mmol) and dimethylthiocarbamoyl chloride (0.67 g, 5.4 mmol) for 16 h. Cool and wash the mixture with 1N aqueous HCl, saturated aqueous NaHCO$_3$ and brine. Concentrate in vacuo and purify by chromatography on silica gel eluting with hexane/EtOAc (1:0 to 3:2 gradient) to give the desired intermediate as a yellow oil that solidifies on standing (0.69 g, 96%). MS (ES+) m/z: 399 (M+H)$^+$.

7-Chloro-6-dimethylcarbamoylthio-9-fluoro-3-(2,2,2-trifluoroacetyl)-2,3,4,5-tetrahydro-1H-benzo[d]azepine: Heat 7-chloro-6-(O-dimethylthiocarbamoyl)-9-fluoro-3-(2,2,2-trifluoroacetyl)-2,3,4,5-tetrahydro-1H-benzo[d]azepine (0.69 g, 1.73 mmol) in diphenyl ether (6 mL) at 245° C. for 2.5 h. Cool the mixture and load onto a column of silica gel. Wash diphenyl ether off with hexane and elute with hexane/EtOAc (1:0 to 3:2 gradient) to give the desired intermediate (0.44 g, 64%). MS (ES+) m/z: 399 (M+H)$^+$.

3-tert-Butoxycarbonyl-7-chloro-6-dimethylcarbamoylthio-9-fluoro-2,3,4,5-tetrahydro-1H-benzo[d]azepine: Heat 7-chloro-6-dimethylcarbamoylthio-9-fluoro-3-(2,2,2-trifluoroacetyl)-2,3,4,5-tetrahydro-1H-benzo[d]azepine (0.2 g, 0.5 mmol) in methanol (50 mL) with potassium carbonate (0.28 g, 2 mmol) at reflux for 5 h. Cool the mixture, add dropwise a solution of di-tert-butyl-dicarbonate (0.22 g, 1.0 mmol) in dichloromethane (20 mL) and stir 17 h. Evaporate the mixture onto silica gel and purify by chromatography eluting with hexane/EtOAc (1:0 to 3:2 gradient) to give the title compound (0.12 g, 62%). MS (ES+) m/z: 303 (M+H–Boc)$^+$.

EXAMPLES 608-611

Examples 608-611 may be prepared essentially as described in Example 350 by using 3-tert-butoxycarbonyl-7-chloro-6-ethylcarbamoylthio-2,3,4,5-tetrahydro-1H-benzo[d]azepine and the appropriately substituted chloromethylheterocycle or bromomethylheterocycle. MS (ES+) data are shown in the Table below.

| Ex. | SR | Compound | MS (ES+ or APCI+) |
|---|---|---|---|
| 608 | benzothiazol-6-ylmethylthio | 7-Chloro-6-(benzothiazol-6-yl-methylthio)-2,3,4,5-tetrahydro-1H-benzo[d]azepine Hydrochloride | 361 (M + H)$^+$ |
| 609 | 2-phenyl-benzothiazol-6-yl-methylthio | 7-Chloro-6-(2-phenyl-benzothiazol-6-yl-methylthio)-2,3,4,5-tetrahydro-1H-benzo[d]azepine Hydrochloride | 437 (M + H)$^+$ |
| 610 | 2-benzyl-benzothiazol-6-yl-methylthio | 7-Chloro-6-(2-benzyl-benzothiazol-6-yl-methylthio)-2,3,4,5-tetrahydro-1H-benzo[d]azepine Hydrochloride | 451 (M + H)$^+$ |

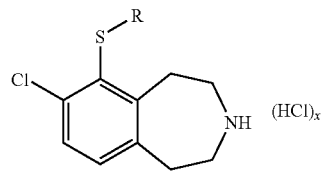

| Ex. | SR | Compound | MS (ES+ or APCI+) |
|---|---|---|---|
| 611 | | 7-Chloro-6-(benzothiophen-6-yl-methylthio)-2,3,4,5-tetrahydro-1H-benzo[d]azepine Hydrochloride | 360 (M + H)⁺ |

EXAMPLE 612

7-Chloro-6-([1,3,4]thiadiazol-2-yl-methylthio)-2,3,4,5-tetrahydro-1H-benzo[d]azepine Hydrochloride

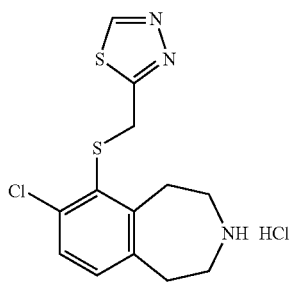

Stir 2-hydroxymethyl-[1,3,4]-thiadiazole (241 mg, 2.1 mmol) in thionylchloride (5 mL) for 1 h and concentrate in vacuo. Treat this residue with the thiolate prepared from 3-tert-butoxycarbonyl-6-dimethylcarbamoylthio-2,3,4,5-tetrahydro-1H-benzo[d]azepine (0.4 g, 1.04 mmol) and potassium hydroxide (1.37 g, 24.5 mmol) in methanol (3.5 mL) according to General Procedure 7 to give 3-tert-butoxycarbonyl-7-chloro-6-([1,3,4]thiadiazol-2-yl-methylthio)-2,3,4,5-tetrahydro-1H-benzo[d]azepine (0.3 g, 70%). Treat an aliquot with trifluoroacetic acid to obtain the mass spectrum. MS (ES+) m/z: 312 (M+H)⁺.

Use a method similar to the General Procedure 1-5 to deprotect 3-tert-butoxycarbonyl-7-chloro-6-([1,3,4]thiadiazol-2-yl-methylthio)-2,3,4,5-tetrahydro-1H-benzo[d]azepine (300 mg, 0.73 mmol). Use a method similar to the General Procedure 2-2 to give the title compound (208 mg, 82%). MS (ES+) m/z: 312 (M+H)⁺.

EXAMPLE 613

7-Chloro-6-(thiazol-5-ylmethylthio)-2,3,4,5-tetrahydro-1H-benzo[d]azepine Succinate

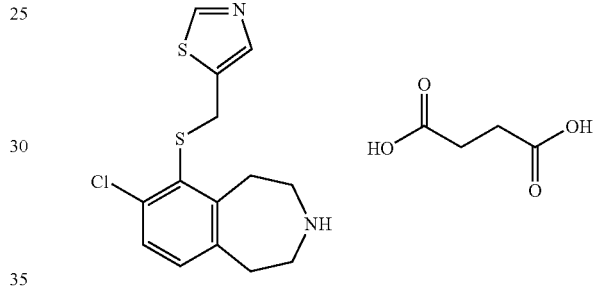

Use a method similar to General Procedure 7, using 3-tert-butoxycarbonyl-7-chloro-6-dimethylcarbamoylthio-2,3,4,5-tetrahydro-1H-benzo[d]azepine and 5-chloromethylthiazole to give, after deprotection and salt formation by methods similar to the General Procedures 1-5 and 2-1, the title compound as a white solid (700 mg, 80% overall). HRMS (ES+) m/z: 311.0427 (M+H)⁺.

EXAMPLE 614

7-Chloro-6-[2-(cyclohexylmethylamino)-thiazol-5-ylmethylthio]-2,3,4,5-tetrahydro-1H-benzo[d]azepine Succinate

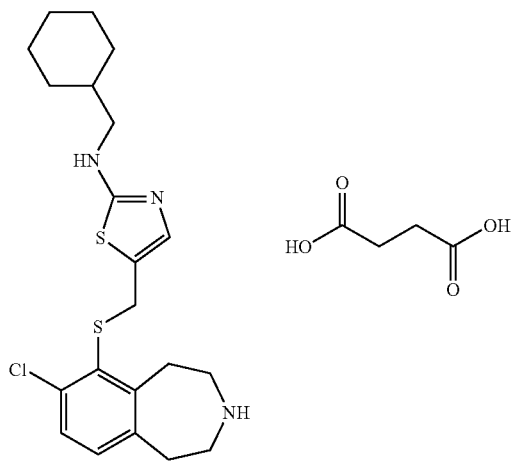

513

Use a method similar to General Procedure 7 using 3-tert-butoxycarbonyl-6-dimethylcarbamoylthio-2,3,4,5-tetrahydro-1H-benzo[d]azepine and 5-bromomethyl-2-chlorothiazole to give 3-tert-butoxycarbonyl-7-chloro-6-(2-chlorothiazol-5-ylmethylthio)-2,3,4,5-tetrahydro-1H-benzo[d]azepine as a yellow oil (0.9 g, 71%). Dissolve 3-tert-butoxycarbonyl-7-chloro-6-(2-chlorothiazol-5-ylmethylthio)-2,3,4,5-tetrahydro-1H-benzo[d]azepine (120 mg, 0.27 mmol) and cyclohexylmethylamine (1 mL, 7.7 mmol) in absolute ethanol (1 mL) in a heavy walled Pyrex tube. Heat the reaction in an oil bath at 82° C. for 24 h. Cool the reaction mixture and concentrate in vacuo. Purify by chromatography on silica gel eluting with hexane/EtOAc (4:1). Use methods similar to General Procedures 1-5 and 2-1 to deprotect and give the title compound as yellow oil (19 mg, 26% overall). MS (ES+) m/z: 422 (M+H)+.

EXAMPLE 615

(−)-7-Chloro-6-[1-(thiazol-2-yl)-ethylthio]-2,3,4,5-tetrahydro-1H-benzo[d]azepine Succinate

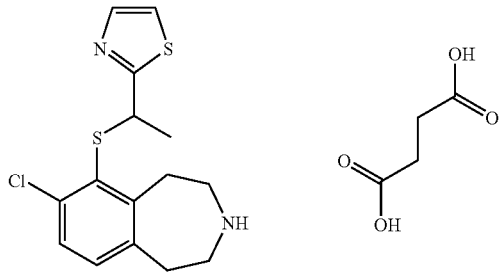

Add potassium hydroxide (3.9 g, 70 mmol) to a solution of 3-tert-butoxycarbonyl-7-chloro-6-dimethylcarbamoylthio-2,3,4,5-tetrahydro-1H-benzo[d]azepine (900 mg, 2.3 mmol) in methanol (25 mL) under a nitrogen atmosphere. Heat the mixture at 80° C. for 1.5 h. Cool the mixture to ambient temperature, then concentrate in vacuo to an oil. Dissolve the oil in EtOAc (50 mL) and wash with saturated aqueous ammonium chloride (30 mL). Separate the organic layer and extract the aqueous layer with EtOAc (3×50 mL). Dry the combined organic extracts over Na$_2$SO$_4$, filter and concentrate in vacuo to an oil (735 mg). Dissolve the oil in anhydrous DMSO (20 mL), then add triethylamine (1.9 mL, 14 mmol) and (±)-1-methanesulfonyloxy-1-thiazol-2-yl-ethyl (1.3 g, 6.3 mmol) at ambient temperature under nitrogen. Heat the mixture at 40° C. for 1 h. Cool the reaction to room temperature, then dilute the mixture with hexane/EtOAc (1:1, 50 mL) and wash with aqueous 5% sodium chloride (3×50 mL). Separate the organic layer and back extract the aqueous layer with EtOAc (3×50 mL). Combine the organic extracts and concentrate in vacuo. Purify the residue by chromatography on silica gel eluting with hexane/EtOAc (19:1 to 7:3 gradient) to obtain (±)-3-tert-butoxycarbonyl-7-chloro-6-[1-(thiazol-2-yl)-ethylthio]-2,3,4,5-tetrahydro-1H-benzo[d]azepine (779 mg, 79%). MS (ES+) m/z: 425.0 (M+H)+.

Separate (±)-3-tert-butoxycarbonyl-7-chloro-6-[1-(thiazol-2-yl)-ethylthio]-2,3,4,5-tetrahydro-1H-benzo[d]azepine (770 mg, 1.8 mmol) by normal phase chiral chromatography [Chiralpak AD, 8×30 cm, eluting with heptane/3A ethanol (9:1)]. Collect the 2$^{nd}$ eluting isomer of 3-tert-butoxycarbonyl-7-chloro-6-[1-(thiazol-2-yl)-ethylthio]-2,3,4,5-tetrahydro-1H-benzo[d]azepine {348 mg, 99% ee [Chiralpak AD-H, 4.6×150 mm, eluant heptane/3A ethanol (9:1)]}.

Use a method similar to the General Procedure 1-5 to deprotect 3-tert-butoxycarbonyl-7-chloro-6-[1-(thiazol-2-yl)-ethylthio]-2,3,4,5-tetrahydro-1H-benzo[d]azepine isomer 2. Purify by chromatography on silica gel eluting with dichloromethane/2M ammonia in methanol (98:2 to 90:10 gradient) to give the free base of the title compound. Use a method similar to the General Procedure 2-1 to obtain the title compound (350 mg, 96%). MS (ES+) m/z: 325.0 (M+H)+. [α]$^{20}_D$ −160° (c 0.5, MeOH).

EXAMPLE 616

7-Chloro-3-methyl-6-(pyridin-2-ylmethylthio)-2,3,4,5-tetrahydro-1H-benzo[d]azepine Succinate

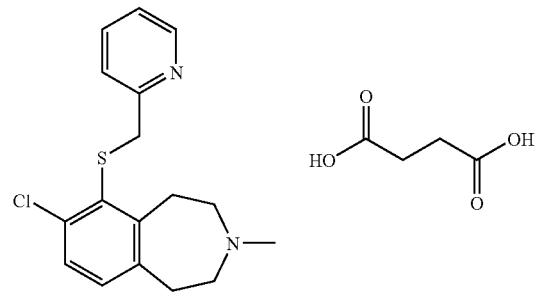

Suspend 7-chloro-6-(pyridin-2-ylmethylthio)-2,3,4,5-tetrahydro-1H-benzo[d]azepine hydrochloride in saturated aqueous NaHCO$_3$ and extract three times with EtOAc. Dry the combined organic extracts over MgSO$_4$. Filter and concentrate in vacuo to give the free base as a yellow oil. Combine the free base (0.2 g, 0.66 mmol), sodium triacetoxyborohydride (0.78 g, 3.7 mmol), formaldehyde (37% solution in water, 0.2 mL, 2.7 mmol), and acetic acid (0.45 mL, 7.9 mmol), in 1,2-dichloroethane (5 mL). Stir at room temperature for 12 h. Concentrate the crude reaction mixture in vacuo and partition the residue between EtOAc/water. Separate the layers and extract the aqueous phase with EtOAc (3×30 mL). Wash the combined organic extracts with 1M aqueous NaOH. Dry over MgSO$_4$, filter and concentrate in vacuo. Purify the crude mixture by chromatography on silica gel eluting with 2M ammonia in methanol/dichloromethane (4:96).

Use a method similar to the General Procedure 2-1 to give the title compound as a sticky glass (140 mg, 48%). HRMS (ES+) m/z: 319.1029 (M+H)+.

EXAMPLES 617 AND 618

7-Chloro-6-(2,2,2-trifluoro-1-pyridin-2-yl-ethylthio)-2,3,4,5-tetrahydro-1H-benzo[d]azepine Hydrochloride Isomer 1 and 7-Chloro-6-(2,2,2-trifluoro-1-pyridin-2-yl-ethylthio)-2,3,4,5-tetrahydro-1H-benzo[d]azepine Hydrochloride Isomer 2

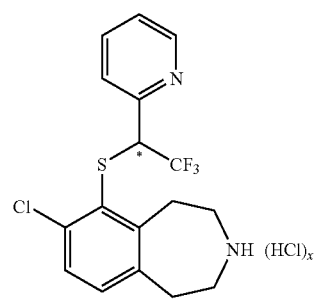

Separate the two enantiomers of (±)-7-chloro-6-(2,2,2-trifluoro-1-pyridin-2-yl-ethylthio)-2,3,4,5-tetrahydro-1H-benzo[d]azepine hydrochloride by normal phase chiral chromatography (Chiralpak AD, 2×25 cm, eluting with heptane/ethanol (85:15) with 0.2% DMEA).

Subject the first eluting isomer to the General Procedure 1-4 to obtain 7-chloro-6-(2,2,2-trifluoro-1-pyridin-2-yl-ethylthio)-2,3,4,5-tetrahydro-1H-benzo[d]azepine hydrochloride isomer 1 [99% ee (Chiralpak AD-H, 4.6×150 mm, eluting with heptane/ethanol (85:15) with 0.2% DMEA, flow rate 0.6 mL/min)]. MS (ES+) m/z: 373.1 (M+H)+.

Subject the second eluting isomer to the General Procedure 14 to obtain 7-chloro-6-(2,2,2-trifluoro-1-pyridin-2-yl-ethylthio)-2,3,4,5-tetrahydro-1H-benzo[d]azepine hydrochloride isomer 2 [99% ee (Chiralpak AD-H, 4.6×150 mm, eluting with heptane/ethanol (85:15) with 0.2% DMEA, flow rate 0.6 mL/min)]. MS (ES+) m/z 373.1 (M+H)+.

EXAMPLE 619

(−)-7-Chloro-6-(1-pyridin-2-yl-propylthio)-2,3,4,5-tetrahydro-1H-benzo[d]azepine Hydrochloride

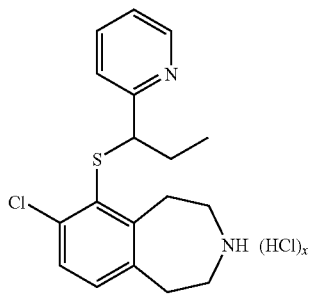

Separate the two enantiomers of (±)-7-chloro-6-(1-pyridin-2-yl-propylthio)-2,3,4,5-tetrahydro-1H-benzo[d]azepine hydrochloride by normal phase chiral chromatography (Chiralcel OJ, 8×33 cm, eluting with heptane/methanol/3A ethanol (85:10:5) with 0.2% DMEA).

Subject the second eluting isomer to the General Procedure 1-4 to obtain the title compound [93% ee (Chiralcel OJ, 4.6×250 mm, eluting with heptane/methanol/3A ethanol (90:5:5) with 0.2% DMEA, flow rate 0.6 mL/min)]. MS (ES+) m/z: 333.1 (M+H)+. [α]$^{20}_D$ −240.6° (c 0.5, MeOH).

EXAMPLE 620

(±)-7-Chloro-6-[1-(4-fluorophenyl)ethylthio]-2,3,4,5-tetrahydro-1H-benzo[d]azepine Hydrochloride

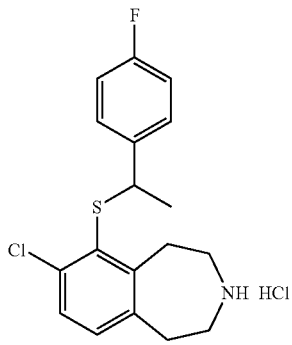

Dissolve 3-tert-butoxycarbonyl-7-chloro-6-dimethylcarbamoylthio-2,3,4,5-tetrahydro-1H-benzo[d]azepine (415 mg, 1.08 mmol) in methanol (20 mL) and add potassium hydroxide (1.938 g, 34.53 mmol). Heat at 60° C. for 4 h. Cool the reaction mixture to ambient temperature, add aqueous saturated ammonium chloride and concentrate in vacuo. Partition the residue between EtOAc and water. Dry the organic phase over anhydrous Na$_2$SO$_4$ and concentrate in vacuo to give 3-tert-butoxycarbonyl-7-chloro-6-mercapto-2,3,4,5-tetrahydro-1H-benzo[d]azepine (0.34 g, 1.086 mmol). Dissolve the crude 3-tert-butoxycarbonyl-7-chloro-6-mercapto-2,3,4,5-tetrahydro-1H-benzo[d]azepine (0.34 g, 1.086 mmol) in anhydrous DMF (10 mL), add sodium hydride (65 mg, 1.63 mmol, 60% in mineral oil) and stir the mixture for 5 min. Add a solution of (±)-1-(4-fluorophenyl)ethyl bromide (332 mg, 1.63 mmol) in anhydrous DMF (5 mL) and heat the solution at 45° C. overnight. Cool to ambient temperature, add water and extract the aqueous phase twice with EtOAc. Dry the combined organic extracts over anhydrous Na$_2$SO$_4$, filter and concentrate in vacuo. Purify the crude mixture by chromatography on silica gel eluting with hexane and hexane/EtOAc (19:1 and 9:1) to give (±)-3-tert-butoxycarbonyl-7-chloro-6-[1-(4-fluorophenyl)ethylthio]-2,3,4,5-tetrahydro-1H-benzo[d]azepine as oil (397 mg, 84%). MS (ES+) m/z: 336 (M+H−Boc)+.

Use a method similar to the General Procedure 1-4 to deprotect (±)-3-tert-butoxycarbonyl-7-chloro-6-[1-(4-fluorophenyl)ethylthio]-2,3,4,5-tetrahydro-1H-benzo[d]azepine (47 mg, 0.108 mmol) and give the title compound as a solid (39 mg, 99%). MS (ES+) m/z: 336 (M+H)+.

EXAMPLES 621-622

Examples 621-622 may be prepared essentially as described in Example 620 using 3-tert-butoxycarbonyl-7-chloro-6-dimethylcarbamoylthio-2,3,4,5-tetrahydro-1H-benzo[d]azepine and the appropriate alkyl bromide. Overall yields and MS (ES+) data are shown in the Table below.

| Ex. | Structure | Compound | Yield (%) | MS (ES+) m/z |
|---|---|---|---|---|
| 621 | 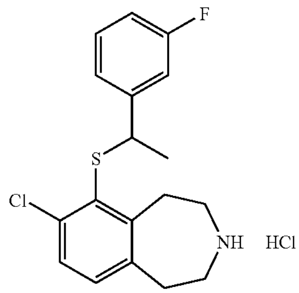 | (±)-7-Chloro-6-[1-(3-fluorophenyl)ethylthio]-2,3,4,5-tetrahydro-1H-benzo[d]azepine Hydrochloride | 75 | 336 (M + H)+ |
| 622 | 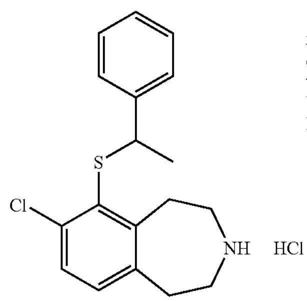 | (±)-7-Chloro-6-(1-methyl-2-phenyl-ethylthio)-2,3,4,5-tetrahydro-1H-benzo[d]azepine Hydrochloride | 80 | 332 (M + H)+ |

EXAMPLES 623 AND 624

7-Chloro-6-[1-(4-fluorophenyl)ethylthio]-2,3,4,5-tetrahydro-1H-benzo[d]azepine Succinate Isomer 1 and 7-chloro-6-[1-(4-fluorophenyl)ethylthio]-2,3,4,5-tetrahydro-1H-benzo[d]azepine Succinate Isomer 2

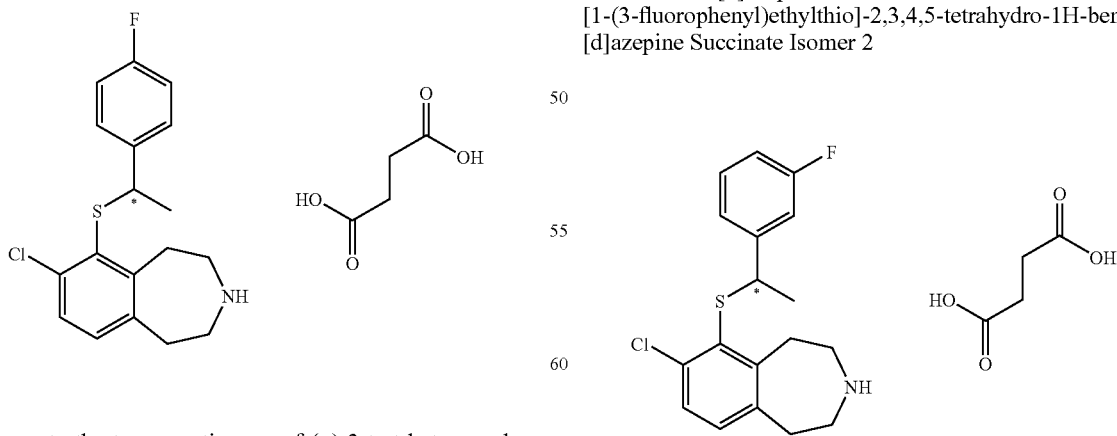

Separate the two enantiomers of (±)-3-tert-butoxycarbonyl-7-chloro-6-[1-(4-fluorophenyl)ethylthio]-2,3,4,5-tetrahydro-1H-benzo[d]azepine by chiral HPLC (Chiralcel OJ-H 4.6×150 mm column, eluting with methanol at 0.6 mL/min).

Subject Isomer 1 ($t_R$=7.3 min, ee >99.9%) to the General Procedure 2-1 to afford 7-chloro-6-[1-(4-fluorophenyl)ethylthio]-2,3,4,5-tetrahydro-1H-benzo[d]azepine succinate isomer 1 as a white solid. MS (ES+) m/z 336 (M+H)+.

Subject Isomer 2 ($t_R$=12.9 min, ee=99.9%) to the General Procedure 2-1 to afford 7-chloro-6-[1-(4-fluorophenyl)ethylthio]-2,3,4,5-tetrahydro-1H-benzo[d]azepine succinate isomer 2 as a white solid. MS (ES+) m/z 336 (M+H)+.

EXAMPLES 625 AND 626

7-Chloro-6-[1-(3-fluorophenyl)ethylthio]-2,3,4,5-tetrahydro-1H-benzo[d]azepine Succinate Isomer 1 and 7-chloro-6-[1-(3-fluorophenyl)ethylthio]-2,3,4,5-tetrahydro-1H-benzo[d]azepine Succinate Isomer 2

Separate the two enantiomers of (±)-3-tert-butoxycarbonyl-7-chloro-6-[1-(3-fluorophenyl)ethylthio]-2,3,4,5-tetrahydro-1H-benzo[d]azepine by chiral HPLC (Chiralcel OJ-H 4.6×150 mm column, eluting with methanol at 0.6 mL/min).

Subject Isomer 1 ($t_R$=5.4 min, ee >99.9%) to the General Procedure 2-1 to afford 7-chloro-6-[1-(3-fluorophenyl)ethylthio]-2,3,4,5-tetrahydro-1H-benzo[d]azepine succinate isomer 1 as a white solid. MS (ES+) m/z 336 (M+H)$^+$.

Subject Isomer 2 ($t_R$=11.2 min, ee=99.7%) to the General Procedure 2-1 to afford 7-chloro-6-[1-(3-fluorophenyl)ethylthio]-2,3,4,5-tetrahydro-1H-benzo[d]azepine succinate isomer 2 as a white solid. MS (ES+) m/z 336 (M+H)$^+$.

EXAMPLE 627

(S)-7-Chloro-6-{1-[4-(3,3-dimethylbutyryl)-phenyl]-ethylthio}-2,3,4,5-tetrahydro-1H-benzo[d]azepine Hydrochloride

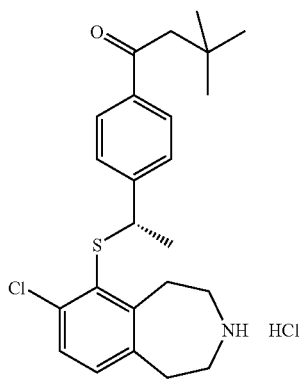

Heat the mixture of 3-tert-butoxycarbonyl-7-chloro-6-dimethylcarbamoylthio-2,3,4,5-tetrahydro-1H-benzo[d]azepine (310 mg, 0.807 mmol) and potassium hydroxide (1.45 g, 25.83 mmol) in methanol (5 mL) at 50° C. for 3 h. Cool the reaction mixture to room temperature and dilute with saturated aqueous NH$_4$Cl and EtOAc. Separate the layers and extract the aqueous layer three times with EtOAc. Dry the combined organic extracts over Na$_2$SO$_4$, filter and concentrate in vacuo. Dissolve the crude 3-tert-butoxycarbonyl-7-chloro-6-mercapto-2,3,4,5-tetrahydro-1H-benzo[d]azepine in anhydrous DMF (2 mL) and cool at 0° C. Add sodium hydride (21 mg, 0.888 mmol) and a solution of (R)-1-[4-(1-bromoethyl)-phenyl]-3,3-dimethylbutan-1-one {prepared by the mixture of (S)-1-[4-(1-hydroxyethyl)-phenyl]-3,3-dimethylbutan-1-one (213 mg, 0.969 mmol), triphenylphosphine (296 mg, 1.130 mmol) and NBS (201 mg, 1.13 mmol) in anhydrous THF (5 mL) at 0° C. and then room temperature}. Stir the mixture at 0° C. for 30 min and quench with water. Dilute with EtOAc and extract the aqueous layer three times with EtOAc. Dry the combined organic extracts over Na$_2$SO$_4$, filter and concentrate in vacuo. Purify the crude mixture by chromatography on silica gel eluting with hexane/EtOAc (85:15) to give (S)-3-tert-butoxycarbonyl-7-chloro-6-{1-[4-(3,3-dimethylbutyryl)-phenyl]-ethylthio}-2,3,4,5-tetrahydro-1H-benzo[d]azepine as yellow oil (197 mg, 47%).

Use a method similar to the General Procedure 1-4, using (S)-3-tert-butoxycarbonyl-7-chloro-6-{1-[4-(3,3-dimethylbutyryl)-phenyl]-ethylthio}-2,3,4,5-tetrahydro-1H-benzo[d]azepine (197 mg, 0.382 mmol) to give the title compound as a white solid (161 mg, 93%). MS (ES+) m/z: 416 (M+H)$^+$; ee=92%, $t_R$=11.27 min (Chiralcel OJ, 4.6×250 mm, 45° C., eluent: 20% isopropanol with 0.05% triethylamine in SFC, flow rate 2 mL/min, UV detector at 234 nm).

EXAMPLE 628

(S)-7-Chloro-6-(1-phenyl-ethylthio)-2,3,4,5-tetrahydro-1H-benzo[d]azepine Hydrochloride

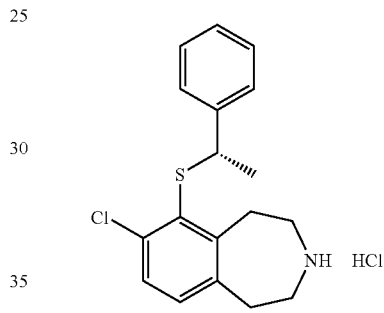

Example 628 may be prepared essentially as described in Example 627 using 3-tert-butoxycarbonyl-7-chloro-6-dimethylcarbamoylthio-2,3,4,5-tetrahydro-1H-benzo[d]azepine and (R)-(1-bromo-ethyl)-benzene (64% yield, MS (ES+) m/z 318 (M+H)$^+$).

EXAMPLE 629

6-(4-Acetyl-benzylthio)-7-chloro-2,3,4,5-tetrahydro-1H-benzo[d]azepine Hydrochloride

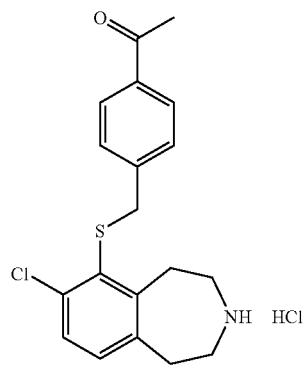

Use a method similar to the General Procedure 7 to react 3-tert-butoxycarbonyl-7-chloro-6-dimethylcarbamoylthio- 2,3,4,5-tetrahydro-1H-benzo[d]azepine (200 mg, 0.521 mmol) with 4-acetylbenzyl bromide (555 mg, 2.605 mmol). Purify the crude mixture by chromatography on silica gel eluting sequentially with hexane and hexane/EtOAc (9:1, 4:1) to obtain 6-(4-acetyl-benzylthio)-3-tert-butoxycarbonyl-7-chloro-2,3,4,5-tetrahydro-1H-benzo[d]azepine (190 mg, 82%).

Use a method similar to the General Procedure 1-4 to deprotect 6-(4-acetyl-benzylthio)-3-tert-butoxycarbonyl-7-chloro-2,3,4,5-tetrahydro-1H-benzo[d]azepine (170 mg, 0.381 mmol) and give the title compound as a white solid (140 mg, 96%). MS (ES+) m/z: 346 (M+H)+.

EXAMPLES 630-634

Examples 630-634 may be prepared essentially as described in Example 629 using 3-tert-butoxycarbonyl-7-chloro-6-dimethylcarbamoylthio-2,3,4,5-tetrahydro-1H-benzo[d]azepine and the appropriate benzyl bromide. Overall yields and MS (ES+) data are shown in the Table below.

| Ex. | R | Compound | Yield (%) | MS (ES+) m/z |
|---|---|---|---|---|
| 630 | Ethyl | 7-Chloro-6-(4-propionyl-benzoyl-thio)-2,3,4,5-tetrahydro-1H-benzo[d]azepine Hydrochloride | 87 | 360 (M + H)+ |
| 631 | n-Propyl | 6-(4-Butyryl-benzylthio)-7-chloro-2,3,4,5-tetrahydro-1H-benzo[d]azepine Hydrochloride | 81 | 374 (M + H)+ |
| 632 | i-Propyl | 7-Chloro-6-(4-isobutyryl-benzylthio)-2,3,4,5-tetrahydro-1H-benzo[d]azepine Hydrochloride | 69 | 374 (M + H)+ |
| 633 | i-Butyl | 7-Chloro-6-[4-(3-methyl-butyryl)-benzylthio]-2,3,4,5-tetrahydro-1H-benzo[d]azepine Hydrochloride | 68 | 388 (M + H)+ |
| 634 | 2-Pyridyl | 7-Chloro-6-[4-(pyridine-2-carbonyl)-benzylthio]-2,3,4,5-tetrahydro-1H-benzo[d]azepine Hydrochloride | 38 | 409 (M + H)+ |

EXAMPLE 635

7-Chloro-6-[4-(pyridine-3-carbonyl)-benzylthio]-2,3,4,5-tetrahydro-1H-benzo[d]azepine Hydrochloride

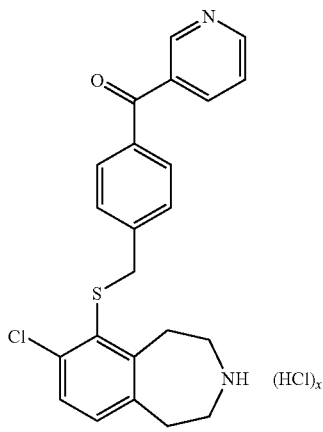

Dissolve 3-tert-butoxycarbonyl-7-chloro-6-dimethylcarbamoylthio-2,3,4,5-tetrahydro-1H-benzo[d]azepine (150 mg, 0.39 mmol) in methanol (10 mL) and add potassium hydroxide (0.7 g, 12.47 mmol). Heat at 60° C. for 4 h. Cool the reaction mixture to ambient temperature, add aqueous saturated ammonium chloride and concentrate in vacuo. Partition the residue between EtOAc and water. Dry the organic phase over anhydrous $Na_2SO_4$ and concentrate in vacuo to give 3-tert-butoxycarbonyl-7-chloro-6-mercapto-2,3,4,5-tetrahydro-1H-benzo[d]azepine (0.12 g). Dissolve the crude 3-tert-butoxycarbonyl-7-chloro-6mercapto-2,3,4,5-tetrahydro-1H-benzo[d]azepine (0.12 g, 5.2 mmol) in anhydrous DMSO (6 mL) and add triethylamine (0.325 mL, 2.34 mmol) and 4-(pyridine-3-carbonyl)-benzyl methanesulfonate (114 mg, 0.39 mmol). Heat the solution at 40° C. overnight. Cool to ambient temperature, dilute the mixture with hexane/EtOAc (1:1, 100 mL), and wash the organic solution sequentially with brine and ice-cold water. Dry the organic layer over anhydrous $Na_2SO_4$, filter and concentrate in vacuo. Purify the crude mixture by chromatography on silica gel eluting with hexane and hexane/EtOAc (1:1) to give 3-tert-butoxycarbonyl-7-chloro-6-[4-(pyridine-3-carbonyl)-benzylthio]-2,3,4, 5-tetrahydro-1H-benzo[d]azepine as oil (123 mg, 64%).

Use a method similar to the General Procedure 1-4 to deprotect 3-tert-butoxycarbonyl-7-chloro-6-[4-(pyridine-3-carbonyl)-benzylthio]-2,3,4,5-tetrahydro-1H-benzo[d]azepine (113 mg, 0.22 mmol) and give the title compound as a solid (105 mg, 99%). MS (ES+) m/z: 409 (M+H)+.

EXAMPLES 636-638

Examples 636-638 may be prepared essentially as described in Example 635 using 3-tert-butoxycarbonyl-7-chloro-6-dimethylcarbamoylthio-2,3,4,5-tetrahydro-1H-benzo[d]azepine and the appropriate methanesulfonate. Overall yields and MS (ES+) data are shown in the Table below.

| Ex. | Structure | Compound | Yield (%) | MS (ES+) m/z |
|---|---|---|---|---|
| 636 | 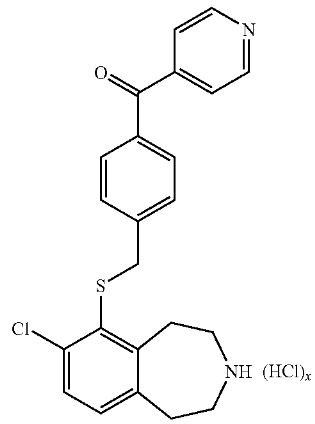 | 7-Chloro-6-[4-(pyridine-4-carbonyl)-benzylthio]-2,3,4,5-tetrahydro-1H-benzo[d]azepine Hydrochloride | 39 | 409 (M + H)+ |
| 637 | 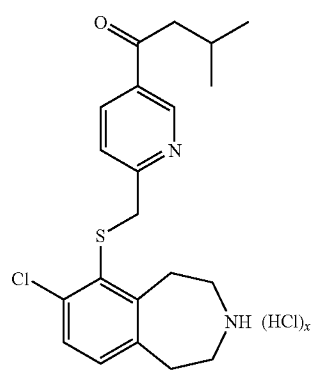 | 7-Chloro-6-[5-(3-methyl-butyryl)-pyridin-2-yl-methylthio]-2,3,4,5-tetrahydro-1H-benzo[d]azepine Hydrochloride | 69 | 389 (M + H)+ |
| 638 | 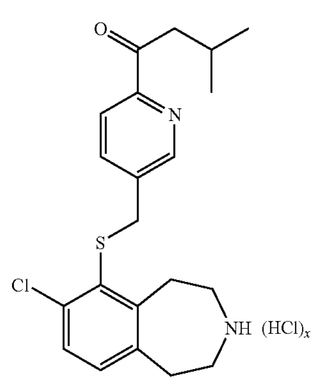 | 7-Chloro-6-[6-(3-methyl-butyryl)-pyridin-3-yl-methylthio]-2,3,4,5-tetrahydro-1H-benzo[d]azepine Hydrochloride | 57 | 389 (M + H)+ |

EXAMPLE 639

7-Chloro-6-[4-(3-cyanobenzoyl)-benzylthio]-3,4,5-tetrahydro-1H-benzo[d]azepine Hydrochloride

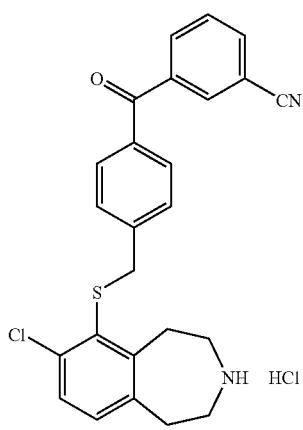

Dissolve 3-tert-butoxycarbonyl-7-chloro-6-dimethylcarbamoylthio-2,3,4,5-tetrahydro-1H-benzo[d]azepine (200 mg, 0.52 mmol) in methanol (12 mL) and add potassium hydroxide (0.935 g, 16.66 mmol). Heat at 60° C. for 4 h Cool the reaction mixture to ambient temperature, add aqueous saturated ammonium chloride and concentrate in vacuo. Partition the residue between EtOAc and water. Dry the organic phase over anhydrous $Na_2SO_4$ and concentrate in vacuo to give 3-tert-butoxycarbonyl-7-chloro-6-mercapto-2,3,4,5-tetrahydro-1H-benzo[d]azepine (0.16 g, 5.2 mmol). Dissolve the crude 3-tert-butoxycarbonyl-7-chloro-6-mercapto-2,3,4,5-tetrahydro-1H-benzo[d]azepine (0.16 g, 0.52 mmol) in anhydrous DMSO (5 mL) and add triethylamine (0.435 mL, 3.12 mmol) and 4-(3-cyano-benzoyl)benzyl bromide (289 mg, 0.96 mmol). Heat the solution at 40° C. overnight. Cool to ambient temperature, dilute the mixture with hexane/EtOAc (1:1, 100 mL), and wash the organic solution sequentially with brine and ice-cold water. Dry the organic layer over anhydrous $Na_2SO_4$, filter and concentrate in vacuo. Purify the crude mixture by chromatography on silica gel eluting with hexane and hexane/EtOAc (9:1, 4:1) to give 3-tert-butoxycarbonyl-7-chloro-6-[4-(3-cyanobenzoyl)-benzylthio]-2,3,4,5-tetrahydro-1H-benzo[d]azepine as oil (212 mg, 77%).

Use a method similar to the General Procedure 1-4 to deprotect 3-tert-butoxycarbonyl-7-chloro-6-[4-(3-cyanobenzoyl)-benzylthio]-2,3,4,5-tetrahydro-1H-benzo[d]azepine (200 mg, 0.37 mmol) and give the title compound as a solid (136 mg, 77%). MS (ES+) m/z: 433 (M+H)+.

EXAMPLE 640

7-Chloro-6-[4-(4-cyanobenzoyl)-benzylthio]-2,3,4,5-tetrahydro-1H-benzo[d]azepine Hydrochloride

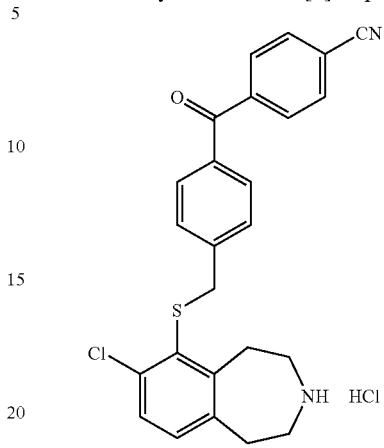

20. Example 640 may be prepared essentially as described in Example 639 using 3-tert-butoxycarbonyl-7-chloro-6-dimethylcarbamoylthio-2,3,4,5-tetrahydro-1H-benzo[d]azepine and 4-(4-cyano-benzoyl)benzyl bromide (49% yield, MS (ES+) m/z 433 (M+H)+).

EXAMPLE 641

7-Chloro-6-(4-tert-butylthiocarbamoyl-benzylthio)-2,3,4,5-tetrahydro-1H-benzo[d]azepine Hydrochloride

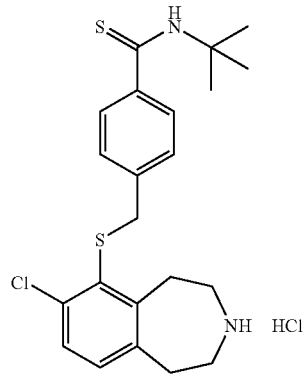

Combine 7-chloro-6-(4-tert-butylcarbamoyl-benzylthio)-2,3,4,5-tetrahydro-1H-benzo[d]azepine (53 mg, 0.13 mmol) with 2,4-bis(4-methoxyphenyl)-1,3-dithia-2,4-diphosphetane-2,4-disulfide (Lawesson's reagent) (53 mg, 0.13 mmol) in anhydrous 1,4-dioxane (1 mL) in a sealed tube and heat at 100° C. for 2 h. Cool the reaction mixture to room temperature, concentrate in vacuo and purify the residue by SCX chromatography to obtain 7-chloro-6-(4-tert-butylthiocarbamoyl-benzylthio)-2,3,4,5-tetrahydro-1H-benzo[d]azepine as a yellow oil. Purify by reverse phase preparative HPLC [Zorbax SB-Phenyl 21.2×250 mm, 5 micron, 22 mL/min of 0.1% aqueous HCl/acetonitrile (9:1 to 1:9) over 30 min, detector at 230 nm].

Use a method similar to the General Procedure 2-2 to obtain the title compound as a yellow solid (36 mg, 58%). MS (ES+) m/z: 419 (M+H)+.

EXAMPLE 642

7-Chloro-6-[4-(4-fluorobenzylthiocarbamoyl)-benzylthio]-2,3,4,5-tetrahydro-1H-benzo[d]azepine Succinate

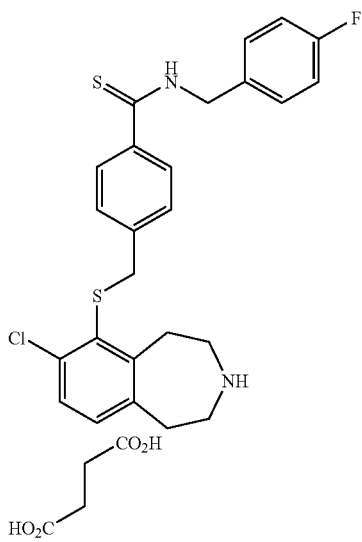

Combine 7-chloro-6-[4-(4-fluorobenzylcarbamoyl)-benzylthio]-2,3,4,5-tetrahydro-1H-benzo[d]azepine (23 mg, 0.05 mmol) with 2,4-bis(4-methoxyphenyl)-1,3-dithia-2,4-diphosphetane-2,4-disulfide (Lawesson's reagent) (23 mg, 0.05 mmol) in anhydrous 1,4-dioxane (1 mL) in a sealed tube and heat at 100° C. for 2 h Cool the reaction mixture to room temperature, concentrate in vacuo and purify the residue by SCX chromatography to obtain 7-chloro-6-[4-(4-fluorobenzylthiocarbamoyl)-benzylthio]-2,3,4,5-tetrahydro-1H-benzo[d]azepine as a yellow oil.

Use a method similar to the General Procedure 2-1 to obtain the title compound as a white solid (10 mg, 42%). MS (ES+) m/z: 471 (M+H)⁺.

EXAMPLE 643

7-Chloro-6-(6-cyclohexylamino-pyridin-3-ylmethylthio)-2,3,4,5-tetrahydro-1H-benzo[d]azepine Succinate

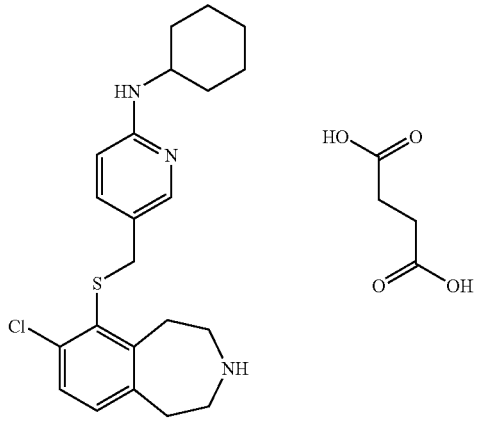

Use a method similar to General Procedure 7, using 3-tert-butoxycarbonyl-7-chloro-6-dimethylcarbamoylthio-2,3,4,5-tetrahydro-1H-benzo[d]azepine (2 g, 5.2 mmol) and 2-chloro-5-(chloromethyl)pyridine (843 mg, 5.2 mmol) to give 3-tert-butoxycarbonyl-7-chloro-6-(6-chloro-pyridin-3-ylmethylthio)-2,3,4,5-tetrahydro-1H-benzo[d]azepine (2.2 g, 95%). MS (ES+) m/z: 439.1 (M+H)⁺.

Slurry palladium(II) acetate (434 mg, 1.9 mmol), BINAP (1.2 g, 1.9 mmol), sodium-tert-butoxide (644 mg, 6.7 mmol), cyclohexylamine (1.4 g, 14.4 mmol) and 3-tert-butoxycarbonyl-7-chloro-6-(6-chloro-pyridin-3-ylmethylthio)-2,3,4,5-tetrahydro-1H-benzo[d]azepine (2.1 g, 4.8 mmol) in anhydrous toluene (70 mL). Degas the slurry under house vacuum, then buble nitrogen. Heat the mixture to 95° C. for 16 h under a nitrogen atmosphere. Cool the mixture to room temperature, dilute with EtOAc (50 mL) and filter through Celite®. Concentrate the filtrate to an oil and purify by chromatography on silica gel eluting with hexane/EtOAc (19:1 to 13:7 gradient) to obtain 3-tert-butoxycarbonyl-7-chloro-6-(6-cyclohexylamino-pyridin-3-ylmethylthio)-2,3,4,5-tetrahydro-1H-benzo[d]azepine (800 mg, 33%). MS (ES+) m/z: 502.2 (M+H)⁺.

Use a method similar to the General Procedure 1-5 to deprotect 3-tert-butoxycarbonyl-7-chloro-6-(6-cyclohexylamino-pyridin-3-ylmethylthio)-2,3,4,5-tetrahydro-1H-benzo[d]azepine (790 mg, 1.6 mmol). Purify by chromatography on silica gel eluting with dichloromethane/2M ammonia in methanol (99:1 to 95:5 gradient) to give the free base of the title compound. Use a method similar to the General Procedure 2-1 to obtain the title compound (670 mg, 82%). MS (ES+) m/z: 402.1 (M+H)⁺.

EXAMPLE 644

7-Chloro-6-(6-trifluoroethylamino-pyridin-3-ylmethylthio)-2,3,4,5-tetrahydro-1H-benzo[d]azepine Succinate

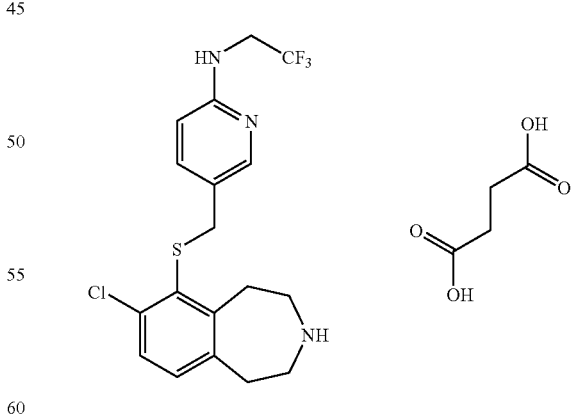

Example 644 may be prepared essentially as described in Example 643 by using 3-tert-butoxycarbonyl-7-chloro-6-(6-chloro-pyridin-3-ylmethylthio)-2,3,4,5-tetrahydro-1H-benzo[d]azepine and 2,2,2-trifluoroethylamine (10% yield, MS (ES+) m/z 502.2 (M+H)⁺).

EXAMPLE 645

7-Chloro-6-(6-cyclohexylmethylamino-pyridin-3-ylmethylthio)-2,3,4,5-tetrahydro-1H-benzo[d]azepine Succinate

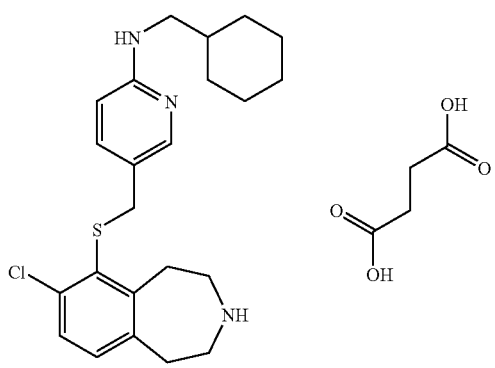

Add cyclohexylmethylamine (3 mL) to a flask containing 3-tert-butoxycarbonyl-7-chloro-6-(6-chloro-pyridin-3-ylmethylthio)-2,3,4,5-tetrahydro-1H-benzo[d]azepine (340 mg, 0.8 mmol) and ammonium chloride (50 mg, 0.92 mmol). Heat the contents in a sealed flask at 170° C. for 7 h. Cool the flask to room temperature, dilute with EtOAc (50 mL) and wash with water (20 mL). Collect the organic layer and concentrate in vacuo. Purify the residue by chromatography on silica gel eluting with hexane/EtOAc (19:1 to 4:1 gradient) to obtain 3-tert-butoxycarbonyl-7-chloro-6-(6-cyclohexylmethylamino-pyridin-3-ylmethylthio)-2,3,4,5-tetrahydro-1H-benzo[d]azepine (160 mg, 40%).

Use a method similar to the General Procedure 1-5 to deprotect 3-tert-butoxycarbonyl-7-chloro-6-(6-cyclohexylmethylamino-pyridin-3-ylmethylthio)-2,3,4,5-tetrahydro-1H-benzo[d]azepine. Purify by chromatography on silica gel eluting with dichloromethane/2M ammonia in methanol (99:1, 98:2, 96:4 gradient) to give the free base of the title compound. Use a method similar to the General Procedure 2-1 to obtain the title compound (115 mg, 70%). MS (ES+) m/z: 416.0 (M+H)+.

EXAMPLE 646

7-Chloro-6-(2,2-difluoro-2-phenyl-ethylthio)-2,3,4,5-tetrahydro-1H-benzo[d]azepine Hydrochloride

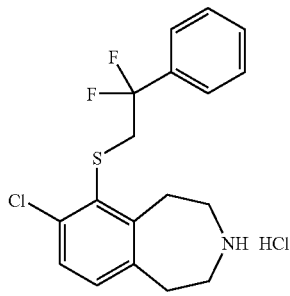

Dissolve 3-tert-butoxycarbonyl-7-chloro-6-dimethylcarbamoylthio-2,3,4,5-tetrahydro-1H-benzo[d]azepine (200 mg, 0.52 mmol) in methanol (10 mL) and add potassium hydroxide (0.934 g, 16.64 mmol). Heat at 60° C. for 4 h. Cool the reaction mixture to ambient temperature, add aqueous saturated ammonium chloride and concentrate in vacuo. Partition the residue between EtOAc and water. Dry the organic phase over anhydrous Na$_2$SO$_4$ and concentrate in vacuo to give 3-tert-butoxycarbonyl-7-chloro-6-mercapto-2,3,4,5-tetrahydro-1H-benzo[d]azepine (0.163 g). Dissolve the crude 3-tert-butoxycarbonyl-7-chloro-6-mercapto-2,3,4,5-tetrahydro-1H-benzo[d]azepine (0.163 g, 0.52 mmol) in anhydrous DMSO (5 mL) and add triethylamine (0.43 mL, 3.12 mmol) and 2,2-difluoro-2-phenylethyl trifluoromethanesulfonate (151 mg, 0.52 mmol). Heat the solution at 40° C. overnight. Cool to ambient temperature, add water and extract the aqueous phase twice with EtOAc. Dry the combined organic extracts over anhydrous Na$_2$SO$_4$, filter and concentrate in vacuo. Purify the crude mixture by chromatography on silica gel eluting with hexane and hexane/EtOAc (19:1, 9:1 and 4:1) to give 3-tert-butoxycarbonyl-7-chloro-6-(2,2-difluoro-2-phenyl-ethylthio)-2,3,4,5-tetrahydro-1H-benzo[d]azepine as oil (132 mg, 56%).

Use a method similar to the General Procedure 1-4 to deprotect 3-tert-butoxycarbonyl-7-chloro-6-(2,2-difluoro-2-phenyl-ethylthio)-2,3,4,5-tetrahydro-1H-benzo[d]azepine (132 mg, 0.29 mmol) and give the title compound as a solid (111 mg, 98%). MS (ES+) m/z: 354 (M+H)+.

EXAMPLE 647

7-Chloro-6-(2,2-difluoro-2-pyridin-2-yl-ethylthio)-2,3,4,5-tetrahydro-1H-benzo[d]azepine Hydrochloride

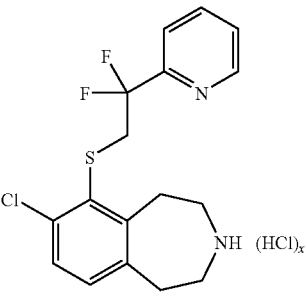

Example 647 may be prepared essentially as described in Example 646 using 3-tert-butoxycarbonyl-7-chloro-6-dimethylcarbamoylthio-2,3,4,5-tetrahydro-1H-benzo[d]azepine and 2,2-difluoro-2-pyridin-2-yl-ethyl trifluoromethanesulfonate (prepared by following the procedure described in *J. Med. Chem.* 2003, 46, 461-473) (66% yield, MS (ES+) m/z 355 (M+H)+).

EXAMPLE 648

7-Chloro-6-[3-(2-oxo-2,3-dihydro-indol-1-yl)-propylthio]-2,3,4,5-tetrahydro-1H-benzo[d]azepine Succinate

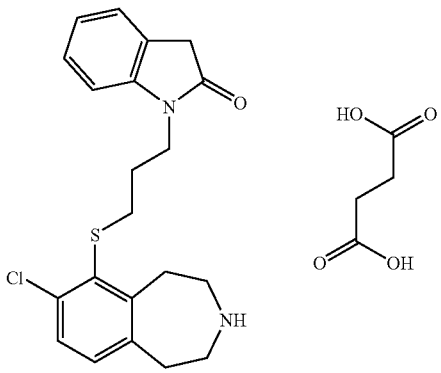

Add potassium hydroxide (899 mg, 16.64 mmol) in one portion to a solution of 3-tert-butoxycarbonyl-7-chloro-6-dimethylcarbamoylthio-2,3,4,5-tetrahydro-1H-benzo[d]azepine (200 mg, 0.52 mmol) in methanol (10 mL). Heat the reaction to 50° C. under nitrogen for 24 h, then cool to room temperature and add 1-(3-chloro-propyl)-1,3-dihydro-indol-2-one (217 mg, 1.04 mmol). Stir the reaction at room temperature for 4 days. Remove solvents in vacuo, add dichloromethane (20 mL) and water (20 mL). Remove the organic layer and dry using an ISCO® phase separator then concentrate in vacuo to give 3-tert-butoxycarbonyl-7-chloro-6-[3-(2-oxo-2,3-dihydro-indol-1-yl)-propylthio]-2,3,4,5-tetrahydro-1H-benzo[d]azepine as orange powder. MS (ES+) m/z: 509 (M+Na)+.

Dissolve 3-tert-butoxycarbonyl-7-chloro-6-[3-(2-oxo-2,3-dihydro-indol-1-yl)-propylthio]-2,3,4,5-tetrahydro-1H-benzo[d]azepine (0.52 mmol) in dichloromethane (10 mL), then add TFA (2 mL) dropwise and stir for 2 h. Remove solvents in vacuo, then free base using an SCX column, eluting with 7M ammonia in methanol. Purify using UV-guided reverse phase HPLC [Supelco Discovery C18 column (21.2×100 mm, 5 µm packing), 20 mL/min flow rate, eluting with water/acetonitrile/acetic acid gradient over 15 min, fraction collection triggered using UV detector (220 and 254 nm)] followed by SCX column, eluting with 7M ammonia in methanol, then Mass-guided reverse phase HPLC [Supelco Discovery C18 column (21.2×100 mm, 5 ppm packing), 25 mL/min flow rate, eluting with water/acetonitrile/acetic acid gradient over 12 min, fraction collection triggered by Electrospray MS] and SCX column. Concentrate in vacuo, then use a method similar to the General Procedure 2-1 and freeze dry to give the title compound as a light pink solid (51 mg, 19%). MS (ES+) w/z: 387 (M+H)+.

EXAMPLES 649-650

Examples 649-650 may be prepared essentially as described in Example 648 using 3-tert-butoxycarbonyl-7-chloro-6-dimethylcarbamoylthio-2,3,4,5-tetrahydro-1H-benzo[d]azepine and the appropriately substituted alkyl chloride. Overall yields and MS (ES+) data are shown in the Table below.

| Ex. | Structure | Compound | Yield (%) | MS (ES+) m/z |
|---|---|---|---|---|
| 649 | 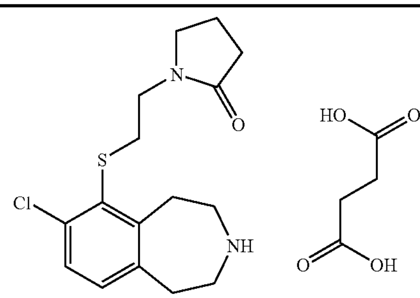 | 7-Chloro-6-[2-(2-oxo-pyrrolidin-1-yl)-ethylthio]-2,3,4,5-tetrahydro-1H-benzo[d]azepine Succinate | 71 | 325 (M + H)+ |
| 650 | 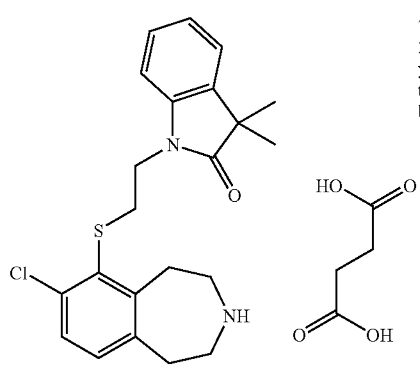 | 7-Chloro-6-[2-(3,3-dimethyl-2-oxo-2,3-dihydro-indol-1-yl)-ethylthio]-2,3,4,5-tetrahydro-1H-benzo[d]azepine Succinate | 32 | 401 (M + H)+ |

EXAMPLE 651

7-Chloro-6-[3-(3,3-dimethyl-2-oxo-2,3-dihydro-indol-1-yl)-propylthio]-2,3,4,5-tetrahydro-1H-benzo[d]azepine Succinate

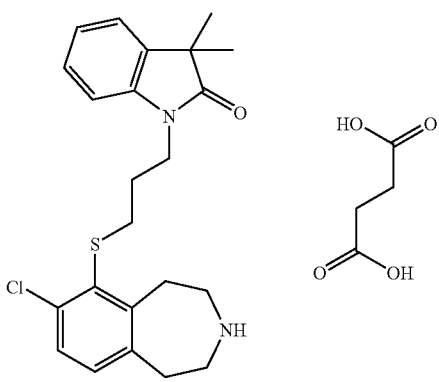

Add potassium hydroxide (170 mg, 3.03 mmol) in one portion to a solution of 3-tert-butoxycarbonyl-7-chloro-6-dimethylcarbamoylthio-2,3,4,5-tetrahydro-1H-benzo[d]azepine (187 mg, 0.49 mmol) in methanol (10 mL). Heat the reaction at reflux under nitrogen overnight. Then add further portion of KOH (867 mg, 15.45 mmol) and heat at reflux for 3 h. Then cool to room temperature and add 1-(3-bromopropyl)-1,3-dihydro-3,3-dimethyl-indol-2-one (274 mg, 0.97 mmol, prepared by following the procedure described in *Perkin 1* 2000, 769-774). Stir the reaction at room temperature overnight. Remove solvents in vacuo, add water and extract with diethyl ether (2×50 mL). Combine the organic extracts, wash with water (2×50 mL) and brine (50 mL). Dry over $MgSO_4$ and concentrate in vacuo. Purify by chromatography on silica gel eluting with isohexane/EtOAc (1:0 to 1:1 gradient over 40 min) to give 3-tert-butoxycarbonyl-7-chloro-6-[3-(3,3-dimethyl-2-oxo-2,3-dihydro-indol-1-yl)-propylthio]-2,3,4,5-tetrahydro-1H-benzo[d]azepine as a colourless oil (330 mg), 50% contaminated with 1-(3-methoxypropyl)-1,3-dihydro-3,3-dimethyl-indol-2-one. MS (ES+) m/z: 537 $(M+Na)^+$.

Dissolve 3-tert-butoxycarbonyl-7-chloro-6-[3-(3,3-dimethyl-2-oxo-2,3-dihydro-indol-1-yl)-propylthio]-2,3,4,5-tetrahydro-1H-benzo[d]azepine (240 mg, 0.52 mmol) in dichloromethane (10 mL), then add TFA (1 mL) dropwise and stir at room temperature overnight. Remove solvents in vacuo to give a straw coloured oil (580 mg), then free base using an SCX column, eluting with 7M ammonia in methanol. Concentrate in vacuo, then use a method similar to the General Procedure 2-1 and freeze dry to give the title compound as a solid (196 mg, 82%). MS (ES+) m/z: 415 $(M+H)^+$.

EXAMPLES 652-654

Examples 652-654 may be prepared essentially as described in Example 651 using 3-tert-butoxycarbonyl-7-chloro-6-dimethylcarbamoylthio-2,3,4,5-tetrahydro-1H-benzo[d]azepine and the appropriate alkyl bromide. Examples 655-657 may be prepared essentially as described in Example 651 using the appropriate alkyl chloride. Overall yields and MS (ES+) data are shown in the Table below.

| Ex. | Structure | Compound | Yield (%) | MS (ES+) m/z |
|---|---|---|---|---|
| 652 | 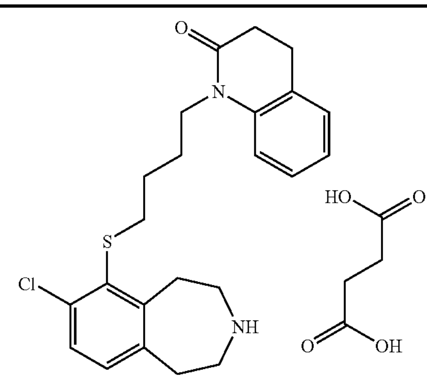 | 7-Chloro-6-[4-(2-oxo-3,4-dihydro-2H-quinolin-1-yl)-butylthio]-2,3,4,5-tetrahydro-1H-benzo[d]azepine Succinate | 71 | 414 $(M + H)^+$ |
| 653 | 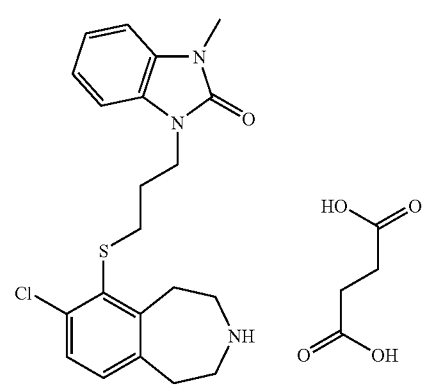 | 7-Chloro-6-[3-(3-methyl-2-oxo-2,3-dihydro-benzoimidazol-1-yl)-propylthio]-2,3,4,5-tetrahydro-1H-benzo[d]azepine Succinate | 31 | 402 $(M + H)^+$ |

-continued

| Ex. | Structure | Compound | Yield (%) | MS (ES+) m/z |
|---|---|---|---|---|
| 654 | 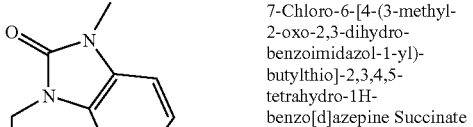 | 7-Chloro-6-[4-(3-methyl-2-oxo-2,3-dihydro-benzoimidazol-1-yl)-butylthio]-2,3,4,5-tetrahydro-1H-benzo[d]azepine Succinate | 31 | 416 (M + H)+ |
| 655 | 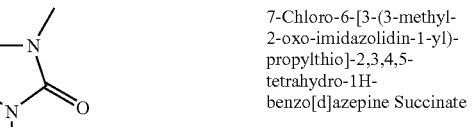 | 7-Chloro-6-[3-(3-methyl-2-oxo-imidazolidin-1-yl)-propylthio]-2,3,4,5-tetrahydro-1H-benzo[d]azepine Succinate | 29 | 354 (M + H)+ |
| 656 | 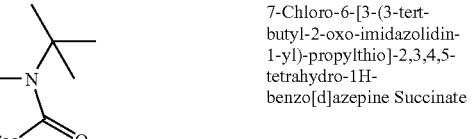 | 7-Chloro-6-[3-(3-tert-butyl-2-oxo-imidazolidin-1-yl)-propylthio]-2,3,4,5-tetrahydro-1H-benzo[d]azepine Succinate | 31 | 396 (M + H)+ |
| 657 | 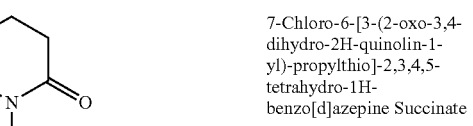 | 7-Chloro-6-[3-(2-oxo-3,4-dihydro-2H-quinolin-1-yl)-propylthio]-2,3,4,5-tetrahydro-1H-benzo[d]azepine Succinate | 66 | 400 (M + H)+ |

EXAMPLE 658

7-Chloro-6-[3-(2-oxo-2,3-dihydro-benzoimidazol-1-yl)-propylthio]-2,3,4,5-tetrahydro-1H-benzo[d] azepine Succinate

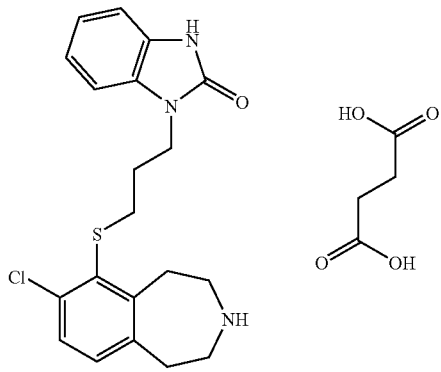

Add potassium hydroxide (933 mg, 16.6 mmol) in one portion to a solution of 3-tert-butoxycarbonyl-7-chloro-6-dimethylcarbamoylthio-2,3,4,5-tetrahydro-1H-benzo[d]azepine (200 mg, 0.52 mmol) in methanol (10 mL). Heat the reaction at reflux under nitrogen 4 h. Then cool to room temperature and add 1-(3-bromo-propyl)-3-isopropenyl-1,3-dihydro-benzoimidazol-2-one (142 mg, 0.52 mmol). Stir the reaction at room temperature overnight. Remove solvents in vacuo, extract into diethyl ether (2×50 mL), wash with water (2×50 mL) and brine (50 mL). Dry over MgSO$_4$, filtrate and concentrate in vacuo to give 3-tert-butoxycarbonyl-7-chloro-6-[3-(2-oxo-2,3-dihydro-benzoimidazol-1-yl)-propylthio]-2,3,4,5-tetrahydro-1H-benzo[d]azepine as an oil (209 mg, 76%). MS (ES+) m/z: 550 (M+Na)$^+$.

Dissolve 3-tert-butoxycarbonyl-7-chloro-6-[3-(2-oxo-2,3-dihydro-benzoimidazol-1-yl)-propylthio]-2,3,4,5-tetrahydro-1H-benzo[d]azepine (209 mg, 0.396 mmol) in dichloromethane (10 mL), then add TFA (0.5 mL) dropwise and stir at room temperature overnight. Remove solvents in vacuo then free base using an SCX column, eluting with 7M ammonia in methanol. Concentrate in vacuo, then use a method similar to the General Procedure 2-1 and freeze dry to give the title compound as a solid (140 mg, 70%). MS (ES+) m/z: 388 (M+H)$^+$.

EXAMPLE 659

7-Chloro-6-[3-(3,3-dimethyl-2-oxo-2,3-dihydro-1H-indol-5-yl)-propylthio]-2,3,4,5-tetrahydro-1H-benzo[d]azepine Succinate

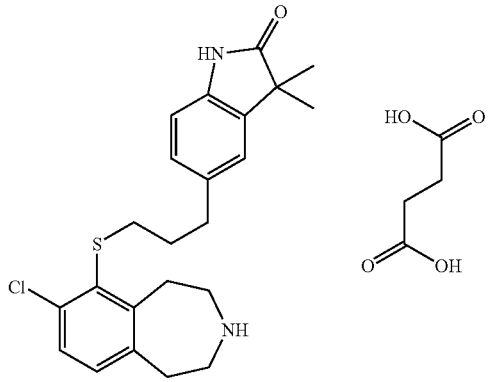

Under nitrogen atmosphere, add potassium hydroxide (138 mg, 2.46 mmol) to a stirred solution of 3-tert-butoxycarbonyl-7-chloro-6-dimethylcarbamoylthio-2,3,4,5-tetrahydro-1H-benzo[d]azepine (375 mg, 0.97 mmol) in methanol (10 mL). Heat under reflux for 2 h then add further potassium hydroxide (159 mg, 2.83 mmol) and continue heating under reflux for another 6 h. Cool the reaction mixture and add dropwise via cannula a solution of 5-(3-chloropropyl)-3,3-dimethyl-1,3-dihydro-indol-2-one (245 mg, 1.03 mmol) in methanol (10 mL). Stir at ambient temperature overnight then heat at 50° C. for 5 h. Add potassium iodide (186 mg, 1.12 mmol) to the reaction mixture and then heat under reflux for 5 h. Concentrate in vacuo and partition the residue between water (100 mL) and EtOAc (50 mL). Extract the aqueous phase with EtOAc (2×50 mL). Wash the combined extracts with brine (50 mL), dry over MgSO$_4$, filter and concentrate in vacuo to obtain the crude mixture as a yellow oil. Dilute this oil with dichloromethane then re-concentrate in vacuo and repeat until a solid remains. Dry the solid in a vacuum oven to give 3-tert-butoxycarbonyl-7-chloro-6-[3-(3,3-dimethyl-2-oxo-2,3-dihydro-1H-indol-5-yl)-propylthio]-2,3,4,5-tetrahydro-1H-benzo[d]azepine as a yellow solid (481 mg) that was used without further purification. MS (ES+) m/z: 537 (M+Na)$^+$.

Add trifluoroacetic acid (0.2 mL, 2.6 mmol) to a solution of 3-tert-butoxycarbonyl-7-chloro-6-[3-(3,3-dimethyl-2-oxo-2,3-dihydro-1H-indol-5-yl)-propylthio]-2,3,4,5-tetrahydro-1H-benzo[d]azepine (257 mg, 0.5 mmol) in dichloromethane (5 mL) then stir at ambient temperature over the weekend. Concentrate in vacuo. Dissolve the residue in methanol and load onto an SCX column. Elute with methanol followed by 7M ammonia in methanol. Collect the basic fraction and concentrate in vacuo. Purify the residue by prep-LCMS [Supelco Discovery C18 column (21.2×100 mm, 5 μm packing), 25 mL/min flow rate, eluting with a water/acetonitrile gradient containing acetic acid as modifier over 12 min, fraction collection triggered by Electrospray MS] to give 7-chloro-6-[3-(3,3-dimethyl-2-oxo-2,3-dihydro-1H-indol-5-yl)-propylthio]-2,3,4,5-tetrahydro-1H-benzo[d]azepine as a white solid (101 mg, 25% over 2 steps). MS (ES+) m/z: 415 (M+H)$^+$.

Dissolve 7-chloro-6-[3-(3,3-dimethyl-2-oxo-2,3-dihydro-1H-indol-5-yl)-propylthio]-2,3,4,5-tetrahydro-1H-benzo[d]azepine (101 mg, 0.24 mmol) in a mixture of diethyl ether (3 mL) and methanol (2 mL). Add succinic acid (28.7 mg, 0.24 mmol) and allow the resultant suspension to stir at ambient temperature for 2 h. Concentrate in vacuo and dry the residue in a vacuum oven to afford the title compound as a white solid. MS (ES+) m/z: 415 (M+H)$^+$.

EXAMPLE 660

7-Chloro-6-(N-phenylcarbamoyl-methylthio)-2,3,4,5-tetrahydro-1H-benzo[d]azepine Succinate

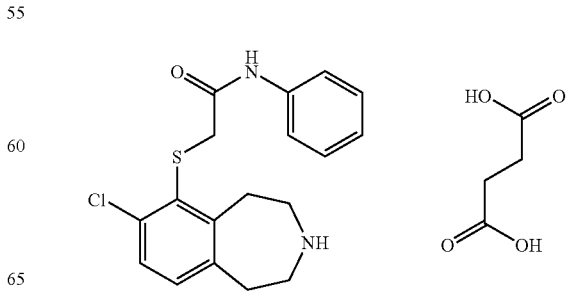

Add potassium hydroxide (890 mg, 15 mmol) in one portion to a solution of 3-tert-butoxycarbonyl-7-chloro-6-dimethylcarbamoylthio-2,3,4,5-tetrahydro-1H-benzo[d]azepine (180 mg, 0.47 mmol) in methanol (10 mL). Heat the reaction at reflux under nitrogen 3 h. Then cool to room temperature, add 2-chloro-N-phenyl-acetamide (79 mg, 0.47 mmol) and stir overnight. Remove solvents in vacuo, extract into diethyl ether (2×50 mL), wash with water (2×50 mL) and brine (50 mL). Dry over MgSO$_4$, filtrate and concentrate in vacuo to give 3-tert-butoxycarbonyl-7-chloro-6-(N-phenylcarbamoyl-methylthio)-2,3,4,5-tetrahydro-1H-benzo[d]azepine as a clear oil (210 mg, 100%). MS (ES+) m/z: 460 (M+Na)$^+$.

Dissolve 3-tert-butoxycarbonyl-7-chloro-6-(N-phenylcarbamoyl-methylthio)-2,3,4,5-tetrahydro-1H-benzo[d]azepine (210 mg, 0.47 mmol) in dichloromethane (10 mL) then add TFA (0.5 mL) dropwise and stir at room temperature for 3 days. Remove solvents in vacuo then free base using an SCX column, eluting with 7M ammonia in methanol. Concentrate in vacuo, then use a method similar to the General Procedure 2-1 and freeze dry to give the title compound as a solid (150 mg, 69%). MS (ES+) m/z: 347 (M+H)$^+$.

EXAMPLE 661

7-Chloro-6-(3-methylcarbamoyl-propylthio)-2,3,4,5-tetrahydro-1H-benzo[d]azepine Succinate

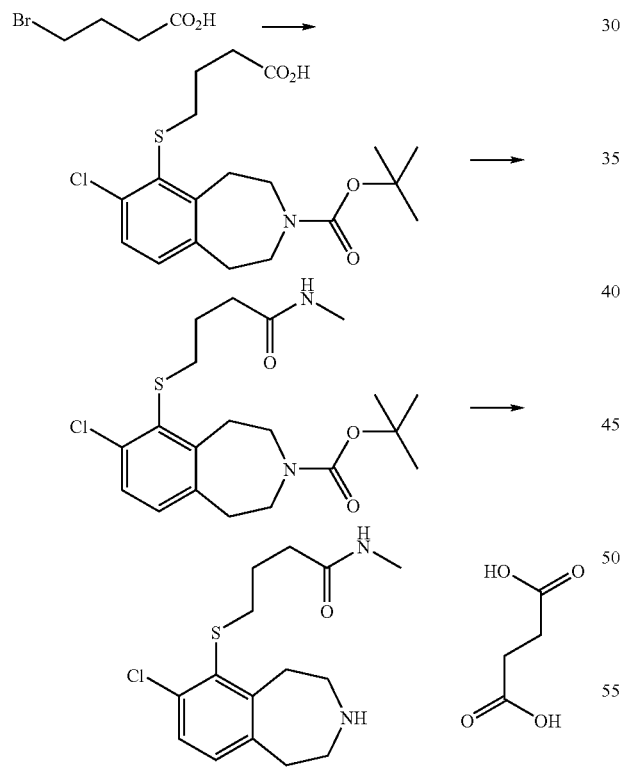

3-tert-Butoxycarbonyl-7-chloro-6-(3-carboxy-propylthio)-2,3,4,5-tetrahydro-1H-benzo[d]azepine: Add potassium hydroxide (700 mg, 12.5 mmol) in one portion to a solution of 3-tert-butoxycarbonyl-7-chloro-6-dimethylcarbamoylthio-2,3,4,5-tetrahydro-1H-benzo[d]azepine (150 mg, 0.39 mmol) in methanol (10 mL). Heat the reaction at reflux under nitrogen 4 h. Then cool to room temperature, add 4-bromo-butyric acid (65 mg, 0.39 mmol) and stir for 3 days. Remove solvents in vacuo, neutralize with ammonium chloride (200 mL) and extract into EtOAc (2×50 mL). Dry over MgSO$_4$, filtrate and concentrate in vacuo to give a clear oil (125 mg). Dissolve the oil in anhydrous DMF (10 mL) and add sodium hydride (30 mg, 0.78 mmol of 60% dispersion in oil) under nitrogen. Stir for 30 min. Add 4-bromo-butyric acid (65 mg, 0.39 mmol) and stir for 30 min. Pour into water (50 mL) and extract with diethyl ether (2×50 mL). Wash the combined organic extracts with brine (50 mL) and dry over MgSO$_4$. Concentrate the filtrate in vacuo to give the desired intermediate as a solid (146 mg, 94%). MS (ES+) m/z: 398 (M+H)$^+$.

3-tert-Butoxycarbonyl-7-chloro-6-(3-methylcarbamoyl-propylthio)-2,3,4,5-tetrahydro-1H-benzo[d]azepine: Add O-benzotriazol-1-yl-N,N,N',N'-tetramethyluronium tetrafluoroborate (123 mg, 0383 mmol) portion wise to a solution of 3-tert-butoxycarbonyl-7-chloro-6-(3-carboxy-propylthio)-2,3,4,5-tetrahydro-1H-benzo[d]azepine (146 mg, 0365 mmol) and methylamine (182 µL, 0.365 mmol) in anhydrous DMF (5 mL) under nitrogen at 0° C. Stir for 15 min then add diisopropylethylamine (127 µL, 0.73 mmol) in anhydrous DMF (1 mL) and continue to stir at, 0° C. for 1 h. Warm to room temperature and continue to stir overnight Pour into water (50 mL) and extract with EtOAc (3×20 mL). Wash the combined organic extracts with saturated aqueous NaHCO$_3$ (50 mL) and brine (50 mL). Dry over MgSO$_4$, filtrate and concentrate in vacuo to give a pale yellow oil (74 mg). MS (ES+) m/z: 398 (M+H)$^+$. Purify using Mass-guided reverse phase HPLC [Supelco Discovery C18 column (21.2×100 mm, 5 µm packing), 25 mL/min flow rate, eluting with water/acetonitrile/acetic acid gradient over 12 min, fraction collection triggered by Electrospray MS]. Concentrate in vacuo to give the desired intermediate as a colourless oil (30 mg, 20%). MS (ES+) m/z: 435 (M+Na)$^+$.

7-Chloro-6-(3-methylcarbamoyl-propylthio)-2,3,4,5-tetrahydro-1H-benzo[d]azepine Succinate: Dissolve 3-tert-butoxycarbonyl-7-chloro-6-(3-methylcarbamoyl-propylthio)-2,3,4,5-tetrahydro-1H-benzo[d]azepine (30 mg, 0.07 mmol) in dichloromethane (10 mL) then add TFA (0.5 mL) dropwise and stir at room temperature for 3 days. Remove solvents in vacuo then free base using an SCX column, eluting with 7M ammonia in methanol. Concentrate in vacuo, then use a method similar to the General Procedure 2-1 and freeze dry to give the title compound as a solid (21 mg, 72%). MS (ES+) m/z: 313 (M+H)$^+$.

EXAMPLE 662

7-Chloro-6-(1-cyano-1-methyl-ethylthio)-2,3,4,5-tetrahydro-1H-benzo[d]azepine Succinate

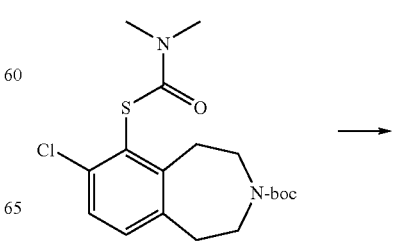

-continued

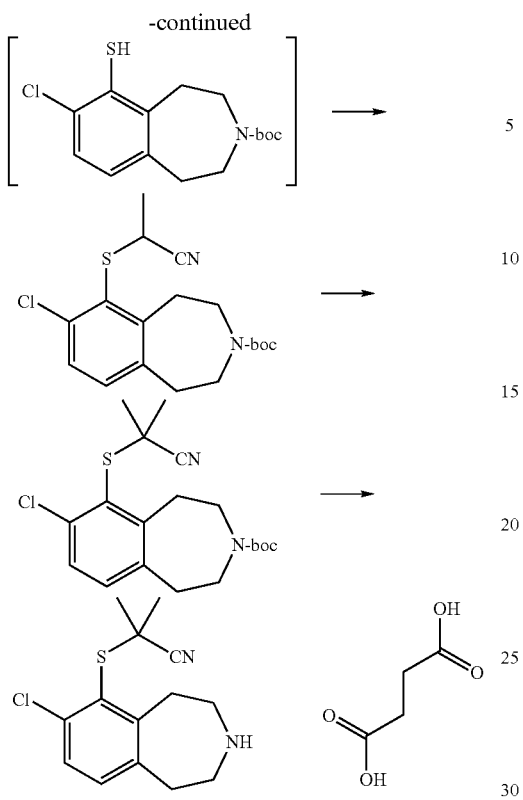

3-tert-Butoxycarbonyl-7-chloro-6-(1-cyano-ethylthio)-2,3,4,5-tetrahydro-1H-benzo[d]azepine: Add potassium hydroxide (10.8 g, 192 mmol) to a solution of 3-tert-butoxycarbonyl-7-chloro-6-dimethylcarbamoylthio-2,3,4,5-tetrahydro-1H-benzo[d]azepine (3 g, 7.8 mmol) in degassed methanol (150 mL) under a nitrogen atmosphere. Heat the mixture at 80° C. for 6 h. Cool the mixture to ambient temperature, then concentrate in vacuo to an oil. Dissolve the oil in EtOAc (50 mL), wash with aqueous saturated ammonium chloride (30 mL). Separate the organic layer and extract the aqueous layer with EtOAc (3×50 mL). Dry the combined organic extracts over $Na_2SO_4$, filter and concentrate in vacuo to an oil (2.4 g). Dissolve the oil in anhydrous DMF (50 mL). Slowly add sodium hydride (470 mg, 11.7 mmol) portionwise over 5 min followed by 2-bromopropionitrile (1 mL, 11.7 mmol). Stir the mixture under nitrogen at ambient temperature for 16 h. Dilute the mixture slowly with EtOAc (100 mL) and wash with cold aqueous saturated ammonium chloride (50 mL). Separate the organic layer and extract the aqueous-layer with EtOAc (3×50 mL). Combine the organic extracts and concentrate in vacuo. Purify the crude mixture by chromatography on silica gel eluting with hexane/EtOAc (19:1 to 3:1 gradient) to obtain the desired intermediate (2.5 g, 89%). MS (ES+) m/z: 267.2 (M-Boc)$^+$.

3-tert-Butoxycarbonyl-7-chloro-6-(1-cyano-1-methyl-ethylthio)-2,3,4,5-tetrahydro-1H-benzo[d]azepine: Slowly add a solution of 3-tert-butoxycarbonyl-7-chloro-6-(1-cyano-ethylthio)-2,3,4,5-tetrahydro-1H-benzo[d]azepine (2.5 g, 6.8 mmol) in anhydrous THF (20 mL) to a slurry of sodium hydride (1.4 g, 34 mmol) in anhydrous THF (50 mL) at 0° C. under a nitrogen atmosphere. Stir the slurry for 5 min, then add iodomethane (12.7 mL, 204 mmol) to the slurry while maintaining the temperature below 30° C. Stir the mixture for 3 h at ambient temperature then quench with methanol (10 mL) and concentrate in vacuo. Purify the crude mixture by chromatography on silica gel eluting with hexane/EtOAc (19:1 to 9:1 gradient) to obtain the desired intermediate (2 g, 79%). MS (ES+) m/z: 281.2 (M+H–Boc)$^+$.

7-Chloro-6-(1-cyano-1-methyl-ethylthio)-2,3,4,5-tetrahydro-1H-benzo[d]azepine Succinate: Use a method similar to the General Procedure 1-5 to deprotect 3-tert-butoxycarbonyl-7-chloro-6-(1-cyano-1-methyl-ethylthio)-2,3,4,5-tetrahydro-1H-benzo[d]azepine (1.4 g, 3.5 mmol). Purify by chromatography on silica gel eluting with dichloromethane/2M ammonia in methanol (99:1 to 90:10 gradient) to give the free base of the title compound. Use a method similar to the General Procedure 2-1 to obtain the title compound (992 mg, 71%). MS (ES+) m/z: 281.2 (M+H)$^+$.

EXAMPLE 663

7-Chloro-6-(1-cyano-cyclopropylthio)-2,3,4,5-tetrahydro-1H-benzo[d]azepine Succinate

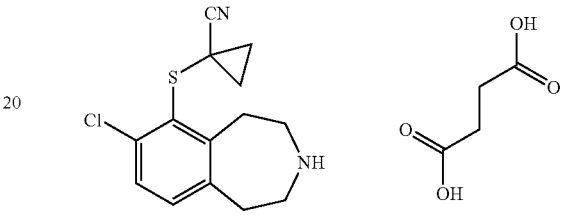

Add potassium hydroxide (5.4 g, 96.2 mmol) to a solution of 3-tert-butoxycarbonyl-7-chloro-6-dimethylcarbamoylthio-2,3,4,5-tetrahydro-1H-benzo[d]azepine (1.5 g, 4.7 mmol) in degassed methanol (75 mL) under a nitrogen atmosphere. Heat the mixture at 80° C. for 6 h Cool the mixture to ambient temperature, then concentrate in vacuo to an oil. Dissolve the oil in EtOAc (50 mL) and wash with saturated aqueous ammonium chloride (30 mL). Separate the organic layer and extract the aqueous layer with EtOAc (3×50 mL). Dry the combined organic extracts over $Na_2SO_4$, filter and concentrate in vacuo to an oil (1.4 g). Dissolve the oil in anhydrous DMF (25 mL), then slowly add sodium hydride (282 mg, 7.1 mmol) and bromoacetonitrile (470 μl, 7.1 mmol). Stir the mixture under nitrogen at ambient temperature for 16 h. Dilute the mixture slowly with EtOAc (100 mL) and wash with cold aqueous saturated ammonium chloride (40 mL). Separate the organic layer and extract the aqueous layer with EtOAc (3×50 mL). Combine the organic extracts and concentrate in vacuo. Purify the residue by chromatography on silica gel eluting with hexane/EtOAc (9:1 to 7:3 gradient) to obtain 3-tert-butoxycarbonyl-7-chloro-6-(1-cyano-methylthio)-2,3,4,5-tetrahydro-1H-benzo[d]azepine (1.34 g, 81%). MS (ES+) m/z: 253.2 (M-Boc)$^+$.

Add sodium bis(trimethylsilyl)amide (5.4 mL, 5.4 mmol, 1M solution in THF) at room temperature under nitrogen to a solution of 3-tert-butoxycarbonyl-7-chloro-6-(1-cyano-methylthio)-2,3,4,5-tetrahydro-1H-benzo[d]azepine (380 mg, 1.1 mmol) in anhydrous toluene (4 mL). Stir the solution for 10 min, then add quickly 1,2-dibromoethane (2.8 mL, 32.4 mmol) followed by anhydrous DMF (4 mL). An exothermic reaction was observed and the reaction temperature increased to 38° C. Stir the mixture for 15 min at ambient temperature, then quench with methanol (2 mL). Concentrate in vacuo and purify by chromatography on silica gel eluting with hexane/EtOAc (9:1) to obtain 3-tert-butoxycarbonyl-7-chloro-6-(1-cyano-cyclopropylthio)-2,3,4,5-tetrahydro-1H-benzo[d]azepine (259 mg).

Use a method similar to the General Procedure 1-5 to deprotect 3-tert-butoxycarbonyl-7-chloro-6-(1-cyano-cyclopropylthio)-2,3,4,5-tetrahydro-1H-benzo[d]azepine. Purify by reverse phase chromatography [Column: Symmetry C18, 19×300 mm, flow rate 30 mL/min, eluting with water with 0.1% TFA/acetonitrile (19:1 to 1:1 gradient)] followed by SCX chromatography to obtain the free base of the title compound. Use a method similar to the General Procedure 2-1 to obtain the title compound (120 mg, 28% yield over 3 steps). MS (ES+) m/z: 279.2 (M+H)+.

EXAMPLE 664

6-(4-tert-Butylcarbamoyl-benzylthio)-7-chloro-9-fluoro-2,3,4,5-tetrahydro-1H-benzo[d]azepine Succinate

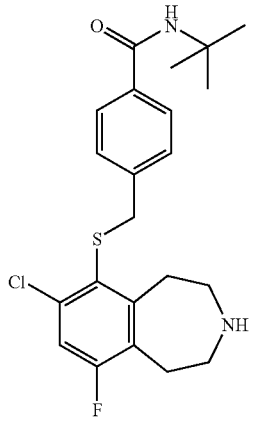
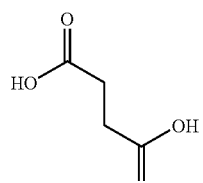

Use a method similar to Example 456 to react 3-tert-butoxycarbonyl-7-chloro-6-dimethylcarbamoylthio-9-fluoro-2,3,4,5-tetrahydro-1H-benzo[d]azepine with 4-chloromethyl-N-(tert-butyl)-benzamide.

Use methods similar to the General Procedures 1-5 and 2-1 to give the title compound as a white solid. MS (ES+) m/z: 421 (M+H)+.

EXAMPLE 665

7-Chloro-6-[4-(3,3-dimethylbutyryl)-benzylthio]-9-fluoro-2,3,4,5-tetrahydro-1H-benzo[d]azepine Succinate

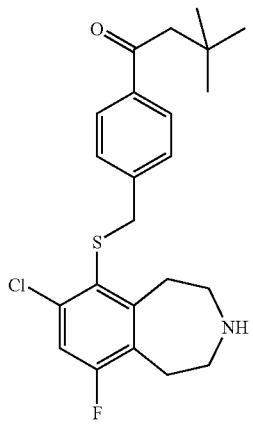
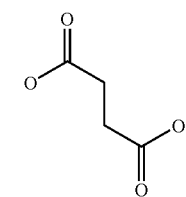

Use a method similar to Example 435 to react 3-tert-butoxycarbonyl-7-chloro-6-dimethylcarbamoylthio-9-fluoro-2,3,4,5-tetrahydro-1H-benzo[d]azepine with 1-(4-bromomethylphenyl)-3,3-dimethylbutan-1-one.

Use methods similar to the General Procedures 1-5 and 2-2 to give the title compound as a white solid. MS (ES+) m/z: 420 (M+H)+.

Preparation 346

4-(2,2-Dimethyl-propane-1-sulfonyl)-

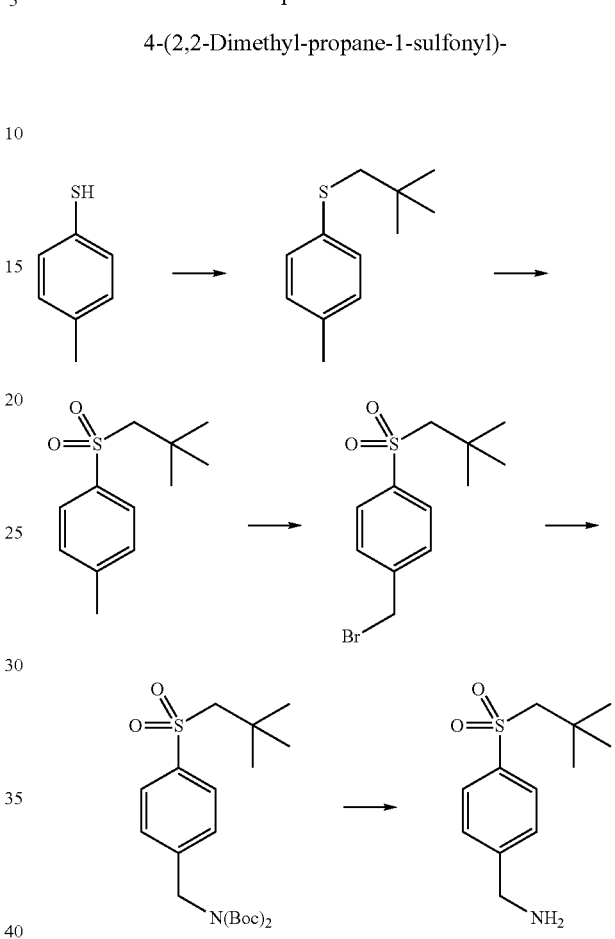

1-(2,2-Dimethyl-propylthio)-4-methyl-benzene: Dissolve 4-methyl-benzenethiol (1.5 g, 12.08 mmol) in anhydrous DMF (6 mL). Cool the solution to 0° C., add sodium hydride (435 mg, 17.21 mmol, 95%) and stir the mixture under nitrogen atmosphere for 15 mm. Add 1-iodo-2,2-dimethylpropane (1.93 mL, 14.5 mmol), stir the mixture for 1 h at 0° C., warm to room temperature and stir overnight. Add water and extract the aqueous phase twice with EtOAc. Wash the combined organic extracts twice with iced-water, dry over Na2SO4, filter and concentrate in vacuo to give the desired intermediate (1.476 g, 63% yield).

1-(2,2-Dimethyl-propane-1-sulfonyl)-4-methyl-benzene: Dissolve 1-(2,2-dimethyl-propylthio)-4-methyl-benzene (1.476 g, 7.6 mmol) in trifluoroacetic acid (9.5 mL). Add dropwise hydrogen peroxide (9.9 mL, 30% in water), cool the mixture to 0° C. and stir 15 min at this temperature and 45 min at room temperature. Concentrate the mixture in vacuo, dilute with saturated aqueous NaHCO3 and extract the aqueous phase twice with EtOAc. Dry the combined organic extracts over Na2SO4, filter and concentrate in vacuo to give the desired intermediate (1.548 g, 90%).

1-Bromomethyl-4-(2,2-dimethyl-propane-1-sulfonyl)-benzene: Use a method similar to the Preparation 213 (Step 2), using 1-(2,2-dimethyl-propane-1-sulfonyl)-4-methyl-benzene (560 mg, 2.47 mmol) to give the desired intermediate.

N-(di-tert-Butoxycarbonyl)-4-(2,2-dimethyl-propane-1-sulfonyl)-benzylamine: Add sodium hydride (60 mg; 2.39 mmol) to a solution of di-tert-butyl-iminodicarboxylate (519 mg, 2.39 mmol) in anhydrous DMF (2 mL) at room temperature under nitrogen and stir for 15 min. Then add a solution of 1-bromomethyl-4-(2,2-dimethyl-propane-1-sulfonyl)-benzene (731 mg, 2.39 mmol) in anhydrous DMF (3 mL) and stir for 1.5 h. Add water and extract the aqueous phase twice with EtOAc. Wash the combined organic extracts with iced-water. Dry the organic layer over $Na_2SO_4$, filter and concentrate in vacuo. Purify by chromatography on silica gel eluting with hexane/EtOAc (88:12) to obtain the desired intermediate (460 mg, 44% over 2 steps).

4-(2,2-Dimethyl-propane-1-sulfonyl)-benzylamine: Add 4N hydrogen chloride in dioxane (2 mL) to a solution of N-(di-tert-butoxycarbonyl)-4-(2,2-dimethyl-propane-1-sulfonyl)-benzylamine (460 mg, 1.04 mmol) in dichloromethane (20 mL) and stir overnight. Concentrate in vacuo, suspend the solid obtained in EtOAc, add saturated aqueous $NaHCO_3$ and stir until both phases are clear. Extract the aqueous phase three times with dichloromethane EtOAc. Dry the combined organic extracts over $Na_2SO_4$, filter and concentrate in vacuo to obtain the title compound as an oil that was used without any further purification (166 mg, 71% yield). MS (ES+) m/z: 242 (M+H)+.

The compounds of Preparations 347-348 may be prepared essentially as described in Preparation 346 using 1-iodo-3,3,3-trifluoropropane (Preparation 347) or 1,1,1-trifluoro-3-iodobutane (Preparation 348). MS (ES+) data are shown in the Table below.

| Prep. | Structure | Compound | MS (ES+) m/z |
|---|---|---|---|
| 347 | 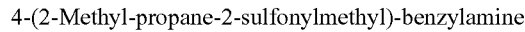 | 4-(3,3,3-Trifluoro-propane-1-sulfonyl)-benzylamine | 268 (M + H)+ |
| 348 | 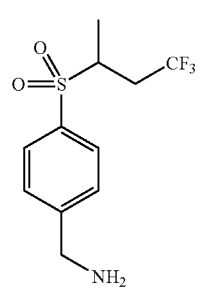 | 4-(4,4,4-Trifluoro-butane-2-sulfonyl)-benzylamine | 282 (M + H)+ |

Preparation 349

4-(2-Methyl-propane-2-sulfonylmethyl)-benzylamine

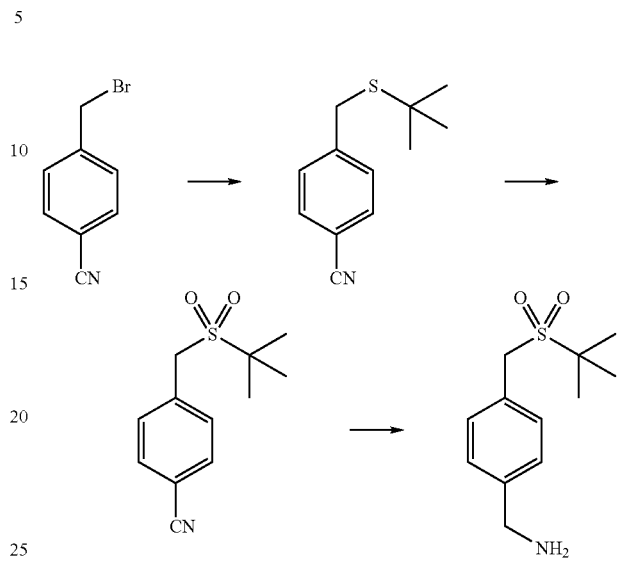

4-tert-Butylthiomethyl-benzonitrile: Add sodium hydride (359 mg, 14.21 mmol) to a solution of 2-methyl-2-propanethiol (900 mg, 9.98 mmol) in anhydrous DMF (15 mL) under nitrogen. Stir the mixture for 15 min, add 4-bromomethyl-benzonitrile (2.348 g, 11.97 mmol) and stir the resulting mixture overnight at room temperature. Add water and extract the aqueous phase twice with EtOAc. Wash the combined organic extracts twice with iced-water, dry over $Na_2SO_4$, filter and concentrate in vacuo. Purify by chromatography on silica gel eluting with hexane/EtOAc 92:8 to give the desired intermediate (1.42 g, 69% yield).

4-(2-Methyl-propane-2-sulfonylmethyl)-benzonitrile: Dissolve 4-tert-butylthiomethyl-benzonitrile (1.42 g, 6.9 mmol) in trifluoroacetic acid (9 mL). Add dropwise hydrogen peroxide (9 mL, 30% in water), cool the mixture to 0° C. and stir 15 min at this temperature and 45 min at room temperature. Concentrate the mixture in vacuo, dilute with saturated aqueous $NaHCO_3$ and extract the aqueous phase twice with EtOAc. Dry the combined organic extracts over $Na_2SO_4$, filter and concentrate in vacuo to give the desired intermediate (1.46 g, 89%).

4-(2-Methyl-propane-2-sulfonylmethyl)-benzylamine: Dissolve 4-(2-methyl-propane-2-sulfonylmethyl)-benzonitrile (300 mg, 1.26 mmol) in methanol (50 mL). Add concentrated HCl (10 drops), 10% Pd/C (Degussa type E101, 60 mg) and submit the mixture to hydrogenation at atmospheric pressure for 1 h. Filter over Celite® and wash with methanol. Concentrate the filtrate in vacuo to give the hydrochloride salt of the title compound as a solid that was washed with diethyl ether (366 mg, 87%). Partition the solid between saturated $NaHCO_3$ and EtOAc and extract the aqueous phase twice with EtOAc. Dry the combined organic extracts over $Na_2SO_4$, filter and concentrate in vacuo to give the title compound (195 mg, 74%). MS (ES+) m/z: 242 (M+H)+.

The compound of Preparation 350 may be prepared essentially as described in Preparation 349 using 4-(2-bromoethyl)-benzonitrile. MS (ES+) data are shown in the Table below.

| Prep. | Structure | Compound | MS (ES+) m/z |
|---|---|---|---|
| 350 | 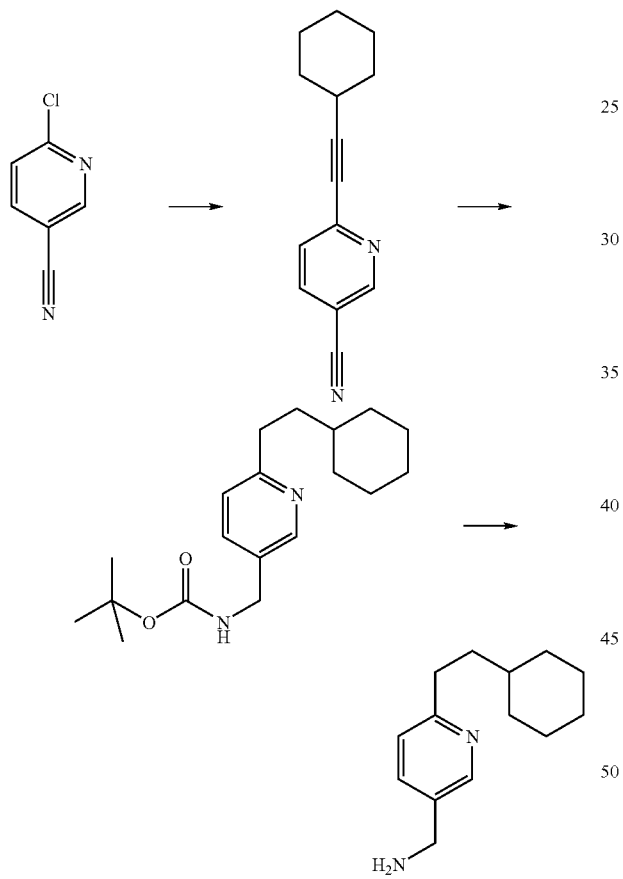 | 4-[2-(2-Methyl-propane-2-sulfonyl)-ethyl]-benzylamine | 256 (M + H)+ |

Preparation 351

3-Aminomethyl-6-(2-cyclohexyl-ethyl)-pyridine

6-Cyclohexylethynyl-nicotinonitrile: Add cyclohexylacetylene (1.54 mL, 11.6 mmol), dichlorobis(triphenylphosphine)palladium (200 mg, 0.28 mmol), copper iodide (100 mg, 0.53 mmol), and triethylamine (2.0 mL, 14.3 mmol) to a solution of 6-chloronicotinonitrile (1.38 g, 9.9 mmol) in DMF (4 mL). Heat the mixture in a sealed flask for 3 h at 100° C. Cool the mixture to room temperature, dilute with 1:1 hexane/EtOAc (100 mL) and wash with an aqueous 10% sodium chloride solution (3×30 mL). Collect the organic layer, concentrate in vacuo, and purify the residue by silica gel chromatography (90 g silica, hexane/EtOAc 95/5 to 85/15 gradient) to obtain the desired intermediate (1.75 g, 83%)

3-tert-Butoxycarbonyl-aminomethyl-6-(2-cyclohexyl-ethyl)-pyridine: Add 6-cyclohexylethynyl-nicotinonitrile (1.75 g, 8.3 mmol), 10% Pd/c (Degussa type E101, 50% water by wt) (1.0 g), methanol (100 mL), and di-t-butyl dicarbonate (2.3 g, 10.4 mmol) to a pressure vessel under a nitrogen atmosphere. Pressurize the vessel to 30 psi with hydrogen, and stir the mixture for 3 h (monitor the reaction by TLC). Purge the vessel with nitrogen, filter the mixture through Celite® and wash the cake with dichloromethane under a nitrogen atmosphere. Concentrate the filtrate in vacuo. Purify the residue by silica gel chromatography (90 g silica, hexane/EtOAc, 95/5 to 50/50 gradient) to obtain the desired intermediate (1.05 mg, 40%). MS (ES+) m/z: 319.2 (M+H)+.

3-Aminomethyl-6-(2-cyclohexyl-ethyl)-pyridine: Add trifluoroacetic acid (2.0 mL) to a solution of 3-tert-butoxycarbonyl-aminomethyl-6-(2-cyclohexyl-ethyl)-pyridine (1.05 g, 3.3 mmol) in methanol (20 mL). Stir the solution for 1 h at room temperature under a nitrogen atmosphere. Concentrate the solution in vacuo and purify the residue via SCX chromatography to obtain the desired intermediate (670 mg, 93%). MS (ES+) m/z: 219.2 (M+H)+.

Preparation 352

2-Aminomethyl-5-(2-cyclohexyl-ethyl)-pyridine

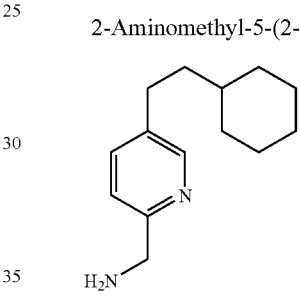

The title compound may be prepared essentially as described in Preparation 351 by using 5-chloro-pyridine-2-carbonitrile (24% yield, MS (ES) m/z 219.2 (M+H)+.

EXAMPLE 666

7-Chloro-6-[4-(2,2-dimethyl-propane-1-sulfonyl)-benzylamino]-2,3,4,5-tetrahydro-1H-benzo[d]azepine (L)-Tartrate

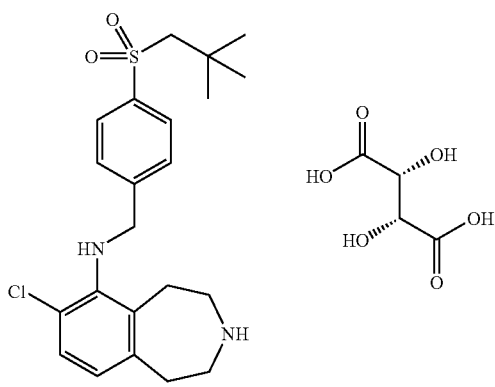

Use a method similar to the General Procedure 5-2 to couple 7-chloro-3-(2,2,2-trifluoroacetyl)-6-trifluoromethanesulfonyloxy-2,3,4,5-tetrahydro-1H-benzo[d] azepine (158 mg, 0.37 mmol) with 4-(2,2-dimethyl-propane-1-sulfonyl)-benzylamine (166 mg, 0.73 mmol) by using tris(dibenzylideneacetone)dipalladium(0) (68 mg, 0.074 mmol), BINAP (92 mg, 0.148 mmol) and cesium carbonate (169 mg, 0.518 mmol) in anhydrous toluene (15 mL). Purify by chromatography on silica gel eluting with hexane/EtOAc (8:2) and then by reversed HPLC [Zorbax Bonus RP, 5 □M 21.2× 100 mm, eluting with water/acetonitrile (0.05% TFA in each), UV detector (230 nm)] to give 7-chloro-6-[4-(2,2-dimethyl-propane-1-sulfonyl)-benzylamino]-3-(2,2,2-trifluoro-acetyl)-2,3,4,5-tetrahydro-1H-benzo[d]azepine as an oil (153 mg, 80%). MS (ES+) m/z: 517 (M+H)$^+$.

Use methods similar to the General Procedures 1-2 and 2-6 to give the title compound as a white solid. MS (ES+) m/z: 421 (M+H)$^+$.

Examples 667-672 may be prepared essentially as described in Example 666 using 7-chloro-3-(2,2,2-trifluoro-acetyl)-6-trifluoromethanesulfonyloxy-2,3,4,5-tetrahydro-1H-benzo[d]azepine and the appropriate amine. Examples 673-674 may be prepared essentially as described in Example 666 using 7-chloro-3-(2,2,2-trifluoroacetyl)-6-trifluoromethanesulfonyloxy-2,3,4,5-tetrahydro-1H-benzo[d] azepine and the appropriate amine but the succinate salt was prepared as described in General Procedure 2-1. MS (ES+) data are shown in the Table below.

| Ex. | Structure | Compound | MS (ES+) m/z |
|---|---|---|---|
| 667 | 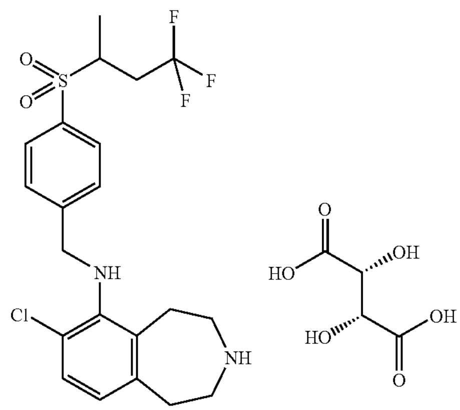 | 7-Chloro-6-[4-(4,4,4-trifluorobutane-2-sulfonyl)-benzylamino]-2,3,4,5-tetrahydro-1H-benzo[d]azepine (L)-Tartrate | 461 (M + H)$^+$ |
| 668 | 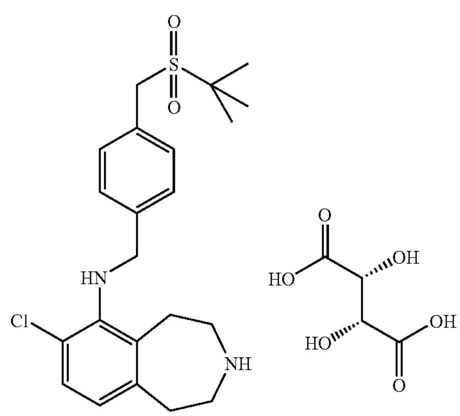 | 7-Chloro-6-[4-(2-methyl-propane-2-sulfonylmethyl)-benzylamino]-2,3,4,5-tetrahydro-1H-benzo[d]azepine (L)-Tartrate | 421 (M + H)$^+$ |
| 669 | 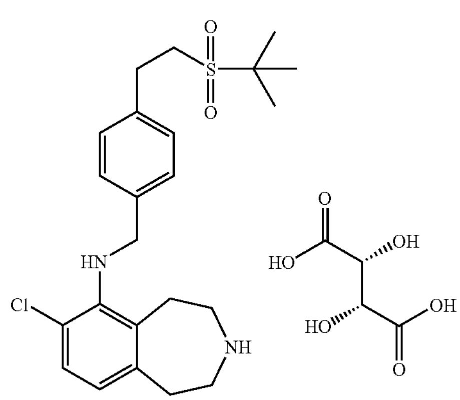 | 7-Chloro-6-[4-(2-methyl-propane-2-sulfonylethyl)-benzylamino]-2,3,4,5-tetrahydro-1H-benzo[d]azepine (L)-Tartrate | 435 (M + H)$^+$ |

-continued

| Ex. | Structure | Compound | MS (ES+) m/z |
|---|---|---|---|
| 670 | 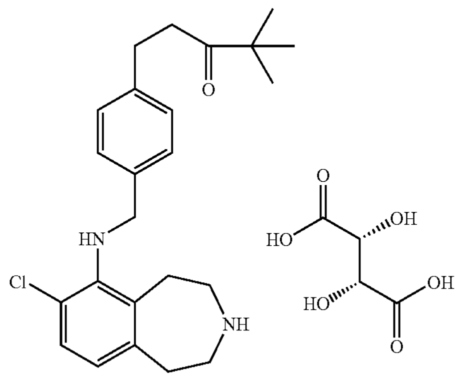 | 7-Chloro-6-[4-(4,4-dimethyl-3-oxo-pentyl)-benzylamino]-2,3,4,5-tetrahydro-1H-benzo[d]azepine (L)-Tartrate | 399 (M + H)+ |
| 671 | 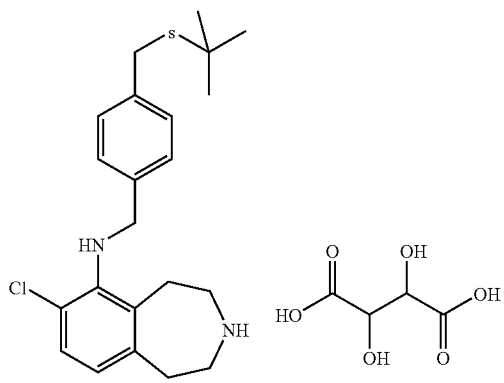 | 7-Chloro-6-[4-(t-butylthiomethyl-benzylamino]-2,3,4,5-tetrahydro-1H-benzo[d]azepine (L)-Tartrate | 389 (M + H)+ |
| 672 | 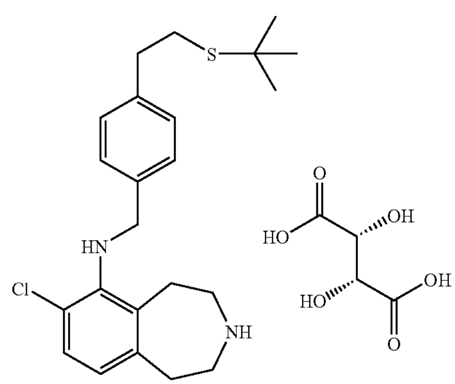 | 7-Chloro-6-[4-(t-butylthioethyl-benzylamino]-2,3,4,5-tetrahydro-1H-benzo[d]azepine (L)-Tartrate | 403 (M + H)+ |
| 673 | 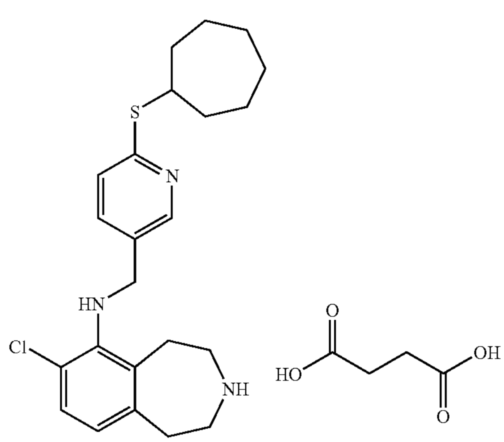 | 7-Chloro-6-[(6-cycloheptylthio-pyridin-3-ylmethyl)-amino]-2,3,4,5-tetrahydro-1H-benzo[d]azepine Succinate | 416 (M + H)+ |

| Ex. | Structure | Compound | MS (ES+) m/z |
|---|---|---|---|
| 674 | 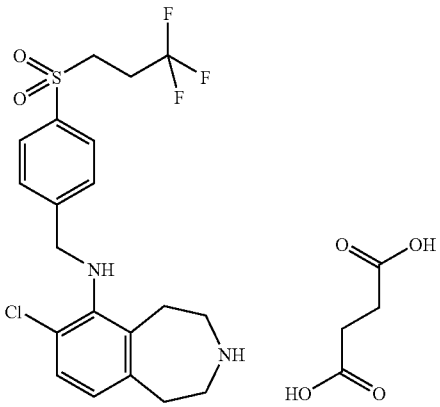 | 7-Chloro-6-[4-(3,3,3-trifluoropropane-1-sulfonyl)-benzylamino]-2,3,4,5-tetrahydro-1H-benzo[d]azepine Succinate | 447 (M + H)+ |

Examples 675-676 may be prepared essentially as described in Example 604 using 7-chloro-3-(2,2,2-trifluoro-acetyl)-6-trifluoromethanesulfonyloxy-2,3,4,5-tetrahydro-1H-benzo[d]azepine and the appropriate amine but the (L)-tartrate salt was prepared as described in General Procedure 2-6. MS (ES+) data are shown in the Table below.

Examples 677-684 may be prepared essentially as described in Example 563 by using 3-tert-butoxycarbonyl-6-(4-carboxy-3-fluoro-benzylamino)-7-chloro-2,3,4,5-tetrahydro-1H-benzo[d]azepine and the appropriate amine. Examples 685-689 may be prepared essentially as described in Example 563 by using 3-tert-butoxycarbonyl-6-(4-car-

| Ex. | Structure | Compound | MS (ES+) m/z |
|---|---|---|---|
| 675 | 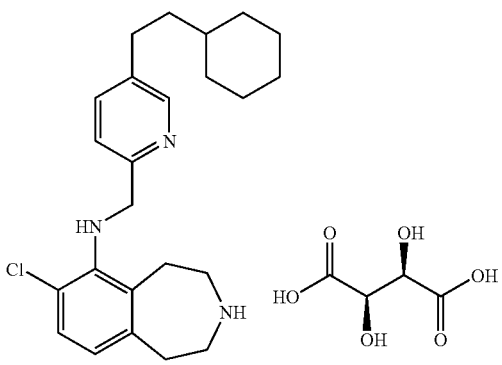 | 7-Chloro-6-(5-cyclohexylethyl-pyridin-2-yl-methylamino)-2,3,4,5-tetrahydro-1H-benzo[d]azepine (L)-Tartrate | 398 (M + H)+ |
| 676 | 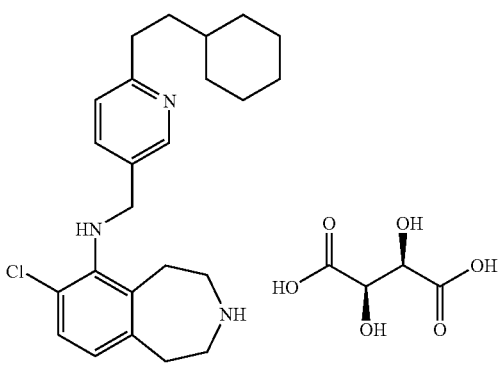 | 7-Chloro-6-(6-cyclohexylethyl-pyridin-3-yl-methylamino)-2,3,4,5-tetrahydro-1H-benzo[d]azepine (L)-Tartrate | 398 (M + H)+ | boxy-benzylamino)-7-chloro-2,3,4,5-tetrahydro-1H-benzo[d]azepine and the appropriate amine. MS (ES+) data are shown in the Table below.

| Ex. | Structure | Compound | MS (ES+) m/z |
|---|---|---|---|
| 677 | 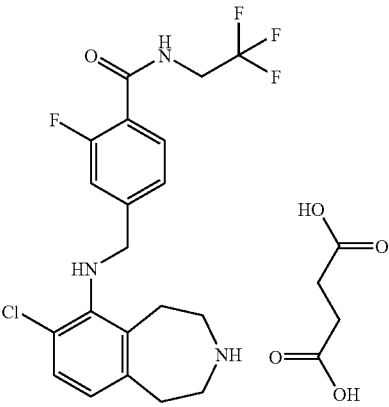 | 7-Chloro-6-[4-(2,2,2-trifluoroethylcarbamoyl)-3-fluoro-benzylamino]-2,3,4,5-tetrahydro-1H-benzo[d]azepine Succinate | 430 (M + H)+ |
| 678 | 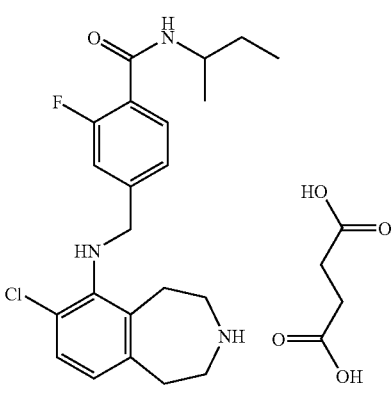 | 7-Chloro-6-[4-(2-butylcarbamoyl)-3-fluoro-benzylamino]-2,3,4,5-tetrahydro-1H-benzo[d]azepine Succinate | 404 (M + H)+ |
| 679 | 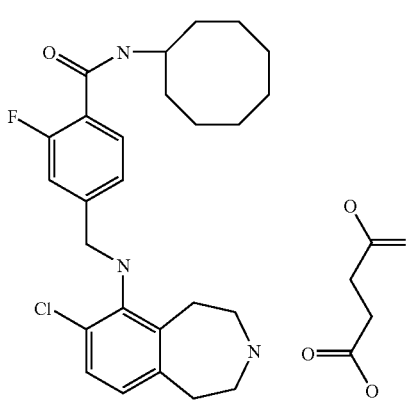 | 7-Chloro-6-[4-(2-cycloheptylcarbamoyl)-3-fluoro-benzylamino]-2,3,4,5-tetrahydro-1H-benzo[d]azepine Succinate | 458 (M + H)+ |

-continued

| Ex. | Structure | Compound | MS (ES+) m/z |
|---|---|---|---|
| 680 | 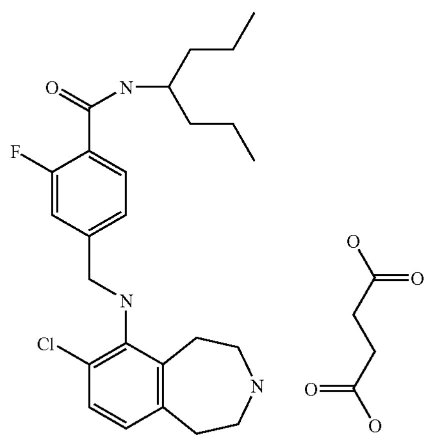 | 7-Chloro-6-[4-(4-heptylcarbamoyl)-3-fluoro-benzylamino]-2,3,4,5-tetrahydro-1H-benzo[d]azepine Succinate | 446 (M + H)+ |
| 681 | 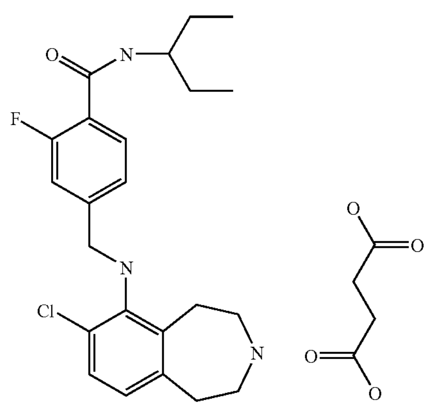 | 7-Chloro-6-[4-(3-pentylcarbamoyl)-3-fluoro-benzylamino]-2,3,4,5-tetrahydro-1H-benzo[d]azepine Succinate | 418 (M + H)+ |
| 682 | 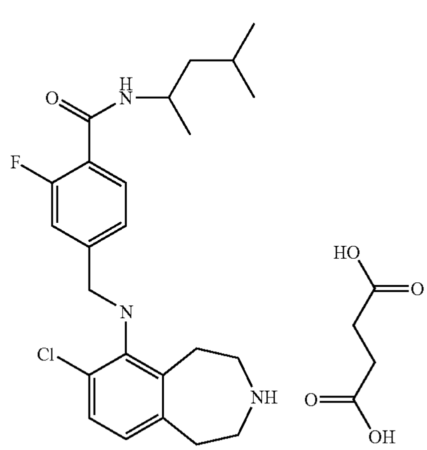 | 7-Chloro-6-[4-(4-methyl-2-pentylcarbamoyl)-3-fluoro-benzylamino]-2,3,4,5-tetrahydro-1H-benzo[d]azepine Succinate | 432 (M + H)+ |

-continued
| Ex. | Structure | Compound | MS (ES+) m/z |
|---|---|---|---|
| 683 | 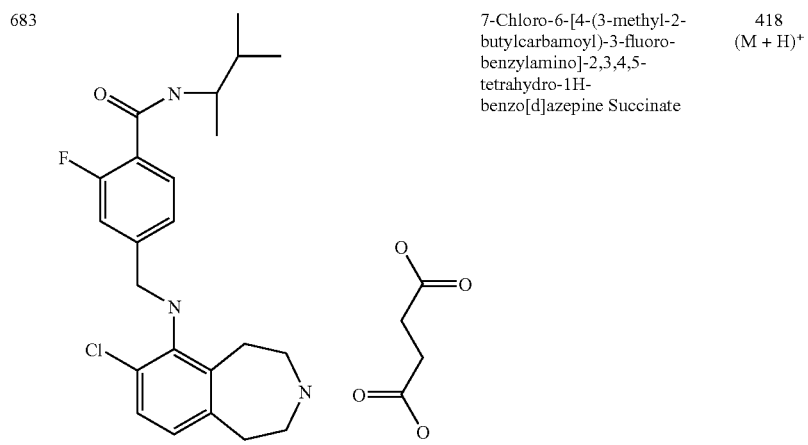 | 7-Chloro-6-[4-(3-methyl-2-butylcarbamoyl)-3-fluoro-benzylamino]-2,3,4,5-tetrahydro-1H-benzo[d]azepine Succinate | 418 (M + H)+ |
| 684 | 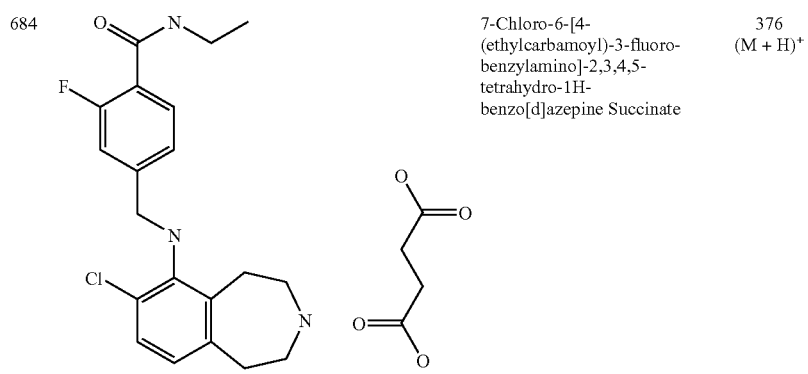 | 7-Chloro-6-[4-(ethylcarbamoyl)-3-fluoro-benzylamino]-2,3,4,5-tetrahydro-1H-benzo[d]azepine Succinate | 376 (M + H)+ |
| 685 | 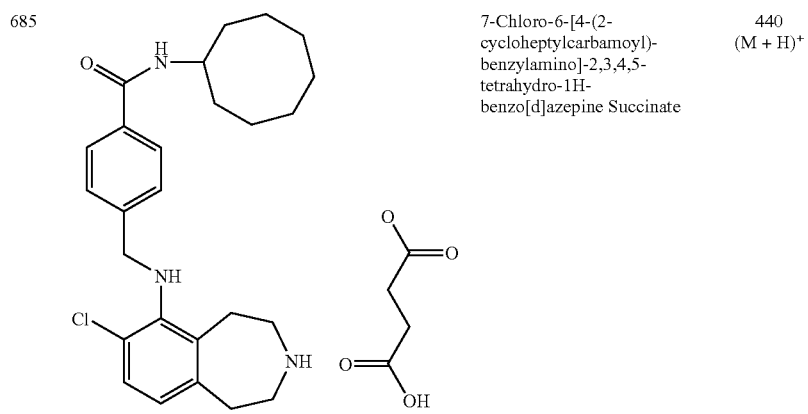 | 7-Chloro-6-[4-(2-cycloheptylcarbamoyl)-benzylamino]-2,3,4,5-tetrahydro-1H-benzo[d]azepine Succinate | 440 (M + H)+ |

-continued
| Ex. | Structure | Compound | MS (ES+) m/z |
|---|---|---|---|
| 686 | 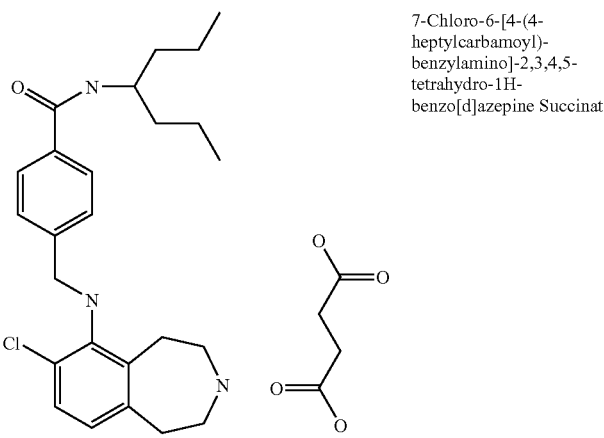 | 7-Chloro-6-[4-(4-heptylcarbamoyl)-benzylamino]-2,3,4,5-tetrahydro-1H-benzo[d]azepine Succinate | 428 (M + H)+ |
| 687 | 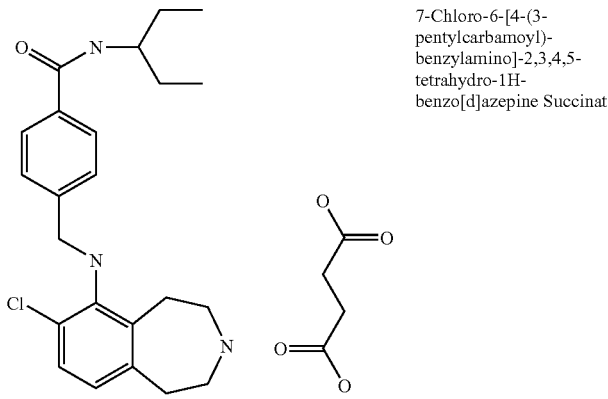 | 7-Chloro-6-[4-(3-pentylcarbamoyl)-benzylamino]-2,3,4,5-tetrahydro-1H-benzo[d]azepine Succinate | 400 (M + H)+ |
| 688 | 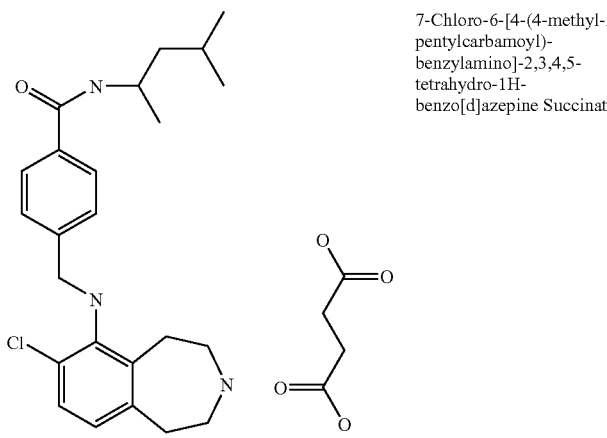 | 7-Chloro-6-[4-(4-methyl-2-pentylcarbamoyl)-benzylamino]-2,3,4,5-tetrahydro-1H-benzo[d]azepine Succinate | 414 (M + H)+ |

-continued

| Ex. | Structure | Compound | MS (ES+) m/z |
|---|---|---|---|
| 689 | 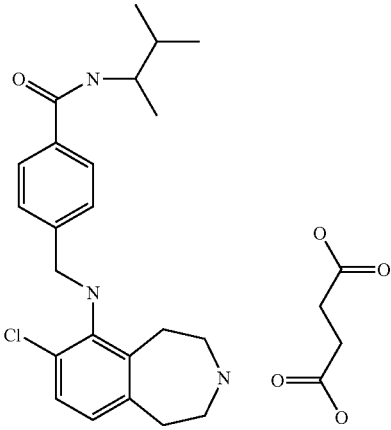 | 7-Chloro-6-[4-(3-methyl-2-butylcarbamoyl)-benzylamino]-2,3,4,5-tetrahydro-1H-benzo[d]azepine Succinate | 400 (M + H)+ |

The compounds of the present invention are relatively selective for the 5-HT$_{2C}$ receptor. The compounds of the present invention are particularly relatively selective for the 5-HT$_{2C}$ receptor in comparison to other 5-HT receptor subtypes and specifically the 5-HT$_{2A}$ and 5-HT$_{2B}$ receptors. This selectivity is demonstrated in the following agonist activity assays and receptor binding assays.

Agonist Activity Assays (G alpha q-GTPγ[$^{35}$S] Binding Assays)

The 5-HT$_2$ receptors are functionally coupled to specific G-proteins. Agonist activation of 5-HT$_2$ G-protein-coupled receptors results in the release of GDP from the α-subunit (G alpha q or G alpha i) of the G-protein and the subsequent binding of GTP. The binding of the stable analog GTPγ[$^{35}$S] is an indicator of receptor activation (i.e. agonist activity).

The G alpha q-GTPγ[$^{35}$S] binding assay is used to determine the in vitro potency (EC$_{50}$) and maximal efficacy (E$_{max}$, normalized to the 5-HT response) of a test compound at the 5-HT$_{2A}$, 5-HT$_{2B}$, and 5-HT$_{2C}$ receptors. The area under the dose response curve (AUC) is also determined for each receptor subtype and used to measure the test compound's selectivity for the 5-HT$_{2C}$ receptor over the 5-HT$_{2A}$ and 5-HT$_{2B}$ receptors, expressed as Selectivity Ratios (AUC 2C/2A and AUC 2C/2B, respectively). The Selectivity Ratios allow the assessment of selectivity based on both potency and efficacy. A selectivity measure that incorporates both potency and efficacy at the 5-HT$_{2C}$ receptor, as compared to the 5-HT$_{2A}$ and 5-HT$_{2B}$ receptors, is considered important due to the adverse events associated with 5-HT$_{2A}$ and 5-HT$_{2B}$ agonist activity (see introduction).

Membrane Preparation: Grow AV12 cells stably transfected with the human 5-HT$_{2A}$, 5-HT$_{2B}$, or 5-HT$_{2C}$ receptors in suspension, harvest by centrifugation, wash the cell pellet with phosphate buffered saline, pH 7.4, pellet the cells again, remove the supernatant, freeze the cell pellet on dry ice and store at −70° C. Thaw stock cell pellet and resuspend in 50 mM Tris, pH 7.4, aliquot into 1-2 mL volumes and refreeze at −70° C. for subsequent assays. (As is appreciated in the art, optimal cell quantities used per aliquot will vary with the individual transfected cell line used. In one embodiment, 5-HT$_{2A}$ and 5-HT$_{2C}$ transfected cells are typically used at about 6×10$^8$ cells per aliquot, while 5-HT$_{2B}$ cells are typically used at about 7.5×10$^8$ cells per aliquot).

On the day of assay, thaw membranes, wash the membranes with assay buffer (50 mM Tris-HCl (pH 7.4), 10 mM MgCl$_2$, 100 mM NaCl, and 0.2 mM EDTA), resuspend in assay buffer and incubate for 10 min. at 37° C. to hydrolyze any residual endogenous 5-HT. Wash the membranes again with assay buffer, and resuspend in assay buffer at a concentration to provide aliquots of about 1-4×10$^6$ cell equivalents per well (typically about 1-2×10$^6$ cell equivalents for assays with 5-HT$_{2A}$ or 5-HT$_{2C}$ receptor assays, and about 3-4×10$^6$ cell equivalents for assays with 5-HT$_{2B}$ receptor assays). Homogenize the cells with a tissue grinder and use the homogenate directly in the assay as described below.

G alpha q-GTPγ[$^{35}$S] Binding Assays: The immunoadsorption scintillation proximity assay (ISPA) of [$^{35}$S]-GTPγS binding to G alpha q is modified from published conditions (DeLapp et al, JPET 289 (1999) 946-955). Dissolve test compounds in DMSO and dilute in assay buffer to provide a range of concentrations to generate a concentration response curve. In wells of a 96 well microtiter plate, mix diluted test compound, GDP (0.1 μM final concentration), and [$^{35}$S]-GTPγS (between 0.5 and 1.0 nM final concentration). Add an aliquot of membranes to the incubation mixture and mix the plates to initiate agonist stimulation of the nucleotide exchange (200 μl final volume). Incubate the microtiter plates for 30 min. at room temperature. Quench the incubation with IGEPAL® CA-630 detergent (0.27% final concentration). Add affinity purified polyclonal rabbit anti-G alpha q antibody (about 1-2 μg per well), and anti-rabbit Ig scintillation proximity assay beads (Amersham; about 1.25 mg per well; 300 μl final volume). Seal the plates and incubate the mixture for 3 h at room temperature. Centrifuge the microtiter plates briefly to pellet beads. Quantitate the GTPγ[$^{35}$S] binding by microtiter plate scintillation spectrometry (Wallac Trilux MicroBeta™ scintillation counter).

Data Analysis: For each concentration response curve for a test compound at a given receptor, analyze the data with GraphPad Prism™ software (v3.O2; GraphPad Software, San Diego, Calif.) running on a personal computer with Micro Soft Windows OS®, using nonlinear regression analysis curve fitting to determine the EC$_{50}$ and E$_{max}$ (normalized to 5-HT control curves). Determine the Area Under the agonist concentration-response Curve (AUC) with GraphPad Prism™ by the trapezoidal method.

To calculate the Selectivity Ratios, first, determine the AUC for the test compound for each receptor subtype as described above. Second, normalize the AUC's at each receptor subtype relative to the AUC determined for 5-HT at that receptor. The normalized AUC for a test compound at a given receptor is therefore expressed as a percentage of the AUC determined for 5-HT at that receptor. For example:

$$5HT_{2A} \text{ Normalized } AUC = a = \frac{\left(\begin{array}{c} AUC_{test\ compound} \text{ at} \\ 5HT_{2A} \text{ receptor} \end{array}\right)}{\left(\begin{array}{c} AUC_{5\text{-}HT} \text{ at} \\ 5HT_{2A} \text{ receptor} \end{array}\right)} \times 100\%$$

$$5HT_{2B} \text{ Normalized } AUC = b = \frac{\left(\begin{array}{c} AUC_{test\ compound} \text{ at} \\ 5HT_{2B} \text{ receptor} \end{array}\right)}{\left(\begin{array}{c} AUC_{5\text{-}HT} \text{ at} \\ 5HT_{2B} \text{ receptor} \end{array}\right)} \times 100\%$$

$$5HT_{2C} \text{ Normalized } AUC = c = \frac{\left(\begin{array}{c} AUC_{test\ compound} \text{ at} \\ 5HT_{2C} \text{ receptor} \end{array}\right)}{\left(\begin{array}{c} AUC_{5\text{-}HT} \text{ at} \\ 5HT_{2C} \text{ receptor} \end{array}\right)} \times 100\%$$

Third, calculate the Selectivity Ratios for the test compound as follows:

Selectivity Ratio for 5-HT$_{2C}$ receptor/5-HT$_{2A}$ receptor
(AUC 2C/2A)=c/a

Selectivity Ratio for 5-HT$_{2C}$ receptor/5-HT$_{2B}$ receptor
(AUC 2C/2B)=c/b

For reference purposes, the AUC 2C/2A and AUC 2C/2B for 5-HT are each 1.0. Likewise, the ratios for mCPP (meta-chlorophenylpiperazine) are tested and are found to be 2.1 and 2.1 respectively.

Representative compounds of the present invention are tested in the G alpha q-GTPγ[$^{35}$S] assays for the 5-HT$_{2A}$, 5-HT$_{2B}$, and 5-HT$_{2C}$ receptors essentially as described above and are found to be a highly potent and selective agonists of the 5-HT$_{2C}$ receptor, with EC$_{50}$'s typically less than or equal to 200 nM, and AUC 2C/2A and AUC 2C/2B ratios greater than 1.5. Preferred compounds are those with EC50's less than or equal to 100 nM, and AUC 2C/2A and AUC 2C/2B ratios greater than or equal to 2.0. More preferred are those with EC50's less than or equal to 50 nM, and AUC 2C/2A and AUC 2C/2B ratios greater than or equal to 3.0.

Ligand Binding Assays

The ligand binding affinity of the compounds of the present invention to the 5-HT$_{2C}$ receptor subtype is measured essentially as described by Wainscott (Wainscott, et al., *Journal of Pharmacology and Experimental Therapeutics*, 276:720-727 (1996)). Data is analyzed by nonlinear regression analysis on the concentration response curves using the four parameter logistic equation described by DeLean (DeLean, et al., *Molecular Pharmacology*, 21, 5-16 (1982)). IC$_{50}$ values are converted to K$_i$ values using the Cheng-Prusoff equation (Cheng, et al., *Biochem. Pharmacol.*, 22, 3099-3108 (1973)).

Representative compounds of the present invention are tested essentially as described above and are found to have excellent affinity for the 5-HT$_{2C}$ receptor, with K$_i$'s typically less than or equal to about 200 nM. Preferred compounds are those with K$_i$'s of less than or equal to about 100 nM. More preferred are those with K$_i$'s less than or equal to 50 nM.

Affinities for other receptor subtypes can readily be determined by slight modification of the above described radioligand receptor binding assay using cells transfected with the desired receptor in place of cells transfected with the 5-HT$_{2C}$ receptor subtype and using an appropriate radioligand. The binding affinities for representative compounds of the present invention for a variety of receptors are determined in such assays and the compounds are found to have surprisingly higher affinity for the 5-HT$_{2C}$ receptor. Affinity for the 5-HT$_{2C}$ receptor is found to be significantly higher than for other 5-HT receptor subtypes, and notably higher than the 5-HT$_{2A}$ and 5-HT$_{2B}$ receptor subtypes. Preferred compounds are those with IC$_{50}$'s equal to or greater than 300 nM for the alpha 1 and alpha 2 adrenergic receptors and equal to or greater than 500 nM for D$_1$ and D$_2$ dopaminergic receptors. More preferred compounds are those with IC$_{50}$'s equal to or greater than 1000 nM for the alpha 1 and alpha 2 adrenergic receptors and the D$_1$ and D$_2$ dopaminergic receptors. Still more preferred are those compounds with IC$_{50}$'s equal to or greater than 3000 nM for the alpha 1 and alpha 2 adrenergic receptors and the D$_1$ and D$_2$ dopaminergic receptors.

For the above in vitro assays, exemplified compounds are assayed and found to have either an EC$_{50}$ or a K$_i$ value of equal to or less than 50 nM, and to have AUC 2C/2A and AUC 2C/2B ratios of greater than or equal to 2.0. Exemplified compounds are assayed and found to have alpha 1 and alpha 2 adrenergic receptor IC$_{50}$'s equal to or greater than 300 nM, and D$_1$ and D$_2$ dopaminergic receptor IC$_{50}$'s equal to or greater than 500 nM.

Rat Feeding Assays

The ability of the compounds of the present invention to treat obesity is demonstrated by testing in acute and chronic rat feeding assays.

Animals: Obtain male Long-Evans rats (Harlan Sprague-Dawley, Indianapolis, Ind.) that are approximately one hundred-days old and have been maintained on a calorie rich diet since weaning (TD 95217, 40% calories from fat; Teklad, Madison, Wis.). House the rats individually with a 12 h:12 h light:dark cycle (lights on from about 22:00 h to about 10:00 h) and maintain rats on the same diet (TD 95217) with free access to water, for about 1-2 weeks to acclimate the rats to the environment. Dose rats orally with vehicle (10% acacia with 0.15% saccharin in water) once daily for at least 1 day (typically 1-2 days) to acclimate the rats to the procedures. Randomize the rats into groups so each group has similar mean body weights.

Calorimetric Acute Feeding Assay: At approximately 8:00 h on the day of assay, weigh each rat and transfer to individual chambers of an open circuit calorimetry system (Oxymax, Columbus Instruments International Corporation; Columbus, Ohio), with free access to food (pre-weighed) and water, and begin measuring VO$_2$ and VCO$_2$. At approximately 10:00 h, dose rats orally with vehicle or test compound, return them to their calorimetry chambers, and continue measuring VO$_2$ and VCO$_2$ at regular time intervals (approximately hourly). At approximately 8:00 h the following day, measure rat body weight and the remaining food, assuming the difference in weight of food is equal to the mass of food consumed. Calculate the 24 h energy expenditure (EE) and respiratory quotient (RQ) essentially as described in Chen, Y. and Heiman, M. L., Regulatory Peptide, 92:113-119 (2000). EE during light photoperiod is indicative of the resting metabolic rate and RQ is indicative of the fuel source the animal utilizes (pure carbohydrate metabolism gives an RQ of about 1.0, pure fat metabolism gives an RQ of about 0.7, mixed carbohydrate and fat metabolism gives intermediate values for RQ). Calculate EE as the product of calorific value (CV) and $VO_2$ per body weight (kg); where CV=3.815+1.232*RQ, and RQ is the ratio of $CO_2$ produced ($VCO_2$) to $O_2$ consumed ($VO_2$). Caloric intake is calculated as (mass of 24 h food intake in grams)×(physiological fuel value of the diet in kilocalorie/g) per kg of body weight.

Acute Feeding Assay with a selective 5-$HT_{2C}$ receptor antagonist: The above calorimetric acute feeding assay is conducted with the following modifications. Open circuit calorimetry systems are not used and only the 24 h periodic food intake and body weight are measured. Three groups of rats are used with the first group receiving a subcutaneous dose of saline (0.5 mL) about 15 minutes prior to the oral dose of vehicle, the second group receiving a subcutaneous dose of saline (0.5 mL) about 15 minutes prior to the oral dose of test compound in vehicle, and the third group receiving a subcutaneous injection of a selective 5-$HT_{2C}$ receptor antagonist, 6-chloro-5-methyl-N-{2-[(2-methylpyridin-3-yl-oxy)pyridin-5-yl]aminocarbonyl}-2,3-dihydroindole (3 mg/Kg, in 35% cyclodextrin, 0.5 mL), about 15 min. prior to the oral dose of test compound in vehicle.

Chronic Feeding Assay: At between approximately 8:00 h and 10:00 h on day one of the assay, weigh and orally dose each rat with vehicle or test compound and return the animal to its home cage, with free access to food (pre-weighed) and water. For each of days 2-15, at between approximately 8:00 h and 10:00 h, measure rat body weight and the weight of food consumed in the last 24 h period, and administer daily oral dose of test compound or vehicle. On days −2 and 15 measure total fat mass and lean mass by nuclear magnetic resonance (NMR) using an EchoMRI™ system (Echo Medical Systems, Houston Tex.). (See Frank C. Tinsley, Gersh Z. Taicher, and Mark L. Heiman, "Evaluation of a New Quantitative Magnetic Resonance (QMR) Method for Mouse Whole Body Composition Analysis", Obesity Research, submitted May 1, 2003.)

Representative compounds of the present invention are tested in acute and chronic feeding assays essentially as described above. In the acute assays, the compounds are found to significantly reduce 24 h food intake, which effect is blocked by pre-administration of the 5-$HT_{2C}$ receptor antagonist. The compounds also are found to dose-dependently reduce RQ without significantly changing the energy expenditure during the light photo-period. Thus the compounds are found to reduce caloric intake and increase the proportion of fuel deriving from fat utilization, without significantly changing the resting metabolic rate. In the chronic assay, the compounds are found to significantly decrease cumulative food intake and cumulative body weight change in a dose-dependent manner compared to control animals. The decrease in body weight is found to be due to loss of adipose tissue while lean body mass is not changed.

The ability of the 5-$HT_{2C}$ receptor agonists of the present invention to treat obsessive/compulsive disorder is demonstrated by testing in a variety of in vivo assays as follows:

Marble Burying Assay

Marble burying in mice has been used to model anxiety disorders including obsessive-compulsive disorders (OCD) due to ethological study of the behavior (e.g. Gyertyan I. "Analysis of the marble burying response: Marbles serve to measure digging rather than evoke burying", *Behavioural Pharmacology* 6: 24-31, (1995) and due to the pharmacological effects of clinical standards (c.f., Njung'E K. Handley SL. "Evaluation of marble-burying behavior as a model of anxiety", *Pharmacology, Biochemistry & Behavior*. 38: 63-67, (1991)); Borsini F., Podhorna J., and Marazziti, D. "Do animal models of anxiety predict anxiolytic effects of antidepressants?", *Psychopharmacology* 163: 121-141, (2002)). Thus, drugs used in the treatment of generalized anxiety in humans (e.g. benzodiazepines) as well as compounds used to treat OCD (e.g. SSRIs like fluoxetine) decrease burying.

House experimentally-naïve male, NIH Swiss mice (Harlan Sprague-Dawley, Indianapolis, Ind.) weighing between 28-35 g in groups of 12 for at least three days prior to testing in a vivarium with 12 h light and dark cycles. Conduct experiments during the light cycle in a dimly lit experimental testing room. Dose mice with vehicle or test compound and, after a specified pretreatment interval (generally 30 min.), place each mouse individually on a rotorod (Ugo Basile 7650) operating at a speed of 6 revolutions/min. and observe for falling. After 2 min. on the rotorod, place the mice individually in a 17×28×12 cm high plastic tub with 5 mm sawdust shavings on the floor that are covered with 20 blue marbles (1.5 cm diameter) placed in the center. After 30 min., count the number of marbles buried (2/3 covered with sawdust). Assess the test compound's effect on marble burying with Dunnett's test and the effect on rotorod performance by Fisher's exact test.

Clinically effective standard compounds suppress marble burying at doses that are devoid of motor-impairing effects as measured on the rotorod. The in vivo efficacy of 5$HT_{2C}$ compounds at the 5$HT_{2C}$ receptor is confirmed by the prevention of effects of the 5$HT_{2C}$ agonists on marble burying by co-administration of the 5$HT_{2C}$ receptor antagonist, 6-chloro-5-methyl-N-{2-[(2-methylpyridin-3-yl-oxy)pyridin-5-yl]aminocarbonyl}-2,3-dihydroindole.

Representative compounds of the present invention are assayed in the marble burying assay essentially as described and are surprisingly found to reduce burying behavior in the test mice. The reduction of burying behavior is found to be blocked by co-administration of the 5-$HT_{2C}$ antagonist. In contrast to the compounds of the present invention, the anxiolytic compound chlordiazepoxide and the antipsychotic compound chlorpromazine decrease marble burying only at doses that also disrupt rotorod performance.

Nestlet Shredding

Mice naturally will construct nests of material available in their living environment. Since this behavior is obsessive in nature, it has been used to model OCD (Xia Li, Denise Morrow and Jeffrey M. Witkin, "Decreases in nestlet shredding of mice by serotonin uptake inhibitors: comparison with marble burying", Psychopharmacology, submitted Jul. 14, 2003). House experimentally-naïve male, NIH Swiss mice (Harlan Sprague-Dawley, Indianapolis, Ind.) weighing between 28-35 g in groups of 12 for at least three days prior to testing in a vivarium with a 12 h light/dark cycle. Conduct experiments during the light cycle in an experimental room with normal overhead fluorescent lighting. Dose mice with vehicle or test compound and after a specified pretreatment interval (generally 30 min.), place the mice individually in a 17×28×12 cm high plastic tub with about 5 mm sawdust shavings on the floor along with a pre-weighed multi-ply gauze pad (51 mm square). After 30 min., weigh the remainder of the gauze pad not removed by the mouse. Determine the weight of the gauze used for nestlet construction by subtraction. Compare the results for test compound treated mice to the results for vehicle control treated mice with Dunnett's test.

Clinically effective OCD treatment standard compounds suppress nestlet shredding at doses that are devoid of motor-impairing effects as measured by the rotorod test. The in vivo efficacy of $5HT_{2C}$ compounds at the $5HT_{2C}$ receptor is confirmed bay the prevention of effects of the $5HT_{2C}$ agonists on nestlet shredding by co-administration of the $5HT_{2C}$ receptor antagonist, 6-chloro-5-methyl-N-{2-[(2-methylpyridin-3-yl-oxy)pyridin-5-yl]aminocarbonyl}-2,3-dihydroindole.

Representative compounds of the present invention are assayed essentially as described above and are surprisingly found to suppress nestlet shredding at doses that are devoid of motor-impairing effects as measured by the rotorod test.

In contrast to the compounds of the present invention, the anxiolytic chlordiazepoxide and the psychomotor stimulant d-amphetamine decreases nestlet shredding only at doses that produce motoric side effects (depression or stimulation, respectively).

Schedule-Induced Polydipsia

Food-deprived rats exposed to intermittent presentations of food will drink amounts of water that are far in excess of their normal daily intake and in excess of their intake when given all of their food at one time (Falk J L. "Production of polydipsia in normal rats by an intermittent food schedule", Science 133: 195-196, (1961)). This excessive behavior is persistent and has been used to model OCD.

Maintain Wistar rats on a food restricted diet (to maintain 85% free feeding weight), but with free access to water. Train the rats in a behavioral testing chamber to press a lever to receive a food pellet under a fixed interval schedule, such that the rats are rewarded with a 45 mg food pellet the first time they press a lever after a 120 second interval has elapsed. The fixed interval is then reset to 120 seconds and the process repeated. Thus, during a 90 min. test session, the rats can earn a maximum of 45 pellets. The behavioral chamber is also equipped with a water bottle that is weighed before and after the session to determine the amount of water consumed.

Administer test compounds on Tuesdays and Fridays. Determine control day performances on Thursdays. Administer compounds either orally at 60 min. before the beginning of a test session, or subcutaneously at 20 min. before the beginning of a test session. Compare the rates of lever pressing and water consumption for each animal's performance during sessions after test compound treatment with that animal's performance during control sessions, expressed as a percent of the control rate. Average the individual percent of control rates for each dose and calculate the standard error of the mean.

Clinically effective OCD treatment standard compounds (e.g. chlomipramine, fluoxetine) suppress schedule-induced polydipsia without producing notable changes in motor patterns, food intake, or behavior the following day. The in vivo efficacy of $5HT_{2C}$ compounds at the $5HT_{2C}$ receptor is confirmed by the prevention of effects of the $5HT_{2C}$ agonists on excessive drinking by co-administration of the $5HT_{2C}$ receptor antagonist, 6-chloro-5-methyl-N-{2-[(2-methylpyridin-3-yl-oxy)pyridin-5-yl]aminocarbonyl}-2,3-dihydroindole.

Representative compounds of the present invention are assayed in the schedule-induced polydipsia assay essentially as described above and are surprisingly found to suppress schedule-induced polydipsia without producing notable changes in motor patterns, food intake, or behavior the following day. The behavior suppression is blocked by co-administration of the $5-HT_{2C}$ antagonist.

In contrast to the compounds of the present invention, the psychomotor stimulant d-amphetamine decreases excessive drinking only at behaviorally stimulating doses and these effects are not prevented by the $5HT_{2C}$ receptor antagonist.

While it is possible to administer compounds employed in the methods of this invention directly without any formulation, the compounds are usually administered in the form of pharmaceutical compositions comprising a pharmaceutically acceptable excipient and at least one compound of Formula I or a pharmaceutically acceptable salt thereof. These compositions can be administered by a variety of routes including oral, rectal, transdermal, subcutaneous, intravenous, intramuscular, and intranasal. The compounds employed in the methods of this invention are effective as both injectable and oral compositions. Such compositions are prepared in a manner well known in the pharmaceutical art. See, e.g. REMINGTON'S PHARMACEUTICAL SCIENCES, (16th ed. 1980).

In making the compositions employed in the present invention the active ingredient is usually mixed with at least one excipient, diluted by at least one excipient, or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard-gelatin capsules, suppositories, sterile injectable solutions, and sterile packaged powders.

In preparing a formulation, it may be necessary to mill the compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The compounds are generally effective over a wide dosage range. For examples, dosages per day normally fall within the range of about 0.01 to about 30 mg/kg. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way.

In some instances dosage levels below the lower limit of the aforesaid range may be more than adequate, while in other cases still larger doses may be employed.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Under some circumstances, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compound employed, the type of pharmacokinetic profile desired from the route of administration, and the state of the patient.

We claim:
1. A compound of Formula I:

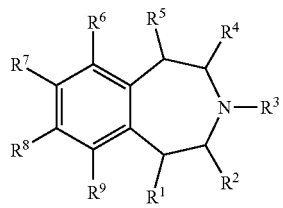

where:
$R^1$ is hydrogen;
$R^2$, $R^3$, and $R^4$ are each hydrogen;
$R^5$ is hydrogen;
$R^6$ is —$NR^{24}R^{25}$;
$R^7$ is halo, cyano, or $CF_3$;
$R^8$ is hydrogen;
$R^9$ is hydrogen;
$R^{24}$ is $(C_1-C_6)$alkoxy$(C_2-C_5)$alkyl optionally substituted with 1 to 6 fluoro substituents, ($C_1-C_6$)alkylthio$(C_2-C_5)$alkyl optionally substituted with 1 to 6 fluoro substituents, $(C_3-C_7)$cycloalkyl$(C_0-C_1)$alkyl-O—$(C_1-C_5)$alkyl, $(C_3-C_7)$cycloalkyl$(C_0-C_1)$alkyl-S—$(C_1-C_5)$alkyl, phenyl$(C_1-C_3)$n-alkyl, $Ph^2$-$(C_1-C_3)$-n-alkyl, $Ar^2(C_0-C_3)$n-alkyl, phenyl$(C_0-C_1)$alkyl-O—$(C_1-C_5)$alkyl, phenyl$(C_0-C_1)$alkyl-S—$(C_1-C_5)$alkyl, $Ph^1$-$(C_0-C_1)$alkyl-C(O)NH—$(C_2-C_4)$alkyl, $Ph^1$-$(C_0-C_1)$alkyl-NH—C(O)NH—$(C_2-C_4)$alkyl, pyridyl-$(C_0-C_1)$alkyl-C(O)NH—$(C_2-C_4)$alkyl, pyridyl-$(C_0-C_1)$alkyl-NH—C(O)NH—$(C_2-C_4)$alkyl, or $Ar^3(C_1-C_2)$alkyl, where $Ar^3$ is a bi-cyclic moiety selected from a group consisting of indanyl, indolyl, dihydrobenzofuranyl, benzofuranyl, benzothiophenyl, benzoxazolyl, benzothiazolyl, benzo[1,3]dioxolyl, naphthyl, dihydrobenzopyranyl, quinolinyl, isoquinolinyl, and benzo[1,2,3]thiadiazolyl, said $Ar^3$ optionally being substituted with $(C_1-C_6)$ alkyl optionally further substituted with 1 to 6 fluoro substituents, phenyl$(C_0-C_1)$alkyl optionally further substituted with 1 to 6 fluoro substituents, or substituted with $(C_3-C_7)$cycloalkyl$(C_0-C_3)$alkyl, or substituted with 1-3 substituents independently selected from the group consisting of halo, oxo, methyl, and —$CF_3$, said phenyl$(C_1-C_3)$ n-alkyl, $Ph^2$-$(C_1-C_3)$ n-alkyl, or $Ar^2(C_0-C_3)$ n-alkyl optionally being substituted on the n-alkyl moiety when present with $(C_1-C_3)$alkyl, dimethyl, gem-ethano, 1 to 2 fluoro substituents, or $(C_1-C_6)$ alkyl-C(O)—, said $Ar^2(C_0-C_3)$ n-alkyl being alternatively optionally substituted with a substituent selected from the group consisting of $(C_3-C_7)$cycloalkyl-$(C_0-C_3)$ alkyl, $Het^1$-$(C_0-C_3)$alkyl, pyridyl-$(C_0-C_3)$alkyl, phenyl-$(C_0-C_3)$alkyl, pyridyl-$(C_0-C_3)$alkyl-NH—, phenyl-$(C_0-C_3)$alkyl-NH—, $(C_1-C_6)$alkyl-S—, and $(C_3-C_7)$cycloalkyl-$(C_0-C_3)$alkyl-S—, and optionally further substituted with one methyl, —$CF_3$, cyano, or —$SCF_3$ substituent, or with 1 to 2 halo substituents, said pyridyl-$(C_0-C_3)$alkyl and phenyl-$(C_0-C_3)$alkyl optionally being further substituted with 1-3 substituents independently selected from halo, —$CH_3$, —$OCH_3$, —$CF_3$, —$OCF_3$, —CN, and —$SCF_3$, and said $Ph^2$-$(C_1-C_3)$ n-alkyl and $Ar^2(C_0-C_3)$ n-alkyl where $Ar^2$ is pyridyl, also optionally being substituted on the phenyl or $Ar^2$ moiety, respectively, with phenyl-CH=CH— or phenyl-C≡C—, said phenyl-CH=CH— or phenyl-C≡C— being optionally further substituted with 1 to 3 substituents independently selected from the group consisting of halo, cyano, —$SCF_3$, $(C_1-C_6)$alkyl optionally further substituted with 1 to 6 fluoro substituents, and $(C_1-C_6)$alkoxy optionally further substituted with 1 to 6 fluoro substituents, and said $Ar^2(C_0-C_3)$ n-alkyl where $Ar^2$ is pyridyl, alternatively, optionally being substituted with $(C_1-C_6)$ alkyl-C(O)— or $R^{28}R^{29}$N—C(O)—, and optionally further substituted with one methyl, —$CF_3$, cyano, or —$SCF_3$ substituent, or with 1 to 2 halo substituents, said phenyl$(C_0-C_1)$alkyl-O—$(C_1-C_5)$alkyl, or phenyl$(C_0-C_1)$alkyl-S—$(C_1-C_5)$alkyl optionally being substituted on the phenyl moiety with $(C_1-C_2)$—S(O)$_2$—, or with 1 to 5 independently selected halo substituents, or with 1 to 3 substituents independently selected from the group consisting of halo, cyano, —SCF$_3$,
($C_1$-$C_6$)alkyl optionally further substituted with 1 to 6 fluoro substituents, and
($C_1$-$C_6$)alkoxy optionally further substituted with 1 to 6 fluoro substituents, and
said pyridyl-($C_0$-$C_1$)alkyl-C(O)NH—($C_2$-$C_4$)alkyl and
pyridyl-($C_0$-$C_1$)alkyl-NH—C(O)NH—($C_2$-$C_4$) alkyl optionally being substituted on the pyridyl moiety with methyl, —CF$_3$, or 1 to 3 halo substituents;

$R^{25}$ is hydrogen, ($C_1$-$C_3$)alkyl optionally substituted with 1 to 6 fluoro substituents, or alkyl;

$R^{26}$ is hydrogen, ($C_1$-$C_4$)alkyl optionally substituted with 1 to 6 fluoro substituents, ($C_3$-$C_7$)cycloalkyl($C_0$-$C_3$)alkyl, Ph$^1$-($C_0$-$C_3$)alkyl, or Het$^2$-($C_0$-$C_3$)alkyl;

$R^{27}$ is hydrogen or ($C_1$-$C_4$)alkyl optionally substituted with 1 to 6 fluoro substituents, or $R^{26}$ and $R^{27}$, taken together with the nitrogen atom to which they are attached, form Het$^1$;

$R^{28}$ is ($C_1$-$C_6$)alkyl optionally substituted with 1 to 6 fluoro substituents, ($C_3$-$C_7$)cycloalkyl-($C_0$-$C_3$)alkyl, tetrahydropyran-3-yl($C_0$-$C_3$)alkyl, tetrahydropyran-4-yl($C_0$-$C_3$)alkyl, tetrahydrofuranyl($C_0$-$C_3$)alkyl, Ph$^1$-($C_0$-$C_2$) n-alkyl, or Ar$^2$—($C_0$-$C_2$) n-alkyl,
said Ph$^1$-($C_0$-$C_2$) n-alkyl and Ar$^2$—($C_0$-$C_2$) n-alkyl optionally being substituted on the alkyl moiety when present with ($C_1$-$C_3$)alkyl, dimethyl, or gem-ethano;

$R^{29}$ is hydrogen or ($C_1$-$C_3$)alkyl;

$R^{30}$ is hydrogen, ($C_1$-$C_6$)alkyl optionally substituted with 1 to 6 fluoro substituents, ($C_3$-$C_7$)cycloalkyl($C_0$-$C_3$)alkyl, Ph$^1$-($C_0$-$C_3$)alkyl, or Ar$^2$($C_0$-$C_3$)alkyl, $R^{31}$ is hydrogen or ($C_1$-$C_6$)alkyl optionally substituted with 1 to 6 fluoro substituents, or $R^{30}$ and $R^{31}$, taken together with the nitrogen atom to which they are attached, form Het$^1$,
said Het$^1$ also optionally being substituted with phenyl optionally further substituted with 1 to 3 halo substituents;

Ar$^2$ is an aromatic heterocycle substituent selected from the group consisting of pyrrolyl, pyrazolyl, imidazolyl, 1,2,3-triazolyl, 1,2,4-triazolyl, furanyl, oxazolyl, isoxazolyl, 1,2,3-oxadiazolyl, 1,2,4-oxadiazolyl, 1,3,4-oxadiazolyl, thiophenyl, thiazolyl, isothiazolyl, 1,2,3-thiadiazolyl, 1,3,4-thiadiazolyl, pyridyl, pyridazinyl, and benzimidazolyl, any of which may optionally be substituted with 1 to 3 substituents independently selected from the group consisting of halo, cyano, —SCF$_3$, ($C_1$-$C_6$)alkyl optionally further substituted with 1 to 6 fluoro substituents, and ($C_1$-$C_6$)alkoxy optionally further substituted with 1 to 6 fluoro substituents, and wherein pyridyl and pyridazinyl may also optionally be substituted with ($C_1$-$C_6$)alkylamino optionally further substituted with 1 to 6 fluoro substituents, ($C_3$-$C_7$)cycloalkyl ($C_0$-$C_3$)alkyl, or ($C_3$-$C_7$)cycloalkyl($C_0$-$C_3$)alkyl-amino;

Het$^1$ is a saturated, nitrogen-containing heterocycle substituent selected from the group consisting of azetidinyl, pyrrolidinyl, piperidinyl, homopiperidinyl, morpholinyl, thiomorpholinyl, homomorpholinyl, and homothiomorpholinyl, any of which may optionally be substituted with ($C_1$-$C_6$)alkyl or with 2 methyl substituents;

Het$^2$ is a saturated, oxygen-containing heterocycle substituent selected from the group consisting of tetrahydrofuranyl, tetrahydropyranyl, and oxepinyl, any of which may optionally be substituted with ($C_1$-$C_6$)alkyl or with 2 methyl substituents;

Ph$^1$ is phenyl optionally substituted with 1 to 5 independently selected halo substituents, or with 1 to 3 substituents independently selected from the group consisting of halo, cyano, —SCF$_3$, ($C_1$-$C_6$)alkyl optionally further substituted with 1 to 6 fluoro substituents, and ($C_1$-$C_6$) alkoxy optionally further substituted with 1 to 6 fluoro substituents;

Ph$^2$ is phenyl substituted with:
 a) 1 to 5 independently selected halo substituents; or
 b) 1 to 3 substituents independently selected from the group consisting of halo, cyano, —SCF$_3$, nitro, hydroxy, ($C_1$-$C_6$)alkyl optionally further substituted with 1 to 6 fluoro substituents, and ($C_1$-$C_6$)alkoxy optionally further substituted with 1 to 6 fluoro substituents; or
 c) 0, 1, or 2 substituents independently selected from the group consisting of halo, cyano, —SCF$_3$, methyl, —CF$_3$, methoxy, —OCF$_3$, nitro, and hydroxy, together with one substituent selected from the group consisting of
  i) ($C_1$-$C_{10}$)alkyl optionally further substituted with 1 to 6 fluoro substituents or mono-substituted with hydroxy, ($C_1$-$C_6$)alkoxy, ($C_1$-$C_6$)alkyl-C(O)—, ($C_1$-$C_6$)alkyl-S(O)—, ($C_1$-$C_6$)alkyl-S(O)$_2$—, ($C_3$-$C_7$)cycloalkyl($C_0$-$C_3$)alkyloxy, ($C_3$-$C_7$)cycloalkyl ($C_0$-$C_3$)alkyl-S(O)—, ($C_3$-$C_7$)cycloalkyl($C_0$-$C_3$) alkyl-S(O)$_2$—, Het$^2$-($C_0$-$C_3$)alkyloxy, Het$^2$-($C_0$-$C_3$)alkyl-S(O), Het$^2$-($C_0$-$C_3$)alkyl-S(O)$_2$, Ph$^1$-($C_0$-$C_3$)alkyloxy, Ph$^1$-($C_0$-$C_3$)alkyl-S(O)—, Ph$^1$-($C_0$-$C_3$)alkyl-S(O)$_2$—,
  ii) $C_1$-$C_{10}$)alkoxy-($C_0$-$C_3$)alkyl optionally further substituted with 1 to 6 fluoro substituents, and optionally further substituted with hydroxy,
  iii) ($C_1$-$C_6$)alkyl-C(O)—($C_0$-$C_3$)alkyl optionally further substituted with 1 to 6 fluoro substituents,
  iv) carboxy,
  v) ($C_1$-$C_6$)alkoxycarbonyl optionally further substituted with 1 to 6 fluoro substituents,
  vi) ($C_1$-$C_6$)alkyl-C(O)—($C_0$-$C_3$)—O— optionally further substituted with 1 to 6 fluoro substituents,
  vii) ($C_1$-$C_6$)alkylthio-($C_0$-$C_3$)alkyl optionally further substituted with 1 to 6 fluoro substituents,
  viii) ($C_1$-$C_6$)alkylsulfinyl-($C_0$-$C_3$)alkyl optionally further substituted with 1 to 6 fluoro substituents,
  ix) ($C_1$-$C_6$)alkylsulfonyl-($C_0$-$C_3$)alkyl optionally further substituted with 1 to 6 fluoro substituents,
  x) ($C_1$-$C_6$)alkylsulfonyl-($C_0$-$C_1$)alkyl-O— optionally further substituted with 1 to 6 fluoro substituents,
  xi) ($C_3$-$C_7$)cycloalkyl($C_0$-$C_3$)alkyl, optionally further substituted on the cycloalkyl with 1 to 4 substituents selected from methyl and fluoro,
  xii) ($C_3$-$C_7$)cycloalkyl($C_0$-$C_3$)alkyl-O—, optionally further substituted on the cycloalkyl with 1 to 4 substituents selected from methyl and fluoro,
  xiii) ($C_3$-$C_7$)cycloalkyl($C_0$-$C_3$)alkyl-C(O)—,
  xiv) ($C_3$-$C_7$)cycloalkyl($C_0$-$C_3$)alkyl-O—C(O)—,
  xv) ($C_3$-$C_7$)cycloalkyl($C_0$-$C_3$)alkyl-S—($C_0$-$C_3$)alkyl,
  xvi) ($C_3$-$C_7$)cycloalkyl($C_0$-$C_3$)alkyl-S(O)—($C_0$-$C_3$) alkyl,
  xvii) ($C_3$-$C_7$)cycloalkyl($C_0$-$C_3$)alkyl-S(O)$_2$—($C_0$-$C_3$)alkyl,
  xviii) Ph$^1$-($C_0$-$C_3$)alkyl, optionally substituted on the alkyl moiety with 1 to 2 fluoro substituents, xix) $Ph^1$-$(C_0$-$C_3)$alkyl-O—, optionally substituted on the alkyl moiety with 1 to 2 fluoro substituents
xx) $Ph^1$-$(C_0$-$C_3)$alkyl-C(O)—,
xxi) $Ph^1$-$(C_0$-$C_3)$alkyl-O—C(O)—,
xxii) $Ph^1$-$(C_0$-$C_3)$alkyl-C(O)—$(C_0$-$C_3)$alkyl-O—,
xxiii) $Ph^1$-$(C_0$-$C_3)$alkylthio,
xxiv) $Ph^1$-$(C_0$-$C_3)$alkylsulfinyl,
xxv) $Ph^1$-$(C_0$-$C_3)$alkylsulfonyl,
xxvi) $Ar^2(C_0$-$C_3)$alkyl,
xxvii) $Ar^2(C_0$-$C_3)$alkyl-O—
xviii) $Ar^2(C_0$-$C_3)$alkyl-S—,
xxix) $Ar^2(C_0$-$C_3)$alkyl-C(O)—,
xxx) $Ar^2(C_0$-$C_3)$alkyl-C(S)—,
xxxi) $Ar^2$—$(C_0$-$C_3)$alkylsulfinyl,
xxxii) $Ar^2$—$(C_0$-$C_3)$alkylsulfonyl,
xxxiii) $Het^1(C_0$-$C_3)$alkyl-C(O)— optionally substituted on the $Het^1$ moiety with $Ph^1$,
xxxiv) $Het^1(C_0$-$C_3)$alkyl-C(S)— optionally substituted on the $Het^1$ moiety with $Ph^1$,
xxxv) N-linked $Het^1$-C(O)—$(C_0$-$C_3)$alkyl-O—,
xxxvi) $Het^2$-$(C_0$-$C_3)$alkyl,
xxxvii) $Het^2$-$(C_0$-$C_3)$alkyloxy,
xxxviii) $Het^2$-$(C_0$-$C_3)$alkyl-S—,
xxxix) $Het^2$-$(C_0$-$C_3)$alkyl-NH—,
xl) $R^{26}R^{27}$N—,
xli) $R^{28}R^{29}$—N—$(C_1$-$C_3)$alkoxy,
xlii) $R^{28}R^{29}$N—C(O)—,
xliii) $R^{28}R^{29}$N—C(O)—$(C_1$-$C_3)$alkyl-O—,
xliv) $R^{28}R^{29}$N—C(S)—,
xlv) $R^{30}R^{31}$N—$S(O)_2$—,
xlvi) HON=$C(CH_3)$—, and
xlvii) HON=$C(Ph^1)$-,
or a pharmaceutically acceptable salt thereof.

2. A compound according to claim 1 wherein $R^7$ is chloro.

3. A compound according to claim 1 wherein $R^{24}$ is $Ph^2$-$(C_1$-$C_3)$ n-alkyl-.

4. A compound according to claim 1 wherein $R^{24}$ is $Ar^2$—$(C_1$-$C_3)$ n-alkyl-.

5. A compound according to claim 1 wherein $R^{24}$ is $Ph^2$-$(C_1$-$C_3)$ n-alkyl- or $Ar^2$—$(C_1$-$C_3)$ n-alkyl-, and $R^{25}$ is hydrogen.

6. A pharmaceutical composition comprising a compound according to claim 1 as an active ingredient in association with a pharmaceutically acceptable carrier, diluent or excipient.

7. A method for the treatment of obesity in mammals, comprising administering to a mammal in need of such treatment an effective amount of a compound according to claim 1.

8. The method of claim 7, where the mammal is human.

9. A method for the treatment of obsessive compulsive disorder in mammals, comprising administering to a mammal in need of such treatment an effective amount of a compound according to claim 1.

10. The method of claim 9, where the mammal is human.

11. A method for the treatment of anxiety in mammals, comprising administering to a mammal in need of such treatment an effective amount of a compound according to claim 1.

12. The method of claim 11, where the mammal is human.

13. The compound according to claim 1 which is 7-chloro-6-[4-(t-butyl-sulfonylmethyl)-benzylamino]-2,3,4,5-tetrahydro-1H-benzo[d]azepine or a pharmaceutically acceptable salt thereof 14. A pharmaceutical composition comprising a compound according to claim 13 as an active ingredient in association with a pharmaceutically acceptable carrier, diluent or excipient.

15. A method for the treatment of obesity in mammals, comprising administering to a mammal in need of such treatment an effective amount of a compound according to claim 13.

16. The method of claim 15, where the mammal is human.

17. A method for the treatment of obsessive compulsive disorder in mammals, comprising administering to a mammal in need of such treatment an effective amount of a compound according to claim 13.

18. The method of claim 17, where the mammal is human.

19. A method for the treatment of depression in mammals, comprising administering to a mammal in need of such treatment an effective amount of a compound according to claim 13.

20. The method of claim 19, where the mammal is human.

21. A method for the treatment of anxiety in mammals, comprising administering to a mammal in need of such treatment an effective amount of a compound according to claim 13.

22. The method of claim 21, where the mammal is human.

* * * * *